United States Patent
Beeley et al.

(10) Patent No.: US 11,865,113 B2
(45) Date of Patent: Jan. 9, 2024

(54) METHODS OF TREATING A PATIENT AFFLICTED WITH NON-ALCOHOLIC STEATOHEPATITIS (NASH)

(71) Applicant: Lipidio Pharmaceuticals Inc., San Diego, CA (US)

(72) Inventors: Nigel R. A. Beeley, Solana Beach, CA (US); J. Gordon Foulkes, Rancho Santa Fe, CA (US); Kieran George Mooney, Lyme, CT (US); Charles Rodney Greenaway Evans, Worthing (GB); Keith Arthur Johnson, Durham, NC (US); Howard G. Welgus, Ballwin, MO (US); Celia P. Jenkinson, San Diego, CA (US)

(73) Assignee: LIPIDIO PHARMACEUTICALS INC., San Diego, CA (US)

( * ) Notice: Subject to any disclaimer, the term of this patent is extended or adjusted under 35 U.S.C. 154(b) by 203 days.

(21) Appl. No.: 16/307,840

(22) PCT Filed: Jun. 6, 2017

(86) PCT No.: PCT/US2017/036224
§ 371 (c)(1),
(2) Date: Dec. 6, 2018

(87) PCT Pub. No.: WO2017/214201
PCT Pub. Date: Dec. 14, 2017

(65) Prior Publication Data
US 2020/0306248 A1 Oct. 1, 2020

Related U.S. Application Data

(60) Provisional application No. 62/483,717, filed on Apr. 10, 2017, provisional application No. 62/351,553, (Continued)

(51) Int. Cl.
*A61K 31/4015* (2006.01)
*A61K 47/10* (2017.01)
(Continued)

(52) U.S. Cl.
CPC ............ *A61K 31/501* (2013.01); *A61K 31/40* (2013.01); *A61K 31/4439* (2013.01); (Continued)

(58) Field of Classification Search
CPC ... A61K 31/4015; A61K 47/10; A61K 9/0014
See application file for complete search history.

(56) References Cited

U.S. PATENT DOCUMENTS 7,335,379 B2 * 2/2008 Carrara .................. A61K 47/08
424/449
2009/0093527 A1 4/2009 Li et al.
(Continued)

OTHER PUBLICATIONS

Kurikawa et al., Biol Pharm Bull. 2013; 36(2):259-67 (Year: 2013).*

(Continued)

*Primary Examiner* — Craig D Ricci
*Assistant Examiner* — Janet L Coppins
(74) *Attorney, Agent, or Firm* — John P. White

(57) ABSTRACT

Pharmaceutical carriers which provide an environment of physical and chemical stability comprising a therapeutically effective amount of an active pharmaceutical ingredient (API) compound of structure I, one or more antioxidants, one or more chelators and a vehicle base comprising water and one or more pharmaceutically acceptable non-aqueous solvents, one or more absorption enhancers, one or more gelling agents and one or more pH buffering agents are described.

(Continued)

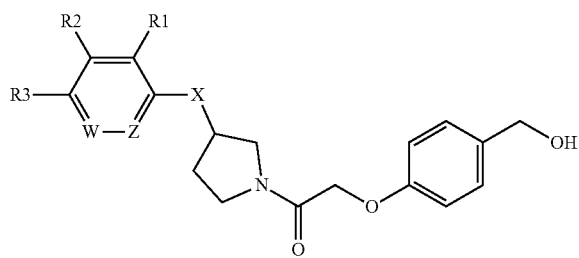

9 Claims, 32 Drawing Sheets

Related U.S. Application Data filed on Jun. 17, 2016, provisional application No. 62/351,174, filed on Jun. 16, 2016, provisional application No. 62/345,972, filed on Jun. 6, 2016, provisional application No. 62/345,963, filed on Jun. 6, 2016.

(51) Int. Cl.
| | | |
|---|---|---|
| *A61K 31/501* | (2006.01) | |
| *A61K 31/40* | (2006.01) | |
| *A61K 31/4439* | (2006.01) | |
| *A61K 47/02* | (2006.01) | |
| *A61K 47/14* | (2017.01) | |
| *A61K 47/18* | (2017.01) | |
| *A61K 47/32* | (2006.01) | |
| *A61K 9/00* | (2006.01) | |
| *A61K 9/06* | (2006.01) | |
| *A61K 45/06* | (2006.01) | |

(52) U.S. Cl.
CPC .............. *A61K 47/02* (2013.01); *A61K 47/10* (2013.01); *A61K 47/14* (2013.01); *A61K 47/183* (2013.01); *A61K 47/32* (2013.01); *A61K 9/0014* (2013.01); *A61K 9/06* (2013.01); *A61K 45/06* (2013.01)

(56) References Cited

U.S. PATENT DOCUMENTS

| | | | |
|---|---|---|---|
| 2009/0118296 A1 | 5/2009 | Black et al. | |
| 2011/0184027 A1* | 7/2011 | Khairatkar-Joshi | A61P 3/08 514/342 |
| 2012/0277280 A1* | 11/2012 | Li | A61P 3/10 514/423 |

OTHER PUBLICATIONS

Alicia Leikin-Frenkel, Ayelet Gonen, Aviv Shaish, Ilana Goldiner, Diana Leikin-Gobbi, Fred M. Konikoff, Dror Harats, Tuvia Gilat, "Fatty Acid Bile Acid Conjugate Inhibits Hepatic Stearoyl Coenzyme A Desaturase and Is Non-atherogenic." Archives of Medical Research, vol. 41, Issue 6, 2010, pp. 397-404, ISSN 0188-4409.

Kurikawa N, Takagi T, Wakimoto S, Uto Y, Terashima H, Kono K, Ogata T, Ohsumi J. "A novel inhibitor of stearoyl-CoA desaturase-1 attenuates hepatic lipid accumulation, liver injury and inflammation in model of nonalcoholic steatohepatitis." Biol Pharm Bull. 2013;36(2):259-67. doi: 10.1248/bpb.b12-00702. PMID: 23370355.

Yoshikazu Uto, "Recent progress in the discovery and development of stearoyl CoA desaturase inhibitors", Chemistry and Physics of Lipids, vol. 197, 2016, pp. 3-12, ISSN 0009-3084.

Safadi R, Konikoff FM, Mahamid M, Zelber-Sagi S, Halpern M, Gilat T, Oren R, Flora Group. "The fatty acid-bile acid conjugate Aramchol reduces liver fat content in patients with nonalcoholic fatty liver disease." Clin Gastroenterol Hepatol. Dec. 2014;12(12) 2085-91.e1. doi:10.1016/j.cgh.2014.04.038. PMID: 24815326.

Ratziu, V. "Novel Pharmacotherapy Options for NASH." Dig Dis Sci. 61, 1398-1405 (2016).

Leikin-Frenkel A, Goldiner I, Leikin-Gobbi D, Rosenberg R, Bonen H, Litvak A, Bernheim J, Konikoff FM, Gilat T. "Treatment of preestablished diet-induced fatty liver by oral fatty acid-bile acid conjugates in rodents." Eur J Gastroenterol Hepatol. Dec. 2008;20(12):1205-13. doi: 10.1097/MEG.0b013e3282fc9743. PMID: 18989145.

T Gilat et al. "Diet Induced Fatty Liver is Prevented and Reversed by Fatty Acid Bile Acid Conjugates (FABACs) via Inhibition of Stearyol Coenzyme A Desaturase 1 in Rodents", Journal of Hepatology (2009), (suppl 1), 22-26.

Sampath H, Flowers MT, Liu X, Paton CM, Sullivan R, Chu K, Zhao M, Ntambi JM. "Skin-specific deletion of stearoyl-CoA desaturase-1 alters skin lipid composition and protects mice from high fat diet-induced obesity." J Biol Chem. Jul. 24, 2009;284(30):19961-73. doi: 10.1074/jbc.M109.014225. Epub May 8, 2009. PMID: 19429677; PMCID: PMC2740422.

Sampath H and Ntambi JM. "Role of stearoyl-CoA desaturase-1 in skin integrity and whole body energy balance." J Biol Chem. Jan. 31, 2014;289(5):2482-8. doi: 10.1074/jbc.R113.516716. Epub Dec. 19, 2013. PMID: 24356954; PMCID: PMC3908384.

Paul Cohen and Jeffrey M. Friedman. "Leptin and the Control of Metabolism: Role for Stearoyl-CoA Desaturase-1 (SCD-1)", The Journal of Nutrition, vol. 134, Issue 9, Sep. 2004, pp. 2455S-2463S.

International Search Report in connection with PCT International Application No. PCT/US2017/036224.

Written Opinion of the International Searching Authority in connection with the PCT International Application No. PCT/US2017/036224.

* cited by examiner

| [palmitate] µM | EC$_{50}$ compound A pM |
|---|---|
| 100 | 43 |
| 33 | 300 |
| 11 | ~871 |
| 3.3 | 577 |
| 1.1 | 610 |
| BSA control | 664 |
| SF media | 838 |

| Compound | % Inhibition of lipid accumulation compared to vehicle |
|---|---|
| CMPD A | 66 |
| CMPD B | 17 |
| CMPD D | 31 |
| CMPD E | 4 |
| CMPD G | 56 |
| CMPD H | 56 |

METHODS OF TREATING A PATIENT AFFLICTED WITH NON-ALCOHOLIC STEATOHEPATITIS (NASH)

CROSS-REFERENCE TO RELATED APPLICATIONS

This application is a § 371 national stage of PCT International Application No. PCT/US2017/036224, filed Jun. 6, 2017 on behalf of GDD Therapeutics, LLC., claiming the benefit of U.S. Provisional Applications Nos. 62/483,717, filed Apr. 10, 2017; 62/351,553, filed Jun. 17; 2016; 62/351,174, filed Jun. 16, 2016; 62/345,972, filed Jun. 6, 2016; 62/345,963, filed Jun. 6, 2016, the contents of each of which are hereby incorporated by reference into the application.

FIELD OF THE INVENTION

The present invention relates to pharmaceutical carriers for pyrrolidine derivatives and pharmaceutical compositions and uses of such formulations, including use as stearoyl-CoA desaturase (SCD-1) inhibitors. It specifically relates to compositions for topical or local use, intended for the treatment and/or prevention of a skin condition associated with abnormal sebum secretion or abnormal sebaceous gland function in a subject. The present invention relates more specifically to a pharmaceutical composition for topical use comprising a pyrrolidine derivative (structure I) having improved pharmaceutical properties over simple formulations typically in use for topical applications. This invention also relates to modifications of the formulation which are unexpectedly advantageous for commercial manufacture of products of this type.

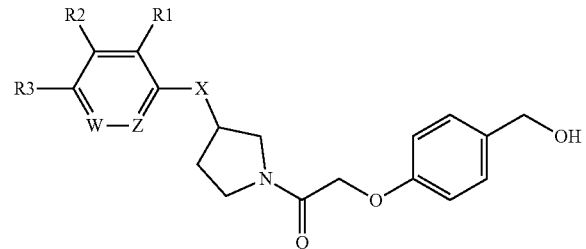

I

Local application of such pharmaceutical compositions is effective for treating a range of skin conditions including, but not limited to, excess sebum production, acne, oily skin, oily hair, shiny or greasy-looking skin, hyper-seborrhea, seborrheic dermatitis, rosacea, sebaceous hyperplasia, and sebaceous carcinoma, as well as related conditions. These pharmaceutical compositions may also be useful in applications involving fat reduction from lipomas and submental fat, and for body sculpting. Treatment of obesity, prediabetic states and diabetes related obesity is also envisaged. Non-alcoholic fatty liver disease (NAFLD) and the more severe Non-alcoholic steatohepatitis (NASH) may also be treated. Additional uses of these pharmaceutical compositions include the treatment of basal-cell skin cancer (BCC), actinic keratosis (AK), squamous-cell skin cancer (SCC), melanoma, Merkel cell carcinoma, and other, less common skin cancers as well as precancerous conditions and diseases of hypopigmentation such as Vitiligo.

BACKGROUND OF THE INVENTION

Stearoyl-CoA desaturase-1 (SCD-1) is a microsomal enzyme that catalyzes the de novo biosynthesis of mono-unsaturated fatty acids from saturated fatty acyl-CoA substrates in mammals. Specifically, SCD-1 introduces a cis-double bond in the C9-C10 position of saturated fatty acids such as palmitoyl-CoA (16:0) and stearoyl-CoA (18:0). The resulting mono unsaturated fatty acids, palmitoyl-CoA (16:1n7) and oleoyl-CoA (18:1n9), are in turn substrates for incorporation into a variety of lipids such as phospholipids, cholesterol esters, and triglycerides. Monounsaturated fatty acids are not only key components of cellular structures, but are also mediators of important biological processes such as signal transduction and cellular differentiation. Studies in mice suggest that SCD-1 activity is important to maintaining the normal functioning of the skin as a result of its major role in lipid synthesis within sebaceous glands. Indeed, global gene deletion of SCD-1 in mice (Miyazaki (2001)) not only results in a hyper-metabolic phenotype with resistance to high fat diet-induced obesity, but also markedly atrophic sebaceous glands with severely impaired sebum output, a similar phenotype to that observed in a spontaneously occurring SCD-1 gene deletion 'asebic' mouse (Zheng (1999)). Interestingly, skin-specific deletion of SCD-1 in mice results in the same resistance to high fat diet-induced obesity and also diminutive sebaceous glands with markedly reduced sebum secretion (Sampath (2009)). SCD-1 expression has been confirmed in the sebaceous glands of human skin by immunohistochemistry (Miyazaki (2003)) and in the immortalized sebaceous gland cell line SZ95 by RT-PCR. U.S. Pat. No. 8,242,286 B2 discloses an SCD-1 inhibitor 2-(4-(hydroxymethyl)phenoxy)-1-(3-(2-(trifluoromethoxyl)phenoxy)pyrrolidin-1-yl)ethanone and its uses, including treating dermatologic and cosmetic conditions such as acne, oily skin, oily hair, shiny skin, greasy-looking skin, greasy-looking hair and seborrheic dermatitis. This patent also discloses medical and cosmetic uses based on the involvement of SCD-1 in obesity, cancer, diabetes and other diseases. However, no pharmaceutical carrier and/or formulation details are reported.

Acne is the most common skin disease. It has a high impact on quality of life and is associated with depression, anxiety, and loss of self-esteem. Of all skin diseases, acne entails direct medical costs second only in magnitude to skin ulcers and wounds. Acne often appears at the onset of puberty, and its prevalence is highest in the middle to late teenage population, although it can persist into middle age, especially in women (Zaenglein (2012)). The overall population prevalence has been estimated at 14% (Tan (2008)), with up to 50 million affect annually in the USA alone. Several treatments already exist for this and related dysfunctions of the skin, but none of them are without significant drawbacks. Thus, by way of example, it is known that a vitamin A derivative, isotretinoin (otherwise known as 13-cis-retinoic acid, Accutane®), is the most efficacious drug in the treatment of severe acne, and acts by inducing atrophy of the sebaceous glands with consequent sebum reduction. However, this substance must be administered systemically to maximize efficacy, since topical administration does not cause sebum reduction. However, such systemic administration causes significant unwanted side effects. Notably, oral isotretinoin is a known severe teratogen, with the potential to cause birth defects due to in utero exposure. Generic versions of the drug are now available in the USA, however women of childbearing potential who are candidates for its use are required to enroll in a special pregnancy prevention program (along with the prescribing physician and pharmacist) and must use multiple forms of birth control. Because of safety concerns and overall benefit vs. risk considerations, isotetinoin use is restricted to the most severe forms of acne which are unresponsive to other treatments. Apart from the very predictable teratogenic effects of isotretinoin, the drug has been associated with suicide ideation, serious gastrointestinal disease, lipid elevations and many common annoying side effects including dryness of skin and mucous membranes, ocular dryness and inflammation, muscle/joint pain. Consequently this drug is contraindicated or otherwise inappropriate or unacceptable for a significant proportion of the population who could benefit from its dramatic sebosuppressive effects.

The pathogenesis of acne involves several elements including excess sebum production, follicular epidermal hyper-proliferation, inflammation, and the presence of the bacterium *Propionibacterium acnes*. Studies have shown a strong correlation between the sebum excretion rate (SER) and untreated acne severity. People with low or normal SER do not get acne or have very mild forms, whereas people with high SER are more acne-prone, and the higher the SER, the more severe the acne. In addition, the reduction in SER produced by systemically administered drugs correlates directly with objective acne improvement measures (Janiczek-Dolphin (2010)). Topical application of 2-(4-(hydroxymethyl)phenoxy)-1-(3-(2-(trifluoromethoxy)phenoxy)pyrrolidin-1-yl)ethanone and/or related analogs can potentially reduce sebum production and inflammation therefore representing novel drugs for the treatment of acne.

Acne represents only one example of the potential therapeutic utility of SCD-1 regulated pathway modulators. Related skin disorders include oily skin, oily hair, shiny or greasy-looking skin, rosacea, hyperseborrhea, seborrheic dermatitis, sebaceous hyperplasia, and sebaceous carcinoma.

Regulation of some of the same biochemical pathways as in the sebaceous glands can also occur in adipose tissue, so yet other applications involve the potential diminution and/or removal of fat cells in conditions such as lipomas and excess submental fat. The SCD-1 inhibitors may also be useful for body sculpting.

Overweight and obesity are typically defined as abnormal or excessive fat accumulation where increases in weight over a healthy level come with major health implications. The degree to which an adult is overweight is assess by their BMI (Body Mass Index) which can range from overweight (BMI=25-30 through to severely obese (BMI>40). Obesity predisposes individuals to development of type 2 diabetes and associated complications such as NASH, NAFLD, diabetic nephropathy, neuropathy and retinopathy and cardiovascular disease co-morbidities. World wide obesity is a pandemic, having doubled since 1980 (WHO http://www.who.int/mediacentre/factsheets/fs311/en/). 13% of adults over 18 are considered to be overweight in 2014 and a further 13% were obese, including 41 million children under the age of 5 Diet and exercise is typically ineffective long-term and the current five approved drugs (orlistat, lorcaserin, phentermine-topiramate, bupropion-naltrexone and the injectable liraglutide) not only lack sufficient efficacy but also carry safety risks (Omran 2017; Khera et al. 2016). The most effective weight-loss procedure continues to be bariatric surgery but only those with morbid obesity and a BMI>40, or other serious health problems such as type 2 diabetes and a BMI of >35, are eligible for the operation (Kozlowski 2016). Topical Stearoyl-CoA desaturase 1 (SCD1) inhibitors are a novel approach to reducing weight through reduction in adipocyte differentiation and lipid accumulation and an increase in energy expenditure without the side effects associated with currently marketed systemic drugs. Mice lacking SCD1 only in the skin are resistant to weight gain and metabolic effects of a high fat diet (Sampath 2009).

Non-alcoholic fatty liver disease (NAFLD) occurs when fat is deposited in the liver due to causes other than alcohol abuse. NAFLD is the most common liver disorder in developed countries (Shaker et al (2014), Rinella (2015)). NAFLD is related to insulin resistance and metabolic syndrome, which have become increasingly common in the United States and throughout the developed world. Up to 80% of obese people have NAFLD (Sanyal (2002)). Non-alcoholic steatohepatitis (NASH) is the most severe form of NAFLD, and is regarded as a major cause of cirrhosis of the liver (Clark et al (2003)). The pathophysiology of NASH begins with fat accumulation in the liver (hepatic steatosis; NAFLD), which in some people progresses to NASH, which is associated with inflammation and fibrosis (steatohepatitis). The causes of this progression remain undefined, but may involve a variety of insults to the liver including toxins and medications. NASH is a progressive disease. Over a 10-year period, up to 20% of patients with NASH will develop cirrhosis of the liver, and 10% will suffer death related to liver disease (McCulough (August 2004)). Treatment of both NASH and NAFLD is envisaged to be advantageous with the SCD1 inhibitors of the present invention.

The SCD-1 inhibitors may also be useful to treat certain types of skin cancer such as basal-cell skin cancer (BCC), squamous-cell skin cancer (SCC), melanoma, Merkel cell carcinoma, and other, less common skin cancers. They may also be useful to treat precancerous conditions such as actinic keratosis (AK). Cancer cells have an abnormally high rate of aerobic glycolysis which not only produces ATP but also abundant molecules for lipid synthesis. Tumor cells are heavily reliant on de novo lipogenesis as fuel sources to maintain their proliferation rate (Peck et al. 2016)). The lipid rich environment in the tumor cell, both normoxic and hypoxic, is sustained through an increase in lipid droplets (LD), formation of which involves SCD1 expression (Koizume and Miyagi 2016). Reduction of SCD1 in tumor cells leads to decreased mono-unsaturated fatty acids, and thus decreases in cell membrane synthesis and proliferation with elevated apoptosis (Mason etal. 2012). An increase in SCD1 expression has been reported in several different tumor types including human cutaneous melanomas (Sumantran et al. 2015). Increased expression of SCD1 has been associated with a worsened prognosis in several tumors and was identified as a signature gene in association three other lipid genes in stage II colorectal cancer (Vargas et al. 2015). Inhibition of SCD1 in melanoma may therefore decrease survival of the melanoma cells and provide a therapeutic alternative for melanoma. Several types of skin cancers start as precursor 'in situ' forms which may evolve into invasive malignancy. For example, actinic keratosis (AK) is a pre-cancerous patch of erythematous, scaly, and crusty skin. These growths are more common in fair-skinned people and those who are frequently in the sun. They usually form when skin gets damaged by ultraviolet (UV) radiation from the sun. AKs are considered potentially pre-cancerous because left untreated, they progress into a type of cancer called squamous cell carcinoma (Werner et al (2015)). As another example, melanoma in situ or lentigo maligna is a precursor of melanoma that consists of malignant cells but does not show invasive growth. The transition to true melanoma is marked by vertical growth and invasion. It is normally found in the elderly, on skin areas with high levels of sun exposure like the face and forearms. Lentigo maligna is a melanoma precursor whose incidence of evolution to invasive melanoma is around 5% (McKenna et al (2006)). Unsaturated fatty acids (oleic acid, linoleic and γ-linolenic acid) have been found to decrease melanogenesis, and linoleic acid is often used to treat melasma. Studies with palmitate and linoleic acid in mouse B16F10 melanoma cells demonstrated that the SCD1 substrate palmitate enhanced levels of tyrosinase, the rate-limiting enzyme in melanogenesis (Ando et al. 2004). Similarly other groups have reported that palmitoleic acid results in reduction of melanin synthesis and tyrosinase activity in B16F10 cells (Yoon et al. 2010), whereas palmitate and stearate stimulated tyrosinase activity in a cell-free assay (Shabani et al. 2010). A SCD1 inhibitor, via reducing the unsaturated:saturated fatty acid ratio, may increase melanogenesis and be used in the treatment of diseases of hypopigmentation such as Vitiligo. There remains, therefore, an unmet need to develop new medicaments against the dysfunctions mentioned above, and in particular pharmaceutical compositions for topical use which make it possible to avoid the drawbacks associated with systemic administration.

SUMMARY OF THE INVENTION

The subject invention provides a pharmaceutical composition comprising a pharmaceutically acceptable carrier which provides an environment of physical and chemical stability and a compound or a pharmaceutically acceptable salt of the compound or ester of the compound or prodrug form of the compound, wherein the compound has the structure I:

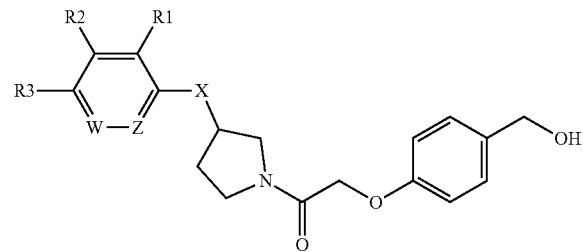

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$;

wherein adjacent substituents $R_1$, $R_2$ and $R_3$ and $R_4$ and $R_5$, if present, may form a saturated or unsaturated 5-membered or 6-membered carbocyclic or heterocyclic ring;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;
wherein optionally substituted alkenyl, if present, may have one or more double bond and each double bond may independently be cis or trans, E or Z, a cis/trans mixture or an E/Z mixture; and
wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The subject invention provides a method of treating a skin condition associated with abnormal sebum secretion or abnormal sebaceous gland function in a subject which comprises topically and periodically applying to an area of the subject's skin affected by the skin condition a composition comprising a pharmaceutically acceptable carrier, which provides an environment of physical and chemical stability, and an amount of a compound or of a pharmaceutically acceptable salt of the compound or ester of the compound or prodrug form of the compound effective to treat the skin condition, wherein the compound has the structure I:

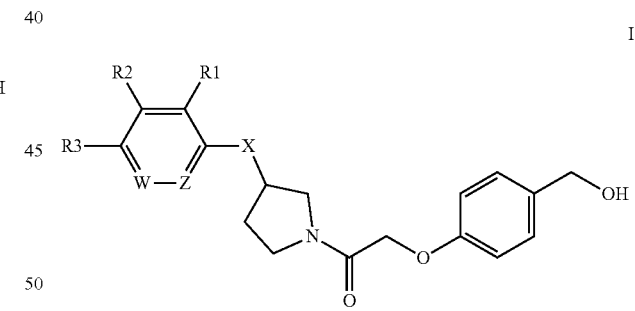

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof;

PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention also provides a method of treating excess fat in a subject which comprises administering to an area of excess fat a composition comprising a pharmaceutically acceptable carrier, which provides an environment of physical and chemical stability, and an amount of a compound or of a pharmaceutically acceptable salt of the compound or ester of the compound or prodrug form of the compound effective to treat the skin condition, wherein the compound has the structure I:

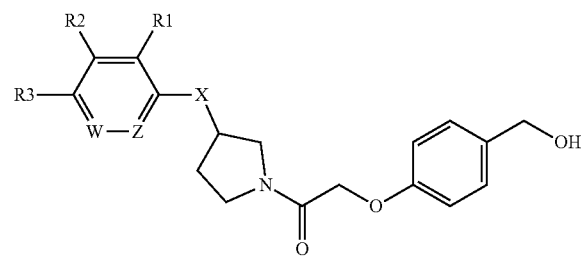

I wherein:
X is O, NH, N-alkyl or N-acyl, S, SO or SO$_2$;
W is independently CR$_4$ or N;
Z is independently CR$_5$ or N;
wherein each of R$_1$, R$_2$ and R$_3$ and R$_4$ and R$_5$, if present, is independently:

H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$;

SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The subject invention provides a method of treating obesity, including pre-diabetic obese states as well as obesity related diabetes, in a subject which comprises topically and periodically applying to an area of the subject's skin a composition comprising a pharmaceutically acceptable carrier, which provides an environment of physical and chemical stability, and an amount of a compound or of a pharmaceutically acceptable salt of the compound or ester of the compound or prodrug form of the compound effective to treat the skin condition, wherein the compound has the structure I:

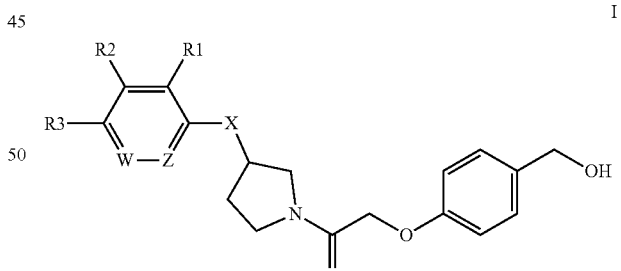

I wherein:
X is O, NH, N-alkyl or N-acyl, S, SO or SO$_2$;
W is independently CR$_4$ or N;
Z is independently CR$_5$ or N;
wherein each of R$_1$, R$_2$ and R$_3$ and R$_4$ and R$_5$, if present, is independently:

H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F;

OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The subject invention provides a method of treating Non-Alcoholic Fatty Liver Disease (NAFLD and the more severe Non-Alcoholic SteatoHepatitis (NASH) in a subject which comprises topically and periodically applying to an area of the subject's skin a composition comprising a pharmaceutically acceptable carrier, which provides an environment of physical and chemical stability, and an amount of a compound or of a pharmaceutically acceptable salt of the compound or ester of the compound or prodrug form of the compound effective to treat the skin condition, wherein the compound has the structure I:

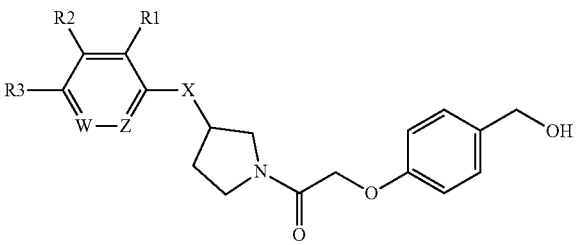

I wherein:
X is O, NH, N-alkyl or N-acyl, S, SO or SO$_2$;
W is independently CR$_4$ or N;
Z is independently CR$_5$ or N;
wherein each of R$_1$, R$_2$ and R$_3$ and R$_4$ and R$_5$, if present, is independently:
H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention provides a method of treating a skin condition associated with cancer in a subject, such basal-cell skin cancer (BCC), squamous-cell skin cancer (SCC), melanoma, Merkel cell carcinoma, and other, less common skin cancers, as well as precancerous conditions (e.g. actinic keratoses) and diseases of hypopigmentation such as Vitiligo, which comprises topically and periodically applying to an area of the subject's skin affected by the skin condition a composition comprising a pharmaceutically acceptable carrier, which provides an environment of physical and chemical stability, and an amount of a compound or of a pharmaceutically acceptable salt of the compound or ester of the compound or prodrug form of the compound effective to treat the skin condition, wherein the compound has the structure I:

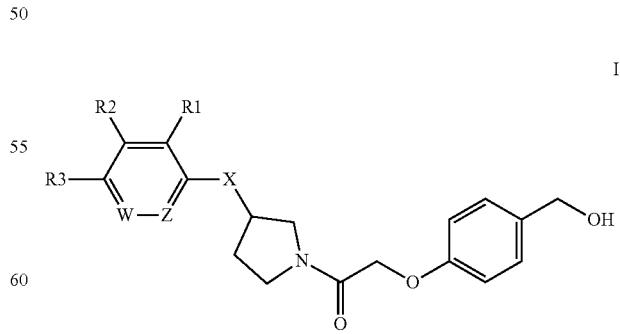

I wherein:
X is O, NH, N-alkyl or N-acyl, S, SO or SO$_2$;
W is independently CR$_4$ or N;
Z is independently CR$_5$ or N;

wherein each of $R_1$, $R_2$ and $R_3$ and $R_4$ and $R_5$, if present, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7C(NR_8)NR_9R_{10}$;

wherein adjacent substituents $R_1$, $R_2$ and $R_3$ and $R_4$ and $R_5$, if present, may form a saturated or unsaturated 5-membered or 6-membered carbocyclic or heterocyclic ring;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The subject application still further provides a compound having the structure I, or a pharmaceutically acceptable salt thereof, or prodrug form thereof,

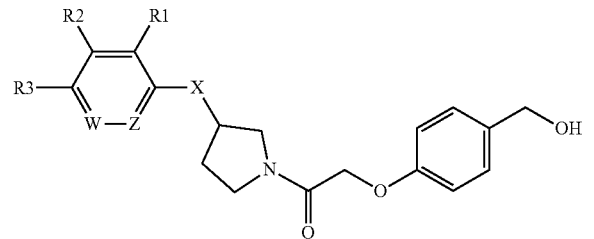

I wherein:
X is NH, N-alkyl or N-acyl;
W is independently $CR_4$ or N;
Z is independently $CR_5$ or N;
wherein each of $R_1$, $R_2$ and $R_3$ and $R_4$ and $R_5$, if present, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7C(NR_8)NR_9R_{10}$;

wherein adjacent substituents $R_1$, $R_2$ and $R_3$ and $R_4$ and $R_5$, if present, may form a saturated or unsaturated 5-membered or 6-membered carbocyclic or heterocyclic ring;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

and wherein Rx is alkyl, cycloalkyl, alkylcycloalkyl, acyl, ester, or thioester.

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The subject application also provides a compound having the structure I, or pharmaceutically acceptable salt thereof, or prodrug form thereof,

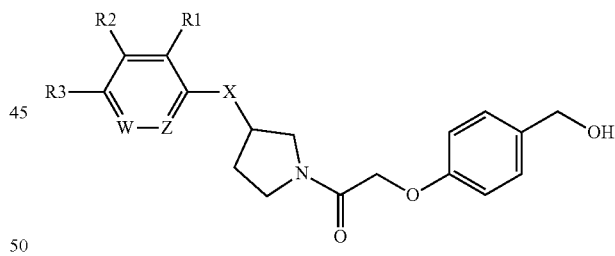

I wherein:
X is S, SO or $SO_2$;
W is independently $CR_4$ or N;
Z is independently $CR_5$ or N;
wherein $R_1$, $R_2$ and $R_3$ and $R_4$ and/or $R_5$, if present, are independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ and esters thereof; $CO_2H$ and esters thereof; $PO_2(OCH_3)H$ and phosphonates thereof; $NO_2$; $NH_2$;

NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and/or R$_5$, if present, may form a saturated or unsaturated 5-membered or 6-membered carbocyclic or heterocyclic ring;

wherein R$_6$, R$_7$, R$_8$, R$_9$ and R$_{10}$, if present, are independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx is alkyl, cycloalkyl, alkylcycloalkyl, acyl, ester, or thioester.

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention still further provides a compound having the structure I, or a pharmaceutically acceptable salt thereof, or prodrug form thereof,

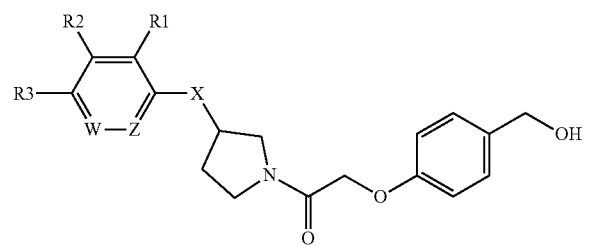

I wherein:
X is O;
W is CR$_4$ or N;
Z is CR$_5$ or N;
wherein at least one of W and Z is N;
wherein each of R$_1$, R$_2$ and R$_3$ and R$_4$ and R$_5$, if present, is independently:

H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention also provides a compound having the structure I, or a pharmaceutically acceptable salt thereof, or prodrug form thereof,

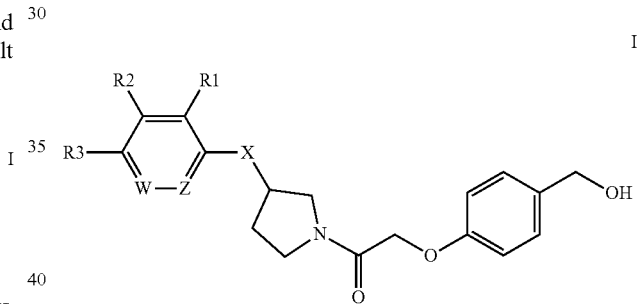

I wherein:
X is O;
W is CR$_4$;
Z is CR$_5$;
wherein each of R$_1$, R$_2$, R$_3$, R$_4$ and R$_5$ is independently:
H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein at least two of R$_1$, R$_2$, R$_3$, R$_4$ and R$_5$ is other than H;

wherein adjacent substituents R$_1$, R$_2$, R$_3$, R$_4$ and R$_5$ may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention further provides a compound having the structure I, or a pharmaceutically acceptable salt thereof, or prodrug form thereof,

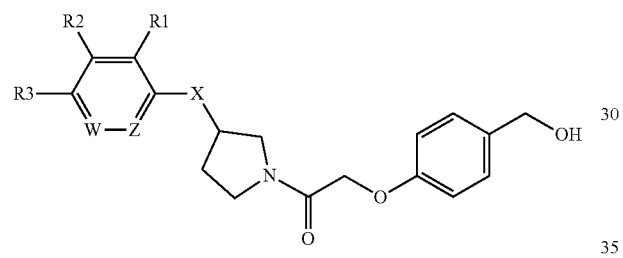

I wherein:
X is O;
W is $CR_4$;
Z is $CR_5$;
wherein one of $R_1$, $R_2$, $R_3$, $R_4$ and $R_5$ is independently:
OH; O-alkyl; O-cycloalkyl; O-alkylcycloalkyl; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$; and the rest of $R_1$, $R_2$, $R_3$, $R_4$ and $R_5$ is H.

wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention yet further provides a compound having the structure I, or a pharmaceutically acceptable salt thereof, or prodrug form thereof,

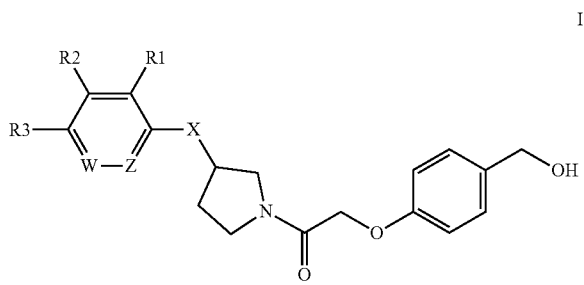

I wherein:
X is O;
W is $CR_4$;
Z is $CR_5$;
wherein each of $R_1$ and $R_5$ is H;
wherein each of $R_2$, $R_3$, and $R_4$ is independently:
H; OH; F; Cl; Br; I; $C_1$ to $C_6$ straight chain or branched chain alkyl; $CH_2F$; $CHF_2$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$;

wherein adjacent substituents $R_2$, $R_3$ and $R_4$ may form a saturated or unsaturated 5-membered or 6-membered carbocyclic or heterocyclic ring;

wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

DETAILED DESCRIPTION OF THE INVENTION

Figure 1A:
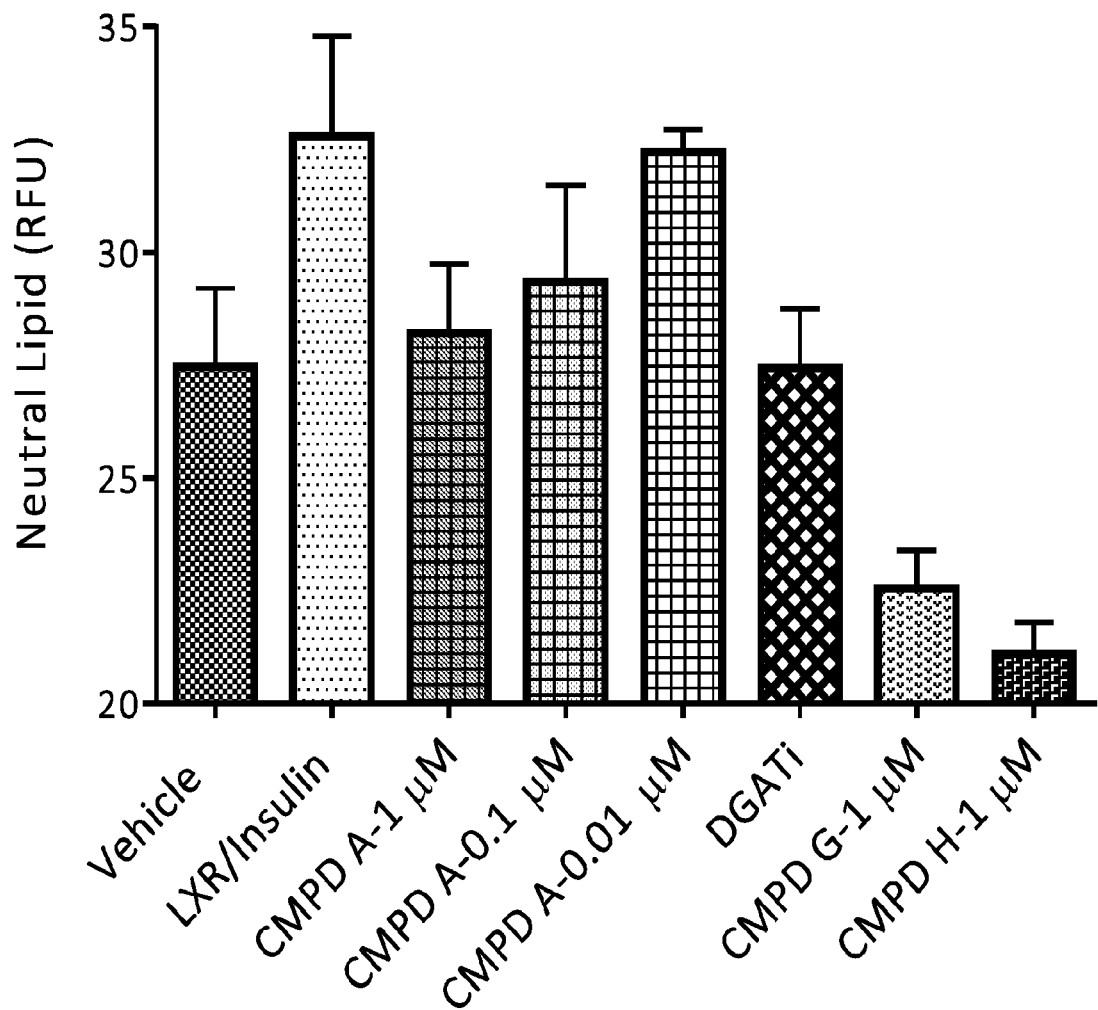
FIG. 1 shows inhibition of neutral lipid accumulation (A) and viability of sebocytes (B), following co-incubation of SCD1 inhibitors Compound A, Compound G and Compound H with an LXR agonist and Insulin for 3 days. Data from a representative experiment from a single donor is shown as mean±s.e.m with each point in quadruplicate.

The subject invention provides a pharmaceutical composition comprising a pharmaceutically acceptable carrier which provides an environment of physical and chemical stability and a compound or a pharmaceutically acceptable salt of the compound or ester of the compound or prodrug form of the compound, wherein the compound has the structure I:

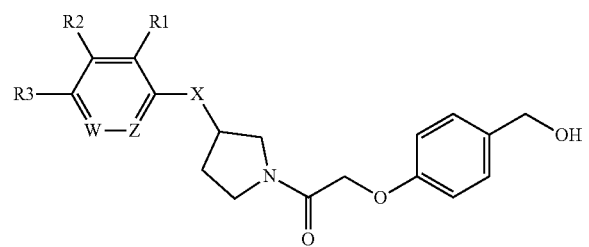

I wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7$C($NR_8$)$NR_9R_{10}$;

wherein adjacent substituents $R_1$, $R_2$ and $R_3$ and $R_4$ and $R_5$, if present, may form a saturated or unsaturated 5-membered or 6-membered carbocyclic or heterocyclic ring;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

In some embodiments, X is O; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7$C($NR_8$)$NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In other embodiments, the compound is one of the following:

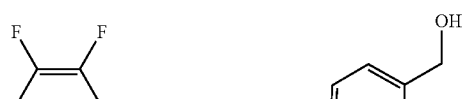

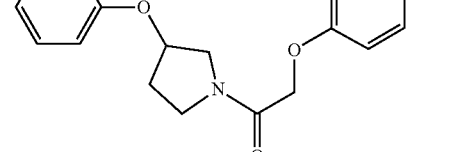

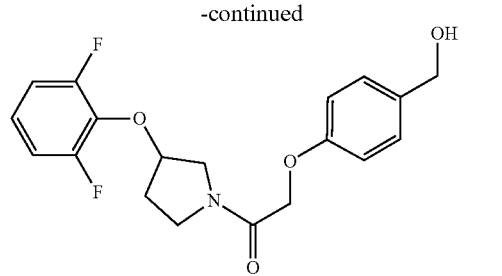
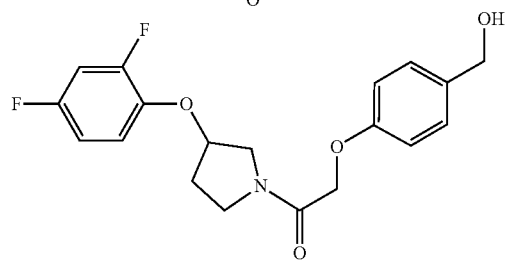
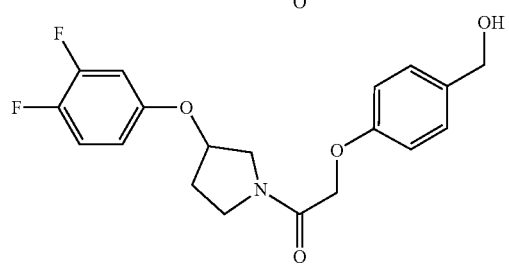
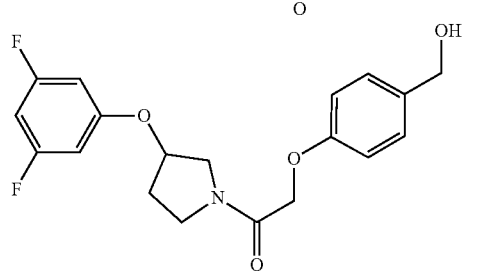
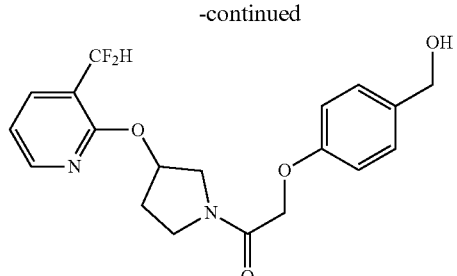
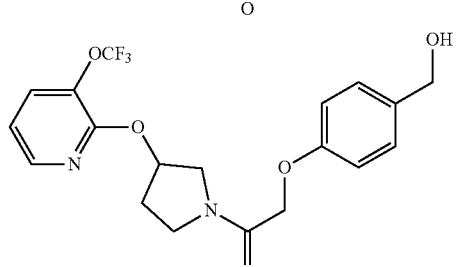
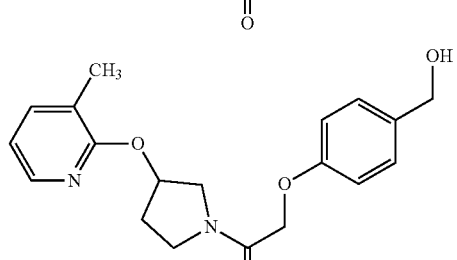
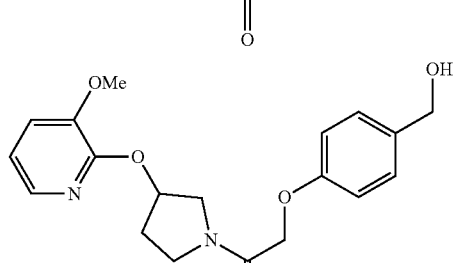
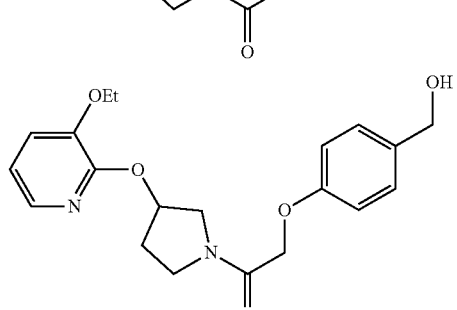
or a pharmaceutically acceptable salt, ester or prodrug form thereof.
In further embodiments, the compound is one of the following:
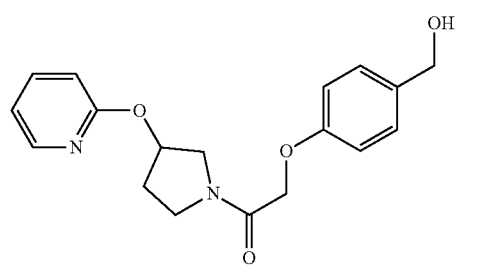
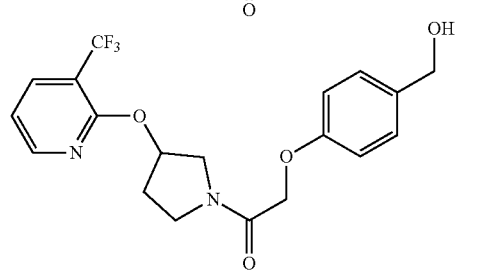
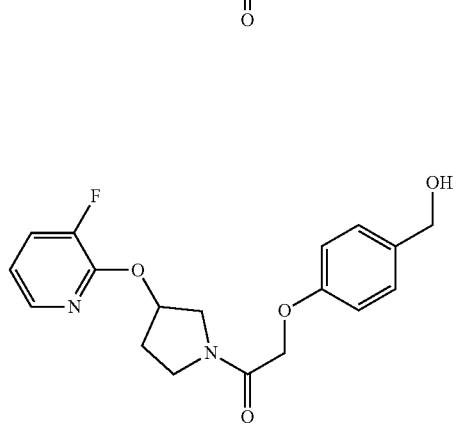

-continued
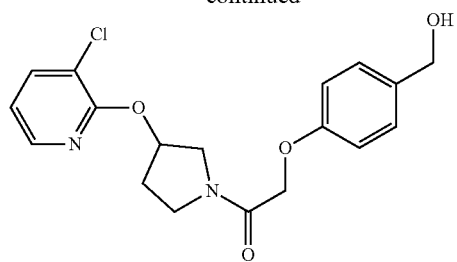
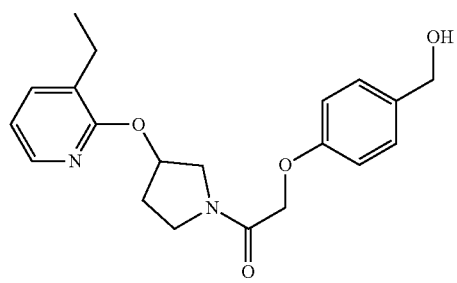
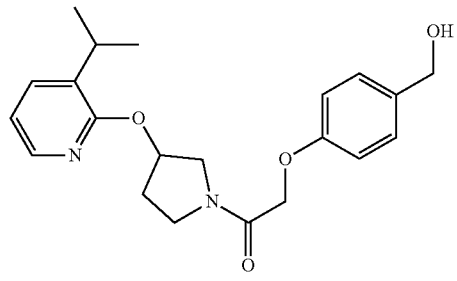
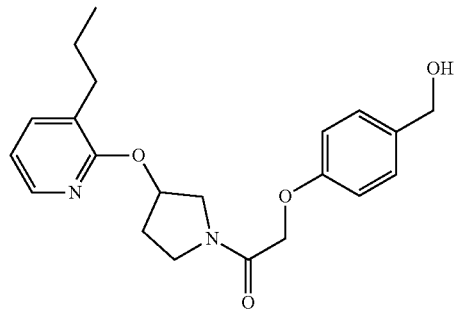
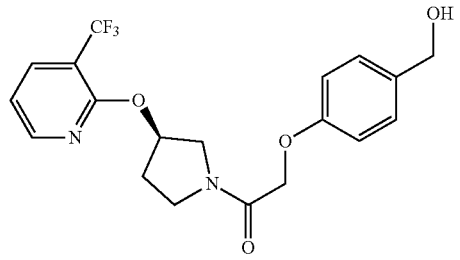
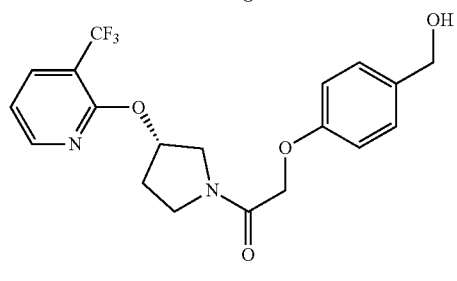
or a pharmaceutically acceptable salt, ester or prodrug form thereof.
In yet other embodiments, the compound is one of the following:
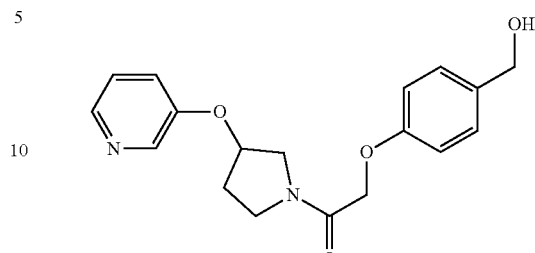
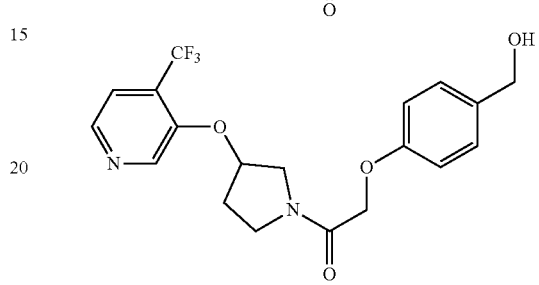
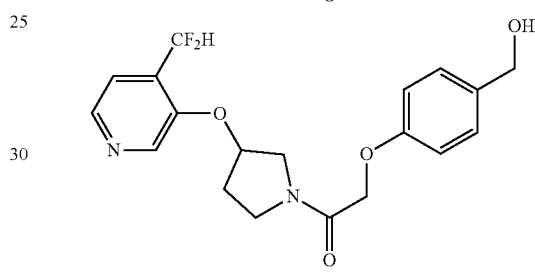
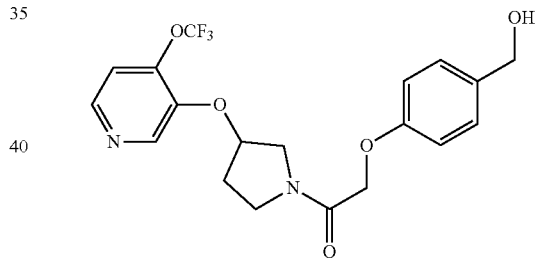
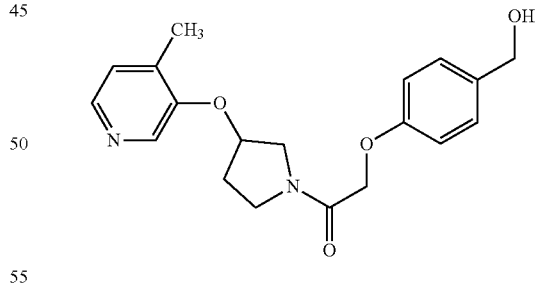
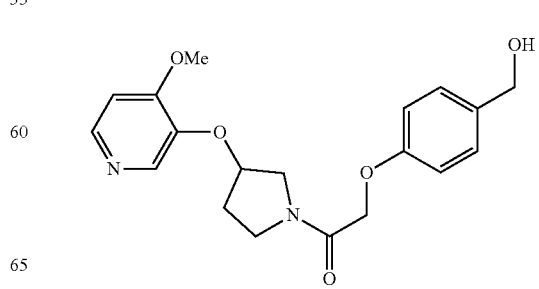

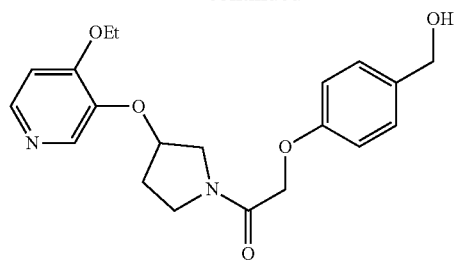
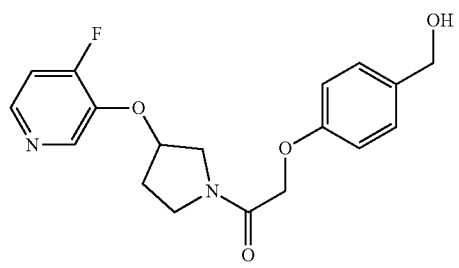
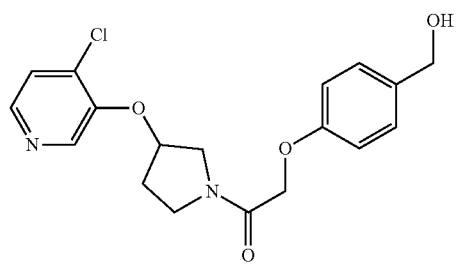
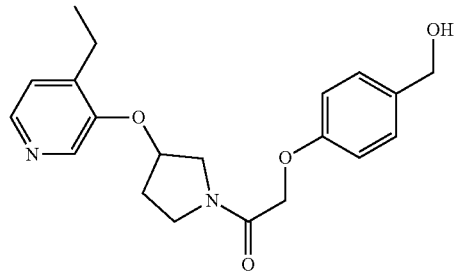
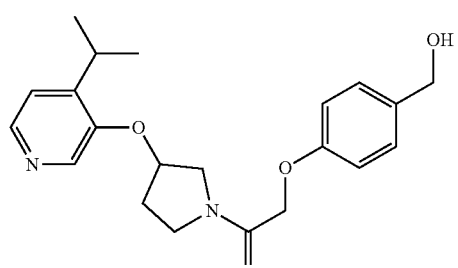
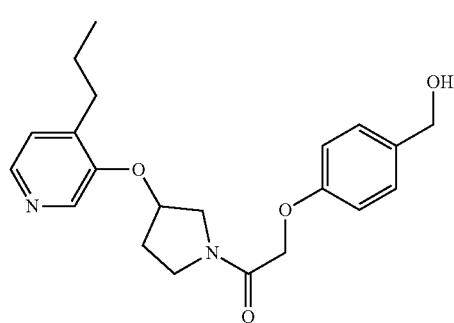
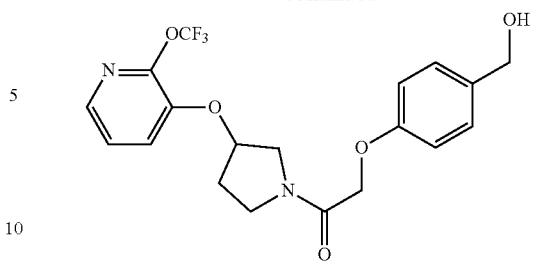
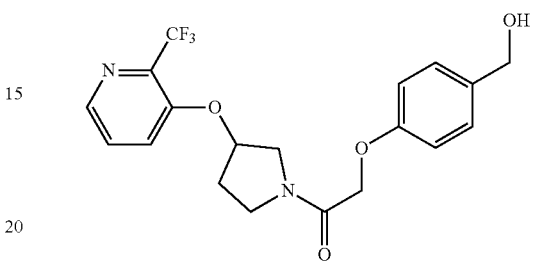
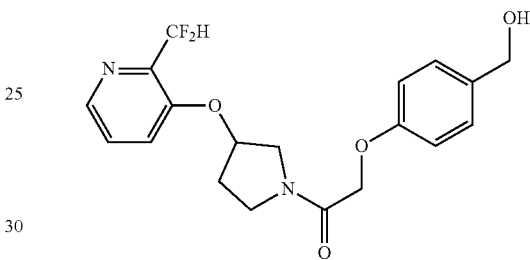
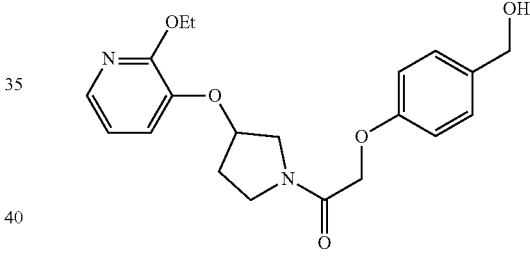
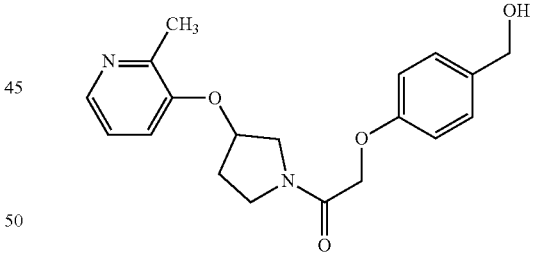
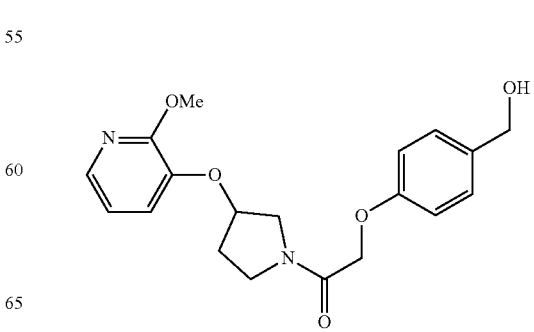

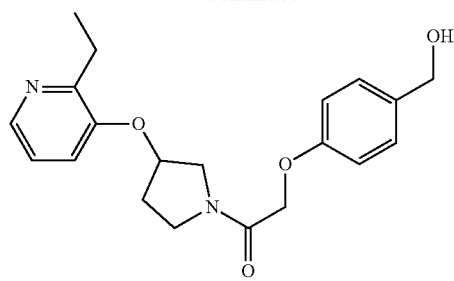
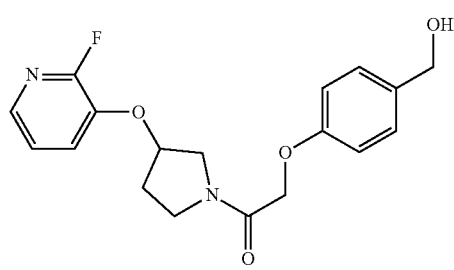
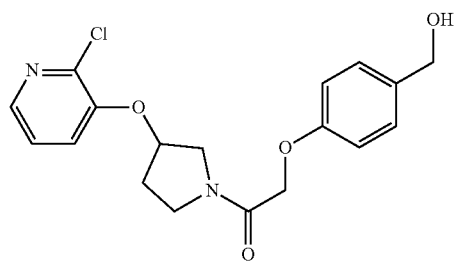
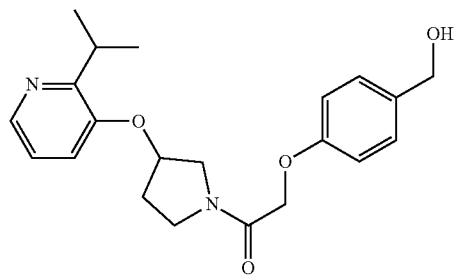
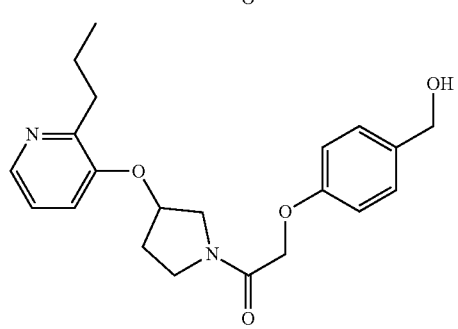
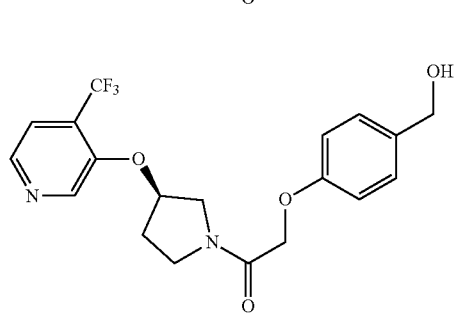
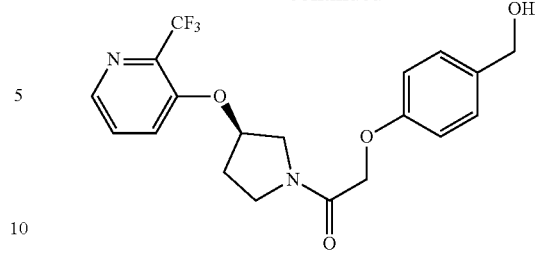

or a pharmaceutically acceptable salt, ester or prodrug form thereof.
In yet further embodiments, the compound is one of the following:
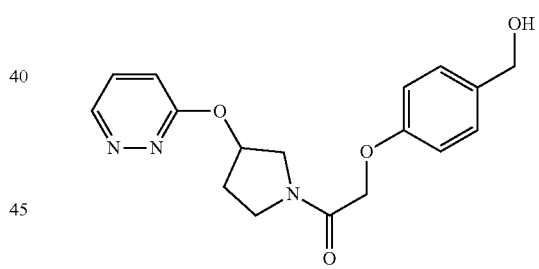
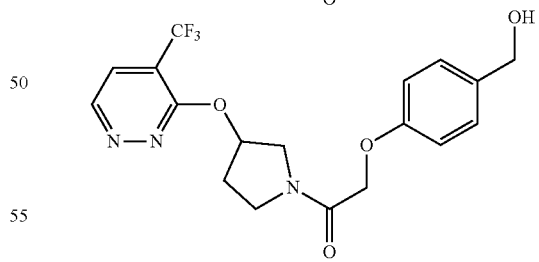

-continued

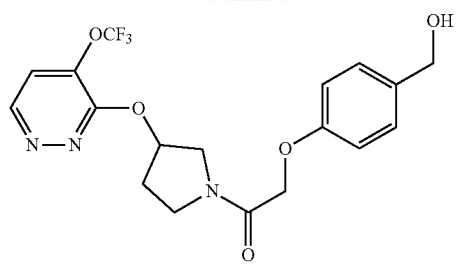

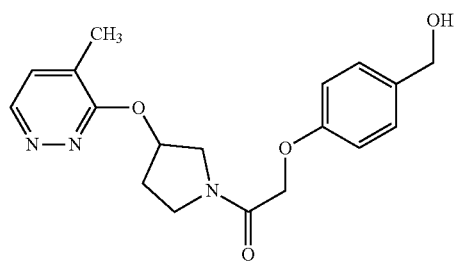

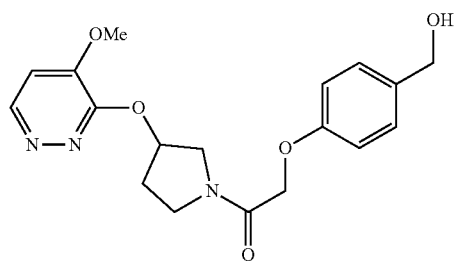

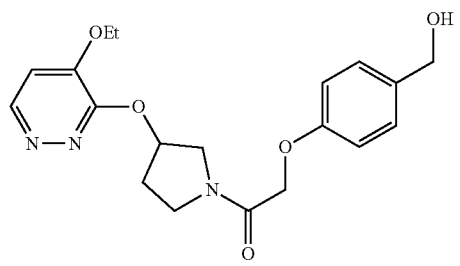

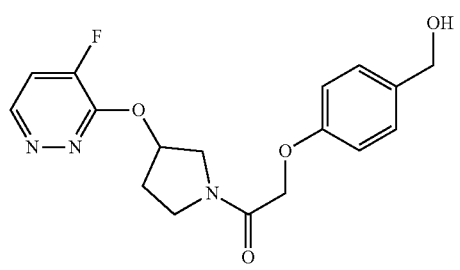

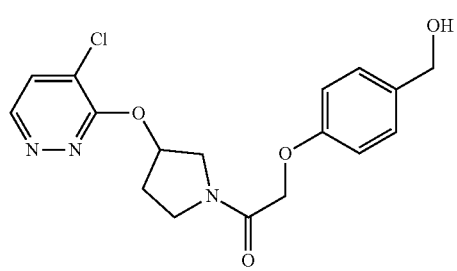

-continued

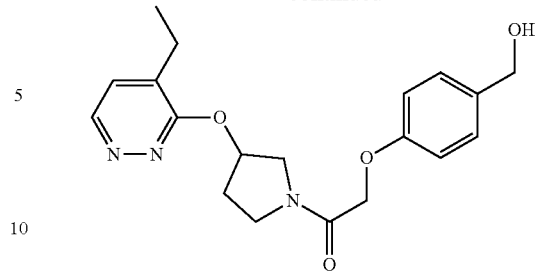

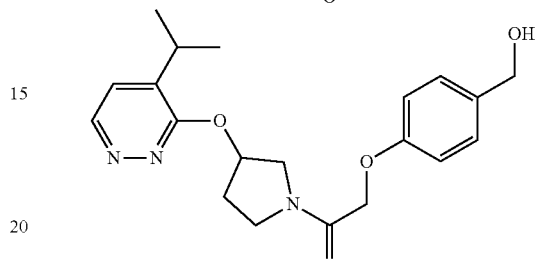



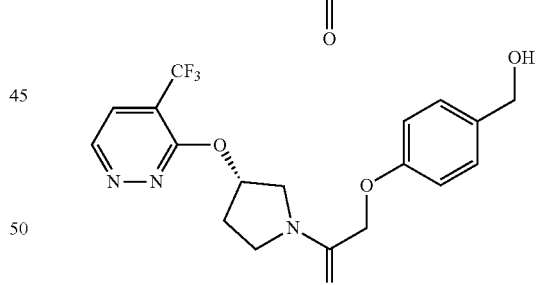

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; CO₂H or a ester thereof; NO₂; NH₂; NHCH(O); NR₆CH(O); NHC(O)R₆; NR₆C(O)R₇; C(O)NR₆R₇; C(NH)NR₆R₇; C(NH)NR₆OH; C(NH)NR₆NO₂; or C(NR₆)NR₇C(NR₈)NR₉R₁₀; adjacent substituents R₁, R₂ and R₃ and R₄ and R₅, if present, may form a saturated or unsaturated 5-membered or 6-membered carbocyclic or heterocyclic ring; and each of R₆, R₇, R₈, R₉ and R₁₀, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In certain embodiments, the compound is one of the following:

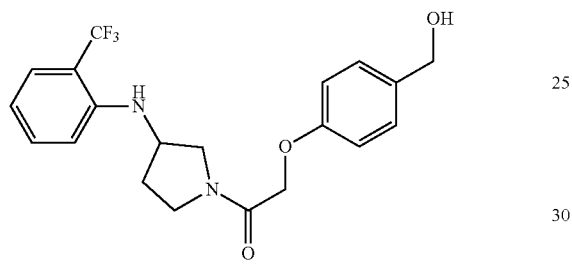

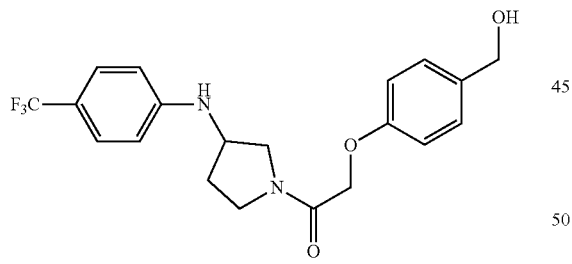

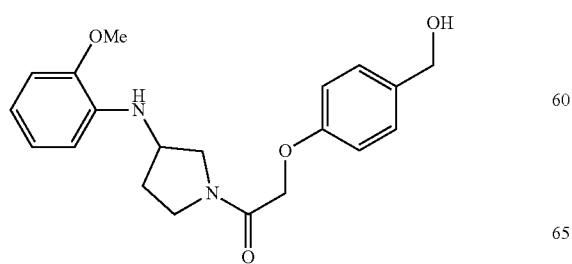

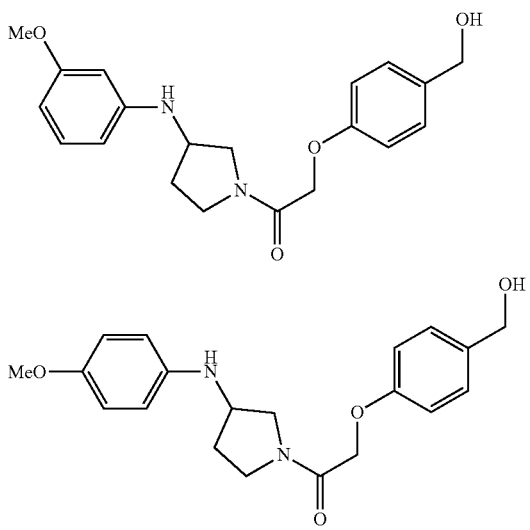

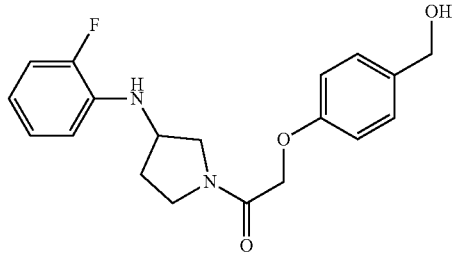

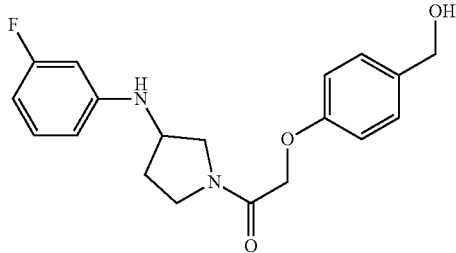

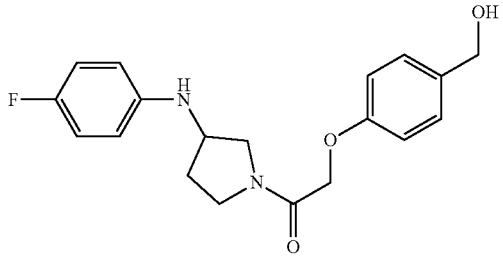

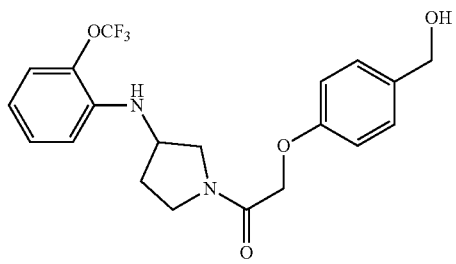

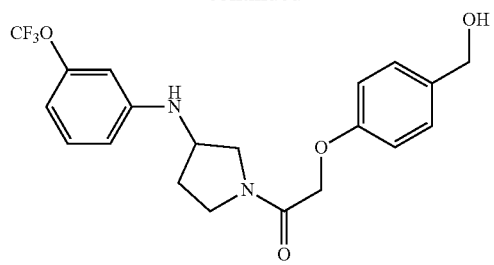
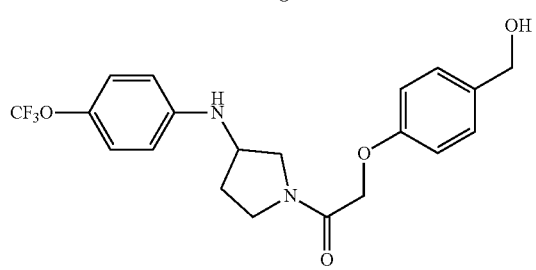
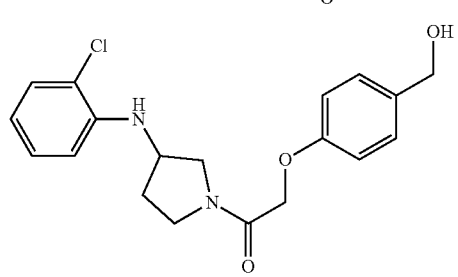
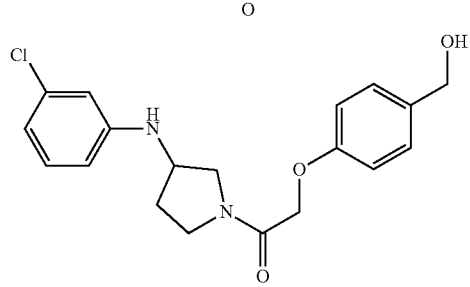
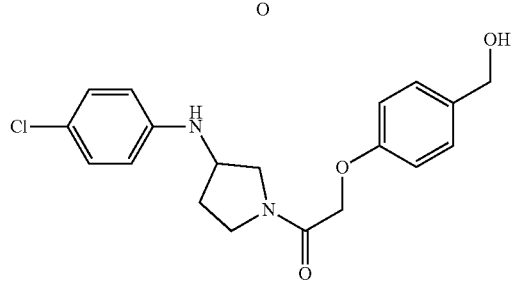
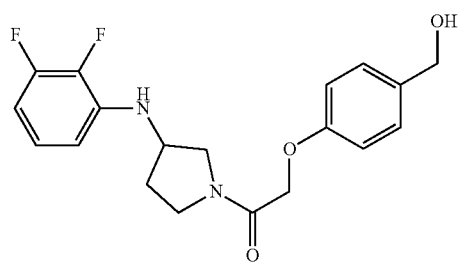
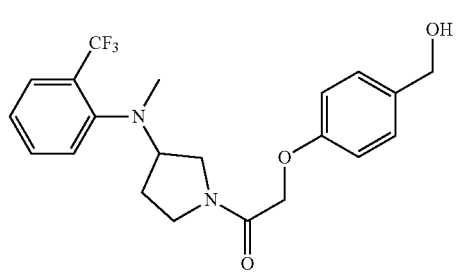
or a pharmaceutically acceptable salt, ester or prodrug form thereof.
In other embodiments, the compound is one of the following:

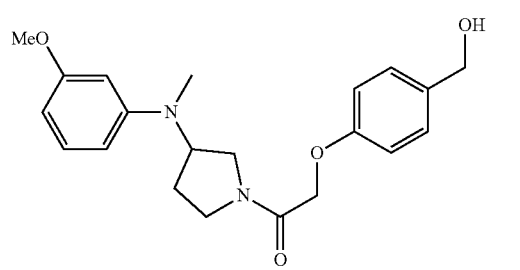
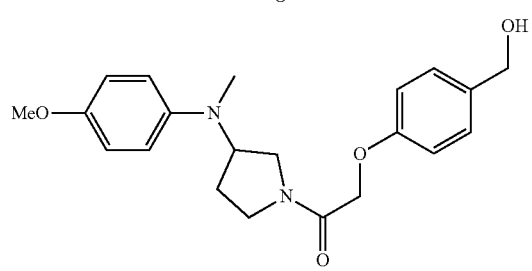
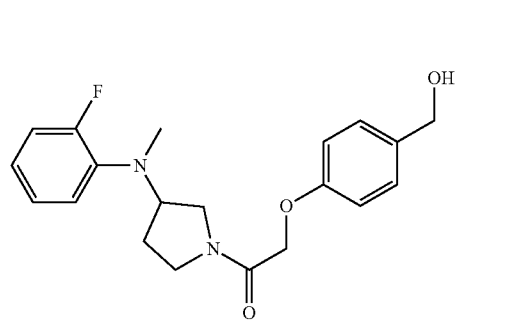
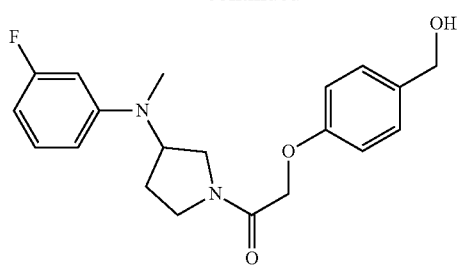
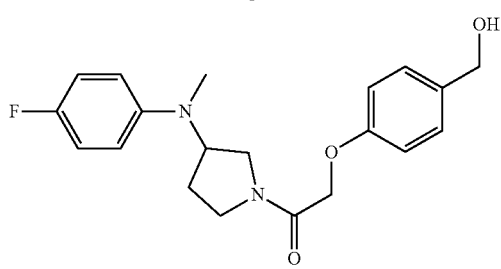
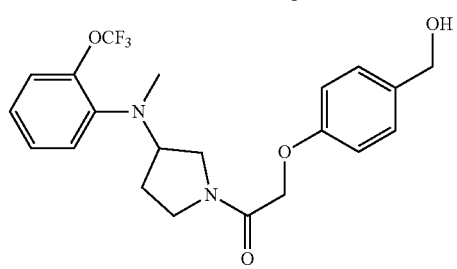
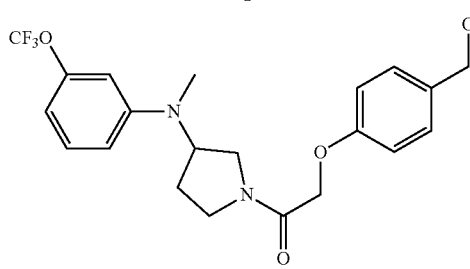
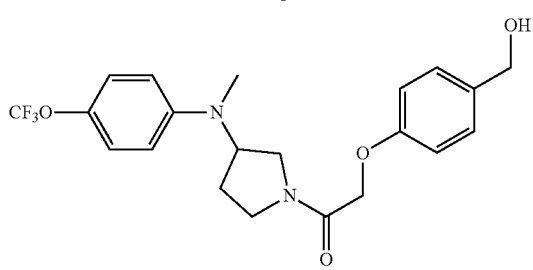

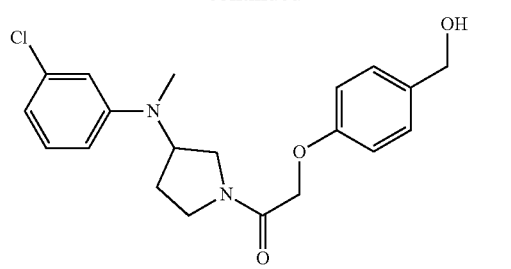
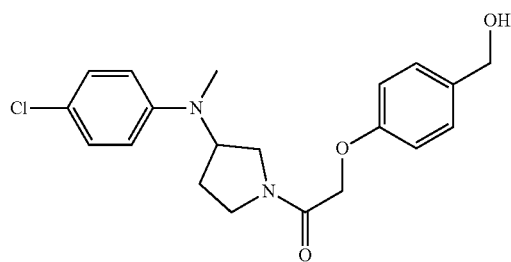
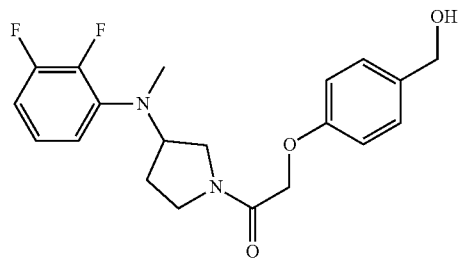
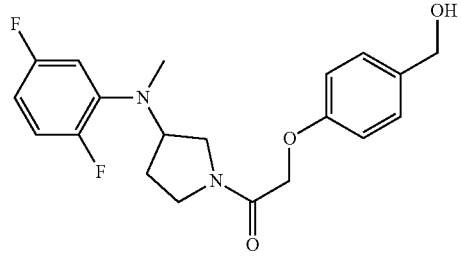
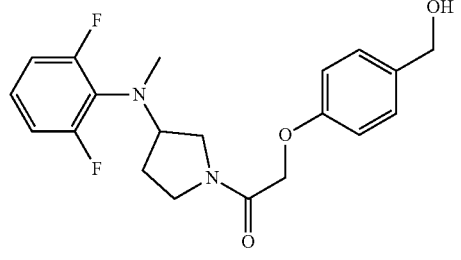
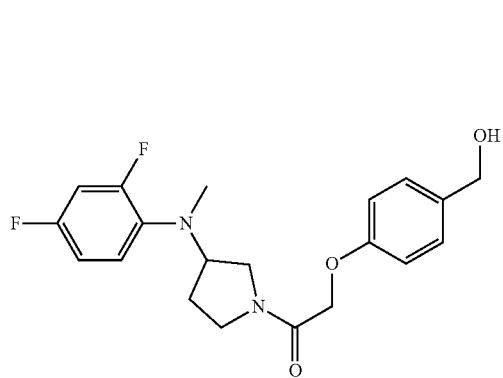
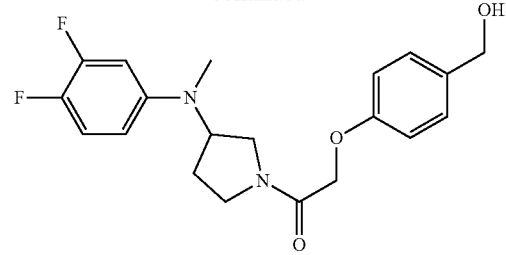
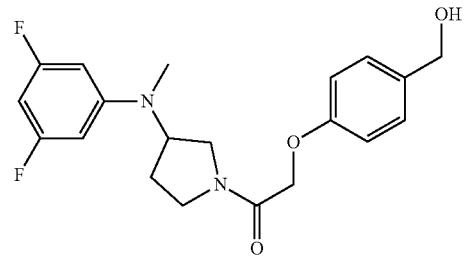
or a pharmaceutically acceptable salt, ester or prodrug form thereof.
In further embodiments, the compound is one of the following:
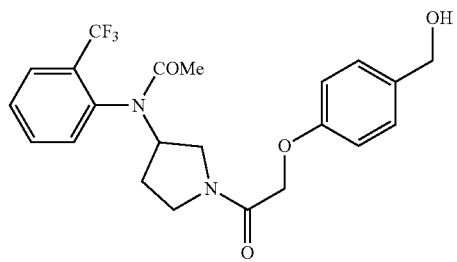
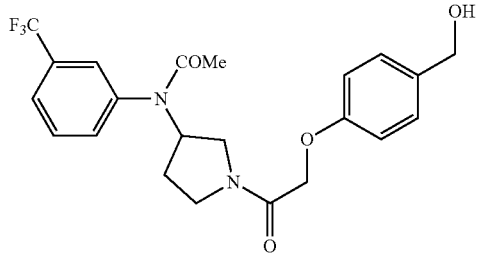
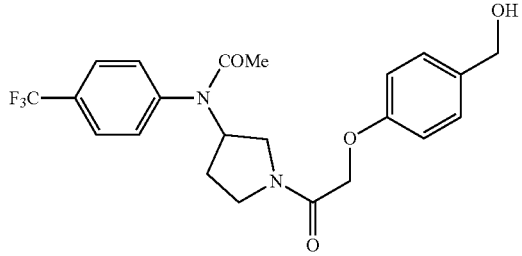
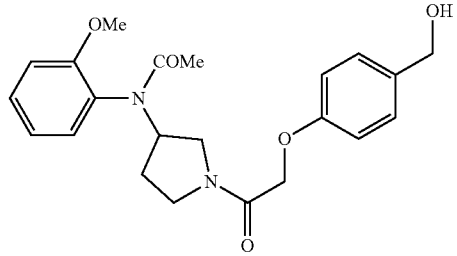

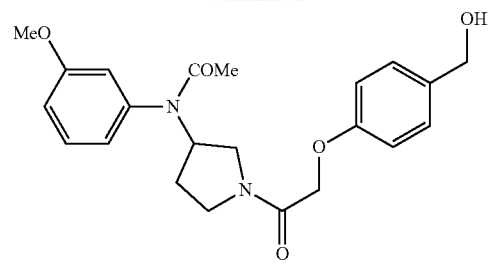
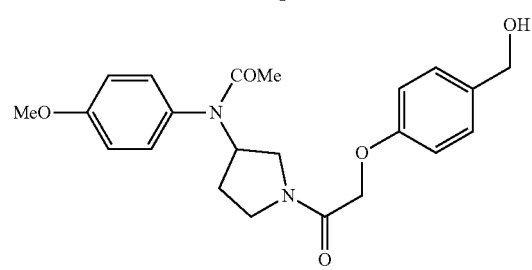
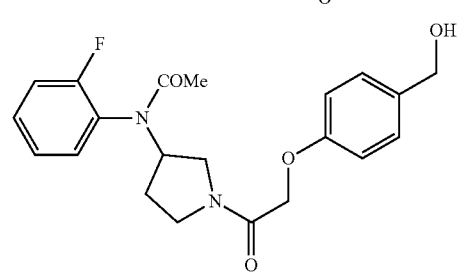
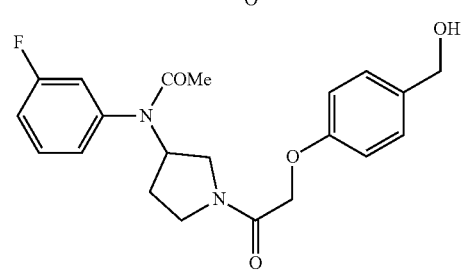
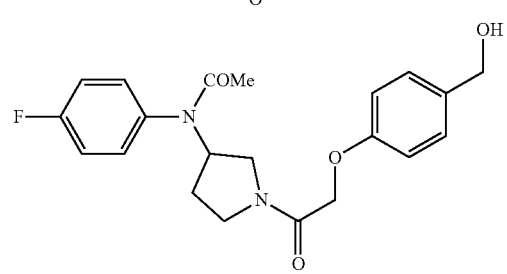
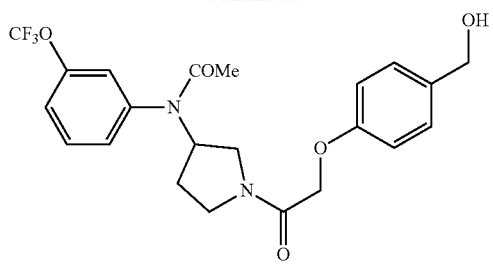
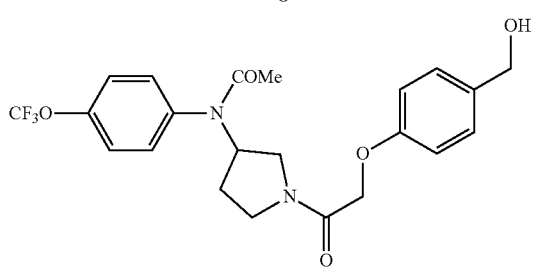
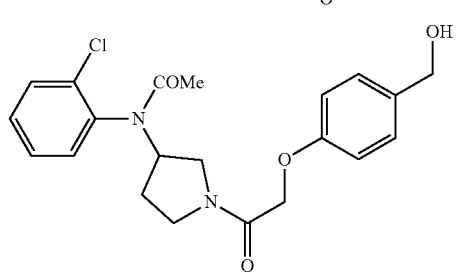
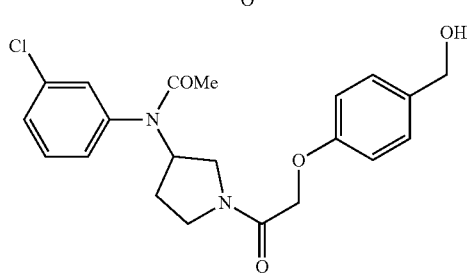
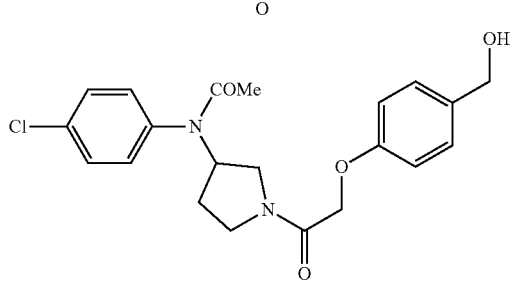
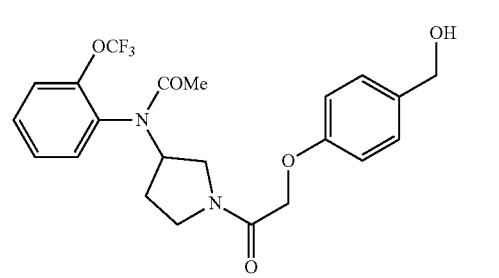

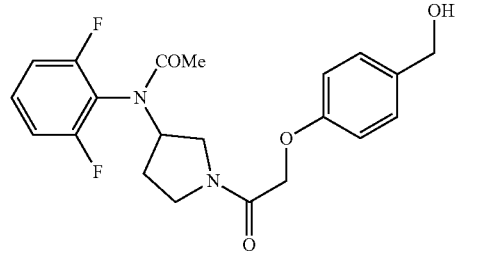
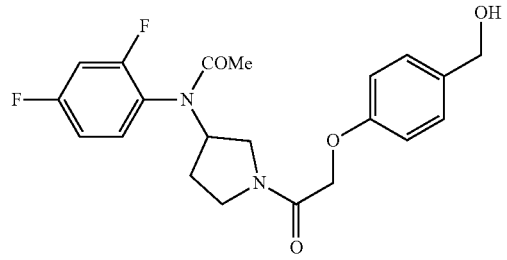
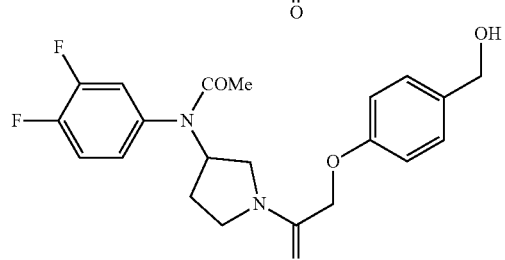
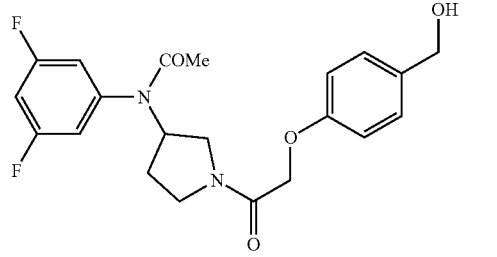
or a pharmaceutically acceptable salt, ester or prodrug form thereof.
In yet further embodiments, the compound is one of the following:
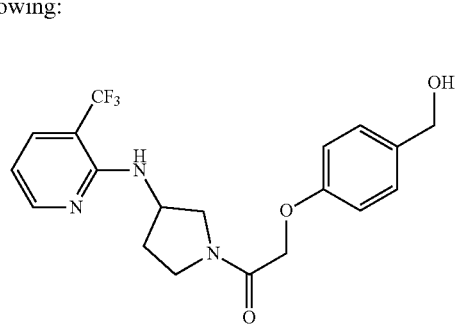
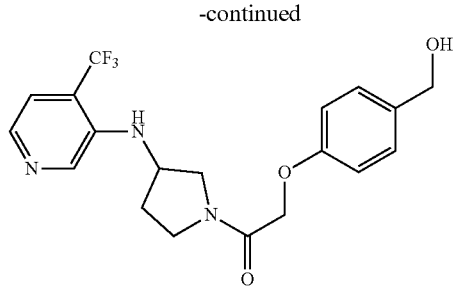
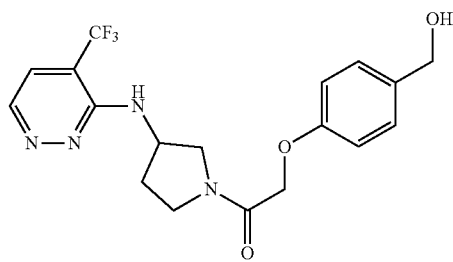
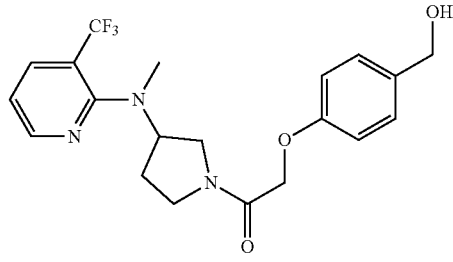
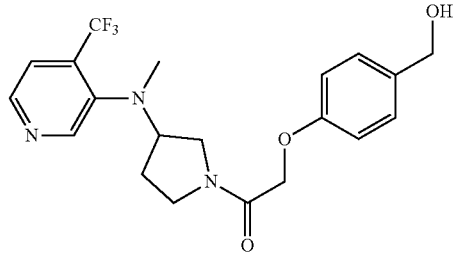
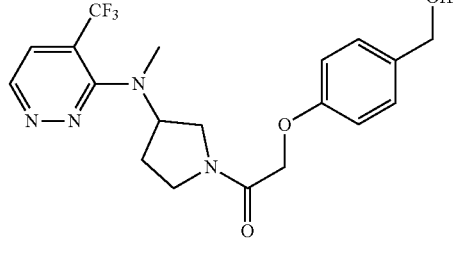
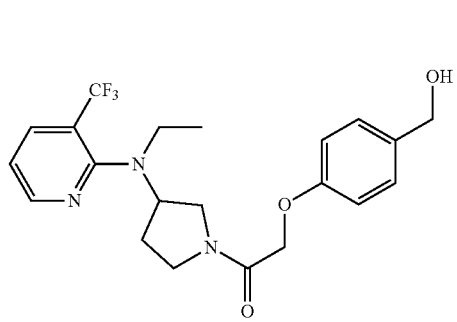

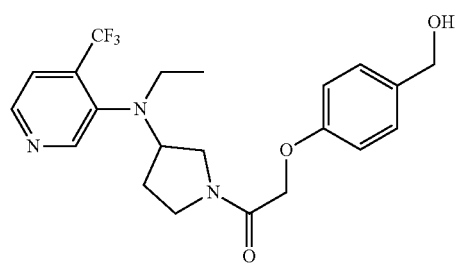

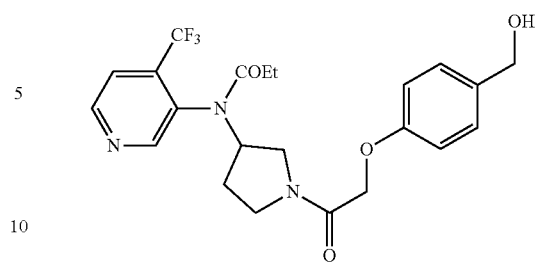

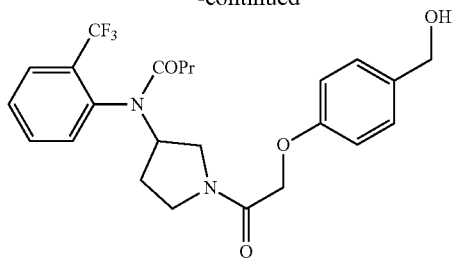
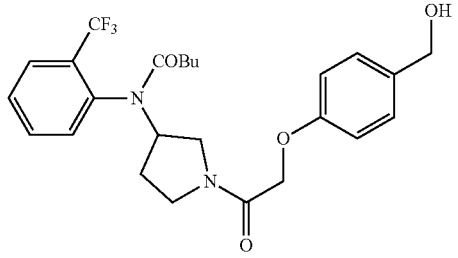
or a pharmaceutically acceptable salt, ester or prodrug form thereof.
In yet other embodiments, the compound is one of the following:
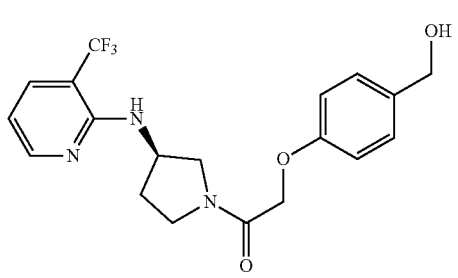
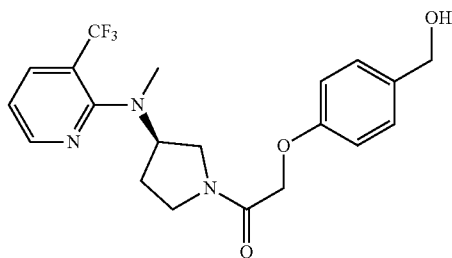
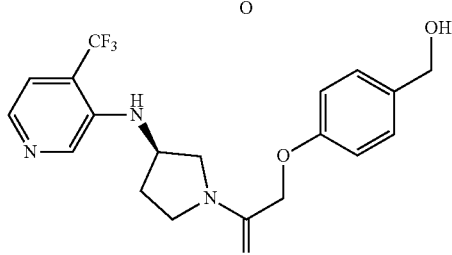
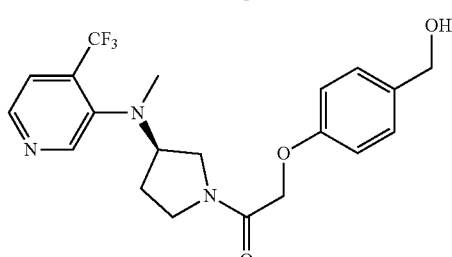
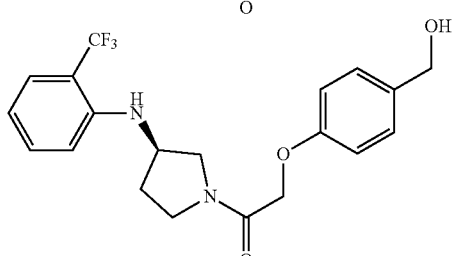
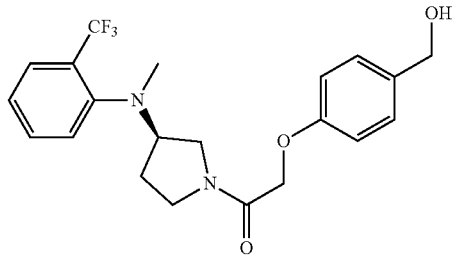
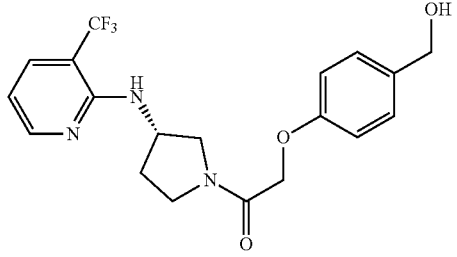

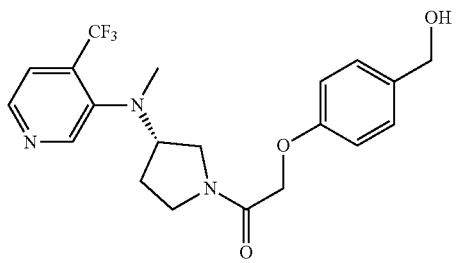

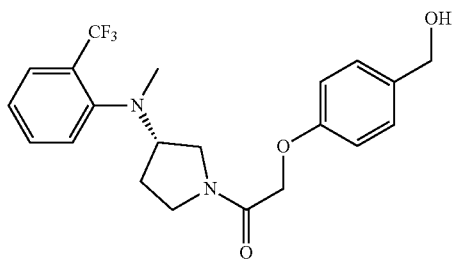

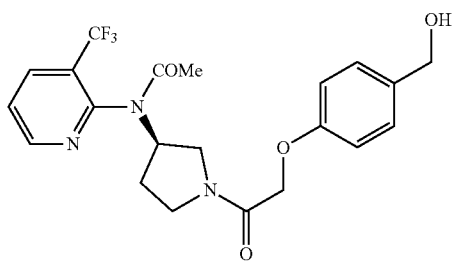

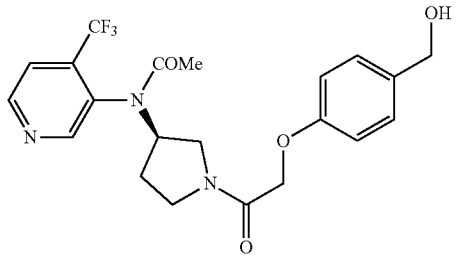

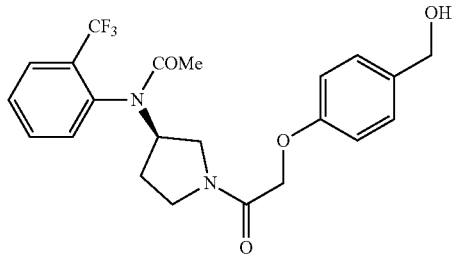

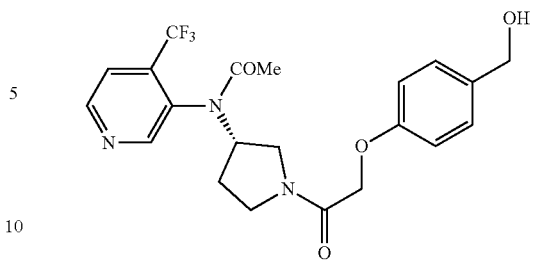

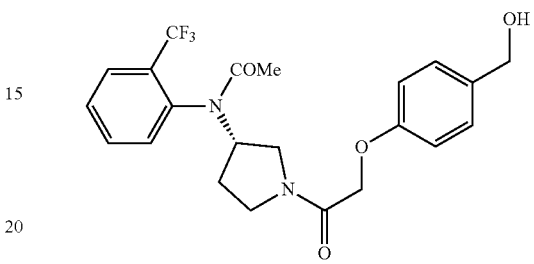

or a pharmaceutically acceptable salt, ester or prodrug form thereof.

In yet further embodiments, X is S, SO or $SO_2$; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_5$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_2$; $SO_3H$ or a ester thereof; $CO_2H$ or a ester thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or $SO_2$. In further embodiments, X is SO. In yet further embodiments X is $SO_2$.

In some embodiments, the compound is one of:

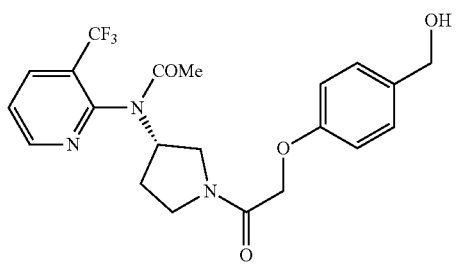

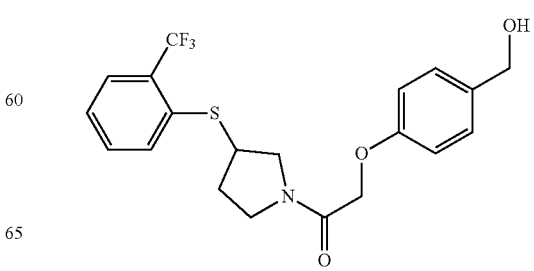

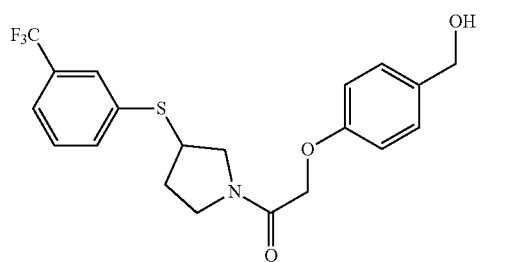
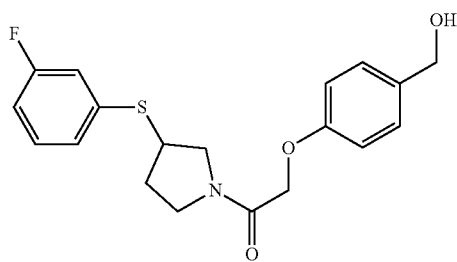
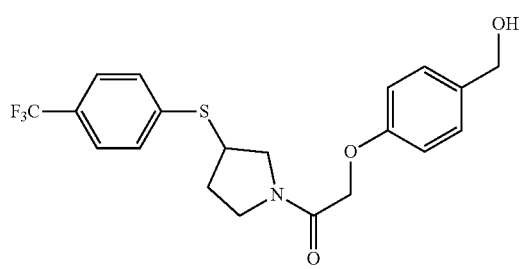 [SMILES: O=C(COc1ccc(CO)cc1)N1CCC(Oc2ccc(C(F)(F)F)cc2)C1]
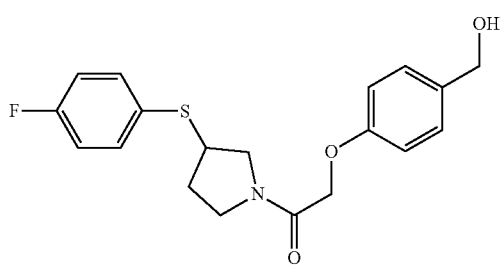
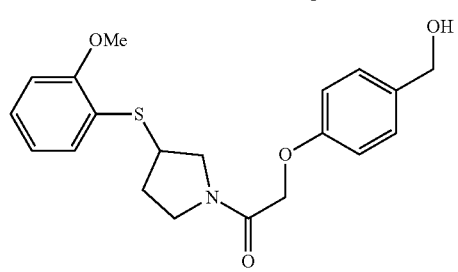
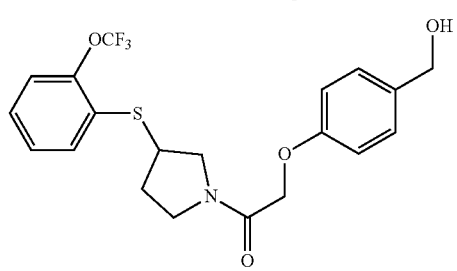
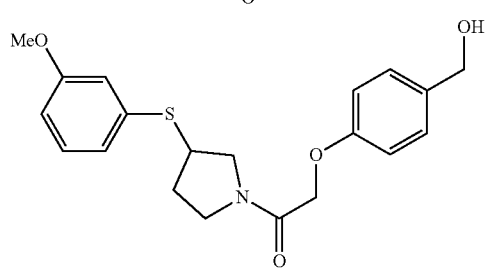
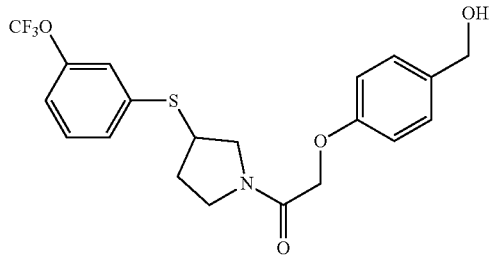
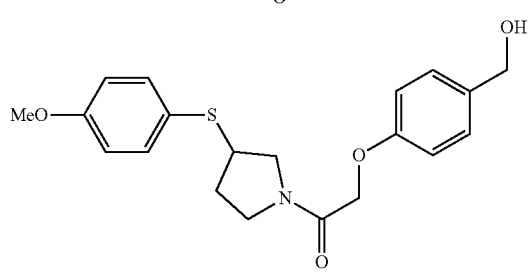
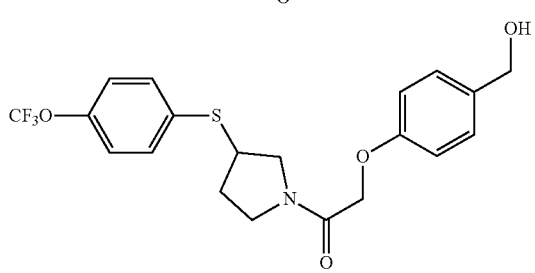
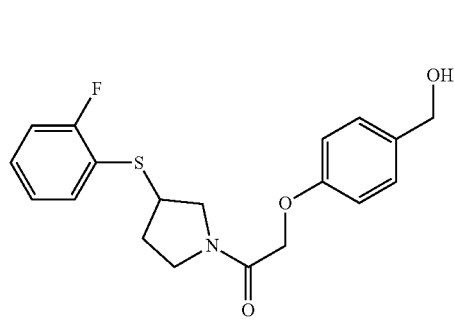 [SMILES: O=C(COc1ccc(CO)cc1)N1CCC(Oc2ccccc2F)C1]
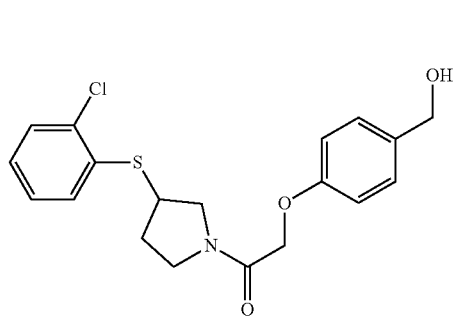

-continued
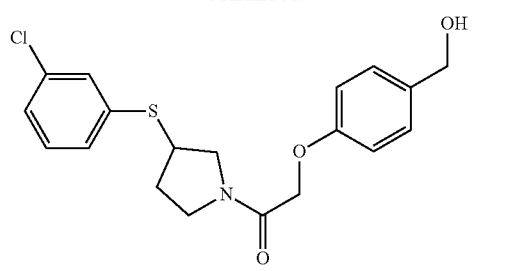
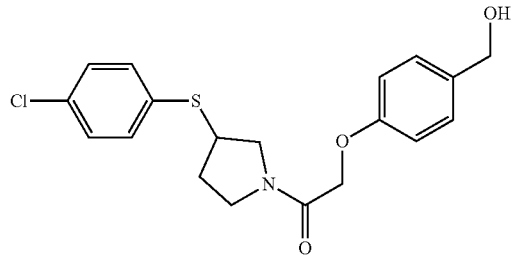
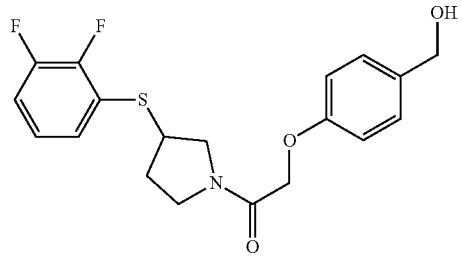
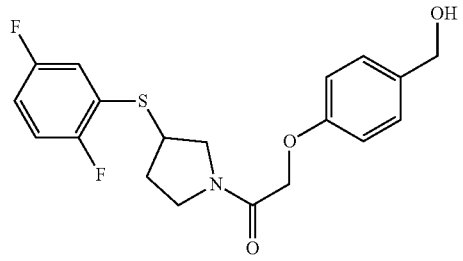
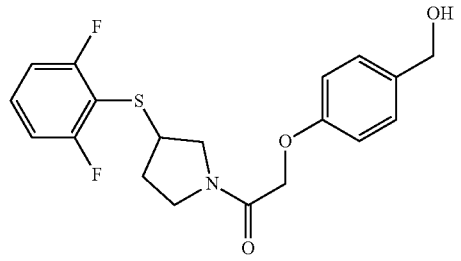
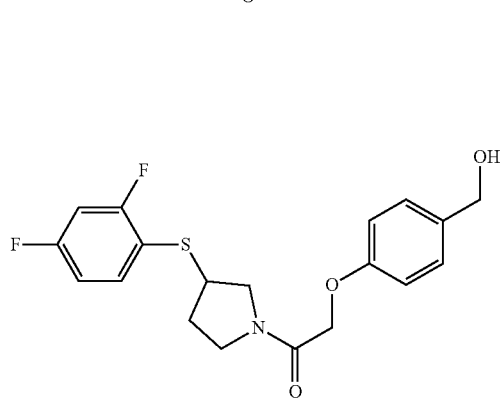
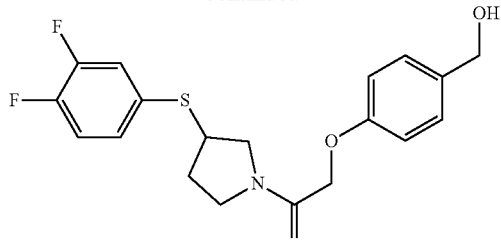
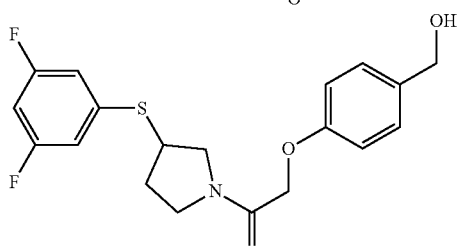
or a pharmaceutically acceptable salt, ester or prodrug form thereof.
In other embodiments, the compound is one of:
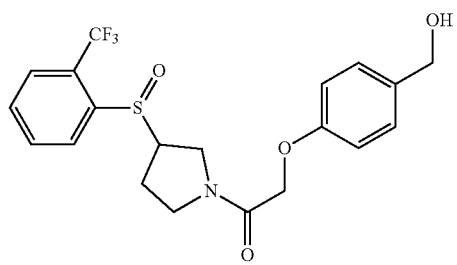
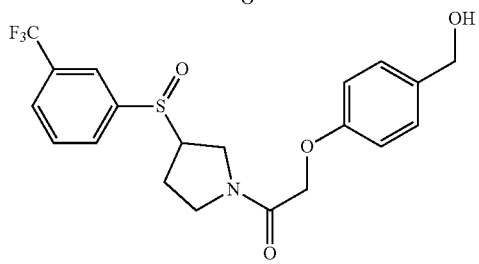
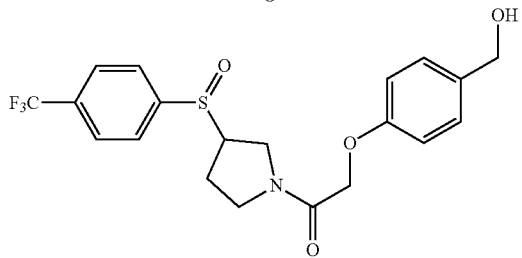
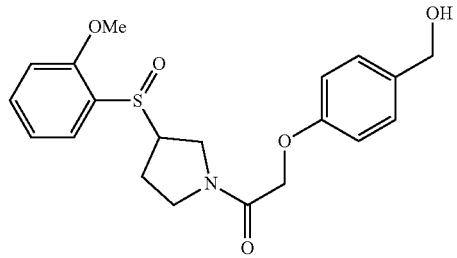

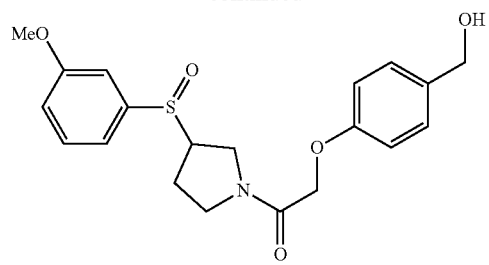
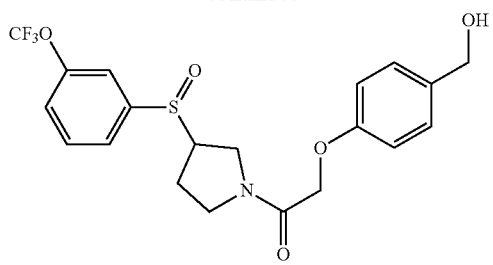
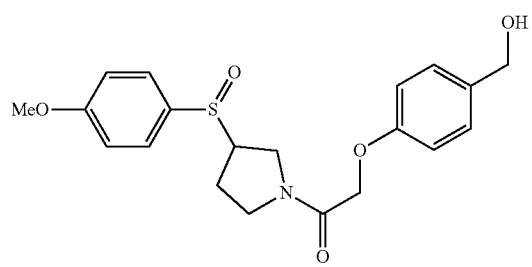
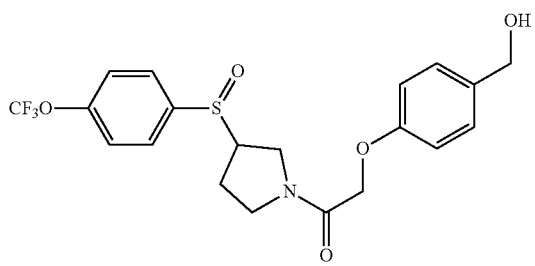
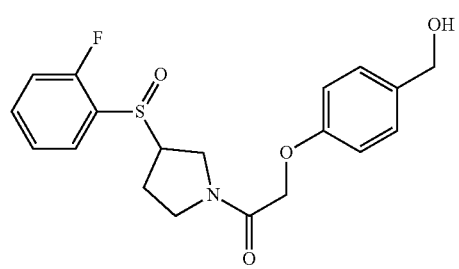
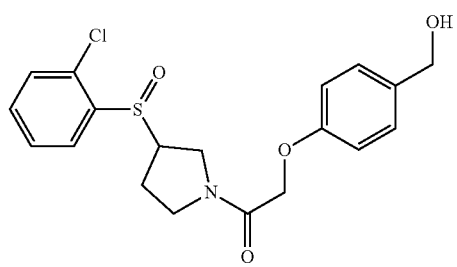
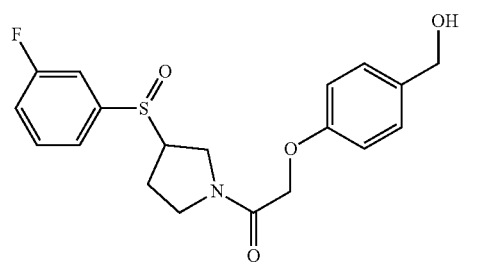
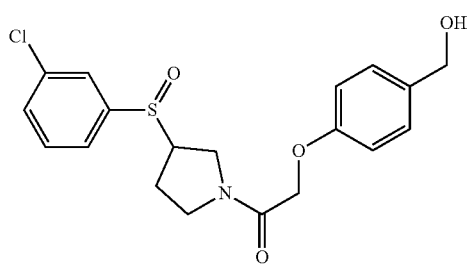
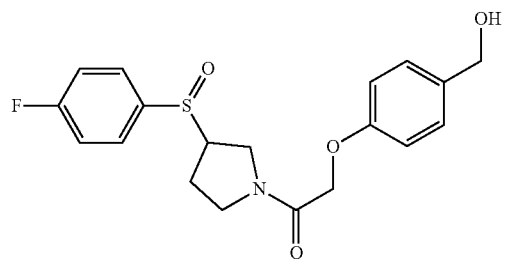
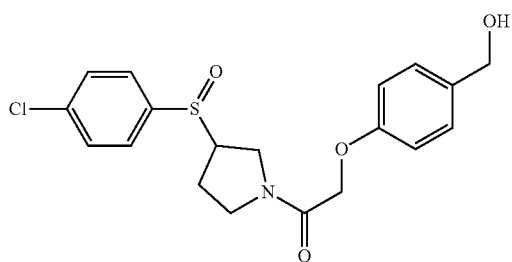
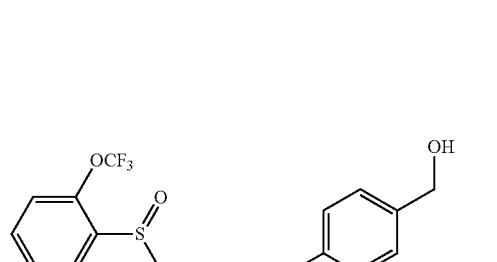
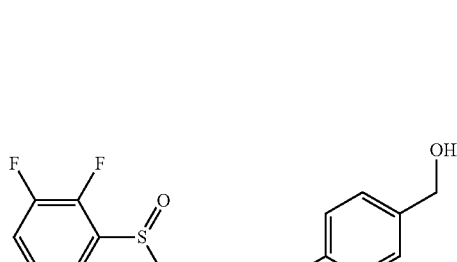

55
-continued
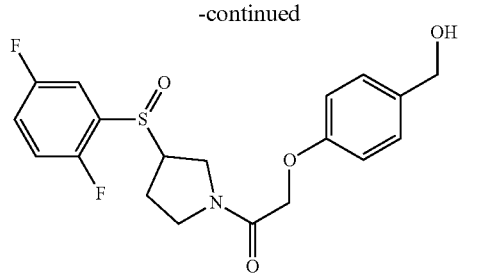
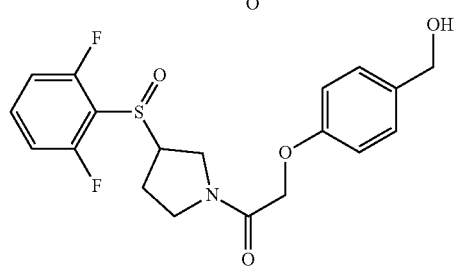
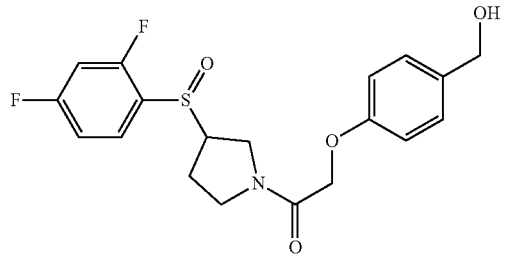
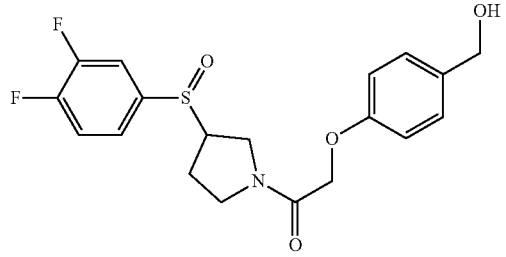
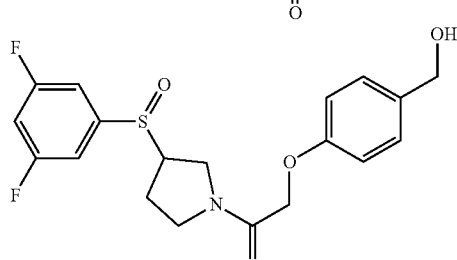
or a pharmaceutically acceptable salt, ester or prodrug form thereof.
In further embodiments, the compound is one of:
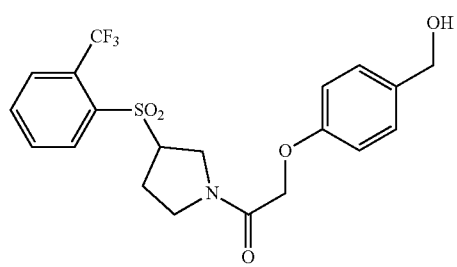
56
-continued
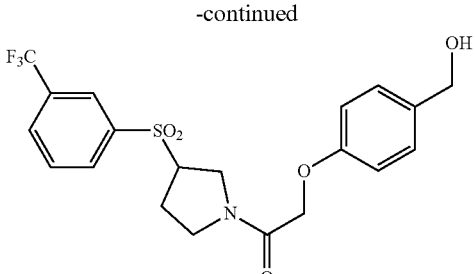
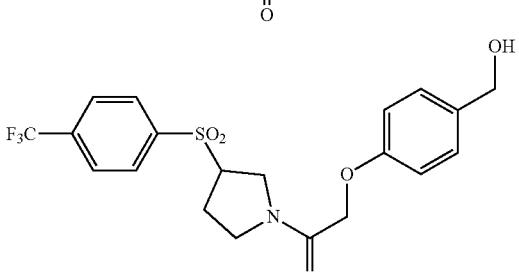
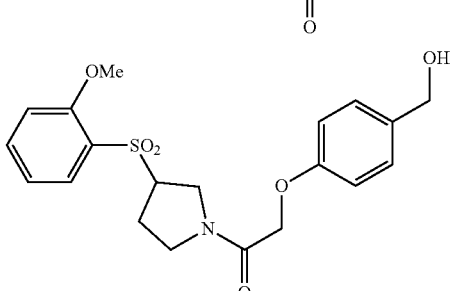
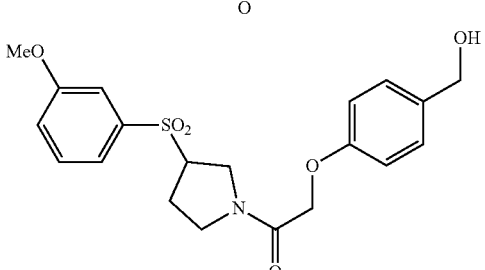
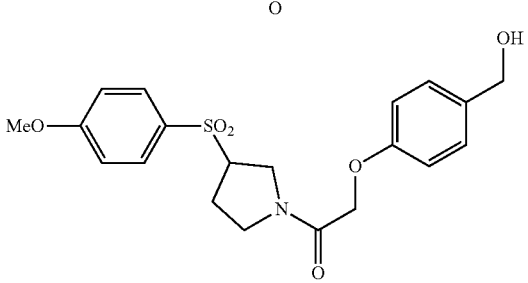
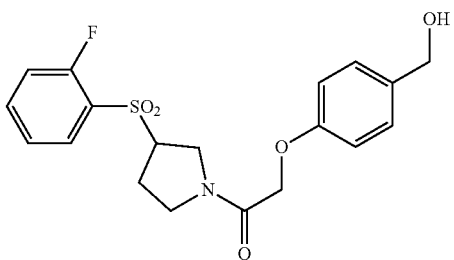

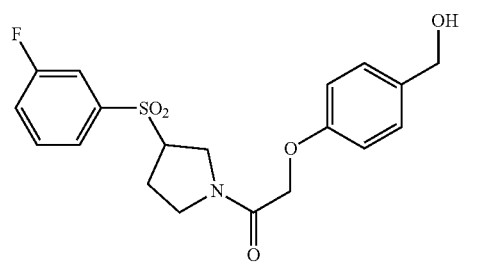
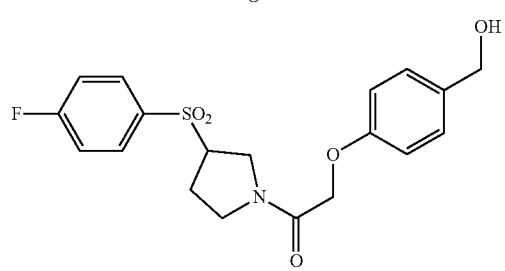
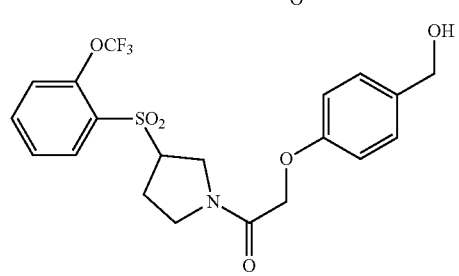
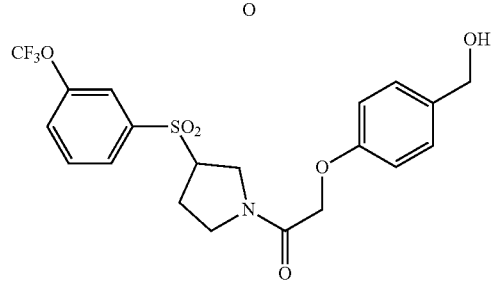
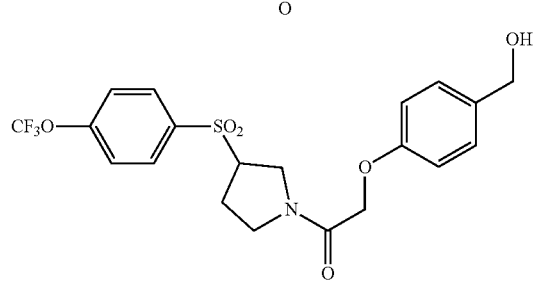
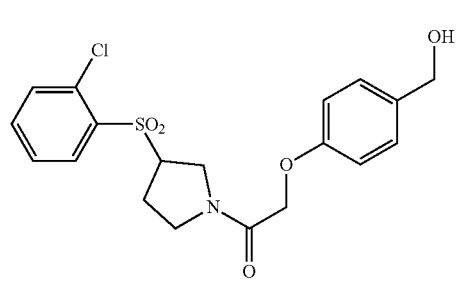
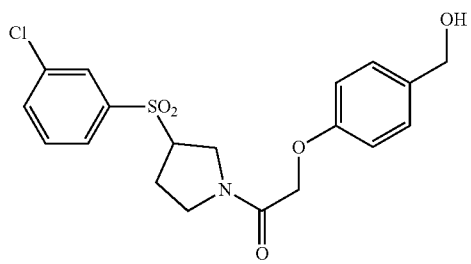
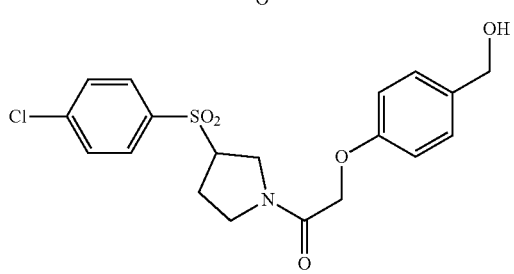
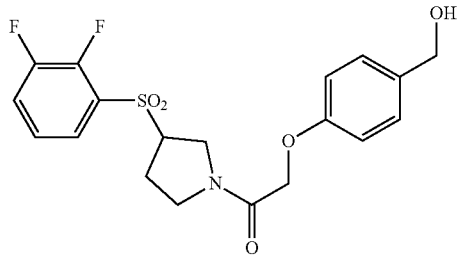
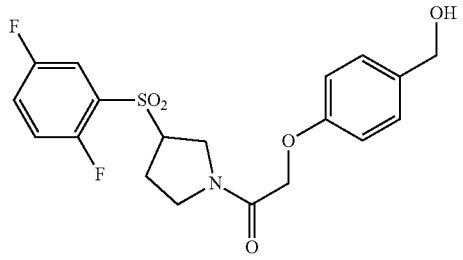
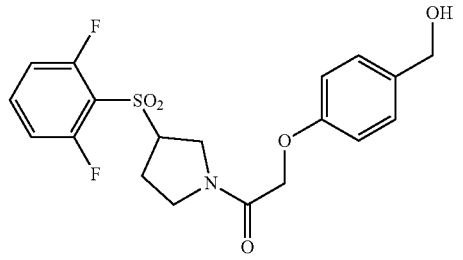
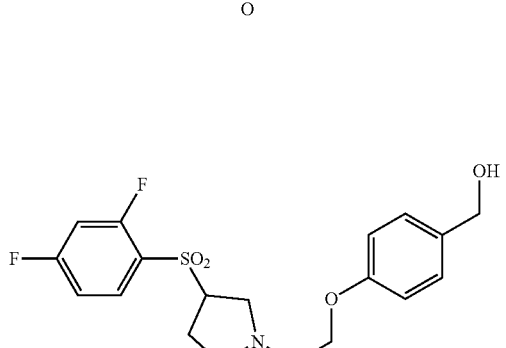

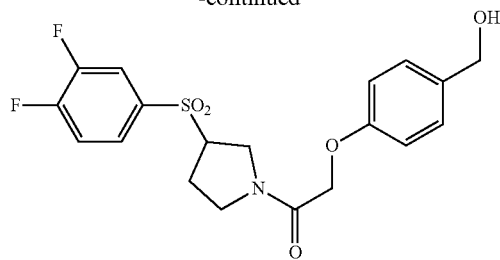
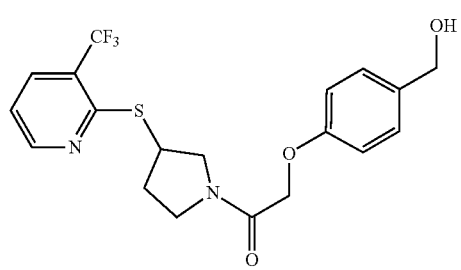
or a pharmaceutically acceptable salt, ester or prodrug form thereof.
In yet further embodiments, the compound is one of:
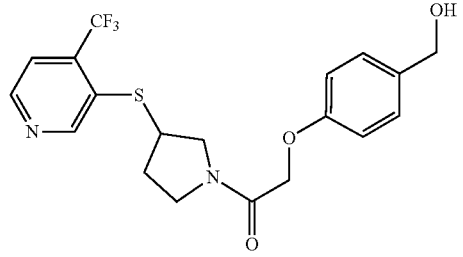
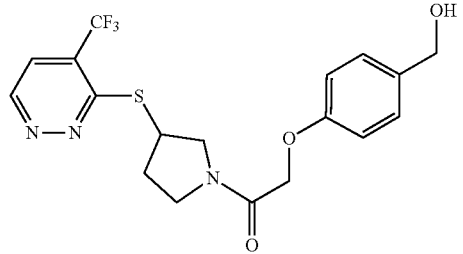
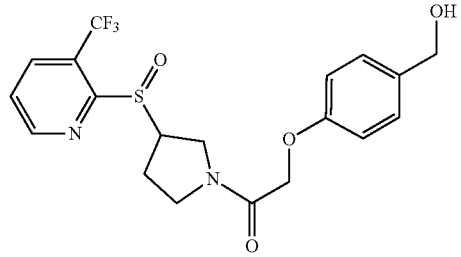
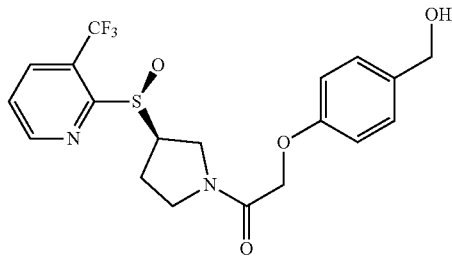
or a pharmaceutically acceptable salt, ester or prodrug form thereof.
In yet further embodiments, the compound is one of:

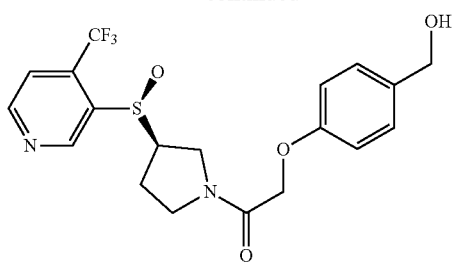
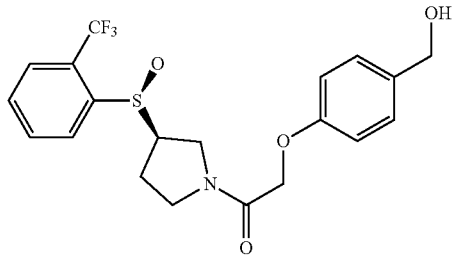
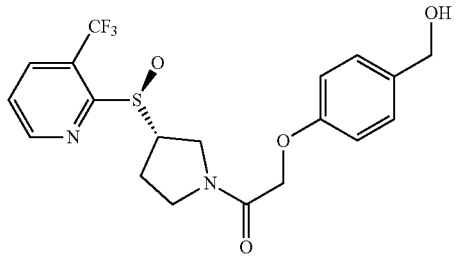
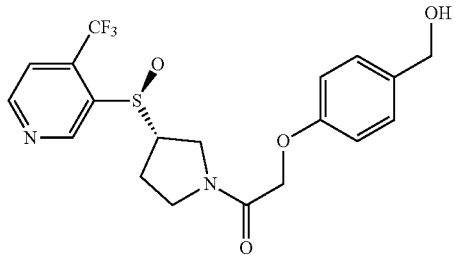
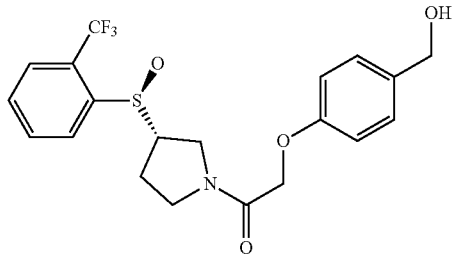
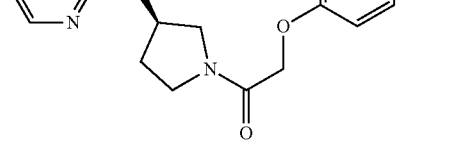
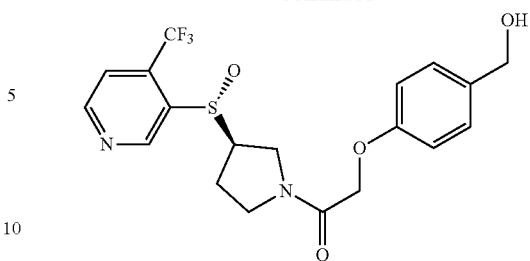

or a pharmaceutically acceptable salt, ester or prodrug form thereof.

In yet further embodiments, the compound has the structure II

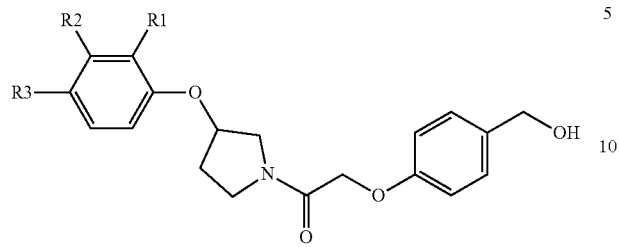

II wherein one of $R_1$ and $R_2$ and $R_3$, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

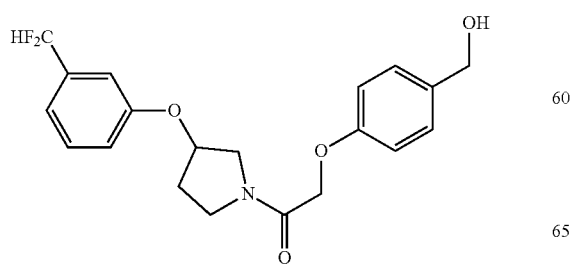

-continued

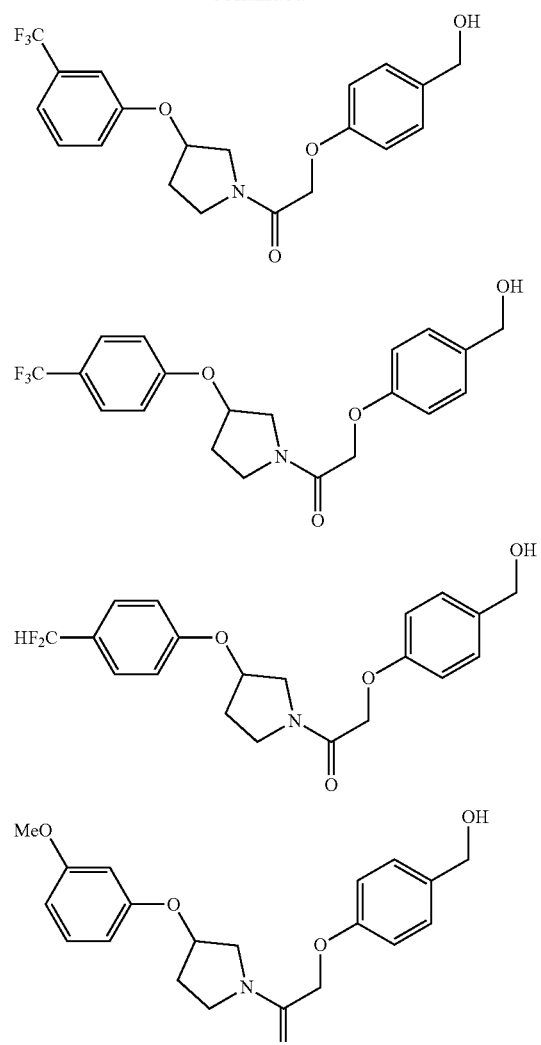

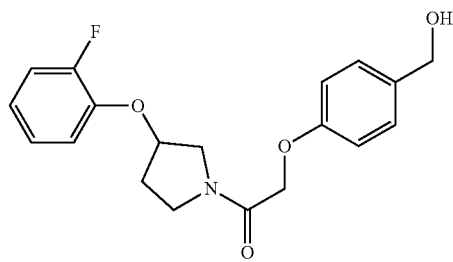

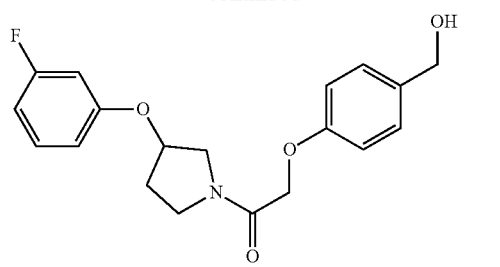 [SMILES: O=C(COc1ccc(CO)cc1)N1CCC(Oc2cccc(F)c2)C1]
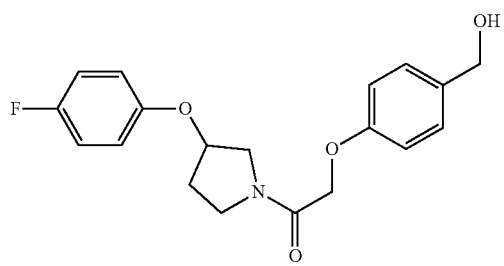 [SMILES: O=C(COc1ccc(CO)cc1)N1CCC(Oc2ccc(F)cc2)C1]
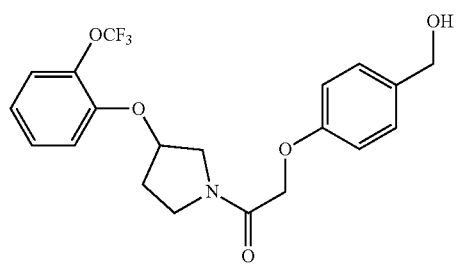 [SMILES: O=C(COc1ccc(CO)cc1)N1CCC(Oc2ccccc2OC(F)(F)F)C1]
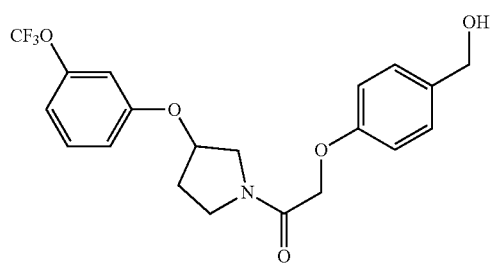
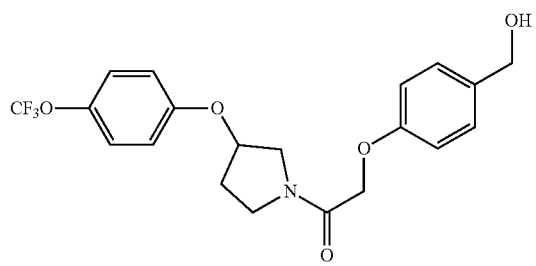
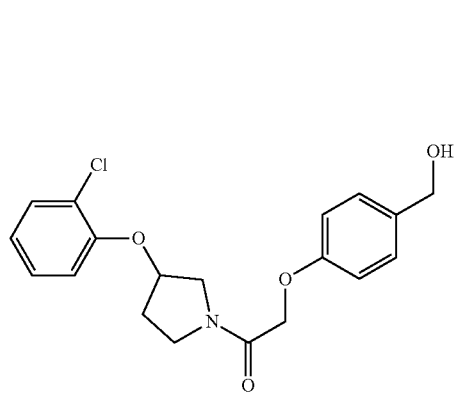
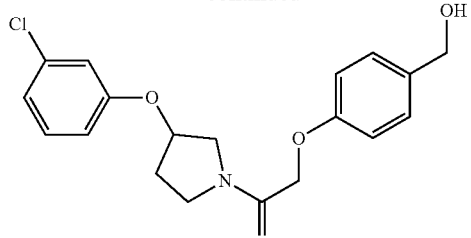
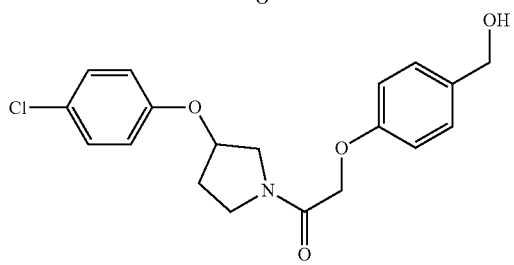
or a pharmaceutically acceptable salt, ester or prodrug form thereof.
In other embodiments the compound is one of the following:
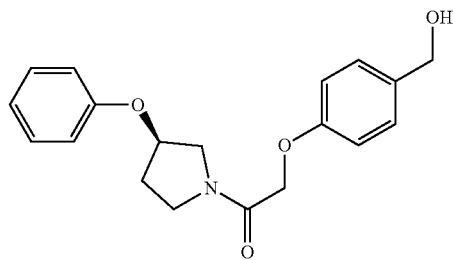
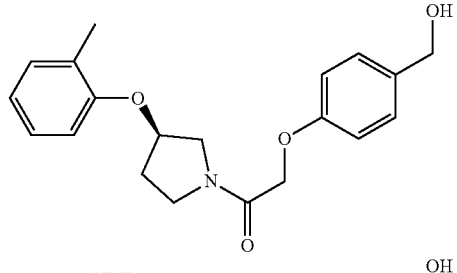
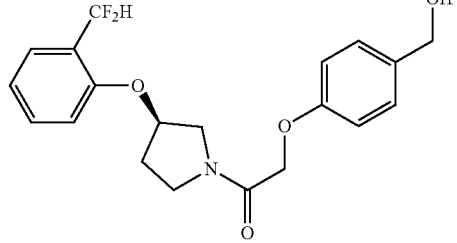
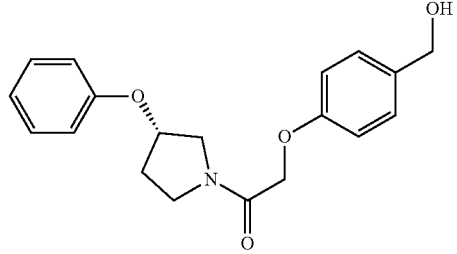 [SMILES: O=C(COc1ccc(CO)cc1)N1CC[C@H](Oc2ccccc2)C1]

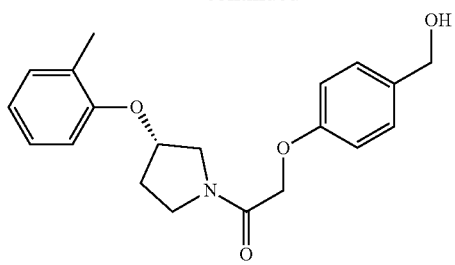 [SMILES: Cc1ccccc1O[C@H]1CCN(C(=O)COc2ccc(CO)cc2)C1]
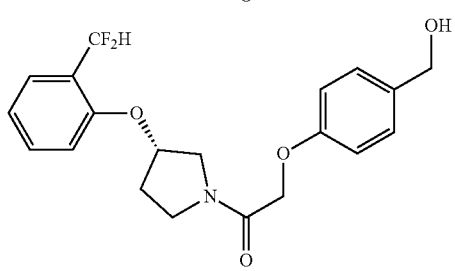
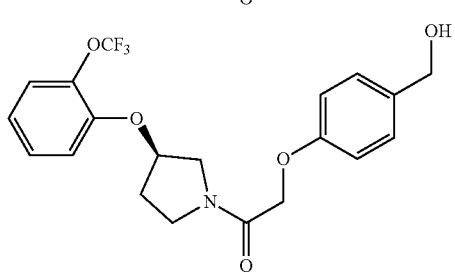
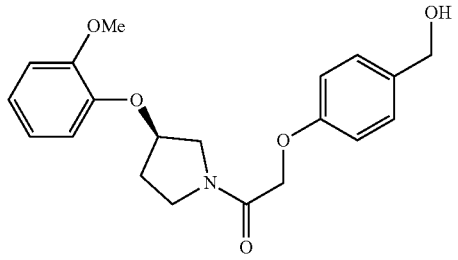
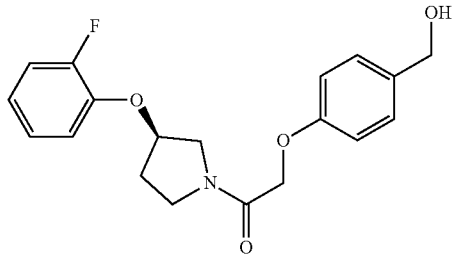
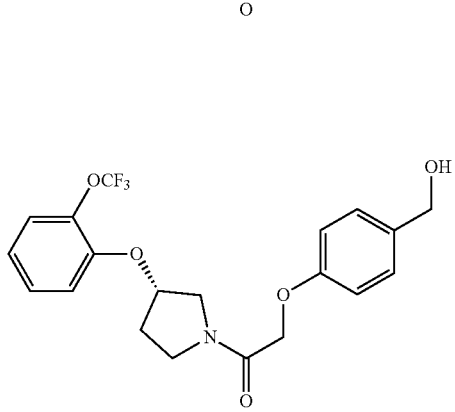
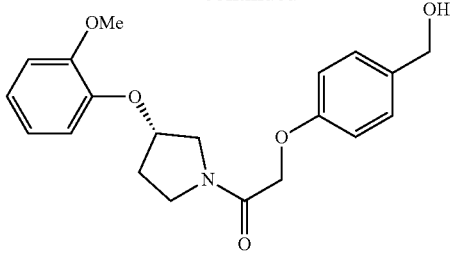
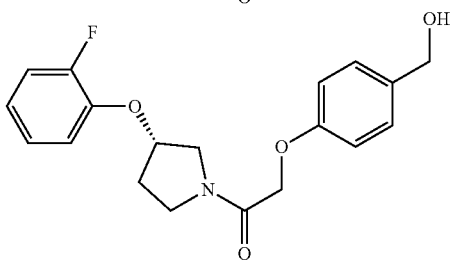
or a pharmaceutically acceptable salt, ester or prodrug form thereof. In alternative embodiments, the
In certain embodiments, the compound is one of the following:
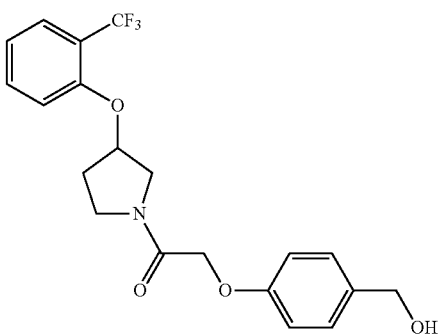
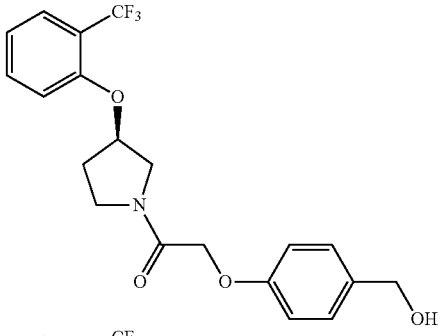
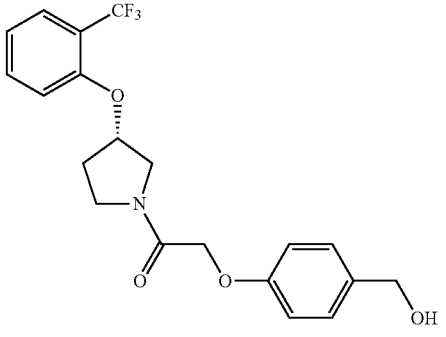

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol. In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50 One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50. In certain embodiments, the pharmaceutical composition comprises both (i) butylated hydroxytoluene (BHT) at a concentration of least 0.05%; and (ii) di-sodium EDTA at a concentration of least 0.001%. In another embodiment, the pharmaceutical composition comprises each of (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50.

In a certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w; and
(vi) a carbomer such as carbomer homopolymer type C980 in the range of 0.5 to 2.0% w/w.

In another certain embodiment, the pharmaceutical composition comprises:
- (i) ethanol in the range of 1.0-20.0% w/w;
- (ii) phenoxyethanol in the range 0.1-5.0% w/w;
- (iii) diethylene glycol monoethyl ether (otherwise known as DEGEE or Transcutol P®) in the range 5.0-40.0% w/w;
- (iv) propylene glycol in the range 5.0-40.0% w/w;
- (v) PEG400 in the range 5.0-40.0% w/w;
- (vi) a carbomer such as carbomer homopolymer type C980 in the range of 0.5 to 2.0% w/w; (vii) butylated hydroxytoluene (BHT) at a concentration of least 0.05%;
- (viii) di-sodium EDTA at a concentration of least 0.001%; and
- (ix) Trolamine to provide an apparent pH in the range 6.50 to 7.50.

In another embodiment, the pharmaceutical composition comprises:
- (i) ethanol in the range of 5.0-15.0% w/w;
- (ii) phenoxyethanol in the range 0.5-2.0% w/w;
- (iii) diethylene glycol monoethyl ether (otherwise known as DEGEE or Transcutol P®) in the range 20.0-30.0% w/w;
- (iv) propylene glycol in the range 15.0-25.0% w/w;
- (v) PEG400 in the range 15.0-25.0% w/w; and
- (vi) a carbomer such as carbomer homopolymer type C980 in the range of 0.75 to 1.5% w/w.

In another embodiment, the pharmaceutical composition comprises:
- (i) ethanol in the range of 5.0-15.0% w/w;
- (ii) phenoxyethanol in the range 0.5-2.0% w/w;
- (iii) diethylene glycol monoethyl ether (otherwise known as DEGEE or Transcutol P®) in the range 20.0-30.0% w/w;
- (iv) propylene glycol in the range 15.0-25.0% w/w;
- (v) PEG400 in the range 15.0-25.0% w/w; and
- (vi) a carbomer such as carbomer homopolymer type C980 in the range of 0.75 to 1.5% w/w.
- (vii) butylated hydroxytoluene (BHT) at a concentration of least 0.1%;
- (viii) di-sodium EDTA at a concentration of least 0.005%; and
- (ix) Trolamine to provide an apparent pH in the range 6.50 to 7.50.

In specific embodiments, the pharmaceutical composition comprises:
- (i) ethanol at a concentration of 10.0% w/w;
- (ii) phenoxyethanol at a concentration of 1% w/w;
- (iii) diethylene glycol monoethyl ether (otherwise known as DEGEE or Transcutol P®) at a concentration of 25.0% w/w;
- (iv) propylene glycol at a concentration of 20.0% w/w;
- (v) PEG400 at a concentration of 21.0% w/w;
- (vi) carbomer homopolymer type C980 at a concentration of 1.0% w/w; and
- (vii) water at a concentration of 19.5-22% w/w.

In yet other specific embodiments, the pharmaceutical composition comprises:
- (i) ethanol at a concentration of 10.0% w/w;
- (ii) phenoxyethanol at a concentration of 1% w/w;
- (iii) diethylene glycol monoethyl ether (otherwise known as DEGEE or Transcutol P®) at a concentration of 25.0% w/w;
- (iv) propylene glycol at a concentration of 20.0% w/w;
- (v) PEG400 at a concentration of 21.0% w/w;
- (vi) carbomer homopolymer type C980 at a concentration of 1.0% w/w;
- (vii) butylated hydroxytoluene (BHT) at a concentration of 0.1% w/w;
- (viii) di-sodium EDTA at a concentration of 0.005% w/w;
- (ix) Trolamine at a concentration of 0.375% w/w; and
- (x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxyl)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6% In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments, the compound is a racemic mixture, a diastereoisomeric mixture, a single enantiomer, an enantiomeric diastereomer, a meso compound, a pure epimer, or a mixture of epimers thereof.

In yet other embodiments, one or more double bonds present in the compound are cis or trans, E or Z, a cis/trans mixture, an E/Z mixture, a combination of E and Z geometries, a combination of E and Z geometric mixtures or other geometric isomers thereof.

In yet further embodiments a second therapeutic agent is present.

The subject invention provides a method of treating a skin condition associated with abnormal sebum secretion or abnormal sebaceous gland function in a subject which comprises topically and periodically applying to an area of the subject's skin affected by the skin condition a composition comprising a pharmaceutically acceptable carrier, which provides an environment of physical and chemical stability, and an amount of a compound or of a pharmaceutically acceptable salt of the compound or ester of the compound or prodrug of the compound effective to treat the skin condition, wherein the compound has the structure I:

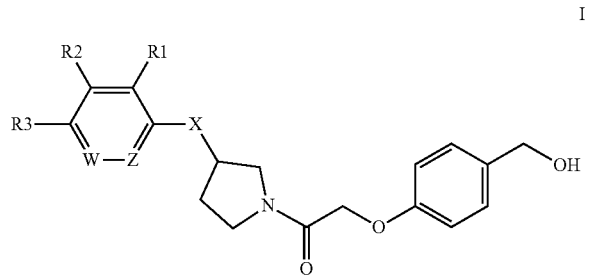

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or $C(NR_6)NR_7C(NR_8)NR_9R_{10}$;
wherein adjacent substituents $R_1$, $R_2$ and $R_3$ and $R_4$ and $R_5$, if present, may form a saturated or unsaturated 5-membered or 6-membered carbocyclic or heterocyclic ring;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;
In some embodiments, X is O; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$;

OCF$_2$CF$_3$; O—(CO)—R$_6$; O—(CNH)—R$_6$; O—(CNR$_6$)—R$_7$; SO$_3$H or a ester thereof; CO$_2$H or a ester thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$; adjacent substituents R$_1$, R$_2$ and R$_3$ and R$_4$ and R$_5$, if present, may form a saturated or unsaturated 5-membered or 6-membered carbocyclic or heterocyclic ring; and each of R$_6$, R$_7$, R$_8$, R$_9$ and R$_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In some embodiments, the compound is one of the following:

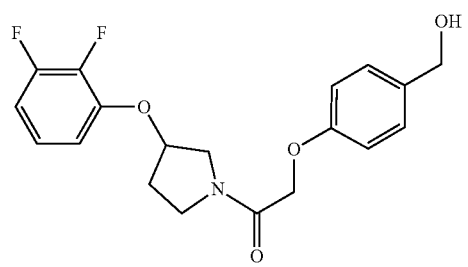

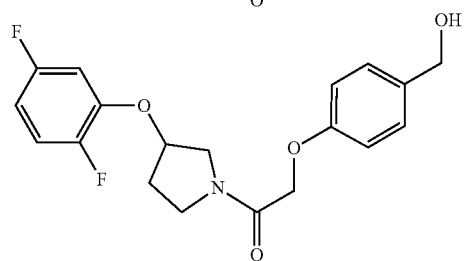

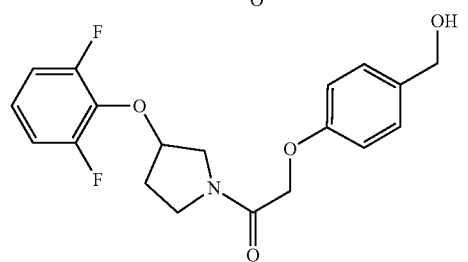

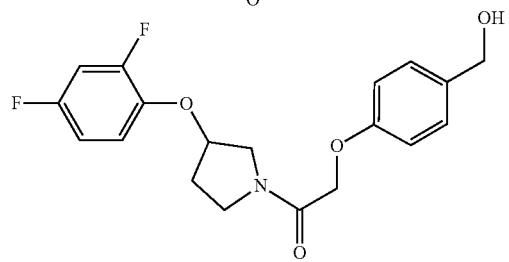

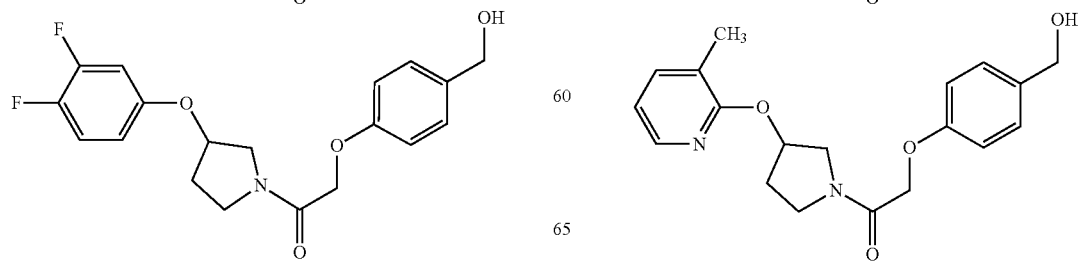

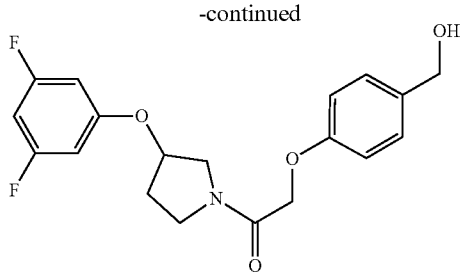

or a pharmaceutically acceptable salt, ester or prodrug form thereof.

In further embodiments, the compound is one of the following:

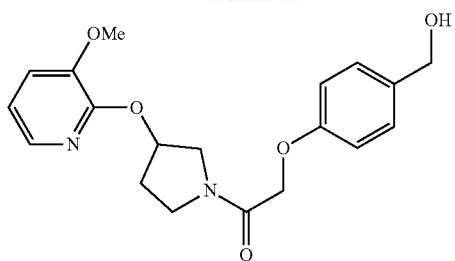
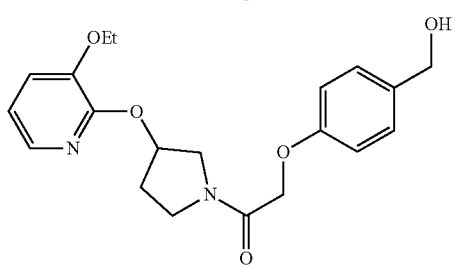
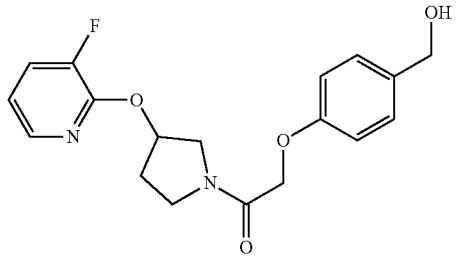
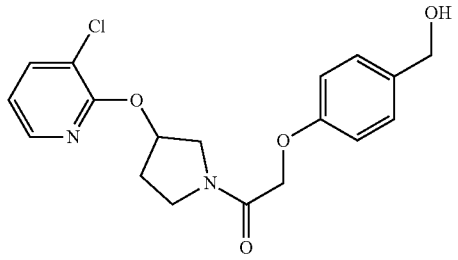
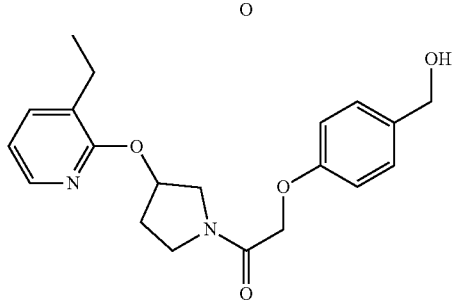
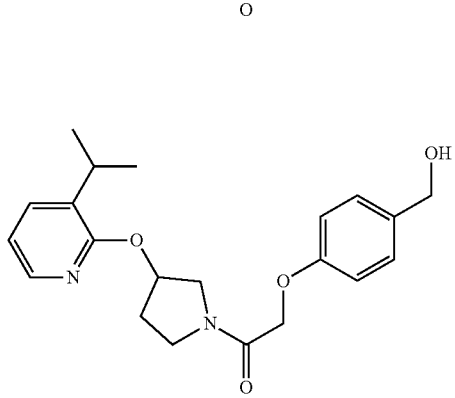
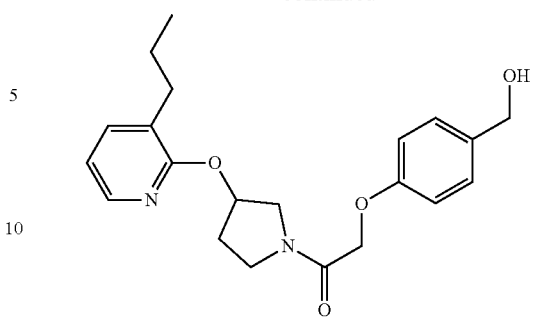
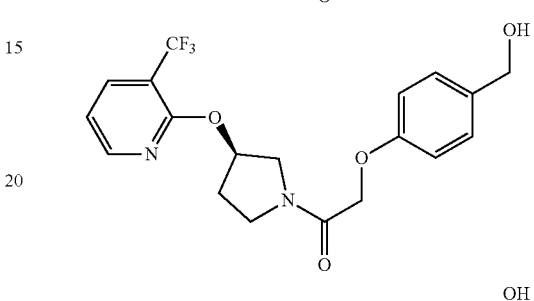
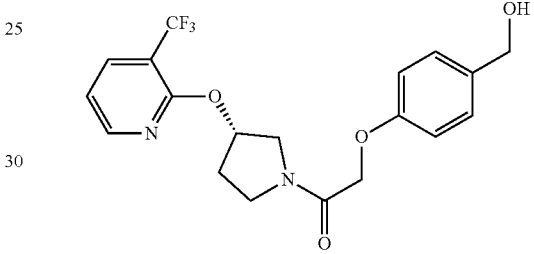
or a pharmaceutically acceptable salt, ester or prodrug form thereof.
In yet other embodiments, the compound is one of the following:
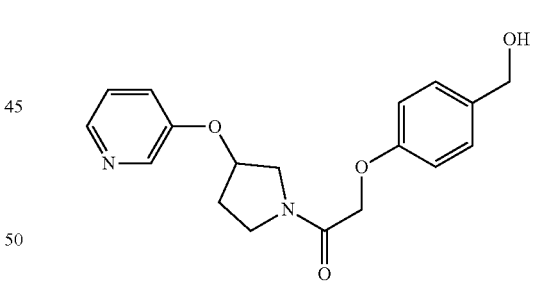
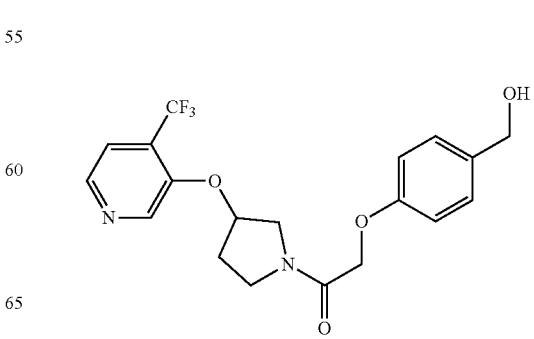

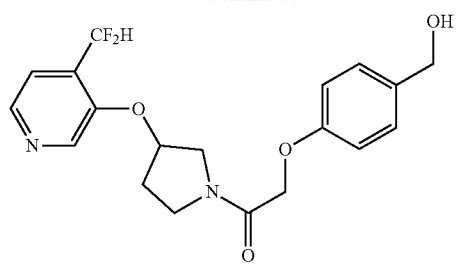
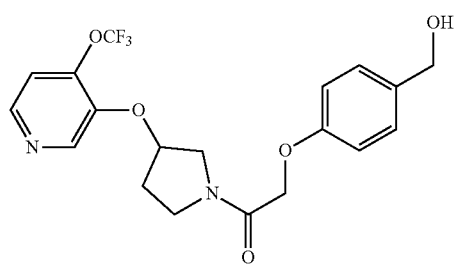
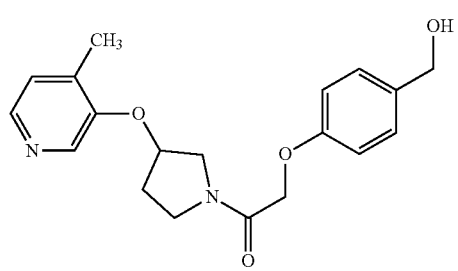
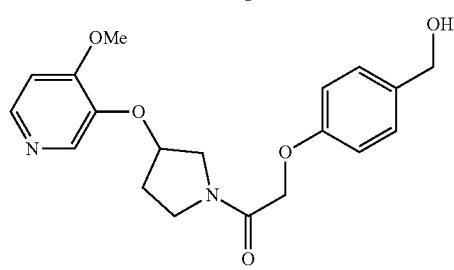
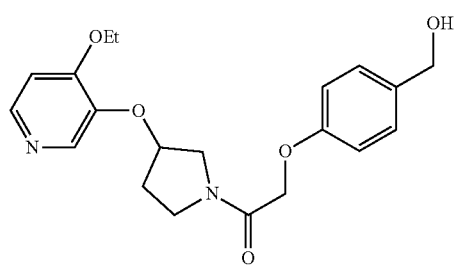
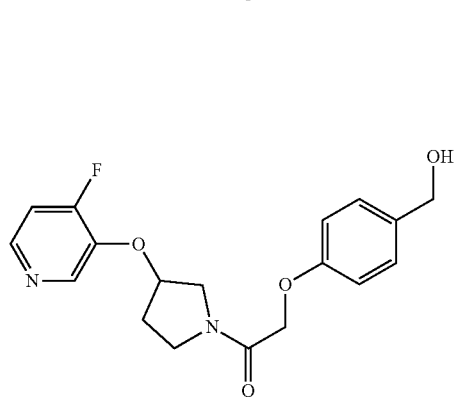
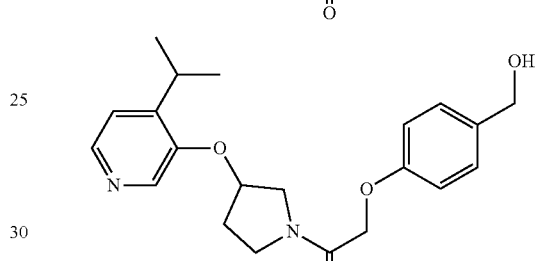

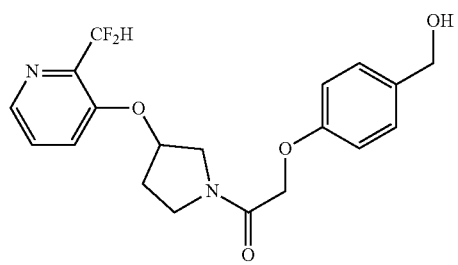 [SMILES: O=C(COc1ccc(CO)cc1)N1CC[C@H](Oc2ccccc2C(F)F)C1]
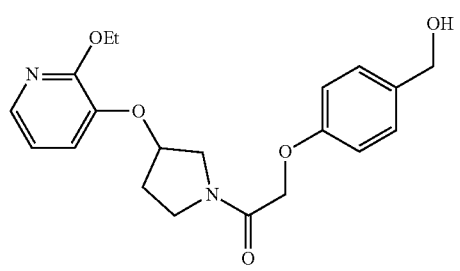
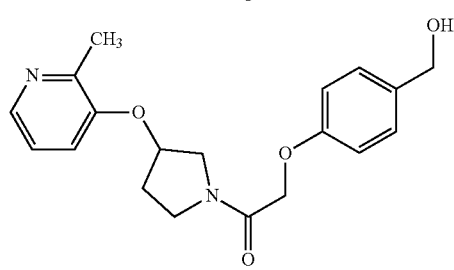
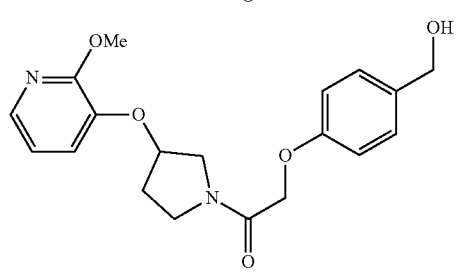
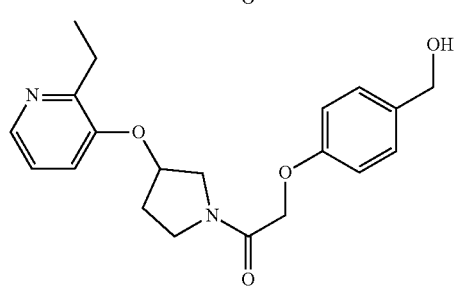
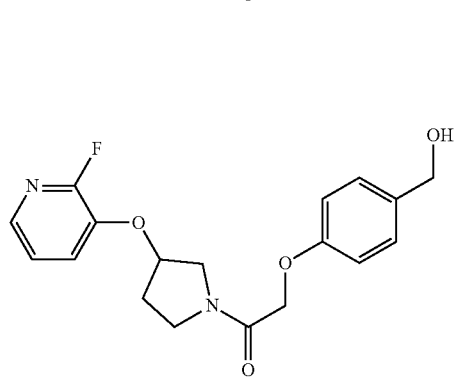
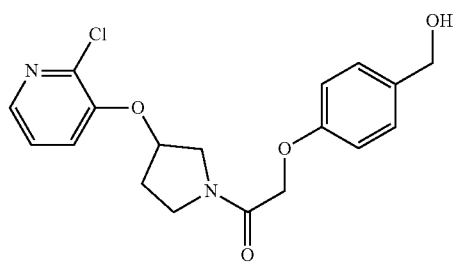
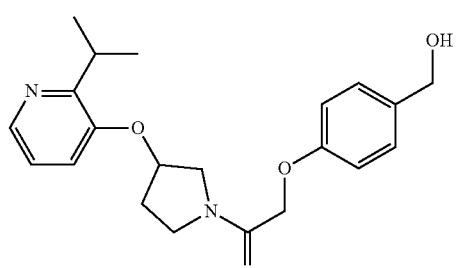
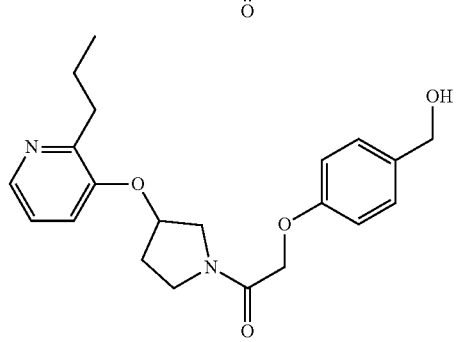
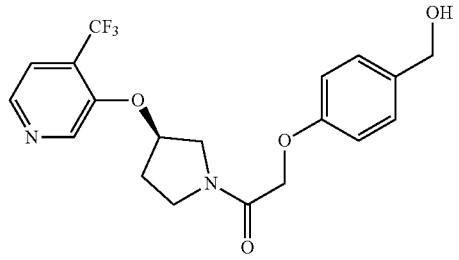
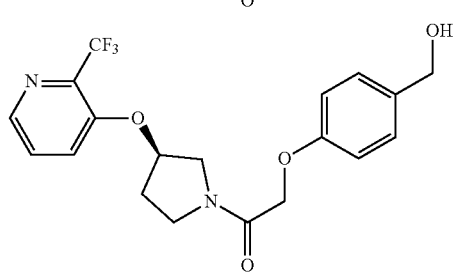
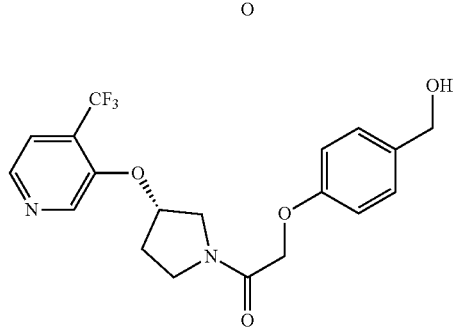

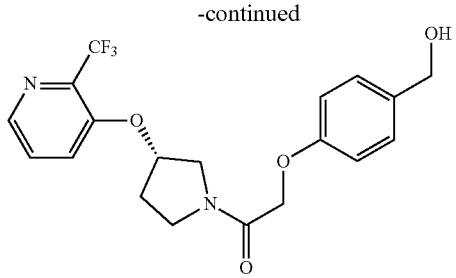
or a pharmaceutically acceptable salt, ester or prodrug form thereof.
In yet further embodiments, the compound is one of the following:
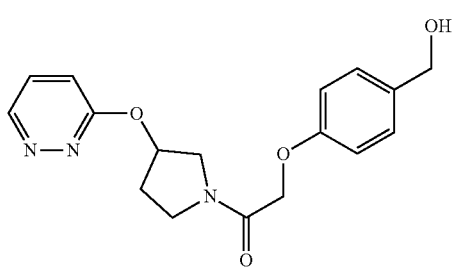
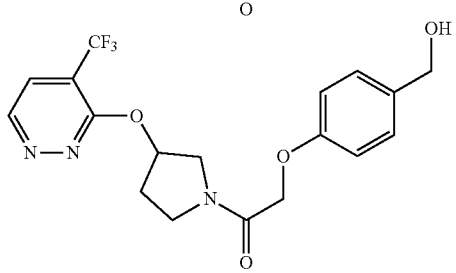
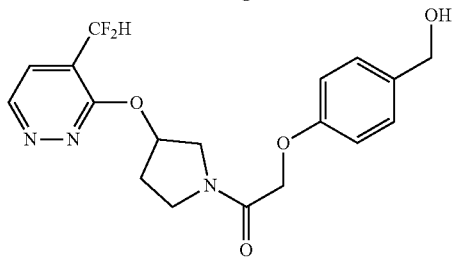
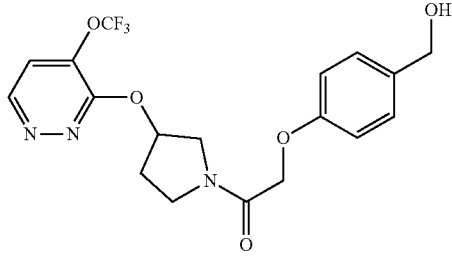
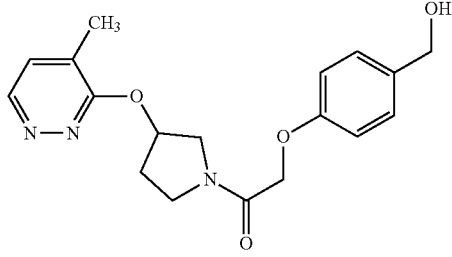
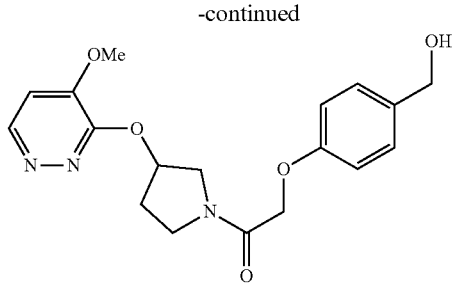
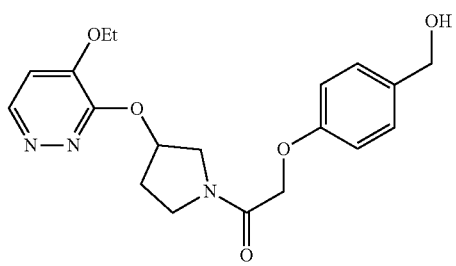
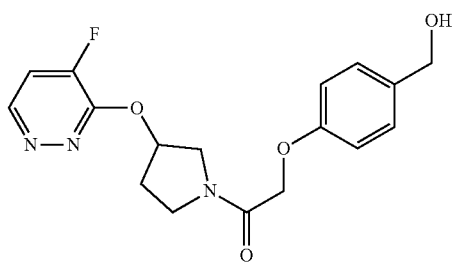
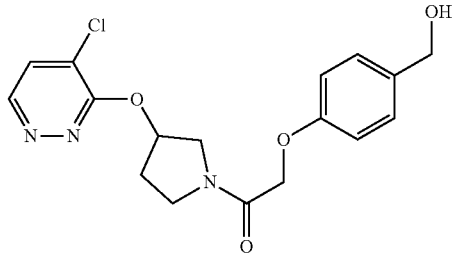

-continued

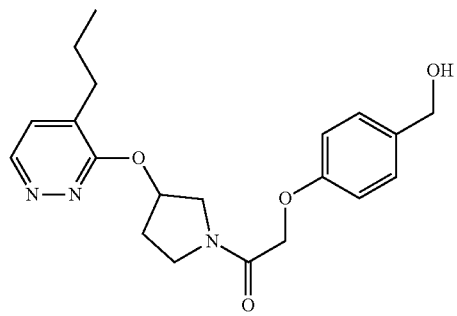

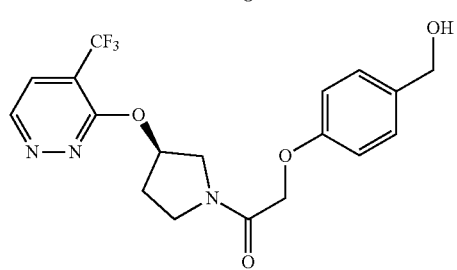

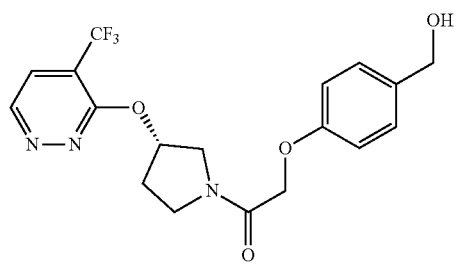

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $NO_2$; $NH_2$; NHCH(O); $NR_6$CH(O); NHC(O)$R_6$; $NR_6$C(O)$R_7$; C(O) $NR_6R_7$; C(NH)$NR_6R_7$; C(NH)$NR_6$OH; C(NH)$NR_6NO_2$; or C($NR_6$)$NR_7$C($NR_8$)$NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In certain embodiments, the compound is one of the following:

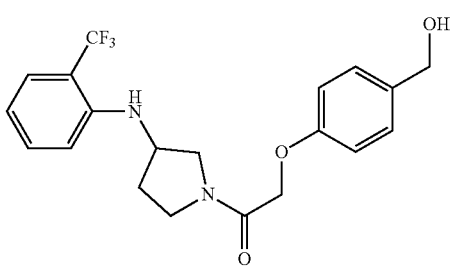

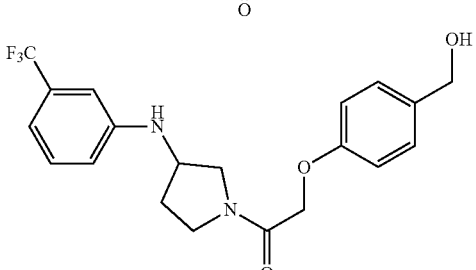

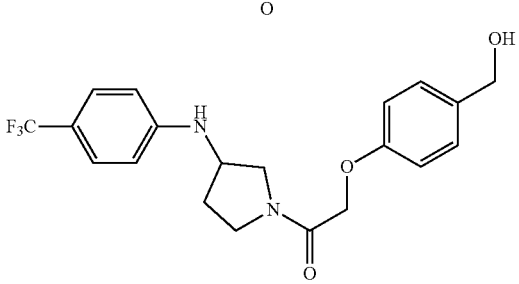

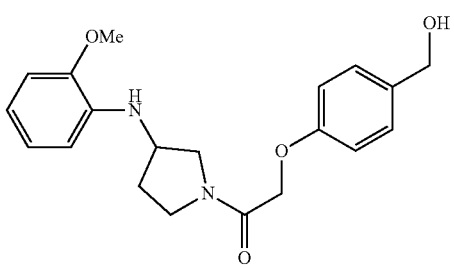

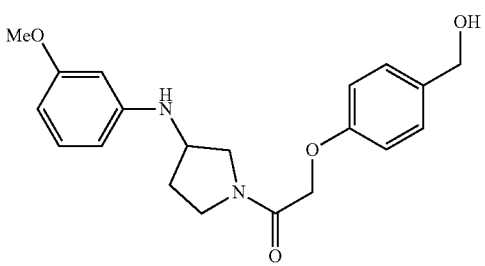

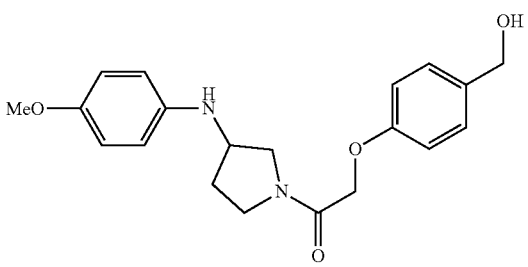

87
-continued
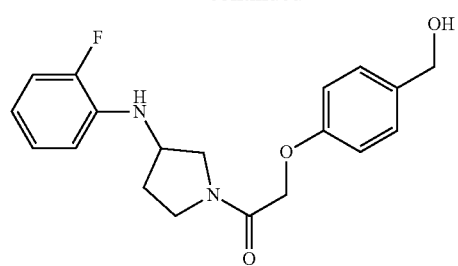
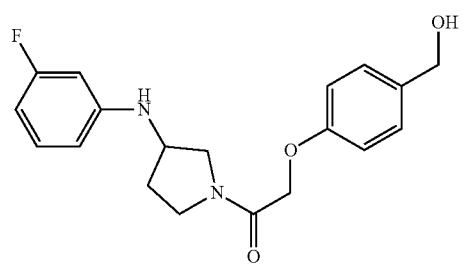
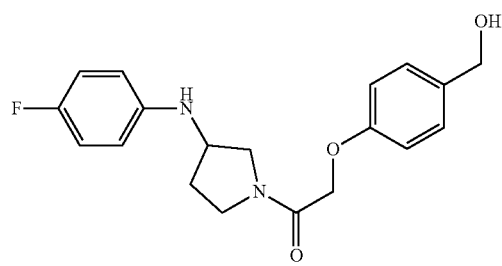
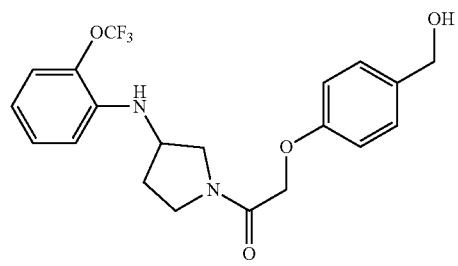
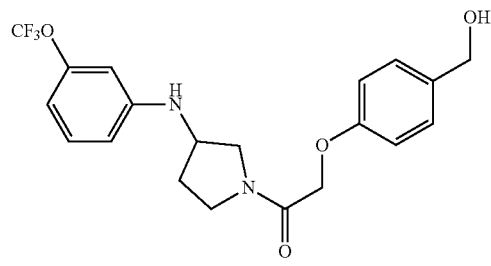
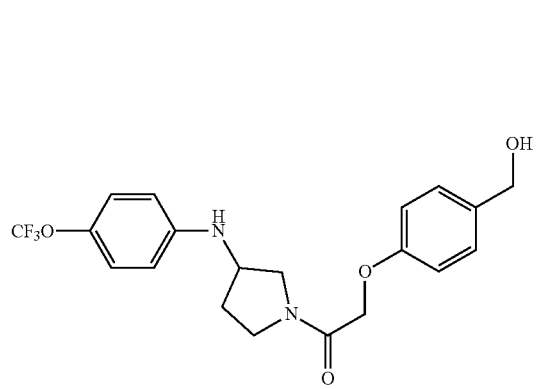
88
-continued
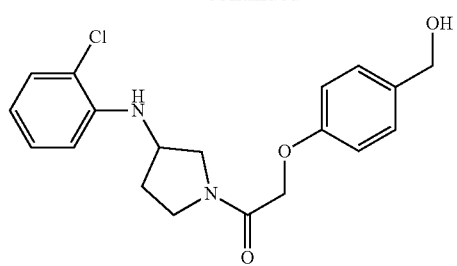
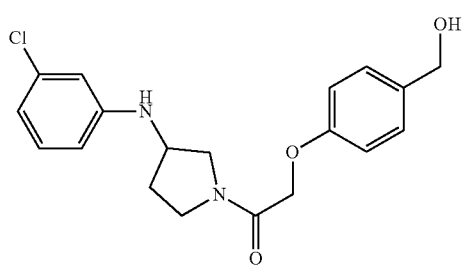
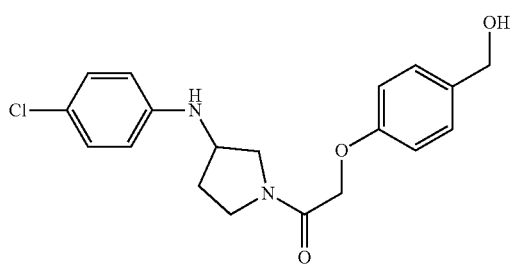
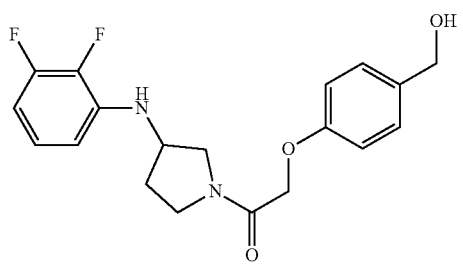
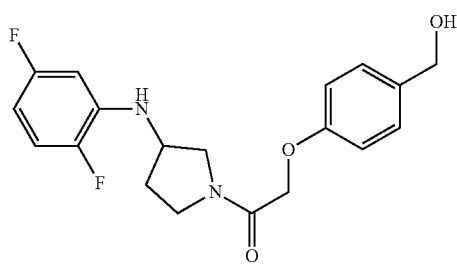
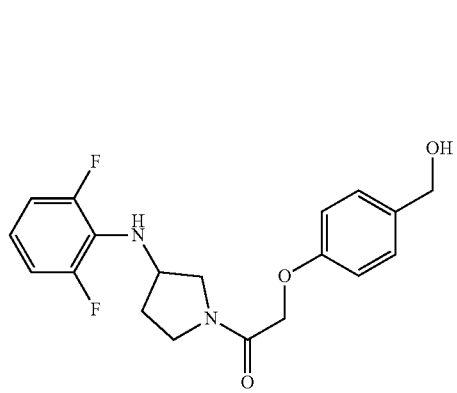

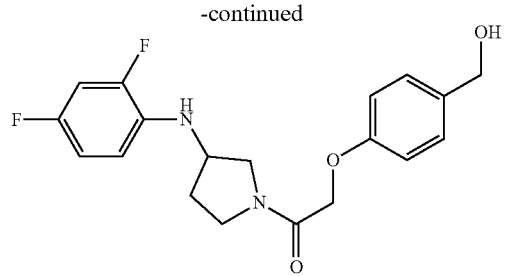
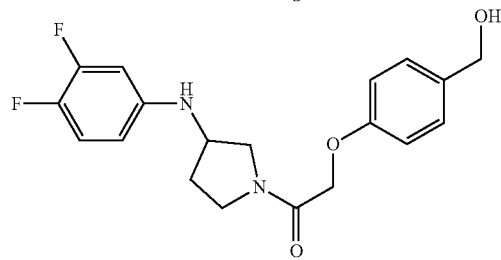
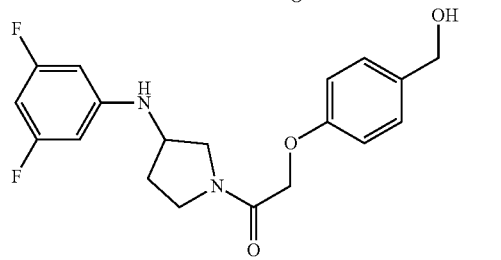
or a pharmaceutically acceptable salt, ester or prodrug form thereof.
In other embodiments, the compound is one of the following:
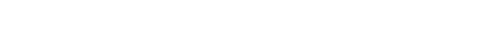
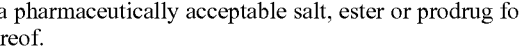
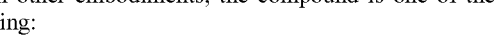
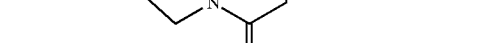
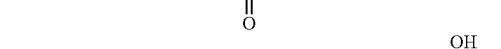
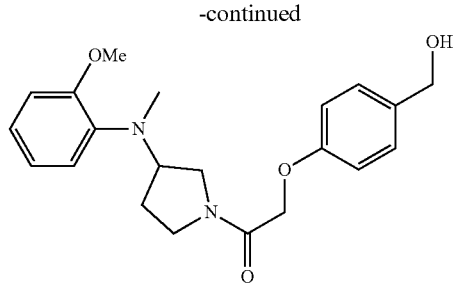
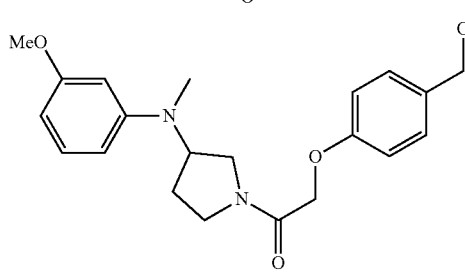
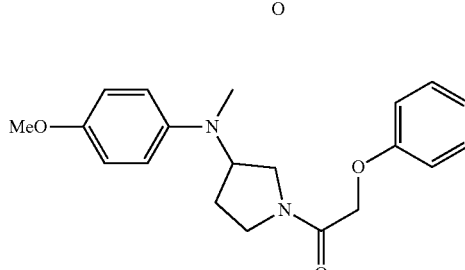
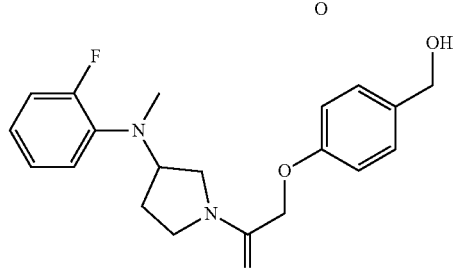
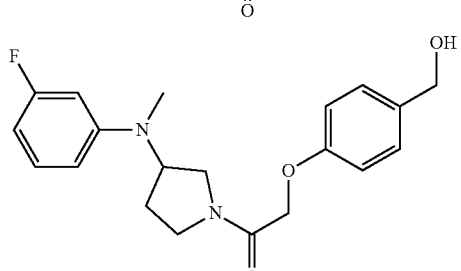
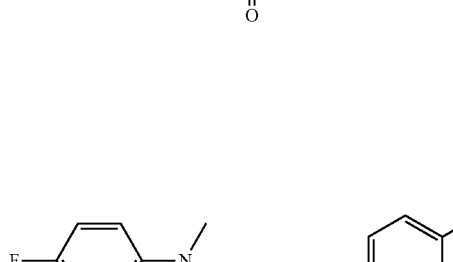
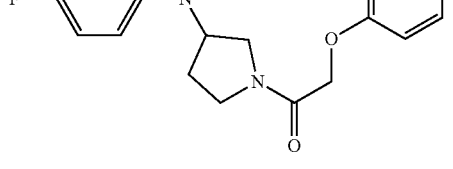

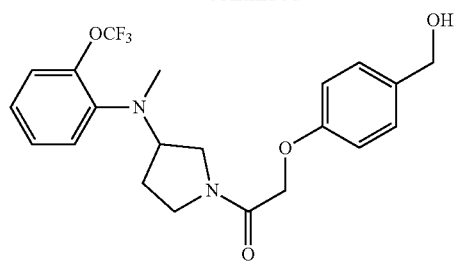
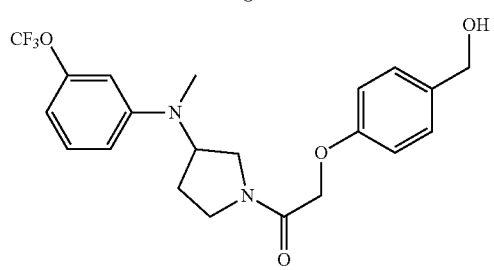
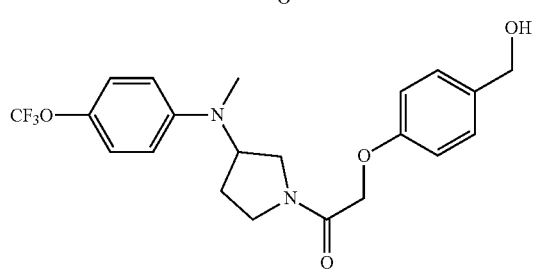
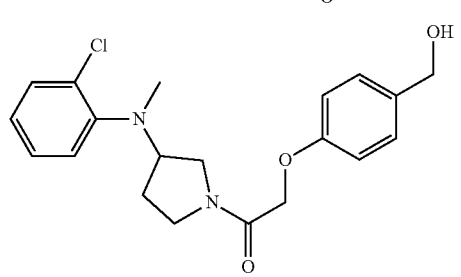
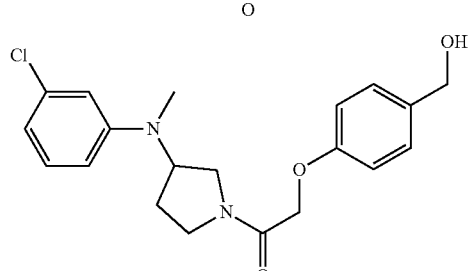
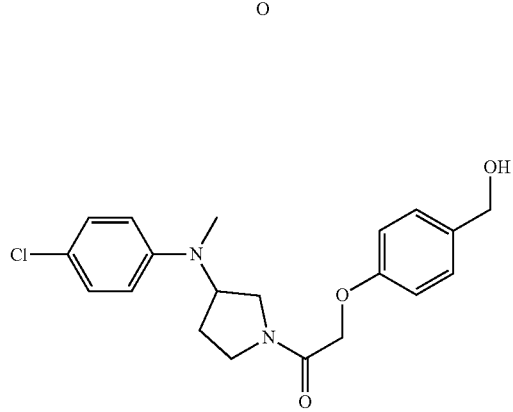
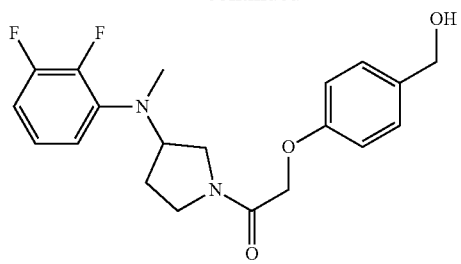
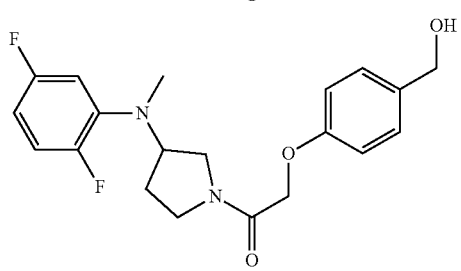
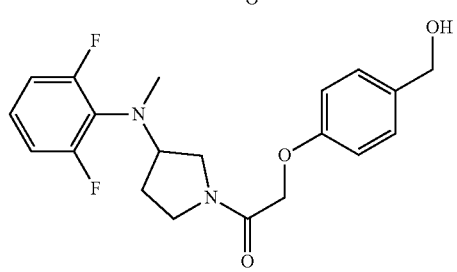
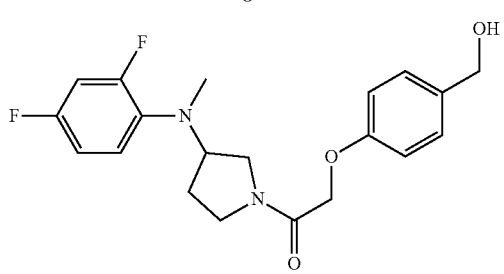
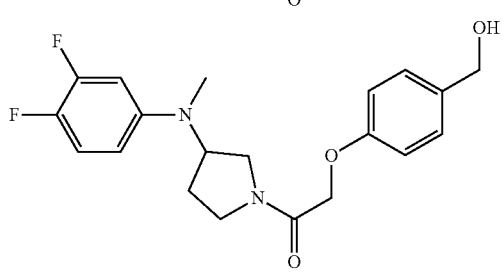
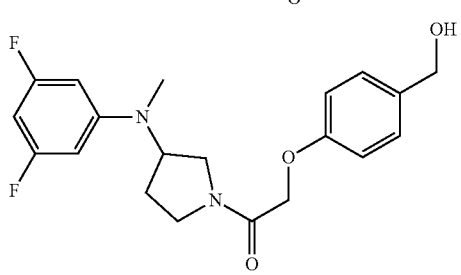
or a pharmaceutically acceptable salt, ester or prodrug form thereof.

In further embodiments, the compound is one of the following:
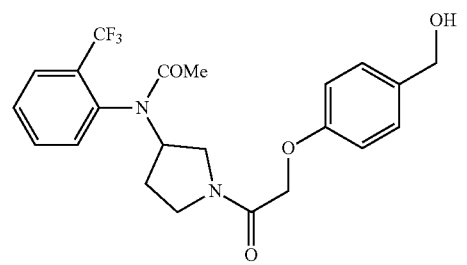
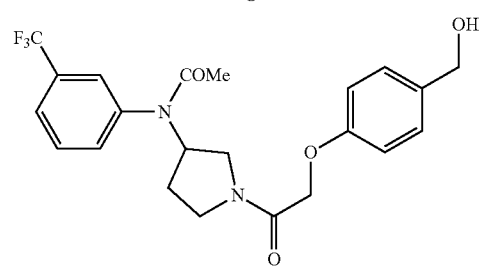
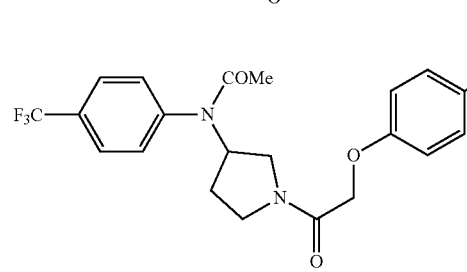
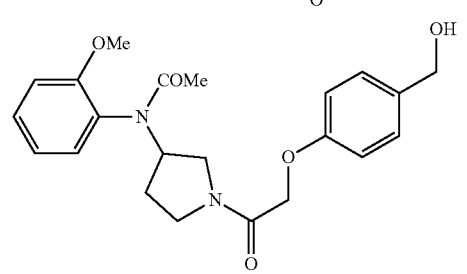
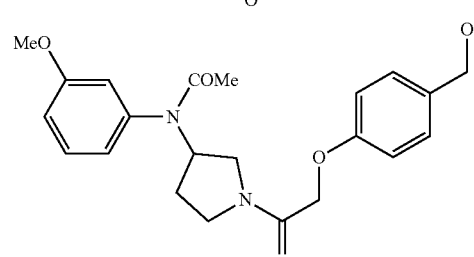
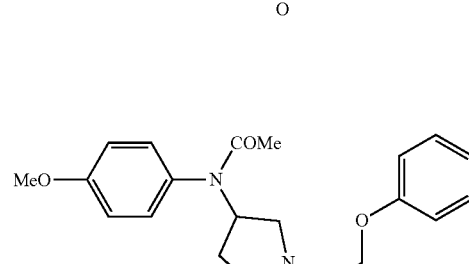
-continued
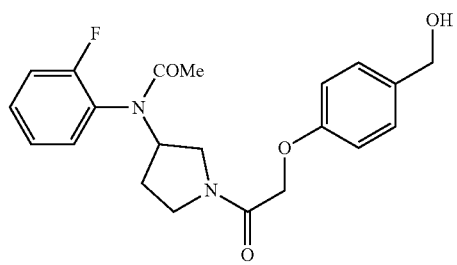
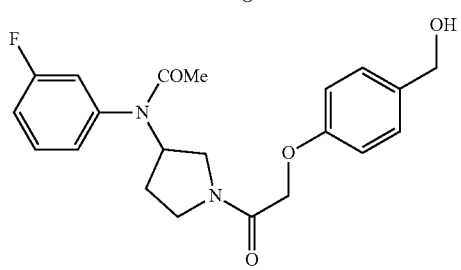
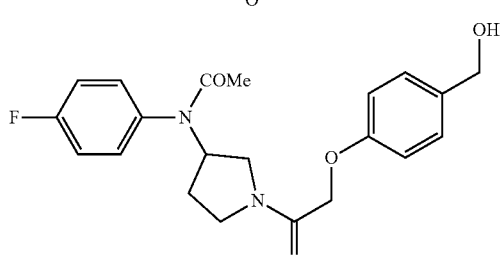
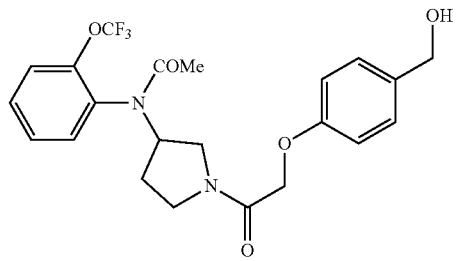
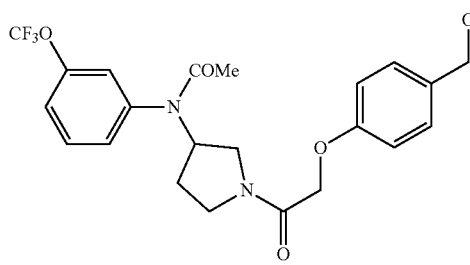
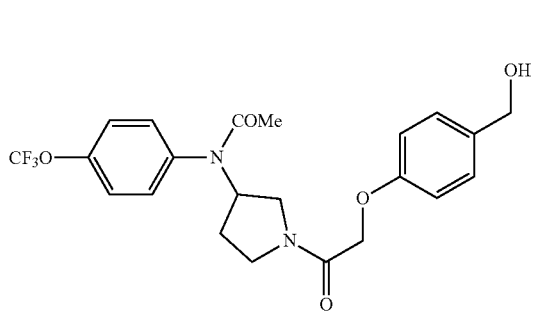

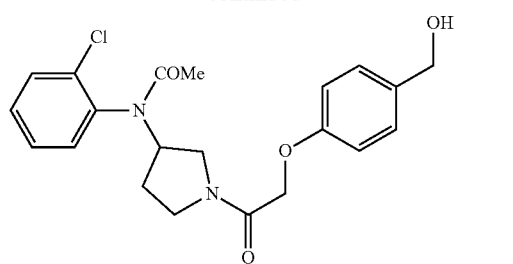
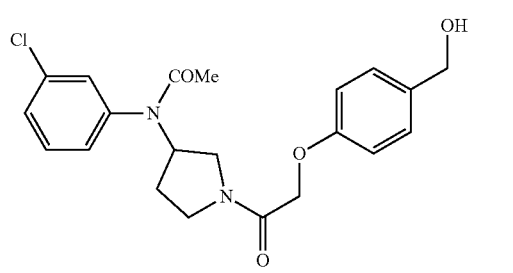
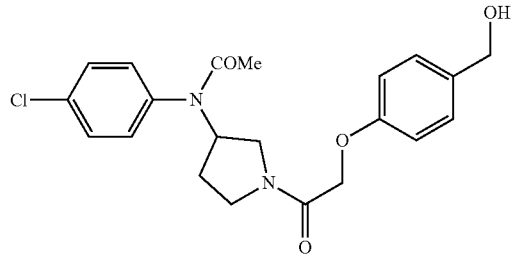
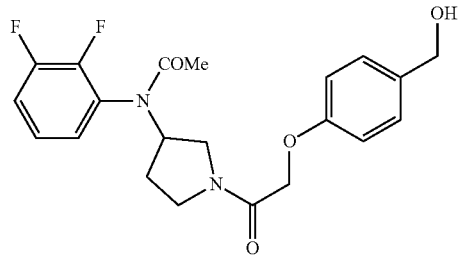
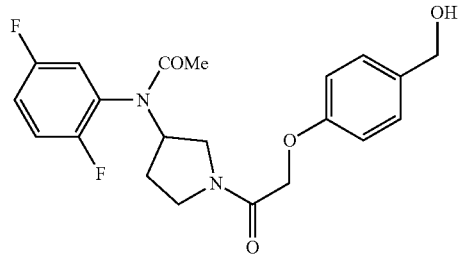
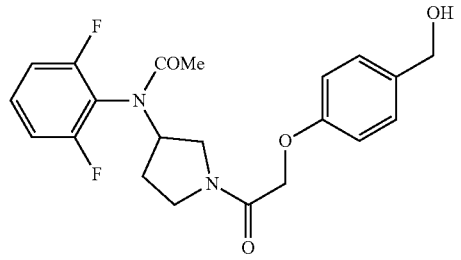
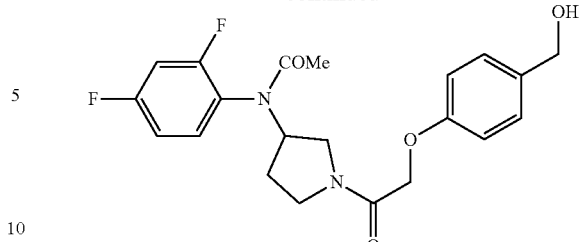
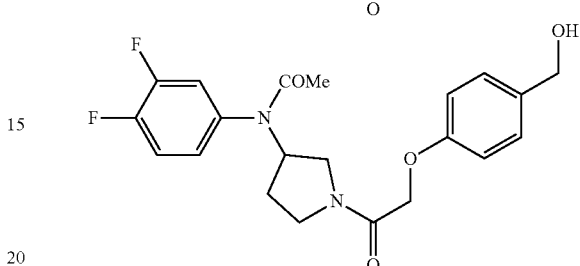

or a pharmaceutically acceptable salt, ester or prodrug form thereof.
In yet further embodiments, the compound is one of the following:

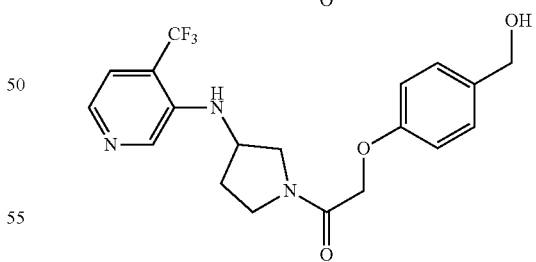
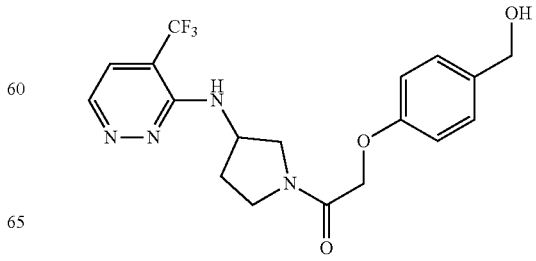

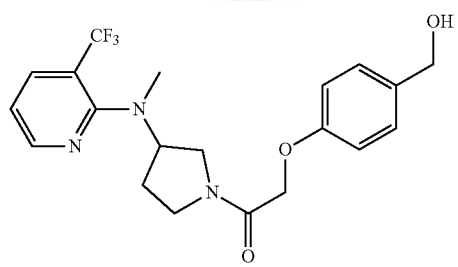

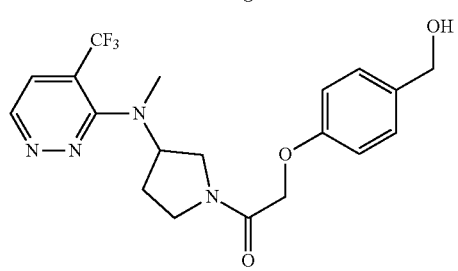
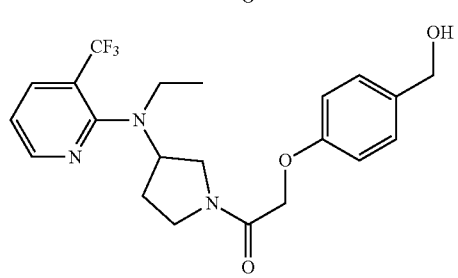

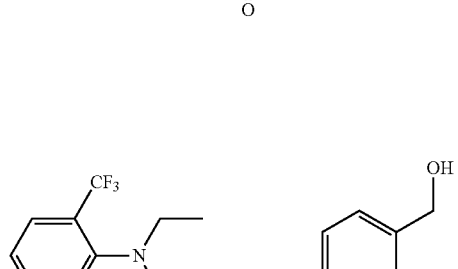
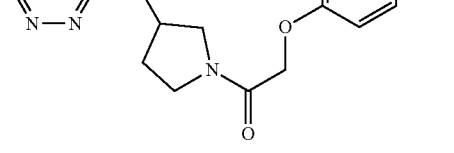
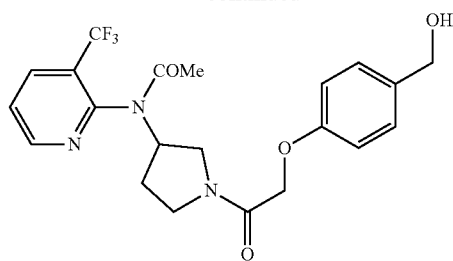
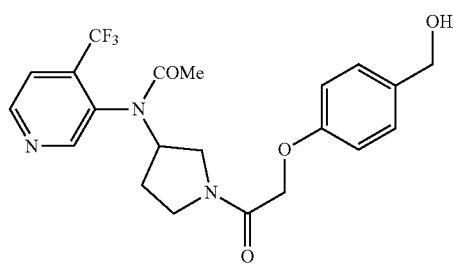
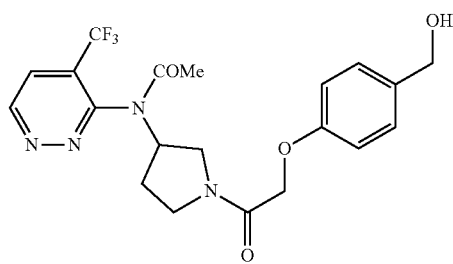
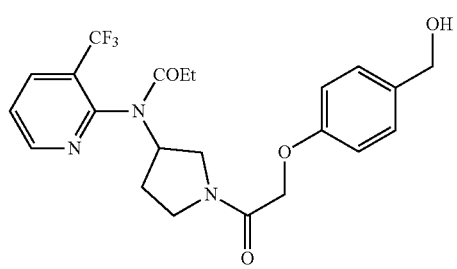
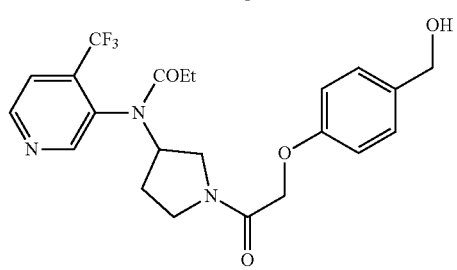
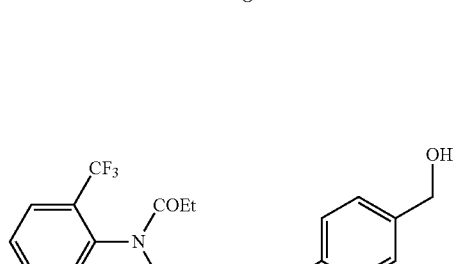
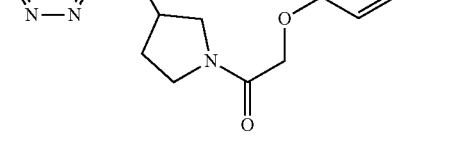

-continued
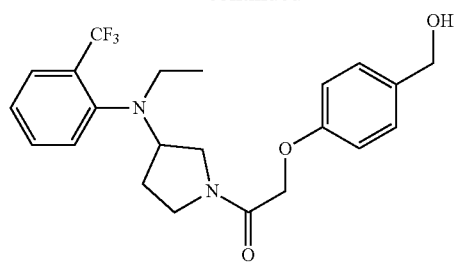
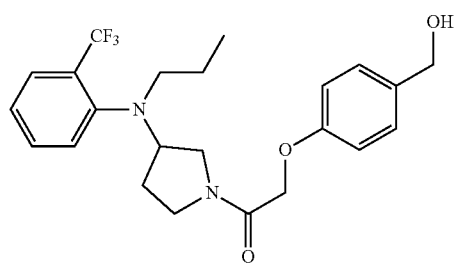
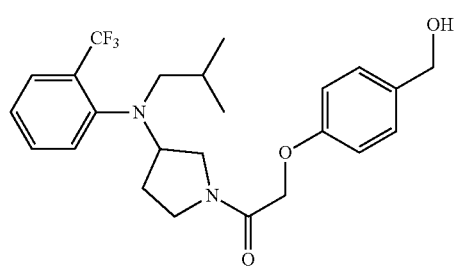
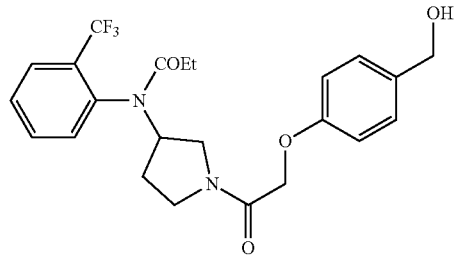
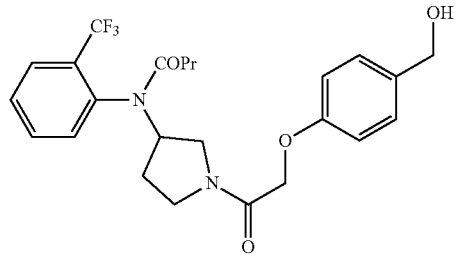
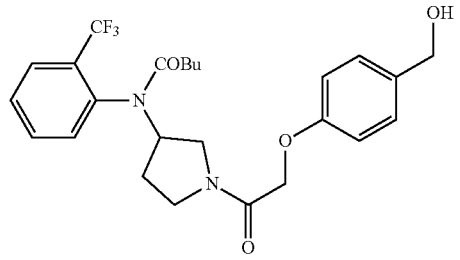
or a pharmaceutically acceptable salt, ester or prodrug form thereof.
In yet other embodiments, the compound is one of the following:
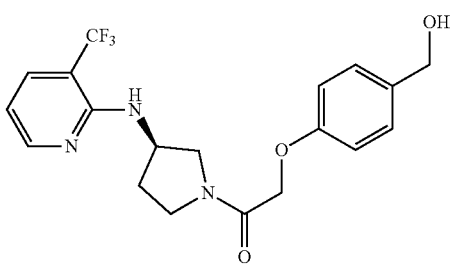
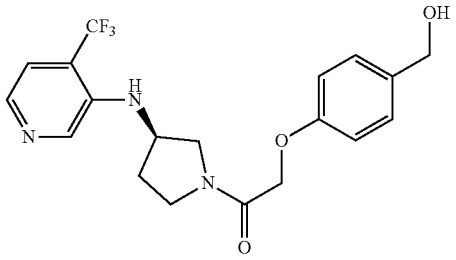
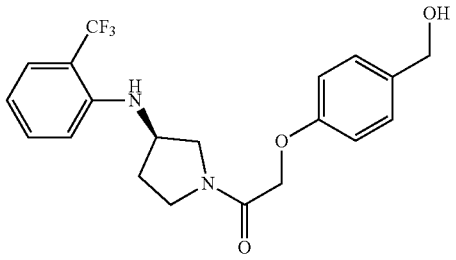
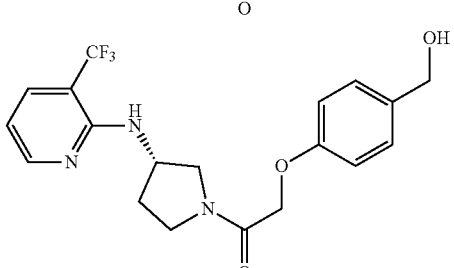
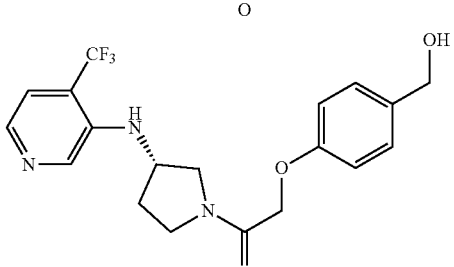
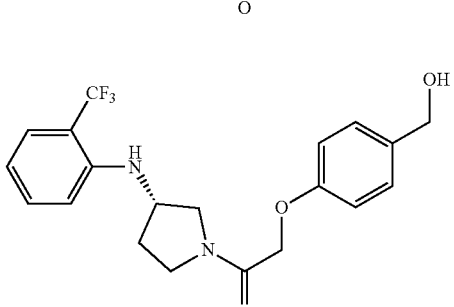

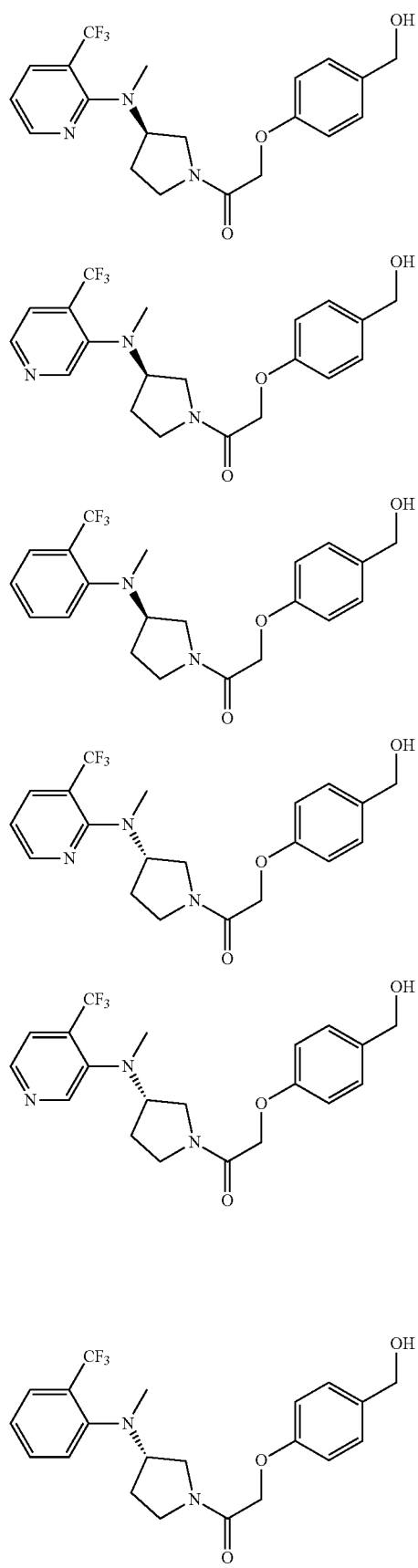
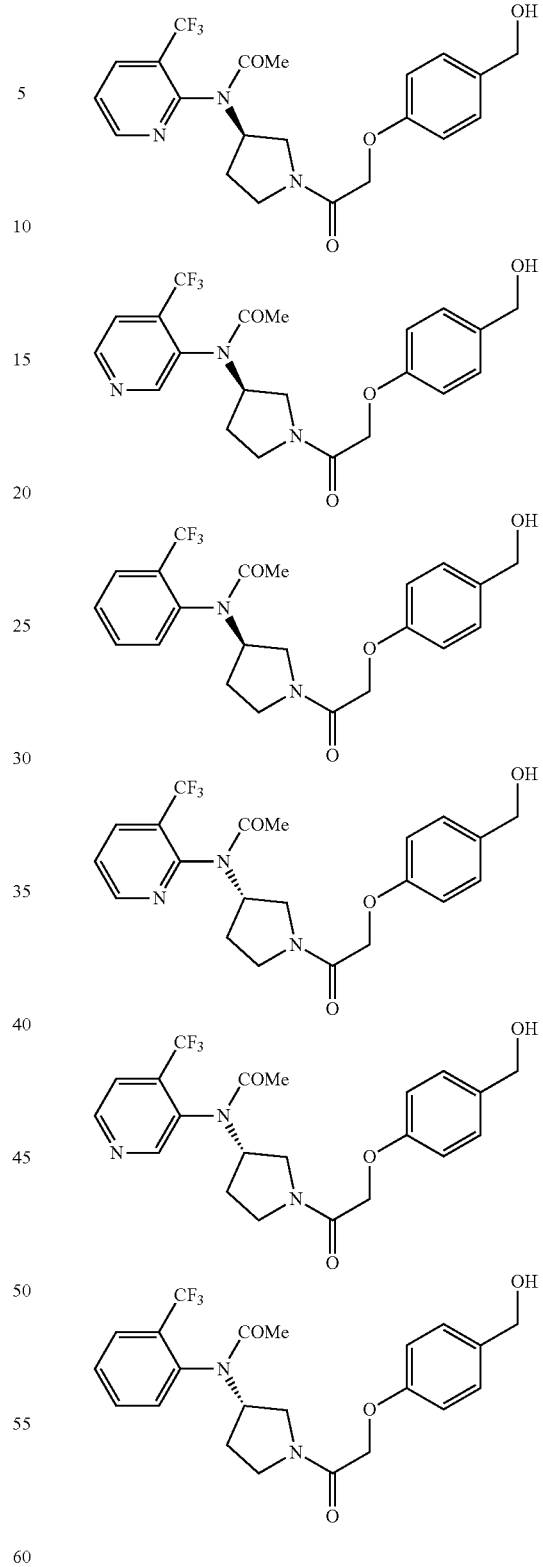
or a pharmaceutically acceptable salt, ester or prodrug form thereof.
In yet further embodiments, X is S, SO or SO; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$;

CHFCH₂; CHFCHF₂; CHFCF₃; CF₂CH₂F; CF₂CHF₂; CF₂CF₃; O-alkyl; O-cycloalkyl; O-alkylcycloalkyl; OCH₂F; OCHF₂; OCF₃; OCH₂CH₂F; OCH₂CHF₂; OCH₂CF₃; OCHFCH₂F; OCHFCHF₂; OCHFCF₃; OCF₂CH₂F; OCF₂CHF₂; OCF₂CF₃; O—(CO)—R₆; O—(CNH)—R₇; O—(CNR₆)—R₇; SO₃H or a ester thereof; CO₂H or a ester thereof; NO₂; NH₂; NHCH(O); NR₆CH(O); NHC(O)R₆; NR₆C(O)R₇; C(O)NR₆R₇; C(NH)NR₆R₇; C(NH)NR₆OH; C(NH)NR₆NO₂; or C(NR₆)NR₇C(NR₈)NR₉R₁₀; adjacent substituents R₁, R₂ and R₃ and R₄ and R₅, if present, may form a saturated or unsaturated 5-membered or 6-membered carbocyclic or heterocyclic ring; and each of R₆, R₇, R₈, R₉ and R₁₀, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or SO₂. In further embodiments, X is SO. In yet further embodiments X is SO₂.

In some embodiments, the compound is one of:

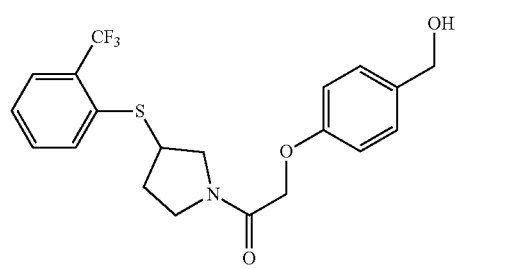

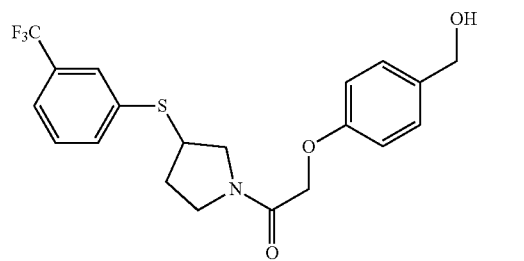

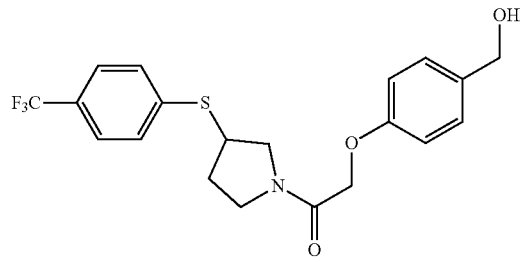

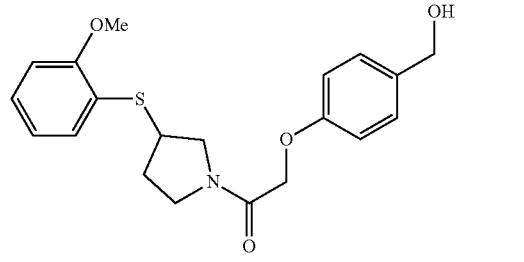

-continued

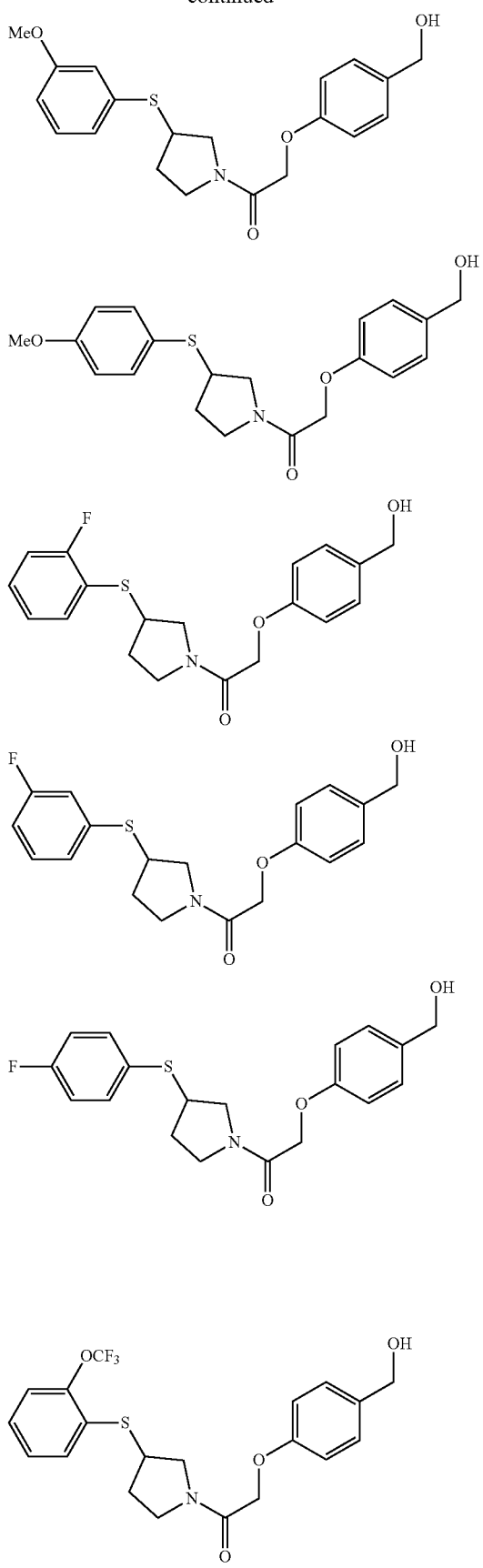

105
-continued
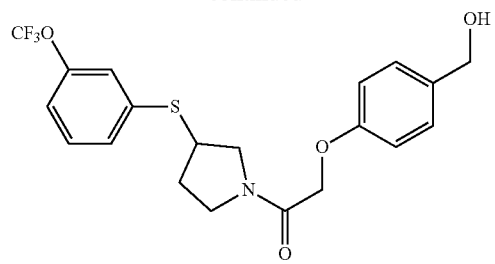
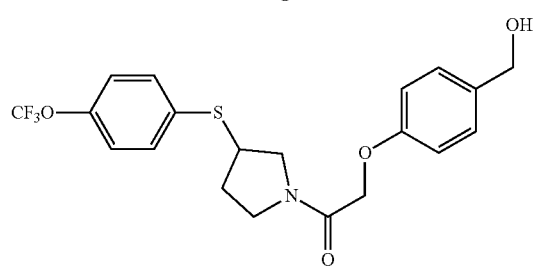
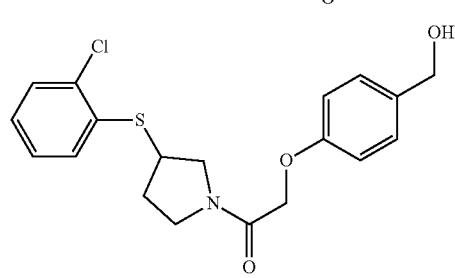
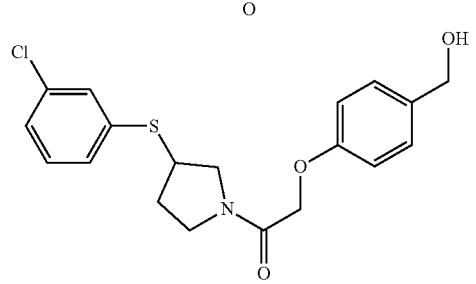
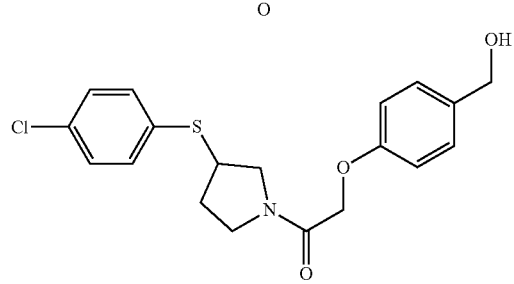
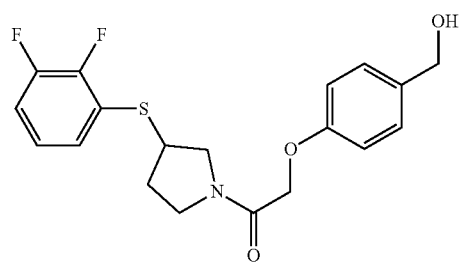
106
-continued
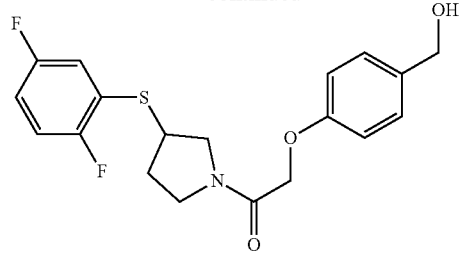
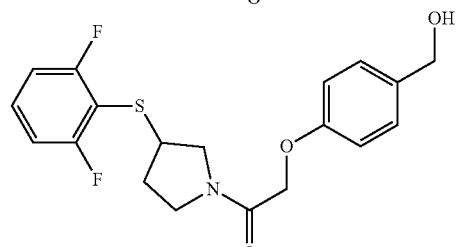
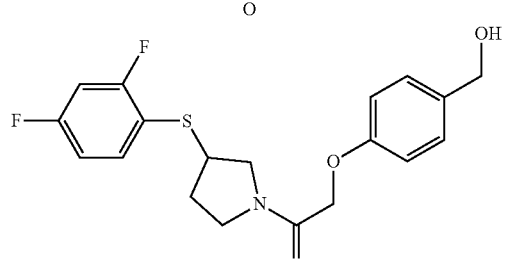
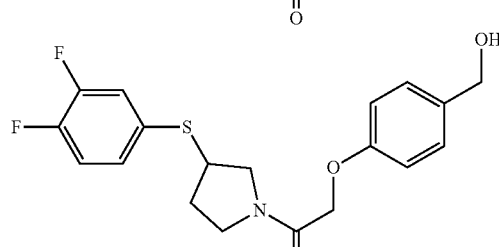
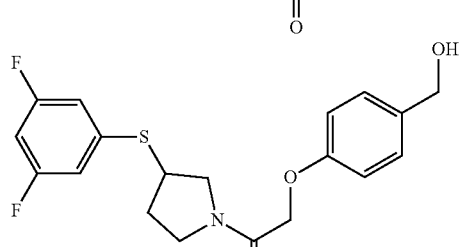
or a pharmaceutically acceptable salt, ester or prodrug form thereof.
In other embodiments, the compound is one of:
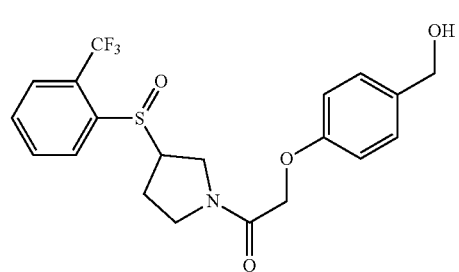

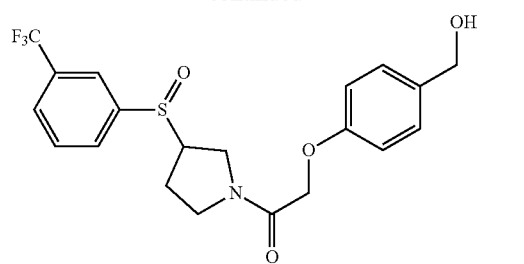
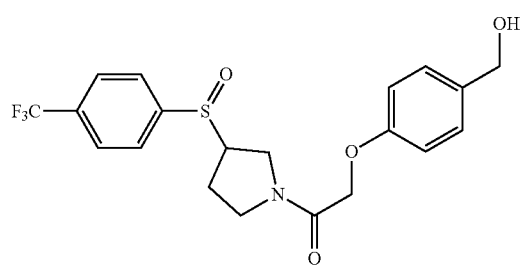
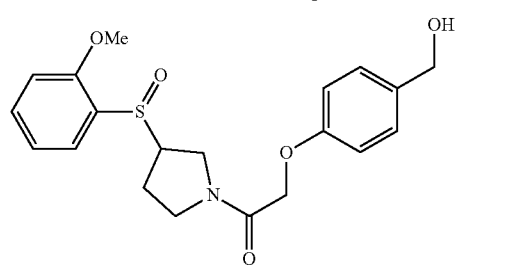
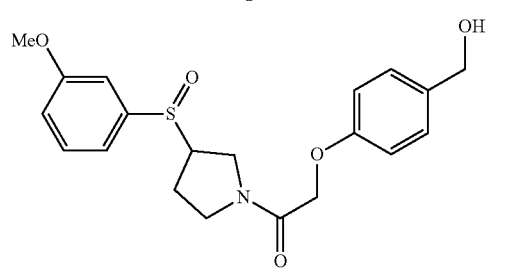
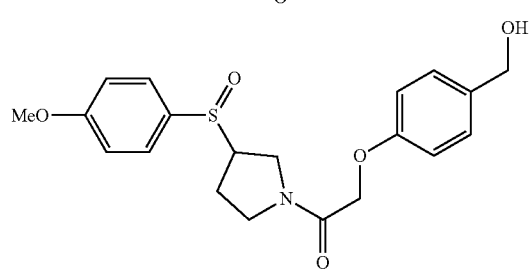
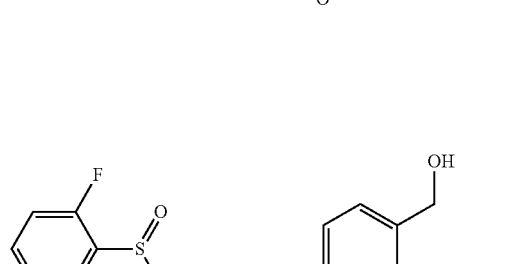
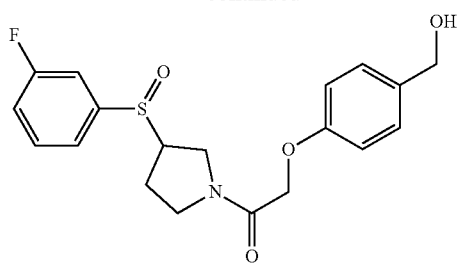
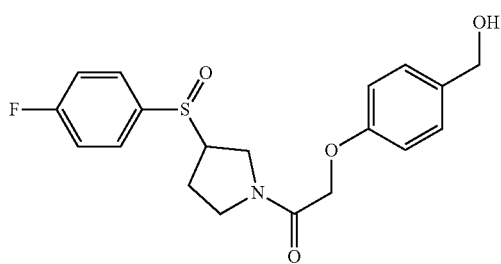
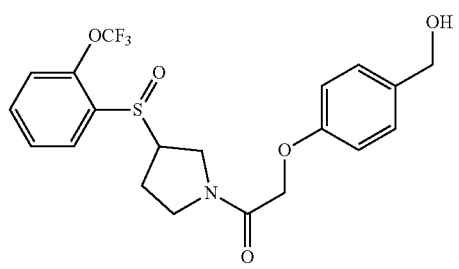
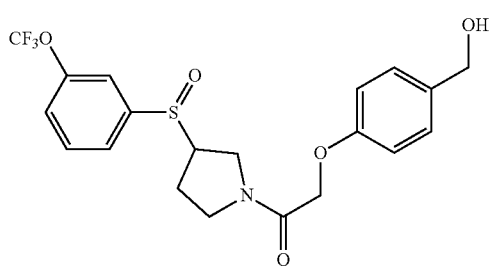
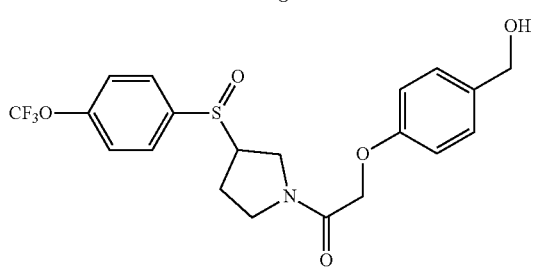
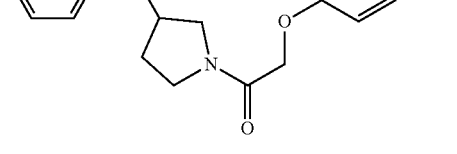

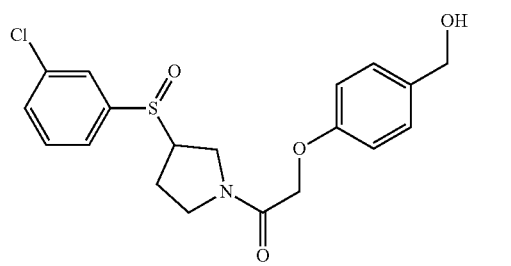
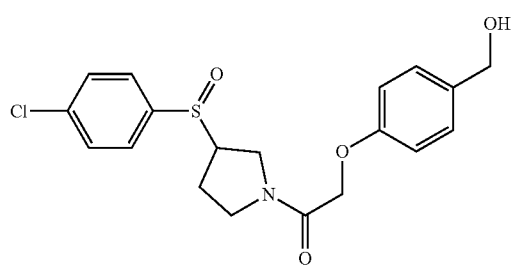
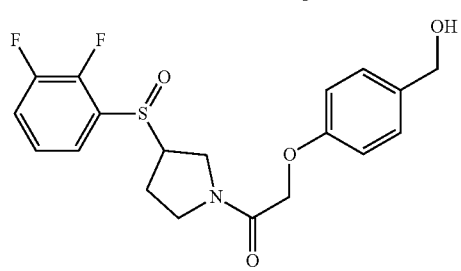
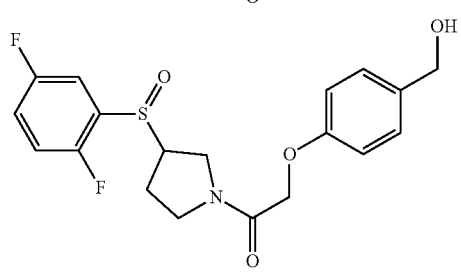
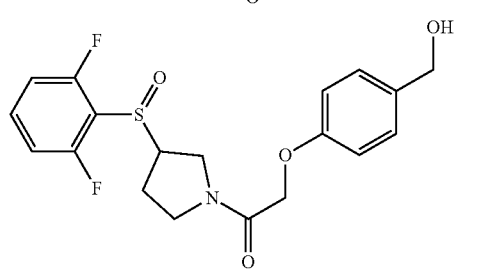
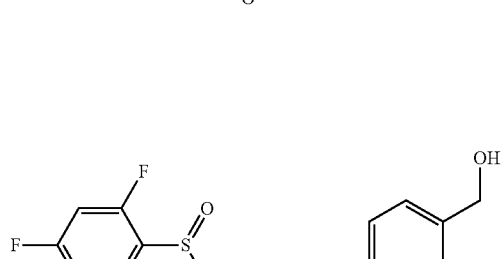
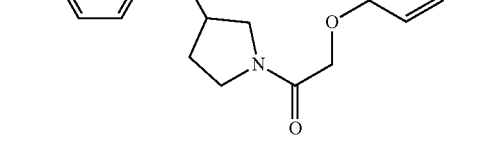
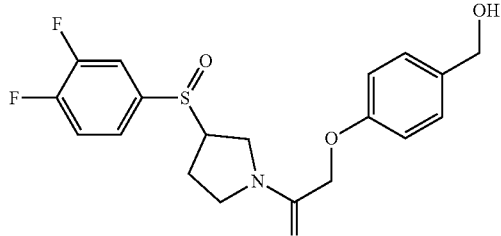
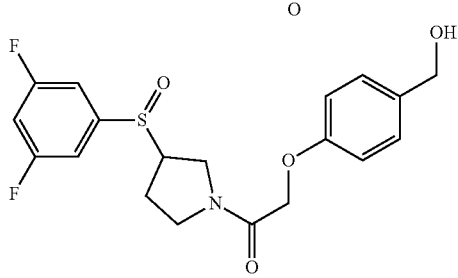
or a pharmaceutically acceptable salt, ester or prodrug form thereof.
In further embodiments, the compound is one of:
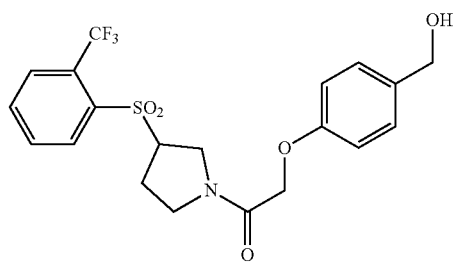
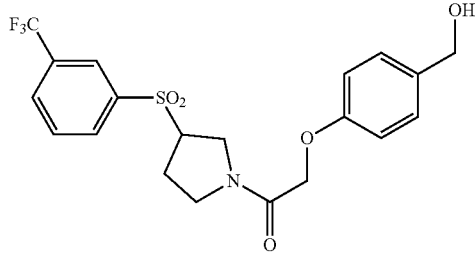
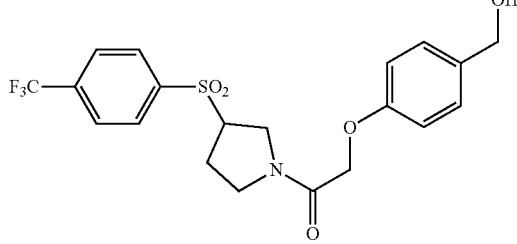
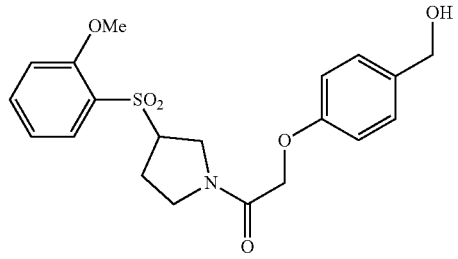

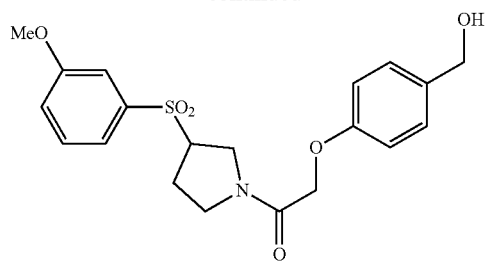
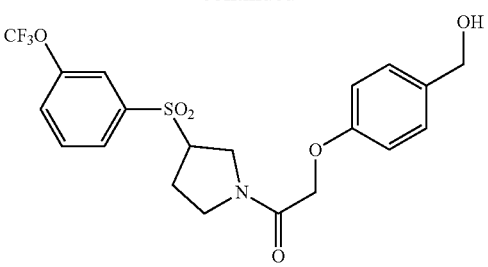
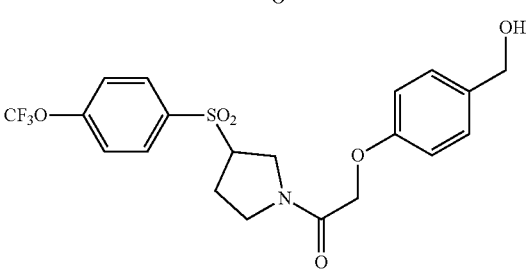
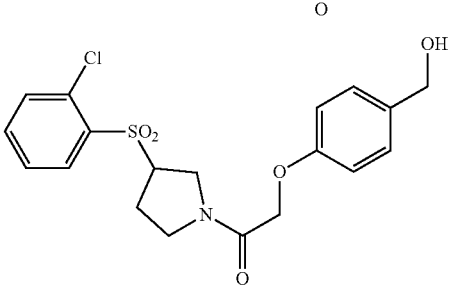
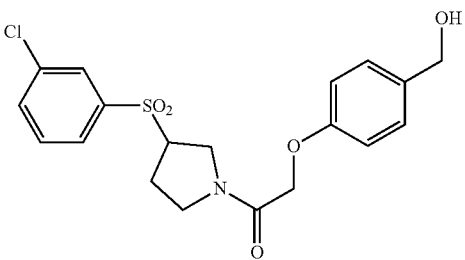
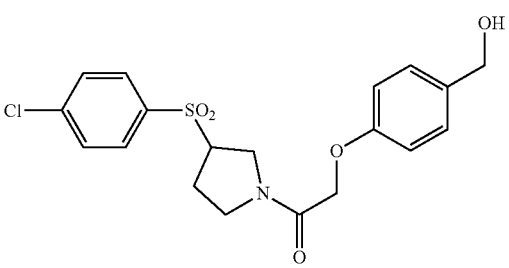
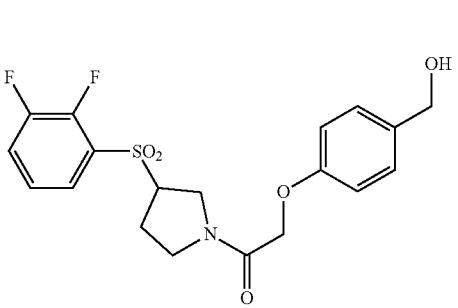

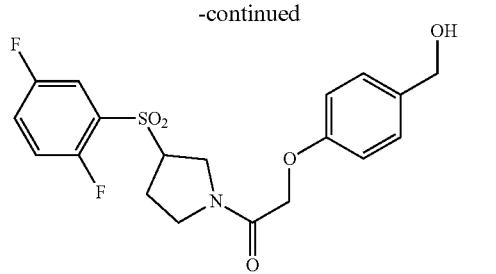
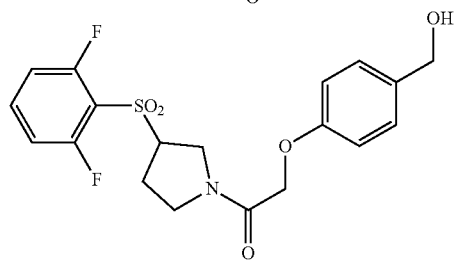
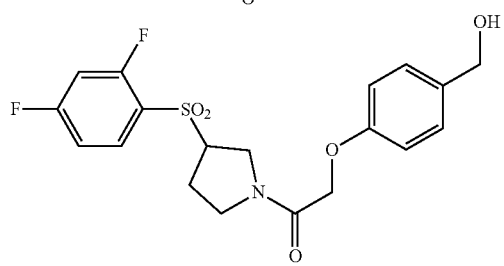
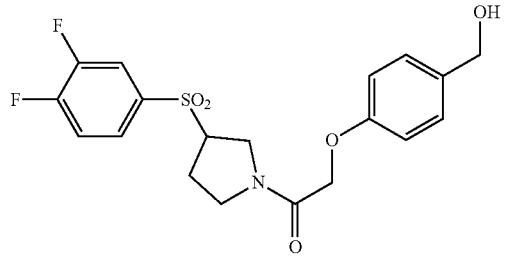
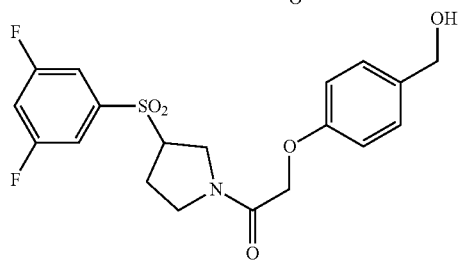
or a pharmaceutically acceptable salt, ester or prodrug form thereof.
In yet further embodiments, the compound is one of:
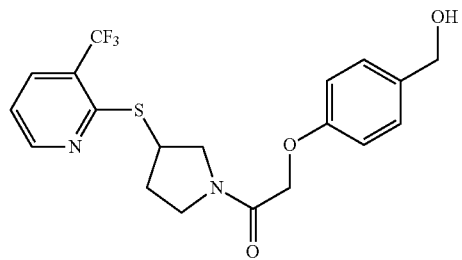
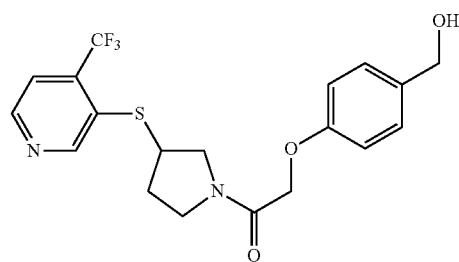
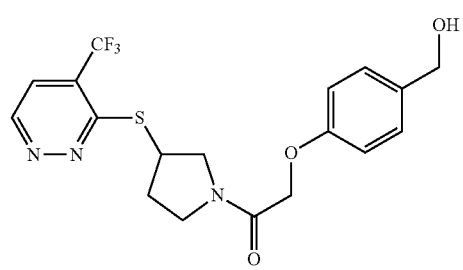
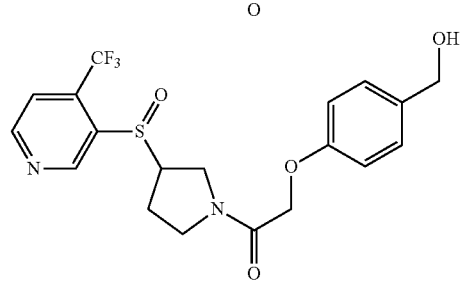

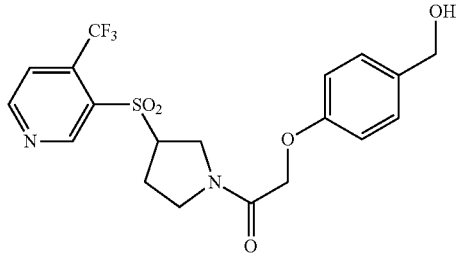
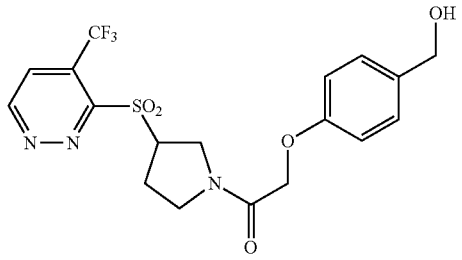
or a pharmaceutically acceptable salt, ester or prodrug form thereof.
In yet other embodiments, the compound is one of:
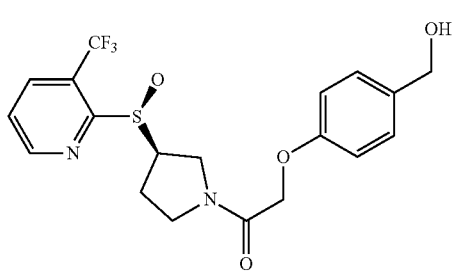
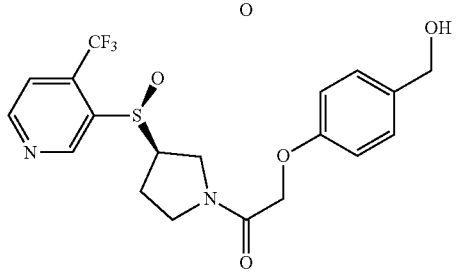
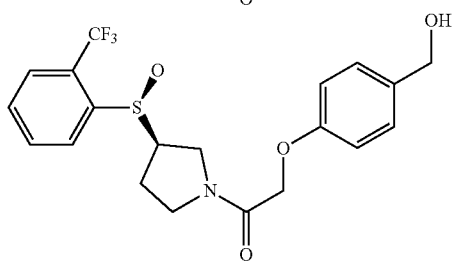
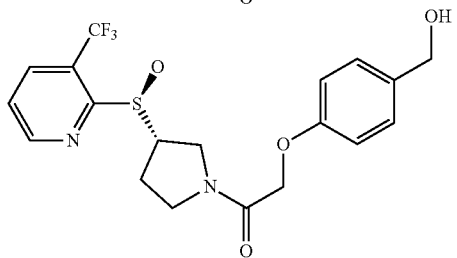
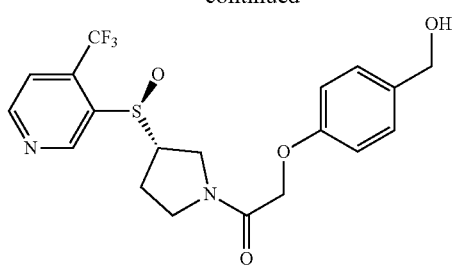
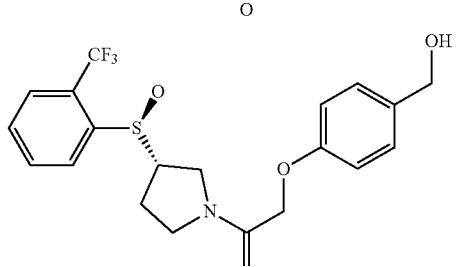
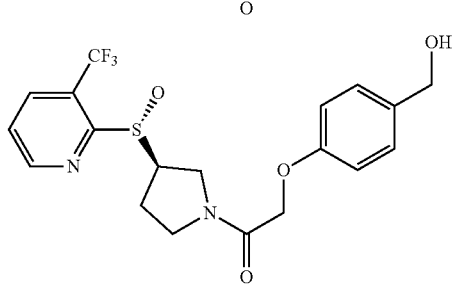
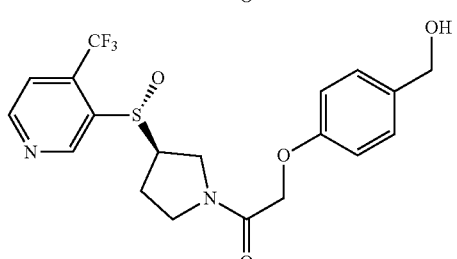
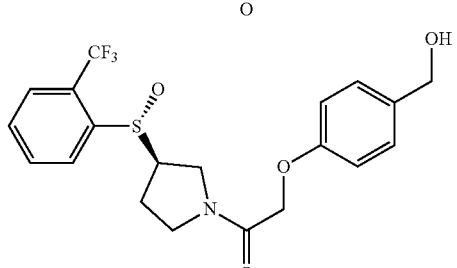
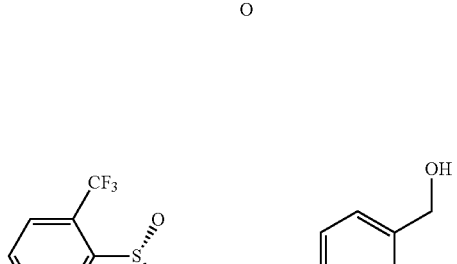
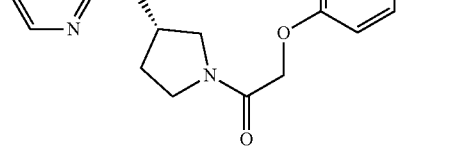

-continued

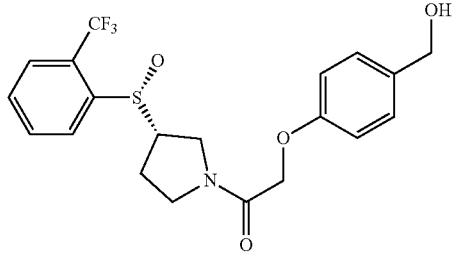

or a pharmaceutically acceptable salt, ester or prodrug form thereof.

In yet further embodiments, the compound has the structure II

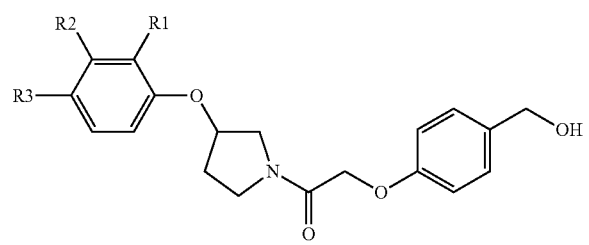

II wherein one of $R_1$ and $R_2$ and $R_3$, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7C(NR_8)NR_9R_{10}$;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;
wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

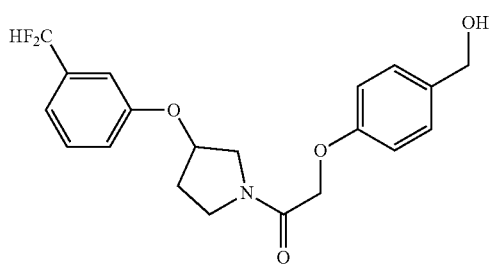

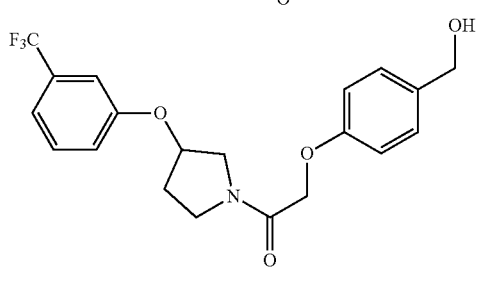

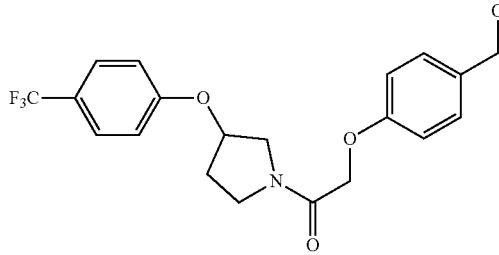

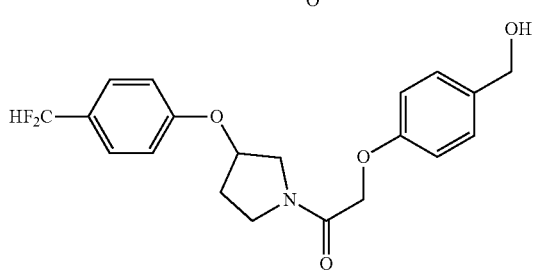

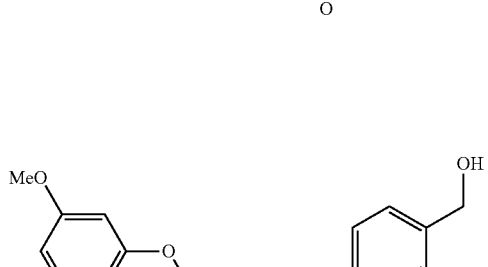

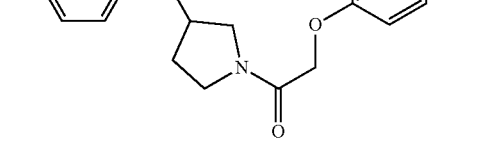

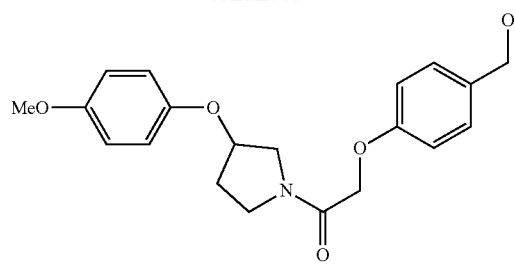
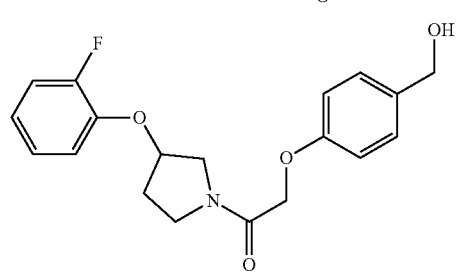
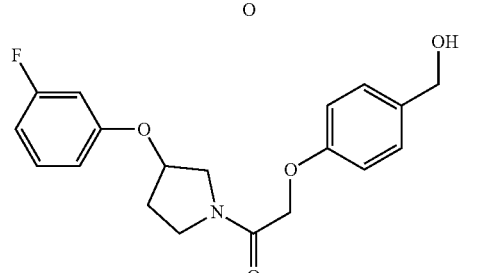
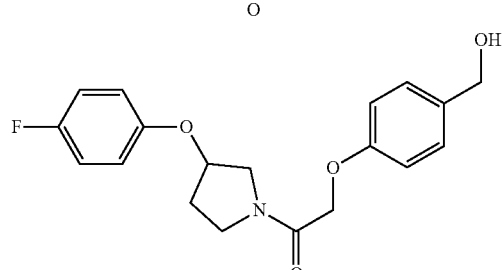
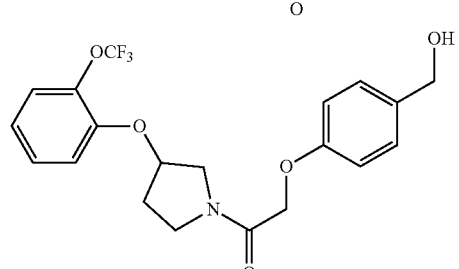
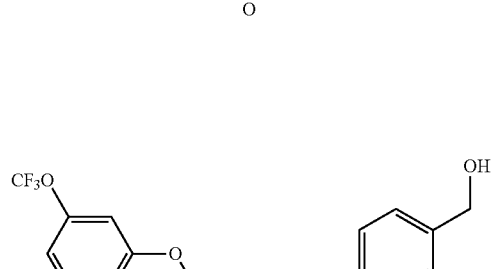
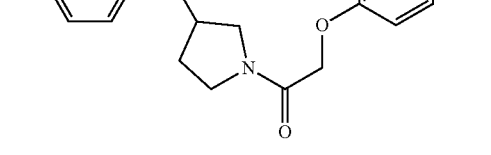
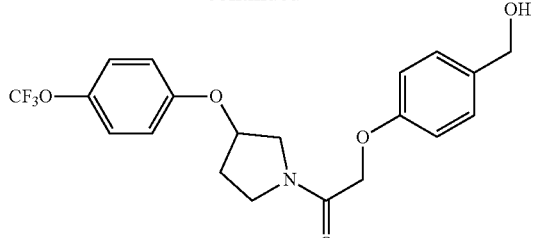
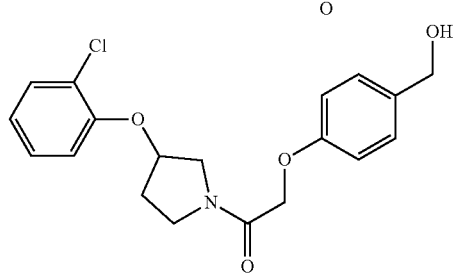
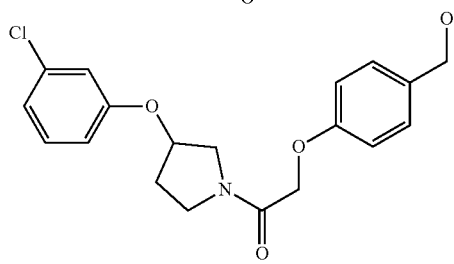
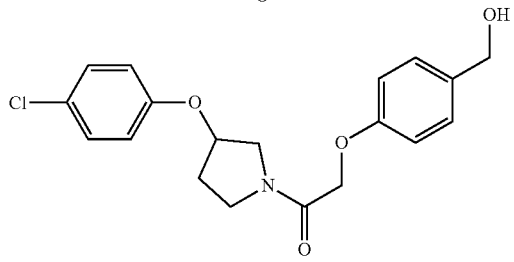
or a pharmaceutically acceptable salt, ester or prodrug form thereof.
In other embodiments the compound is one of the following:
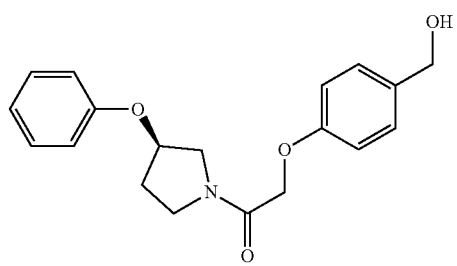 [SMILES: O=C(COc1ccc(CO)cc1)N1CC[C@@H](Oc2ccccc2)C1]
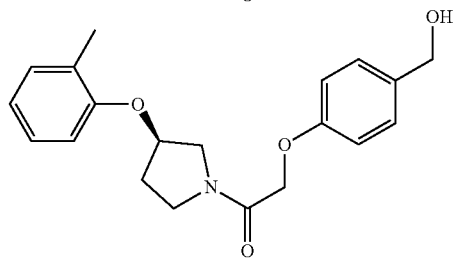

121
-continued
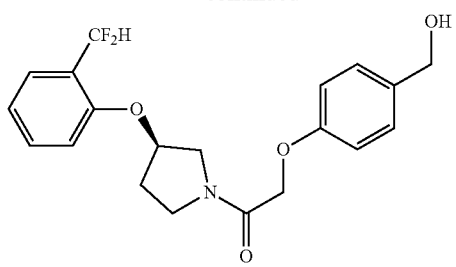 [SMILES: O=C(COc1ccc(CO)cc1)N1CC[C@@H](Oc2ccccc2C(F)F)C1]
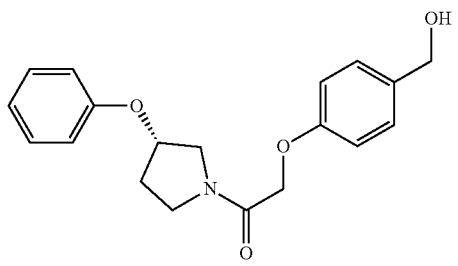
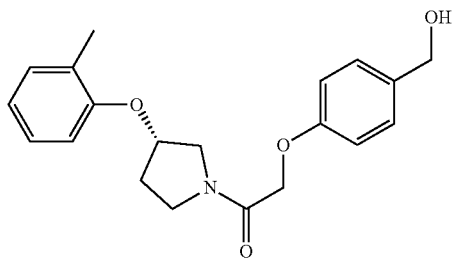
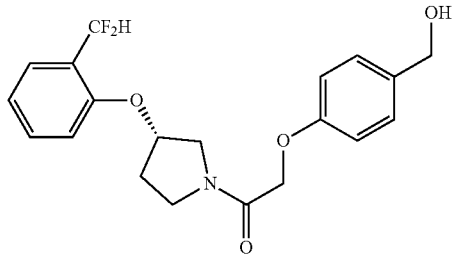
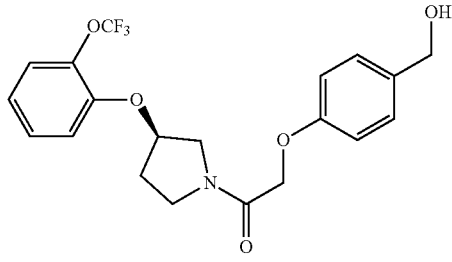 [SMILES: O=C(COc1ccc(CO)cc1)N1CC[C@@H](Oc2ccccc2OC(F)(F)F)C1]
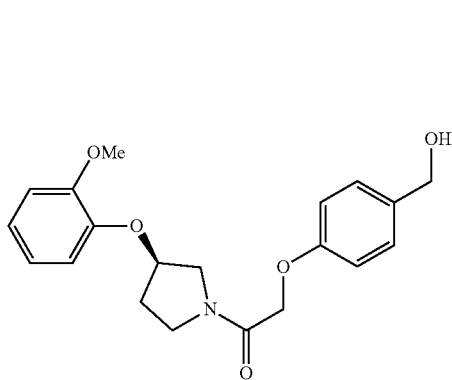 [SMILES: COc1ccccc1O[C@@H]1CCN(C(=O)COc2ccc(CO)cc2)C1]
122
-continued
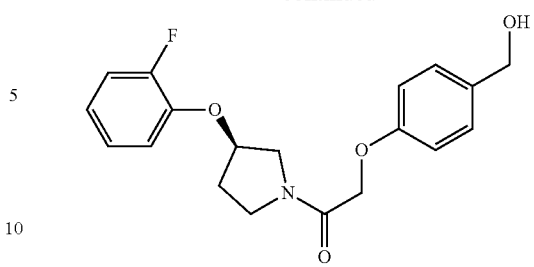
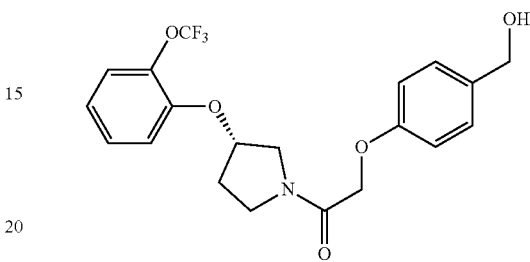
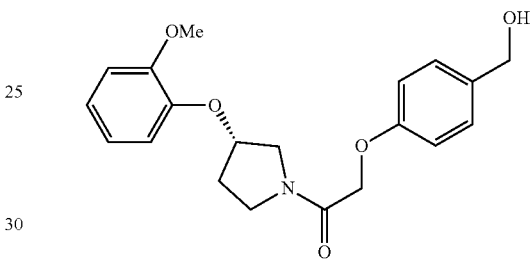
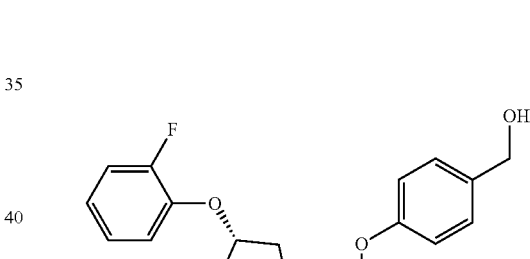
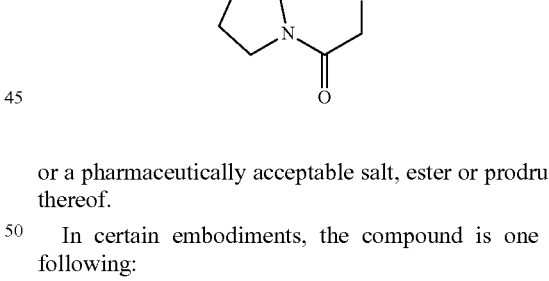
or a pharmaceutically acceptable salt, ester or prodrug form thereof.
In certain embodiments, the compound is one of the following:
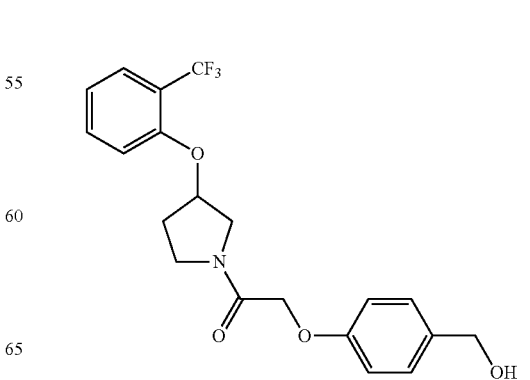

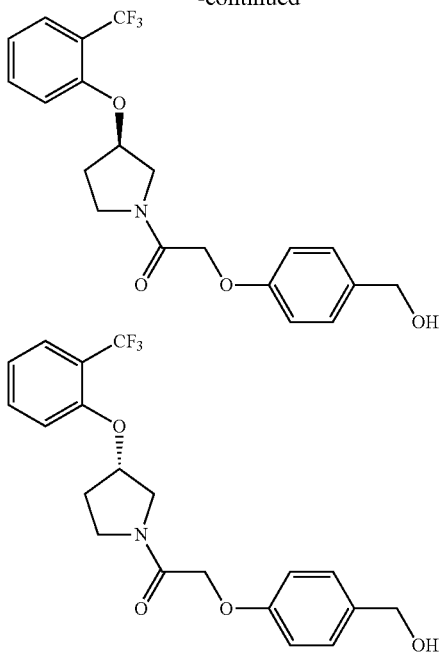

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol. In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50

One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50. In certain embodiments, the pharmaceutical composition comprises both (i) butylated hydroxytoluene (BHT) at a concentration of least 0.05%; and (ii) di-sodium EDTA at a concentration of least 0.001%. In another embodiment, the pharmaceutical composition comprises each of (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50.

In a certain embodiment, the pharmaceutical composition comprises:
- (i) ethanol in the range of 1.0-20.0% w/w;
- (ii) phenoxyethanol in the range 0.1-5.0% w/w;
- (iii) diethylene glycol monoethyl ether (otherwise known as DEGEE or Transcutol P®) in the range 5.0-40.0% w/w;
- (iv) propylene glycol in the range 5.0-40.0% w/w;
- (v) PEG400 in the range 5.0-40.0% w/w; and
- (vi) a carbomer such as carbomer homopolymer type C980 in the range of 0.5 to 2.0% w/w.

In another certain embodiment, the pharmaceutical composition comprises:
- (i) ethanol in the range of 1.0-20.0% w/w;
- (ii) phenoxyethanol in the range 0.1-5.0% w/w;
- (iii) diethylene glycol monoethyl ether (otherwise known as DEGEE or Transcutol P®) in the range 5.0-40.0% w/w;
- (iv) propylene glycol in the range 5.0-40.0% w/w;
- (v) PEG400 in the range 5.0-40.0% w/w;
- (vi) a carbomer such as carbomer homopolymer type C980 in the range of 0.5 to 2.0% w/w; (vii) butylated hydroxytoluene (BHT) at a concentration of least 0.05%;
- (viii) di-sodium EDTA at a concentration of least 0.001%; and
- (ix) Trolamine to provide an apparent pH in the range 6.50 to 7.50.

In another embodiment, the pharmaceutical composition comprises:
- (i) ethanol in the range of 5.0-15.0% w/w;
- (ii) phenoxyethanol in the range 0.5-2.0% w/w;
- (iii) diethylene glycol monoethyl ether (otherwise known as DEGEE or Transcutol P®) in the range 20.0-30.0% w/w;
- (iv) propylene glycol in the range 15.0-25.0% w/w;
- (v) PEG400 in the range 15.0-25.0% w/w; and
- (vi) a carbomer such as carbomer homopolymer type C980 in the range of 0.75 to 1.5% w/w.

In another embodiment, the pharmaceutical composition comprises:
- (i) ethanol in the range of 5.0-15.0% w/w;
- (ii) phenoxyethanol in the range 0.5-2.0% w/w;
- (iii) diethylene glycol monoethyl ether (otherwise known as DEGEE or Transcutol P®) in the range 20.0-30.0% w/w;
- (iv) propylene glycol in the range 15.0-25.0% w/w;
- (v) PEG400 in the range 15.0-25.0% w/w; and
- (vi) a carbomer such as carbomer homopolymer type C980 in the range of 0.75 to 1.5% w/w.
- (vii) butylated hydroxytoluene (BHT) at a concentration of least 0.1%;
- (viii) di-sodium EDTA at a concentration of least 0.005%; and
- (ix) Trolamine to provide an apparent pH in the range 6.50 to 7.50.

In specific embodiments, the pharmaceutical composition comprises:
- (i) ethanol at a concentration of 10.0% w/w;
- (ii) phenoxyethanol at a concentration of 1% w/w;
- (iii) diethylene glycol monoethyl ether (otherwise known as DEGEE or Transcutol P®) at a concentration of 25.0% w/w;
- (iv) propylene glycol at a concentration of 20.0% w/w;
- (v) PEG400 at a concentration of 21.0% w/w;
- (vi) carbomer homopolymer type C980 at a concentration of 1.0% w/w; and
- (vii) water at a concentration of 19.5-22% w/w.

In yet other specific embodiments, the pharmaceutical composition comprises:
- (i) ethanol at a concentration of 10.0% w/w;
- (ii) phenoxyethanol at a concentration of 1% w/w;
- (iii) diethylene glycol monoethyl ether (otherwise known as DEGEE or Transcutol P®) at a concentration of 25.0% w/w;
- (iv) propylene glycol at a concentration of 20.0% w/w;
- (v) PEG400 at a concentration of 21.0% w/w;
- (vi) carbomer homopolymer type C980 at a concentration of 1.0% w/w;
- (vii) butylated hydroxytoluene (BHT) at a concentration of 0.1% w/w;
- (viii) di-sodium EDTA at a concentration of 0.005% w/w;
- (ix) Trolamine at a concentration of 0.375% w/w; and
- (x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxyl)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6% In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments a second therapeutic agent is present.

In some embodiments, the duration of treatment is greater than 28 days.

In further embodiments, the duration of treatment is between one and six months or thereabouts. In yet further embodiments, the duration of treatment is between one and twenty four months or thereabouts; one and eighteen months or thereabouts; one and twelve months or thereabouts; one and three months or thereabouts; one and two months or thereabouts; or one month or thereabouts.

The present invention also provides a method of treating excess fat in a subject which comprises administering to an area of excess fat a composition comprising a pharmaceutically acceptable carrier, which provides an environment of physical and chemical stability, and an amount of a compound or of a pharmaceutically acceptable salt of the compound or ester of the compound or prodrug of the compound effective to treat the skin condition, wherein the compound has the structure I:

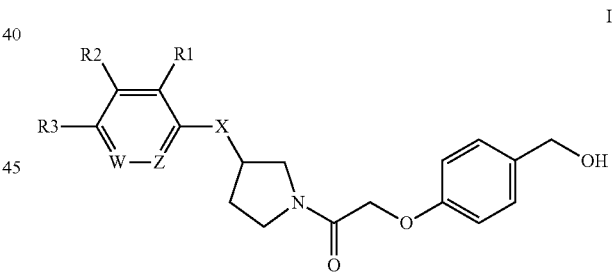

wherein:

X is O, NH, N-alkyl or N-acyl, S, SO or $SO_2$;

W is independently $CR_4$ or N;

Z is independently $CR_5$ or N;

wherein each of $R_1$, $R_2$ and $R_3$ and $R_4$ and $R_5$, if present, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; $NHCH(O)$; $NR_6CH(O)$; $NHC(O)R_6$; $NR_6C(O)R_7$;

C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_1$, R$_2$ and R$_3$ and R$_4$ and R$_5$, if present, may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

In some embodiments, X is O; W is independently CR$_4$ or N; Z is independently CR$_5$ or N; each of R$_1$, R$_2$ and R$_3$ and R$_4$ and R$_5$, if present, is independently: H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$; adjacent substituents R$_1$, R$_2$ and R$_3$ and R$_4$ and R$_5$, if present, may form a saturated or unsaturated 5-membered or 6-membered carbocyclic or heterocyclic ring; and each of R$_6$, R$_7$, R$_8$, R$_9$ and R$_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In some embodiments, the compound is one of the following:

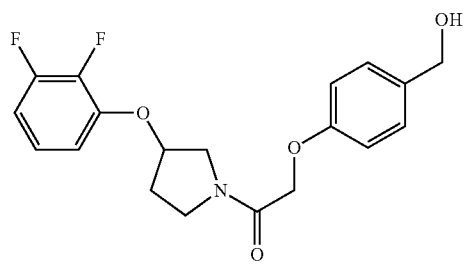

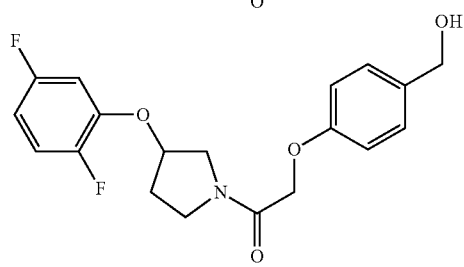

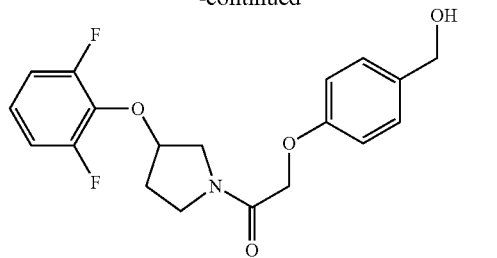

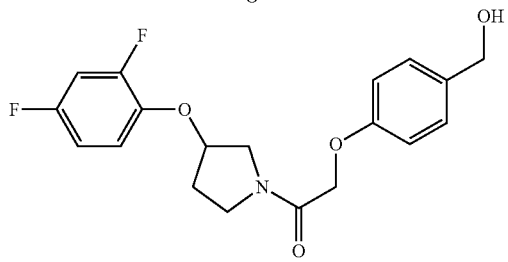

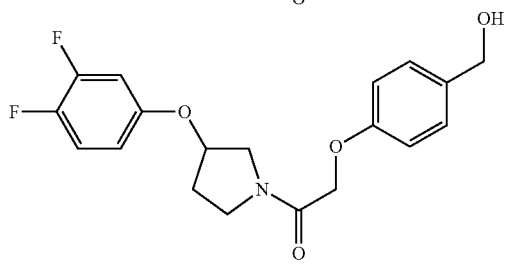

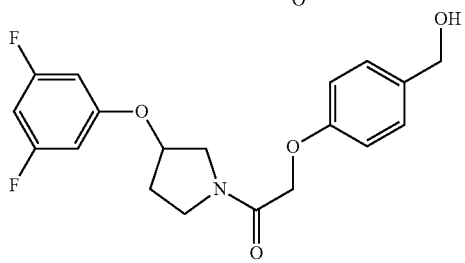

or a pharmaceutically acceptable salt, ester or prodrug form thereof.

In further embodiments, the compound is one of the following:

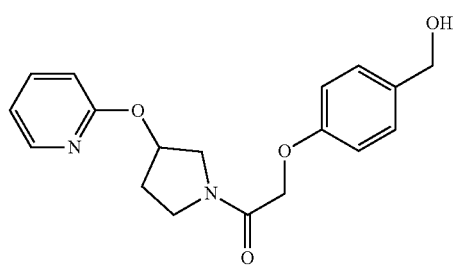

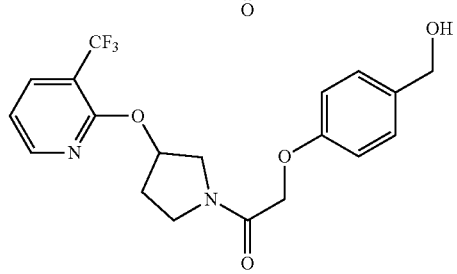

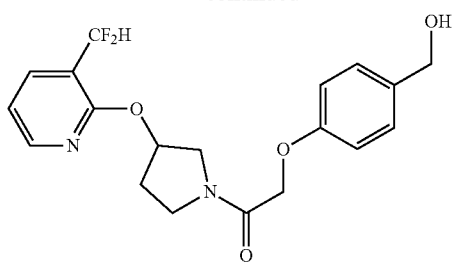
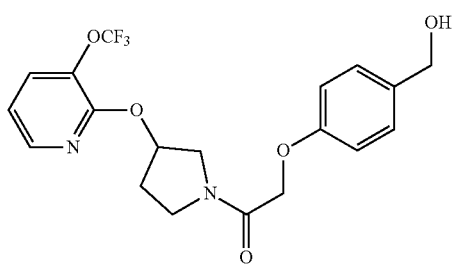
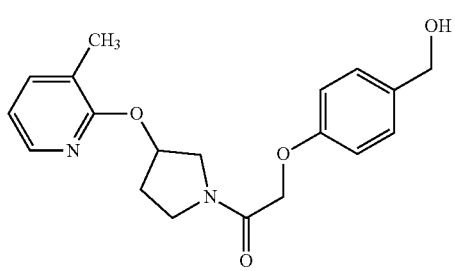
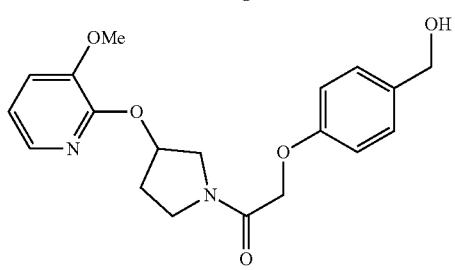
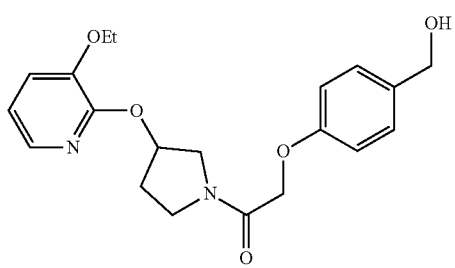
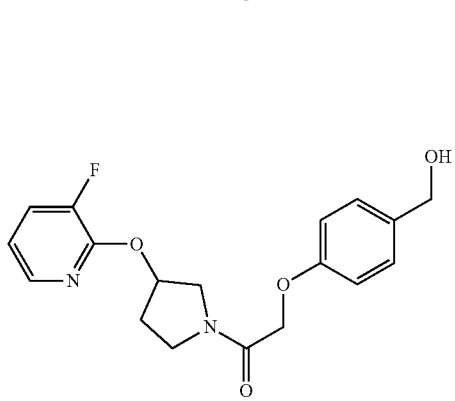
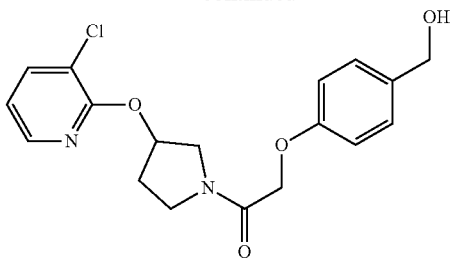
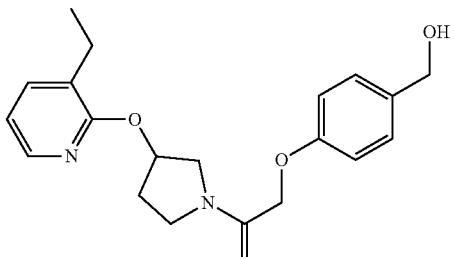
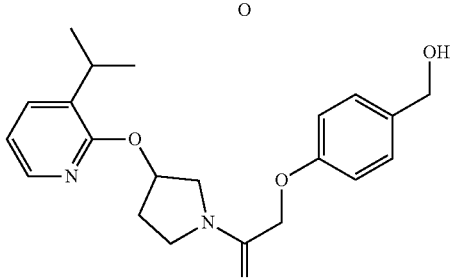
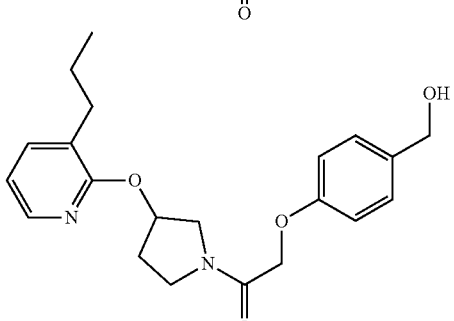
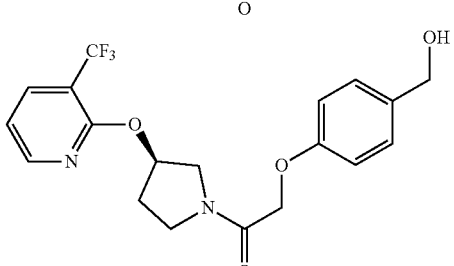
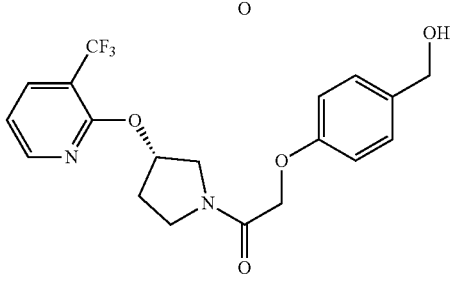
or a pharmaceutically acceptable salt, ester or prodrug form thereof.

In yet other embodiments, the compound is one of the following:
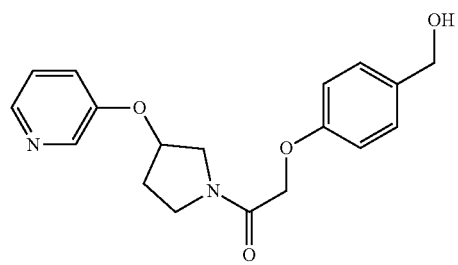
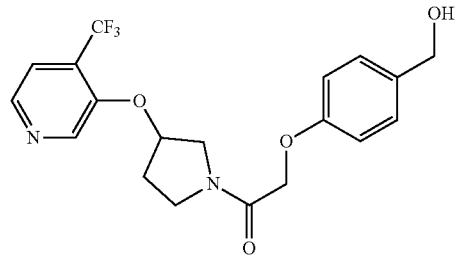
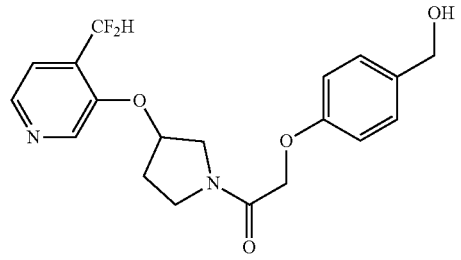
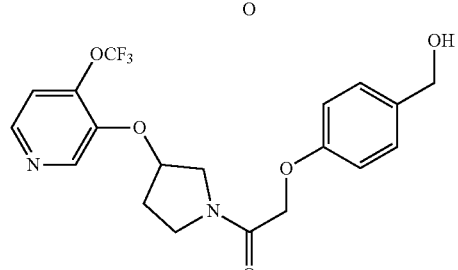
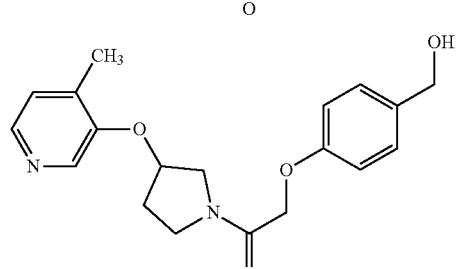
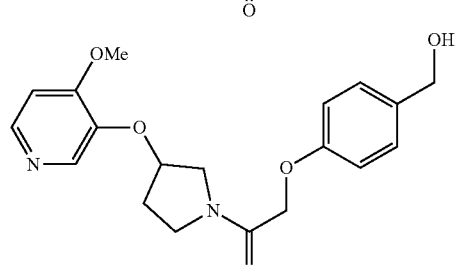
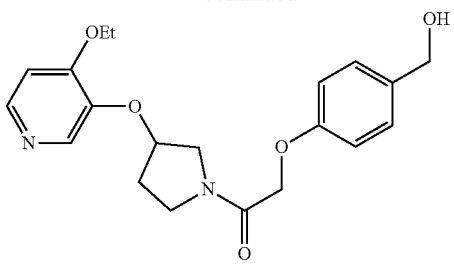
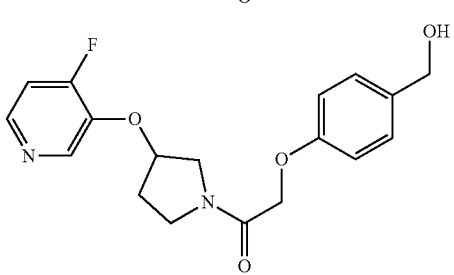
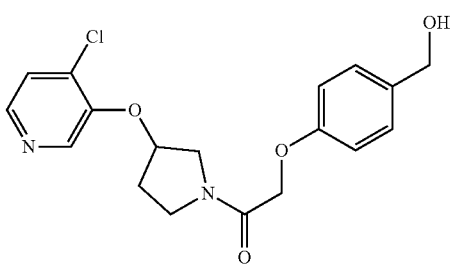
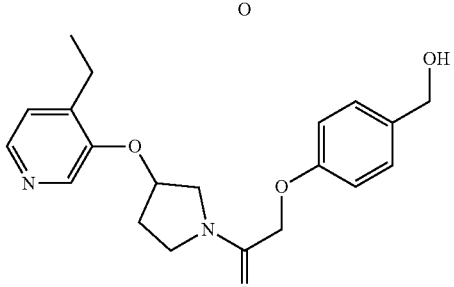
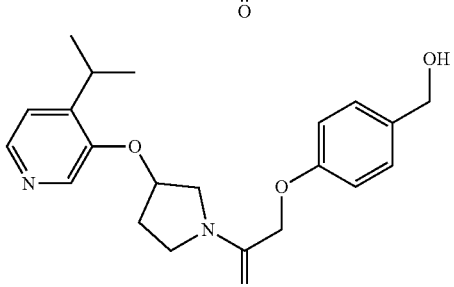
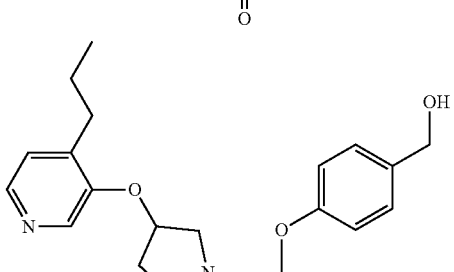

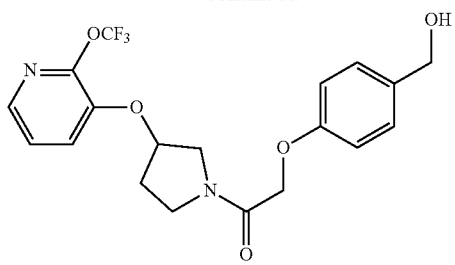

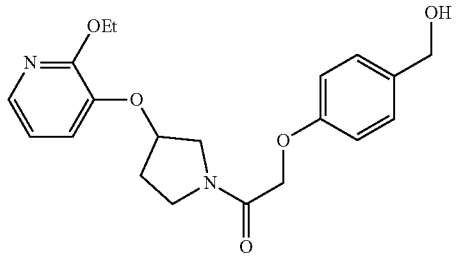
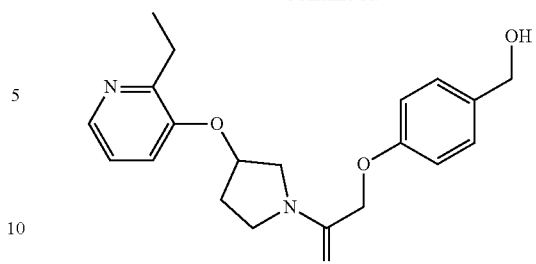
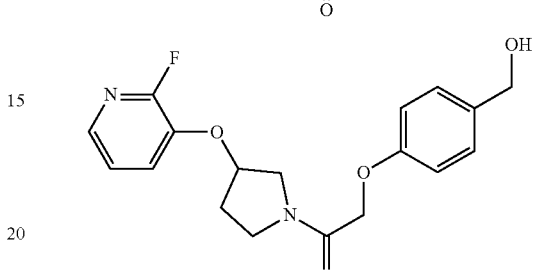
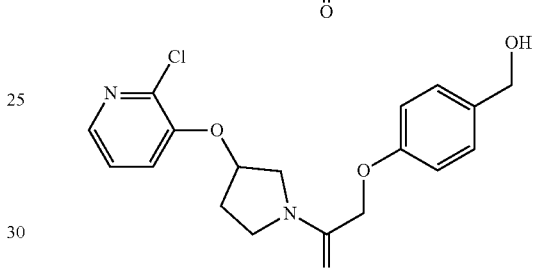

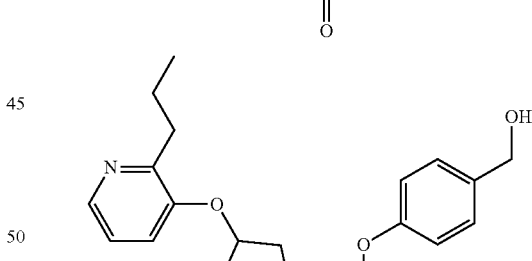
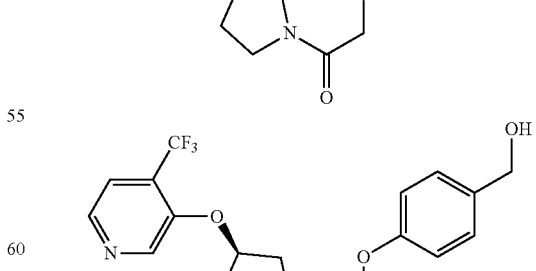

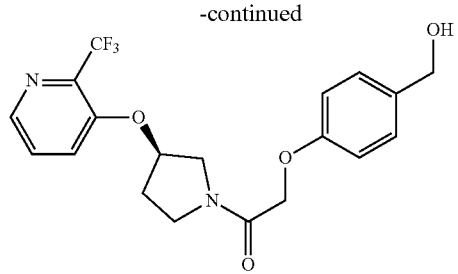
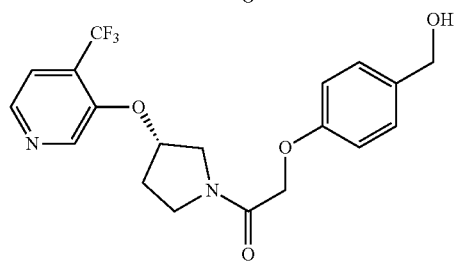
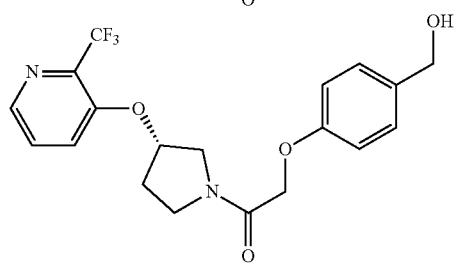
or a pharmaceutically acceptable salt, ester or prodrug form thereof.
In yet further embodiments, the compound is one of the following:
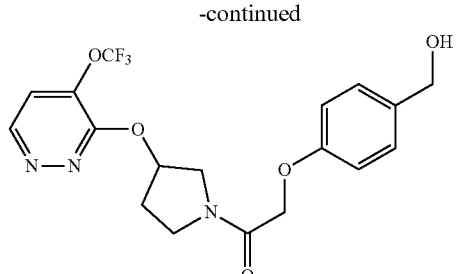
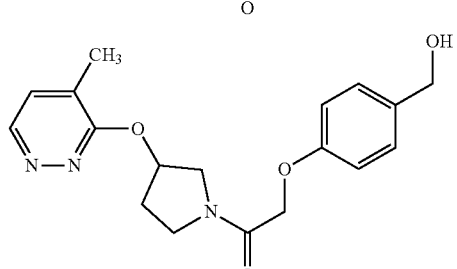
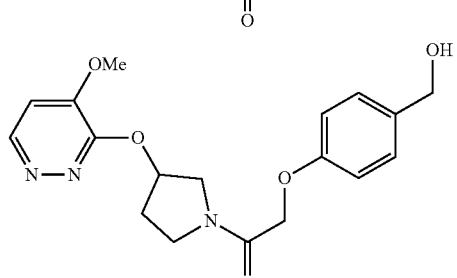
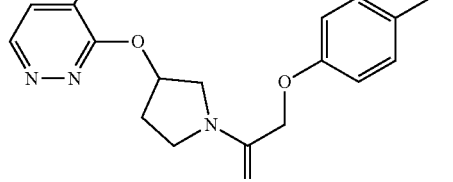
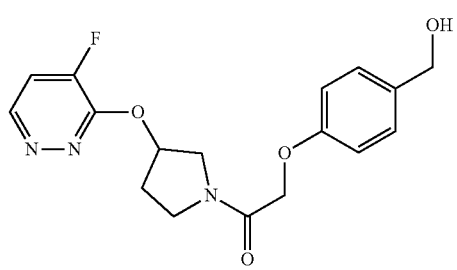
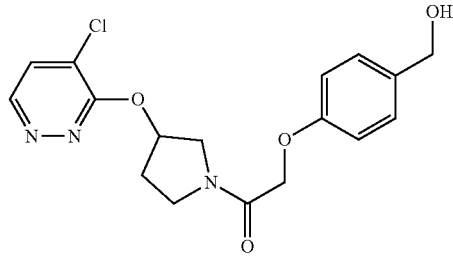

-continued

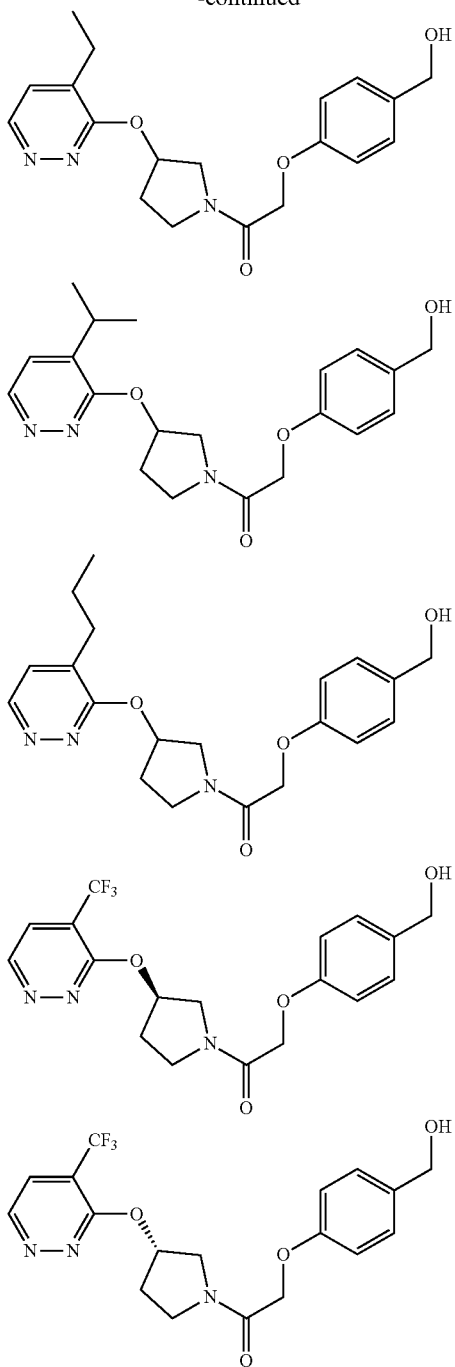

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $NO_2$; $NH_2$; NHCH(O); $NR_6$CH(O); NHC(O)$R_6$; $NR_6$C(O)$R_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In certain embodiments, the compound is one of the following:

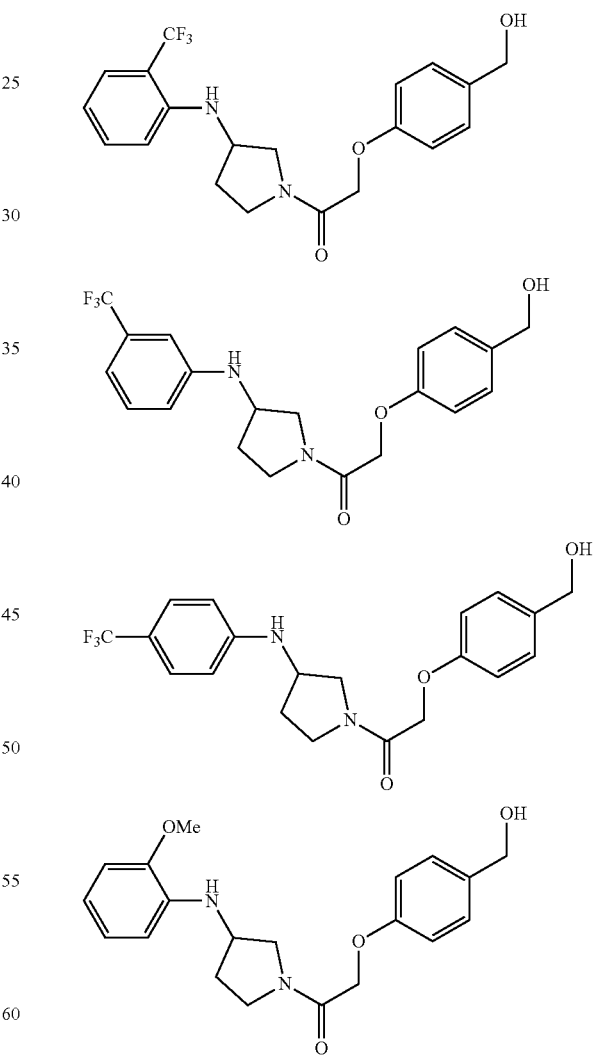

-continued
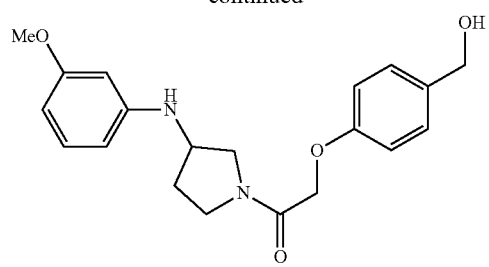
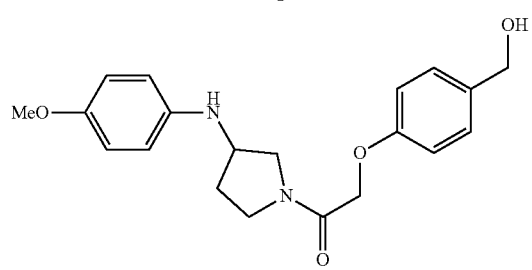
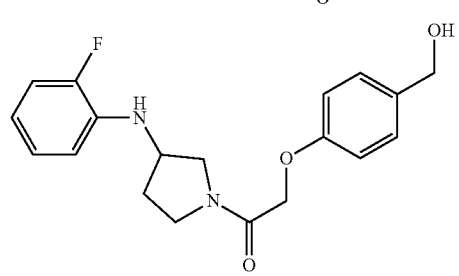
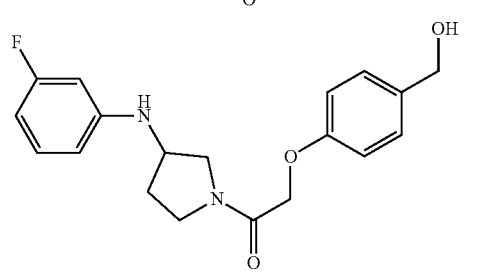
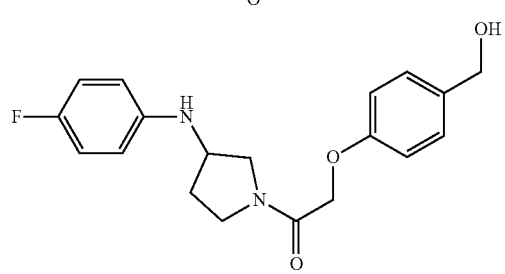
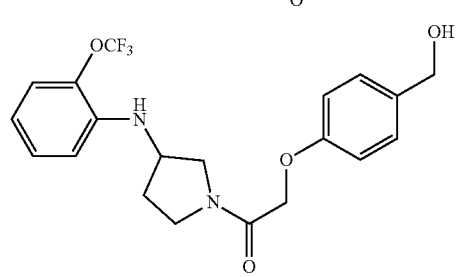
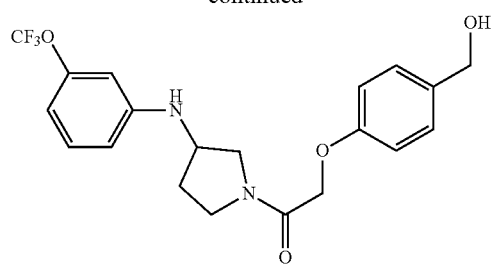
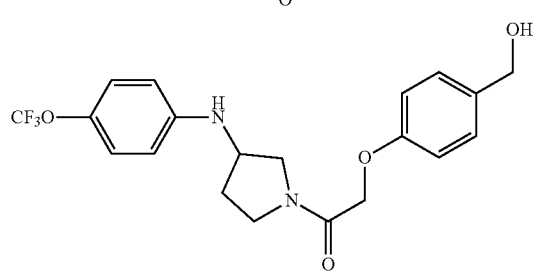
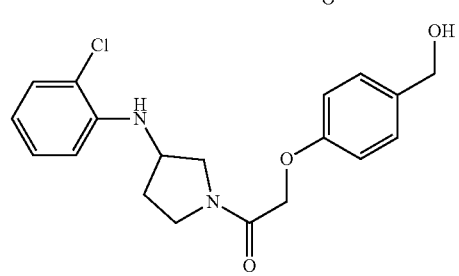
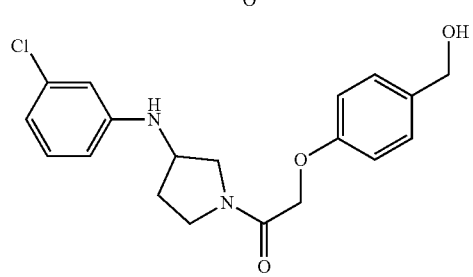
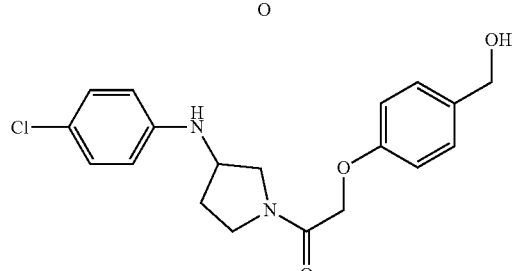
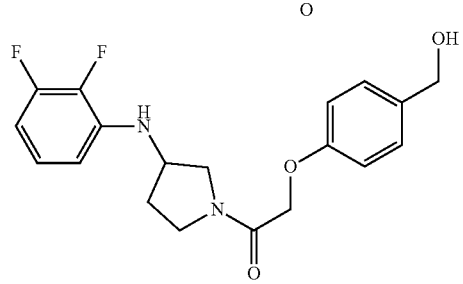

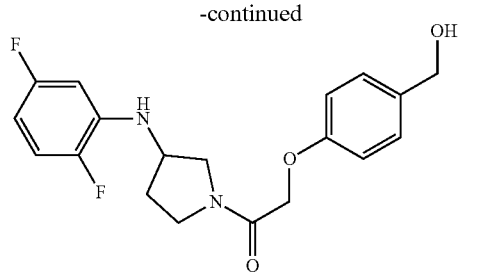
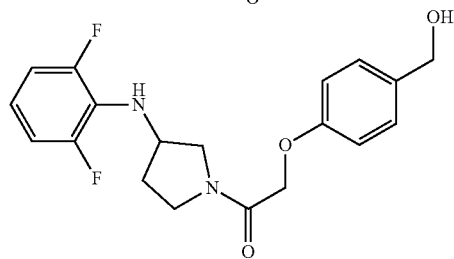
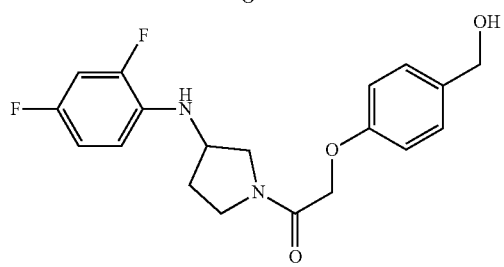
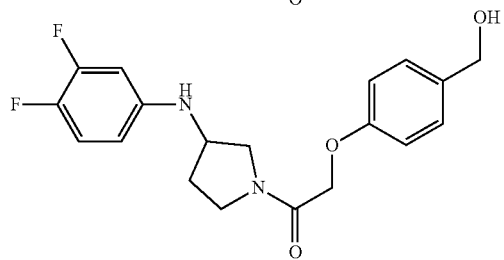
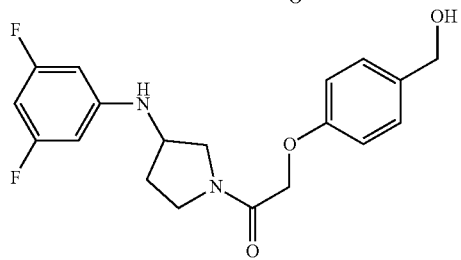
or a pharmaceutically acceptable salt, ester or prodrug form thereof.
In other embodiments, the compound is one of the following:
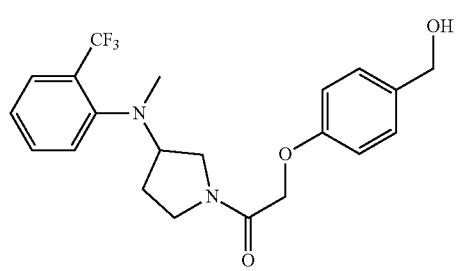
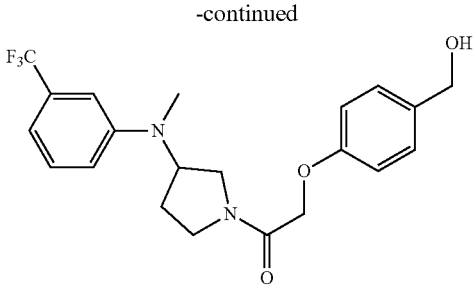
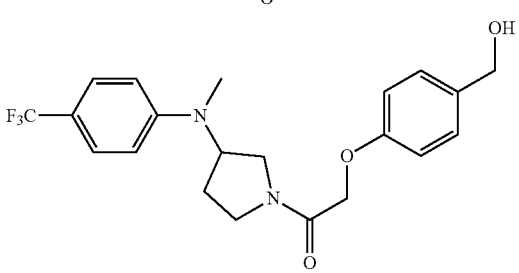
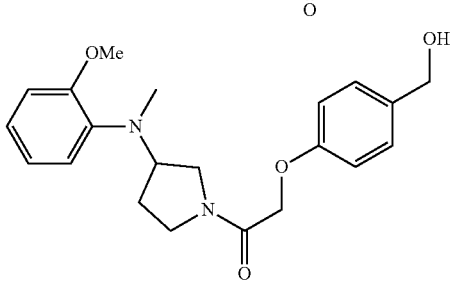
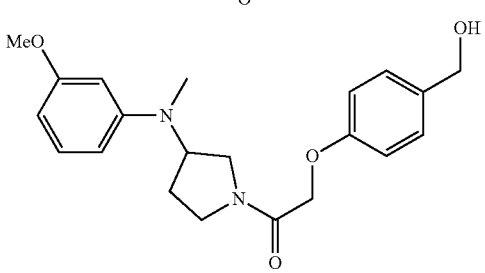
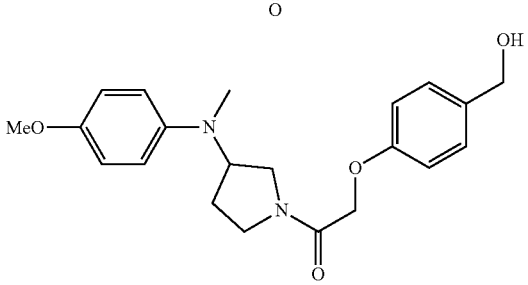

-continued
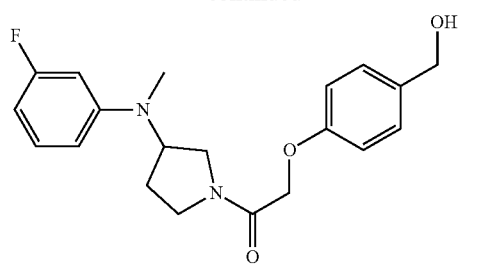
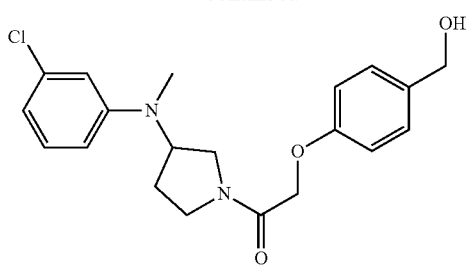
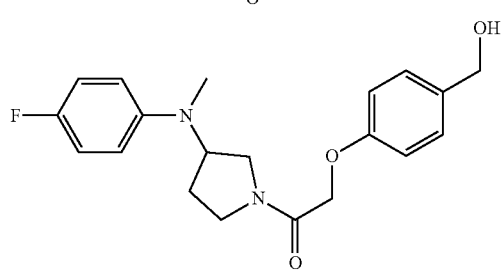
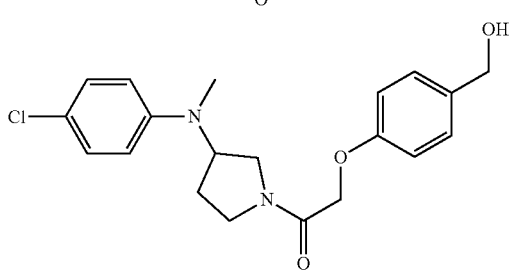
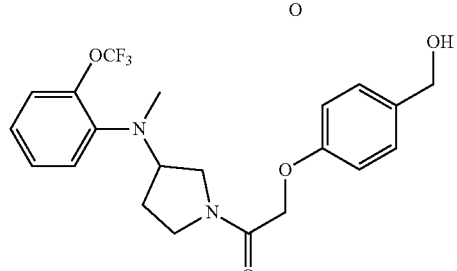
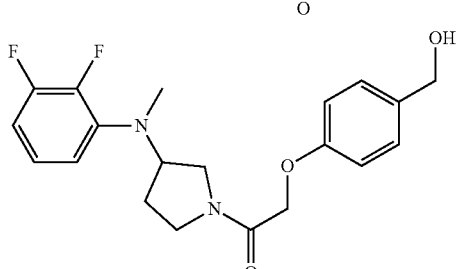
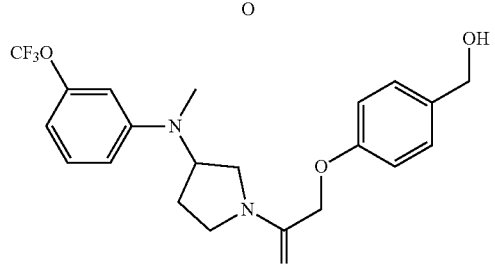
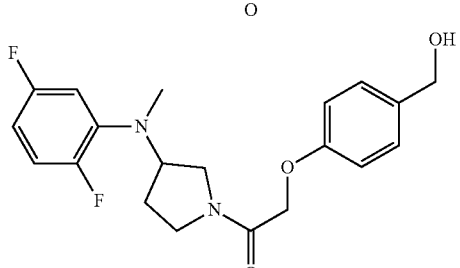
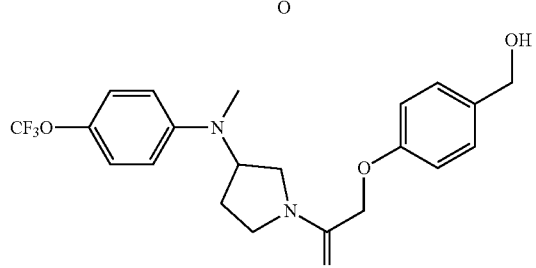
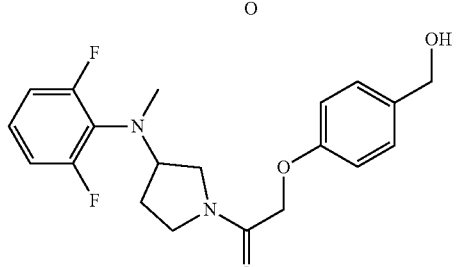
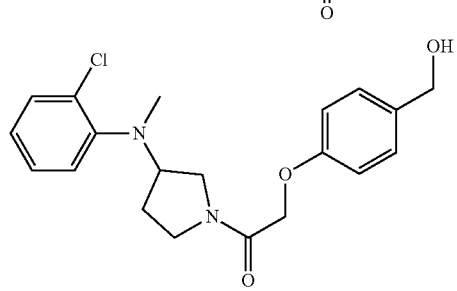
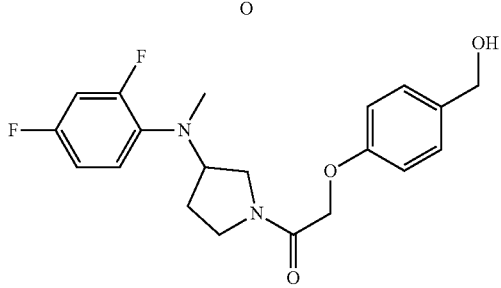

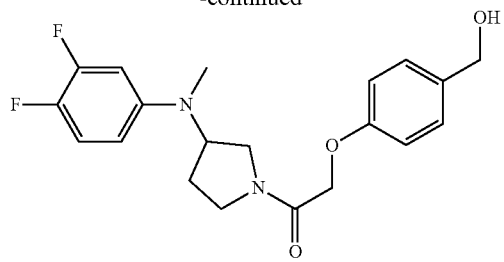
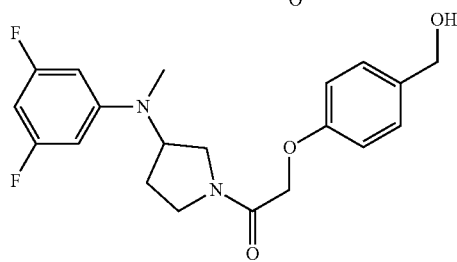
or a pharmaceutically acceptable salt, ester or prodrug form thereof.
In further embodiments, the compound is one of the following:
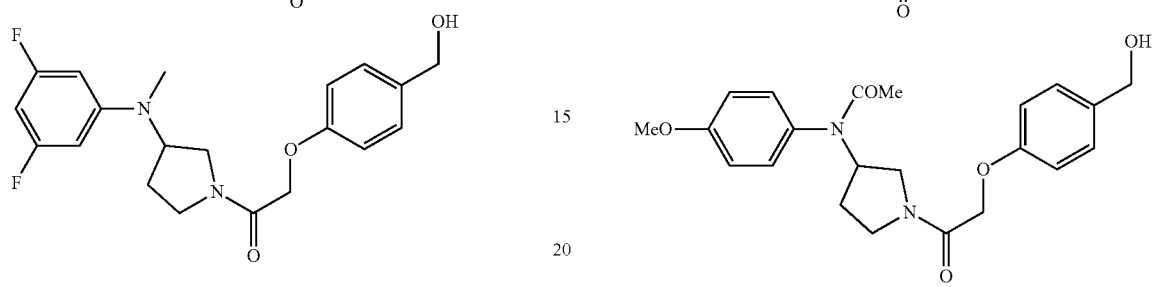
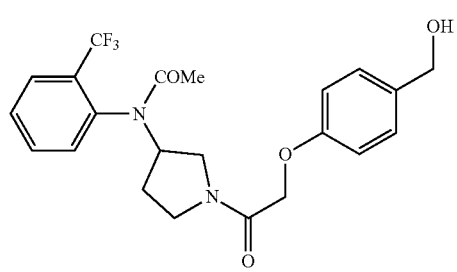
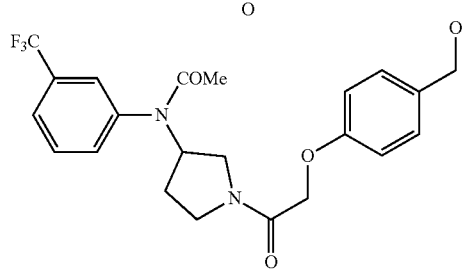
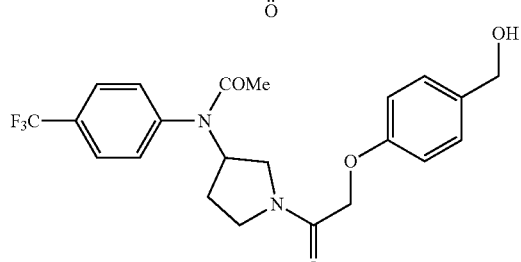
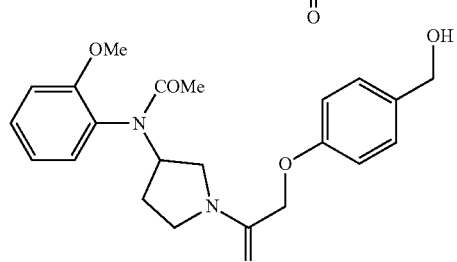
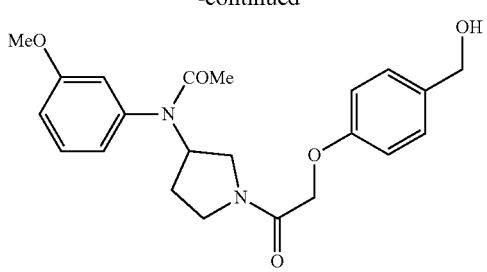
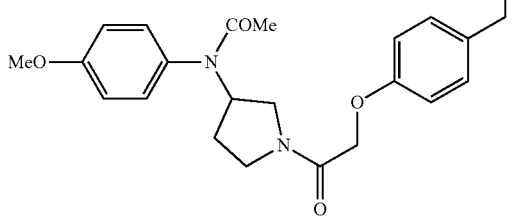
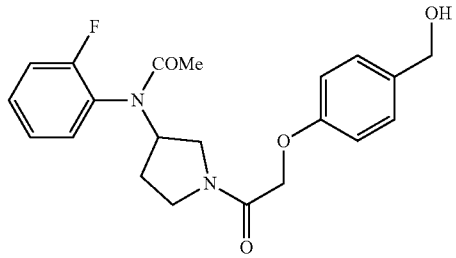
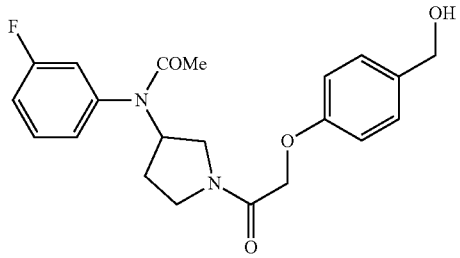
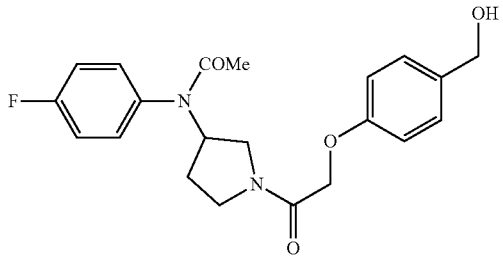
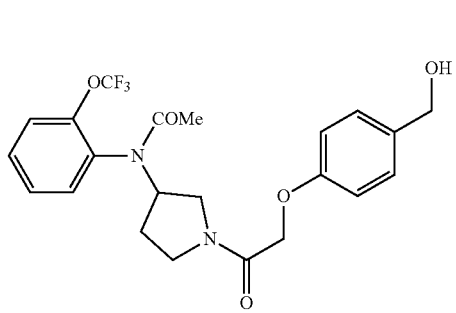

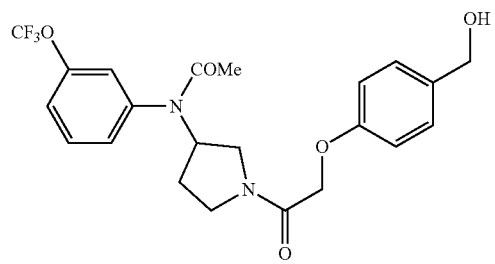
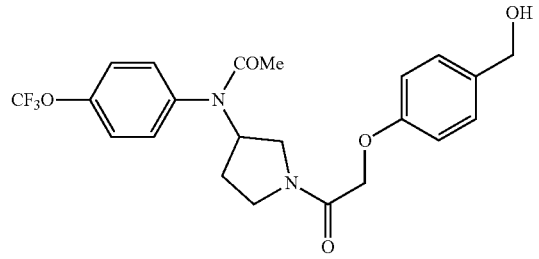
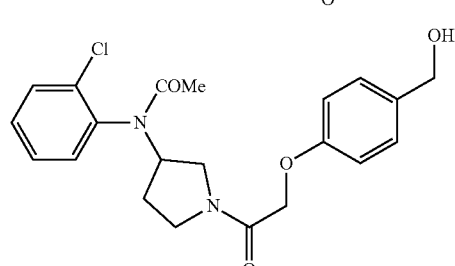
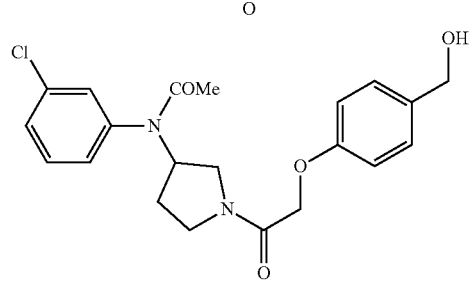
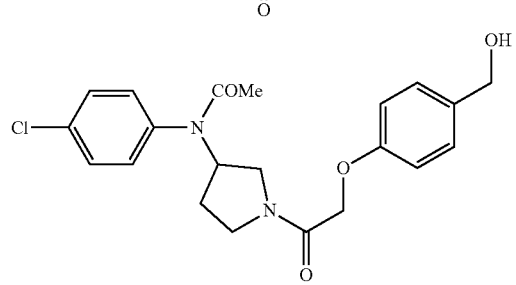
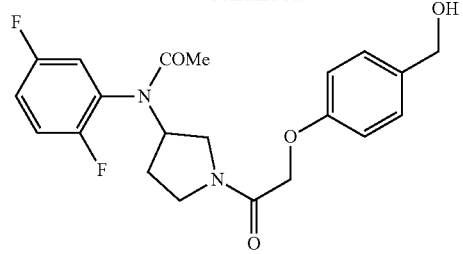
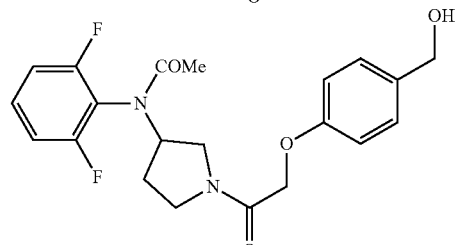
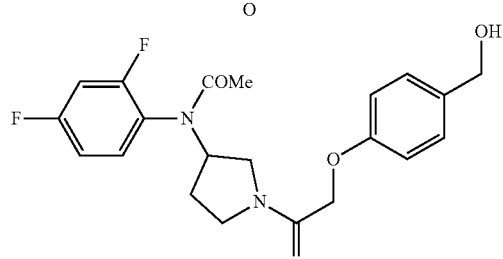
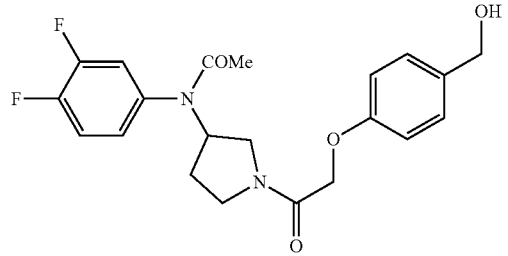
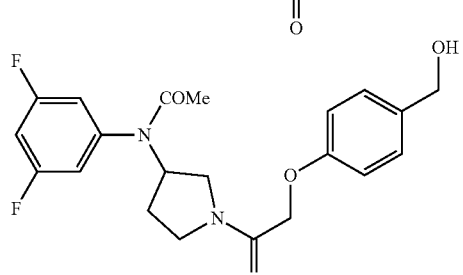
or a pharmaceutically acceptable salt, ester or prodrug form thereof.
In yet other embodiments, the compound is one of the following:
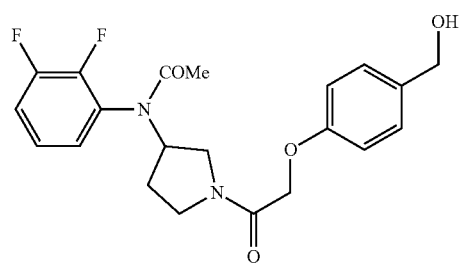
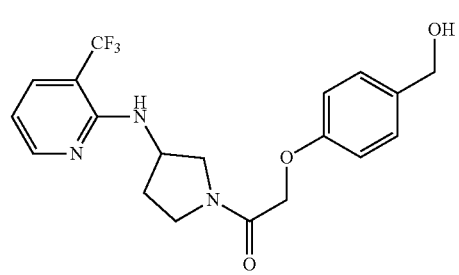

151
-continued
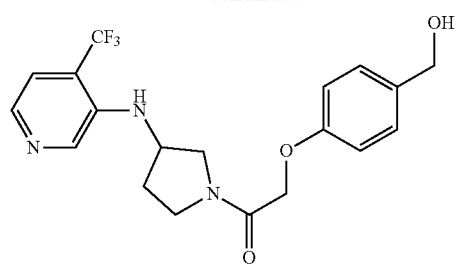
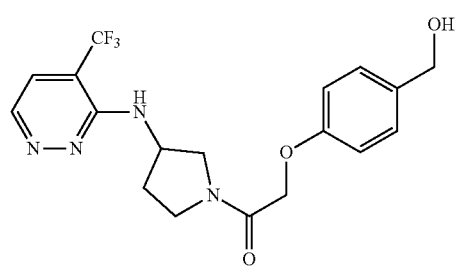
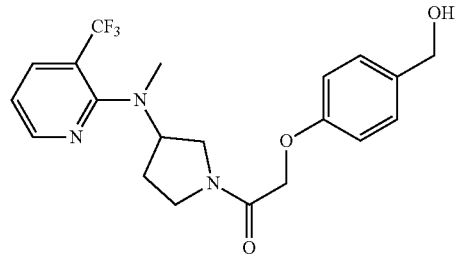
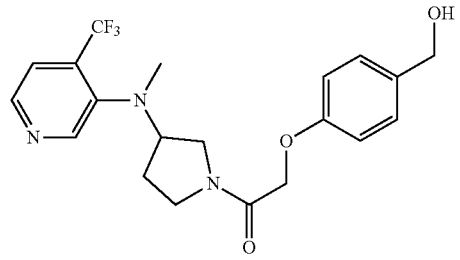
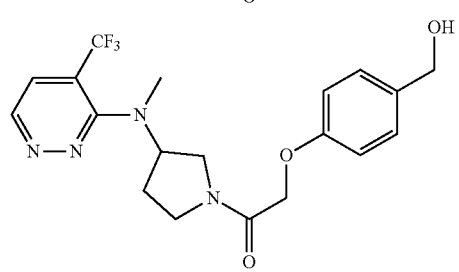

152
-continued

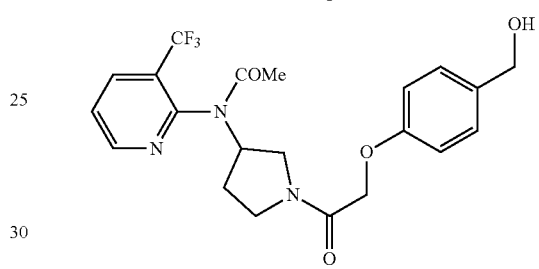
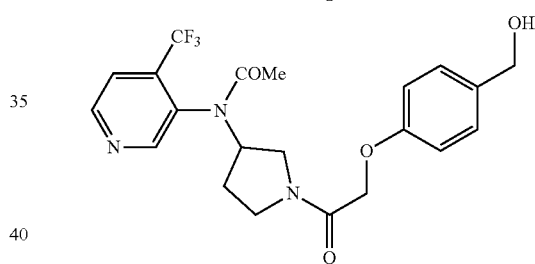
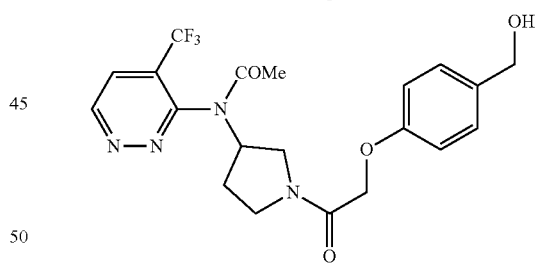

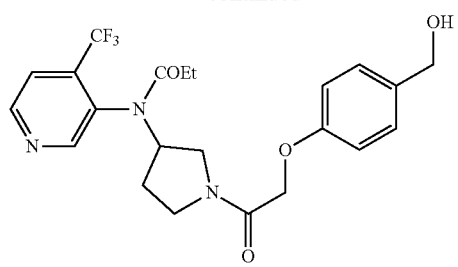
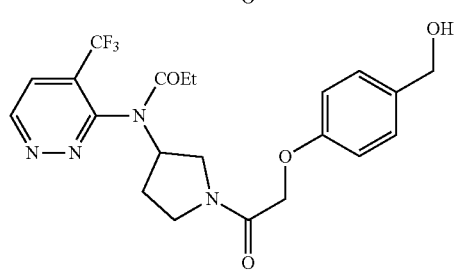
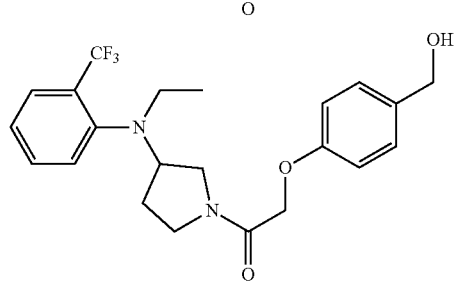
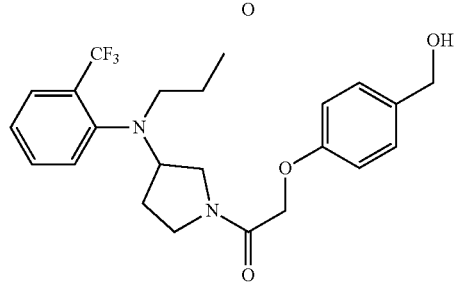
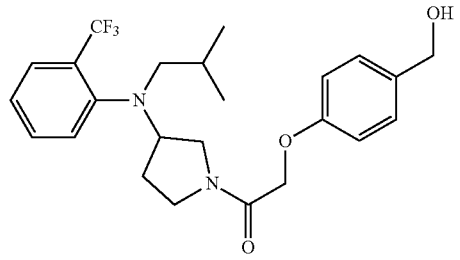
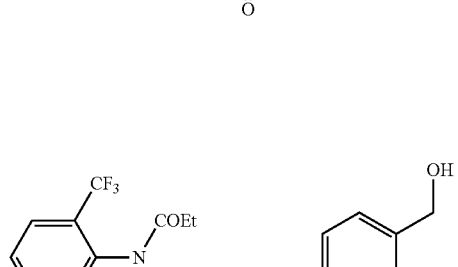
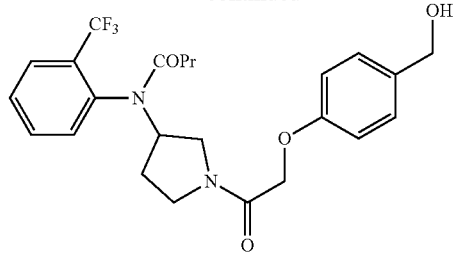
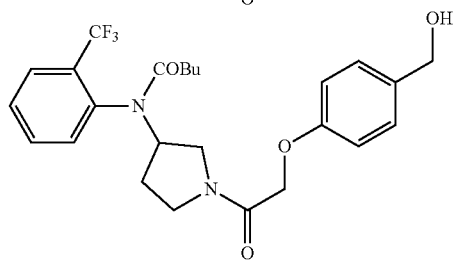
or a pharmaceutically acceptable salt, ester or prodrug form thereof.
In yet other embodiments, the compound is one of the following:
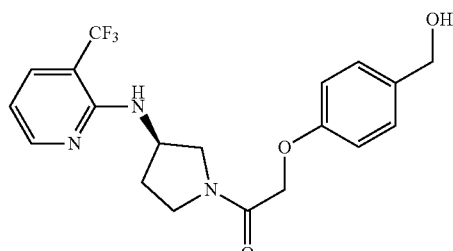
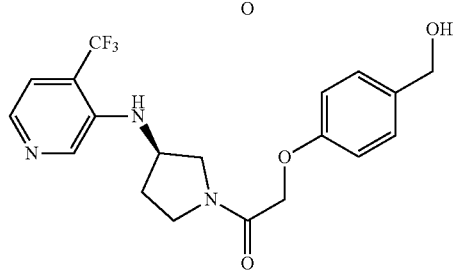
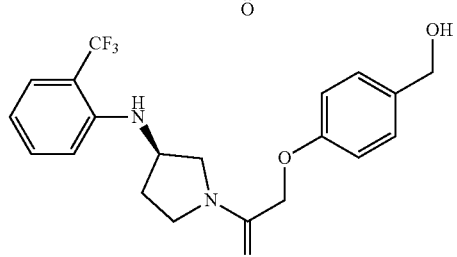
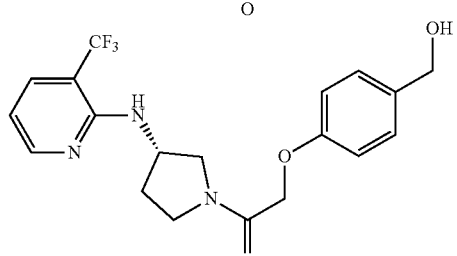

155
-continued
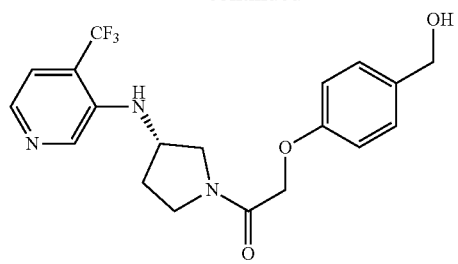
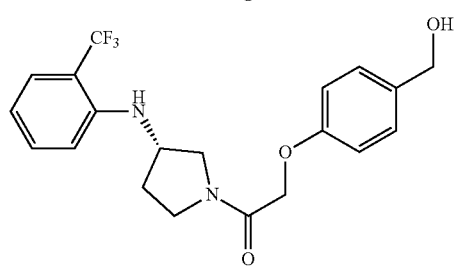
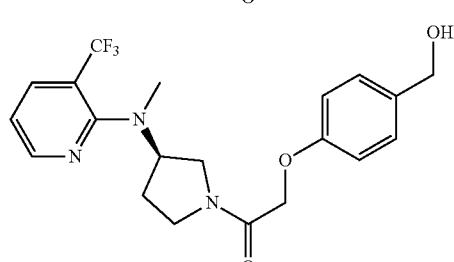
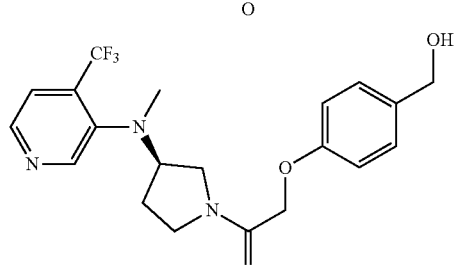
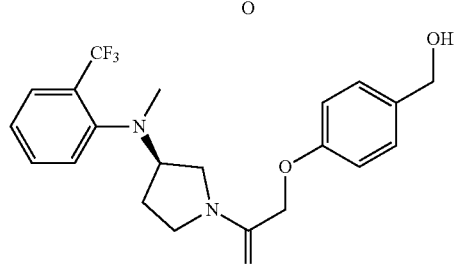
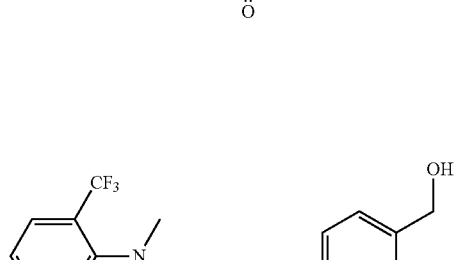
156
-continued
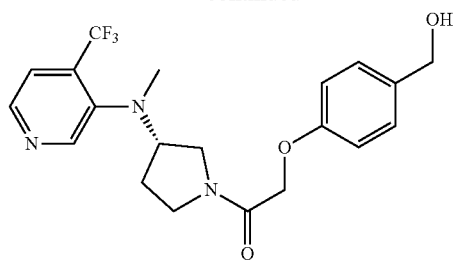
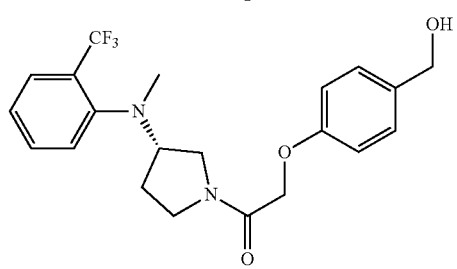
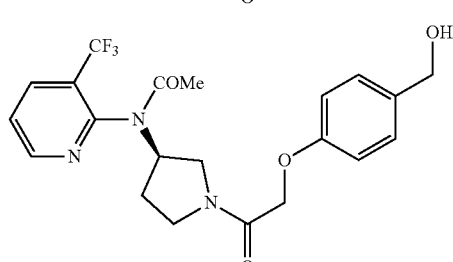
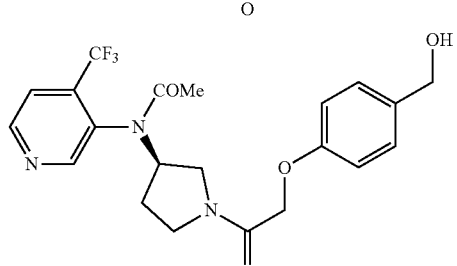
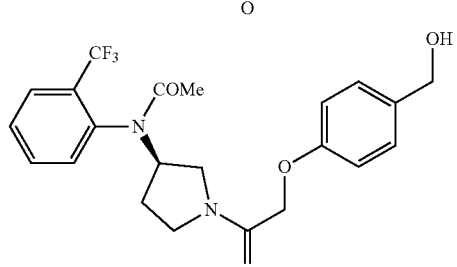
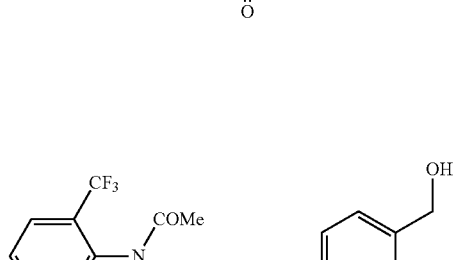

-continued

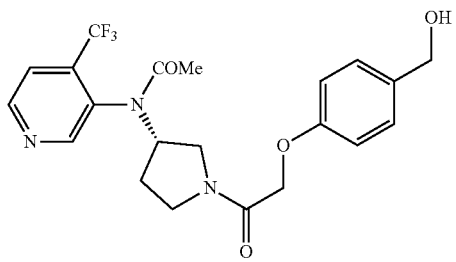

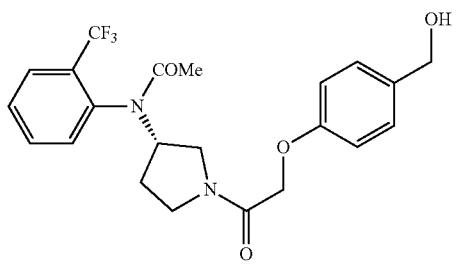

or a pharmaceutically acceptable salt, ester or prodrug form thereof.

In yet further embodiments, X is S, SO or SO$_2$; W is independently CR$_4$ or N; Z is independently CR$_5$ or N; each of R$_1$, R$_2$ and R$_3$ and R$_4$ and R$_5$, if present, is independently: H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR)NR$_9$R$_{10}$; adjacent substituents R$_1$, R$_2$ and R$_3$ and R$_4$ and R$_5$, if present, may form a saturated or unsaturated 5-membered or 6-membered carbocyclic or heterocyclic ring; and each of R$_6$, R$_7$, R$_8$, R$_9$ and R$_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or SO$_2$. In further embodiments, X is SO. In yet further embodiments X is SO$_2$.

In some embodiments, the compound is one of:

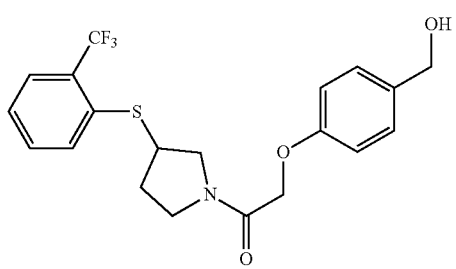 [SMILES: O=C(COc1ccc(CO)cc1)N1CCC(Oc2ccccc2C(F)(F)F)C1]

-continued

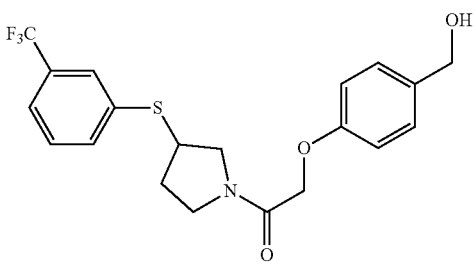

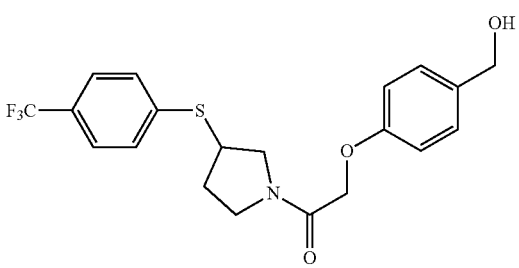

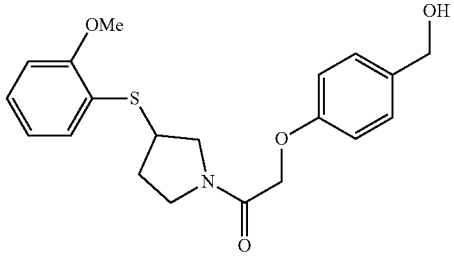

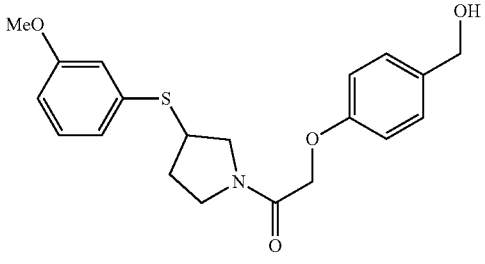

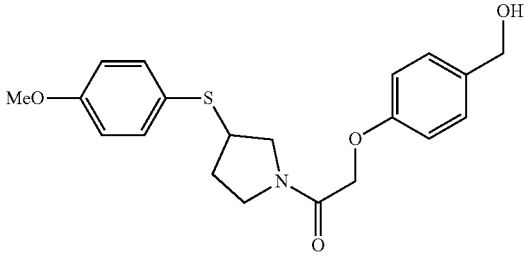

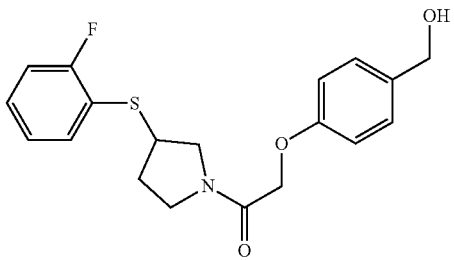

159
-continued
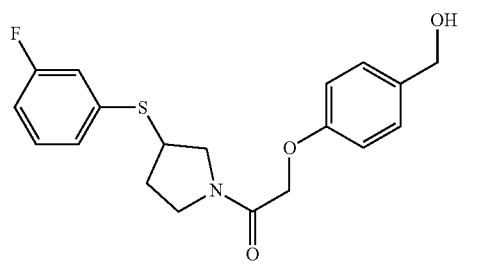
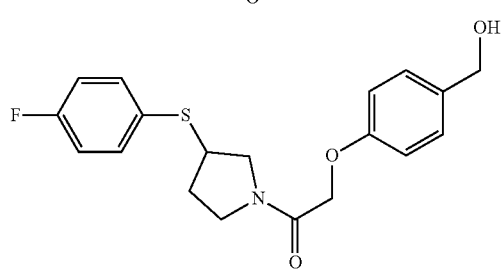
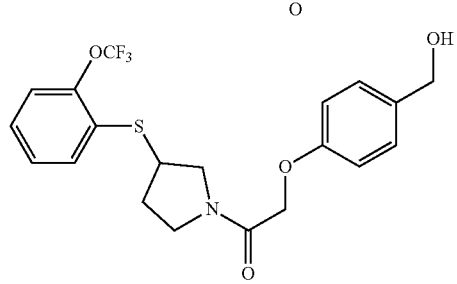
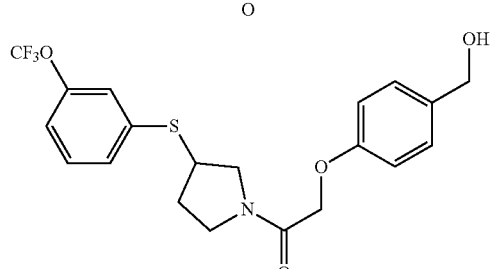
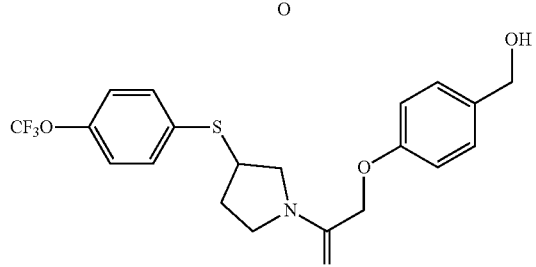
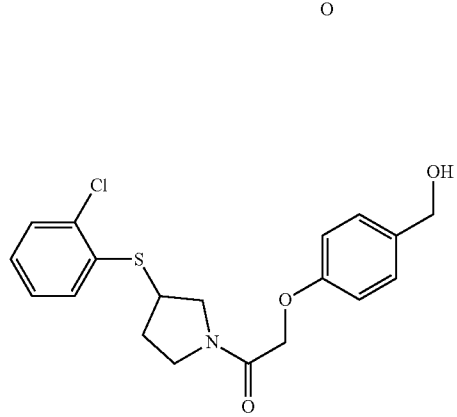
160
-continued
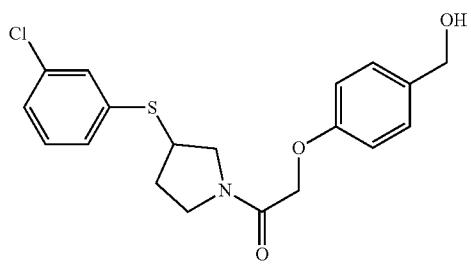
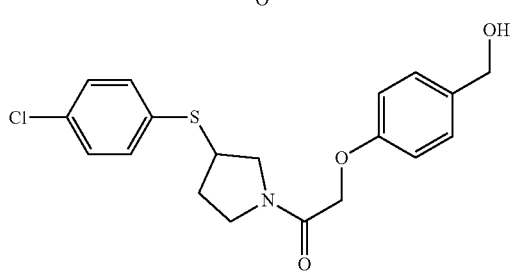
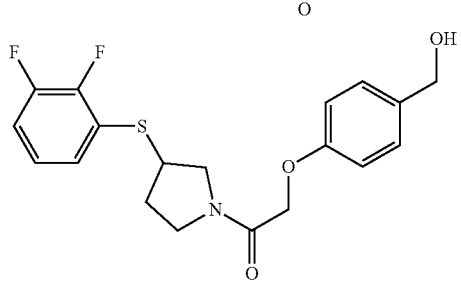
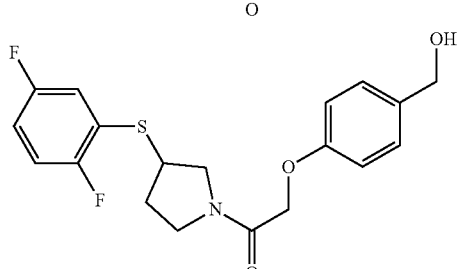
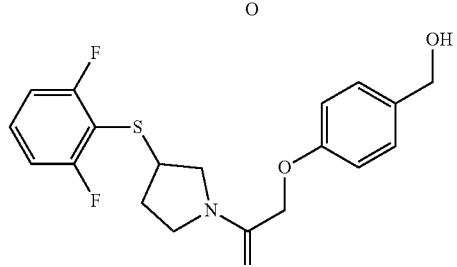
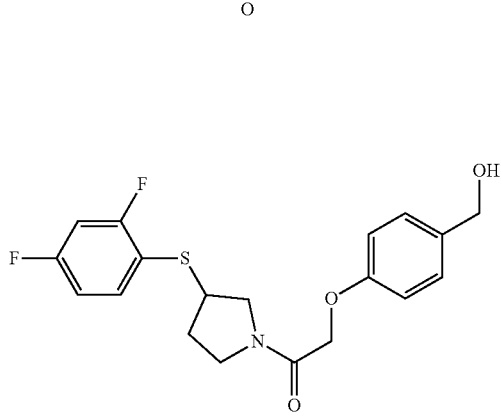

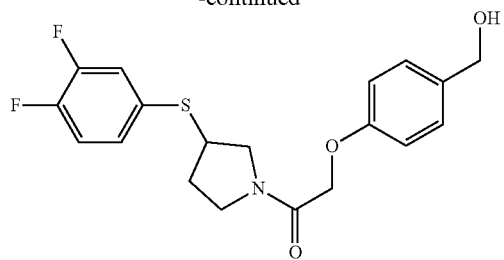
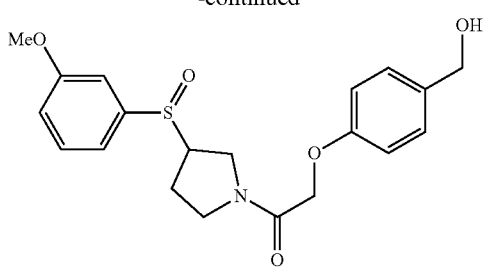
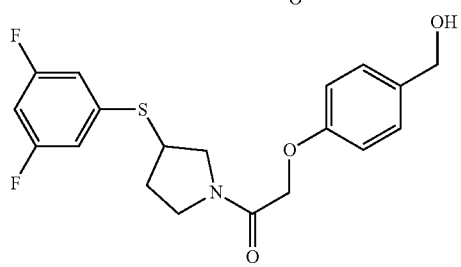
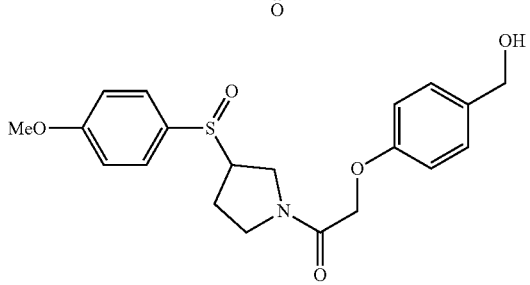
or a pharmaceutically acceptable salt, ester or prodrug form thereof.
In other embodiments, the compound is one of:
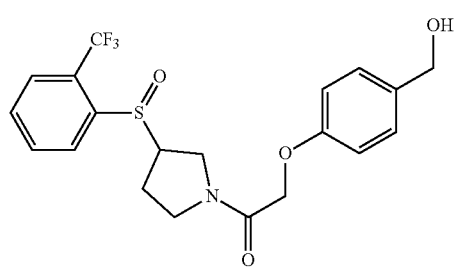
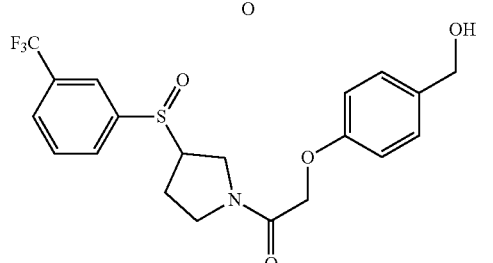
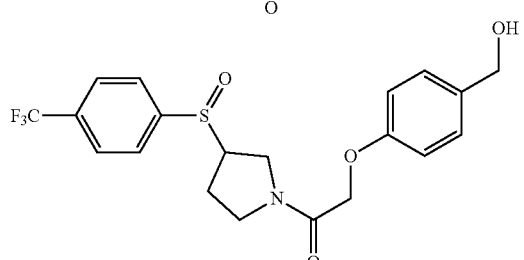
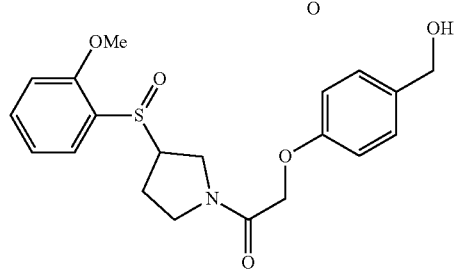
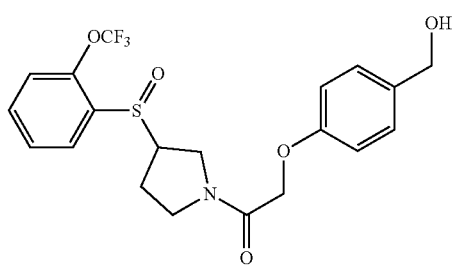

-continued
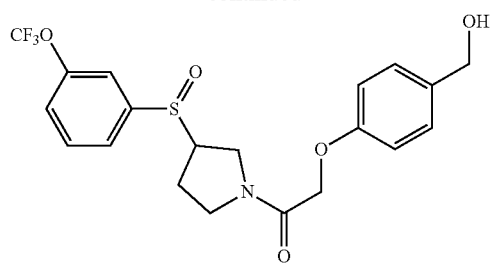
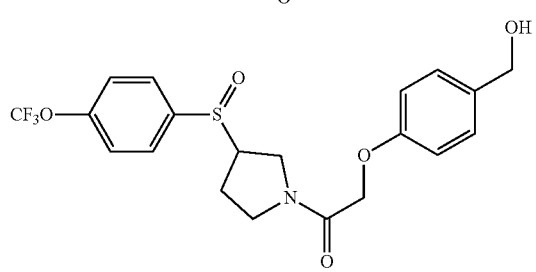
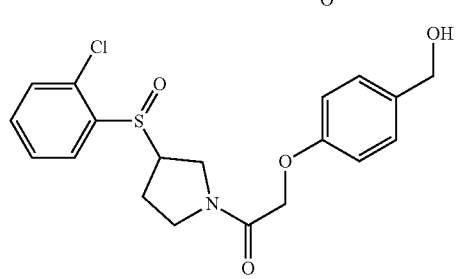
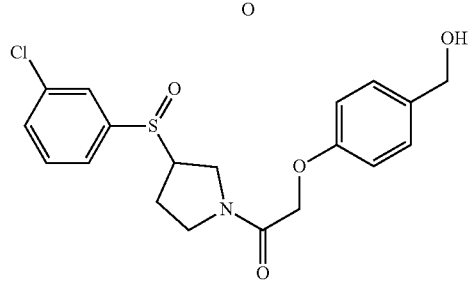
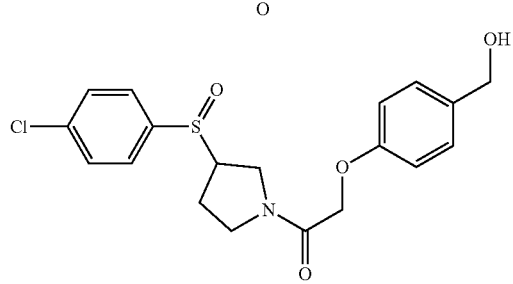
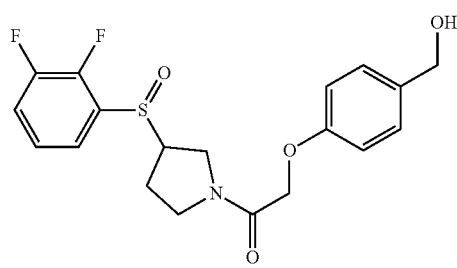
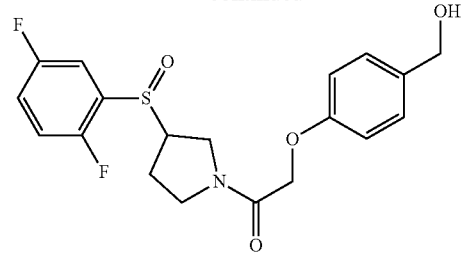
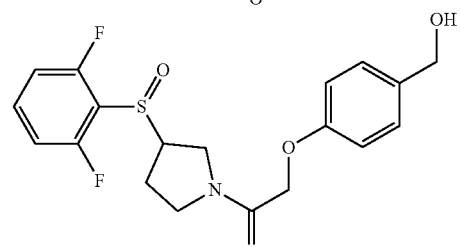
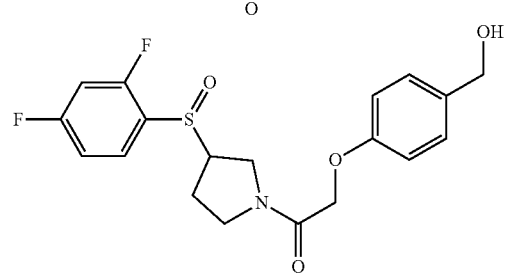
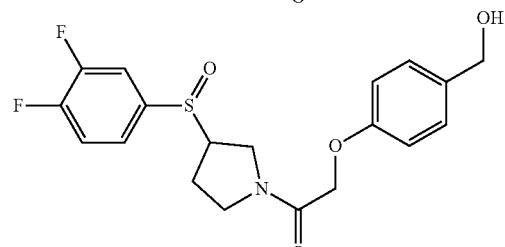
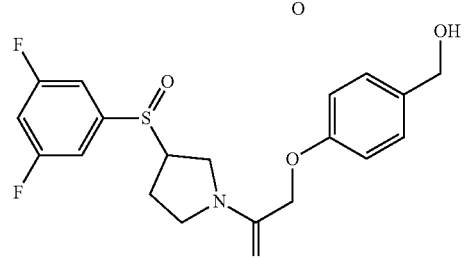
or a pharmaceutically acceptable salt, ester or prodrug form thereof.
In further embodiments, the compound is one of:
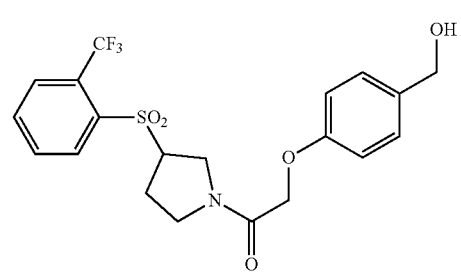

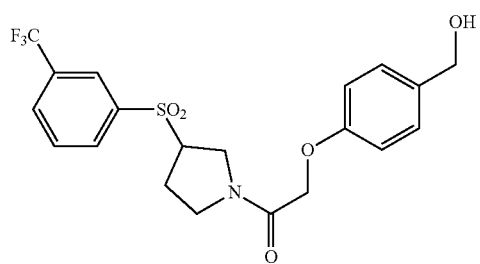
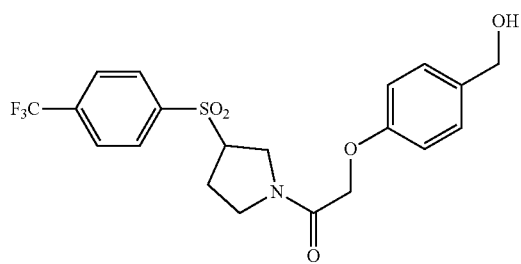
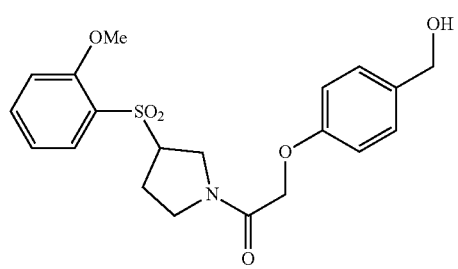
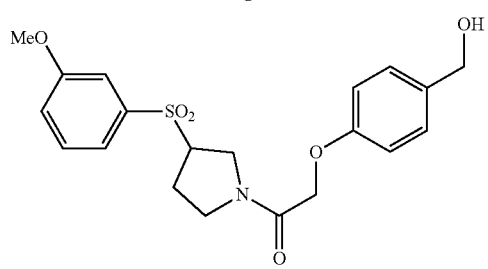
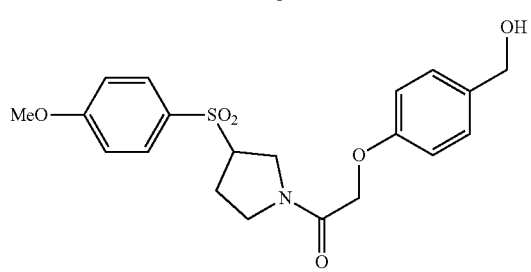
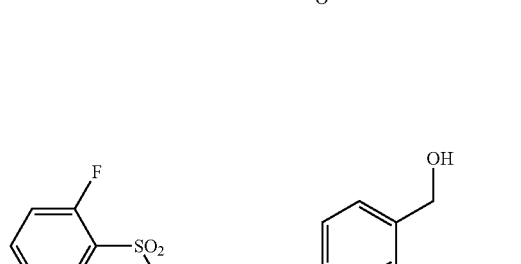
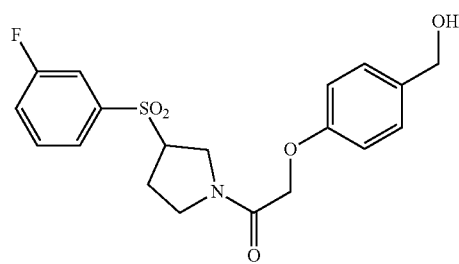
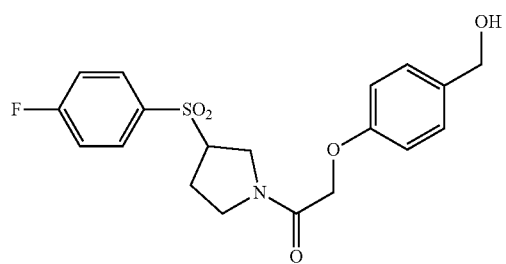
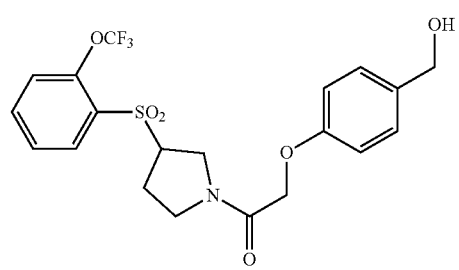
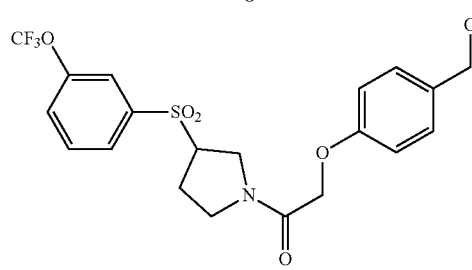
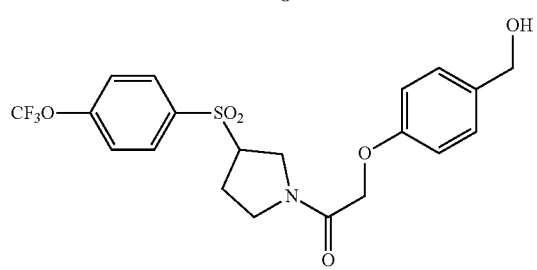
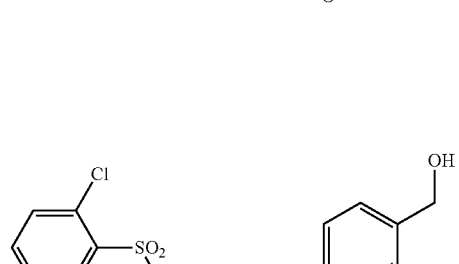

167
-continued
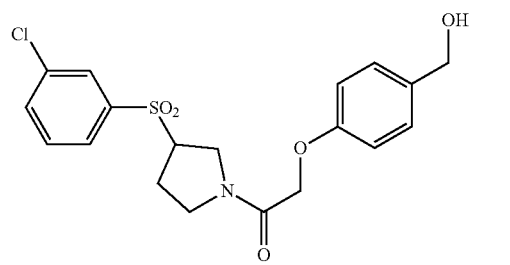
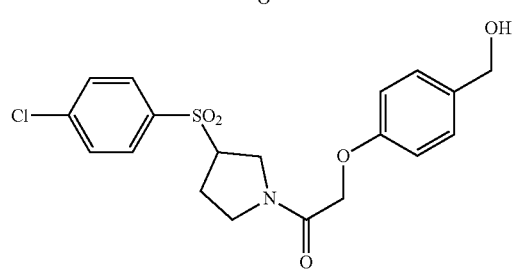
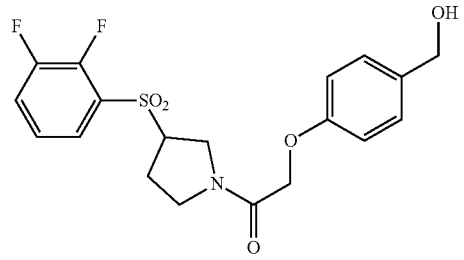
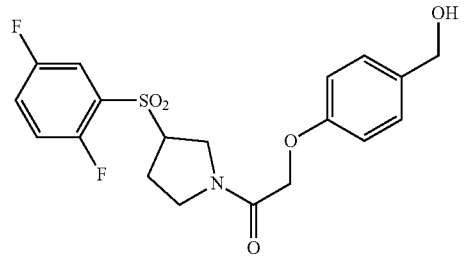
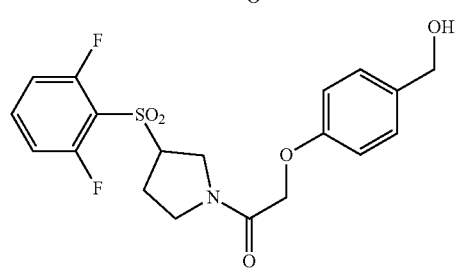
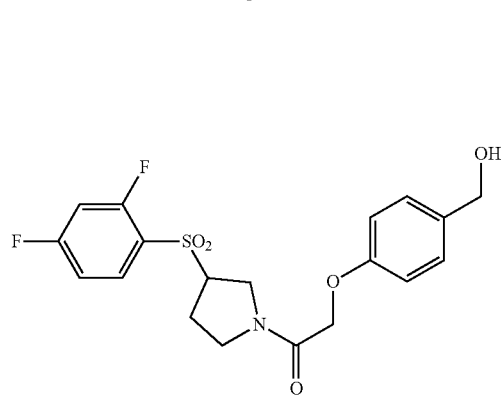
168
-continued
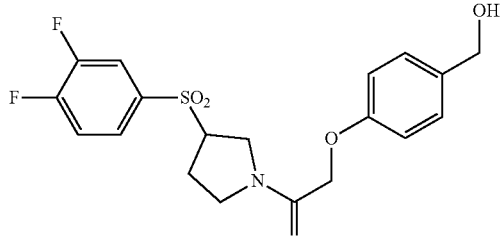
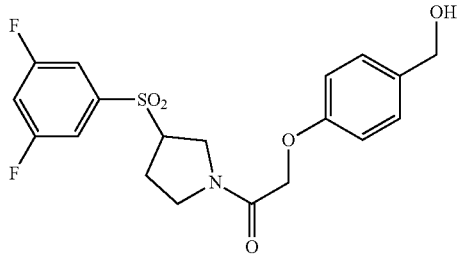
or a pharmaceutically acceptable salt, ester or prodrug form thereof.
In yet further embodiments, the compound is one of:
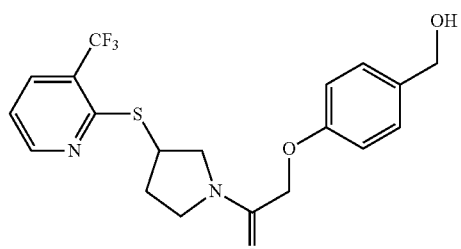
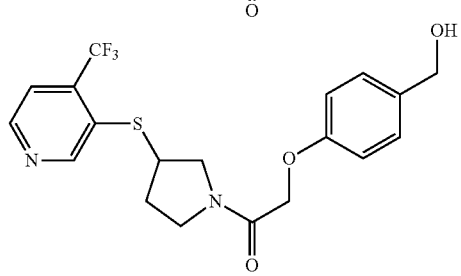
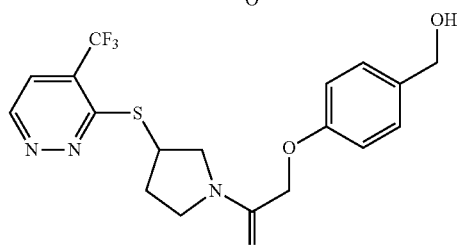
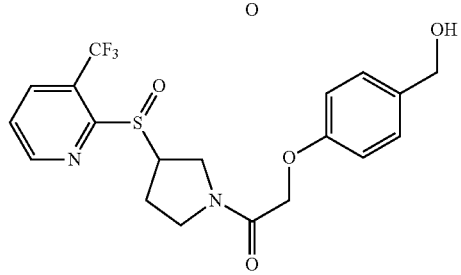

169
-continued
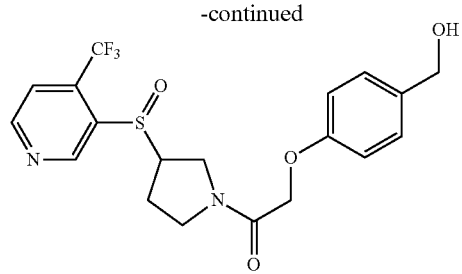
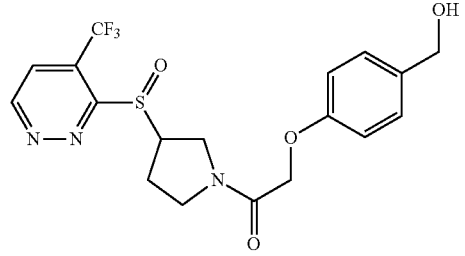
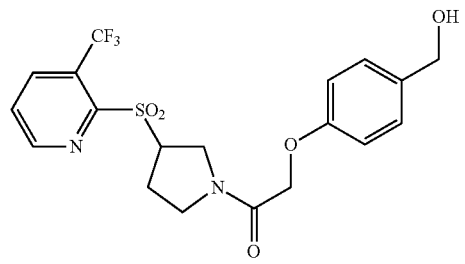
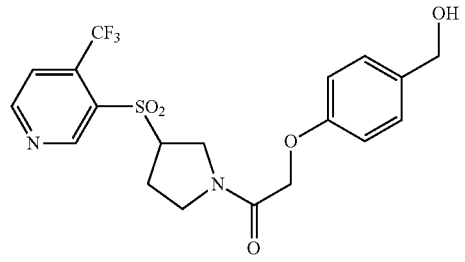
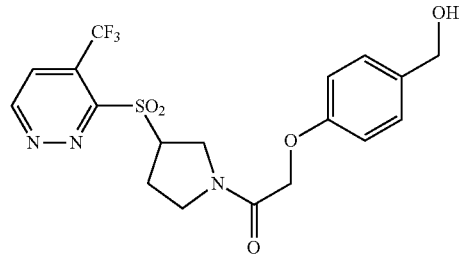
or a pharmaceutically acceptable salt, ester or prodrug form thereof.
In yet other embodiments, the compound is one of the following:
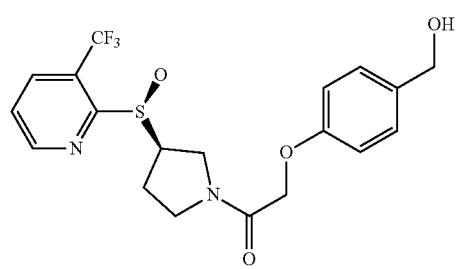
170
-continued
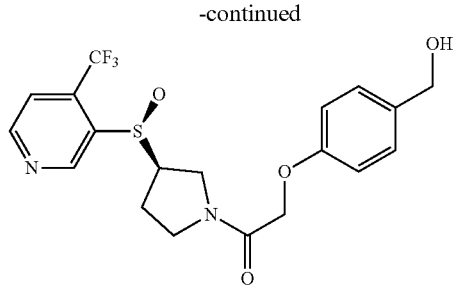
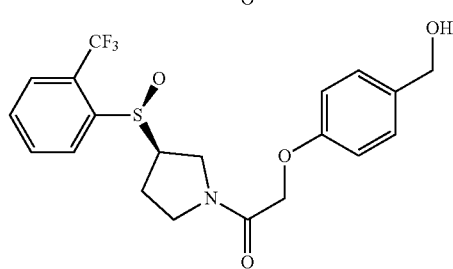
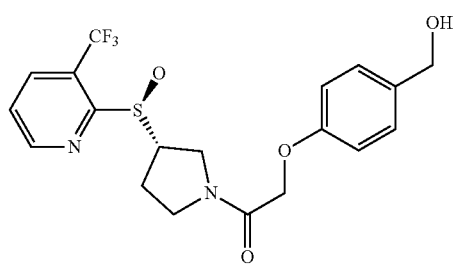
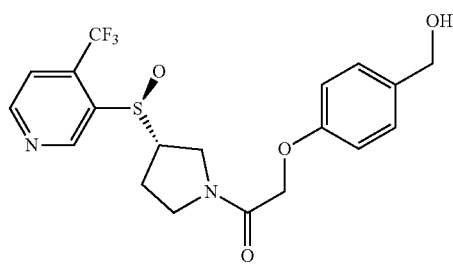
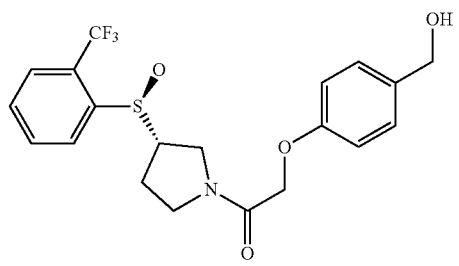
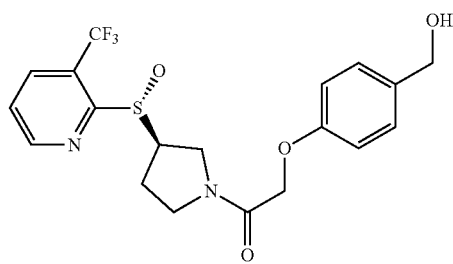

-continued

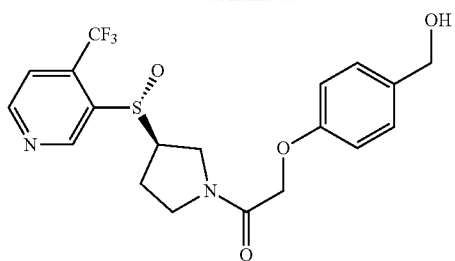

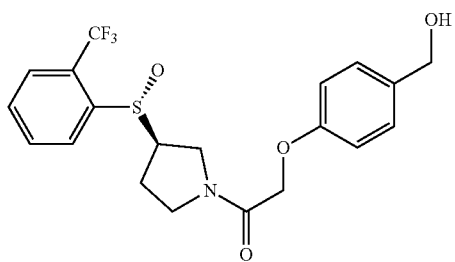

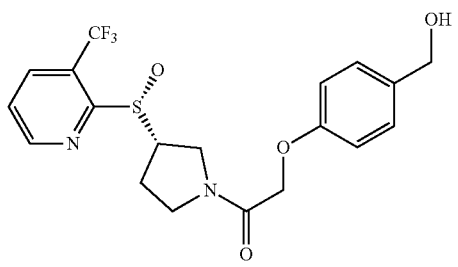

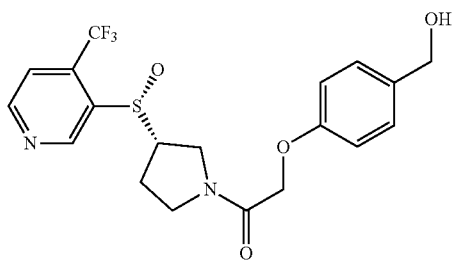

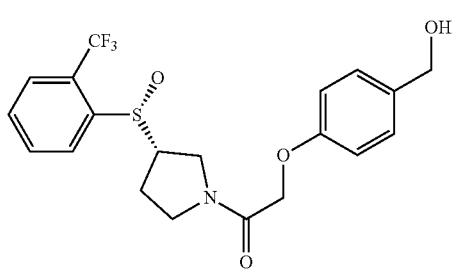

or a pharmaceutically acceptable salt, ester or prodrug form thereof.

In yet further embodiments, the compound has the structure II

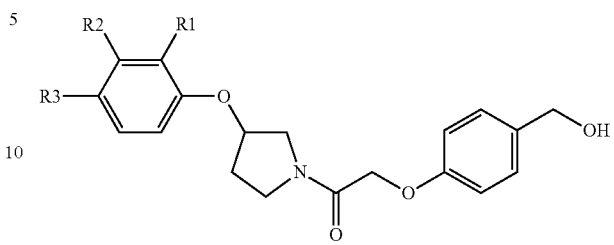

II wherein one of $R_1$ and $R_2$ and $R_3$, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

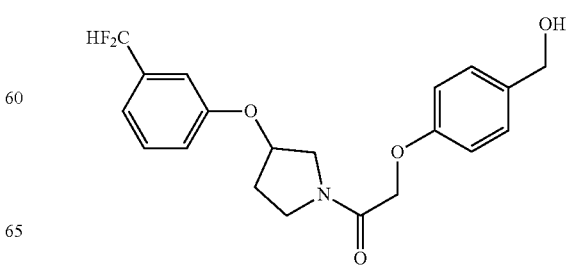

173
-continued
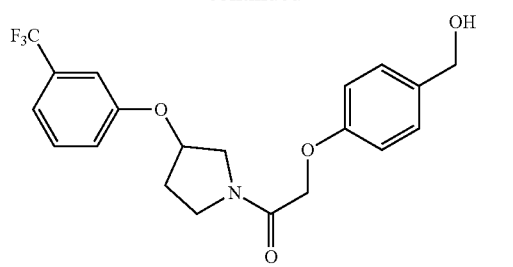
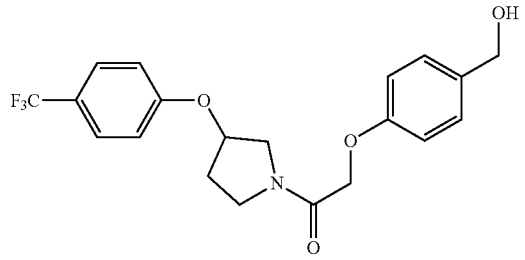
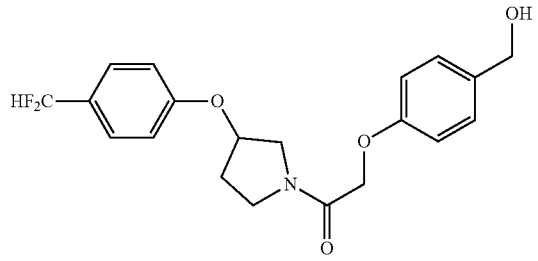
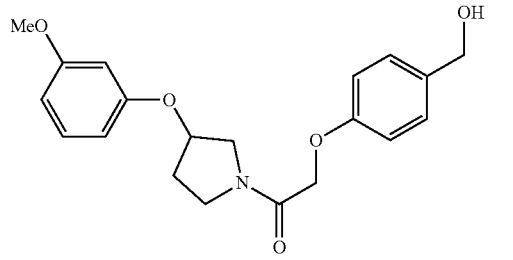
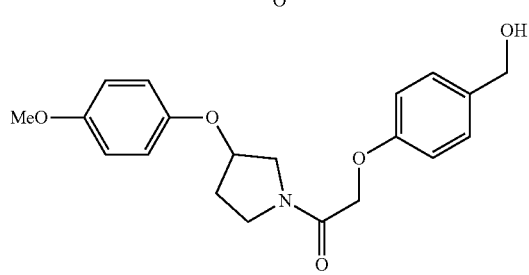
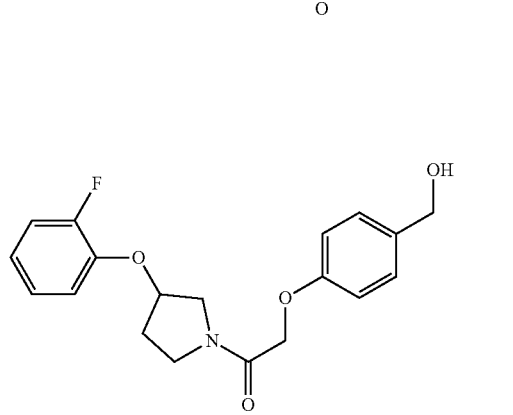
174
-continued
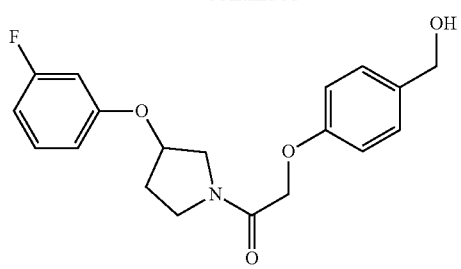
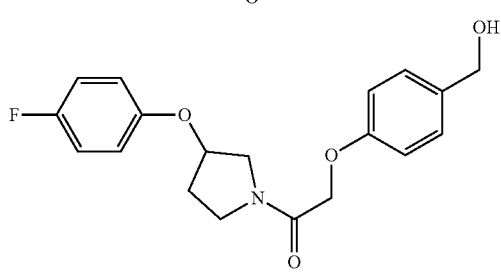
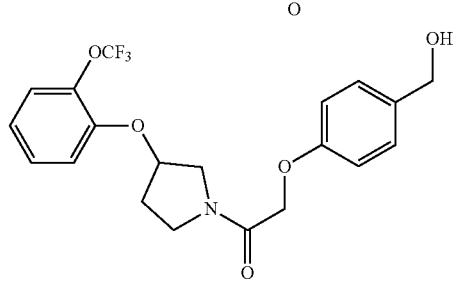
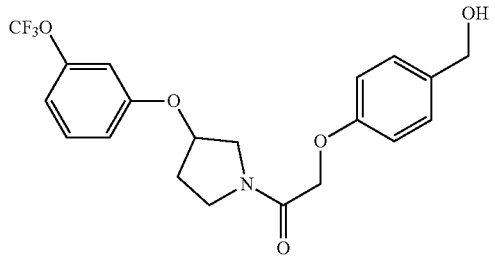
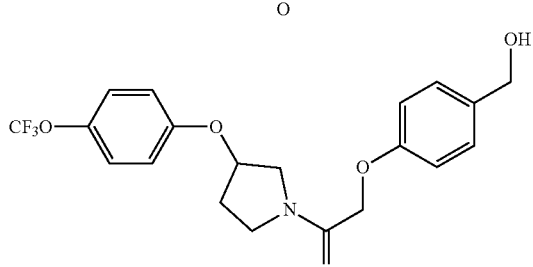
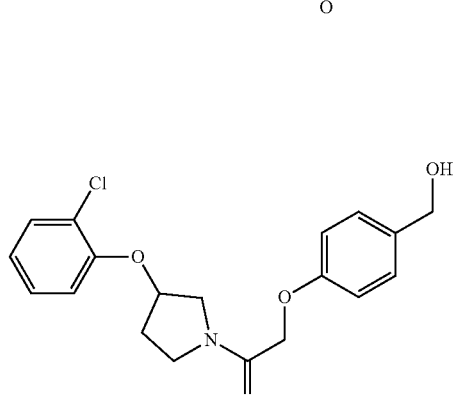

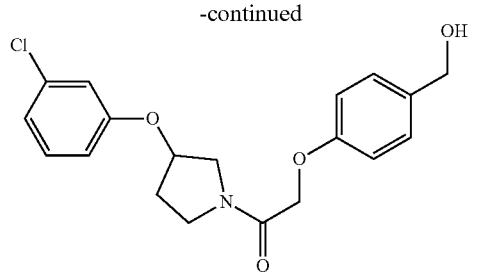
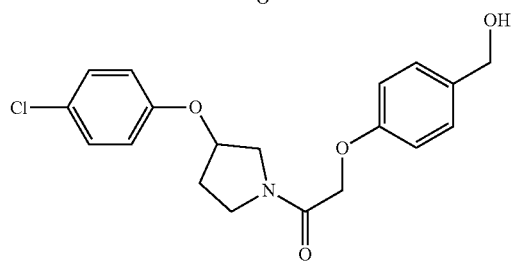
or a pharmaceutically acceptable salt, ester or prodrug form thereof.
In other embodiments the compound is one of the following:
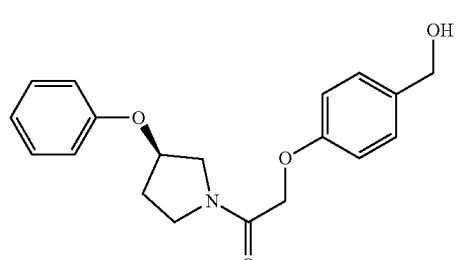
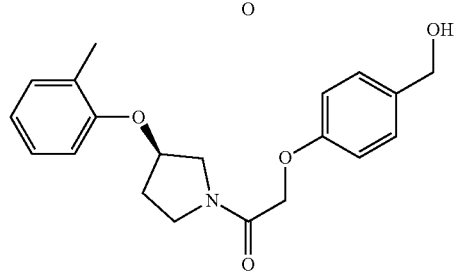
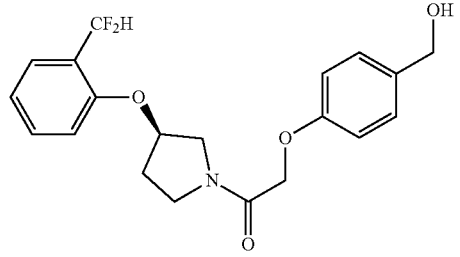
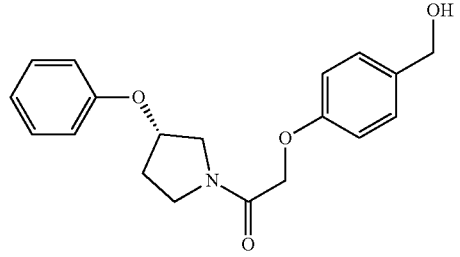
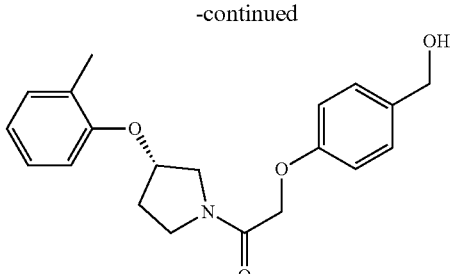
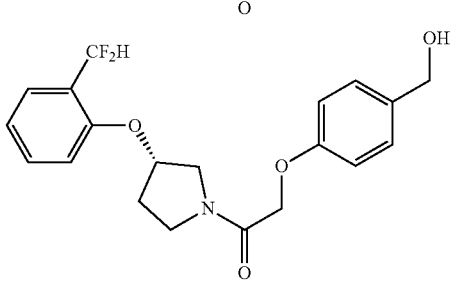

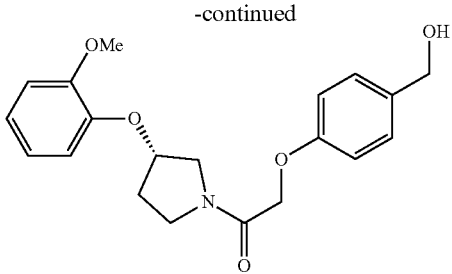

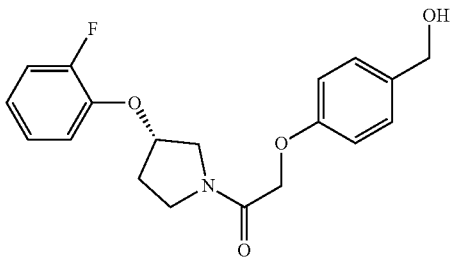

or a pharmaceutically acceptable salt, ester or prodrug form thereof.

In certain embodiments, the compound is one of the following:

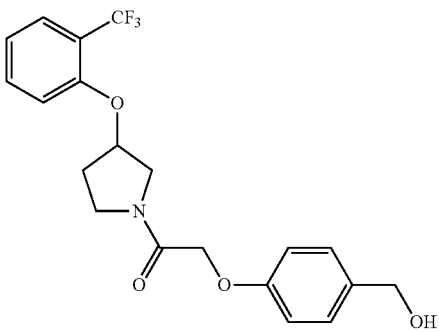

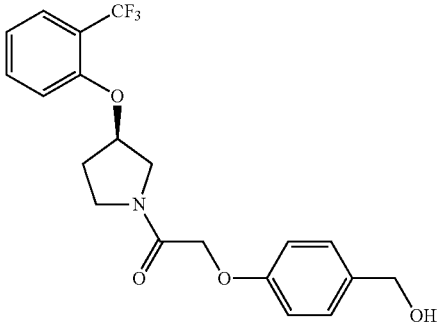

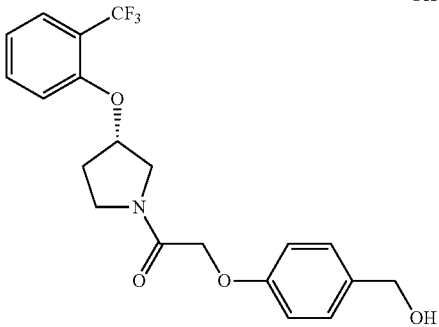

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol. In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50 One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50. In certain embodiments, the pharmaceutical composition comprises both (i) butylated hydroxytoluene (BHT) at a concentration of least 0.05%; and (ii) di-sodium EDTA at a concentration of least 0.001%. In another embodiment, the pharmaceutical composition comprises each of (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50.

In a certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w; and
(vi) a carbomer such as carbomer homopolymer type C980 in the range of 0.5 to 2.0% w/w.

In another certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w;
(vi) a carbomer such as carbomer homopolymer type C980 in the range of 0.5 to 2.0% w/w; (vii) butylated hydroxytoluene (BHT) at a concentration of least 0.05%;
(viii) di-sodium EDTA at a concentration of least 0.001%; and
(ix) Trolamine to provide an apparent pH in the range 6.50 to 7.50.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.
(vii) butylated hydroxytoluene (BHT) at a concentration of least 0.1%;
(viii) di-sodium EDTA at a concentration of least 0.005%; and
(ix) Trolamine to provide an apparent pH in the range 6.50 to 7.50.

In specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w; and
(vii) water at a concentration of 19.5-22% w/w.

In yet other specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;

(vi) carbomer homopolymer type C980 at a concentration of 1.0% w/w;
(vii) butylated hydroxytoluene (BHT) at a concentration of 0.1% w/w;
(viii) di-sodium EDTA at a concentration of 0.005% w/w;
(ix) Trolamine at a concentration of 0.375% w/w; and
(x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxy)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6%

In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments a second therapeutic agent is present.

In some embodiments, the duration of treatment is greater than 28 days.

In further embodiments, the duration of treatment is between one and six months or thereabouts. In yet further embodiments, the duration of treatment is between one and twenty four months or thereabouts; one and eighteen months or thereabouts; one and twelve months or thereabouts; one and three months or thereabouts; one and two months or thereabouts; or one month or thereabouts.

The present invention also provides a method of treating obesity, including pre-diabetic obesity and diabetes related obesity, in a subject which comprises administering to an area of skin, including an area of excess fat, a composition comprising a pharmaceutically acceptable carrier, which provides an environment of physical and chemical stability, and an amount of a compound or of a pharmaceutically acceptable salt of the compound or ester of the compound or prodrug of the compound effective to treat the skin condition, wherein the compound has the structure I:

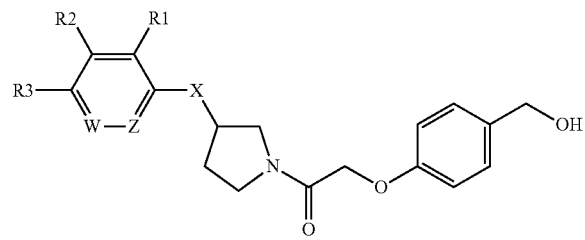

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;
wherein adjacent substituents $R_1$, $R_2$ and $R_3$ and $R_4$ and $R_5$, if present, may form a saturated or unsaturated 5-membered or 6-membered carbocyclic or heterocyclic ring;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;

In some embodiments, X is O; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In some embodiments, the compound is one of the following:

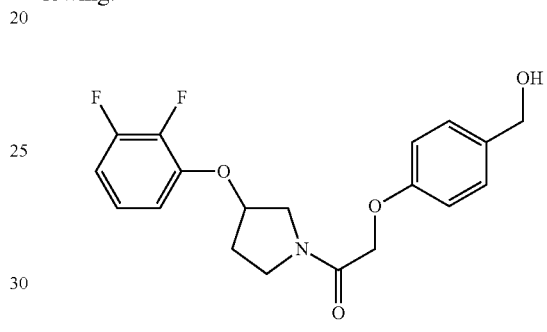

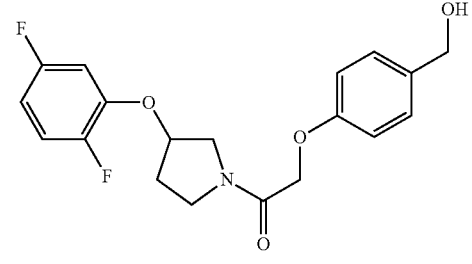

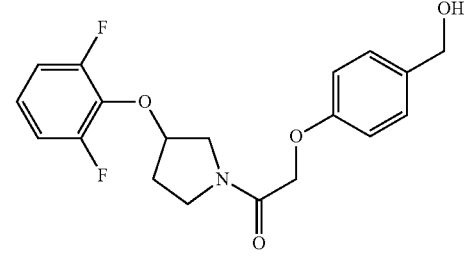

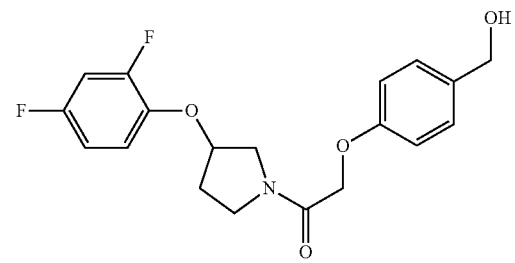

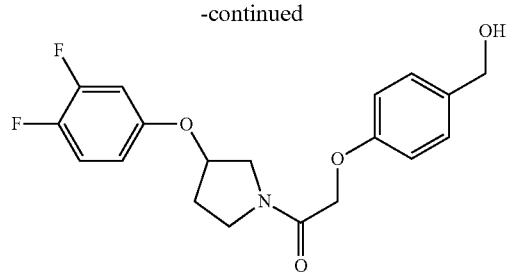
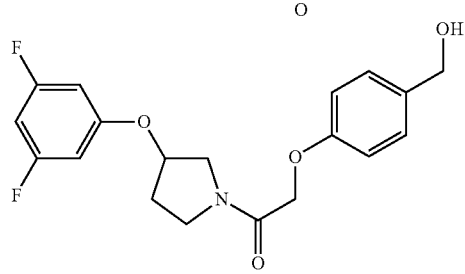
or a pharmaceutically acceptable salt, ester or prodrug form thereof.
In further embodiments, the compound is one of the following:
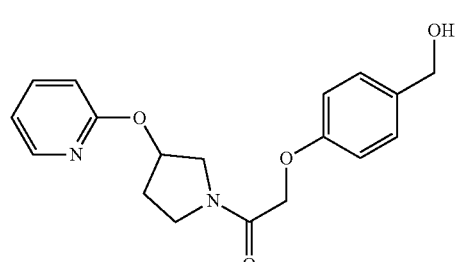
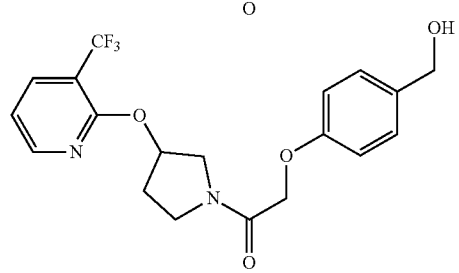
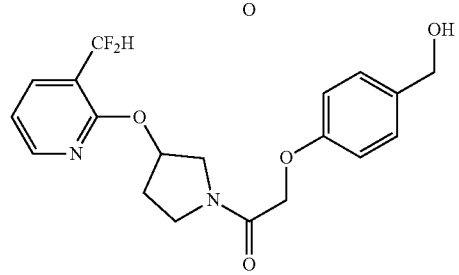
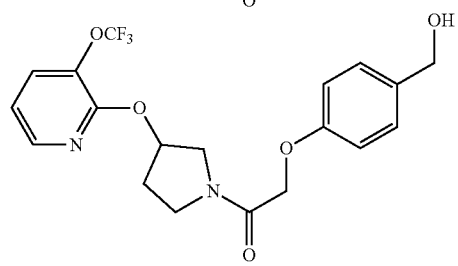
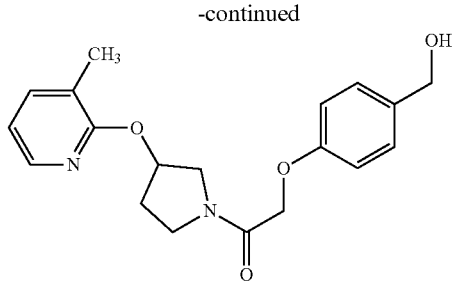
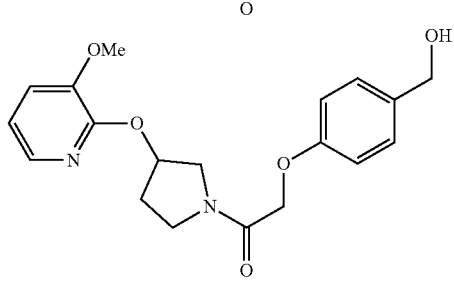

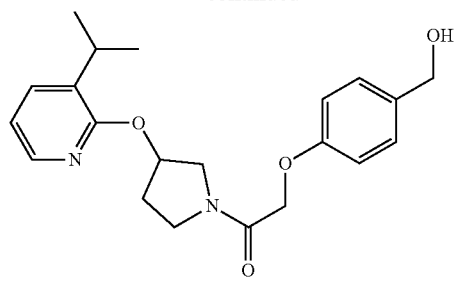
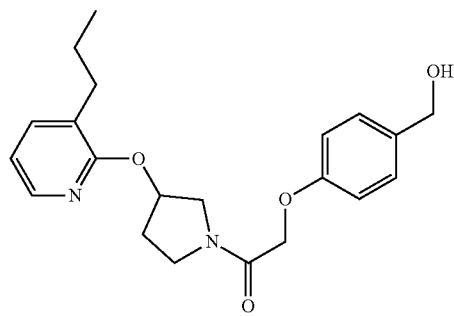
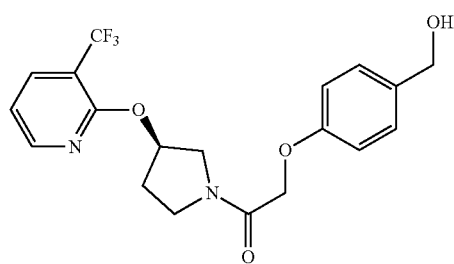 [SMILES: O=C(COc1ccc(CO)cc1)N1CC[C@@H](Oc2ccccc2C(F)(F)F)C1]
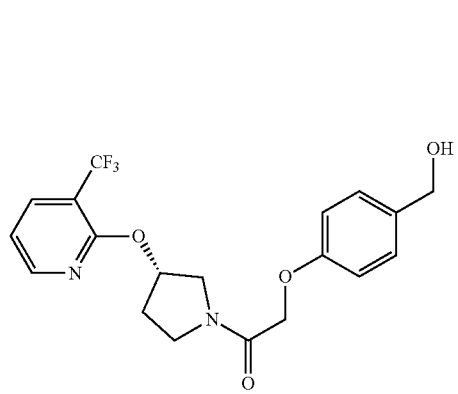
or a pharmaceutically acceptable salt, ester or prodrug form thereof.
In yet other embodiments, the compound is one of the following:

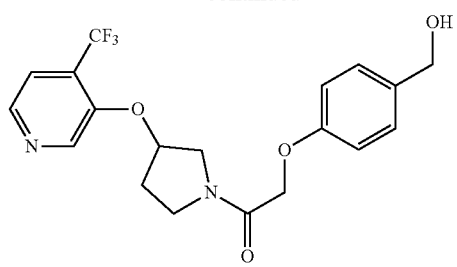
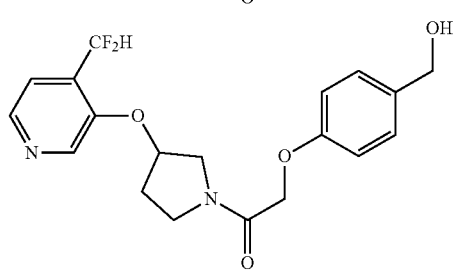
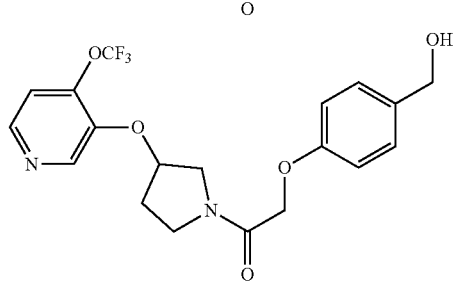
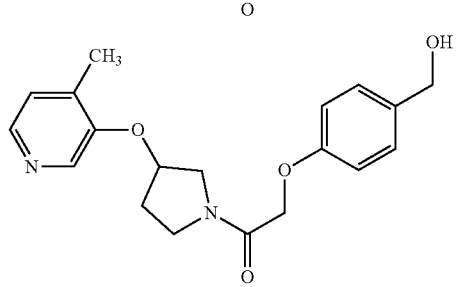
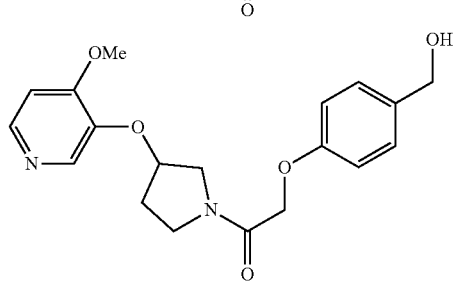
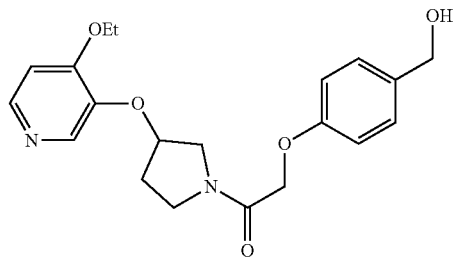

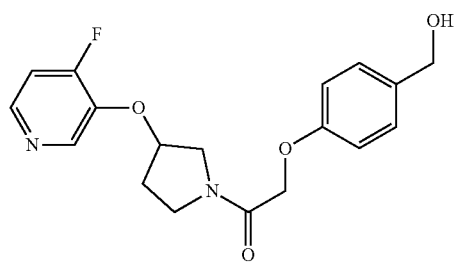
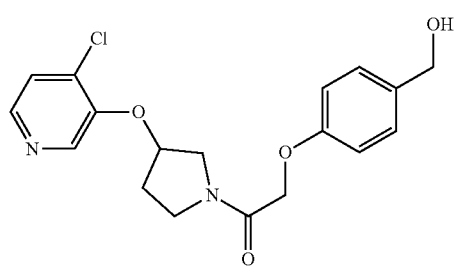
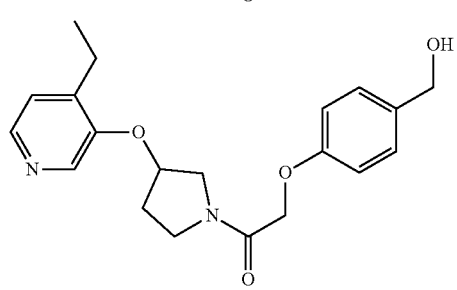
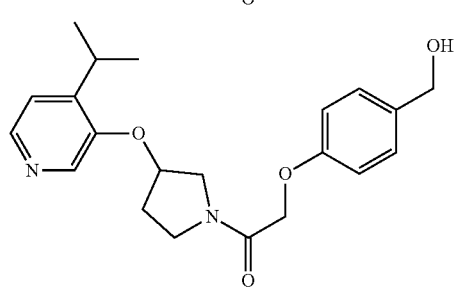
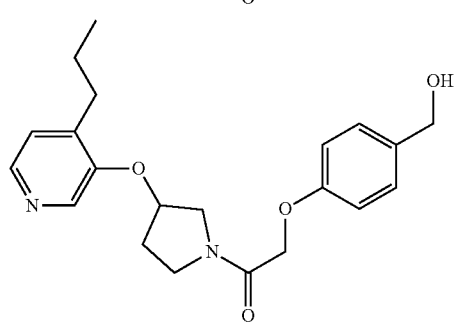
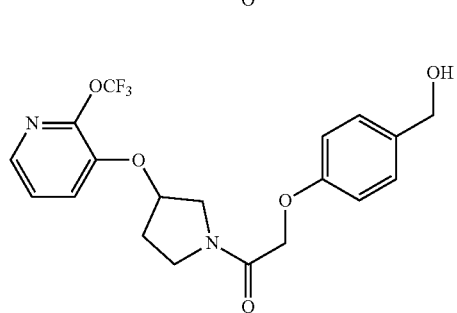
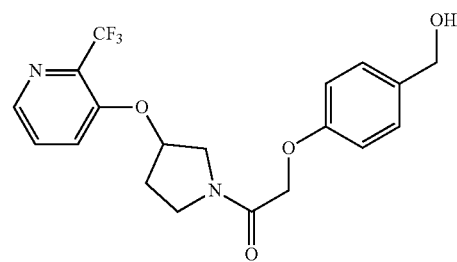
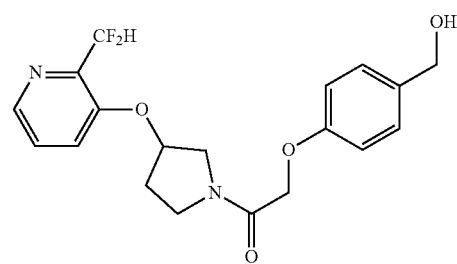
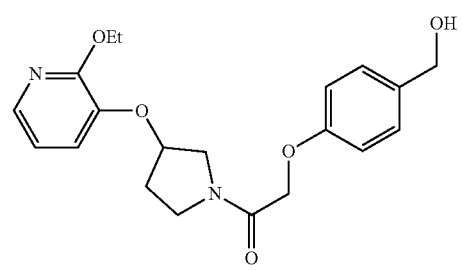
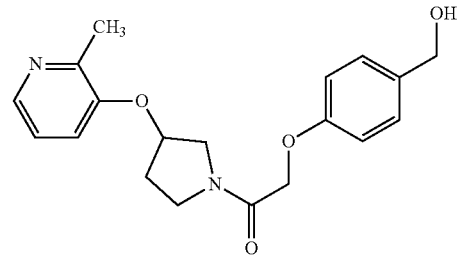
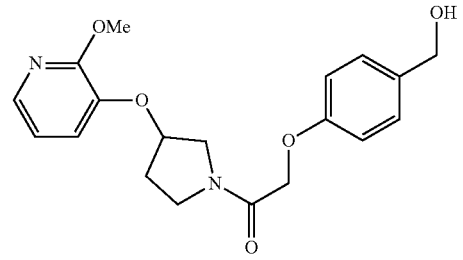
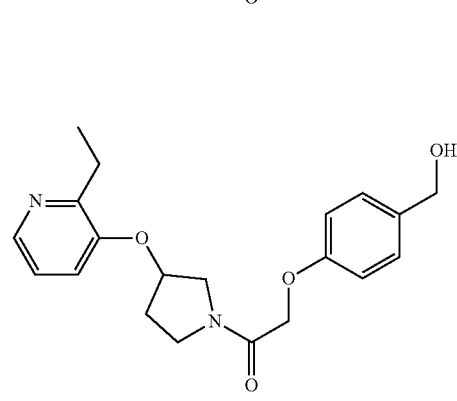

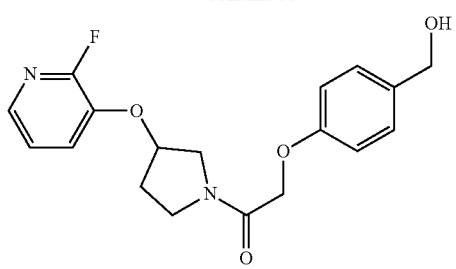
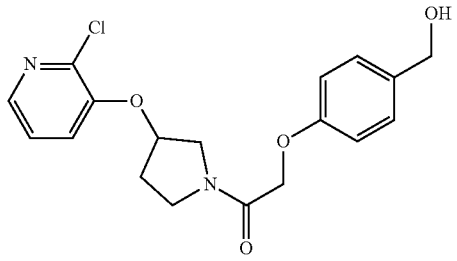
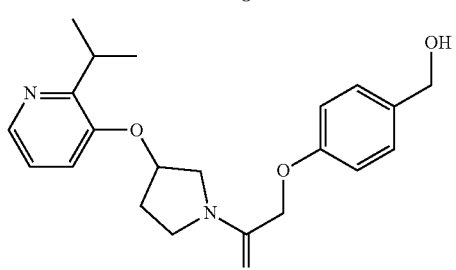
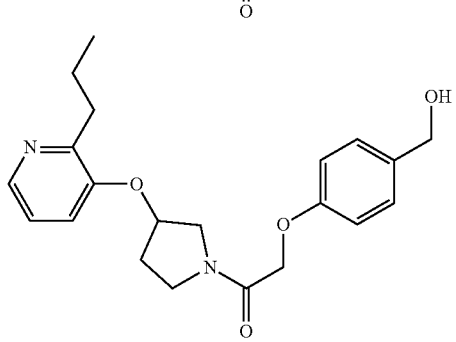
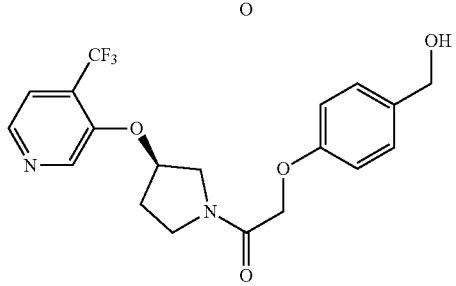
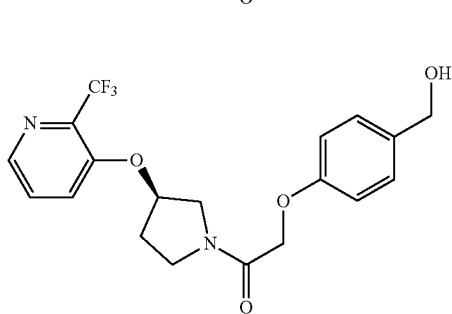
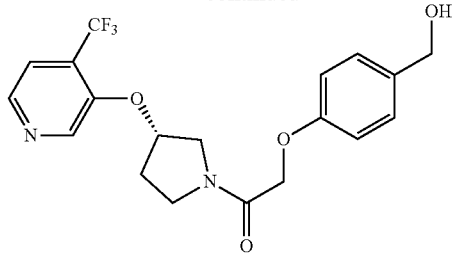 [SMILES: O=C(COc1ccc(CO)cc1)N1CC[C@H](Oc2ccccc2C(F)(F)F)C1]
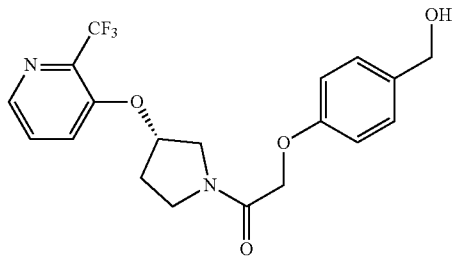
or a pharmaceutically acceptable salt, ester or prodrug form thereof.
In yet further embodiments, the compound is one of the following:
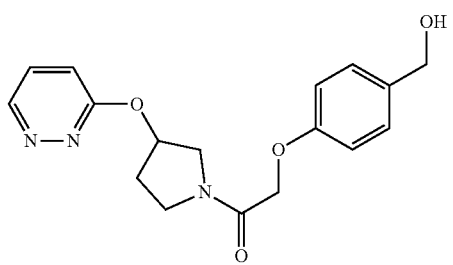
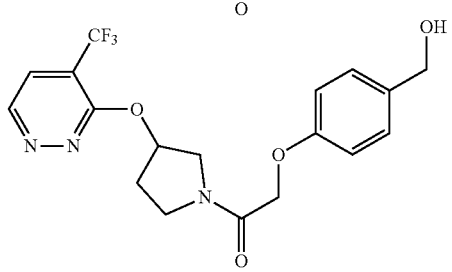
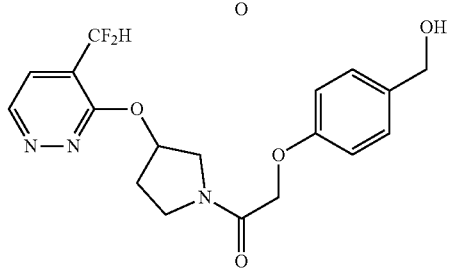
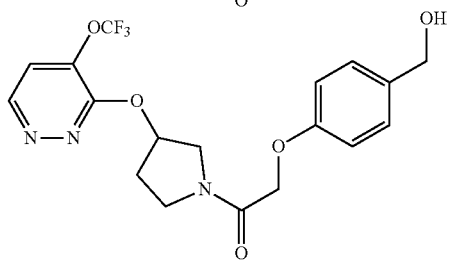

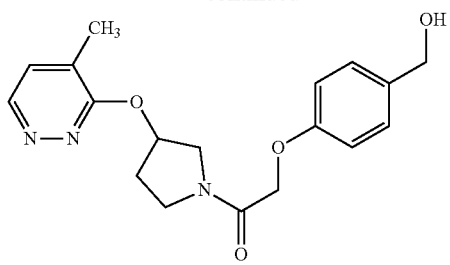
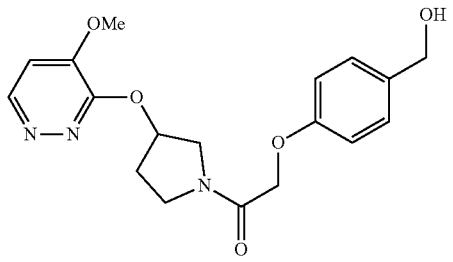
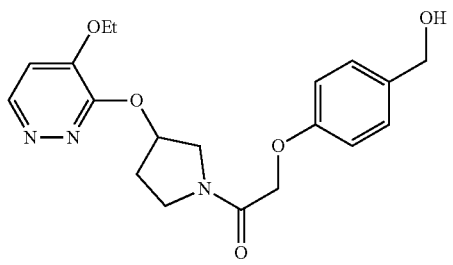
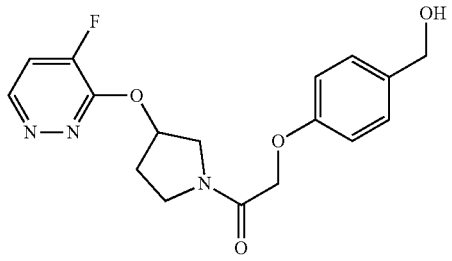
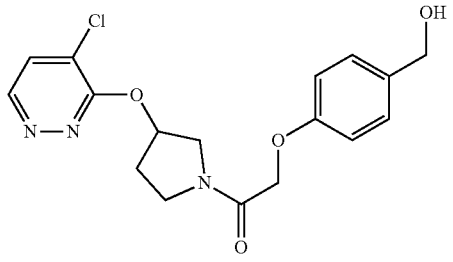
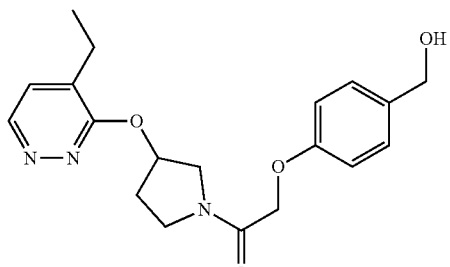
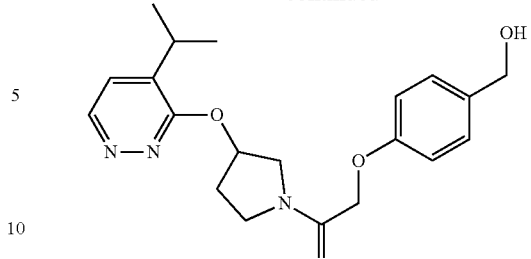
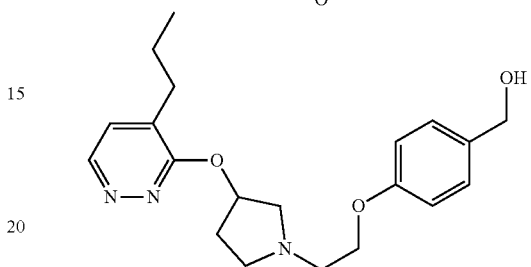
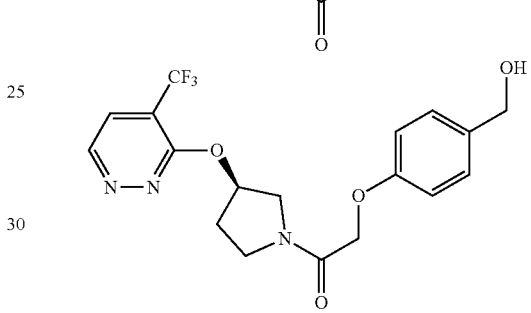
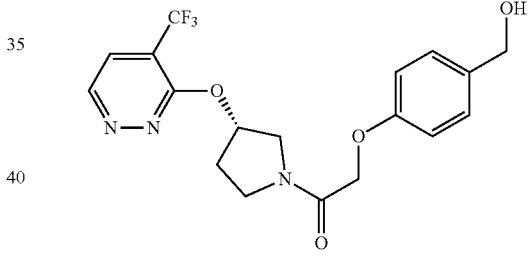

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $NO_2$; $NH_2$; NHCH(O); $NR_6CH(O)$; $NHC(O)R_6$; $NR_6C(O)R_7$; C(O)$NR_6R_7$; $C(NH)NR_6R_7$; $C(NH)NR_6OH$; $C(NH)NR_6NO_2$; or $C(NR_6)NR_7C(NR_8)NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.
In further embodiments, X is NH. In other embodiments, X is N-alkyl or N-acyl. In further embodiments, X is N-alkyl. In yet further embodiments X is N-acyl.
In certain embodiments, the compound is one of the following:
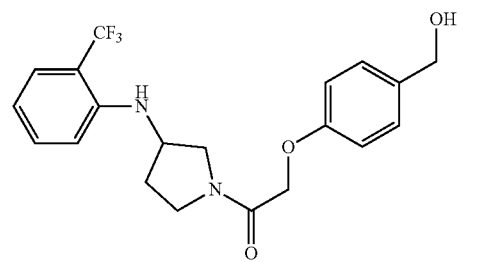
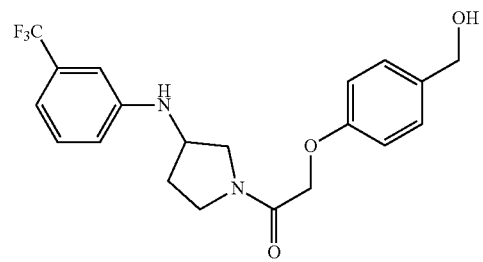
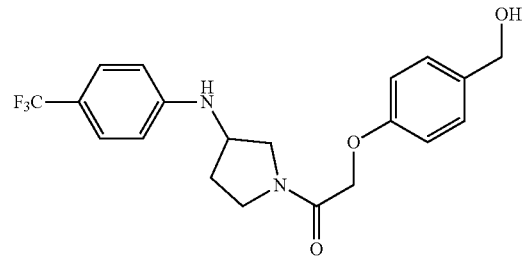
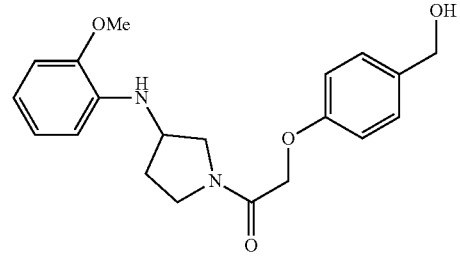
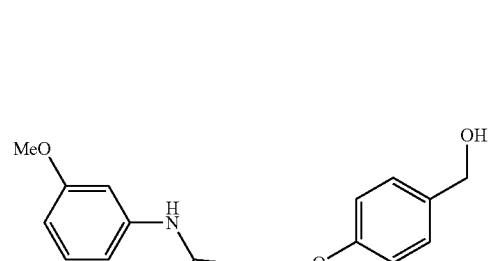
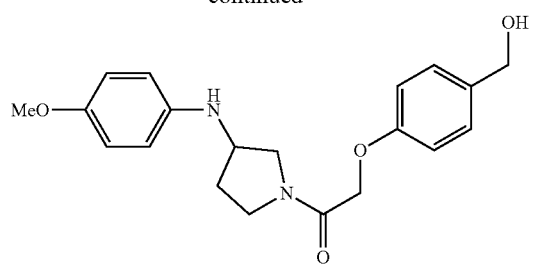
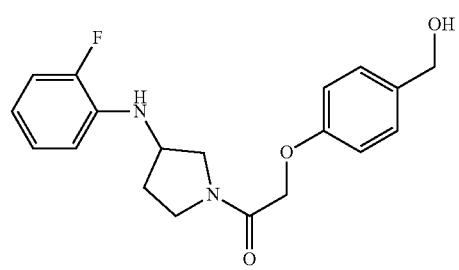
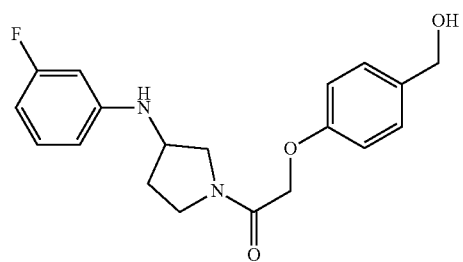
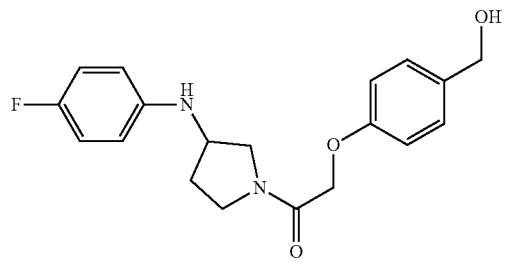
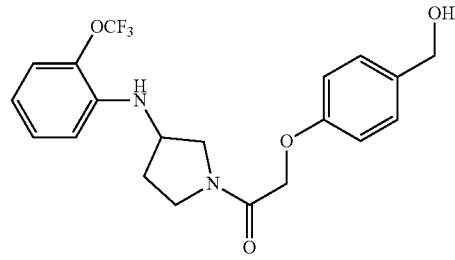

197
-continued
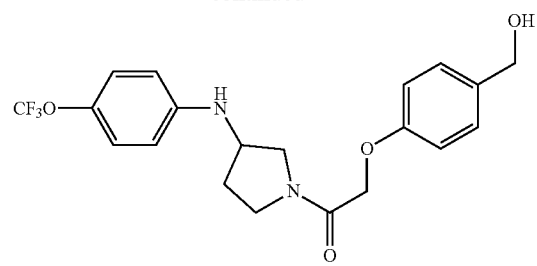
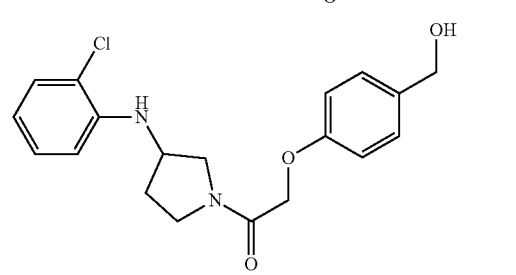
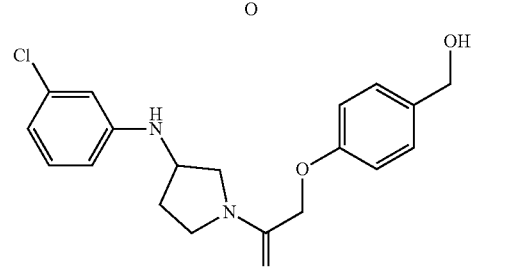
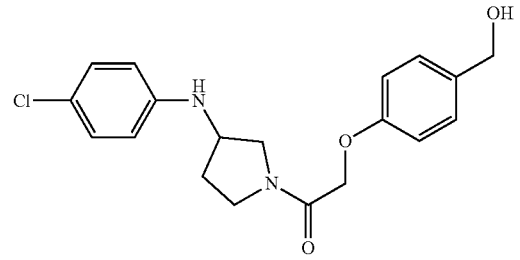
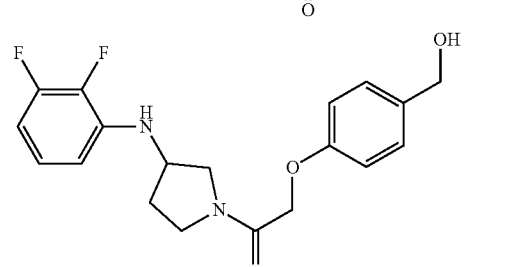
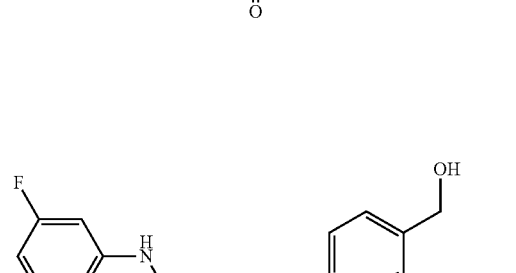
198
-continued
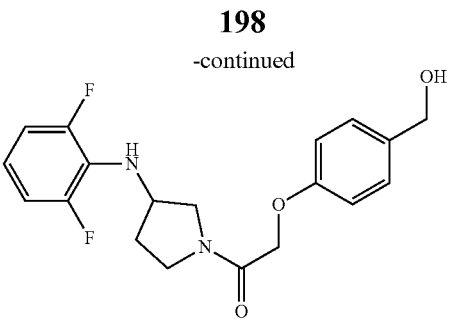
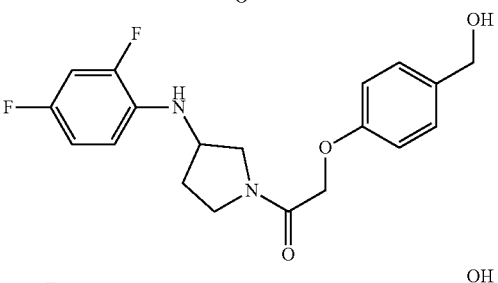
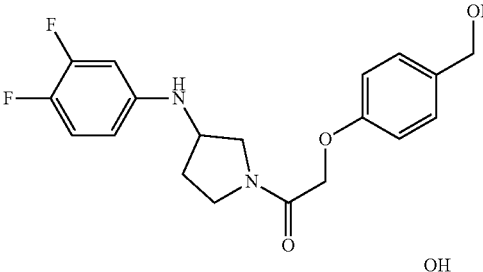
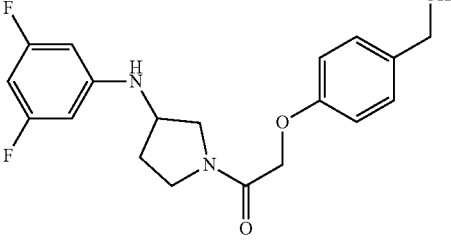
or a pharmaceutically acceptable salt, ester or prodrug form thereof.
In other embodiments, the compound is one of the following:
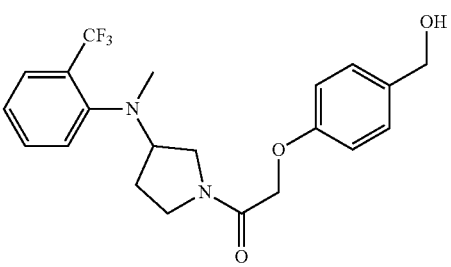
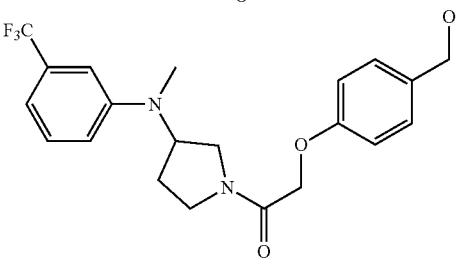

199
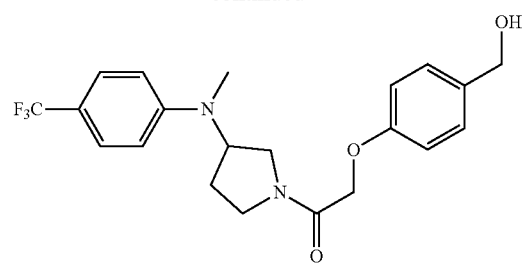
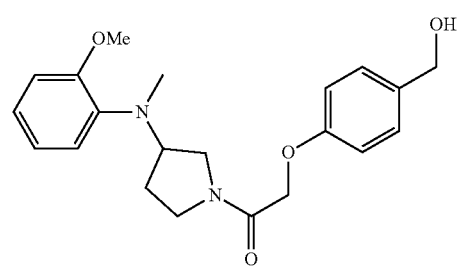
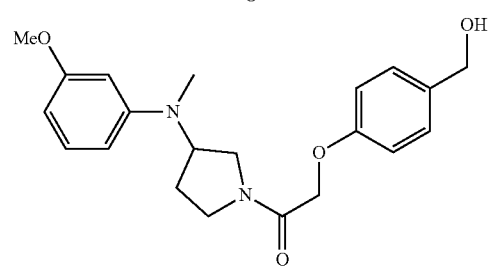
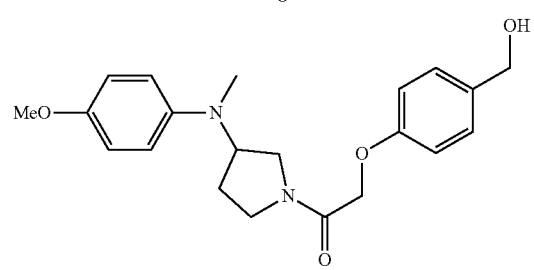
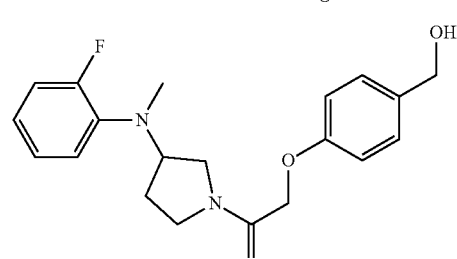
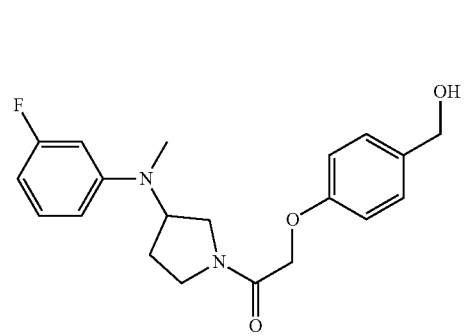
200
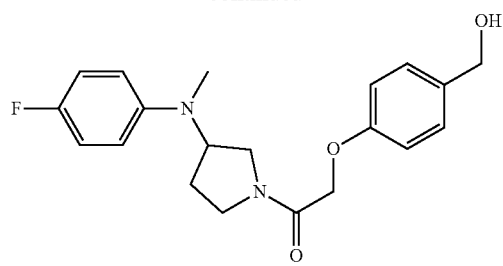
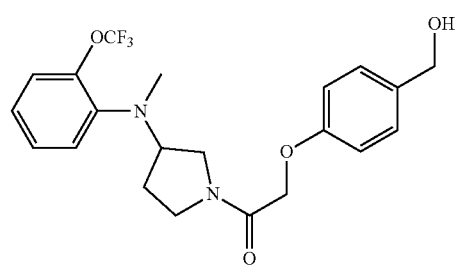
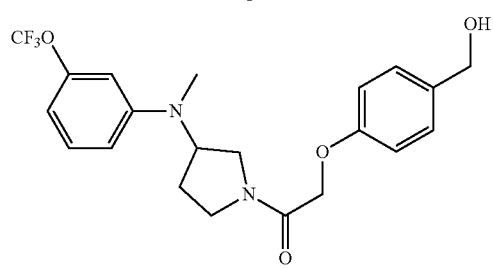
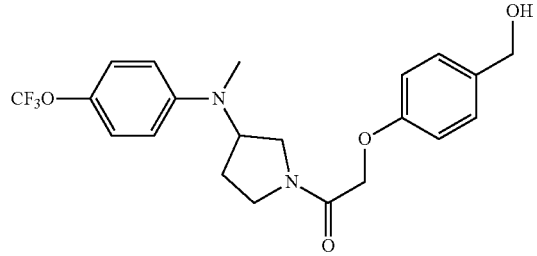
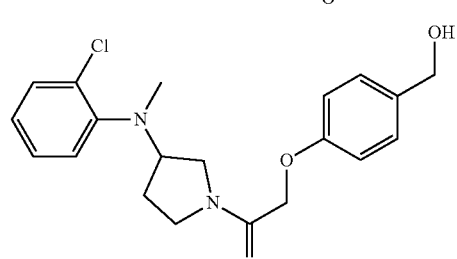
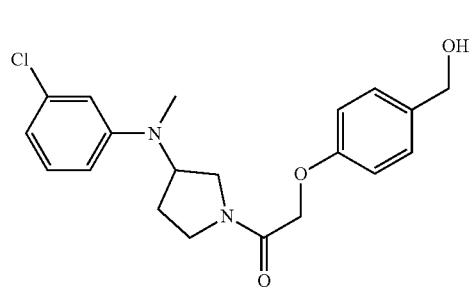

201
-continued
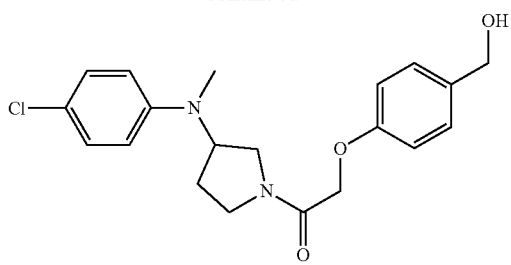
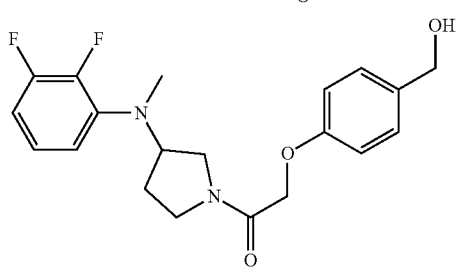
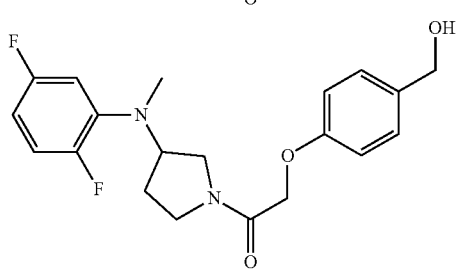
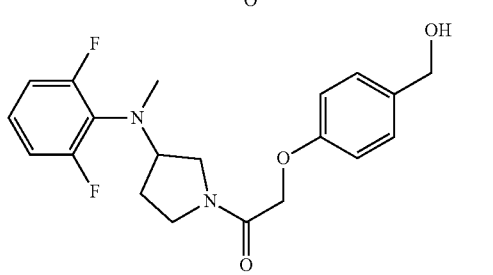
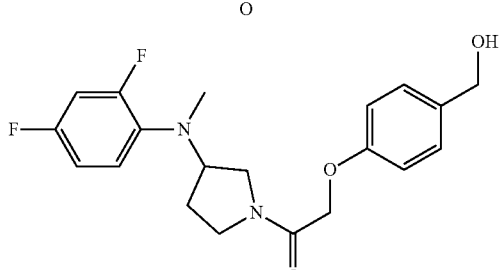
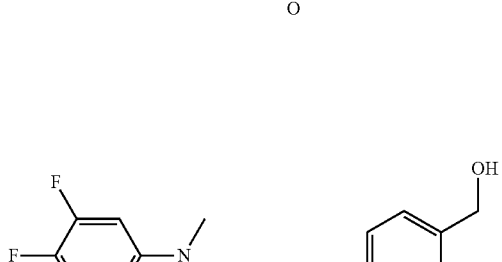
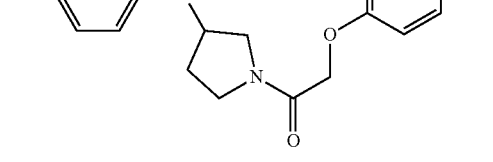
202
-continued
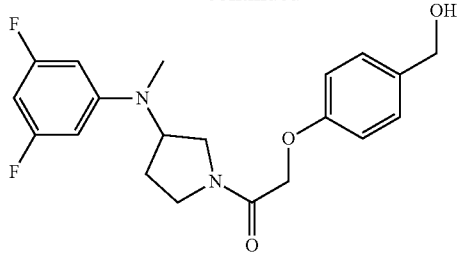
or a pharmaceutically acceptable salt, ester or prodrug form thereof.
In further embodiments, the compound is one of the following:
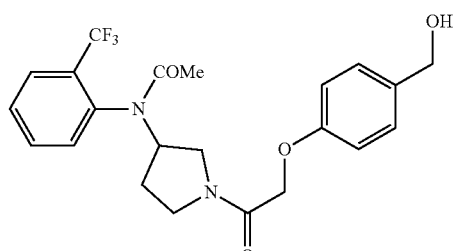
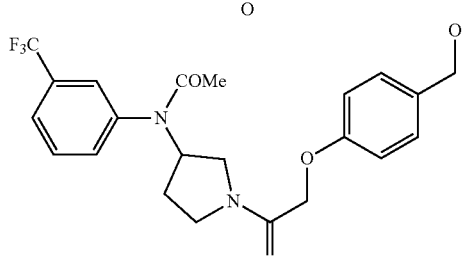
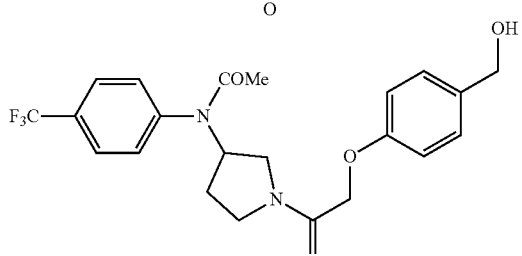
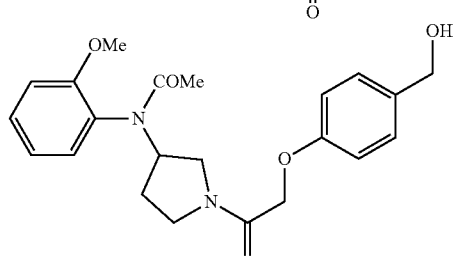
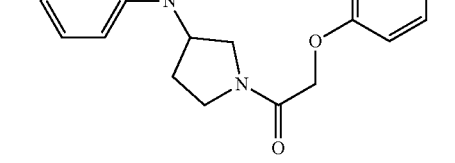

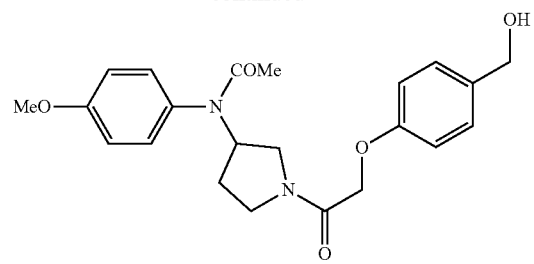
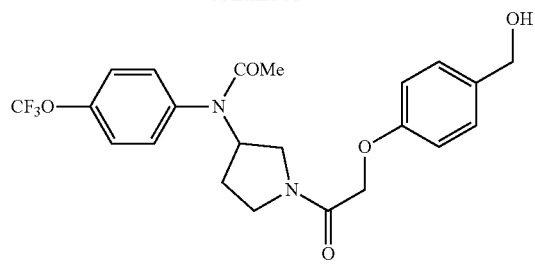
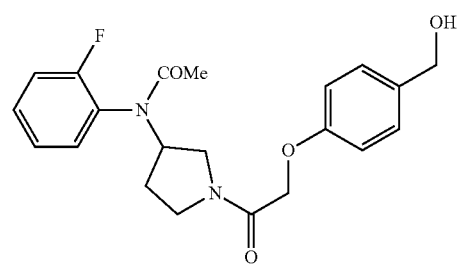
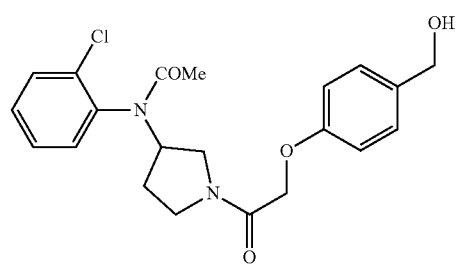
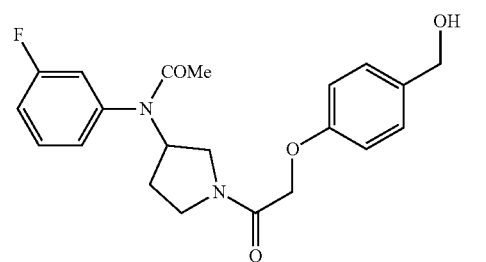
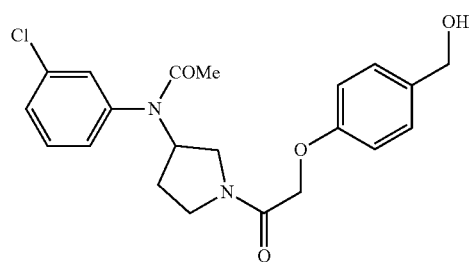
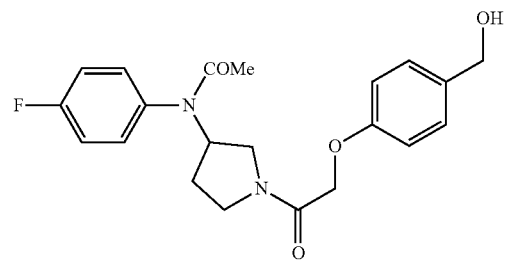
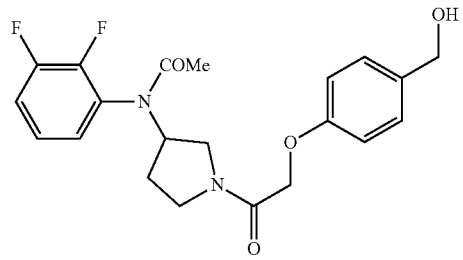
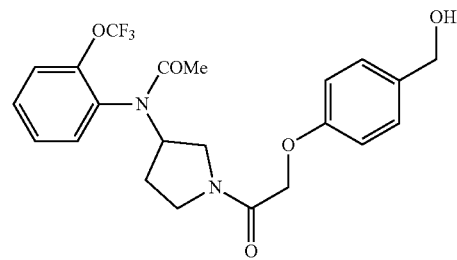
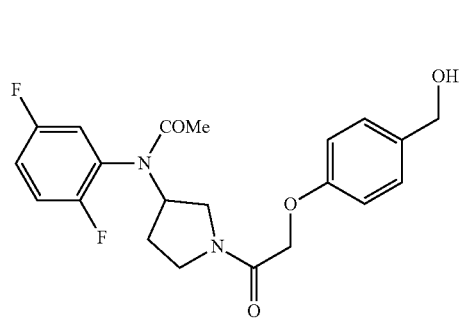
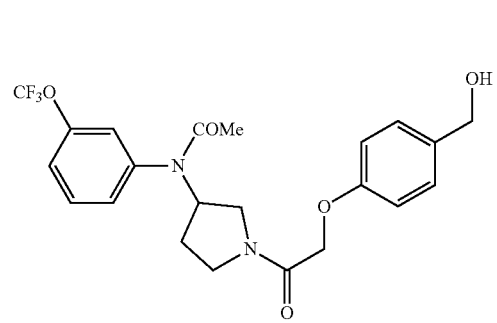

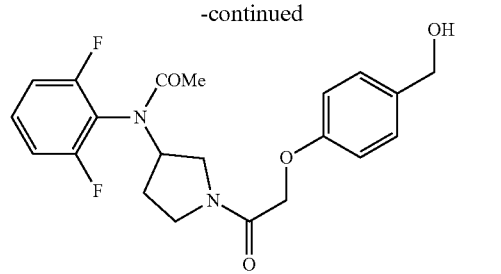
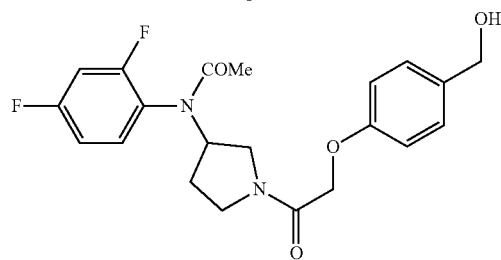
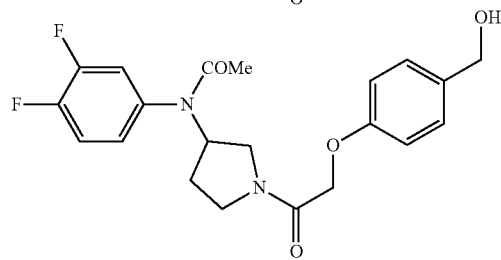
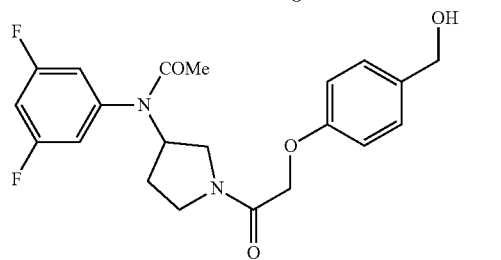
or a pharmaceutically acceptable salt, ester or prodrug form thereof.
In yet further embodiments, the compound is one of the following:
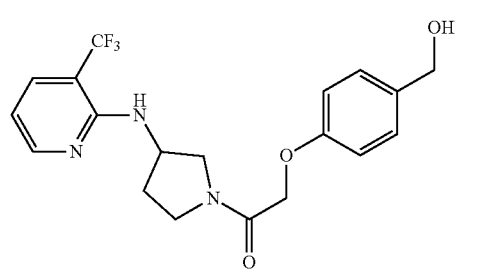
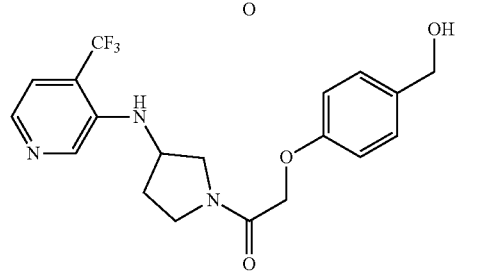
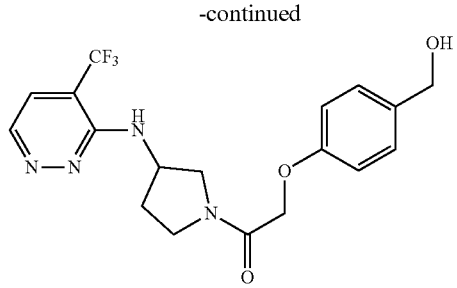
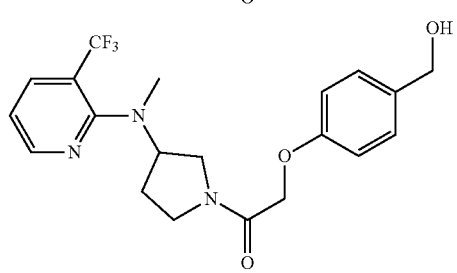
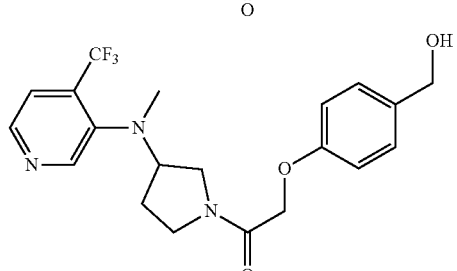
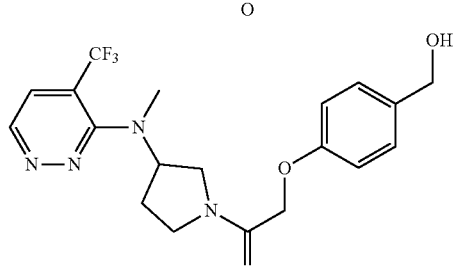
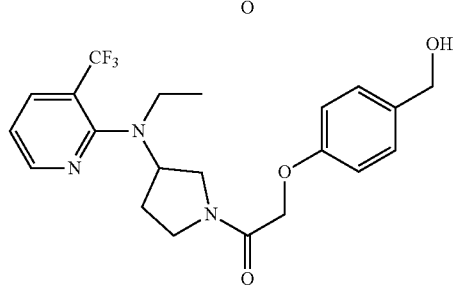

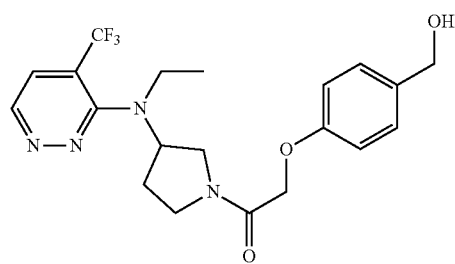
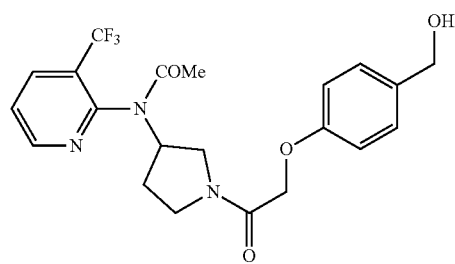
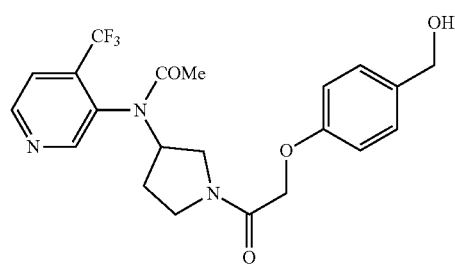
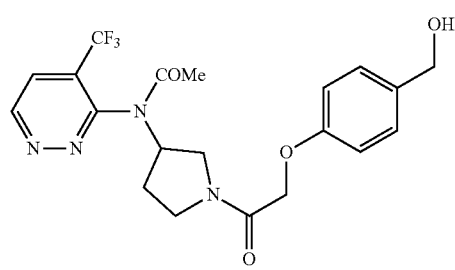
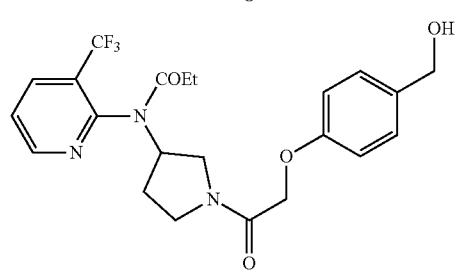
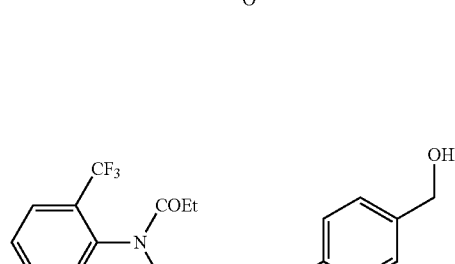
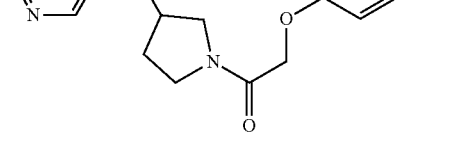
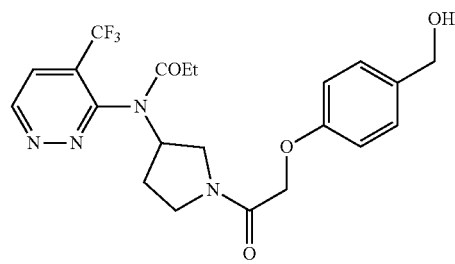
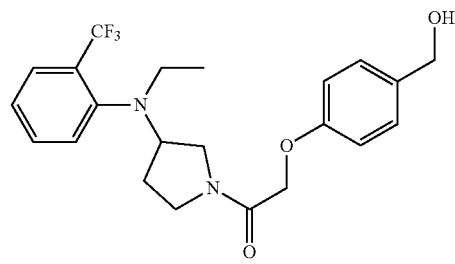
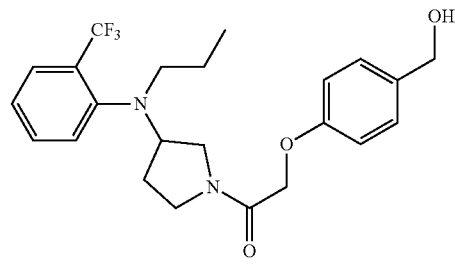
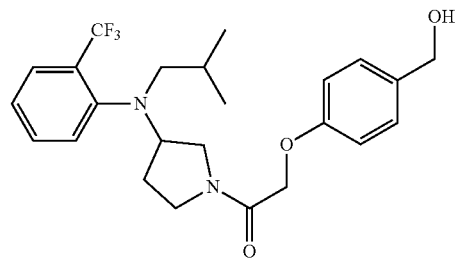
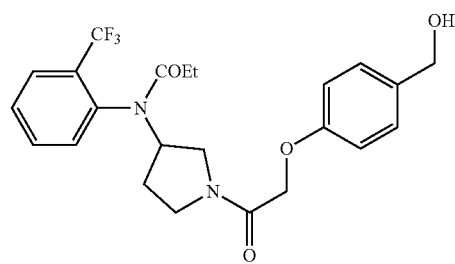
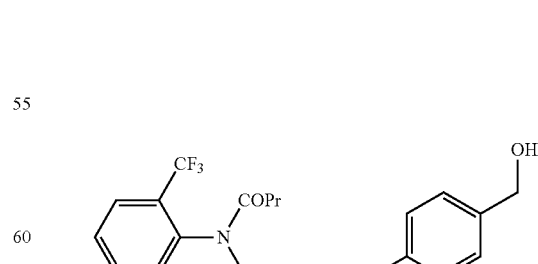
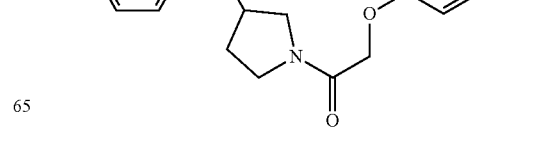

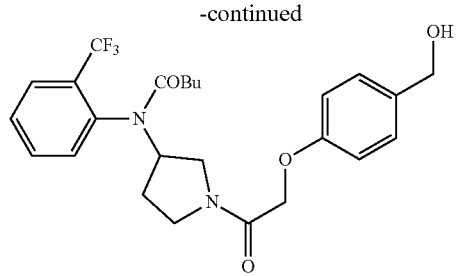
or a pharmaceutically acceptable salt, ester or prodrug form thereof.
In yet other embodiments, the compound is one of the following:
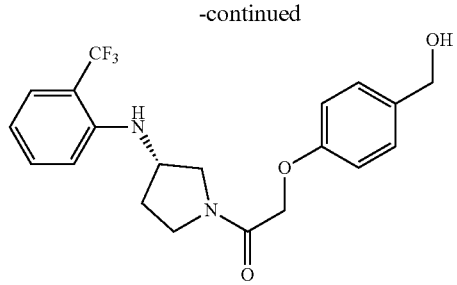
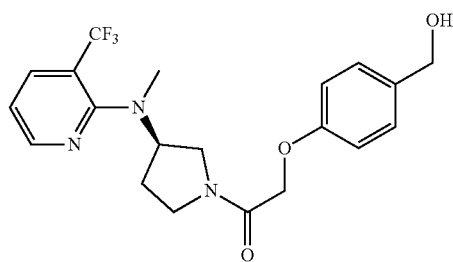
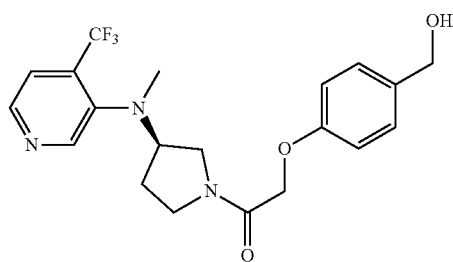
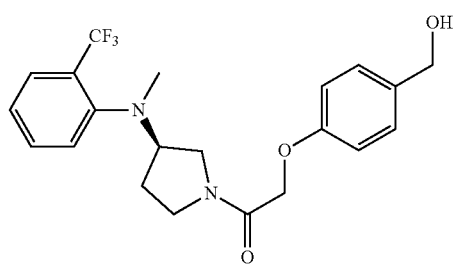
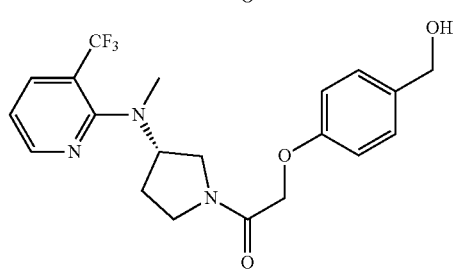
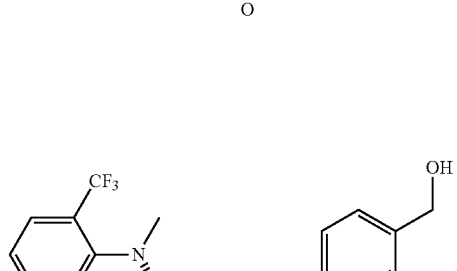
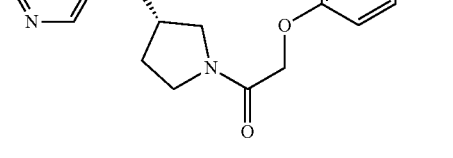

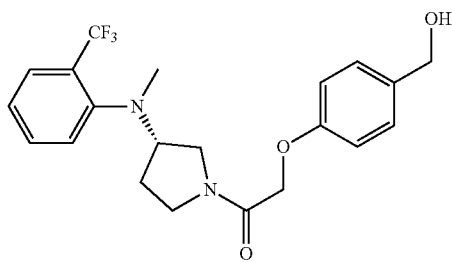
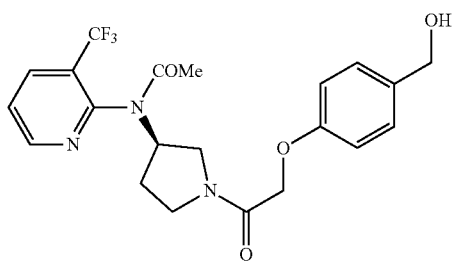
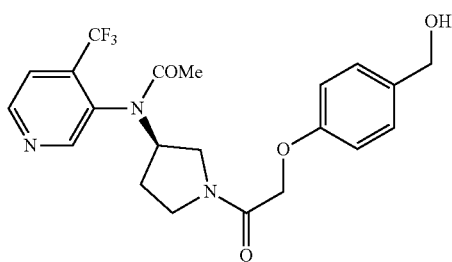
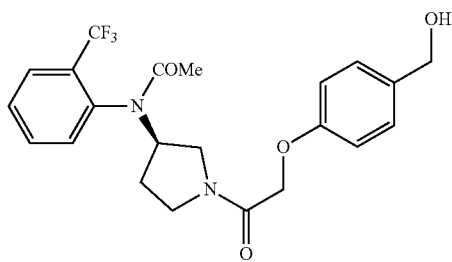
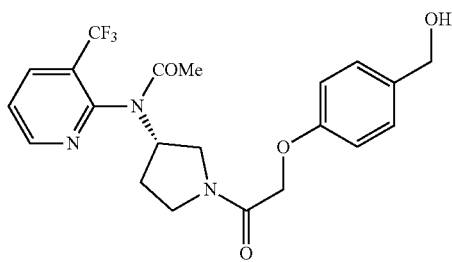
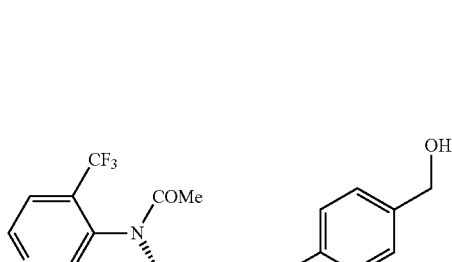
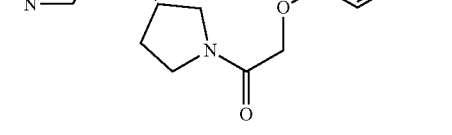

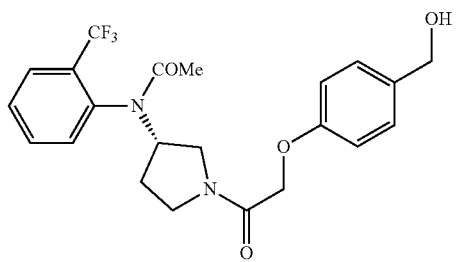

or a pharmaceutically acceptable salt, ester or prodrug form thereof.

In yet further embodiments, X is S, SO or $SO_2$; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or $SO_2$. In further embodiments, X is SO. In yet further embodiments X is $SO_2$.

In some embodiments, the compound is one of:

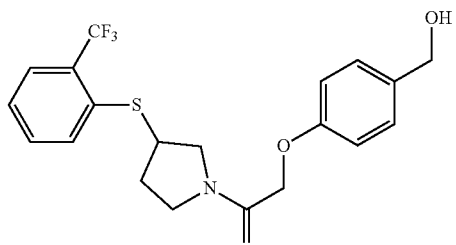

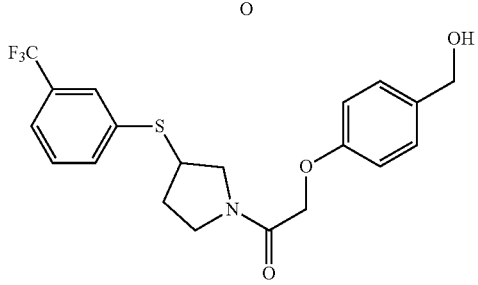

213
-continued
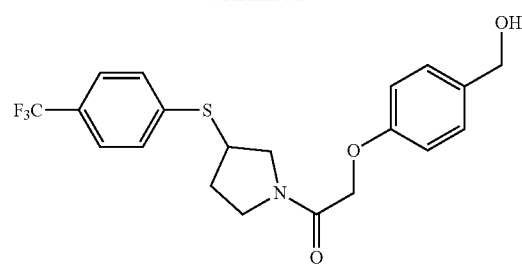
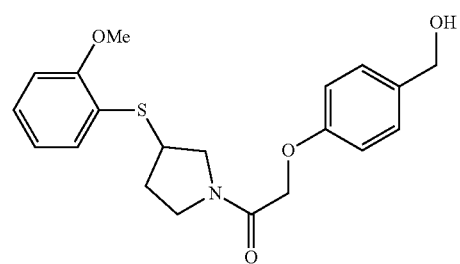
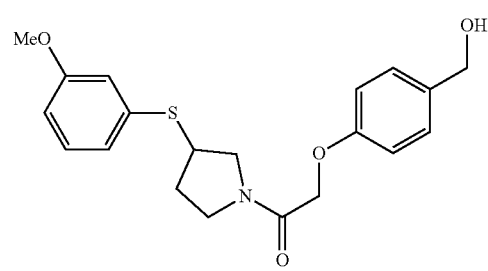
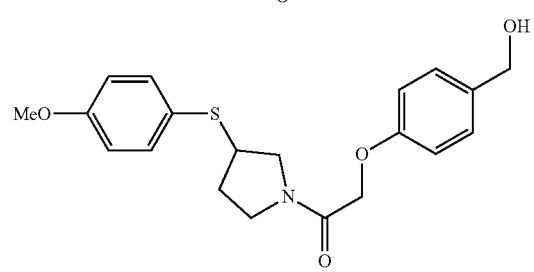
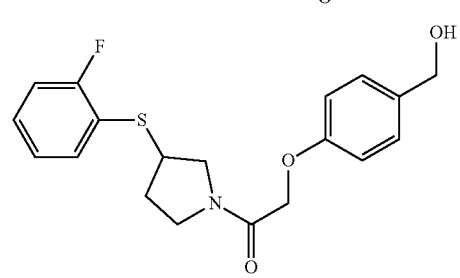
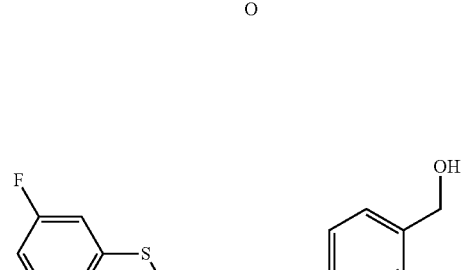
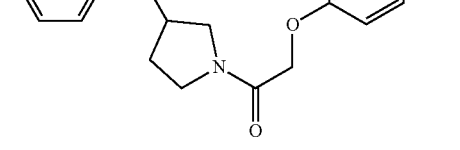
214
-continued
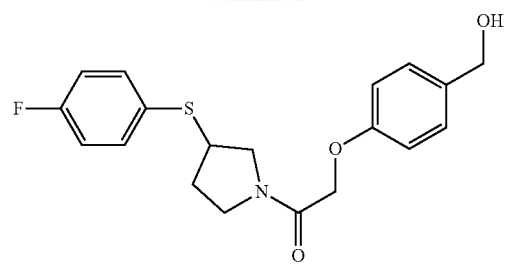
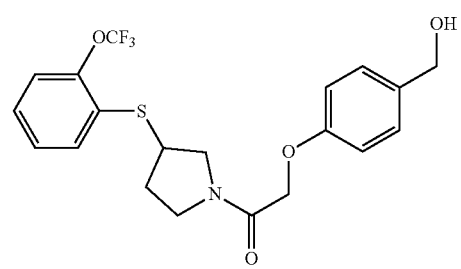
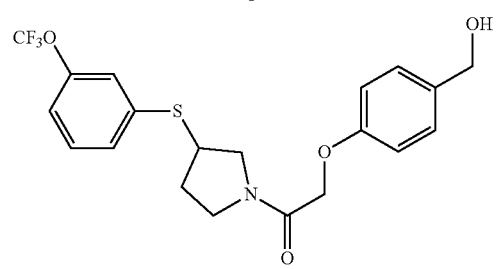
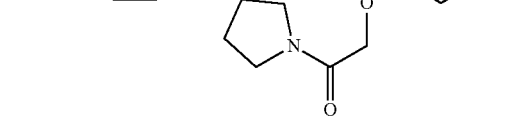
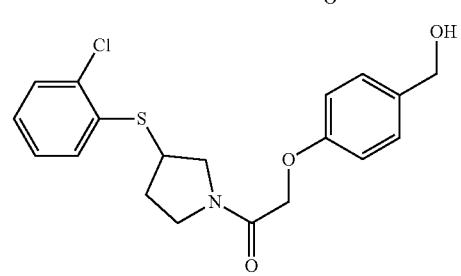
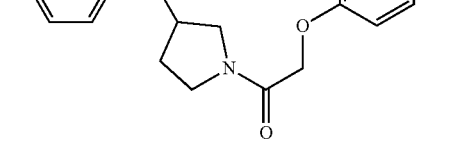

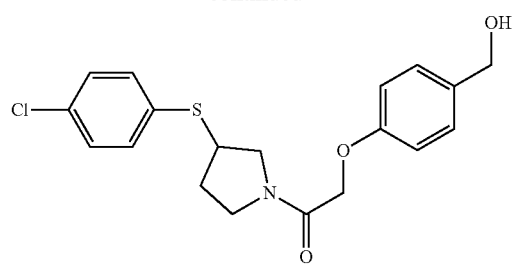
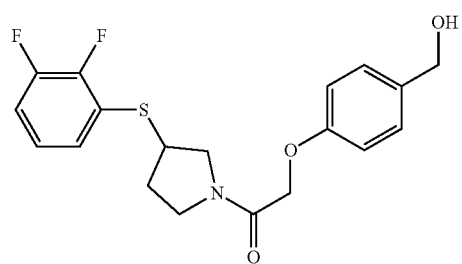 [SMILES: O=C(COc1ccc(CO)cc1)N1CCC(Oc2cccc(F)c2F)C1]

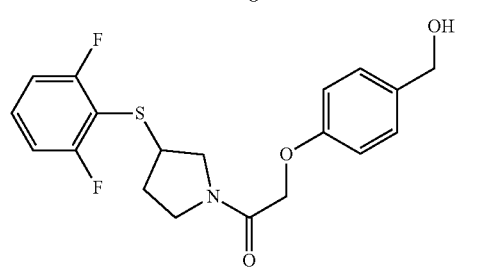
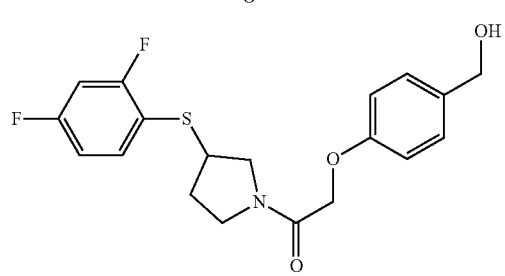
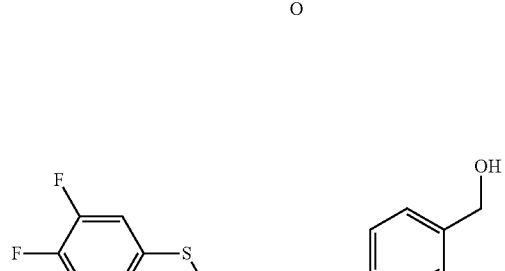
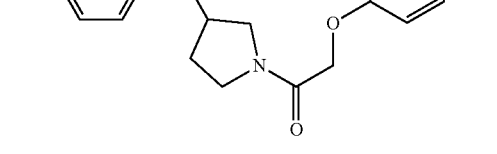
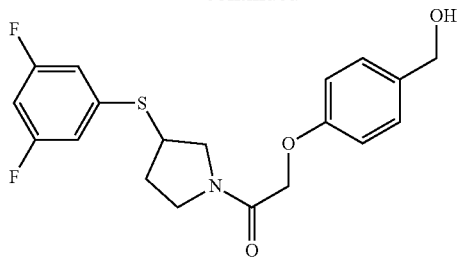
or a pharmaceutically acceptable salt, ester or prodrug form thereof.
In other embodiments, the compound is one of:
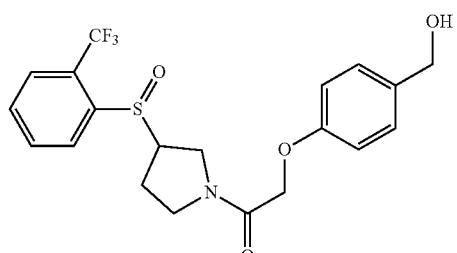
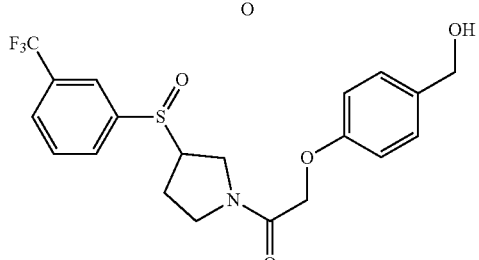
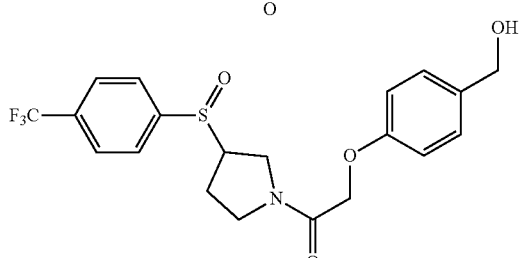
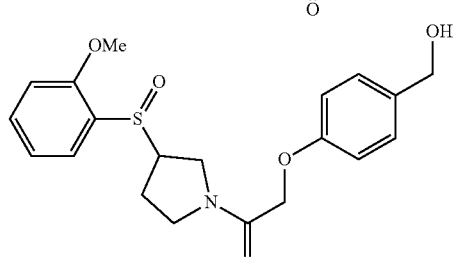
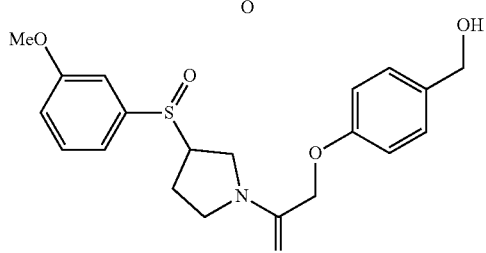

217
-continued
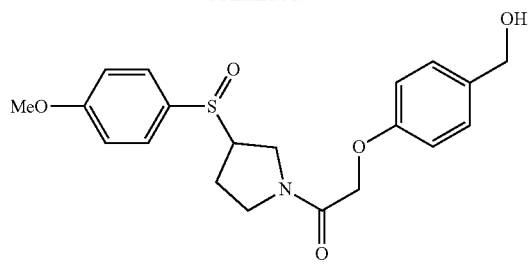
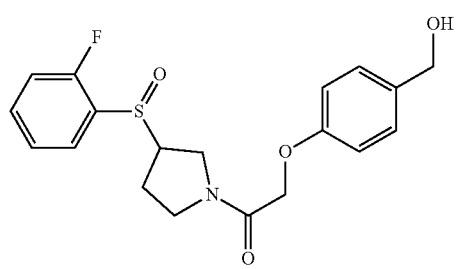
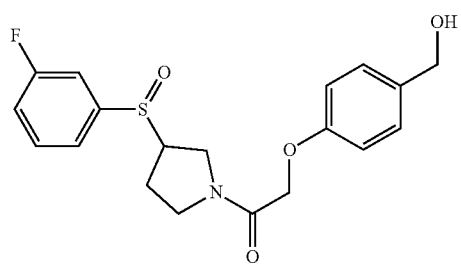
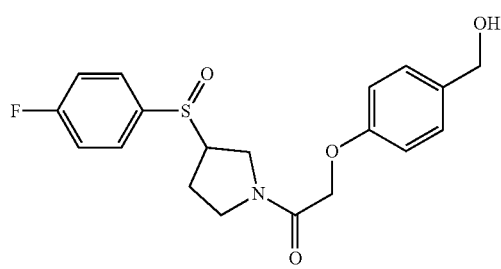
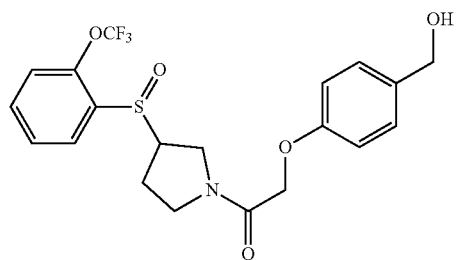
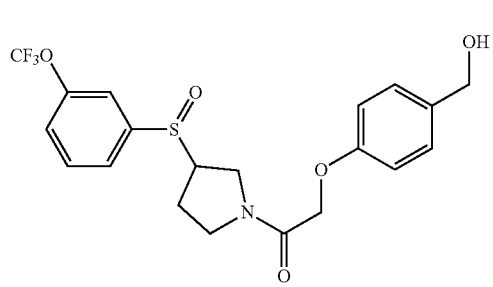
218
-continued
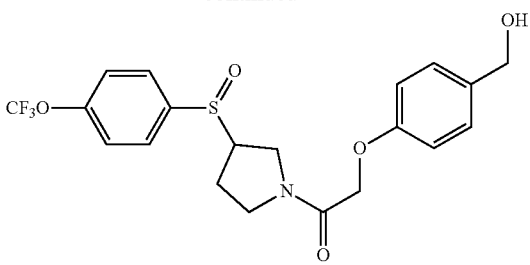
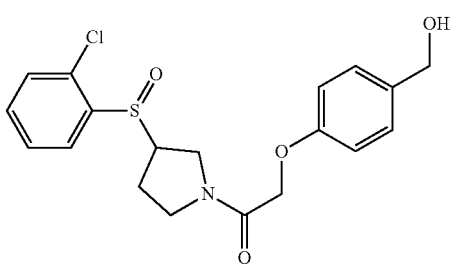
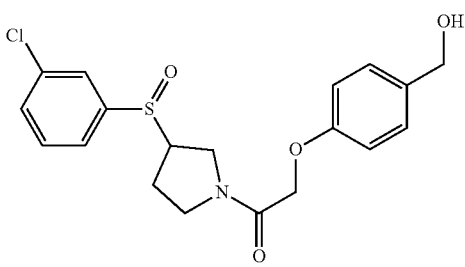
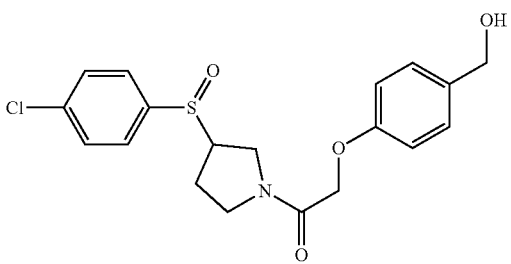
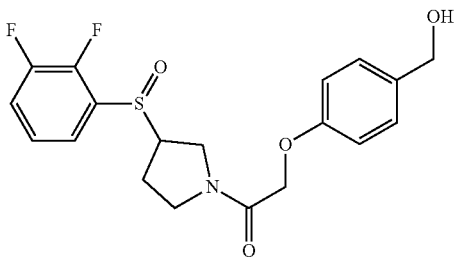
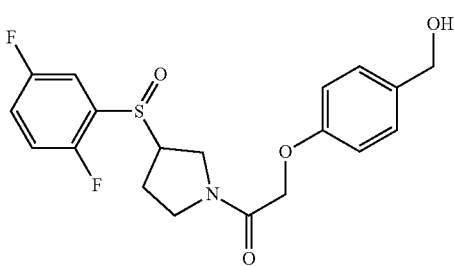

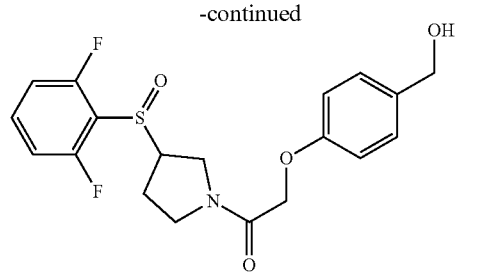
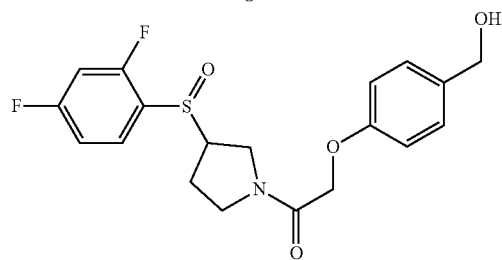
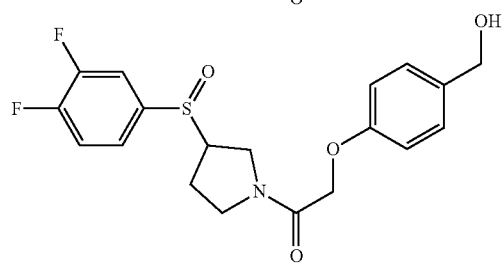
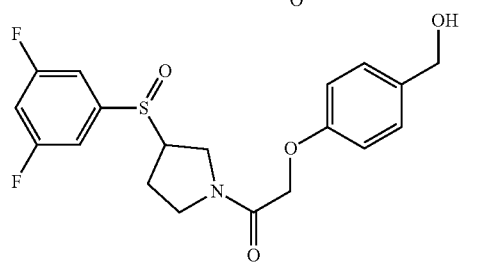
or a pharmaceutically acceptable salt, ester or prodrug form thereof.
In further embodiments, the compound is one of:
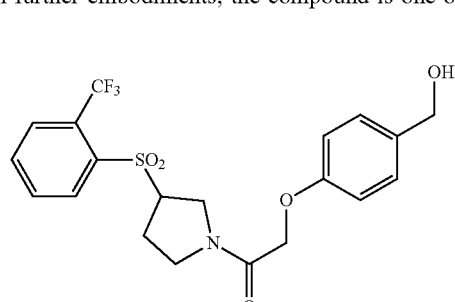
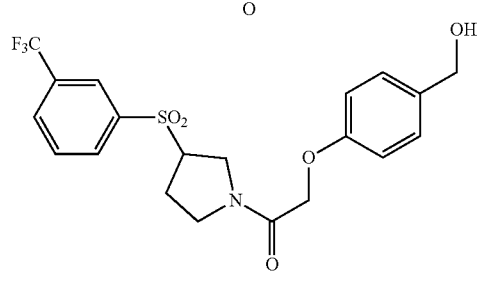
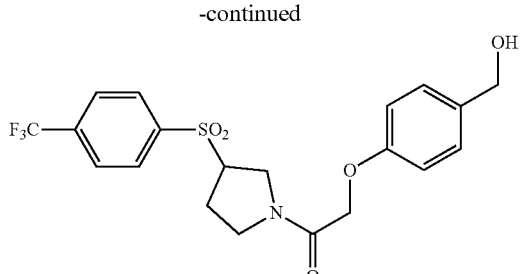
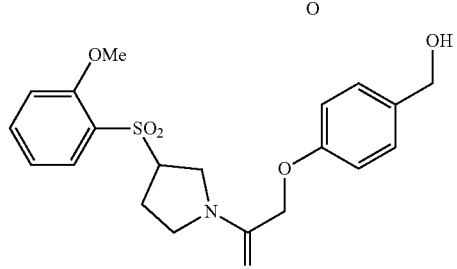
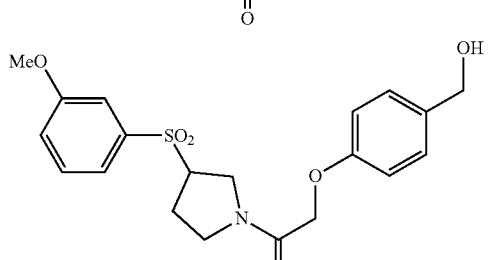
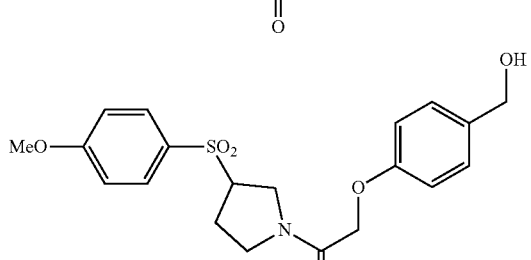
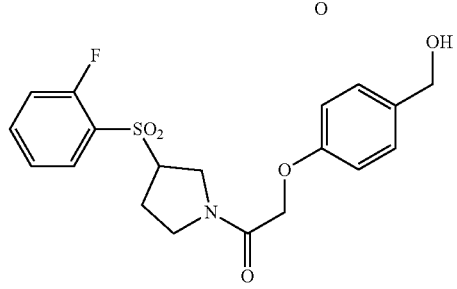
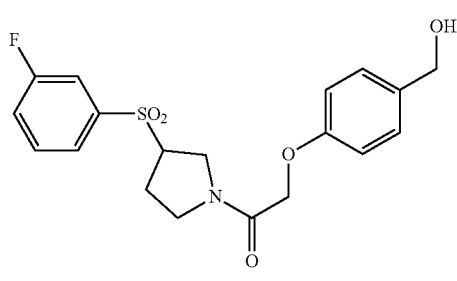

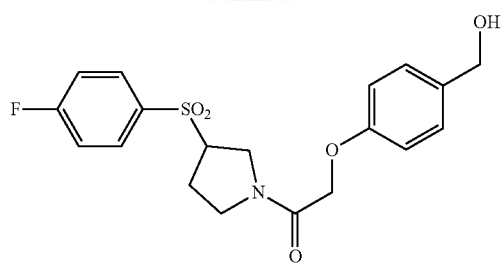
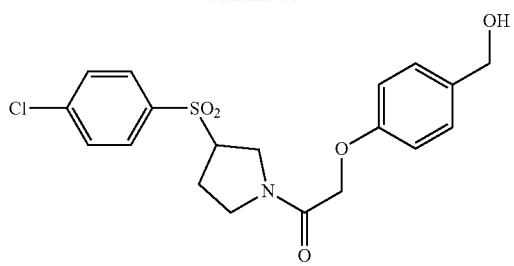
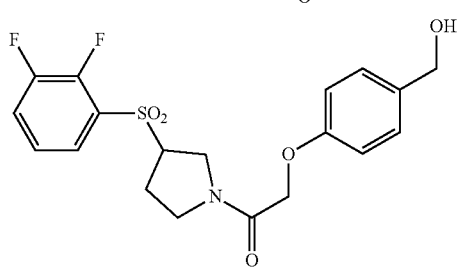
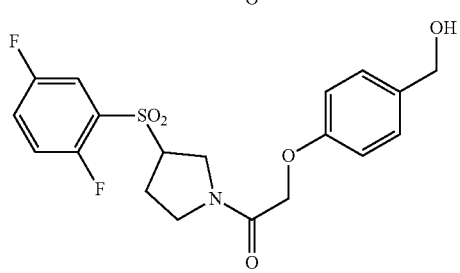
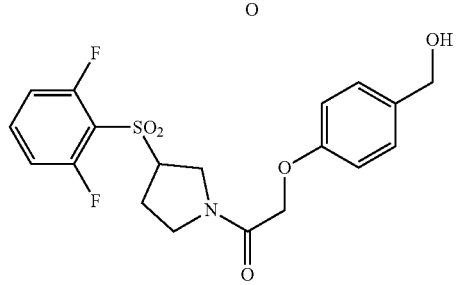
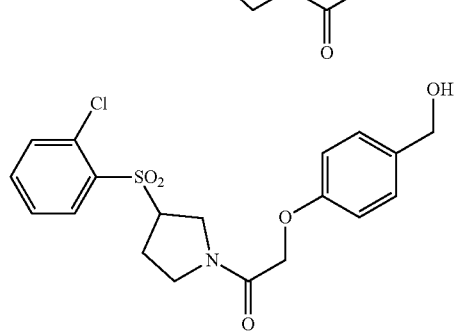
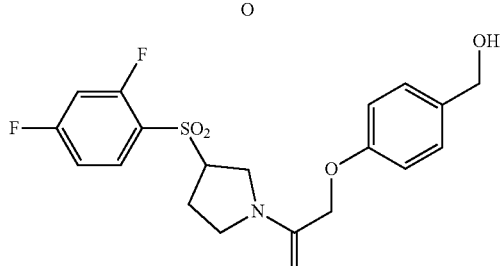
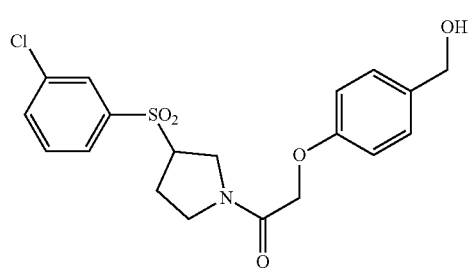
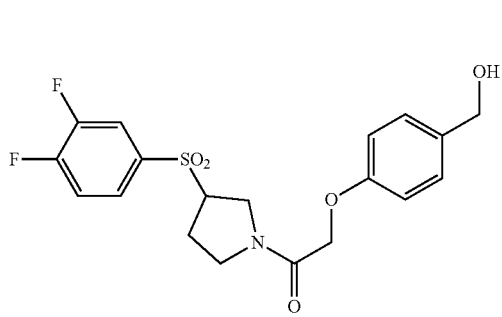 [SMILES: O=C(COc1ccc(CO)cc1)N1CCC(Oc2ccc(F)c(F)c2)C1]

-continued
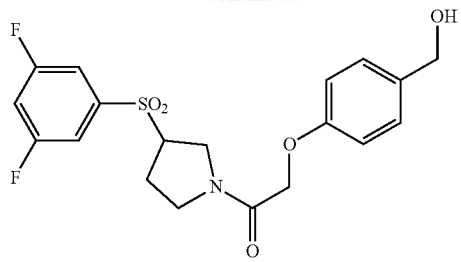 [SMILES: O=C(COc1ccc(CO)cc1)N1CCC(Oc2cc(F)cc(F)c2)C1]
or a pharmaceutically acceptable salt, ester or prodrug form thereof.
In yet further embodiments, the compound is one of:
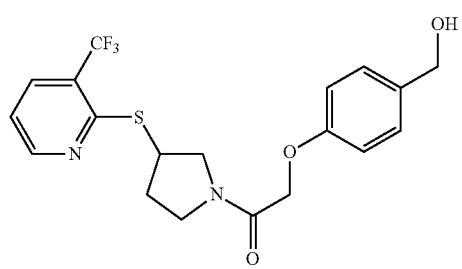
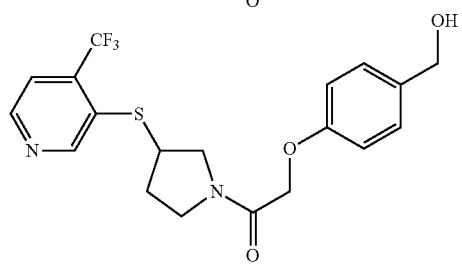
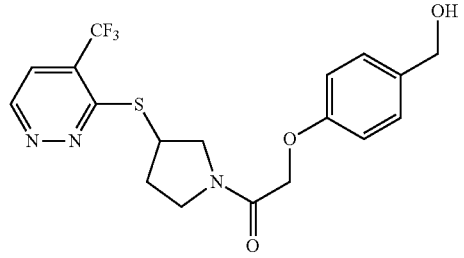
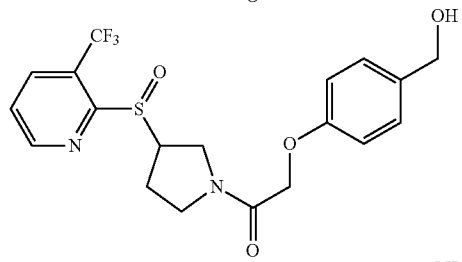
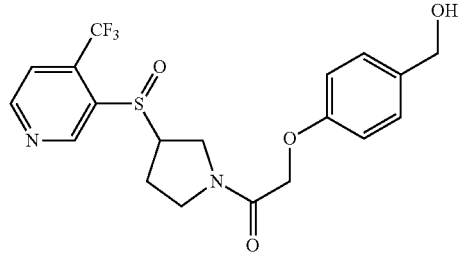
-continued
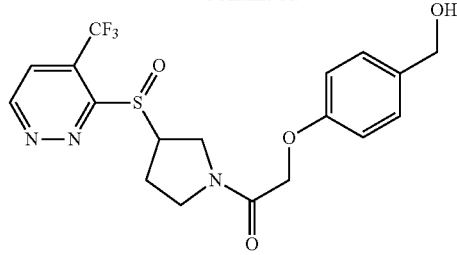
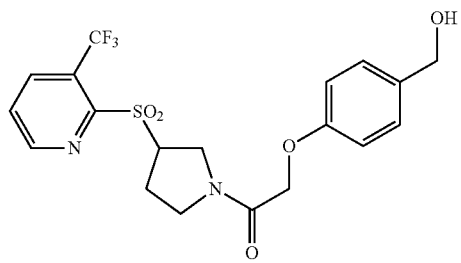
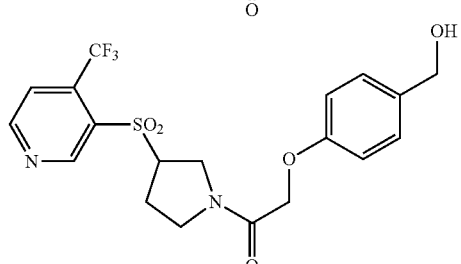
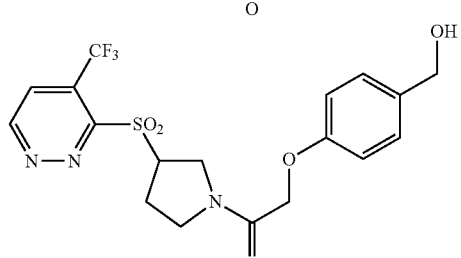
or a pharmaceutically acceptable salt, ester or prodrug form thereof.
In yet other embodiments, the compound is one of:
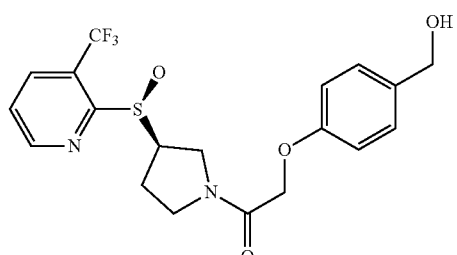
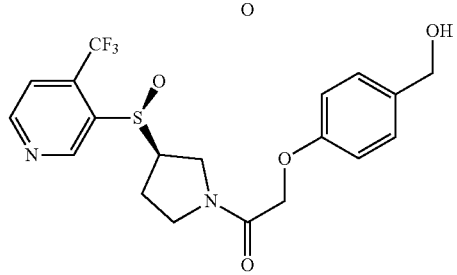

225
-continued

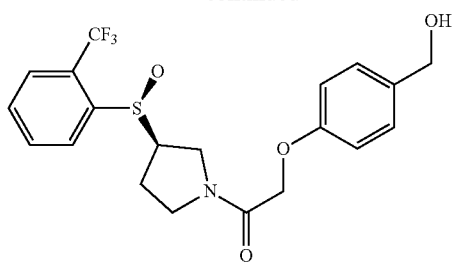

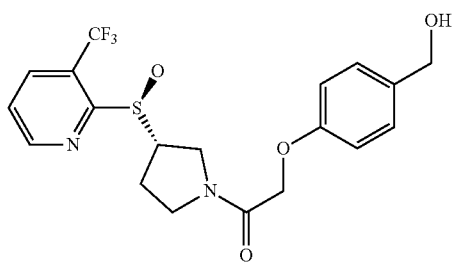

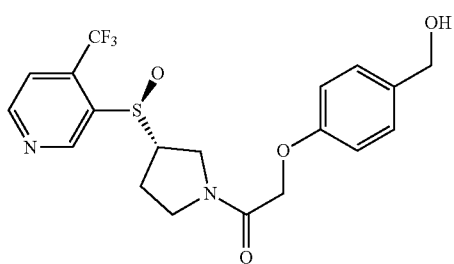

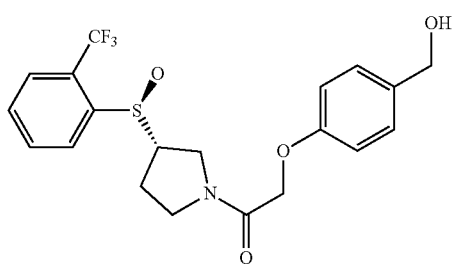

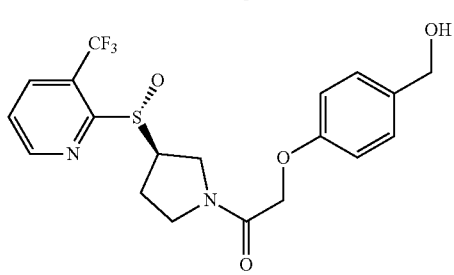


226
-continued

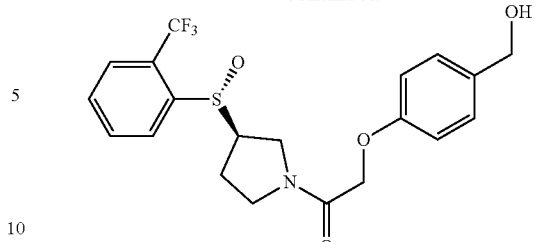

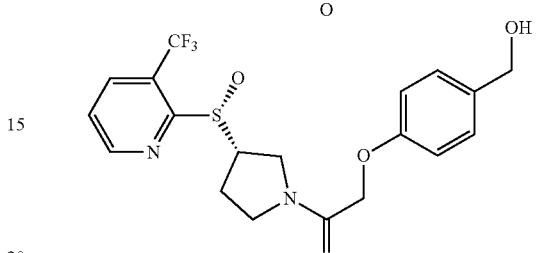

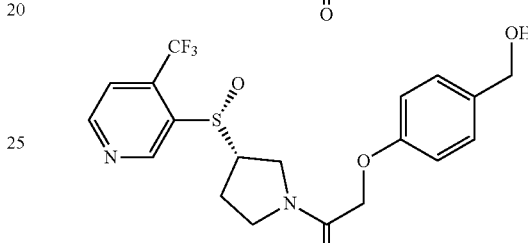

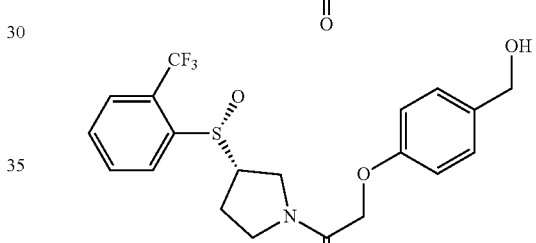

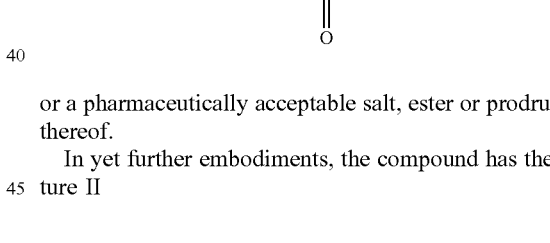

or a pharmaceutically acceptable salt, ester or prodrug form thereof.

In yet further embodiments, the compound has the structure II

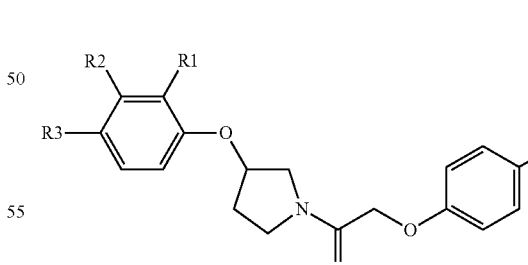

II wherein one of $R_1$ and $R_2$ and $R_3$, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$;

O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

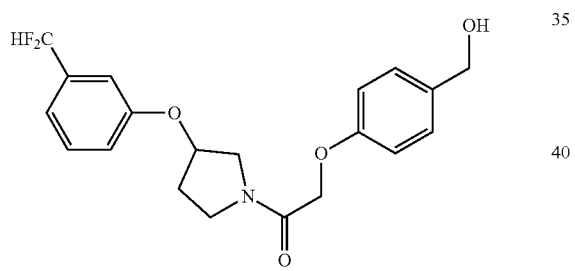

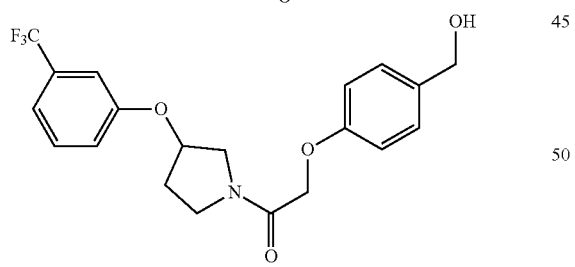



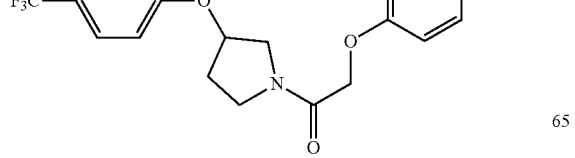

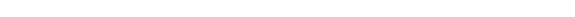

-continued

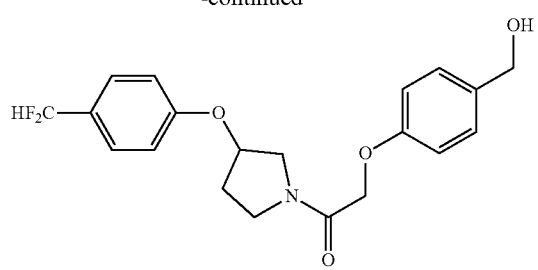

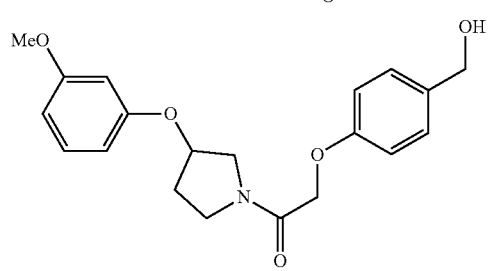

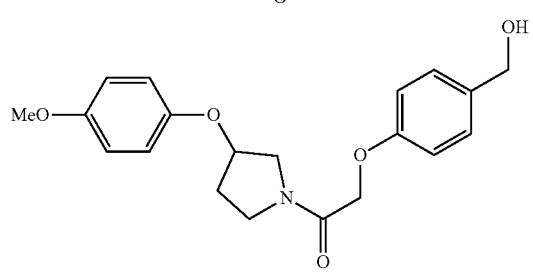

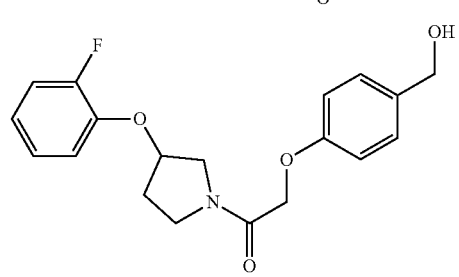

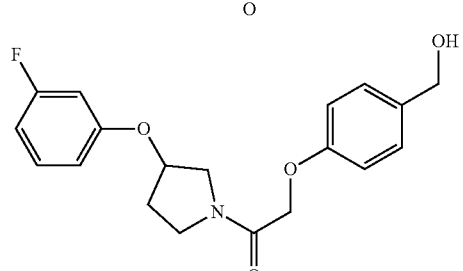

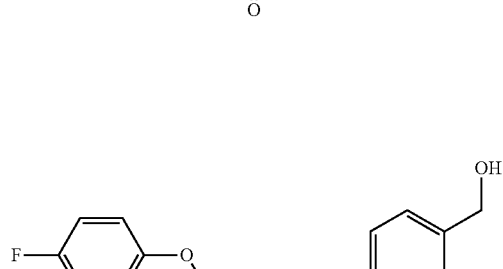

229
-continued
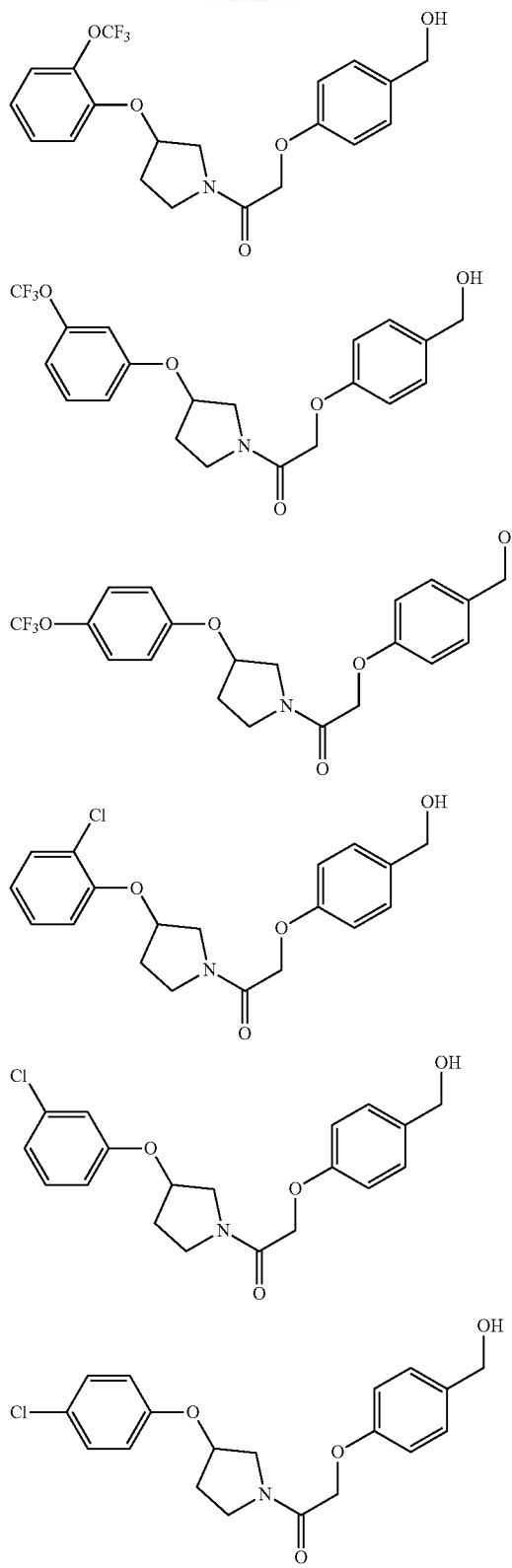
or a pharmaceutically acceptable salt, ester or prodrug form thereof.
230
In other embodiments the compound is one of the following:
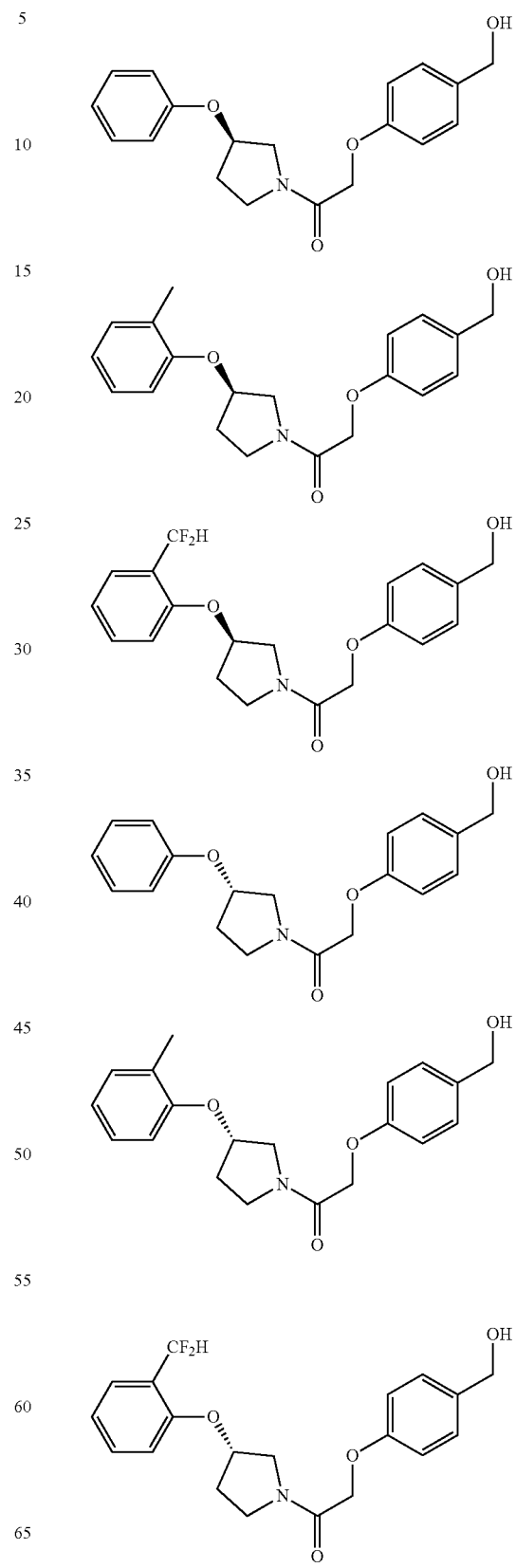

-continued

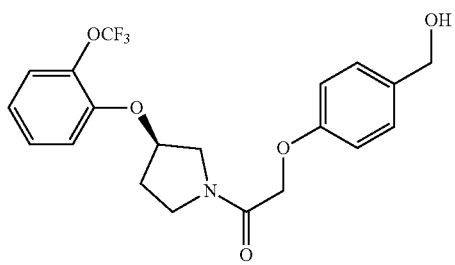
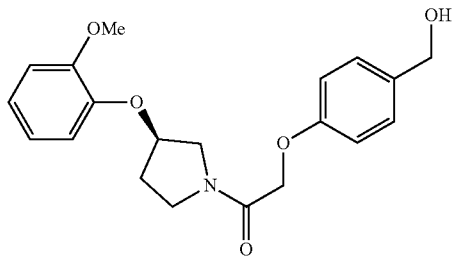
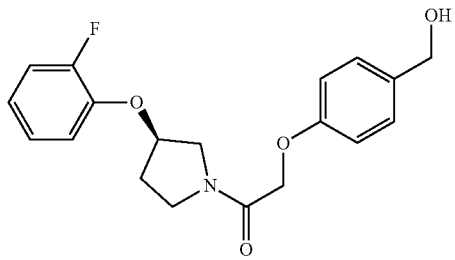
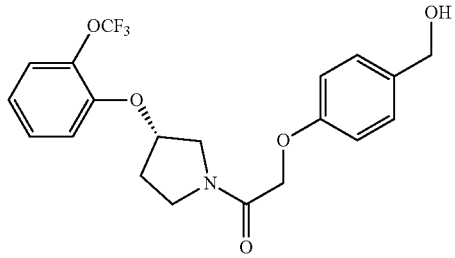
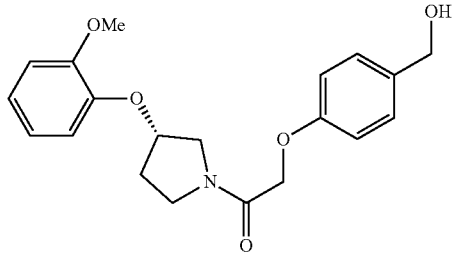
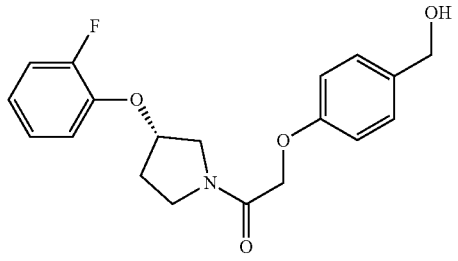

or a pharmaceutically acceptable salt, ester or prodrug form thereof.

In certain embodiments, the compound is one of the following:

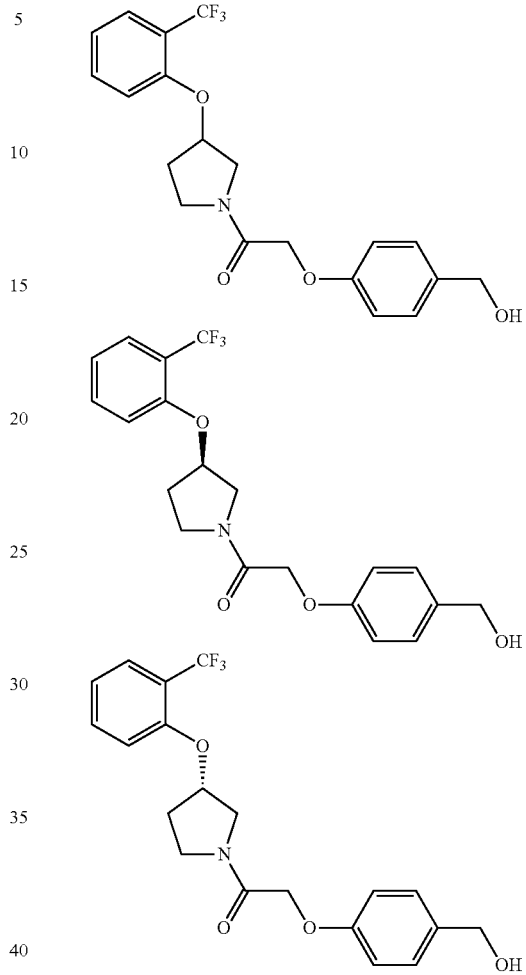

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of at least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol.

In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50

One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of at least 0.05%; (ii) di-sodium EDTA at a concentration of at least 0.001%; and (iii) Trolamine to provide an apparent pH in the range 6.50 to 7.50. In certain embodiments, the pharmaceutical composition comprises both (i) butylated hydroxytoluene (BHT) at a concentration of at least 0.05%; and (ii) di-sodium EDTA at a concentration of at least 0.001%. In another embodiment, the pharmaceutical composition comprises each of (i) butylated hydroxytoluene (BHT) at a concentration of at least 0.05%; (ii) di-sodium EDTA at a concentration of at least 0.001%; and (iii) Trolamine to provide an apparent pH in the range 6.50 to 7.50.

In a certain embodiment, the pharmaceutical composition comprises:
 (i) ethanol in the range of 1.0-20.0% w/w;
 (ii) phenoxyethanol in the range 0.1-5.0% w/w;
 (iii) diethylene glycol monoethyl ether (otherwise known as DEGEE or Transcutol P®) in the range 5.0-40.0% w/w;
 (iv) propylene glycol in the range 5.0-40.0% w/w;
 (v) PEG400 in the range 5.0-40.0% w/w; and
 (vi) a carbomer such as carbomer homopolymer type C980 in the range of 0.5 to 2.0% w/w.

In another certain embodiment, the pharmaceutical composition comprises:
 (i) ethanol in the range of 1.0-20.0% w/w;
 (ii) phenoxyethanol in the range 0.1-5.0% w/w;
 (iii) diethylene glycol monoethyl ether (otherwise known as DEGEE or Transcutol P®) in the range 5.0-40.0% w/w;
 (iv) propylene glycol in the range 5.0-40.0% w/w;
 (v) PEG400 in the range 5.0-40.0% w/w;
 (vi) a carbomer such as carbomer homopolymer type C980 in the range of 0.5 to 2.0% w/w; (vii) butylated hydroxytoluene (BHT) at a concentration of at least 0.05%;
 (viii) di-sodium EDTA at a concentration of at least 0.001%; and
 (ix) Trolamine to provide an apparent pH in the range 6.50 to 7.50.

In another embodiment, the pharmaceutical composition comprises:
 (i) ethanol in the range of 5.0-15.0% w/w;
 (ii) phenoxyethanol in the range 0.5-2.0% w/w;
 (iii) diethylene glycol monoethyl ether (otherwise known as DEGEE or Transcutol P®) in the range 20.0-30.0% w/w;
 (iv) propylene glycol in the range 15.0-25.0% w/w;

(v) PEG400 in the range 15.0-25.0% w/w; and
(vi) a carbomer such as carbomer homopolymer type C980 in the range of 0.75 to 1.5% w/w.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.
(vii) butylated hydroxytoluene (BHT) at a concentration of least 0.1%;
(viii) di-sodium EDTA at a concentration of least 0.005%; and
(ix) Trolamine to provide an apparent pH in the range 6.50 to 7.50.

In specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w; and
(vii) water at a concentration of 19.5-22% w/w.

In yet other specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w;
(vii) butylated hydroxytoluene (BHT) at a concentration of 0.1% w/w;
(viii) di-sodium EDTA at a concentration of 0.005% w/w;
(ix) Trolamine at a concentration of 0.375% w/w; and
(x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxy)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6%

In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments a second therapeutic agent is present.

In some embodiments the BMI (Body Mass Index) of the patient to be treated is a BMI>25, a BMI range of 25-30, a BMI range of 30-40, a range of BMI>40.

In other embodiments the obesity is associated with a prediabetic state, in yet other embodiments the obesity is associated with diabetes In some embodiments, the duration of treatment is greater than 28 days.

In further embodiments, the duration of treatment is between one and six months or thereabouts. In yet further embodiments, the duration of treatment is between one and twenty four months or thereabouts; one and eighteen months or thereabouts; one and twelve months or thereabouts; one and three months or thereabouts; one and two months or thereabouts; or one month or thereabouts.

The present invention also provides a method of treating Non-Alcoholic Fatty Liver Disease (NAFLD) and the more severe Non-Alcoholic SteatoHepatitis (NASH) in a subject which comprises administering to an area of skin, including an area of excess fat, a composition comprising a pharmaceutically acceptable carrier, which provides an environment of physical and chemical stability, and an amount of a compound or of a pharmaceutically acceptable salt of the compound or ester of the compound or prodrug of the compound effective to treat the skin condition, wherein the compound has the structure I:

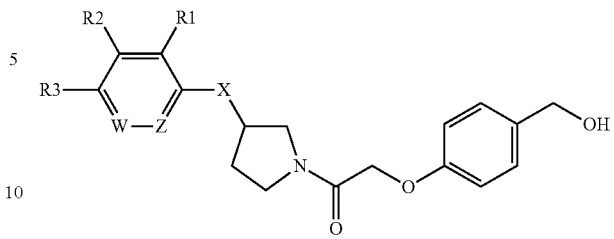

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I, $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR)NR_9R_{10}$;
wherein adjacent substituents $R_1$, $R_2$ and $R_3$ and $R_4$ and $R_5$, if present, may form a saturated or unsaturated 5-membered or 6-membered carbocyclic or heterocyclic ring;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;

In some embodiments, X is O; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.
In some embodiments, the compound is one of the following:
or a pharmaceutically acceptable salt, ester or prodrug form thereof.
In further embodiments, the compound is one of the following:
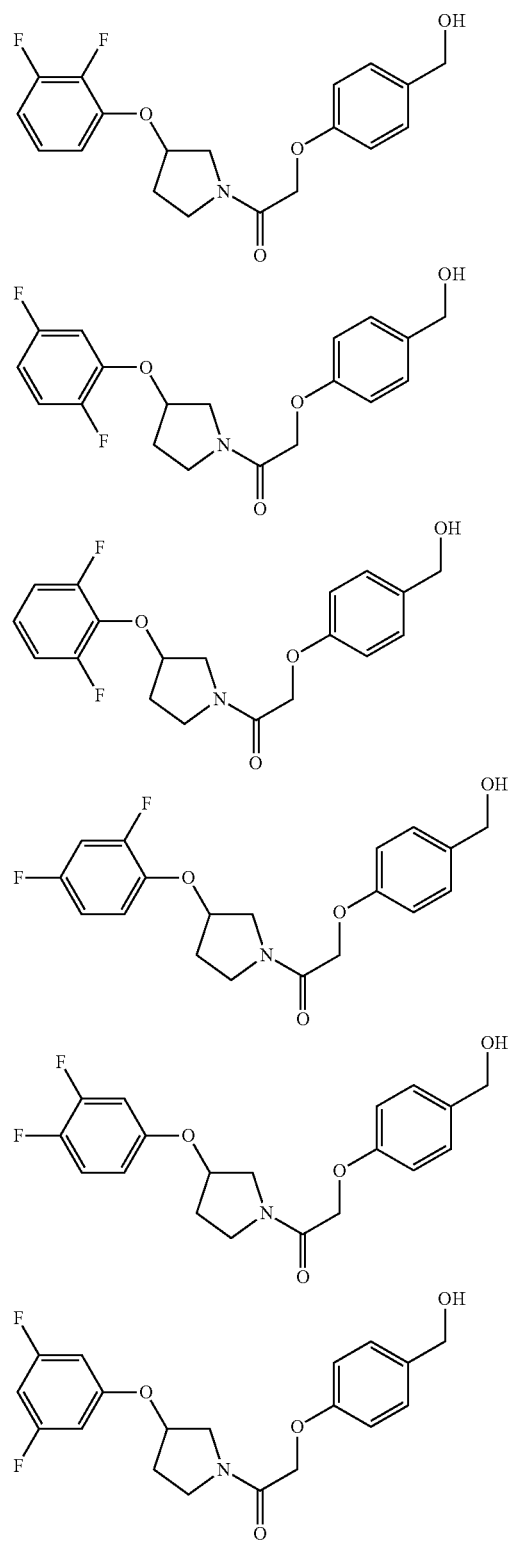
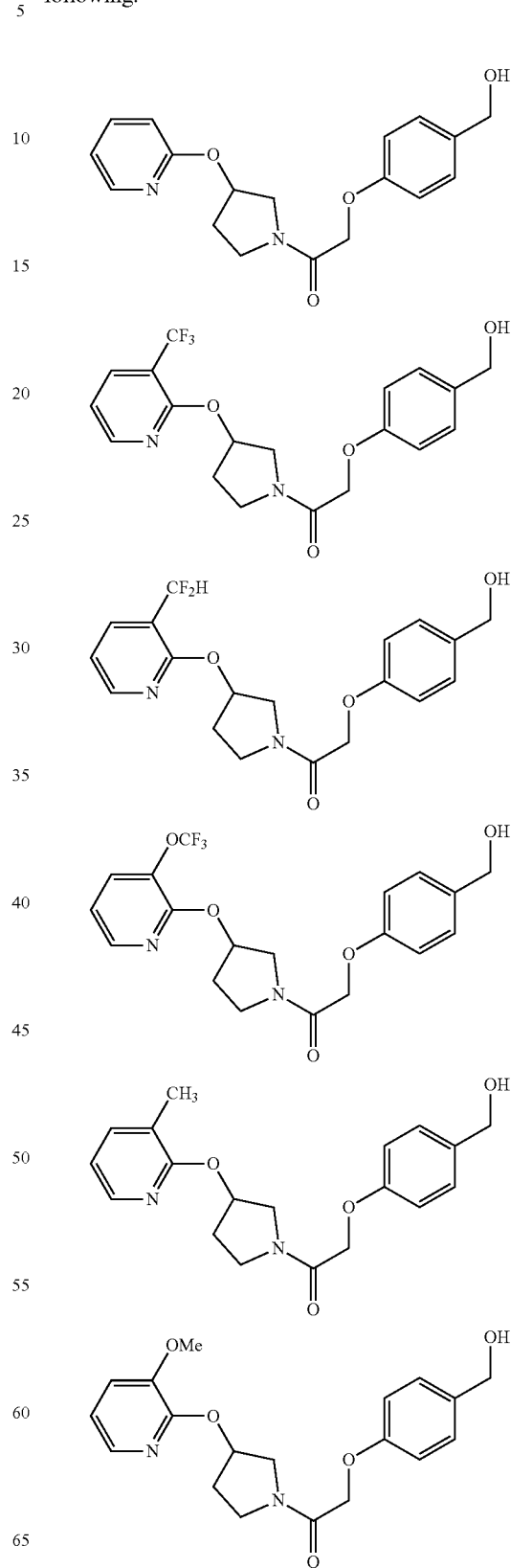

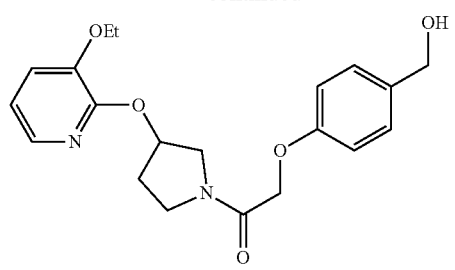 [SMILES: CCOc1cccnc1OC1CCN(C(=O)COc2ccc(CO)cc2)C1]
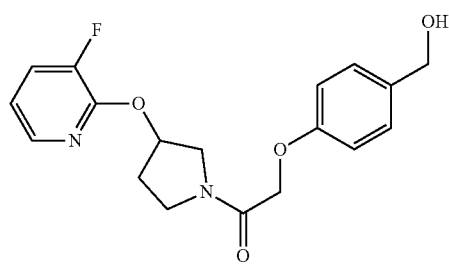 [SMILES: O=C(COc1ccc(CO)cc1)N1CCC(Oc2ncccc2F)C1]
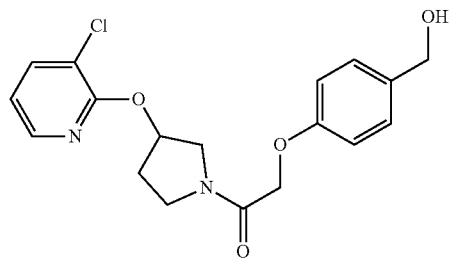 [SMILES: O=C(COc1ccc(CO)cc1)N1CCC(Oc2ncccc2Cl)C1]
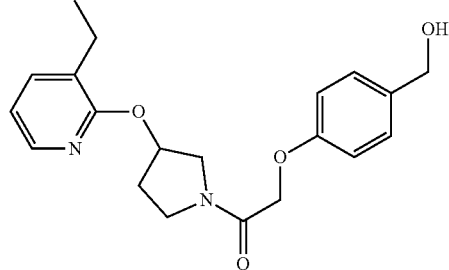 [SMILES: CCc1cccnc1OC1CCN(C(=O)COc2ccc(CO)cc2)C1]
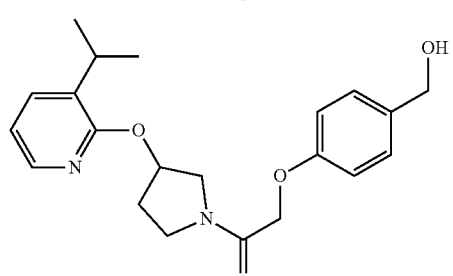
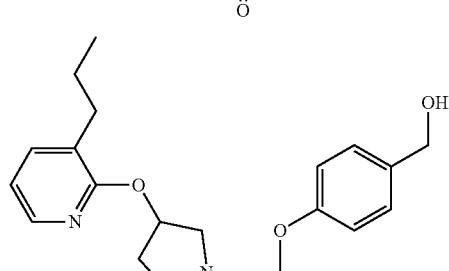
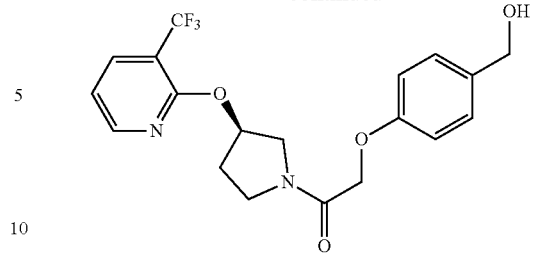
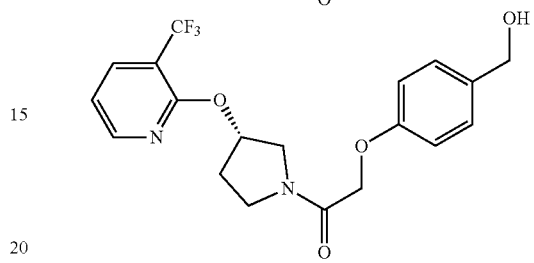
or a pharmaceutically acceptable salt, ester or prodrug form thereof.
In yet other embodiments, the compound is one of the following:
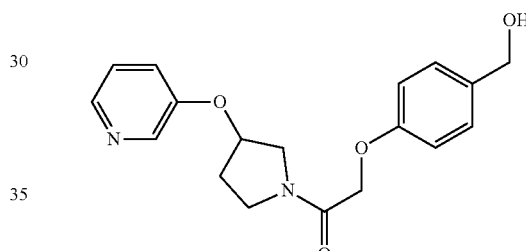
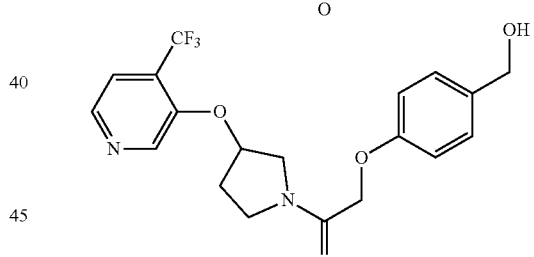
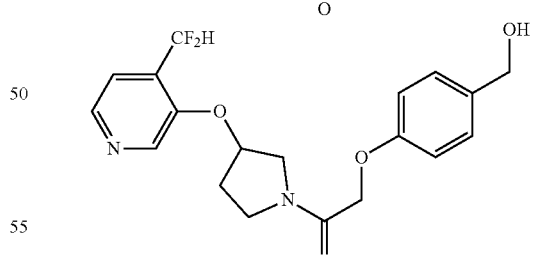
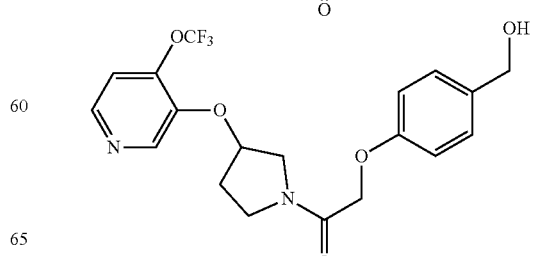

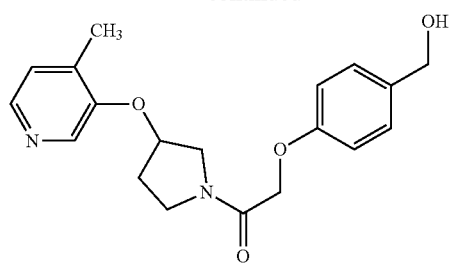 [SMILES: O=C(COc1ccc(CO)cc1)N1CCC(Oc2cnccc2C(F)(F)F)C1]
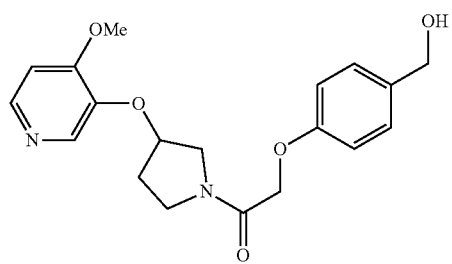 [SMILES: COc1ccncc1OC1CCN(C(=O)COc2ccc(CO)cc2)C1]
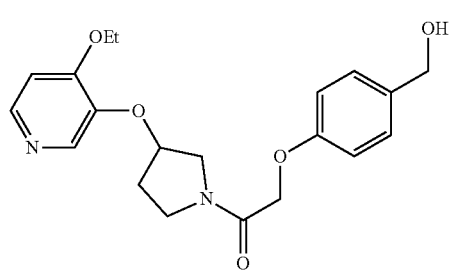
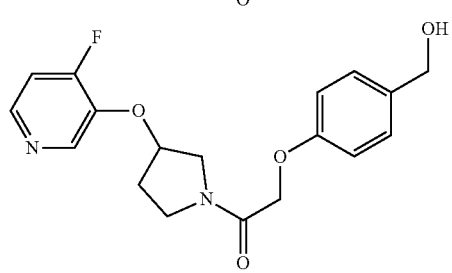 [SMILES: CCc1ccncc1OC1CCN(C(=O)COc2ccc(CO)cc2)C1]
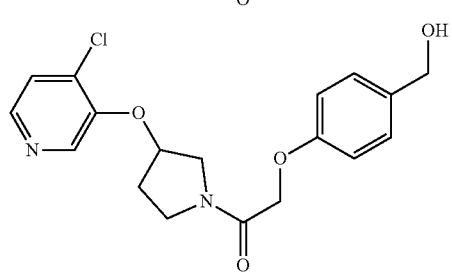
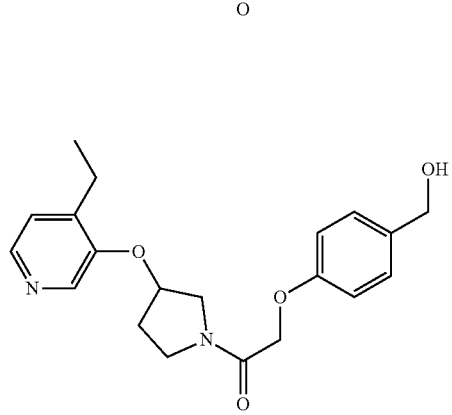
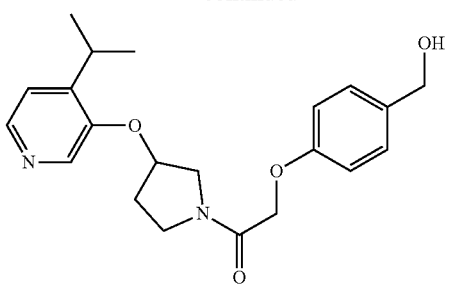 [SMILES: CC(C)c1ccncc1OC1CCN(C(=O)COc2ccc(CO)cc2)C1]
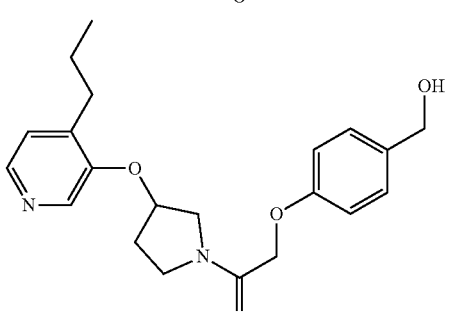
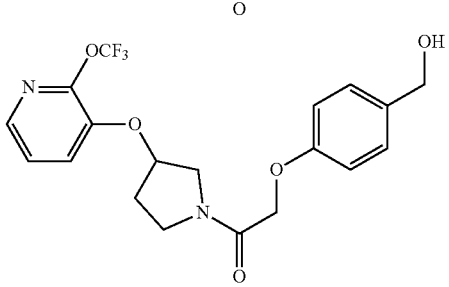
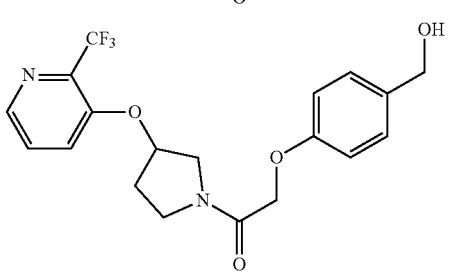
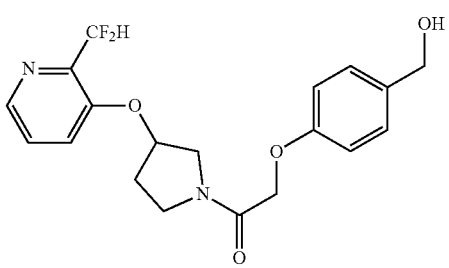
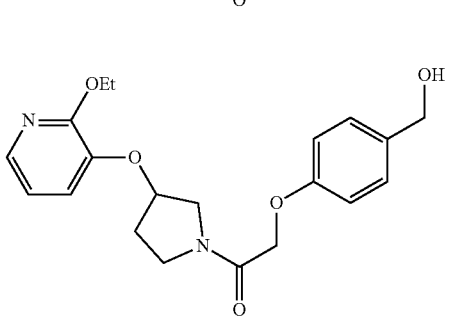

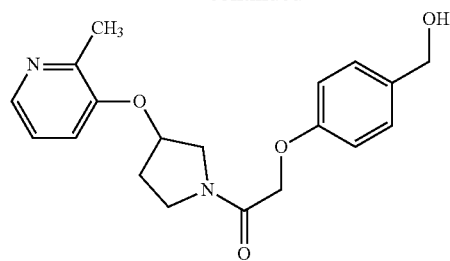
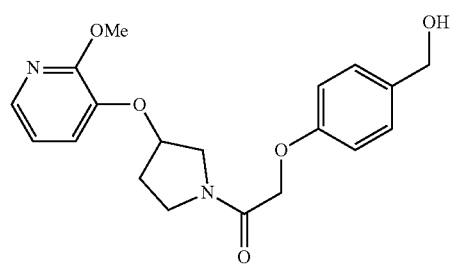
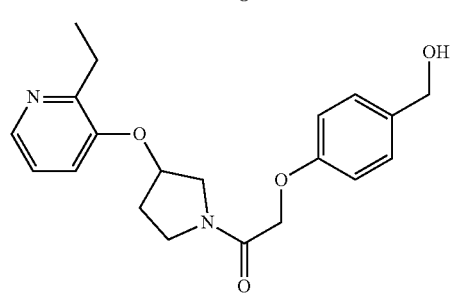
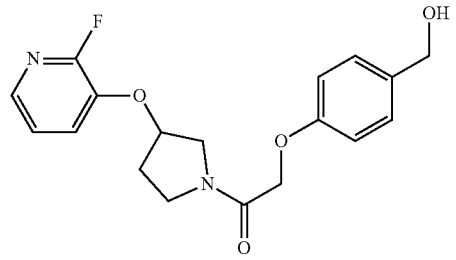
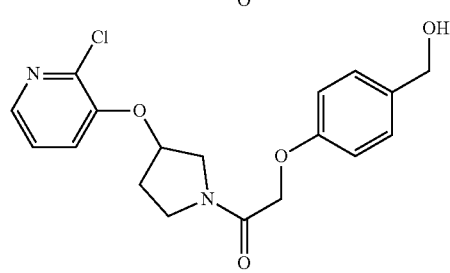
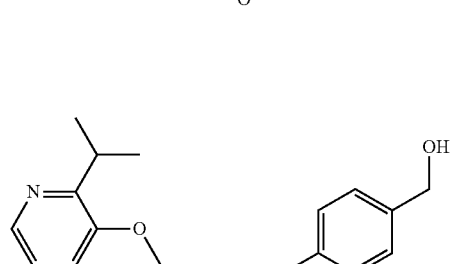
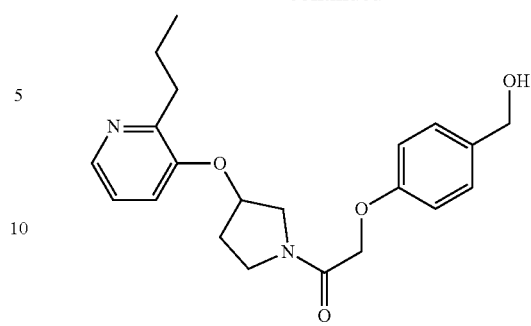
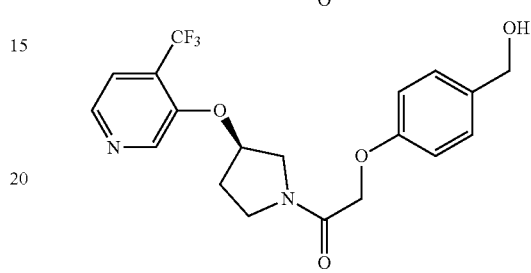
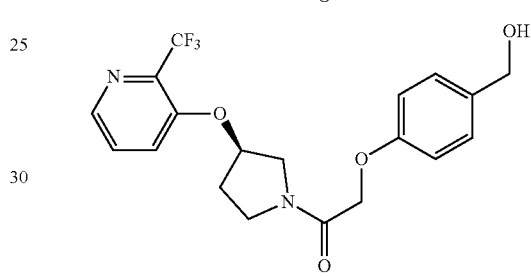
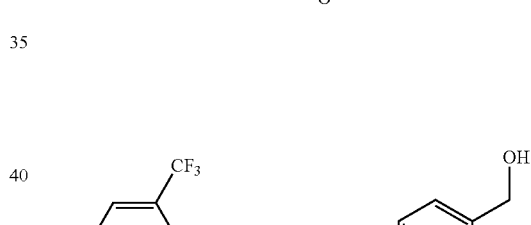
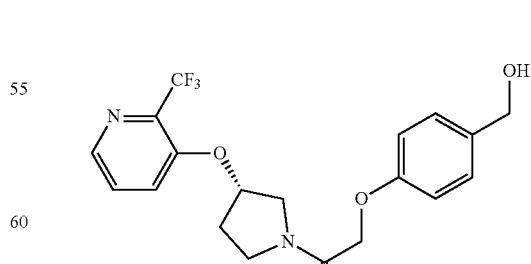
or a pharmaceutically acceptable salt, ester or prodrug form thereof.

In yet further embodiments, the compound is one of the following:
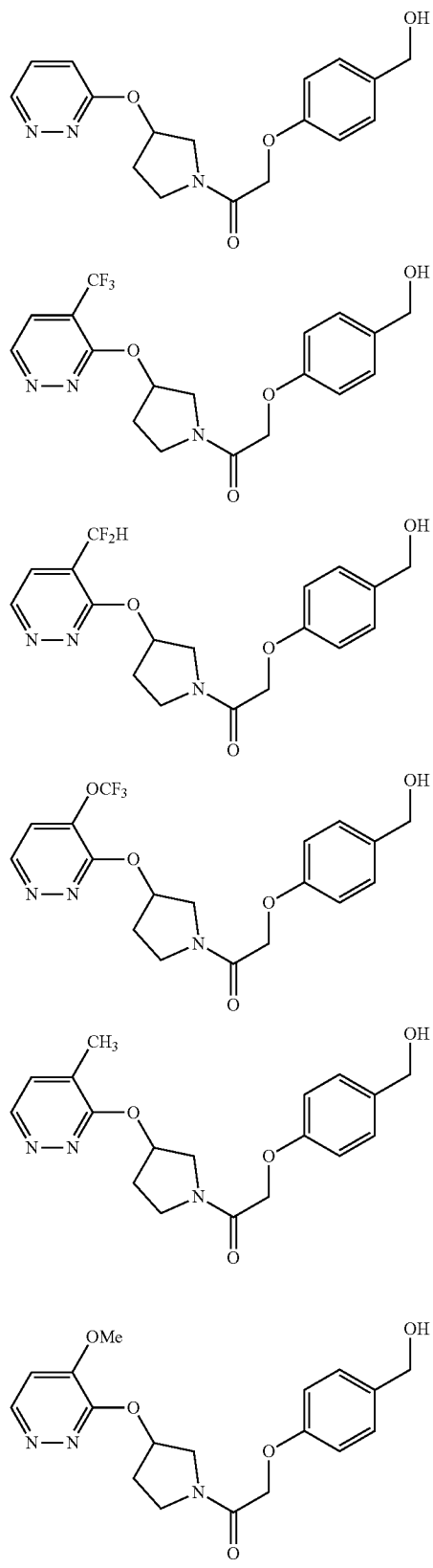
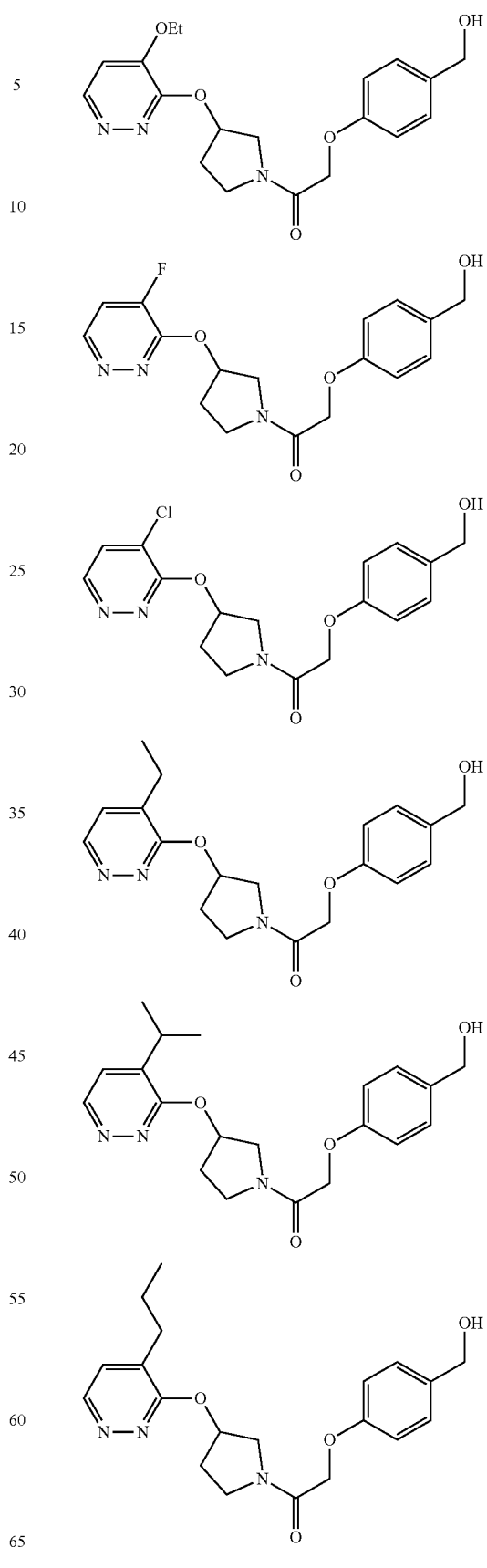

-continued

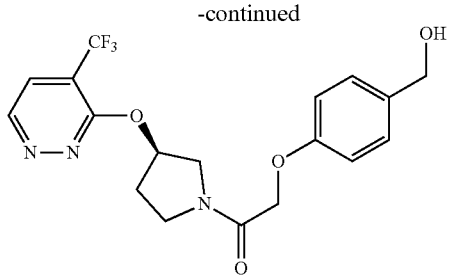

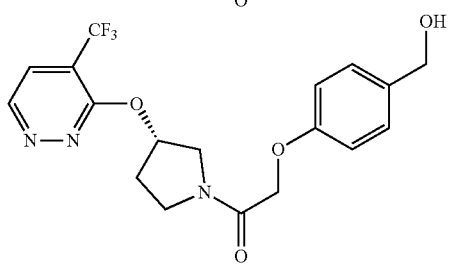

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $NO_2$; $NH_2$; NHCH(O); $NR_6CH(O)$; $NHC(O)R_6$; $NR_6C(O)R_7$; C(O)$NR_6R_7$; $C(NH)NR_6R_7$; $C(NH)NR_6OH$; $C(NH)NR_6NO_2$; or $C(NR_6)NR_7C(NR_8)NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In certain embodiments, the compound is one of the following:

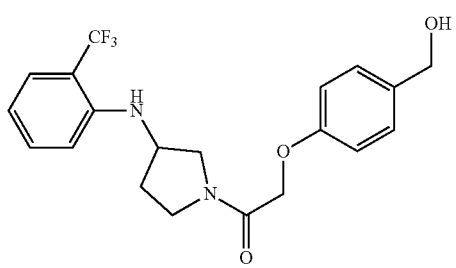

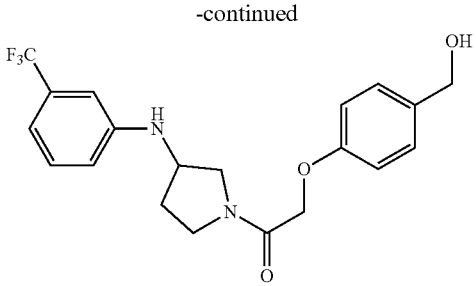

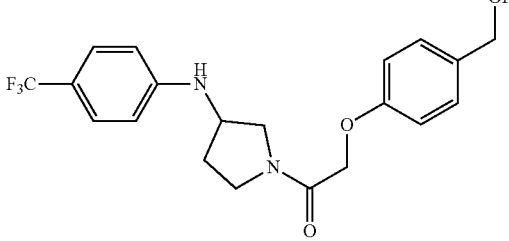

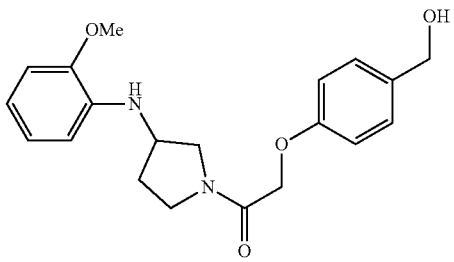

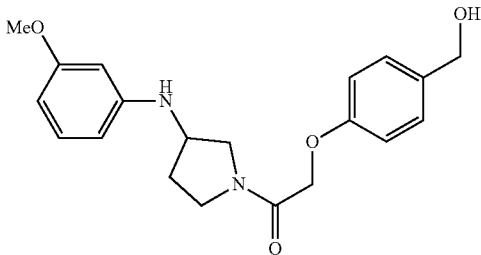

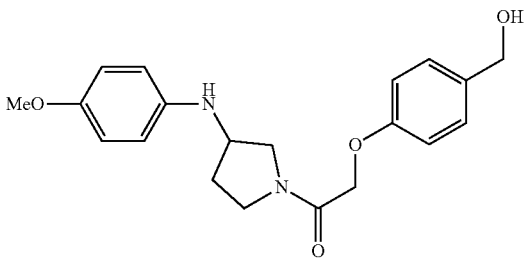

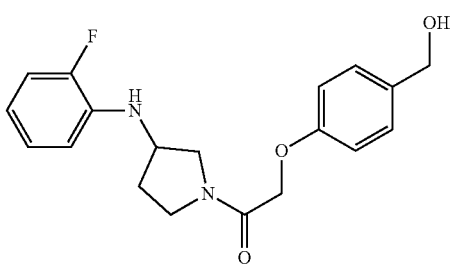

251
-continued
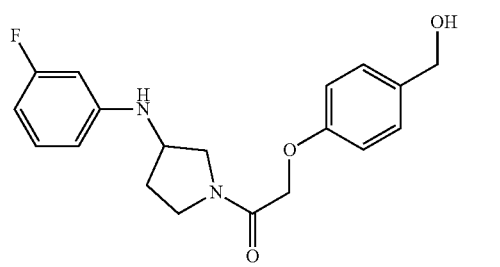
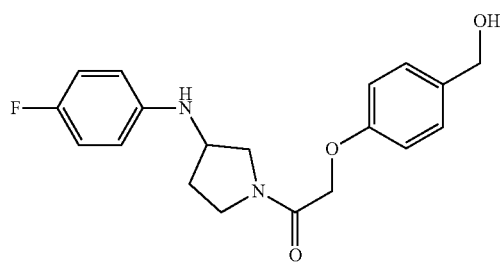
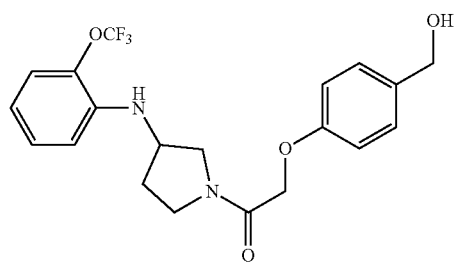
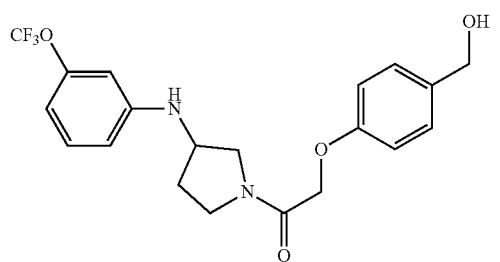
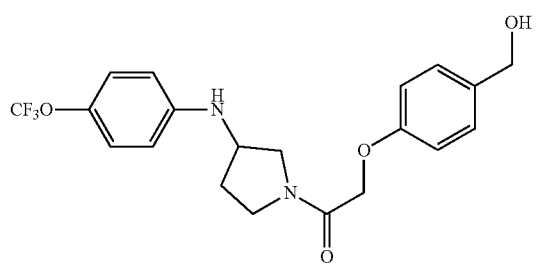
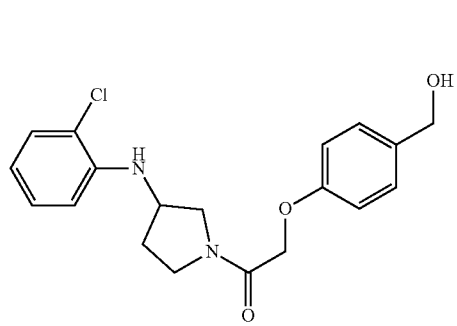
252
-continued
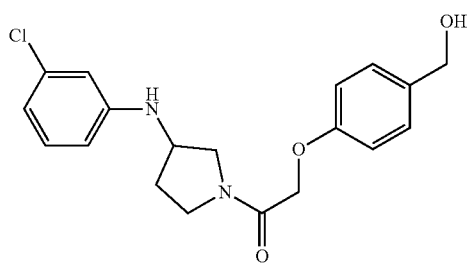
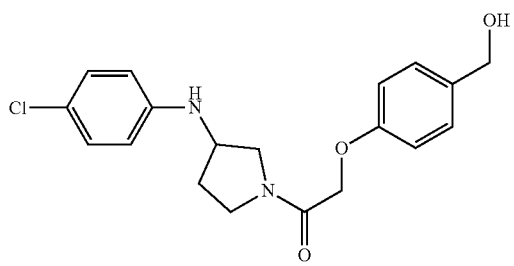
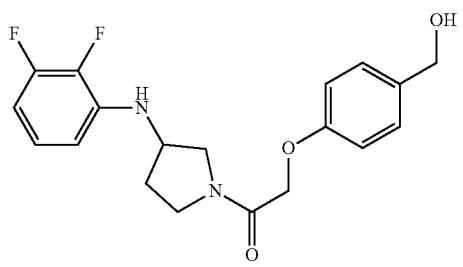
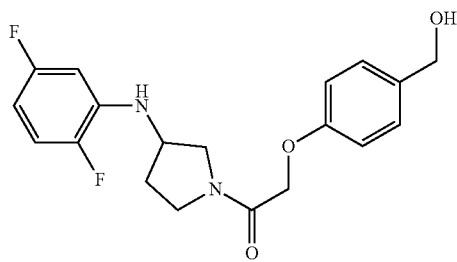
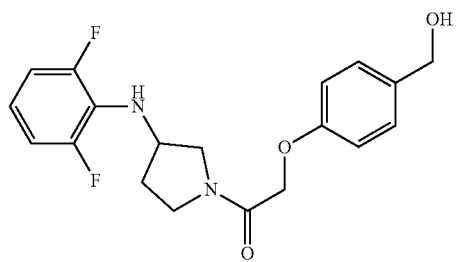
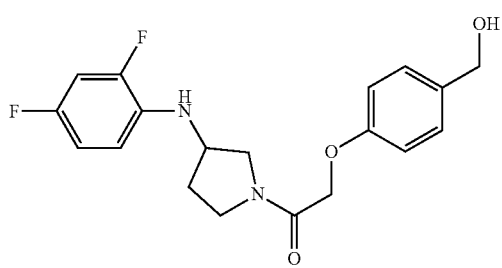

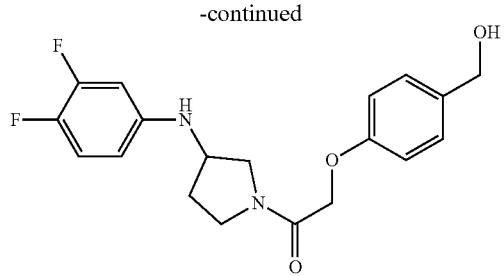
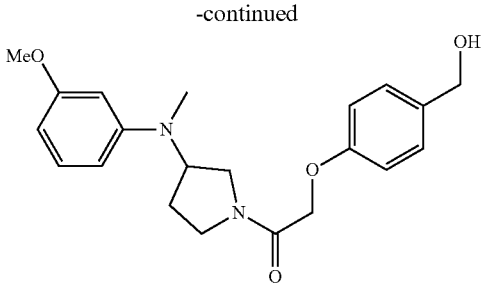
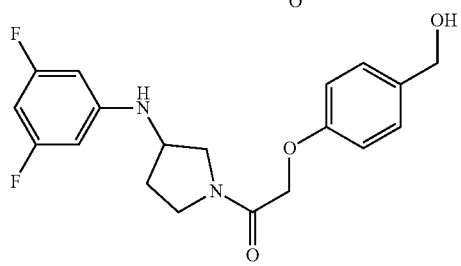
or a pharmaceutically acceptable salt, ester or prodrug form thereof.
In other embodiments, the compound is one of the following:

255
-continued
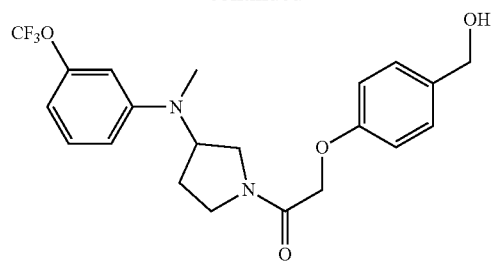
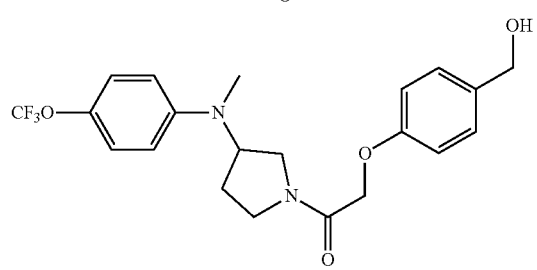
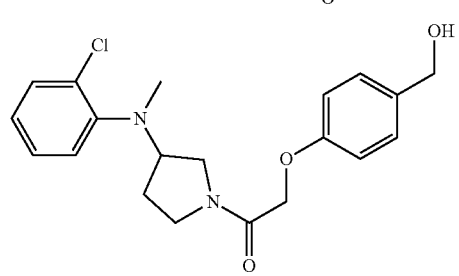
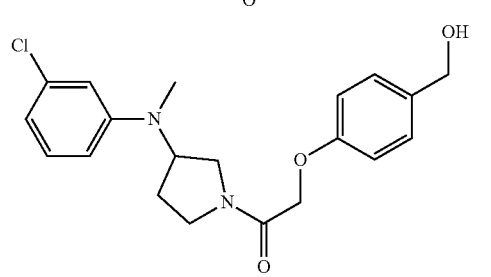
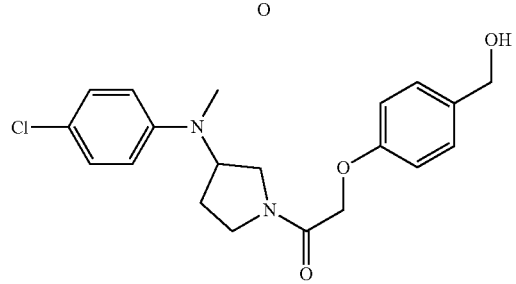
256
-continued
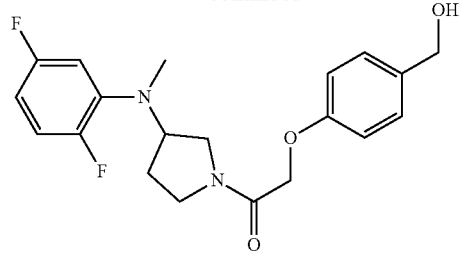
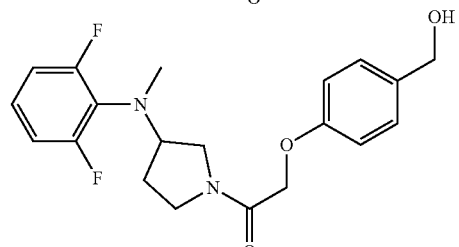
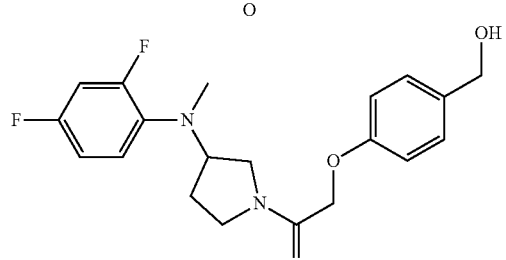
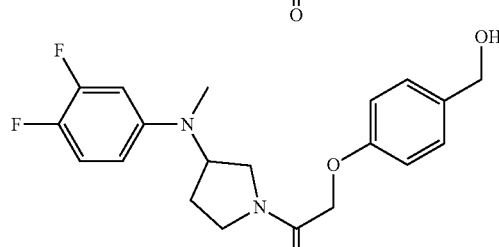
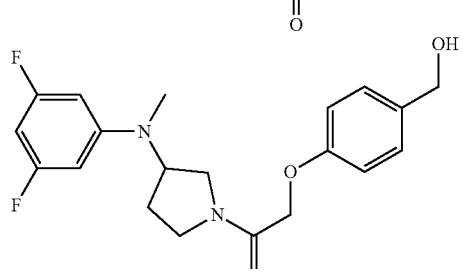
or a pharmaceutically acceptable salt, ester or prodrug form thereof.
In further embodiments, the compound is one of the following:
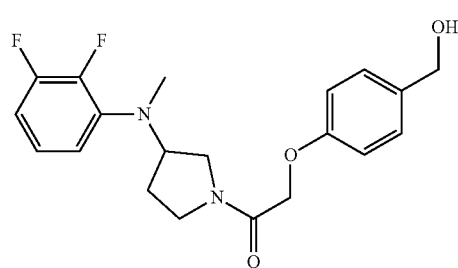
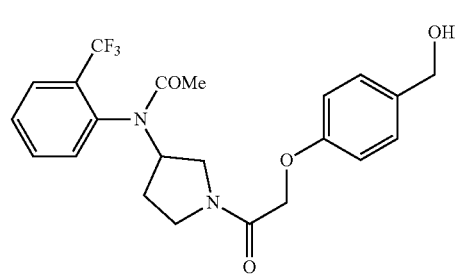

257
-continued
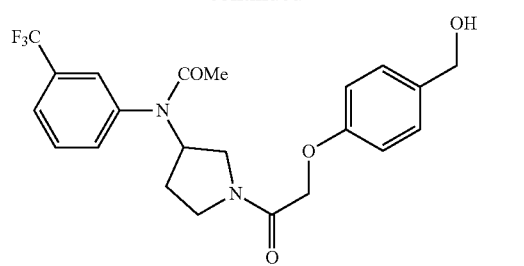

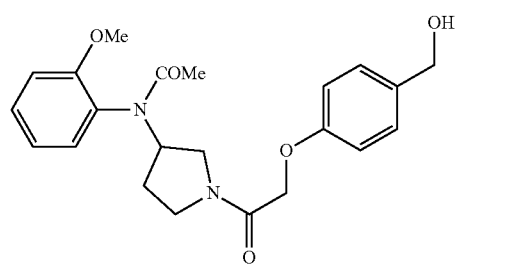
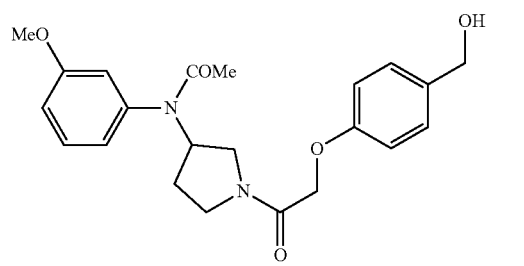
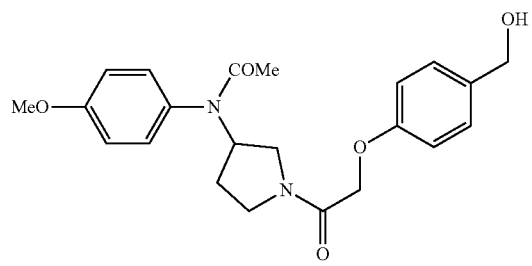
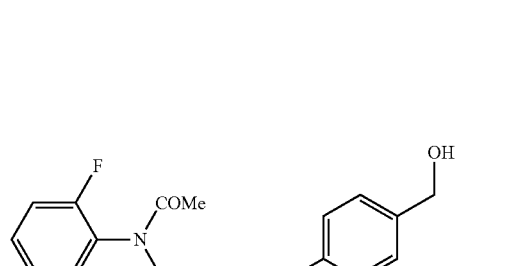
258
-continued
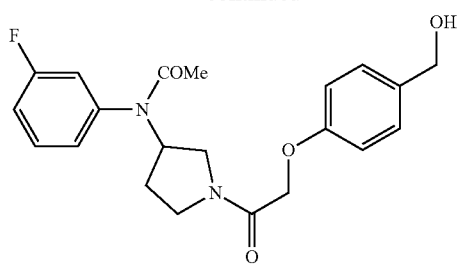
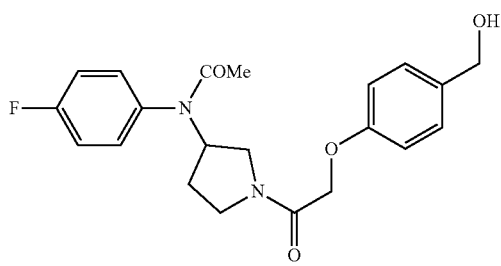
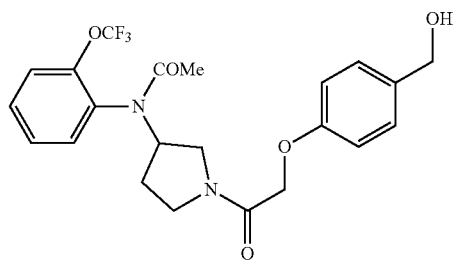
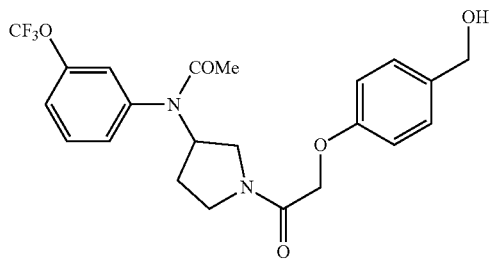
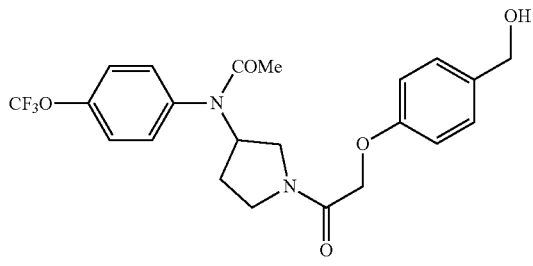
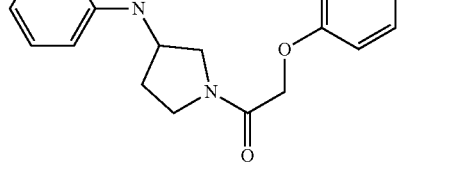

-continued
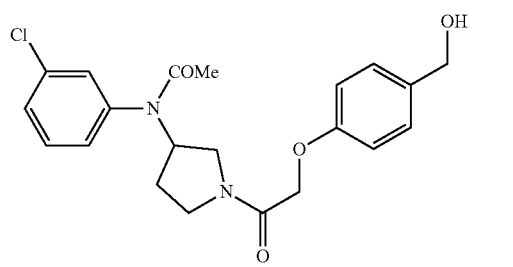
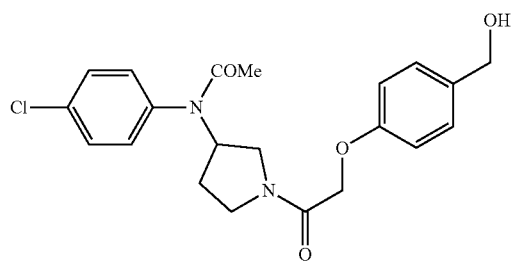
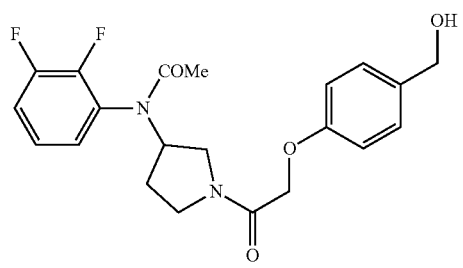
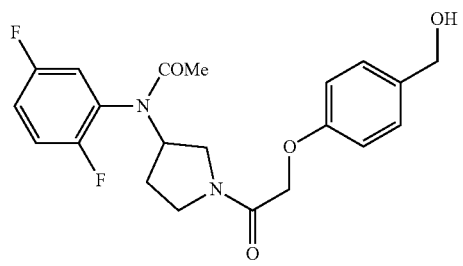
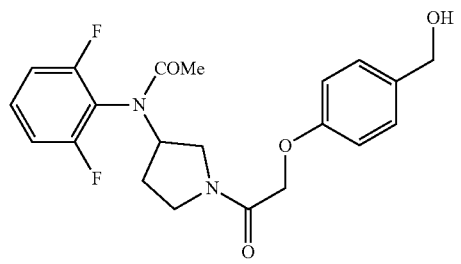
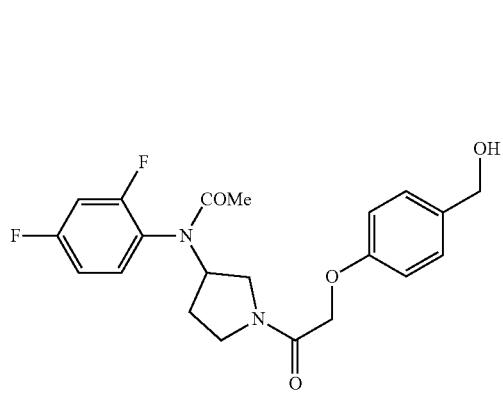
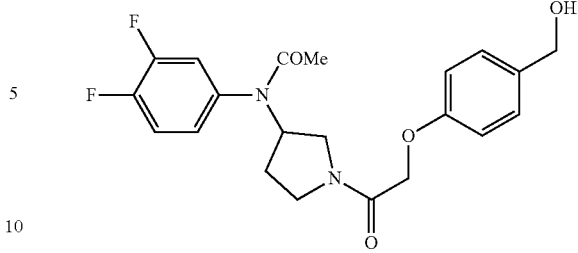
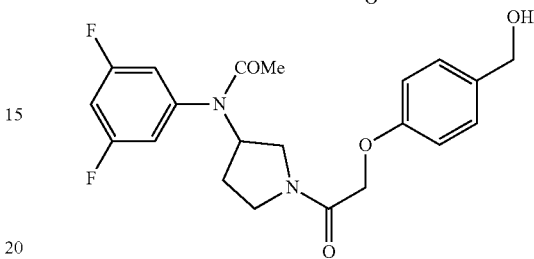
or a pharmaceutically acceptable salt, ester or prodrug form thereof.
In yet further embodiments, the compound is one of the following:
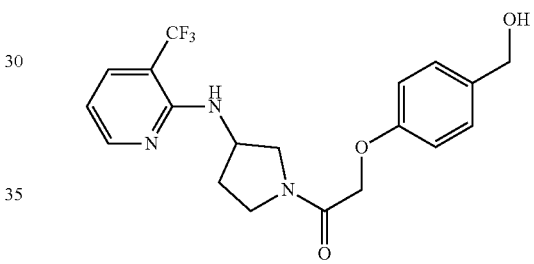
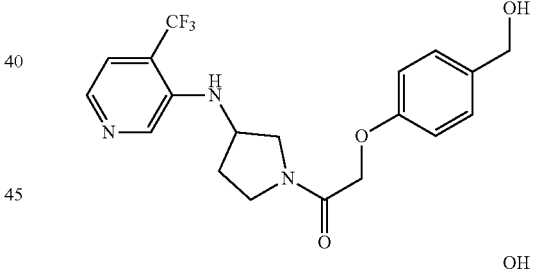
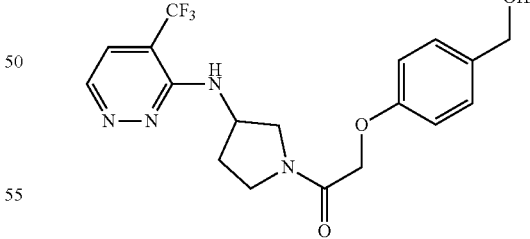
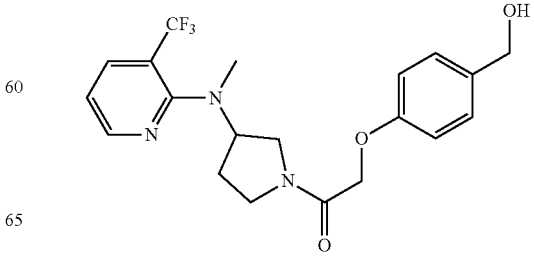

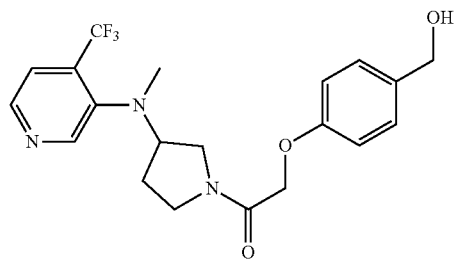
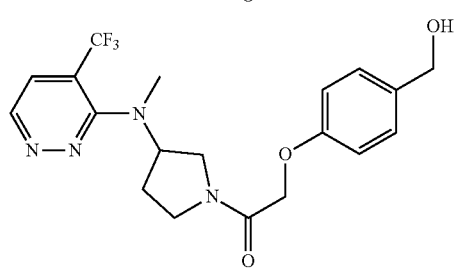
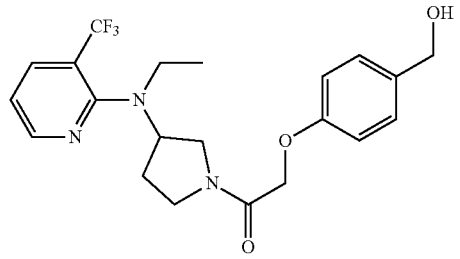
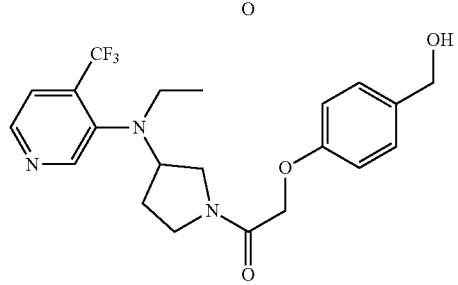
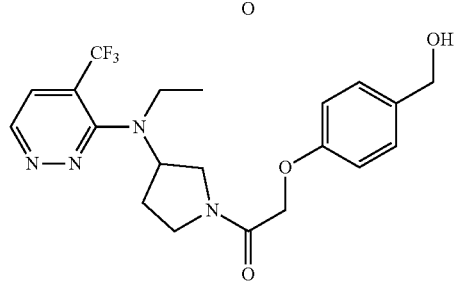
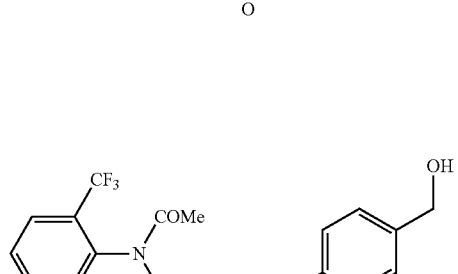
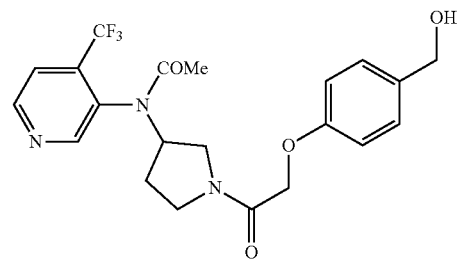
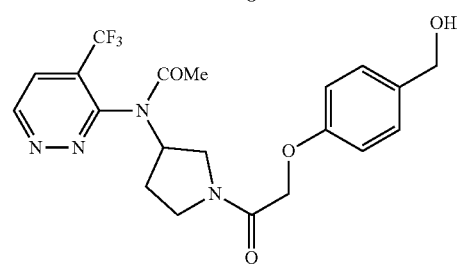
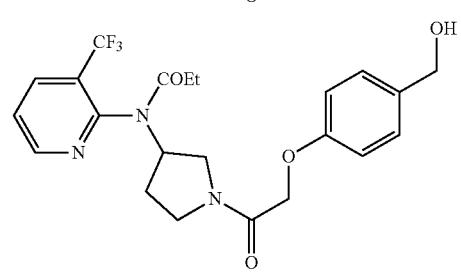
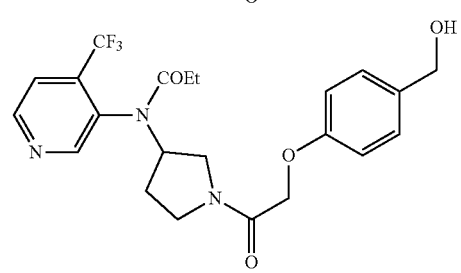
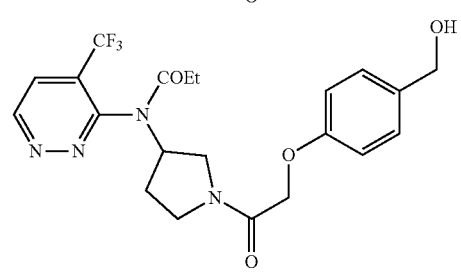
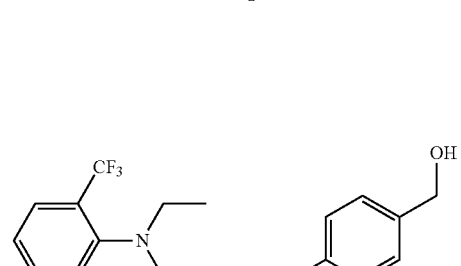

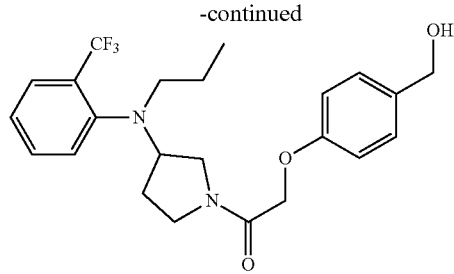
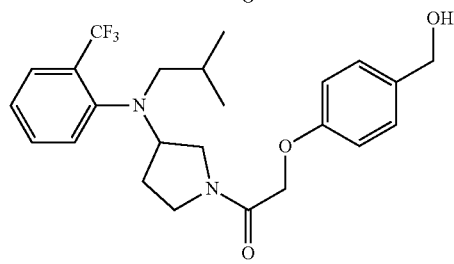
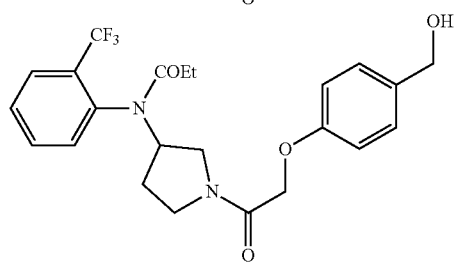
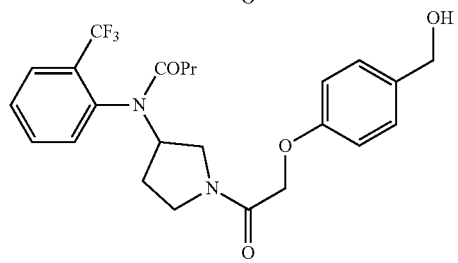
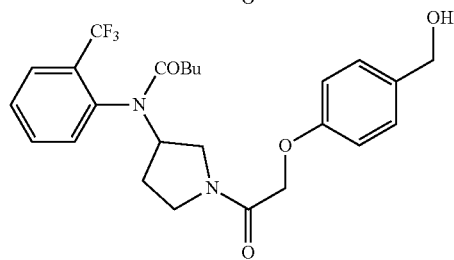
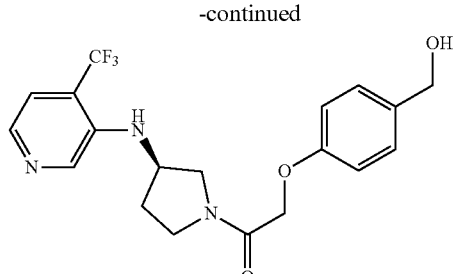
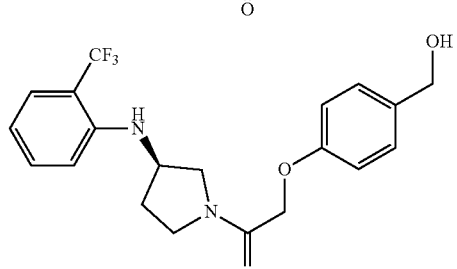
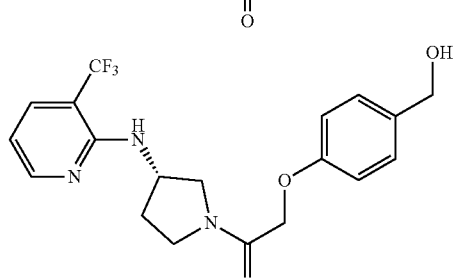
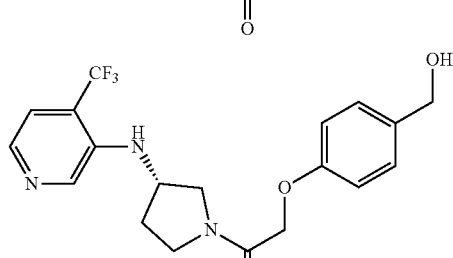
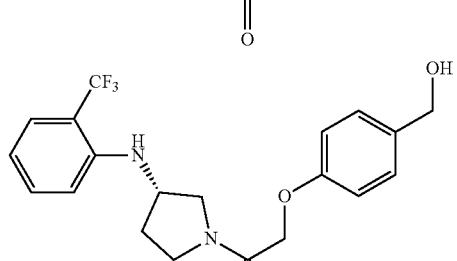
or a pharmaceutically acceptable salt, ester or prodrug form thereof.
In yet other embodiments, the compound is one of the following:
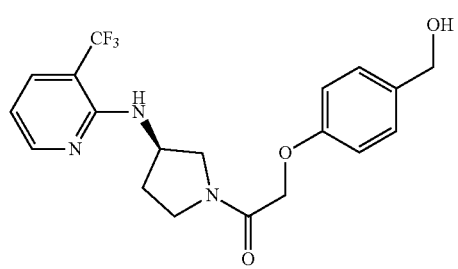
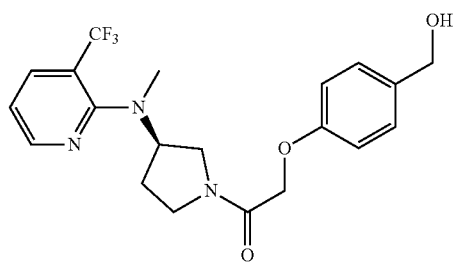

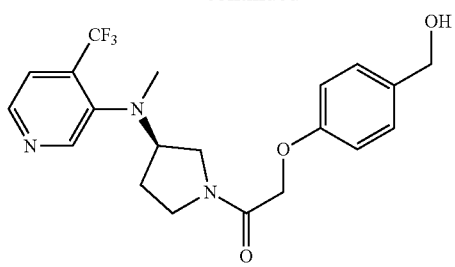
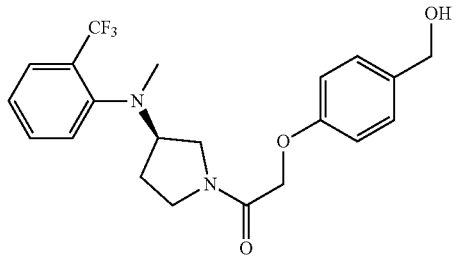
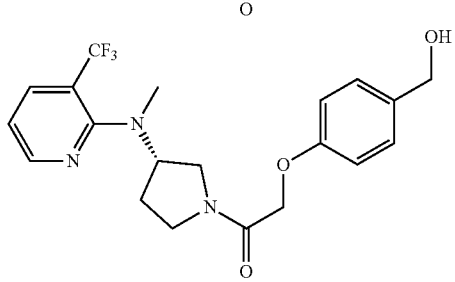
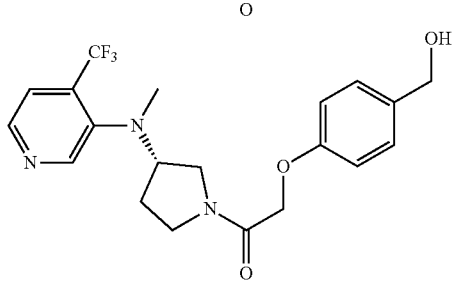
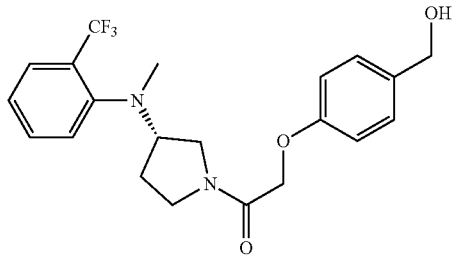
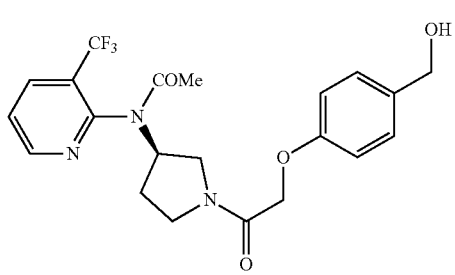

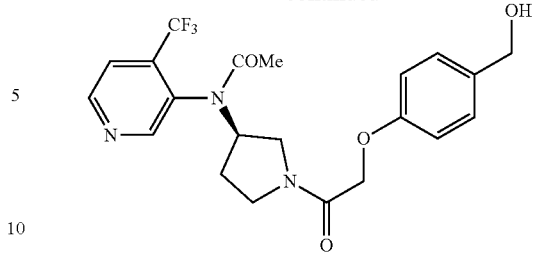
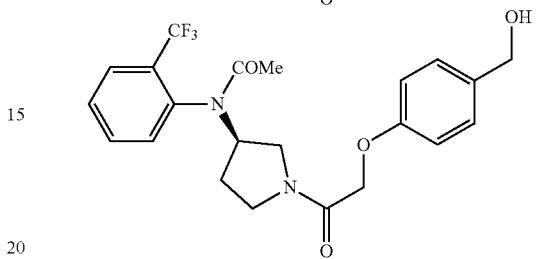
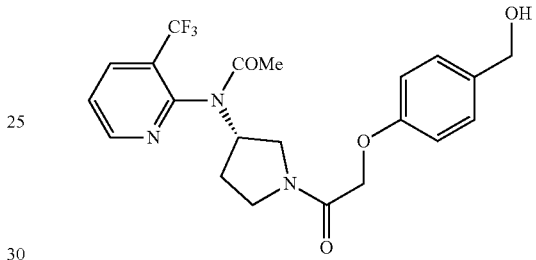
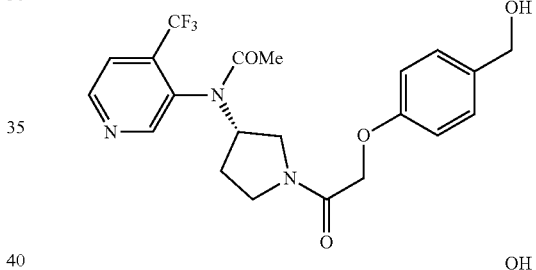
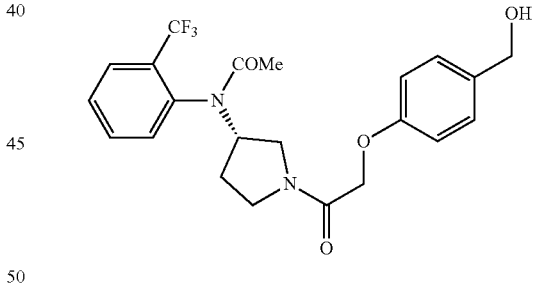

or a pharmaceutically acceptable salt, ester or prodrug form thereof.

In yet further embodiments, X is S, SO or $SO_2$; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR_6)—$R_7$; $SO_3H$ or a ester thereof; $CO_2H$ or a ester thereof; $NO_2$; $NH_2$; NHCH(O); $NR_5CH(O)$; $NHC(O)R_6$; $NR_5C(O)R_7$; $C(O)NR_6R_7$; $C(NH)NR_6R_7$; $C(NH)NR_6OH$; $C(NH)NR_6NO_2$; or $C(NR_5)NR_7C(NR_5)NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or $SO_2$. In further embodiments, X is SO. In yet further embodiments X is $SO_2$.

In some embodiments, the compound is one of:

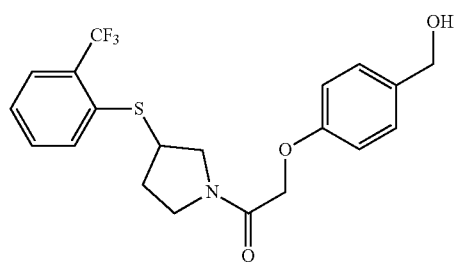

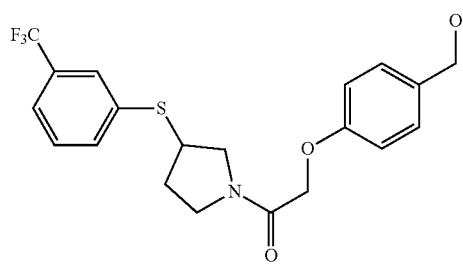

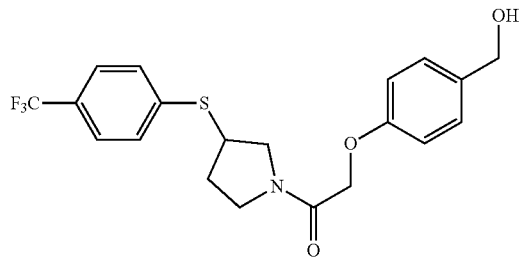

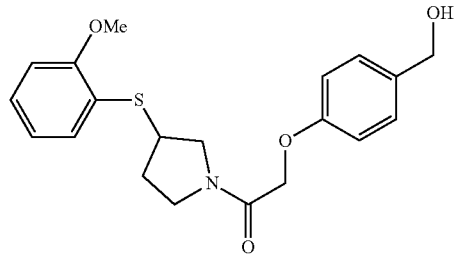

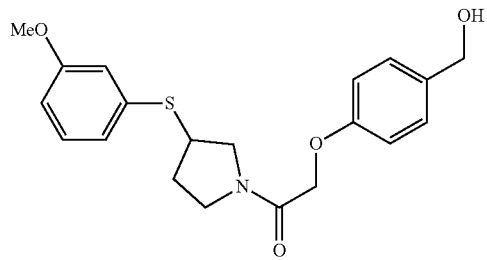

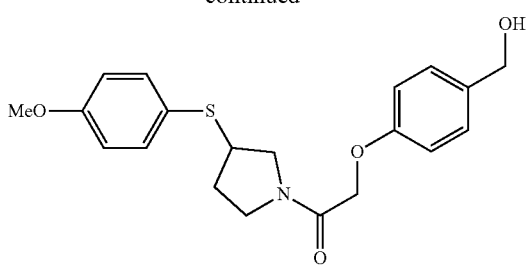

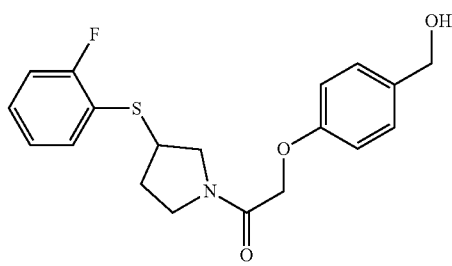

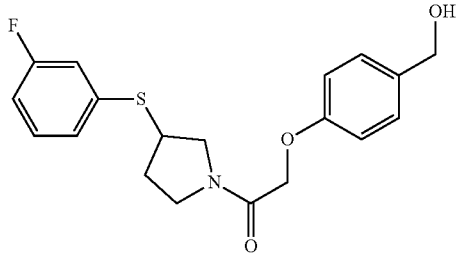

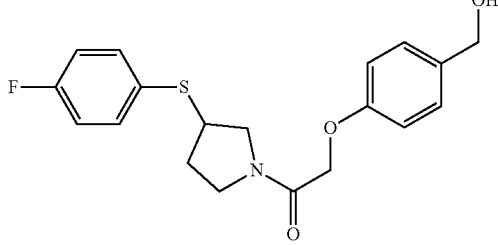

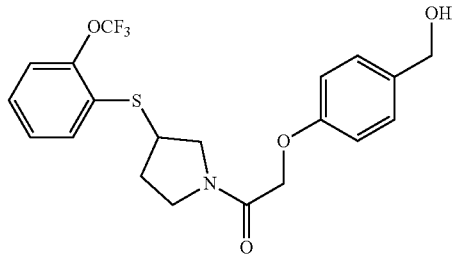

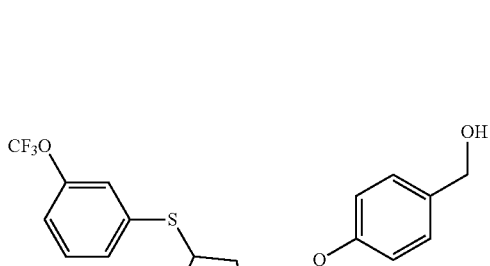

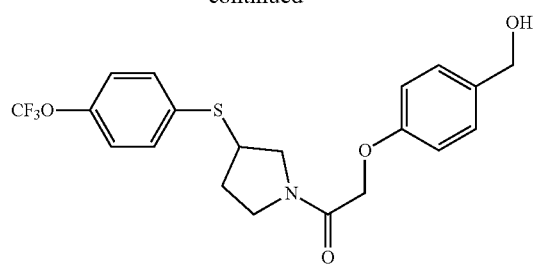
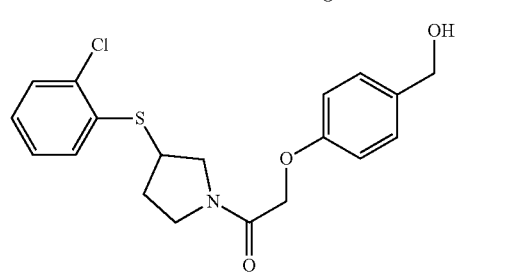
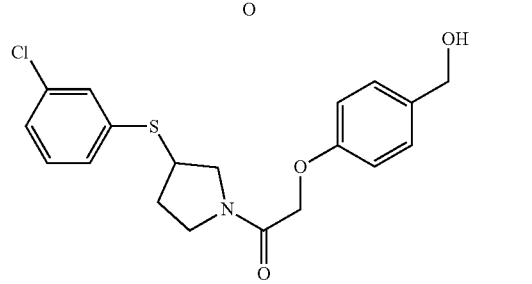
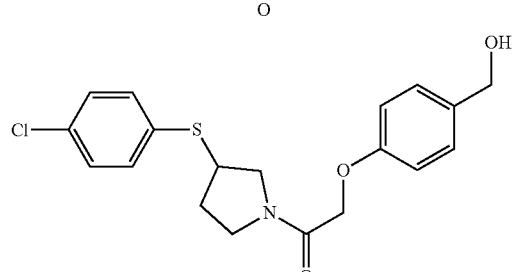
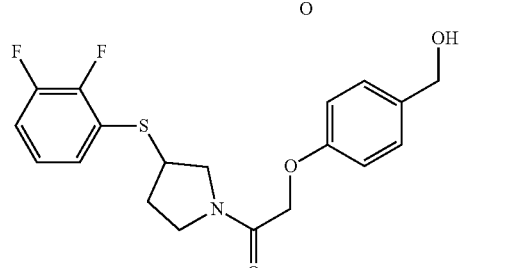
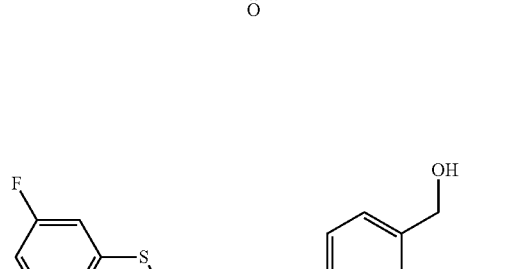
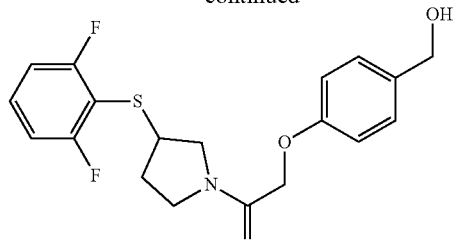
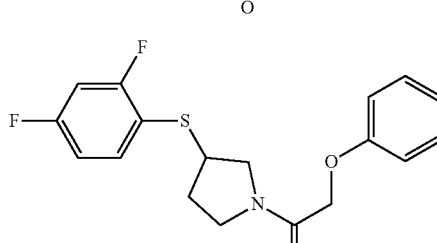
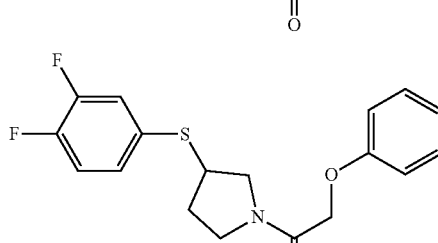
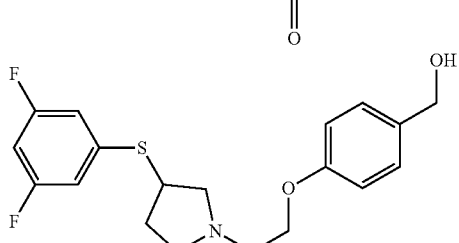
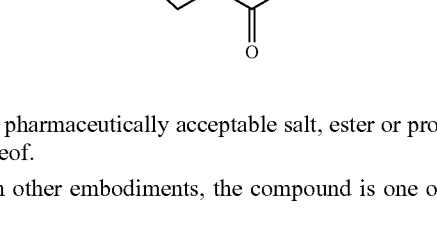
or a pharmaceutically acceptable salt, ester or prodrug form thereof.
In other embodiments, the compound is one of:
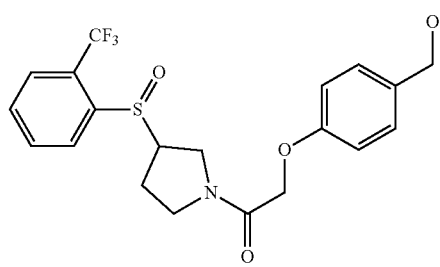
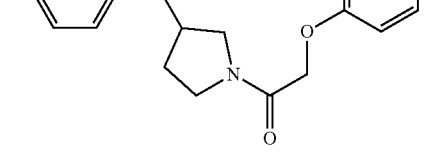

271
-continued
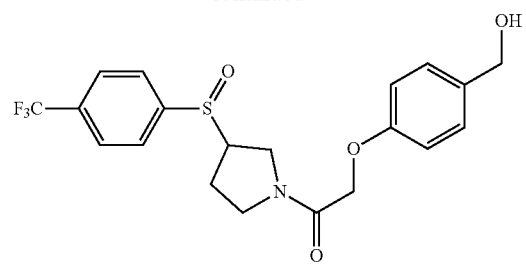
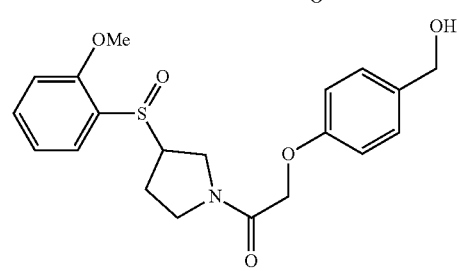
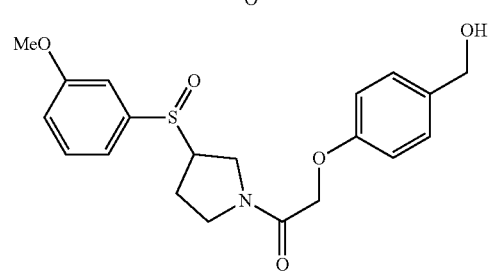
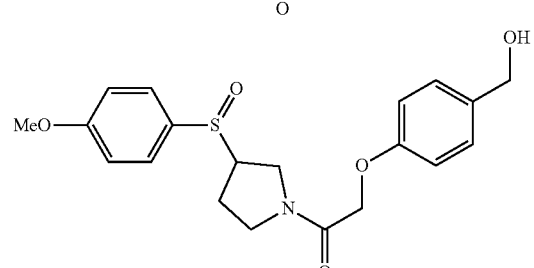
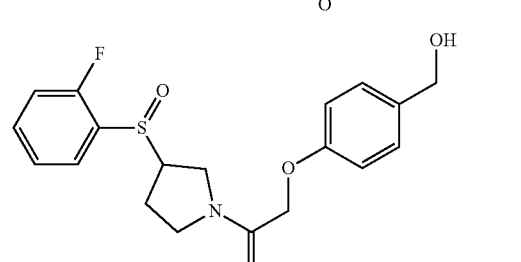
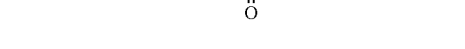
272
-continued
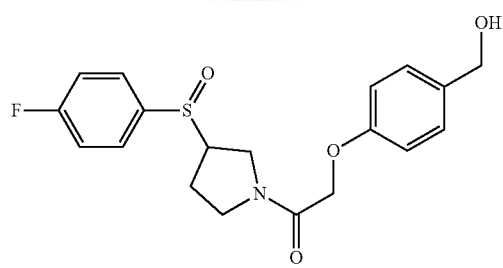
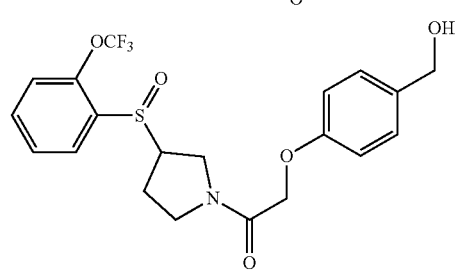
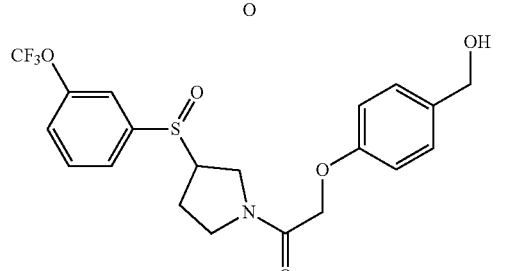
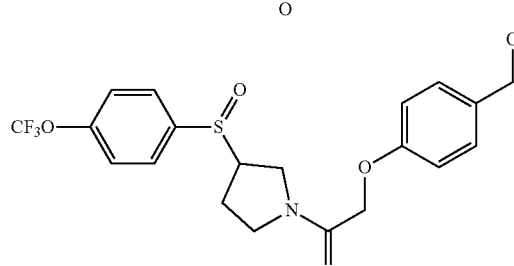
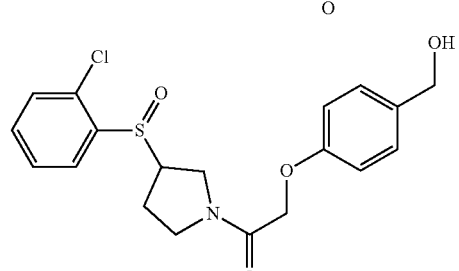
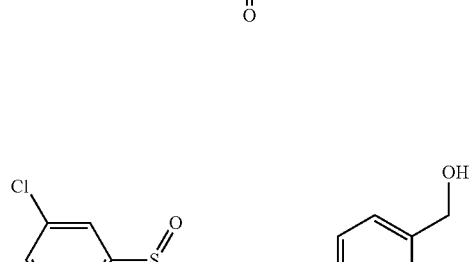
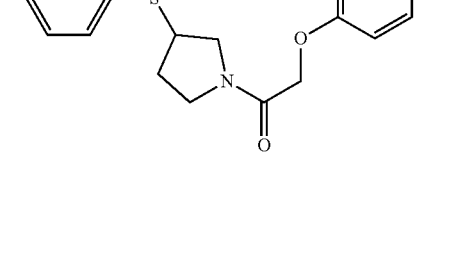

-continued
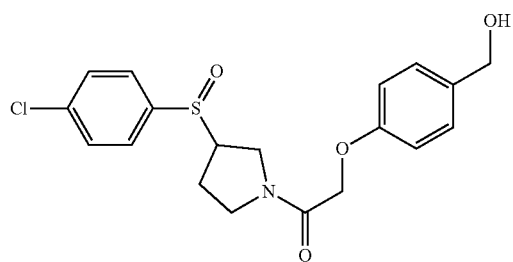
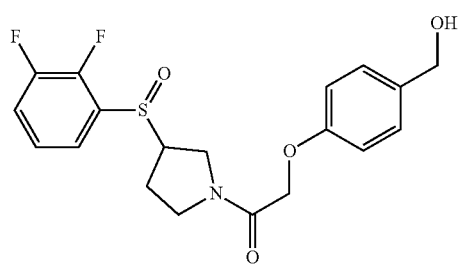
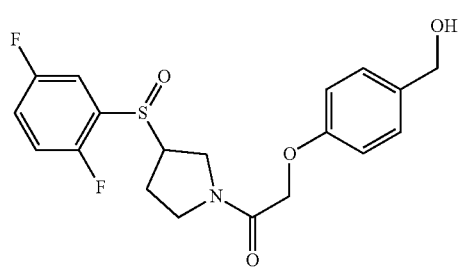

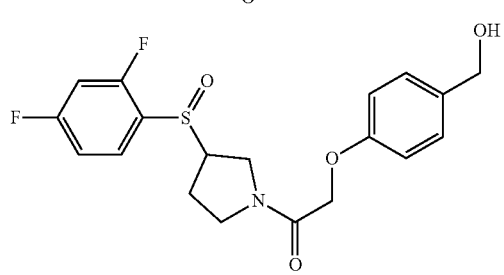
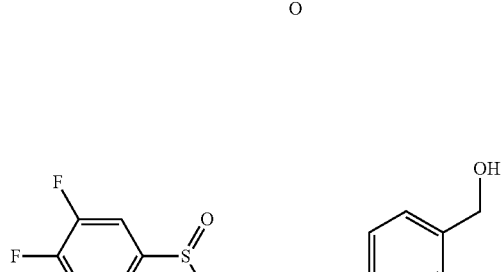
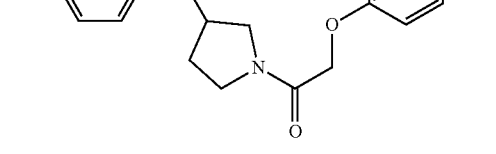
-continued
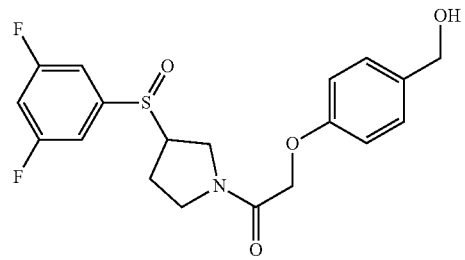
or a pharmaceutically acceptable salt, ester or prodrug form thereof.
In further embodiments, the compound is one of:
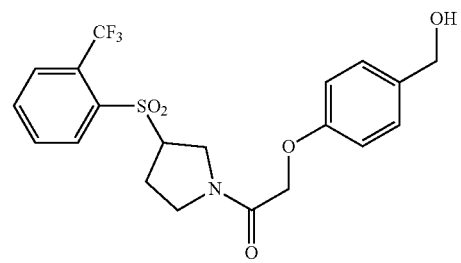
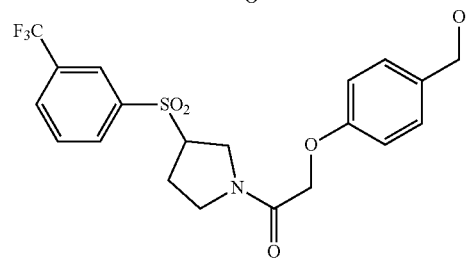
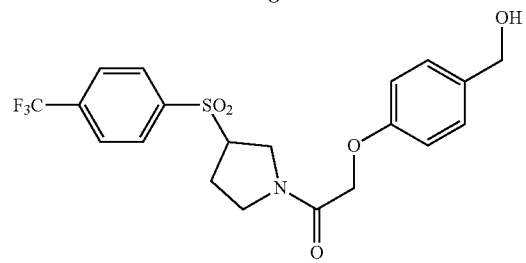
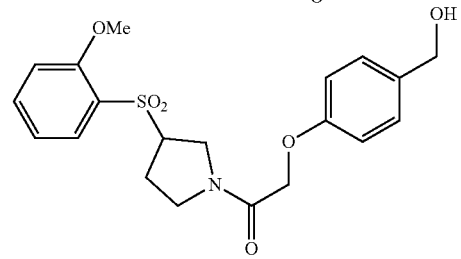
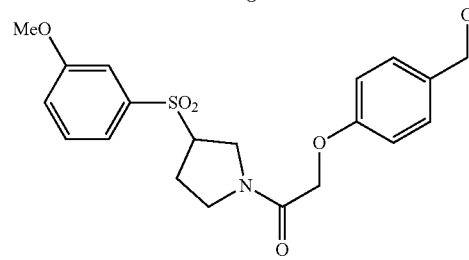

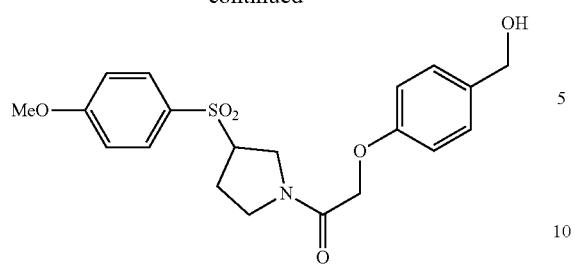
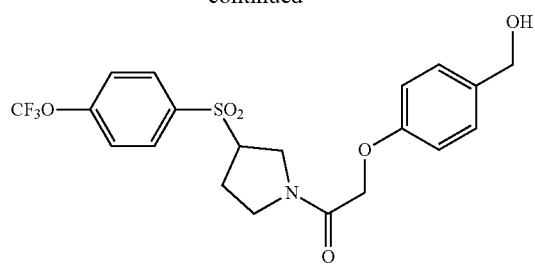
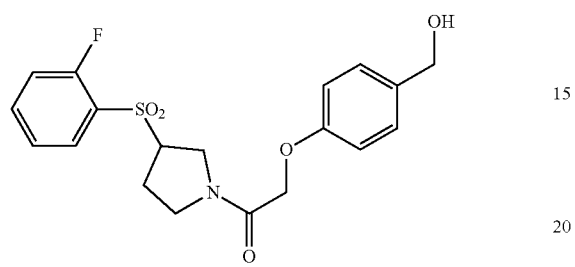
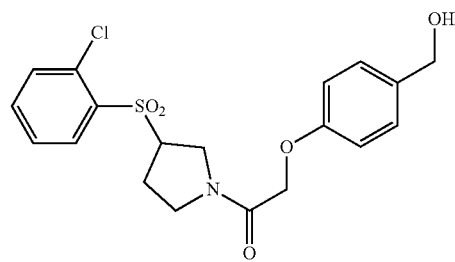
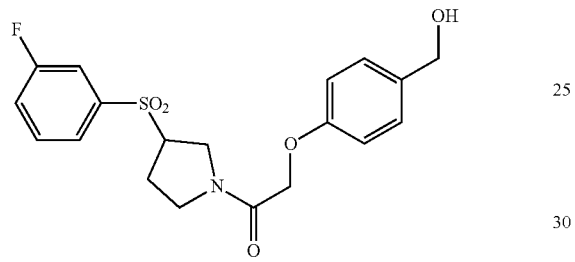
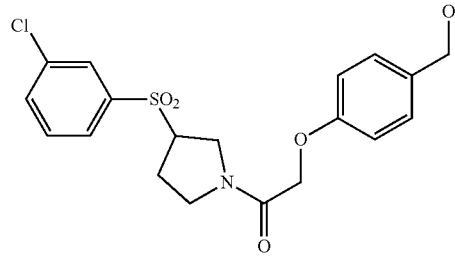
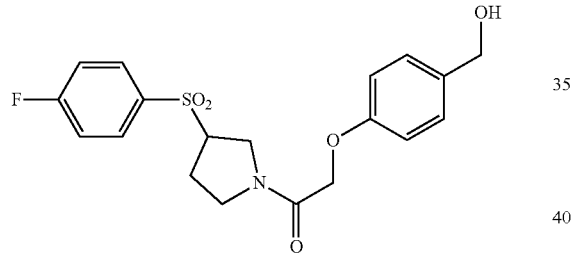
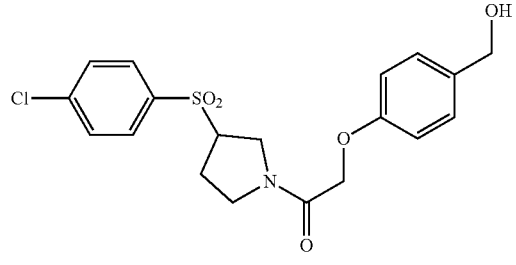
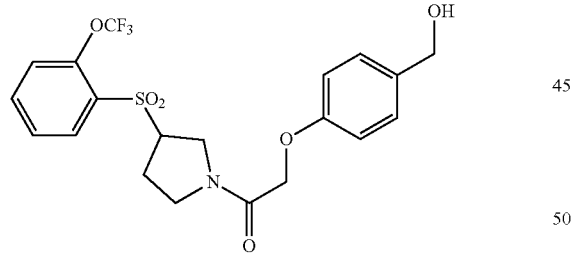
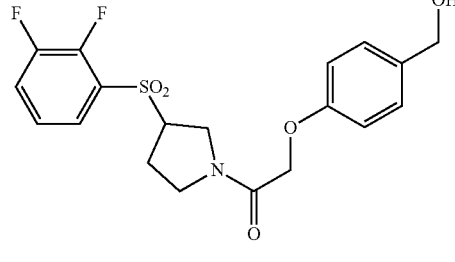
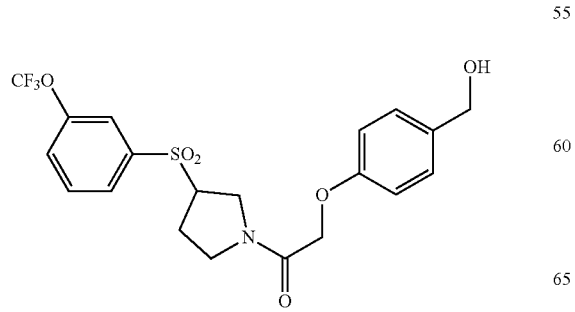
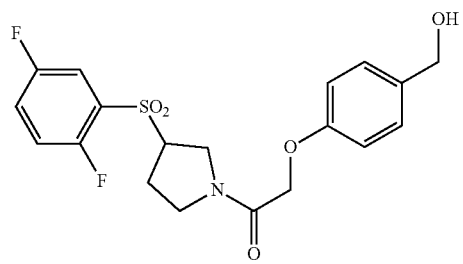

277
-continued
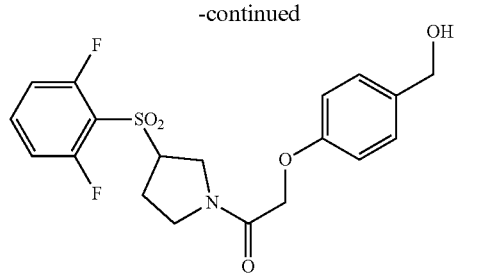
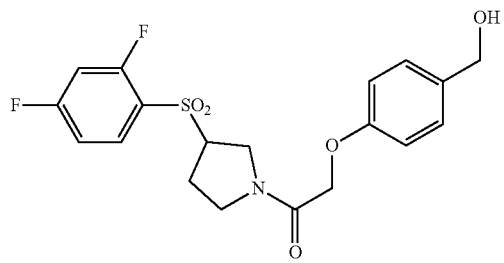
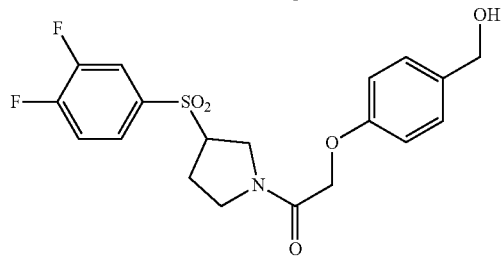
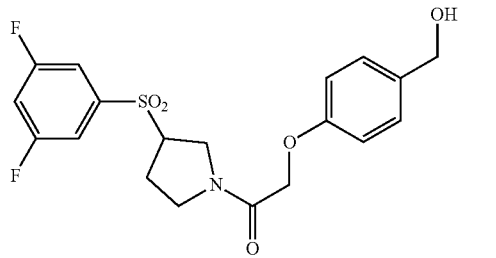
or a pharmaceutically acceptable salt, ester or prodrug form thereof.
In yet further embodiments, the compound is one of:
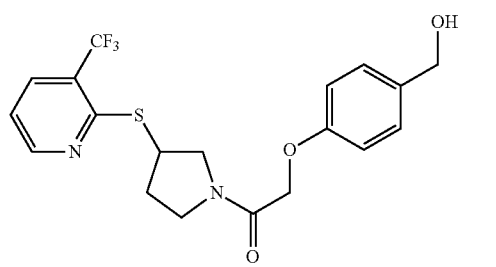
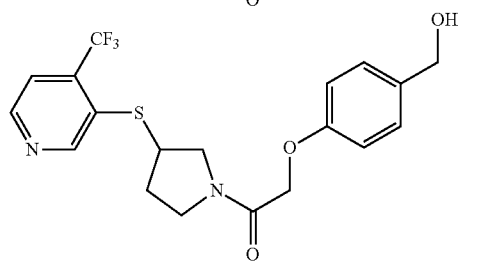
278
-continued
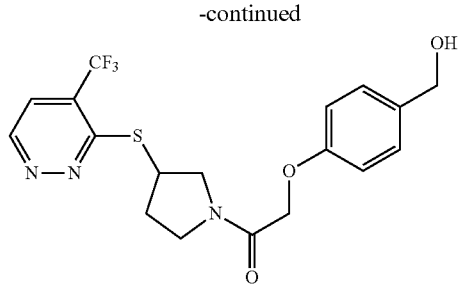
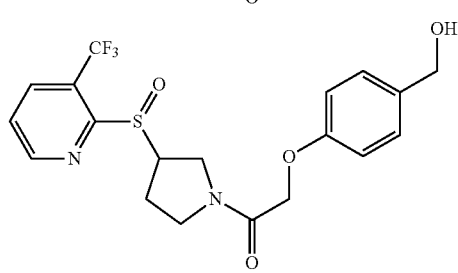
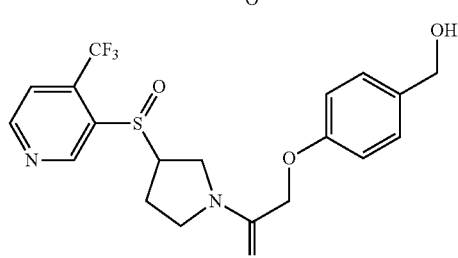
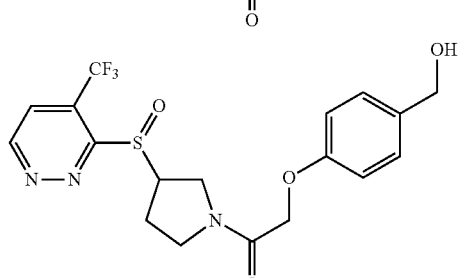
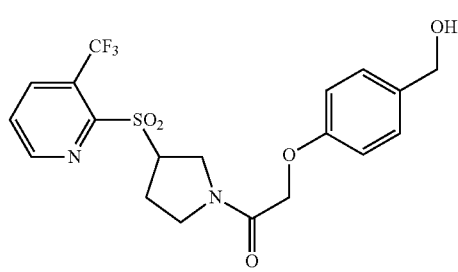
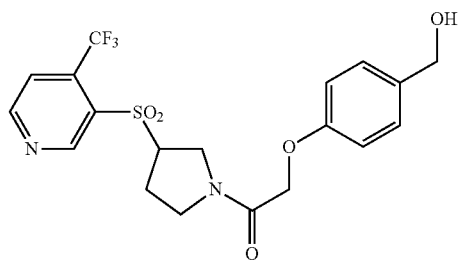

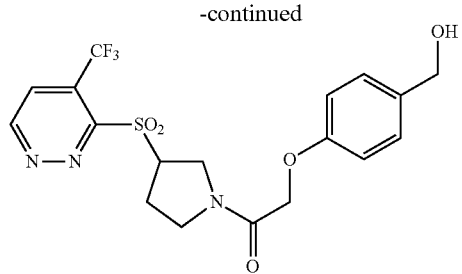
or a pharmaceutically acceptable salt, ester or prodrug form thereof.
In yet other embodiments, the compound is one of the following:
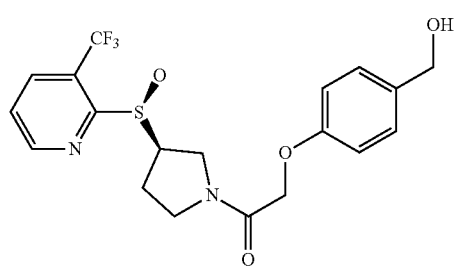
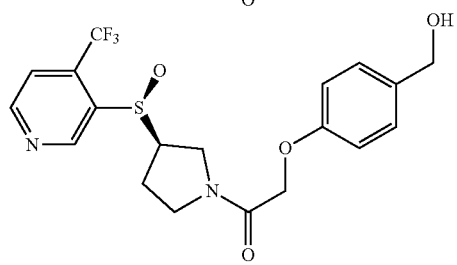
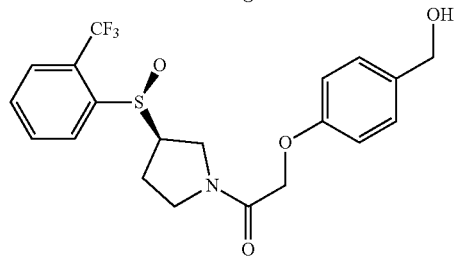
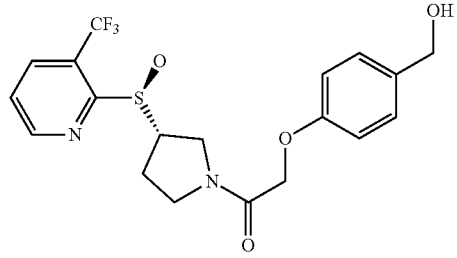
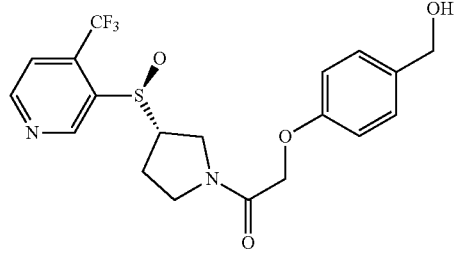
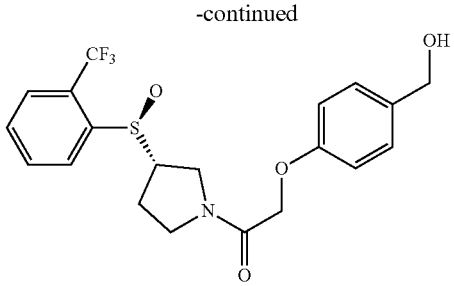
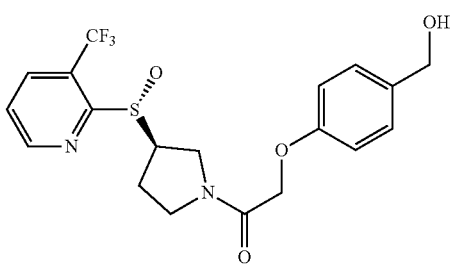
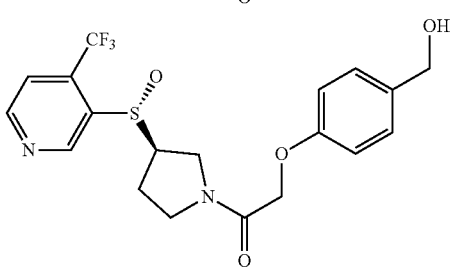
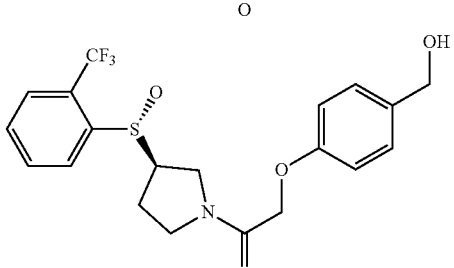
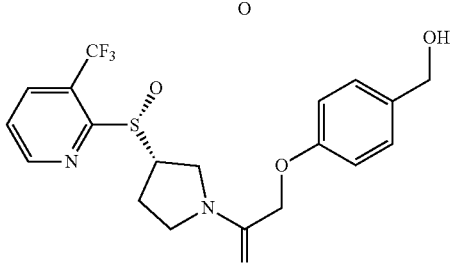
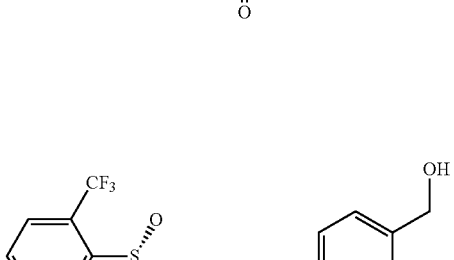
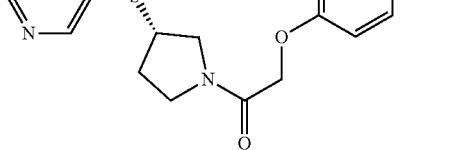

-continued

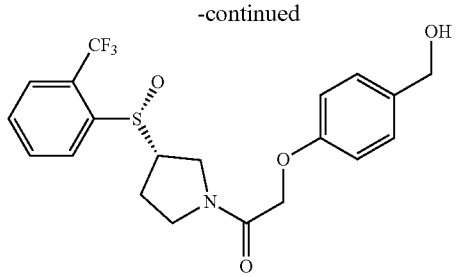

or a pharmaceutically acceptable salt, ester or prodrug form thereof.

In yet further embodiments, the compound has the structure II

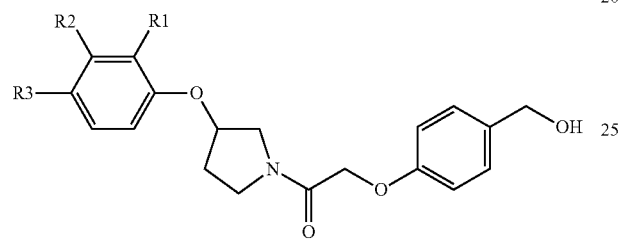

II wherein one of $R_1$ and $R_2$ and $R_3$, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR_6)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6OH$; C(NH)$NR_6NO_2$; or C($NR_6$)$NR_7$C($NR_8$)$NR_9R_{10}$;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

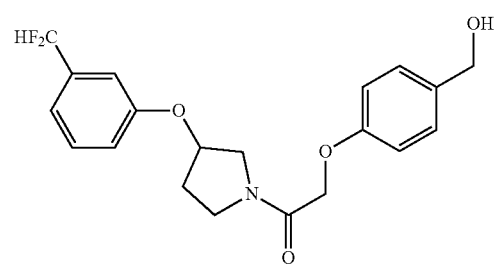

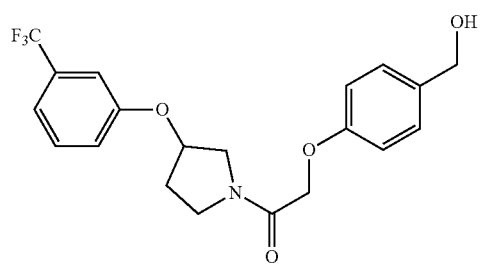

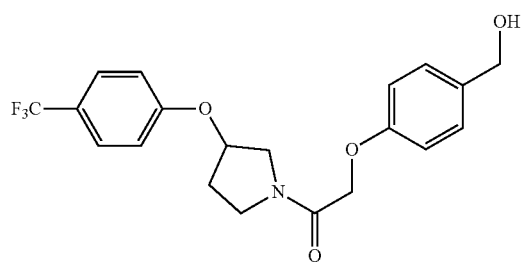

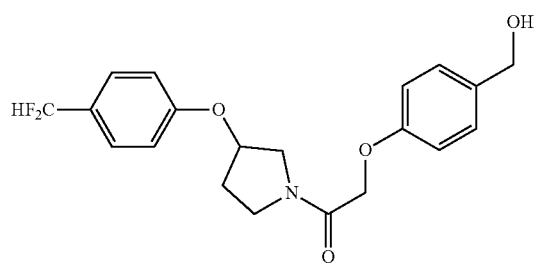

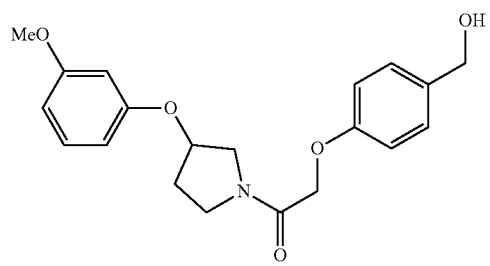

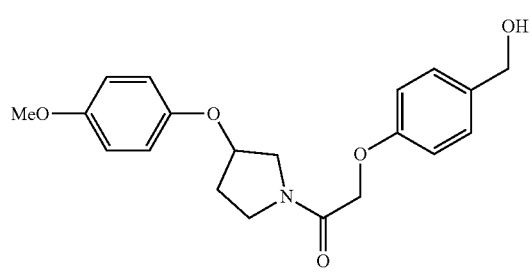

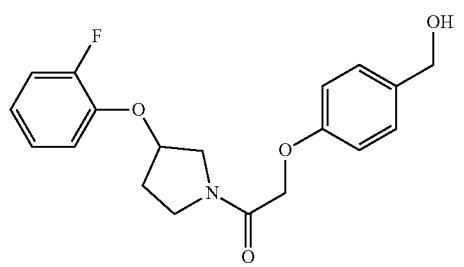
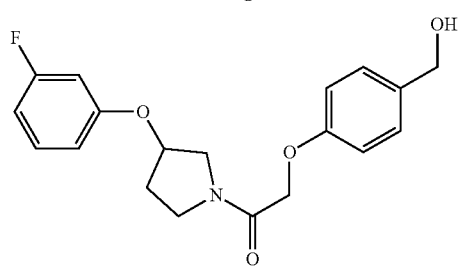
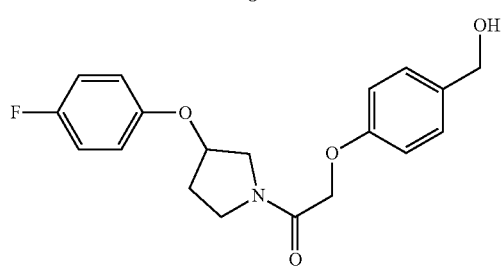
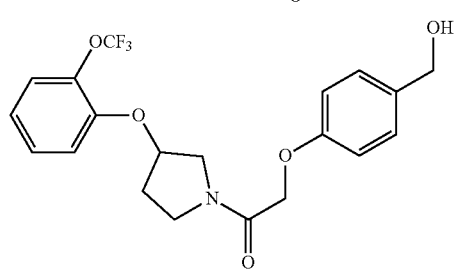
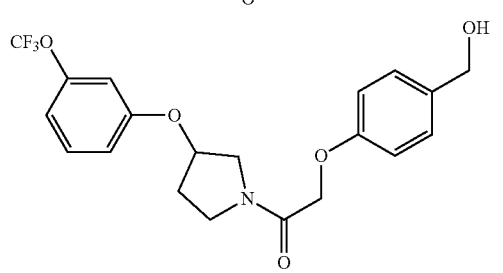
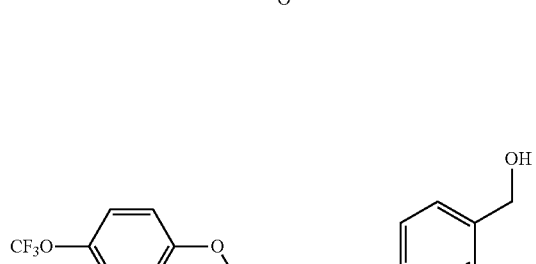
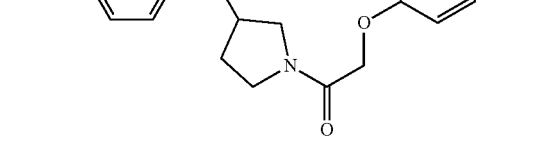
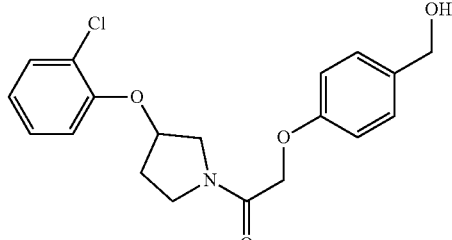
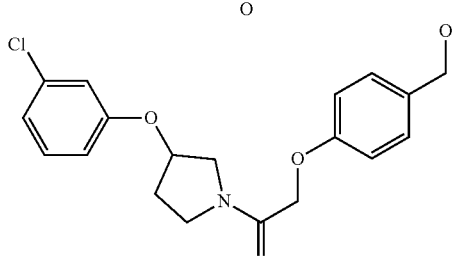
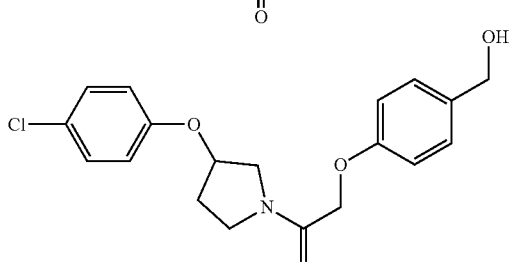
or a pharmaceutically acceptable salt, ester or prodrug form thereof.
In other embodiments the compound is one of the following:
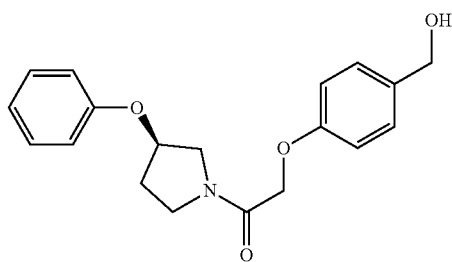
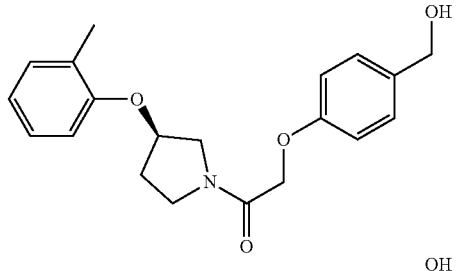
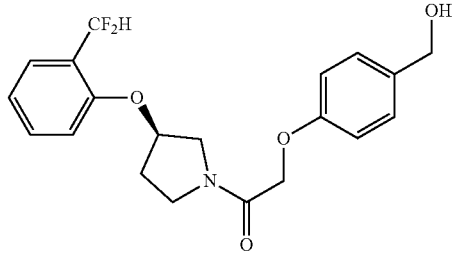

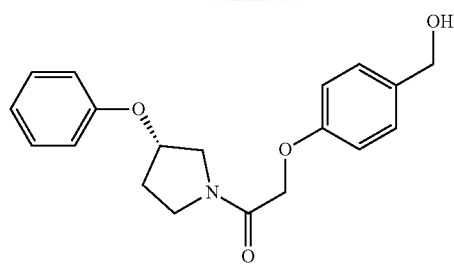
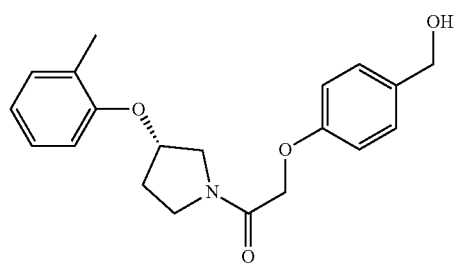
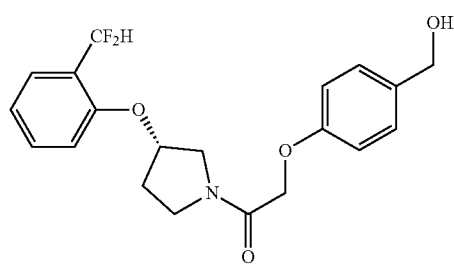
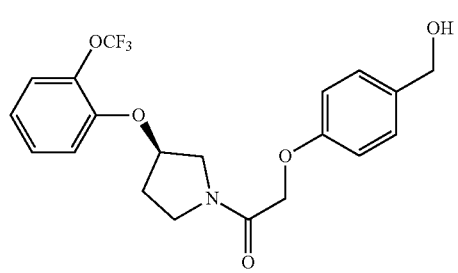
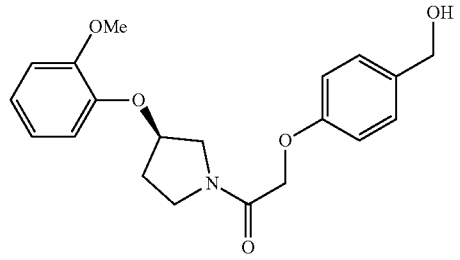
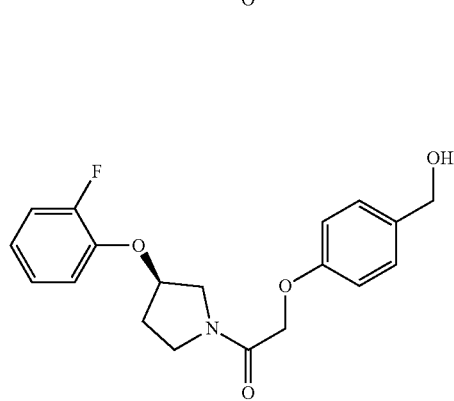
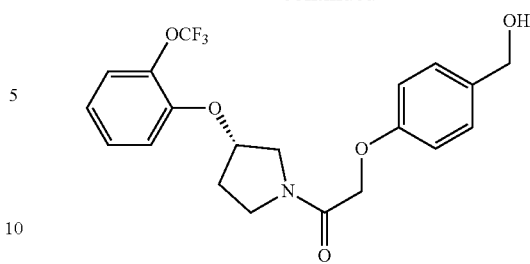
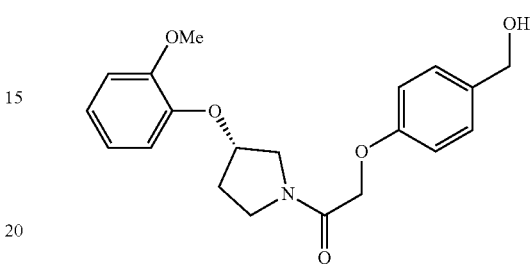
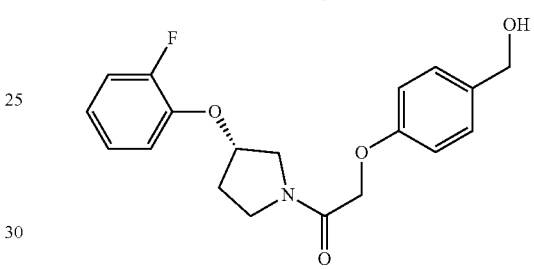
or a pharmaceutically acceptable salt, ester or prodrug form thereof.
In certain embodiments, the compound is one of the following:
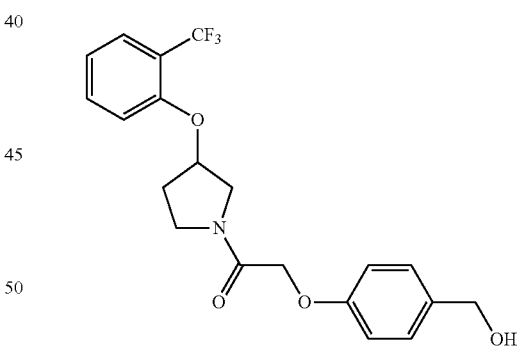
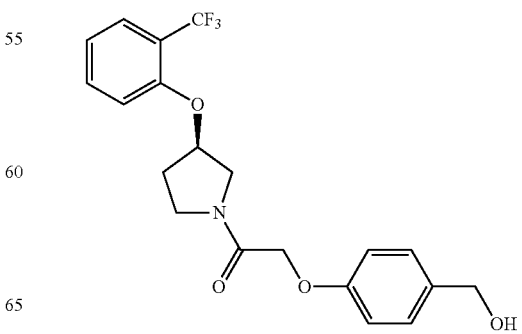

-continued

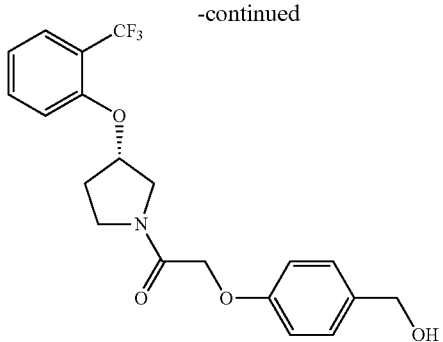

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol. In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50 One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50. In certain embodiments, the pharmaceutical composition comprises both (i) butylated hydroxytoluene (BHT) at a concentration of least 0.05%; and (ii) di-sodium EDTA at a concentration of least 0.001%. In another embodiment, the pharmaceutical composition comprises each of (i) butylated hydroxytoluene (BHT) at a concentration of least 0.05%; (ii)

di-sodium EDTA at a concentration of least 0.001%; and (iii) Trolamine to provide an apparent pH in the range 6.50 to 7.50.

In a certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w; and
(vi) a carbomer such as carbomer homopolymer type C980 in the range of 0.5 to 2.0% w/w.

In another certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w;
(vi) a carbomer such as carbomer homopolymer type C980 in the range of 0.5 to 2.0% w/w;
(vii) butylated hydroxytoluene (BHT) at a concentration of least 0.05%;
(viii) di-sodium EDTA at a concentration of least 0.001%; and
(ix) Trolamine to provide an apparent pH in the range 6.50 to 7.50.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.
(vii) butylated hydroxytoluene (BHT) at a concentration of least 0.1%;
(viii) di-sodium EDTA at a concentration of least 0.005%; and
(ix) Trolamine to provide an apparent pH in the range 6.50 to 7.50.

In specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w; and
(vii) water at a concentration of 19.5-22% w/w.

In yet other specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w;
(vii) butylated hydroxytoluene (BHT) at a concentration of 0.1% w/w;
(viii) di-sodium EDTA at a concentration of 0.005% w/w;
(ix) Trolamine at a concentration of 0.375% w/w; and
(x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxyl)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6%

In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments a second therapeutic agent is present.

In some embodiments, the condition to be treated is NAFLD (Non-Alcoholic Fatty Liver Disease), in other embodiments, the condition to be treated is NASH (Non-Alcoholic SteatoHepatitis, the most severe form of NAFLD)

In some embodiments, the area for topical application is any area of skin, in other embodiments, the area for topical application is an excessively fatty area of skin.

In some embodiments, the duration of treatment is greater than 28 days.

In further embodiments, the duration of treatment is between one and six months or thereabouts. In yet further embodiments, the duration of treatment is between one and twenty four months or thereabouts; one and eighteen months or thereabouts; one and twelve months or thereabouts; one and three months or thereabouts; one and two months or thereabouts; or one month or thereabouts.

The present invention also provides a method of treating cancer or a precancerous state in a subject which comprises administering to an area of skin, including an area of pre-cancerous or cancerous skin a composition comprising a pharmaceutically acceptable carrier, which provides an environment of physical and chemical stability, and an amount of a compound or of a pharmaceutically acceptable salt of the compound or ester of the compound or prodrug of the compound effective to treat the skin condition, wherein the compound has the structure I:

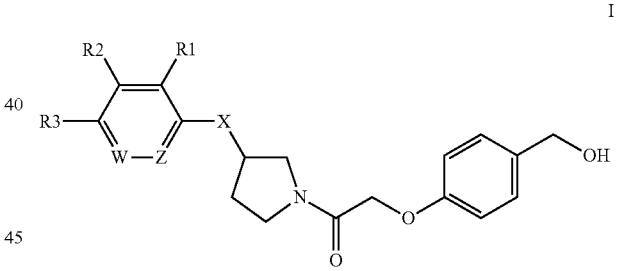

wherein:
X is O, NH, N-alkyl or N-acyl, S, SO or $SO_2$;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(C$NR_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; NHC(O)$R_6$; $NR_6C(O)R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$;

wherein adjacent substituents R₁, R₂ and R₃ and R₄ and R₅, if present, may form a saturated or unsaturated 5-membered or 6-membered carbocyclic or heterocyclic ring;

wherein each of R₆, R₇, R₈, R₉ and R₁₀, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

In some embodiments, X is O; W is independently CR₄ or N; Z is independently CR₅ or N; each of R₁, R₂ and R₃ and R₄ and R₅, if present, is independently: H; OH; F; Cl; Br; I; C₁ to C₆ straight chain or branched chain alkyl; CH₂F; CHF₂; CF₃; CH₂CH₂F; CH₂CHF₂; CH₂CF₃; CHFCH₂F; CHFCHF₂; CHFCF₃; CF₂CH₂F; CF₂CHF₂; CF₂CF₃; O-alkyl; O-cycloalkyl; O-alkylcycloalkyl; OCH₂F; OCHF₂; OCF₃; OCH₂CH₂F; OCH₂CHF₂; OCH₂CF₃; OCHFCH₂F; OCHFCHF₂; OCHFCF₃; OCF₂CH₂F; OCF₂CHF₂; OCF₂CF₃; O—(CO)—R₆; O—(CNH)—R₆; O—(CNR₆)—R₇; SO₃H or a ester thereof; CO₂H or a ester thereof; NO₂; NH₂; NHCH(O); NR₆CH(O); NHC(O)R₆; NR₆C(O)R₇; C(O)NR₆R₇; C(NH)NR₆R₇; C(NH)NR₆OH; C(NH)NR₆NO₂; or C(NR₆)NR₇C(NR₈)NR₉R₁₀; adjacent substituents R₁, R₂ and R₃ and R₄ and R₅, if present, may form a saturated or unsaturated 5-membered or 6-membered carbocyclic or heterocyclic ring; and each of R₆, R₇, R₈, R₉ and R₁₀, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In some embodiments, the compound is one of the following:

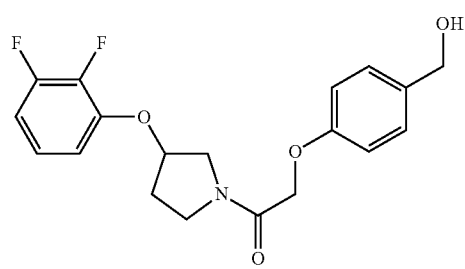

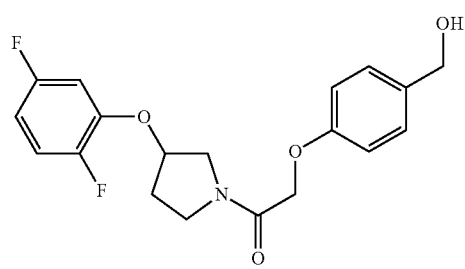

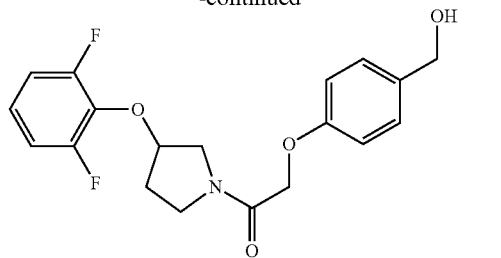

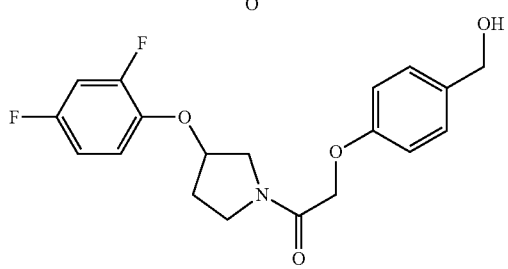

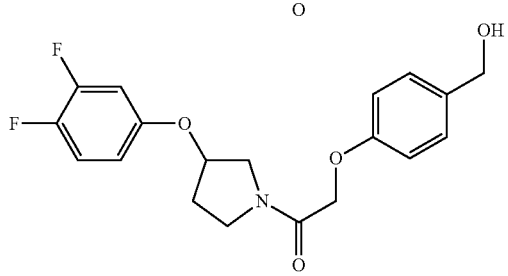

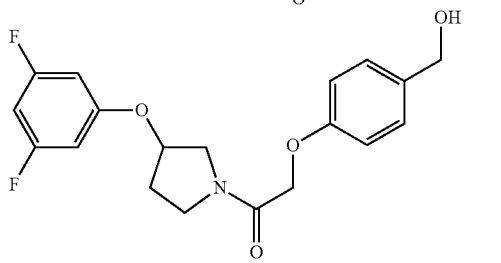

or a pharmaceutically acceptable salt, ester or prodrug form thereof.

In further embodiments, the compound is one of the following:

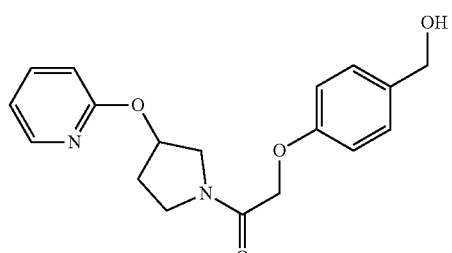

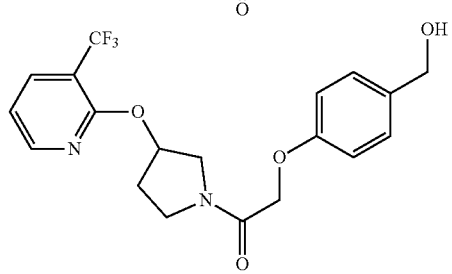

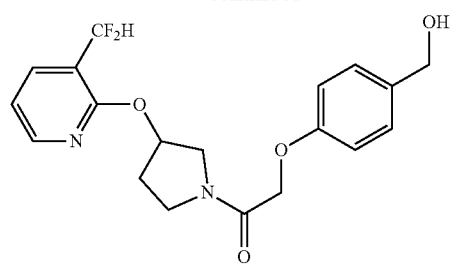
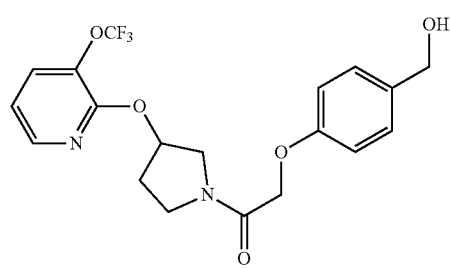
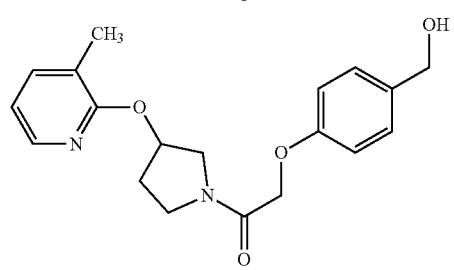
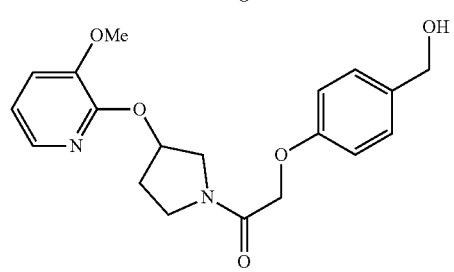
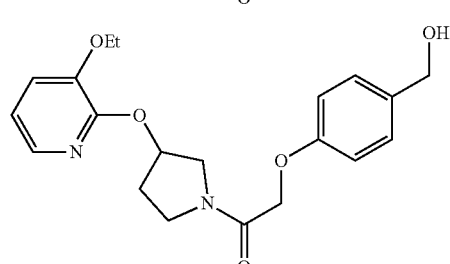
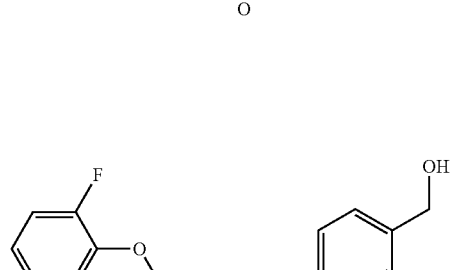
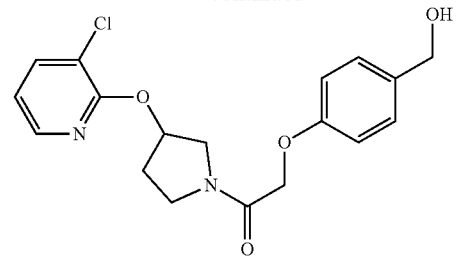
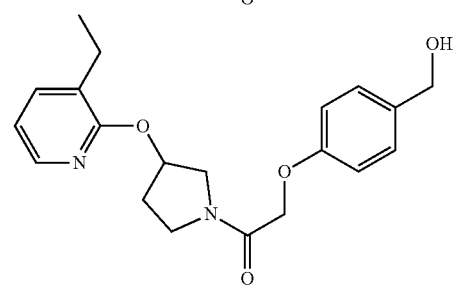
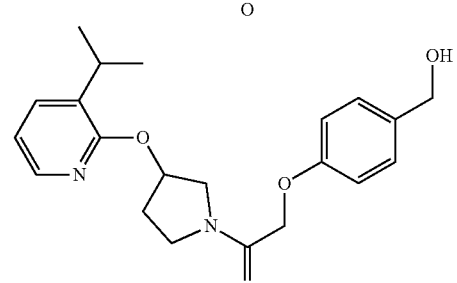
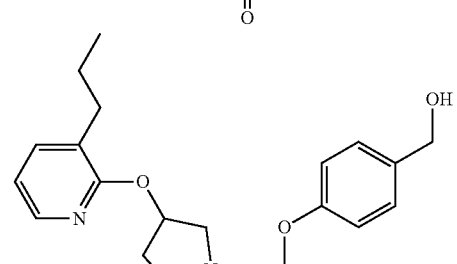
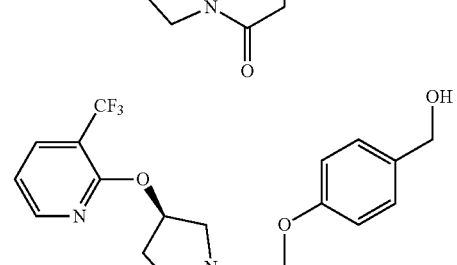
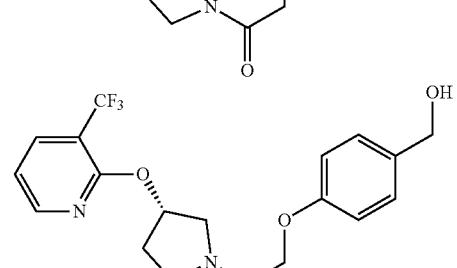
or a pharmaceutically acceptable salt, ester or prodrug form thereof.

In yet other embodiments, the compound is one of the following:
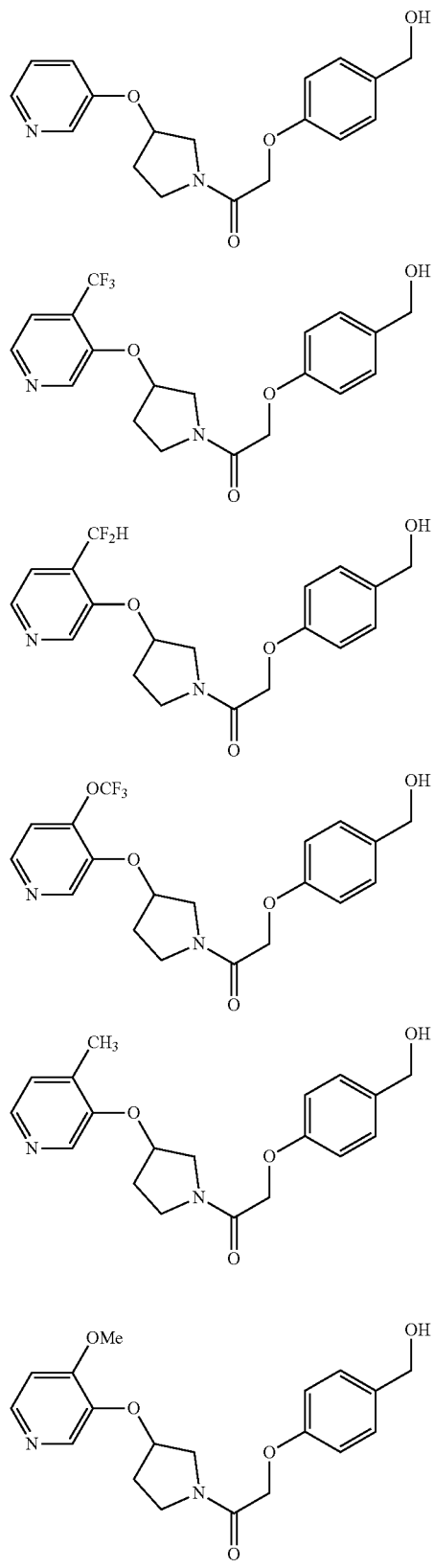
-continued
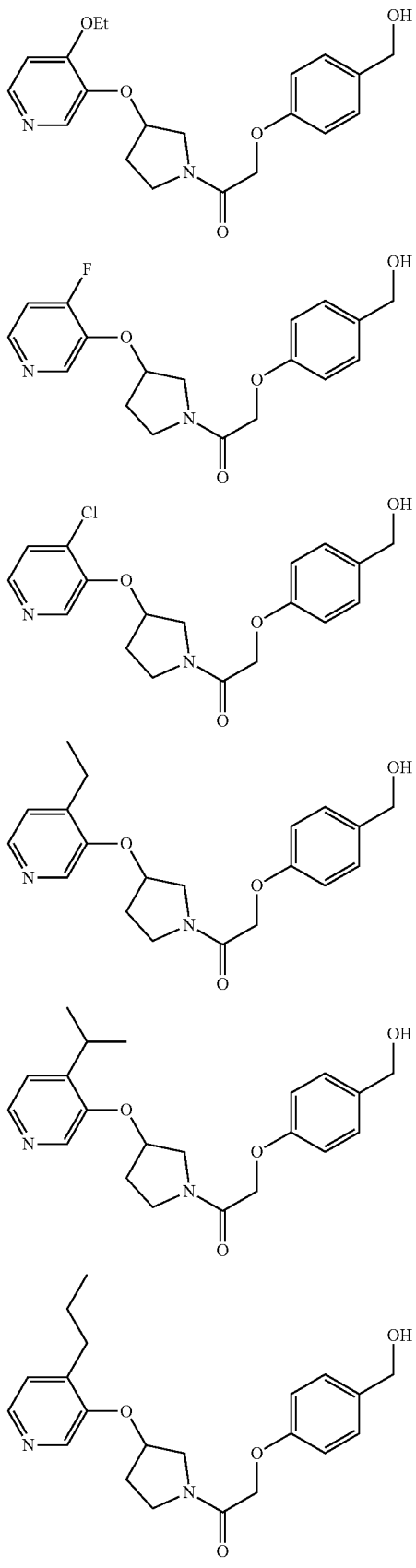

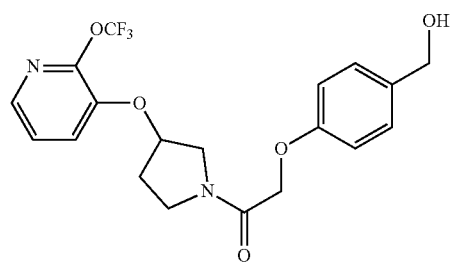 [SMILES: O=C(COc1ccc(CO)cc1)N1CCC(Oc2cccnc2OC(F)(F)F)C1]
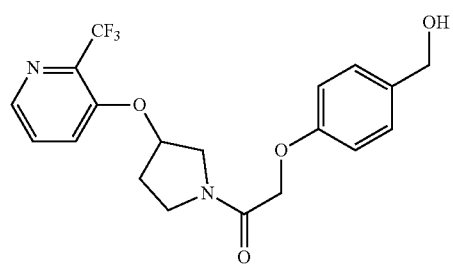 [SMILES: O=C(COc1ccc(CO)cc1)N1CCC(Oc2cccnc2C(F)(F)F)C1]
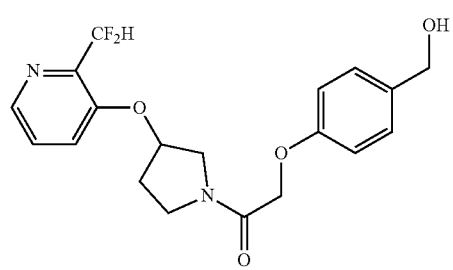 [SMILES: O=C(COc1ccc(CO)cc1)N1CCC(Oc2cccnc2C(F)F)C1]
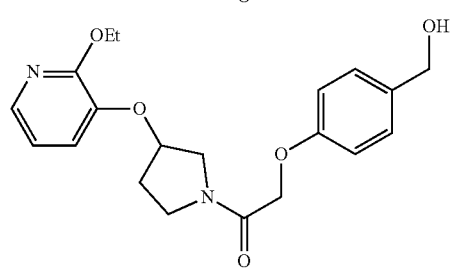
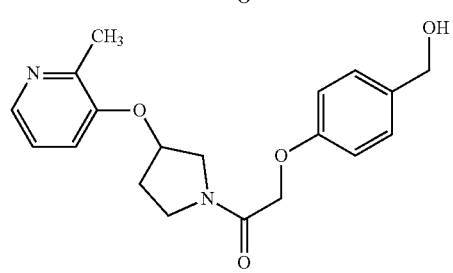
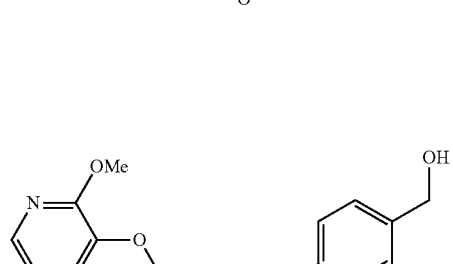
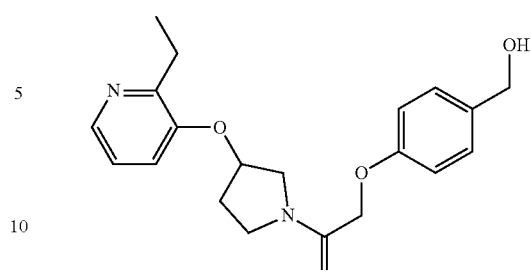
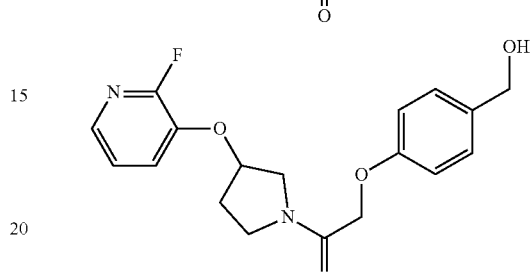
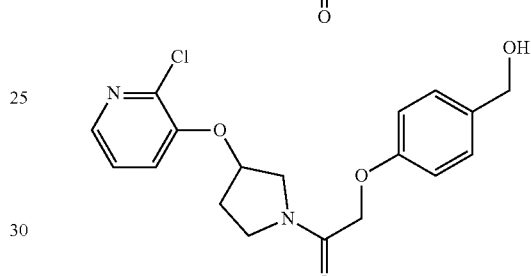
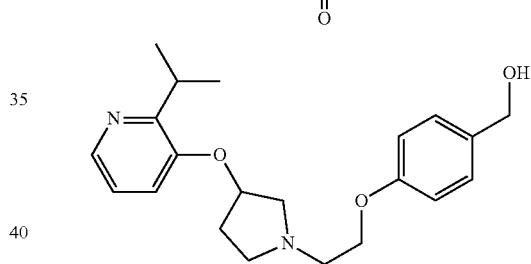
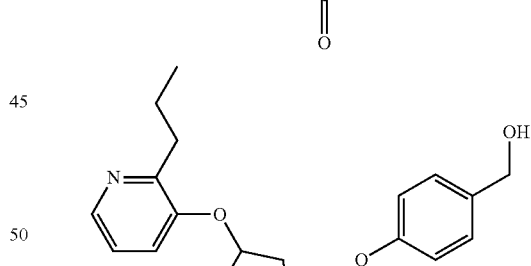
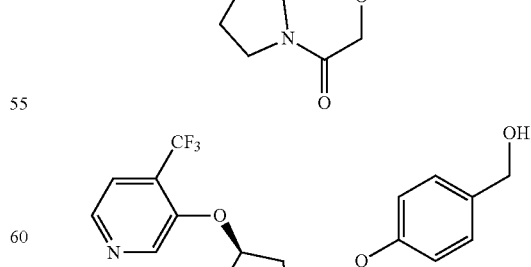
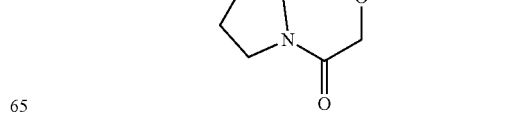

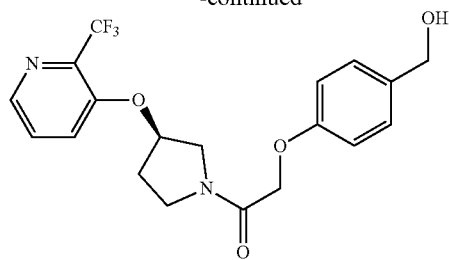
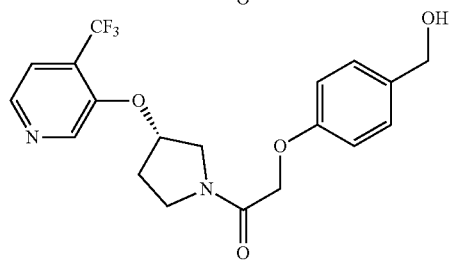
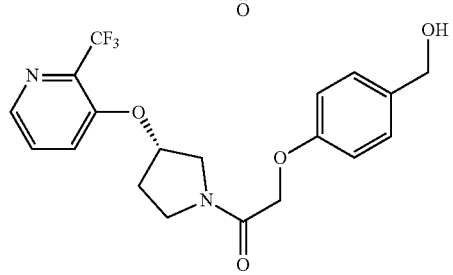
or a pharmaceutically acceptable salt, ester or prodrug form thereof.
In yet further embodiments, the compound is one of the following:
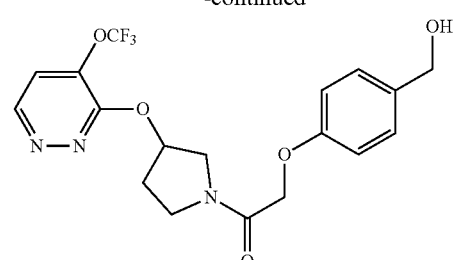
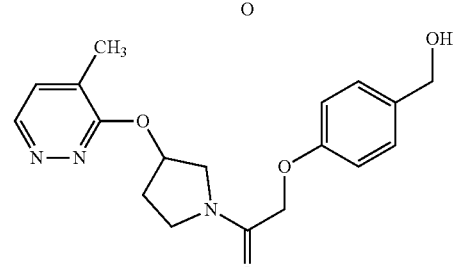
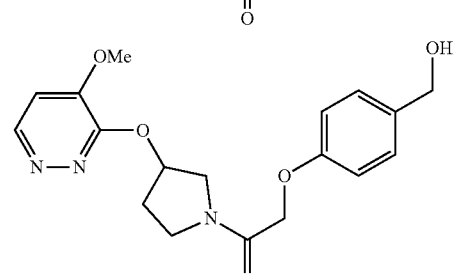
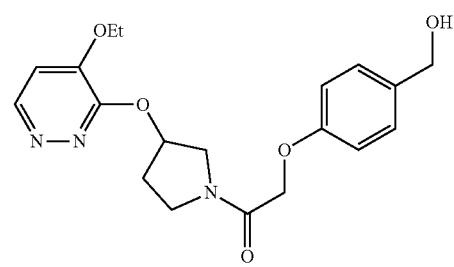
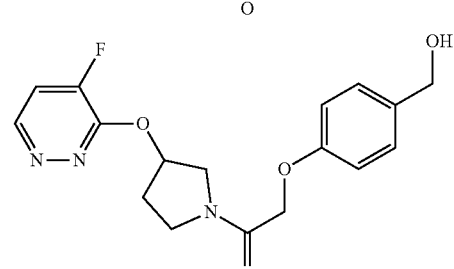
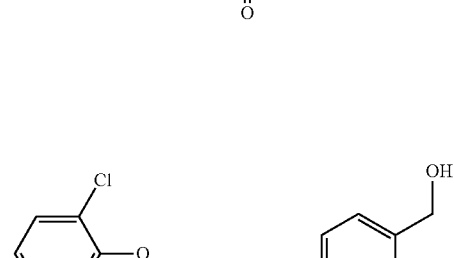
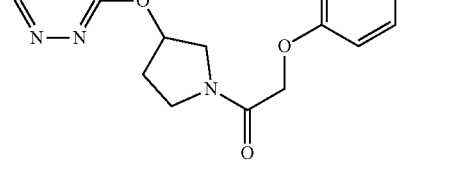

-continued

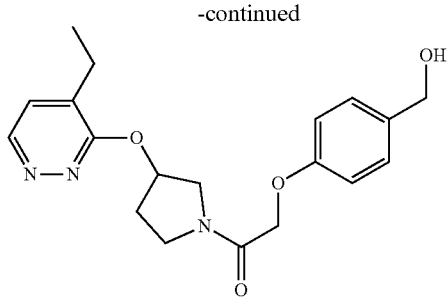
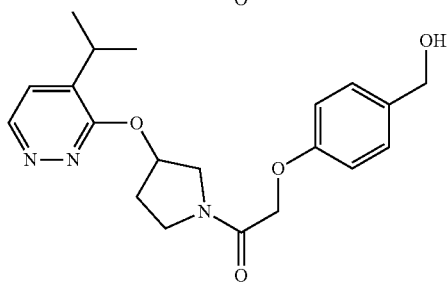
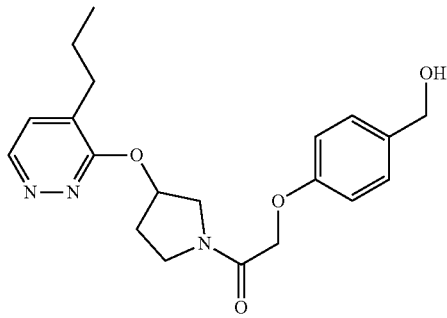
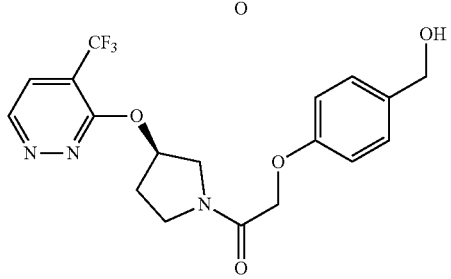
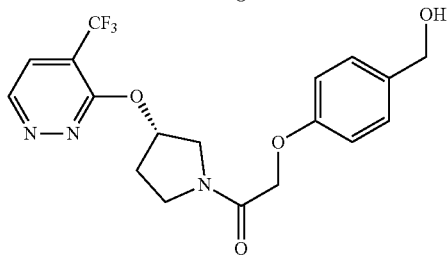

or a pharmaceutically acceptable salt, ester or prodrug form thereof.

In further embodiments, X is NH, N-alkyl or N-acyl; W is independently $CR_4$ or N; Z is independently $CR_5$ or N; each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CN$R_6$)—$R_7$; $SO_3H$ or a ester thereof; $CO_2H$ or a ester thereof; $NO_2$; $NH_2$; NHCH(O); $NR_6$CH(O); NHC(O)$R_6$; $NR_6$C(O)$R_7$; C(O)$NR_6R_7$; C(NH)$NR_6R_7$; C(NH)$NR_6$OH; C(NH)$NR_6NO_2$; or C($NR_6$)$NR_7$C($NR_8$)$NR_9R_{10}$; adjacent substituents $R_1$, $R_2$ and $R_3$ and $R_4$ and $R_5$, if present, may form a saturated or unsaturated 5-membered or 6-membered carbocyclic or heterocyclic ring; and each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In certain embodiments, the compound is one of the following:

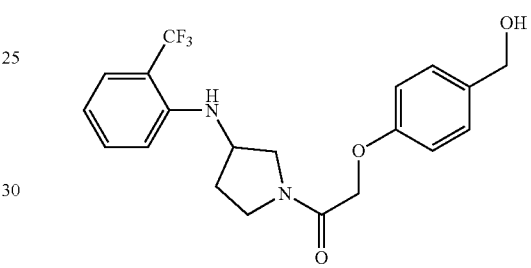
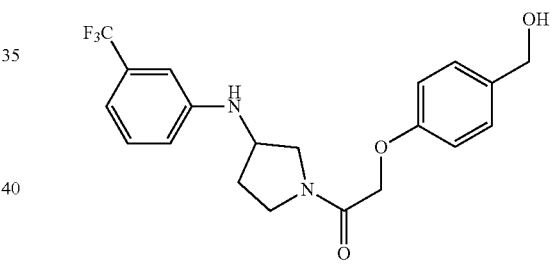
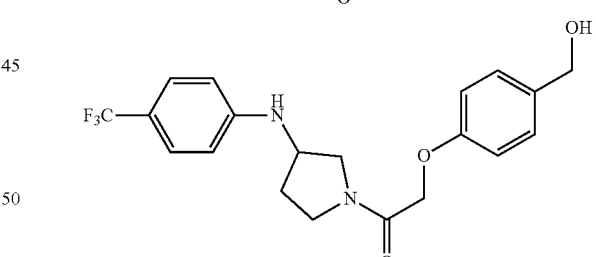
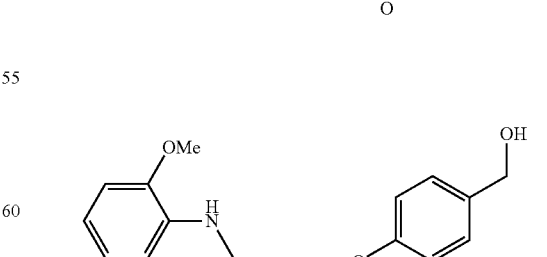
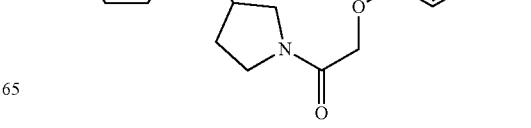

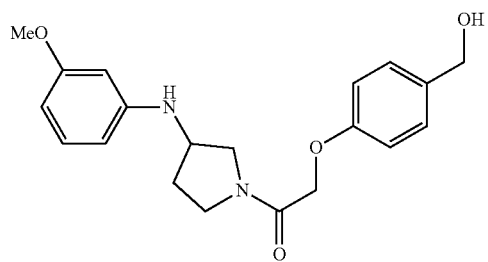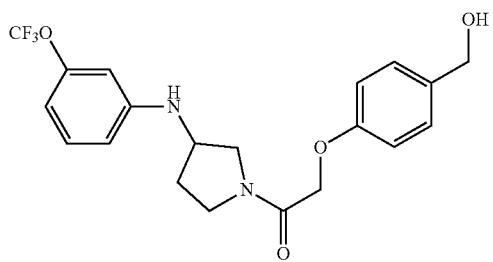

307
-continued
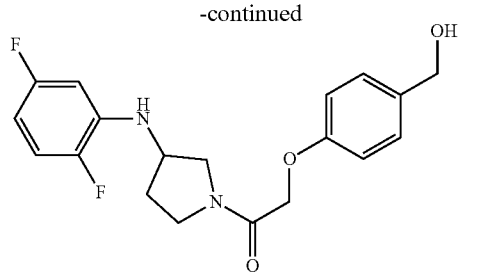
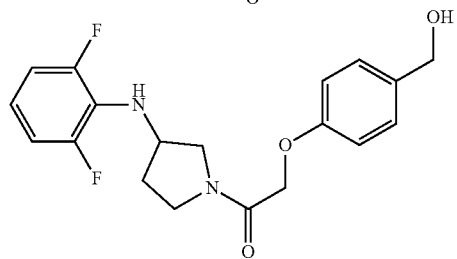
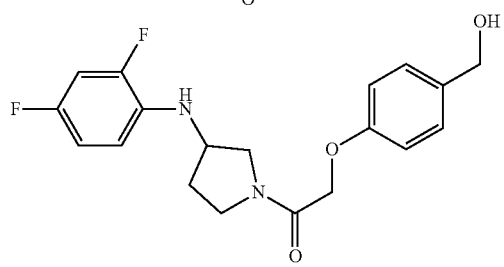
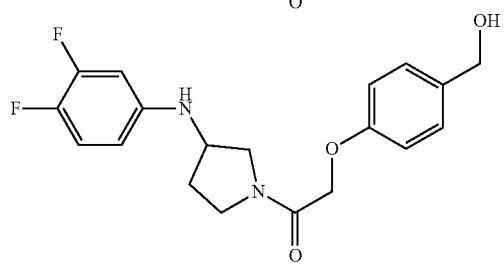
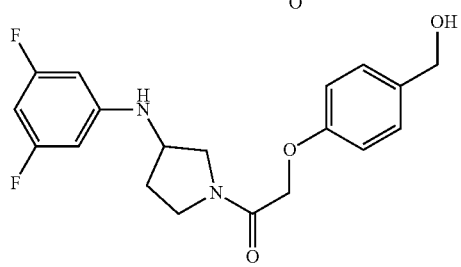
or a pharmaceutically acceptable salt, ester or prodrug form thereof.
In other embodiments, the compound is one of the following:
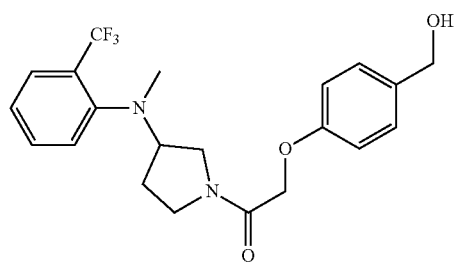
308
-continued
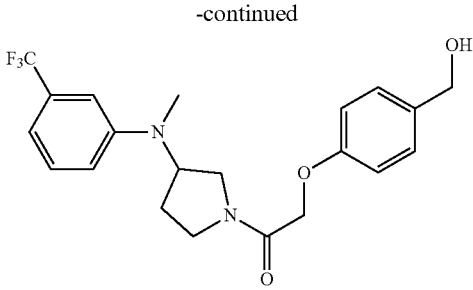
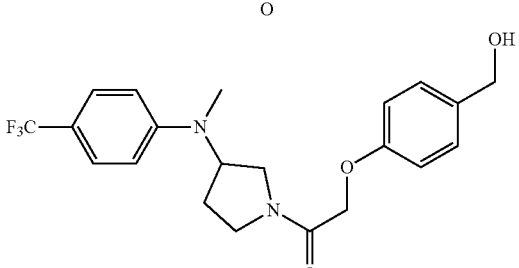
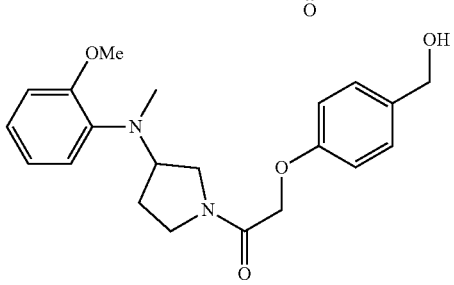
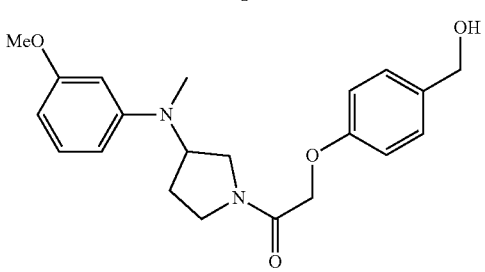
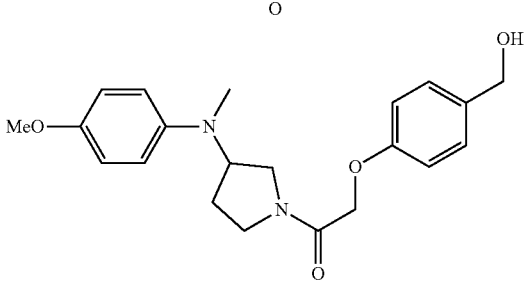
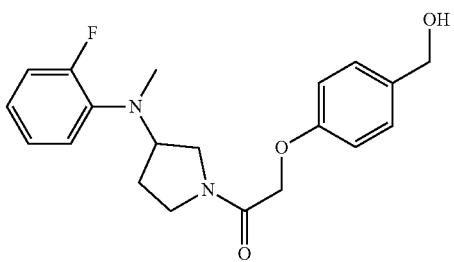

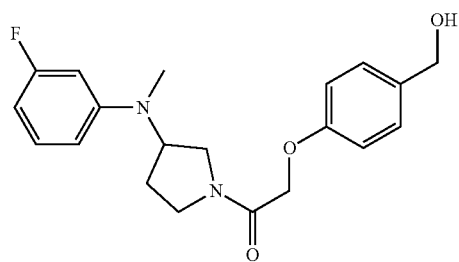
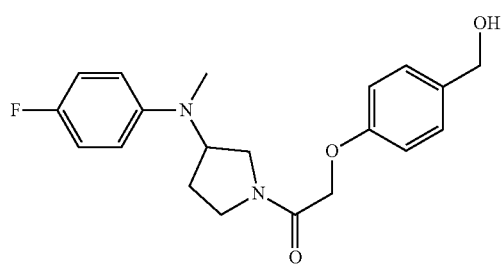
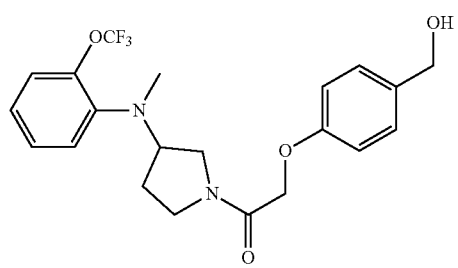
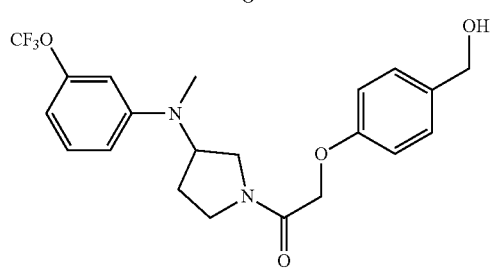
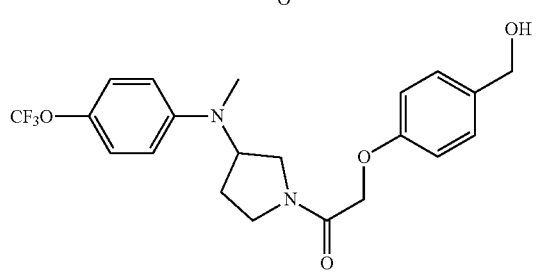
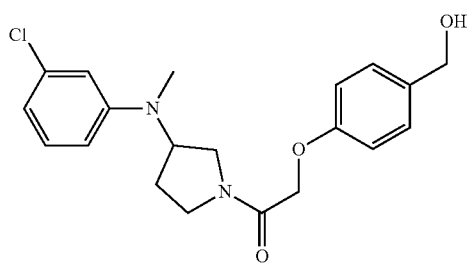
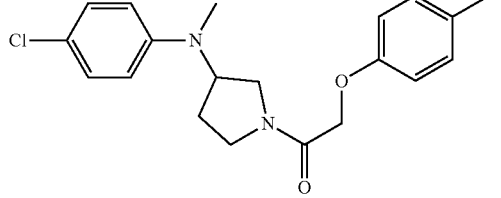
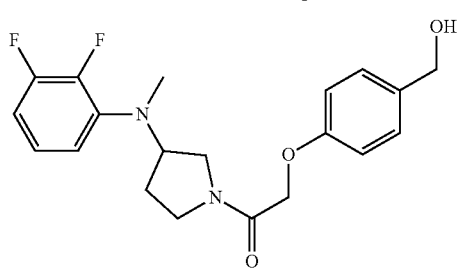
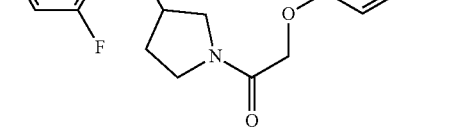
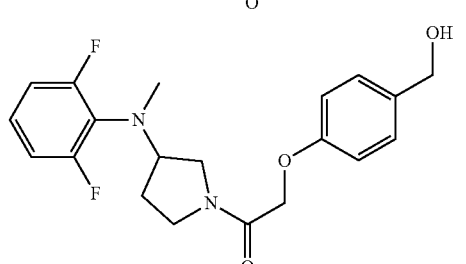

311
-continued
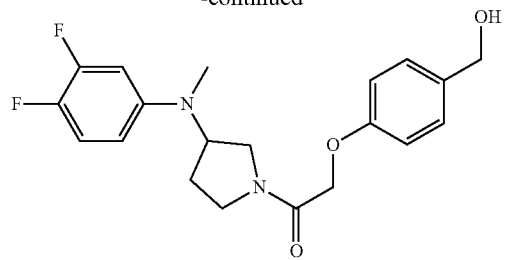
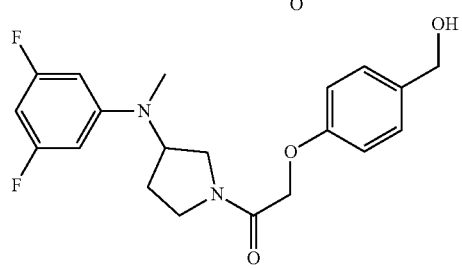
or a pharmaceutically acceptable salt, ester or prodrug form thereof.
In further embodiments, the compound is one of the following:
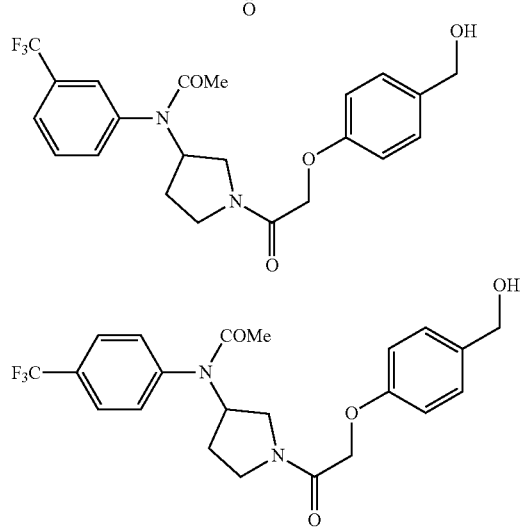
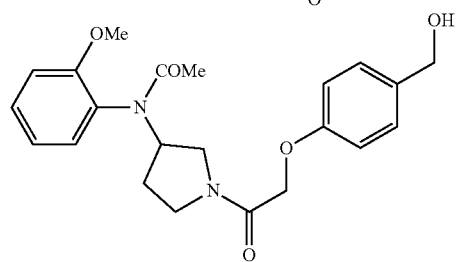
312
-continued
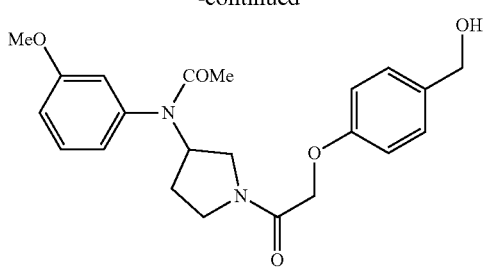
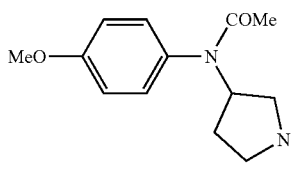
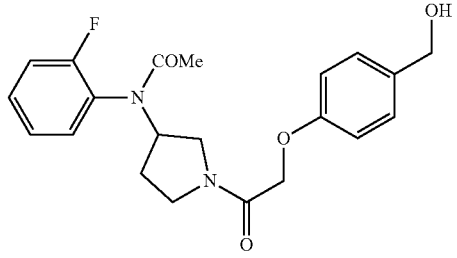
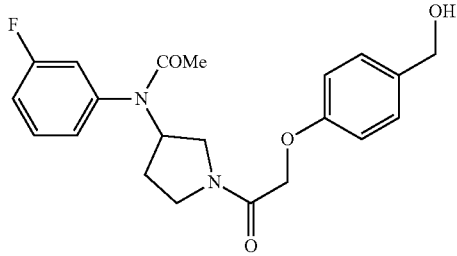
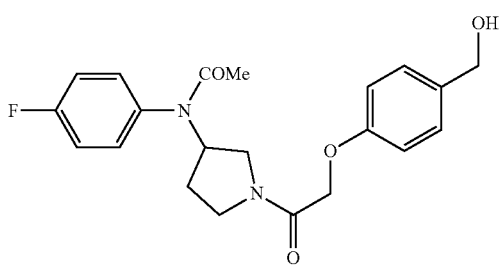
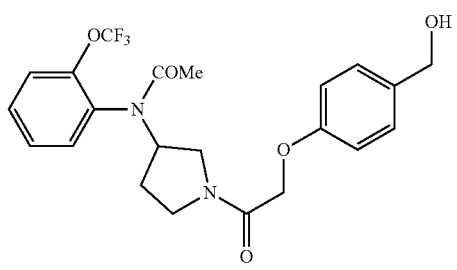

313
-continued
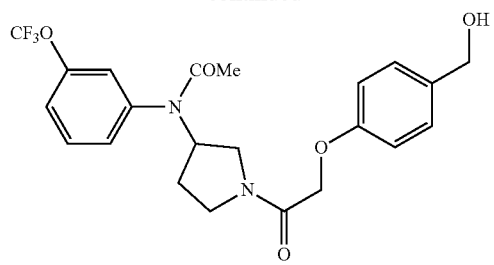
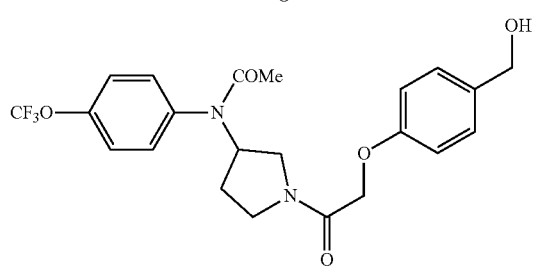
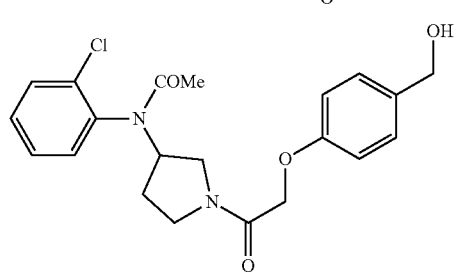
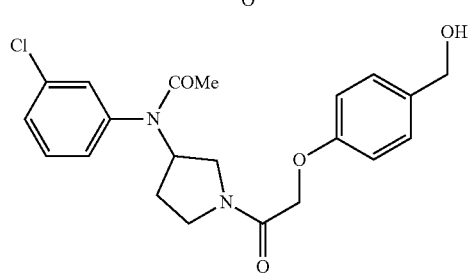
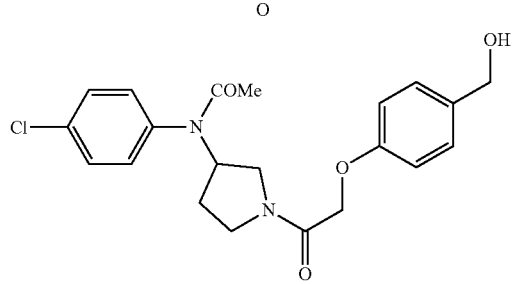
314
-continued
or a pharmaceutically acceptable salt, ester or prodrug form thereof.
In yet further embodiments, the compound is one of the following:
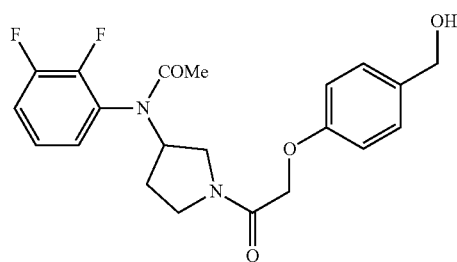
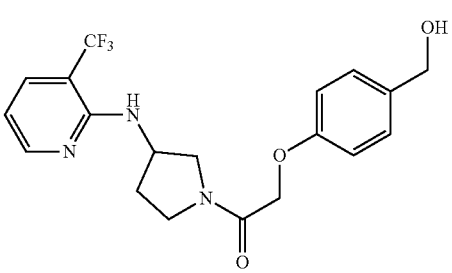

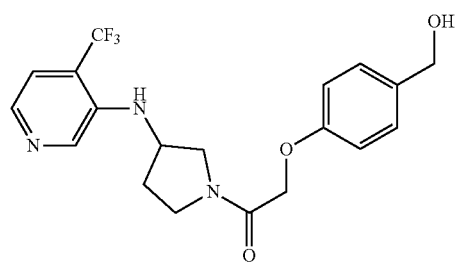
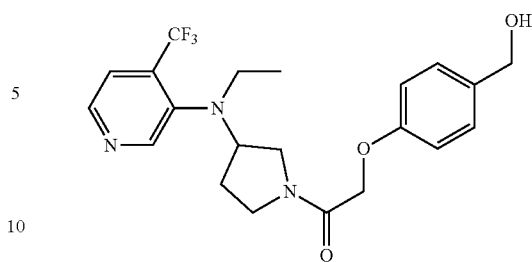
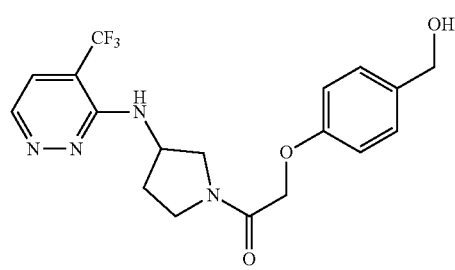
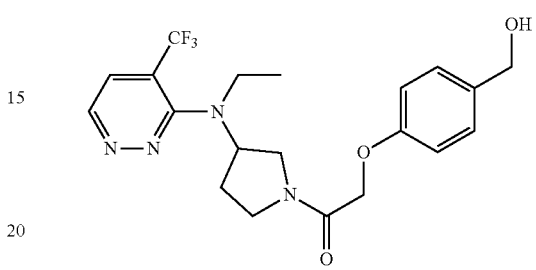
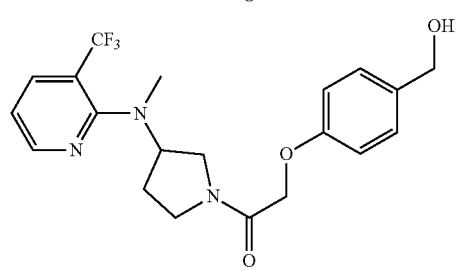
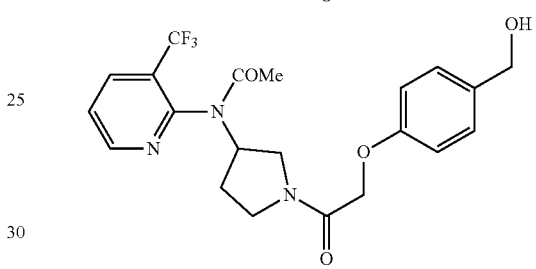
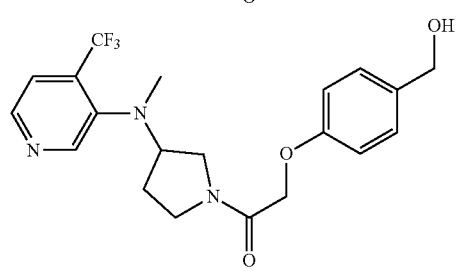
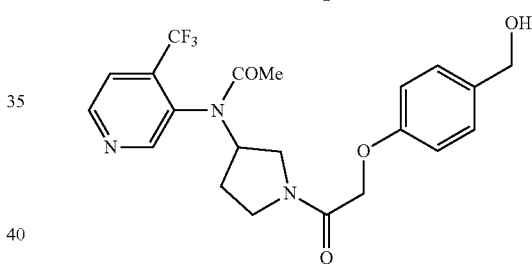
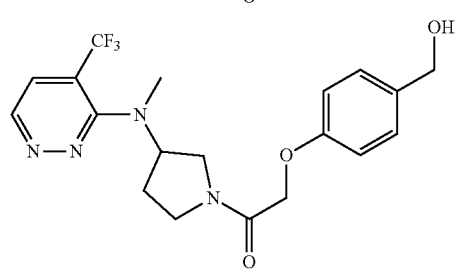
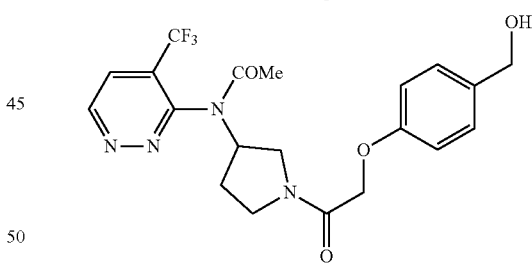
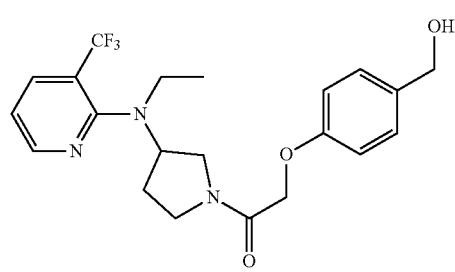
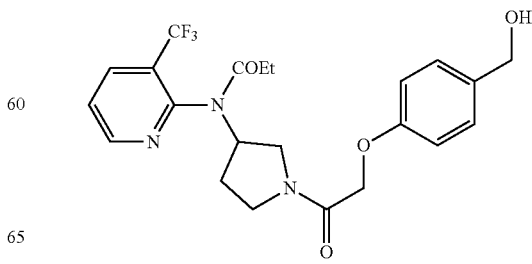

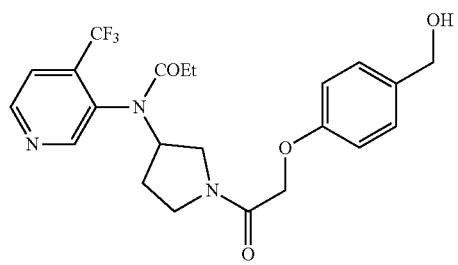
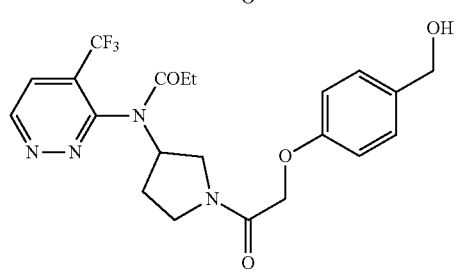
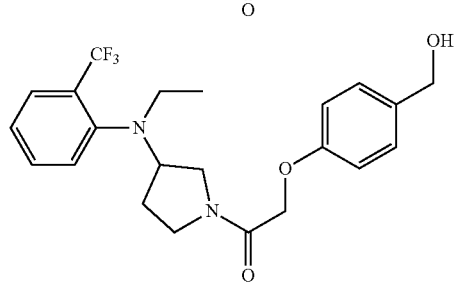
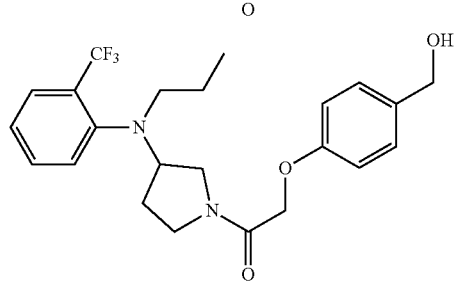
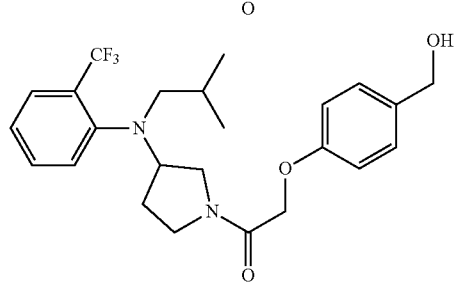
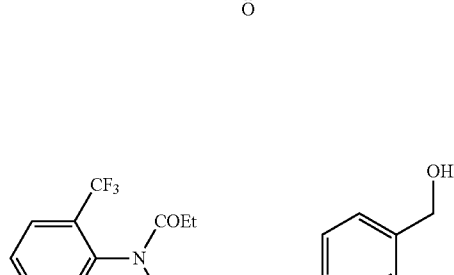
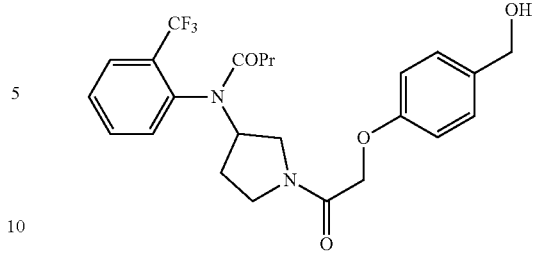
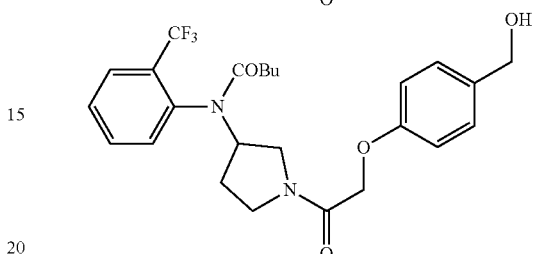
or a pharmaceutically acceptable salt, ester or prodrug form thereof.
In yet other embodiments, the compound is one of the following:
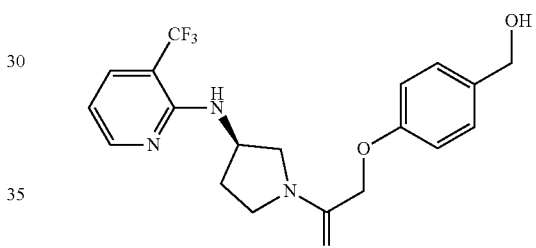
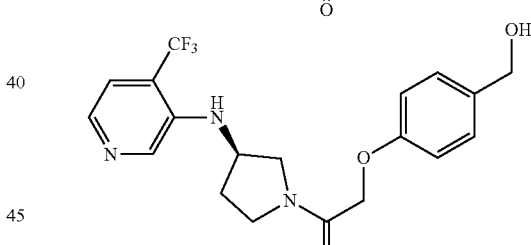
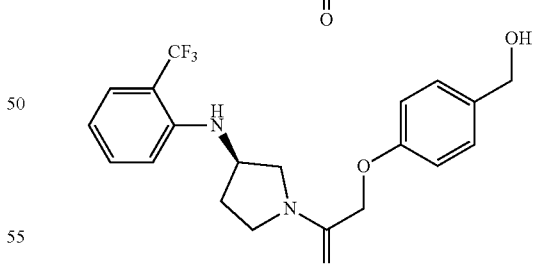
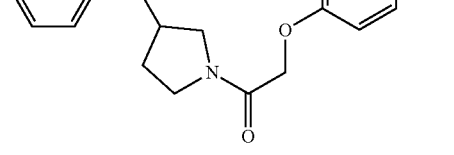

319
-continued
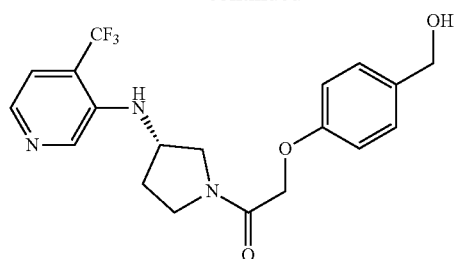
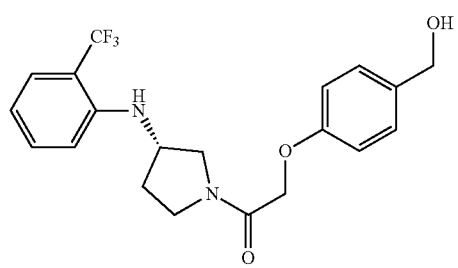
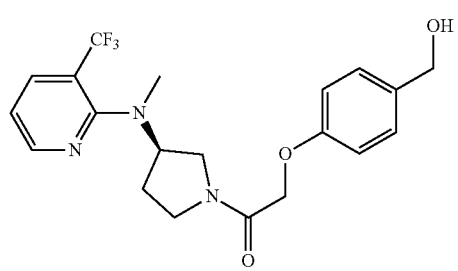
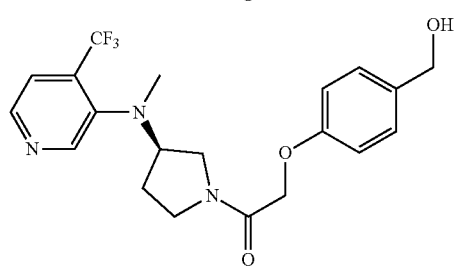
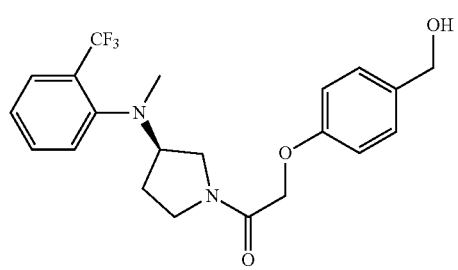
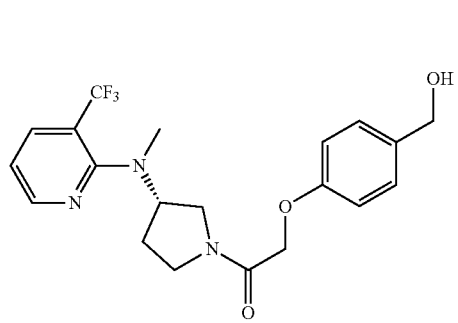
320
-continued
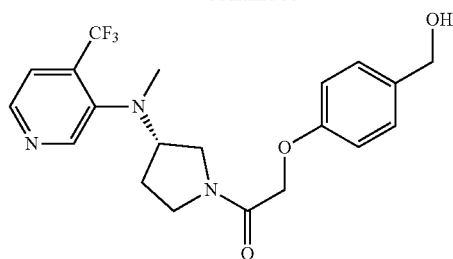
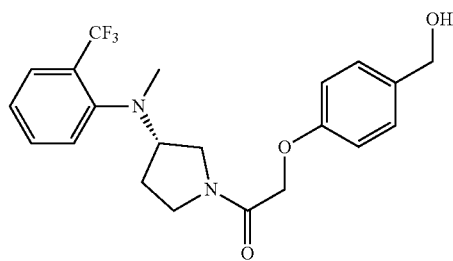
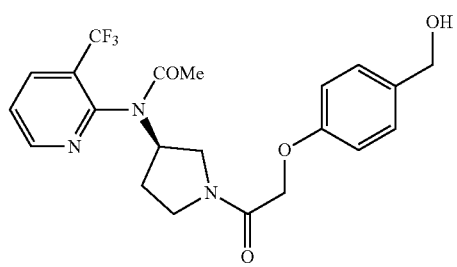
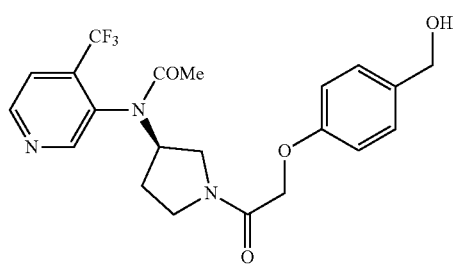
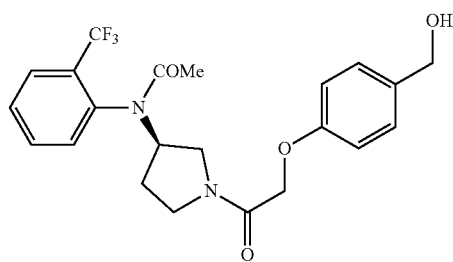

-continued

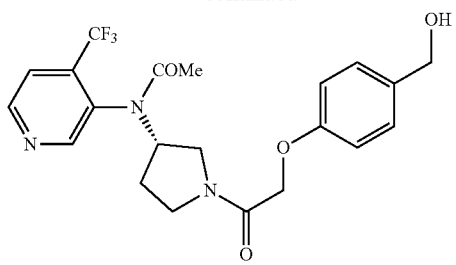

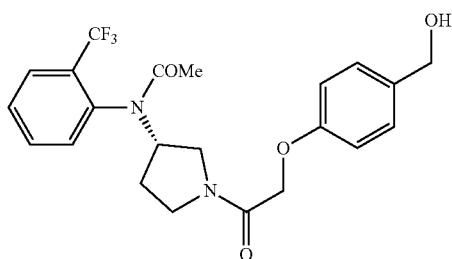

or a pharmaceutically acceptable salt, ester or prodrug form thereof.

In yet further embodiments, X is S, SO or SO$_2$; W is independently CR$_4$ or N; Z is independently CR$_5$ or N; each of R$_1$, R$_2$ and R$_3$ and R$_4$ and R$_5$, if present, is independently: H; OH; F; Cl; Br; I; C$_3$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$; adjacent substituents R$_1$, R$_2$ and R$_3$ and R$_4$ and R$_5$, if present, may form a saturated or unsaturated 5-membered or 6-membered carbocyclic or heterocyclic ring; and each of R$_6$, R$_7$, R$_8$, R$_9$ and R$_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or SO$_2$. In further embodiments, X is SO. In yet further embodiments X is SO$_2$.

In some embodiments, the compound is one of:

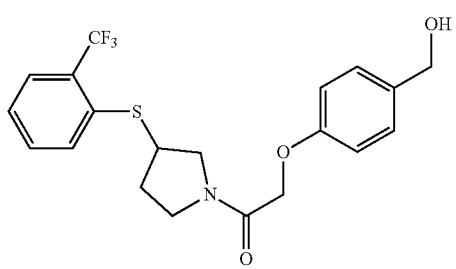

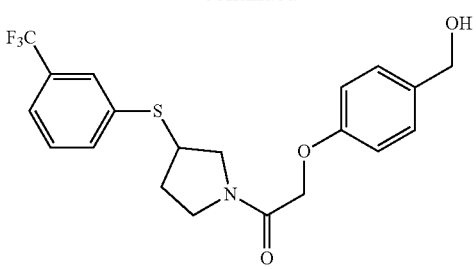

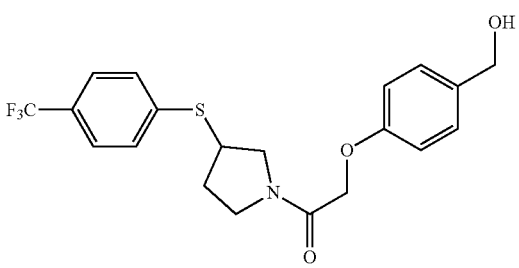

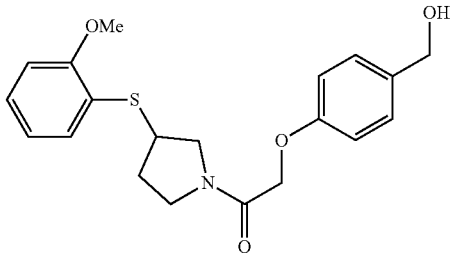

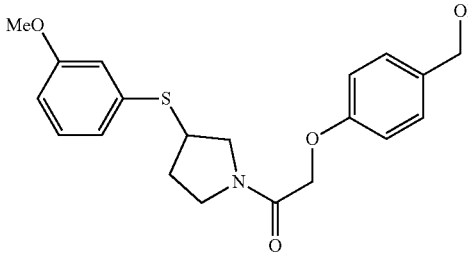

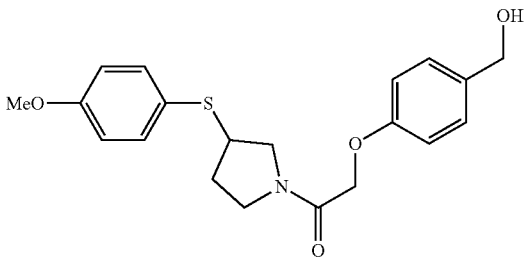

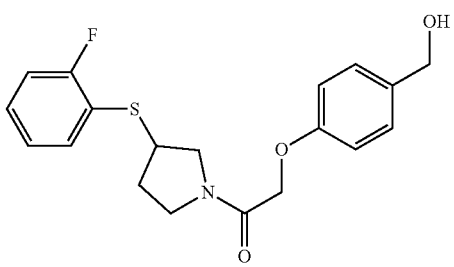

| 323 | 324 |
|---|---|
| -continued | -continued |
| 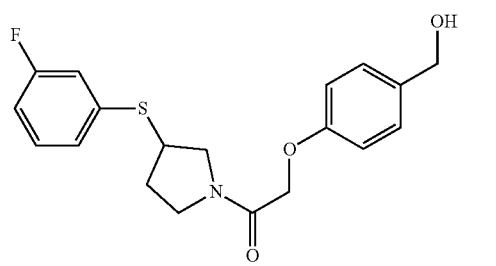 | 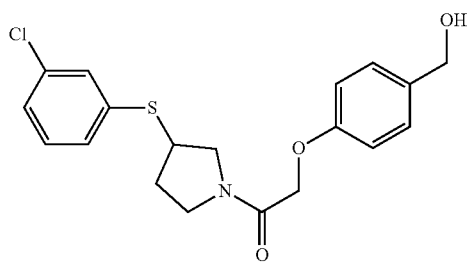 |
| 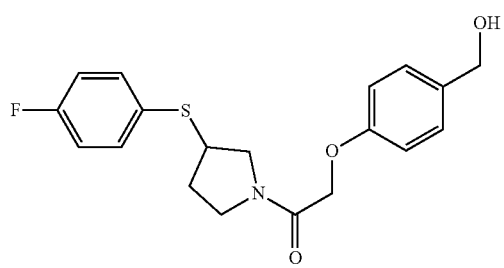 | 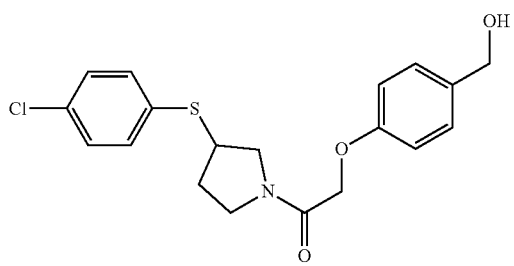 |
| 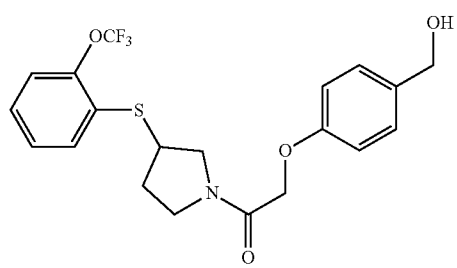 | 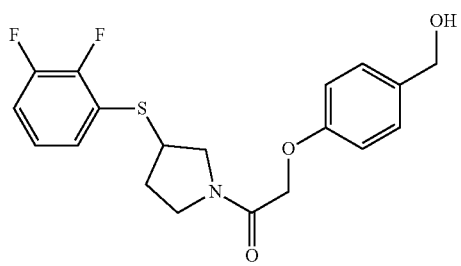 |
| 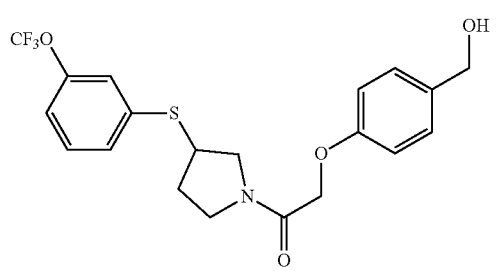 | 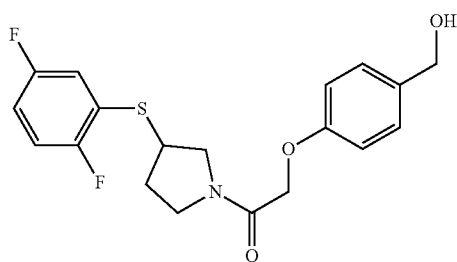 |
| 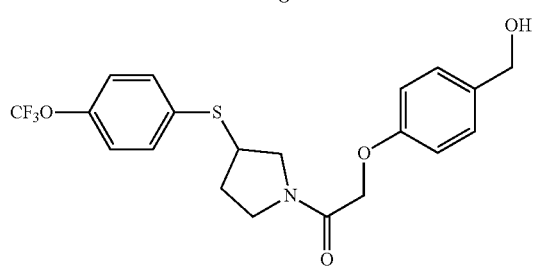 | 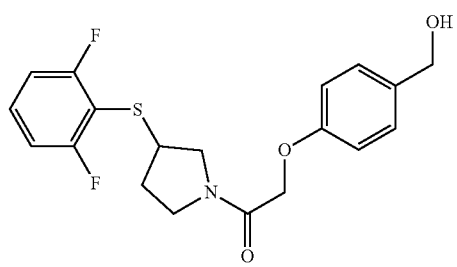 |
| | 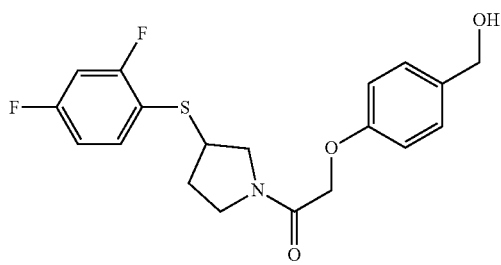 |

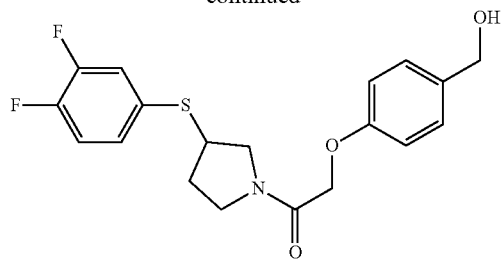
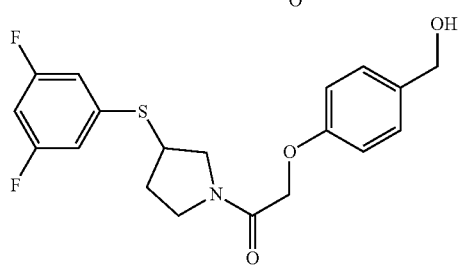
or a pharmaceutically acceptable salt, ester or prodrug form thereof.
In other embodiments, the compound is one of:
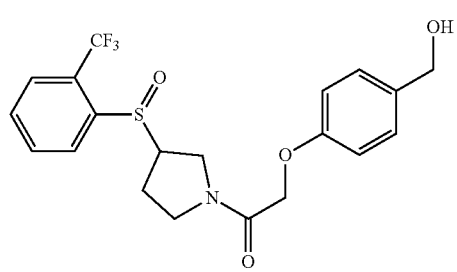
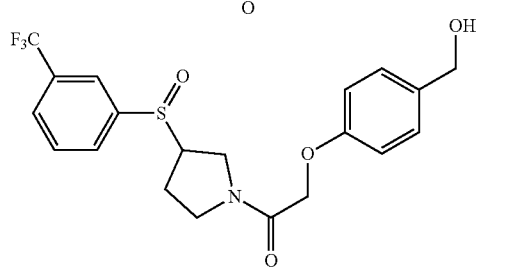
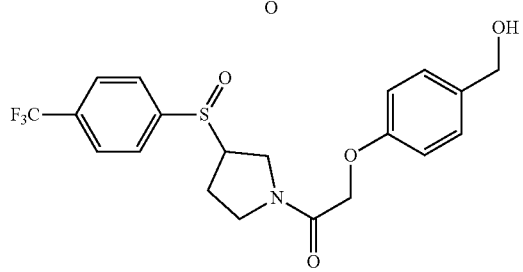
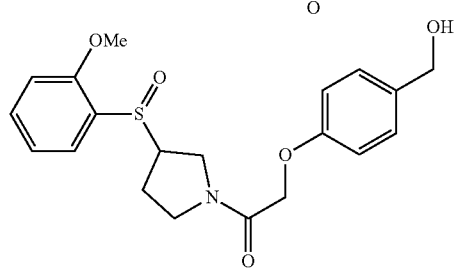
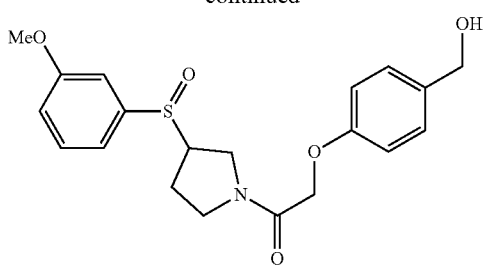
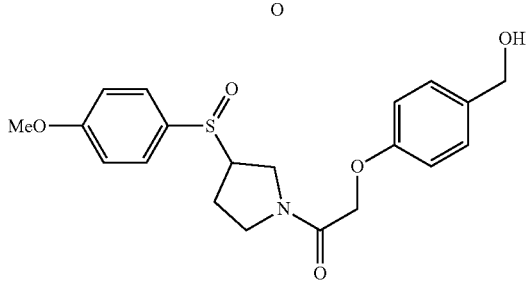
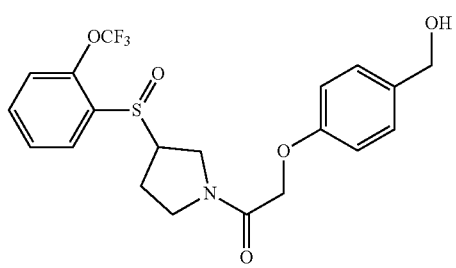

327
-continued
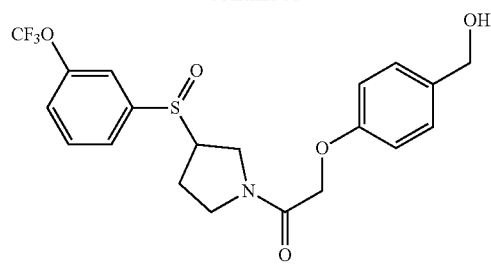
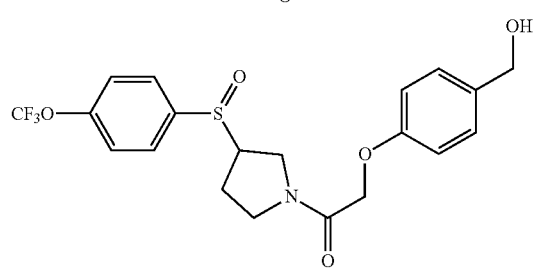
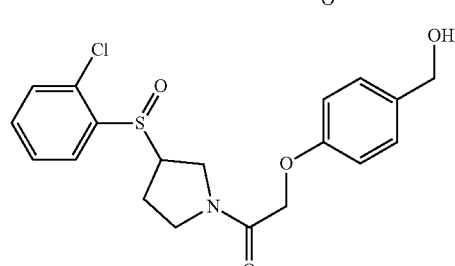
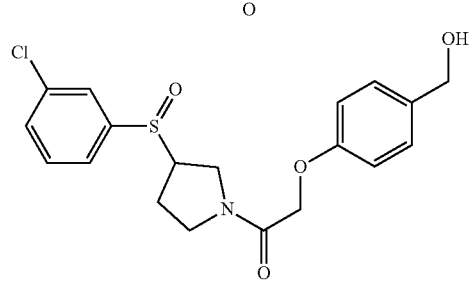
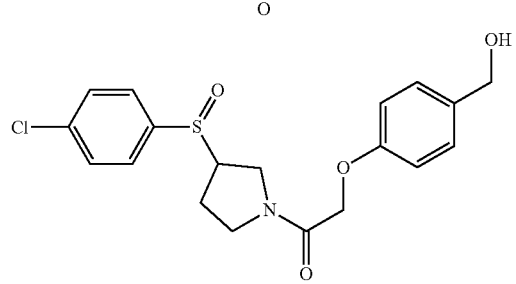
328
-continued
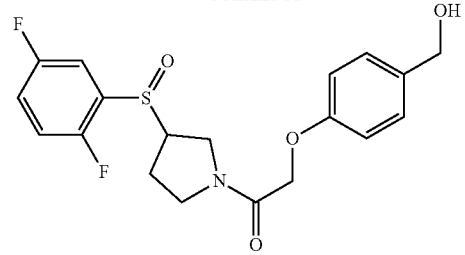
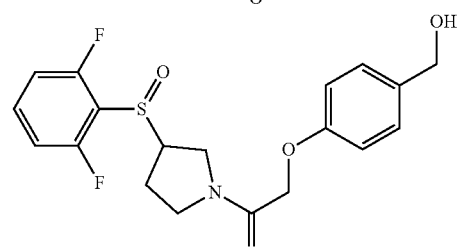
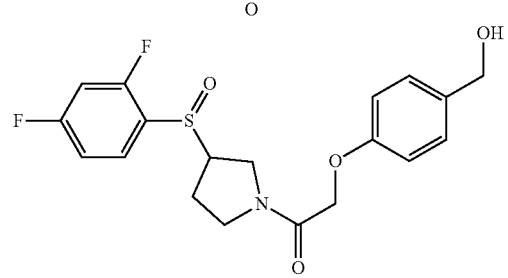
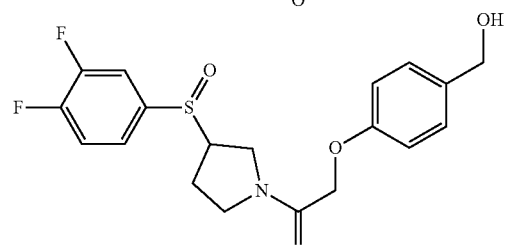
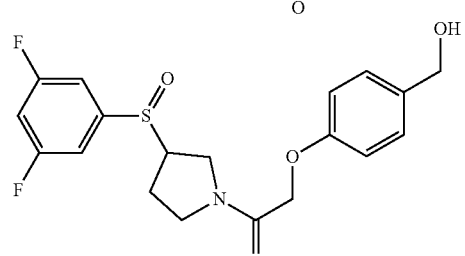
or a pharmaceutically acceptable salt, ester or prodrug form thereof.
In further embodiments, the compound is one of:
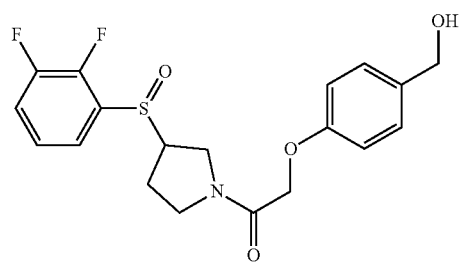
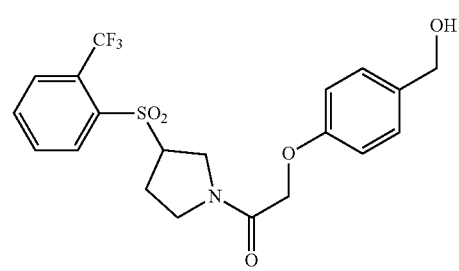

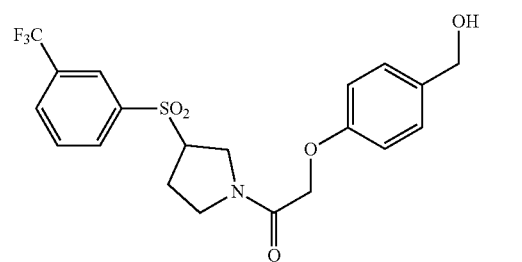
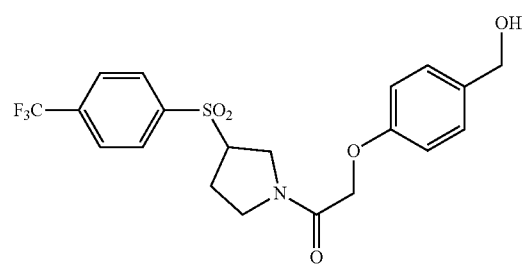
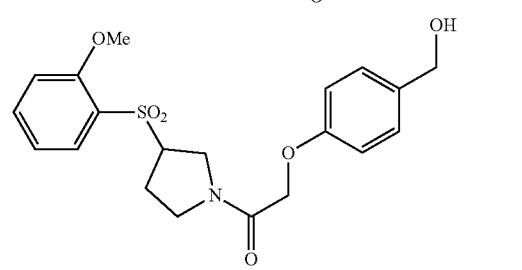
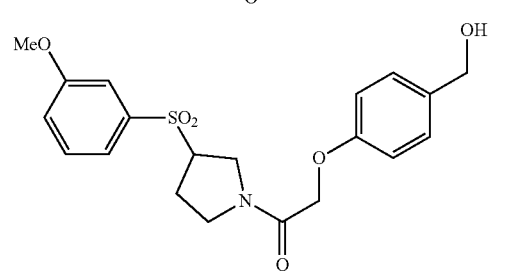
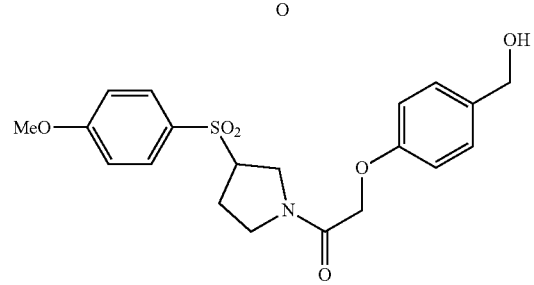
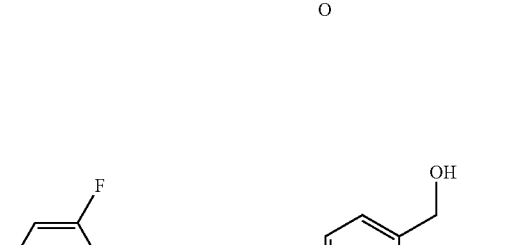
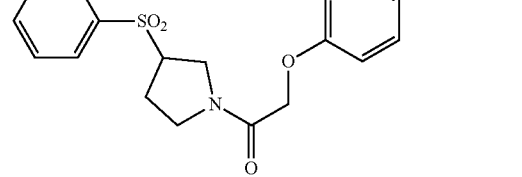
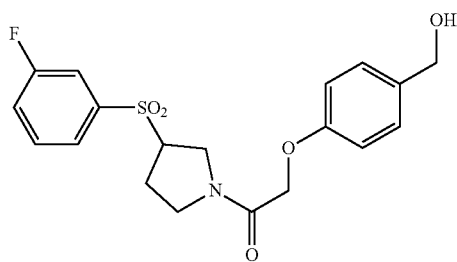
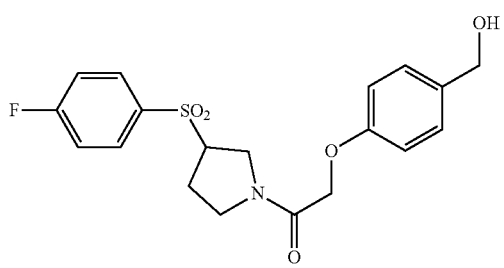
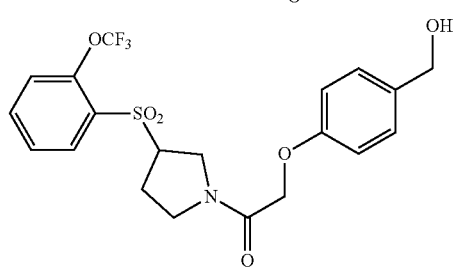
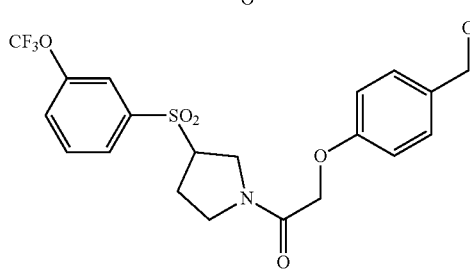
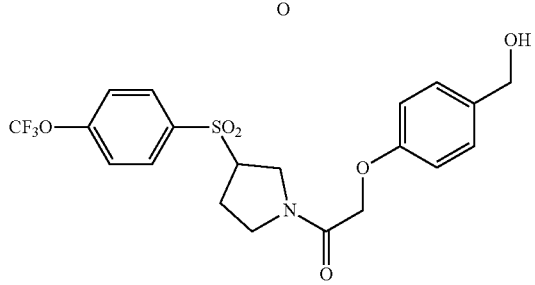
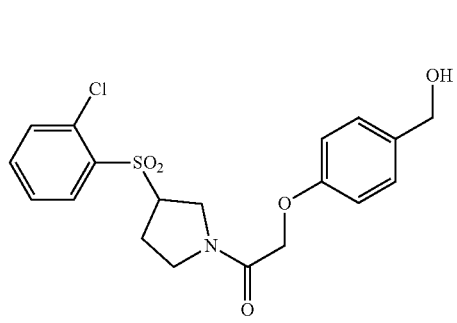

-continued
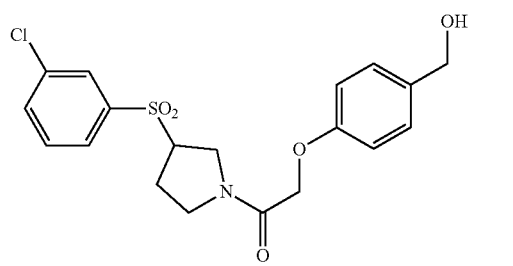
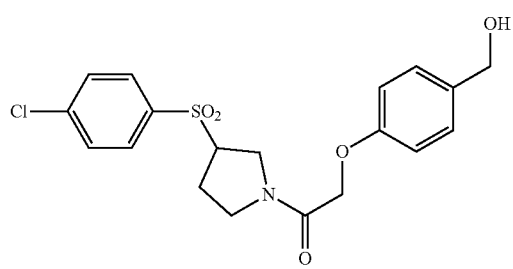
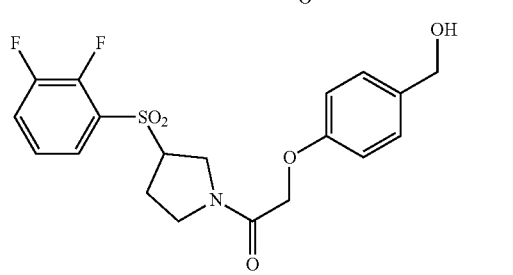
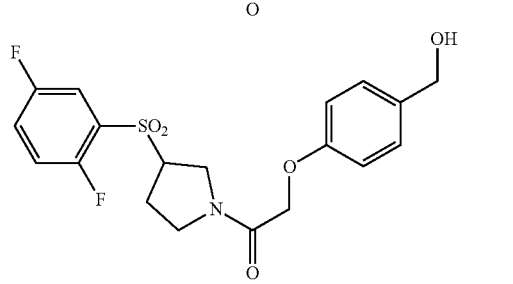
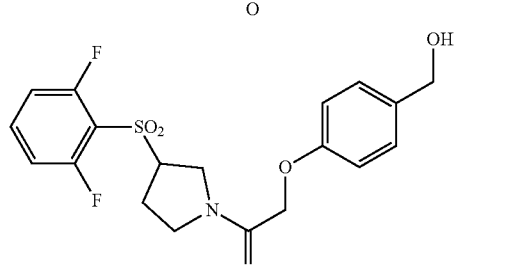
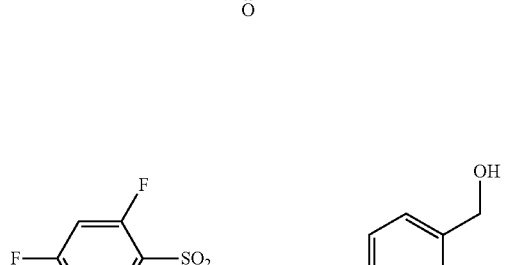
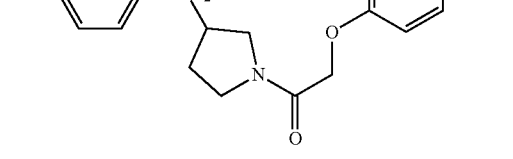
-continued
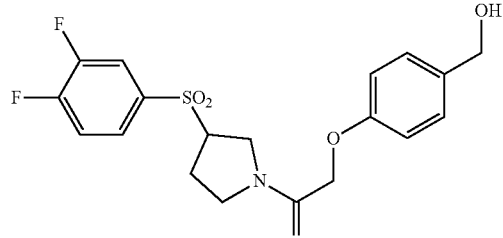
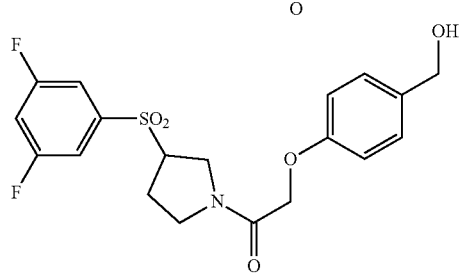
or a pharmaceutically acceptable salt, ester or prodrug form thereof.
In yet further embodiments, the compound is one of:
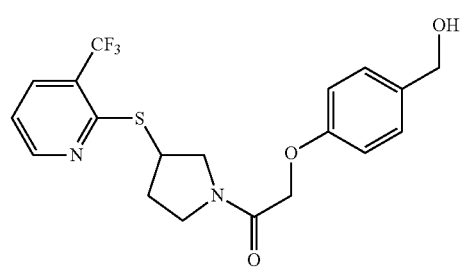
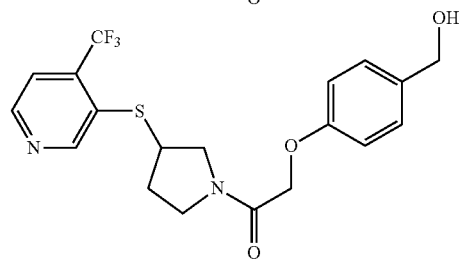
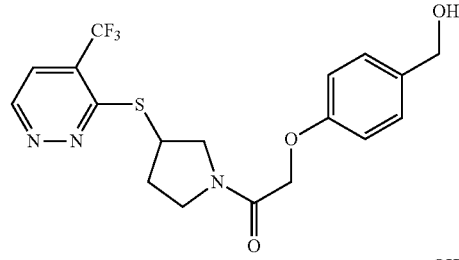
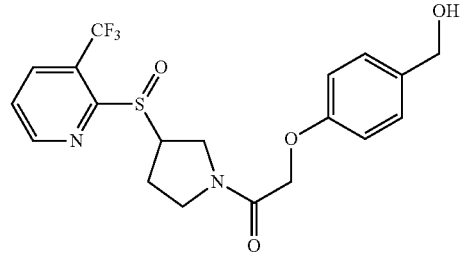

333
-continued
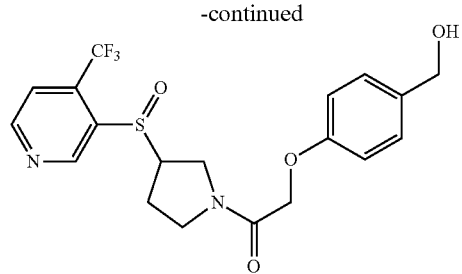
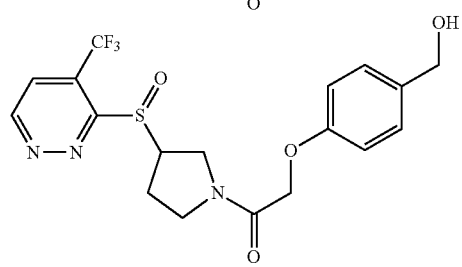
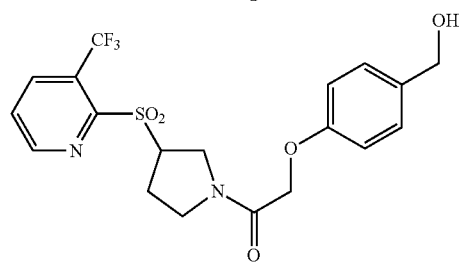
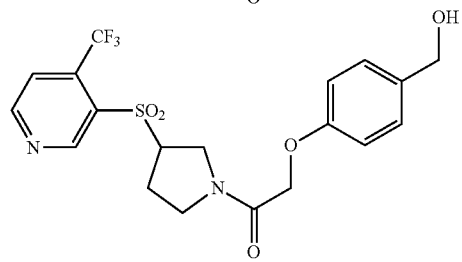
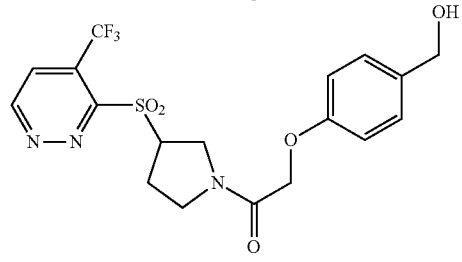
or a pharmaceutically acceptable salt, ester or prodrug form thereof.
In yet other embodiments, the compound is one of the following:
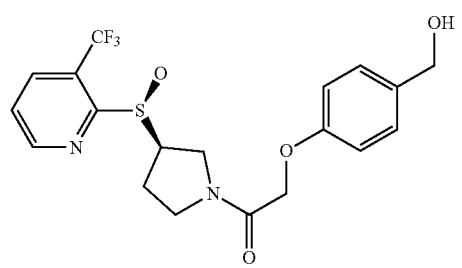
334
-continued
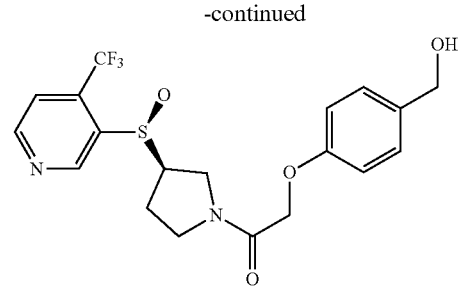
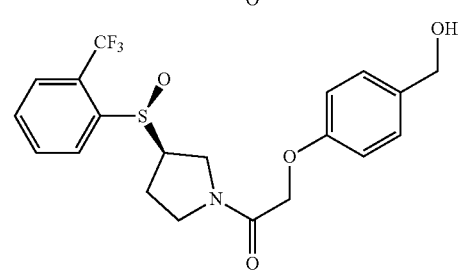
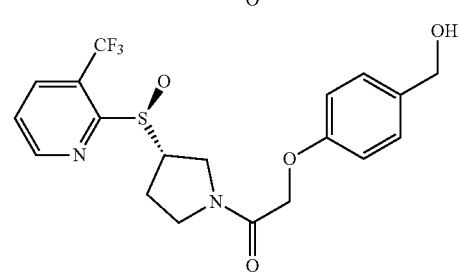
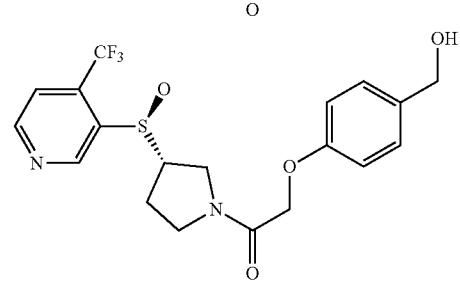
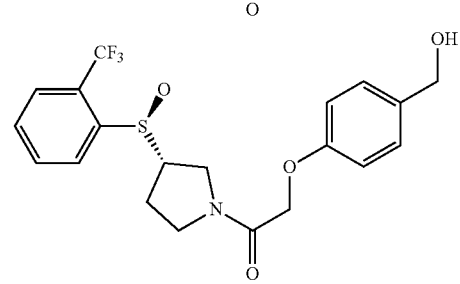
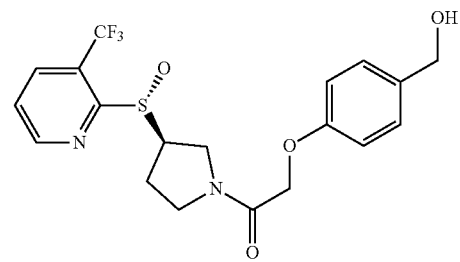

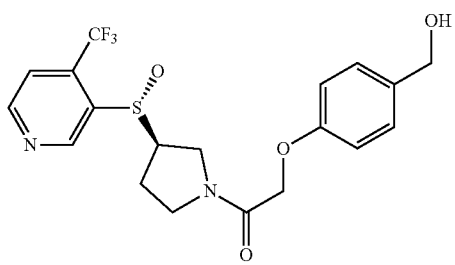
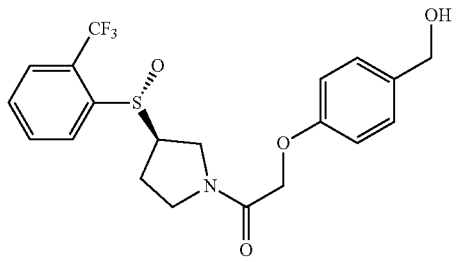
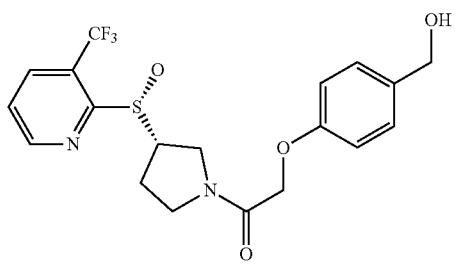
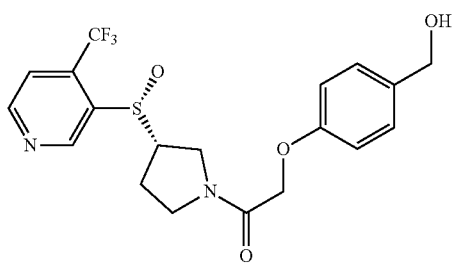
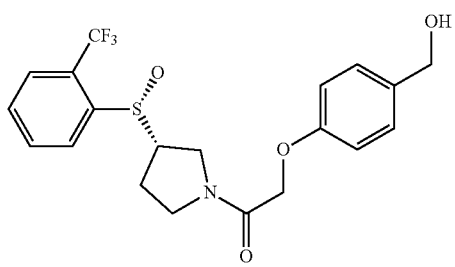

or a pharmaceutically acceptable salt, ester or prodrug form thereof.

In yet further embodiments, the compound has the structure II

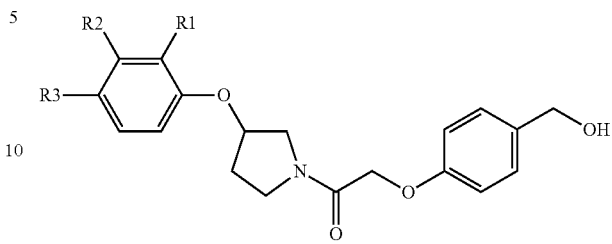

II wherein one of $R_1$ and $R_2$ and $R_3$, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—(CNR$_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments, the compound is one of the following:

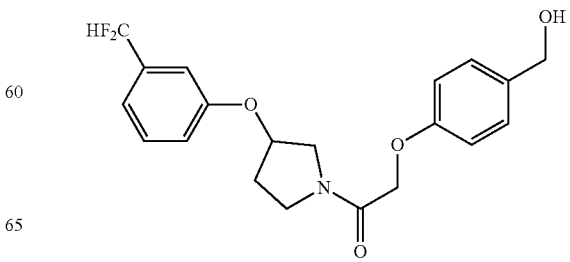

337
-continued
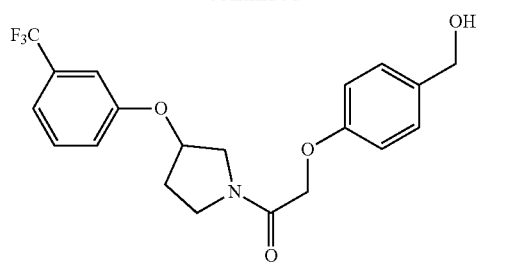
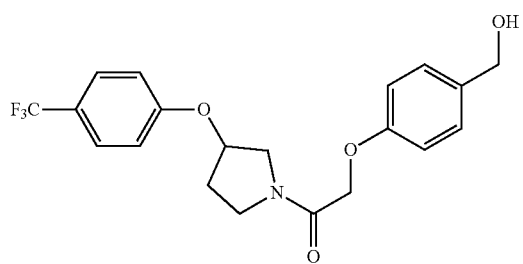
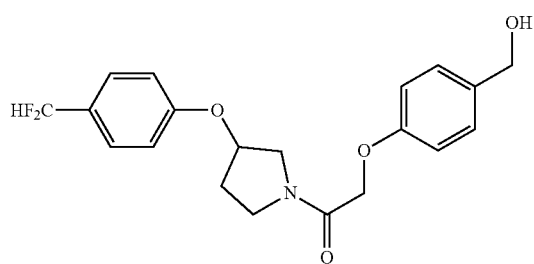
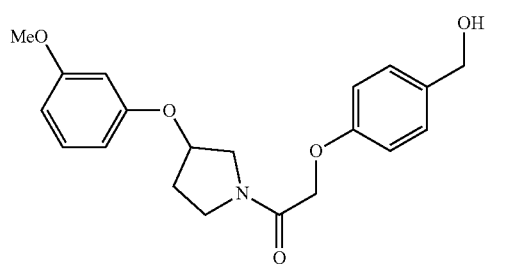
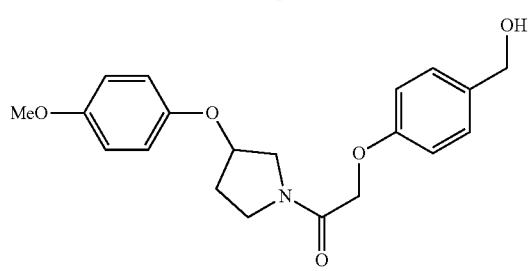
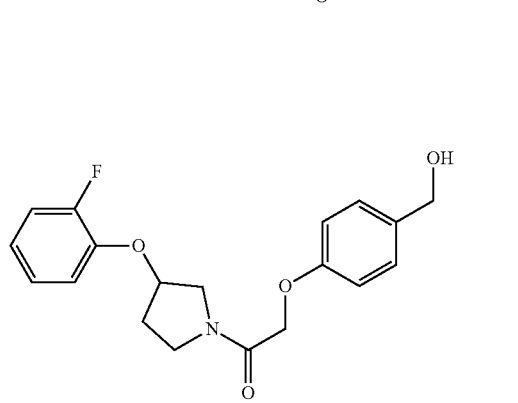
338
-continued
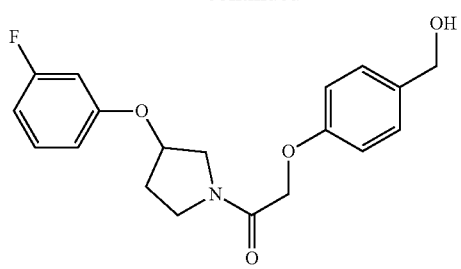
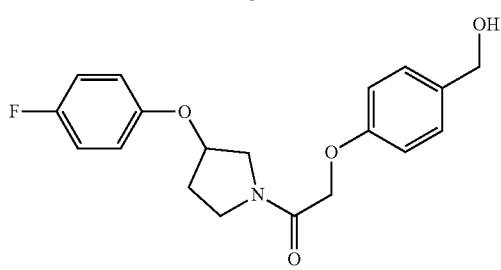
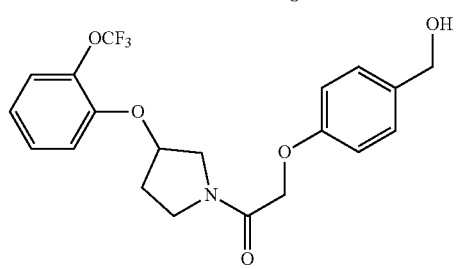
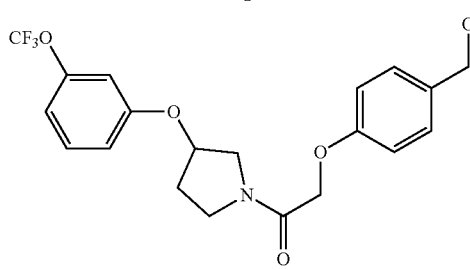
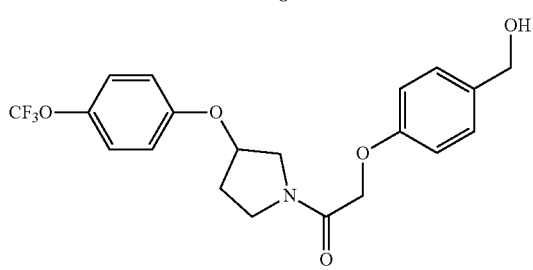
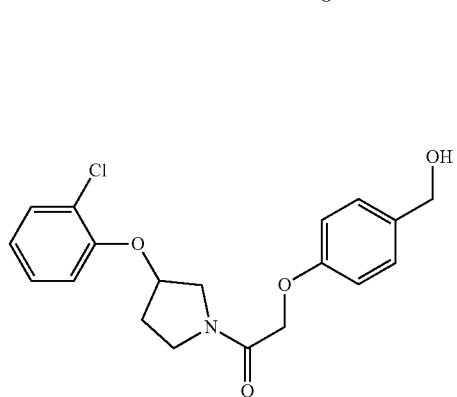

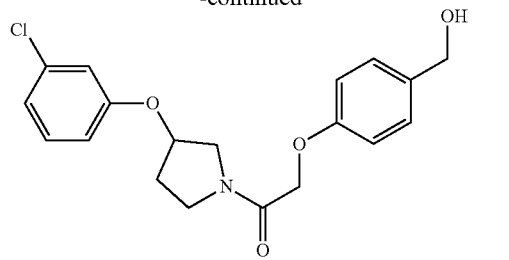
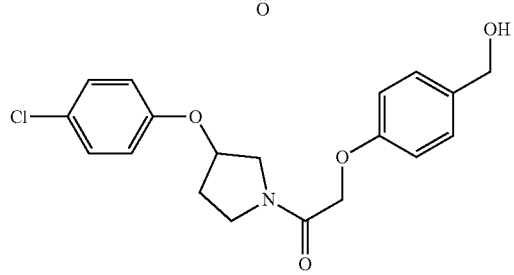
or a pharmaceutically acceptable salt, ester or prodrug form thereof.
In other embodiments the compound is one of the following:
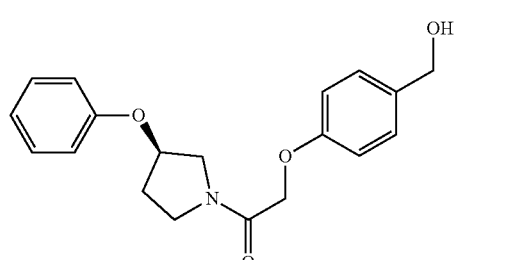
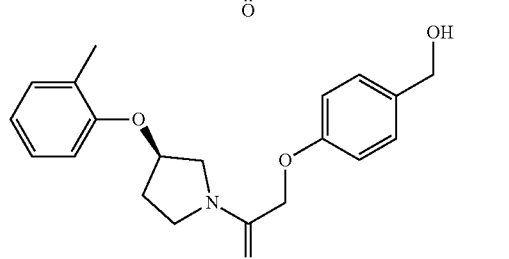
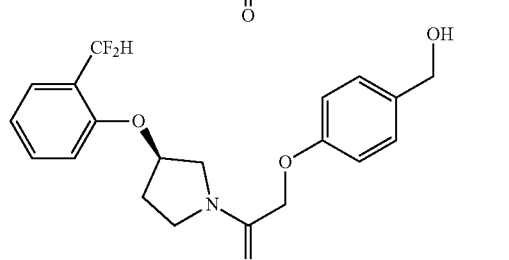
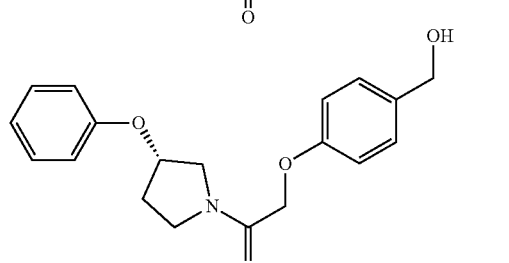
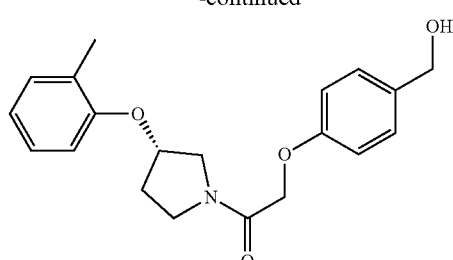
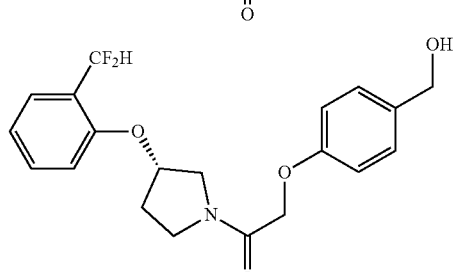
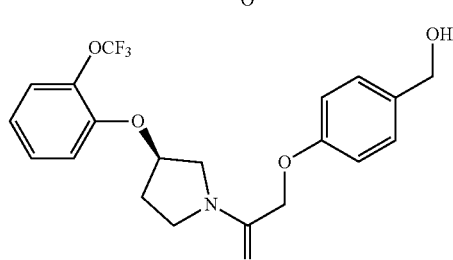

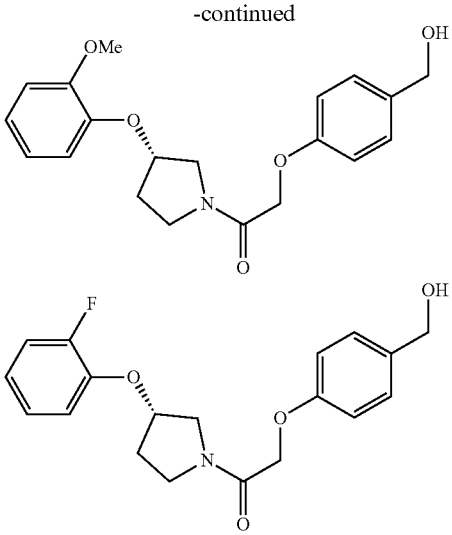

or a pharmaceutically acceptable salt, ester or prodrug form thereof.

In certain embodiments, the compound is one of the following:

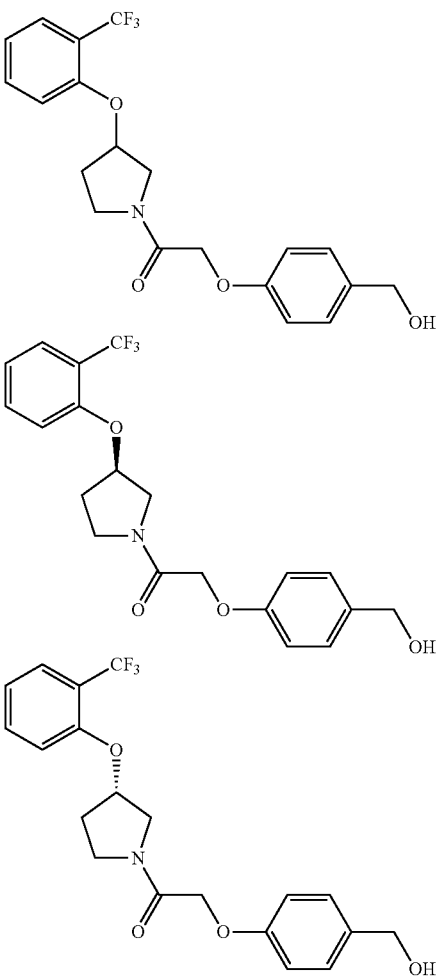

or a pharmaceutically acceptable salt, ester or prodrug form thereof. In alternative embodiments, the asymmetric center is of the R configuration or in the S configuration.

In other embodiments the pharmaceutically acceptable carrier which provides an environment of physical and chemical stability comprises a comprises a combination of one or more antioxidant, one or more chelator and a vehicle base comprising water and one or more pharmaceutically acceptable non-aqueous solvents, one or more absorption enhancers, one or more humectant, one or more gelling agents and one or more pH buffering agent.

The antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, and sodium bisulfate.

A preferred antioxidant is butylated hydroxytoluene (BHT) at a concentration of least 0.05%. In another embodiment the butylated hydroxytoluene (BHT) is at a concentration of at least 0.1%.

The chelator is selected from ethylenediamine tetraacetic acid (EDTA) and its sodium, potassium and calcium salts, sodium pyrophosphate, citric acid, gluconic acid, catechol and various thiol derivatives.

A preferred chelator is di-sodium EDTA at a concentration of least 0.001%. In another embodiment the di-sodium EDTA is at a concentration of at least 0.005%.

One or more non-aqueous solvents is selected from ethanol, acetone, benzyl alcohol, 2-(2-ethoxyethoxy)ethanol, diethylene glycol monoethyl ether, glycerin, propylene glycol, propylene carbonate, acetone, hexylene glycol, isopropyl alcohol, polyethylene glycols (PEGs), methoxypolyethylene glycols, diethyl sebacate, dimethyl isosorbide, propylene carbonate, dimethyl sulfoxide (DMSO), diisopropyl adipate, isopropyl myristate, vegetable oils, a mineral oil, and isopropyl palmitate.

Preferred non-aqueous solvents are ethanol, phenoxyethanol, diethylene glycol monoethyl ether (otherwise known as DEGEE or Transcutol P®), propylene glycol or PEG400.

In one embodiment, the non-aqueous solvent is selected from ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In a further embodiment, the pharmaceutical composition comprises three or more, four or more, or all of: ethanol in the range of 1.0-20.0% w/w, phenoxyethanol in the range 0.1-5.0% w/w, diethylene glycol monoethyl ether (otherwise known as DEGEE or Transcutol P®) in the range 5.0-40.0% w/w, propylene glycol in the range 5.0-40.0% w/w or PEG400 in the range 5.0-40.0% w/w. In yet further embodiments, ethanol is in the range 5.0-15.0% w/w, phenoxyethanol in the range 0.5-2.0% w/w, diethylene glycol monoethyl ether (otherwise known as DEGEE or Transcutol P®) in the range 20.0-30.0% w/w, propylene glycol in the range 15.0-25.0% w/w and/or PEG400 in the range 15.0-25.0% w/w.

One or more pharmaceutically acceptable non-aqueous solvent which can also act as a topical absorption (permeation) enhancer is selected from ethanol, benzyl alcohol, propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl Isosorbide, triethyl citrate, tetrahydrofurfuryl alcohol, glycerol monolaurate, methyl oleate, propylene glycol monolaurate, and oleyl alcohol.

A preferred topical absorption (permeation) enhancer is selected from diethylene glycol monoethyl ether (DEGEE or Transcutol P®), propylene glycol and ethanol. In one embodiment, at least one topical absorption (permeation) enhancer is selected from diethylene glycol monoethyl ether (DEGEE or Transcutol P®) in the range 5.0-40.0% w/w, propylene glycol in the range 5.0-40.0% w/w and ethanol in the range of 1.0-20.0% w/w.

One or more humectant is selected from the groups consisting of hexylene glycol, glycerin, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols.

Preferred one or more humectants are selected from propylene glycol, polyethylene glycols and hexylene glycol. In one embodiment, one or more humectant is selected from propylene glycol, polyethylene glycols and hexylene glycol in the range 5.0-40.0% w/w.

One or more pH buffering agent is selected from Trolamine or Sodium Hydroxide. In one embodiment, the Trolamine or Sodium Hydroxide provides an apparent pH in the range 6.50 to 7.50 One or more gelling agent is selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

Preferred one or more gelling agent is a carbomer such as carbomer homopolymer type C980. In one embodiment, the carbomer homopolymer type C980 is in the range of 0.5 to 2.0% w/w.

In a further embodiment, the pharmaceutical composition comprises two or more of: (i) butylated hydroxytoluene (BHT) at a concentration of at least 0.05%; (ii) di-sodium EDTA at a concentration of at least 0.001%; and (iii) Trolamine to provide an apparent pH in the range 6.50 to 7.50. In certain embodiments, the pharmaceutical composition comprises both (i) butylated hydroxytoluene (BHT) at a concentration of at least 0.05%; and (ii) di-sodium EDTA at a concentration of least 0.001%. In another embodiment, the pharmaceutical composition comprises each of (i) butylated hydroxytoluene (BHT) at a concentration of least 0.05%; (ii) di-sodium EDTA at a concentration of least 0.001%; and (iii) Trolamine to provide an apparent pH in the range 6.50 to 7.50.

In a certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w; and
(vi) a carbomer such as carbomer homopolymer type C980 in the range of 0.5 to 2.0% w/w.

In another certain embodiment, the pharmaceutical composition comprises:
(i) ethanol in the range of 1.0-20.0% w/w;
(ii) phenoxyethanol in the range 0.1-5.0% w/w;
(iii) diethylene glycol monoethyl ether (otherwise known as DEGEE or Transcutol P®) in the range 5.0-40.0% w/w;
(iv) propylene glycol in the range 5.0-40.0% w/w;
(v) PEG400 in the range 5.0-40.0% w/w;
(vi) a carbomer such as carbomer homopolymer type C980 in the range of 0.5 to 2.0% w/w;
(vii) butylated hydroxytoluene (BHT) at a concentration of least 0.05%;
(viii) di-sodium EDTA at a concentration of least 0.001%; and
(ix) Trolamine to provide an apparent pH in the range 6.50 to 7.50.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.

In another embodiment, the pharmaceutical composition comprises:
(i) ethanol in the range of 5.0-15.0% w/w;
(ii) phenoxyethanol in the range 0.5-2.0% w/w;
(iii) diethylene glycol monoethyl ether (otherwise known as DEGEE or Transcutol P®) in the range 20.0-30.0% w/w;
(iv) propylene glycol in the range 15.0-25.0% w/w;
(v) PEG400 in the range 15.0-25.0% w/w; and
(vi) a carbomer such as carbomer homopolymer type C980 in the range of 0.75 to 1.5% w/w.
(vii) butylated hydroxytoluene (BHT) at a concentration of least 0.1%;
(viii) di-sodium EDTA at a concentration of least 0.005%; and
(ix) Trolamine to provide an apparent pH in the range 6.50 to 7.50.

In specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w; and
(vii) water at a concentration of 19.5-22% w/w.

In yet other specific embodiments, the pharmaceutical composition comprises:
(i) ethanol at a concentration of 10.0% w/w;
(ii) phenoxyethanol at a concentration of 1% w/w;
(iii) diethylene glycol monoethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;

(vi) carbomer homopolymer type C980 at a concentration of 1.0% w/w;
(vii) butylated hydroxytoluene (BHT) at a concentration of 0.1% w/w;
(viii) di-sodium EDTA at a concentration of 0.005% w/w;
(ix) Trolamine at a concentration of 0.375% w/w; and
(x) water at a concentration of 19.02-21.52% w/w.

In yet other specific embodiments, the pharmaceutical composition of either of the above two embodiments wherein the compound is 2-(4-(hydroxymethyl)phenoxy)-1-(3-(2-(trifluoromethoxy)phenoxy)pyrrolidin-1-yl)ethanone at a concentration up to 2.50% w/w, particularly at a concentration of 0.25%, 0.75% or 1.75%.

In yet further embodiments the pharmaceutically acceptable carrier is a cream or a lotion, which provides an environment of physical and chemical stability, comprising a combination of one or more antioxidant, one or more chelator and a vehicle base comprising water and one or more pharmaceutically acceptable non-aqueous solvents, one or more oil, one or more structural lipids, one or more absorption enhancers, one or more aqueous emulsifier surfactants, one or more emollients, one or more humectant, one or more gelling agents and one or more pH buffering agent.

One or more oils are selected from hydrogenated castor oil, liquid paraffin, white soft paraffin, corn oil, cottonseed oil, ethyl oleate, petrolatum, sesame oil, peanut oil, soybean oil, safflower oil, olive oil, almond oil, coconut oil, walnut oil, avocado nut oil.

A preferred combination of oils is liquid paraffin at not less than 2% and white soft paraffin at not less than 1%.

In further embodiments one or more antioxidant is selected from the group consisting of alpha tocopherol, beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate.

A preferred antioxidant is butylated hydroxytoluene (BHT) at a concentration of least 0.05%.

In other embodiments one or more structural lipids are selected from stearic acid, stearyl alcohol, cetostearyl alcohol, cetrimide, cetyl alcohol, cetyl esters wax, lanolin, lanolin alcohols, emulsifying wax, microcrystalline wax, white wax, yellow wax, hydrogenated castor oil.

A preferred structural lipid is cetostearyl alcohol at not less than 1%.

In other embodiments one or more oil and aqueous emulsifier surfactants are selected from medium chain triglycerides, Tween 60, Tween 80, Span 60, Brij 721, Brij 72, Aracel 165, Polyoxyethylene castor oil derivatives, Cetomacrogol 1000, Polyoxyethylene stearates.

A preferred combination of surfactants is Brij 721 at not less than 1% with Brij 72 at not less than 2%.

In other embodiments one or more emollients are selected from diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plant oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

A preferred emollient combination is cetostearyl alcohol at not less than 1% and Crodamol GTCC medium chain triglydcerides at not less than 6%

In other embodiments one or more pharmaceutically acceptable non-aqueous solvents which can also act as absorption enhancers are selected from propylene glycol, 2-(2ethoxyethoxy)ethanol, hexylene glycol, PEG400, diisopropyl adipate, diethylene glycol monoethyl ether (DEGEE or Transcutol P®),Dimethylsulfoxide (DMSO), decylmethylsulfoxide, N,N-dimethyl acetamide, N,N-dimethyl formamide, 2-pyrrolidone, 1-methyl-2-pyrrolidone, 5-methyl-2-pyrrolidone, 1,5-methyl-2-pyrrolidone, 1-ethyl-2-pyrrolidone, 2-pyrrolidone-5-carboxylic acid, propylene glycol, ethanol, isopropanol, oleic acid, laurocapram (AZone), limonene, cineole, diethyl-m-toluamide (DEET), sodium dodecylsulfate, di-methyl isosorbide, triethyl citrate, tetrahydrofurfuryl alcohol, glycerol monolaurate, methyl oleate, propylene glycol monolaurate, and oleyl alcohol, alcohol (ethanol), acetone, benzyl alcohol, phenoxyethanol, diethylene glycol monoethyl ether (Transcutol P), glycerin, hexylene glycol, propylene glycol, isopropyl alcohol, polyethylene glycols(PEGs), methoxypolyethylene glycols, diethyl sebacate, dimethyl isosorbide, propylene carbonate, and dimethyl sulfoxide.

A preferred non-aqueous solvent combination is ethanol at not less than 8%, PEG400 at not less than 20%, phenoxyethanol at not less than 1%, diethylene glycol monoethyl ether (Transcutol P) at not less than 12% and glycerol at not less than 8%.

In further embodiments one or more pH buffering agents are selected from sodium citrate, monosodium phosphate, sodium acetate, sodium lactate, sodium tartrate, sodium fumarate at or around pH 5.5 to pH 6.

A preferred buffer system is sodium citrate at 0.01M adjusted to pH 5.5.

In yet further embodiments one or more humectants are selected from glycerol, hexylene glycol, propylene glycol, sorbitol, lactic acid, sodium lactate, mannitol, butylene glycol, panthenol, hyaluronic acid, urea, chitosan, polyols, methyl gluceth-10, methyl gluceth-20, and polyethylene glycols (PEG's).

Preferred humectants are glycerol at not less than 8% and PEG 400 at not less than 20%.

In other embodiments one or more gelling agents are selected from hydroxypropylcellulose, hydroxyethylcellulose, hydroxypropyl methyl cellulose, polyvinyl alcohol, povidone, fatty alcohols, cetylalcohol, stearyl alcohol, cetostearyl alcohol, and myristyl alcohol, carbomer, carboxymethylcellulose, xanthan gum, guar gum, chitosan, carrageenan and alginic acid.

A preferred gelling agent is a carbomer such as carbomer homopolymer type C980 at not less than 0.25%.

In further embodiments the compound (Structure I) is present at a concentration between about 0.005% and about 5% by weight. In certain embodiments the compound is present in the pharmaceutical composition at a concentration between about 0.01% and about 2.5% w/w, and in specific alternative embodiments the pharmaceutical composition is at a concentration of 0.25%, 0.75% or 1.75% w/w.

In yet further embodiments a second therapeutic agent is present.

In other embodiments the cancer is selected from basal-cell skin cancer (BCC), squamous-cell skin cancer (SCC), melanoma, Merkel cell carcinoma, and other, less common skin cancers either individually or collectively.

In yet other embodiments a precancerous state is selected from diseases of hypopigmentation such as Vitiligo In some embodiments, the duration of treatment is greater than 28 days.

In further embodiments, the duration of treatment is between one and six months or thereabouts. In yet further embodiments, the duration of treatment is between one and twenty four months or thereabouts; one and eighteen months or thereabouts; one and twelve months or thereabouts; one and three months or thereabouts; one and two months or thereabouts; or one month or thereabouts.

The subject invention also provides a compound having the structure I, or a pharmaceutically acceptable salt thereof,

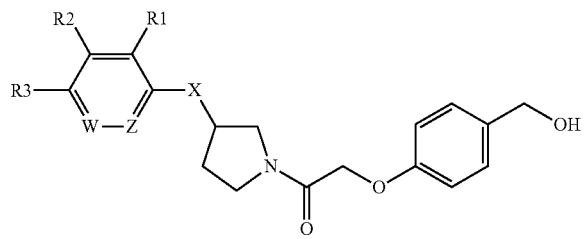

I wherein:
X is NH, N-alkyl or N-acyl;
W is independently $CR_4$ or N;
Z is independently $CR_5$ or N;
wherein each of $R_1$, $R_2$ and $R_3$ and $R_4$ and $R_5$, if present, is independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;
wherein adjacent substituents $R_1$, $R_2$ and $R_3$ and $R_4$ and $R_5$, if present, may form a saturated or unsaturated 5-membered or 6-membered carbocyclic or heterocyclic ring;
wherein each of $R_6$, $R_7$, $R_8$, $R_9$ and $R_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
and wherein Rx is alkyl, cycloalkyl, alkylcycloalkyl, acyl, ester, or thioester.

In some embodiments, X is NH, N-alkyl or N-acyl; W is independently $CR_4$ or N; Z is independently $CR_5$ or N; wherein each of $R_1$, $R_2$ and $R_3$ and $R_4$ and $R_5$, if present, is independently: H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$; wherein adjacent substituents $R_1$, $R_2$ and $R_3$ and $R_4$ and $R_5$, if present, may form a saturated or unsaturated 5-membered or 6-membered carbocyclic or heterocyclic ring; and wherein each of $R_6$, $R_7$, $R_8$, $R_9$ and $R_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is NH. In other embodiments, X is N-alkyl or N-acyl. In further embodiments, X is N-alkyl. In yet further embodiments X is N-acyl.

In some embodiments, the compound is one of the following:

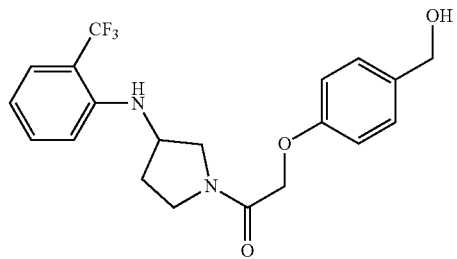

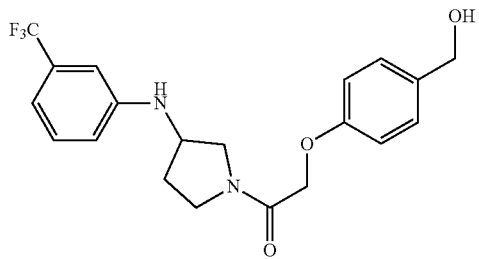

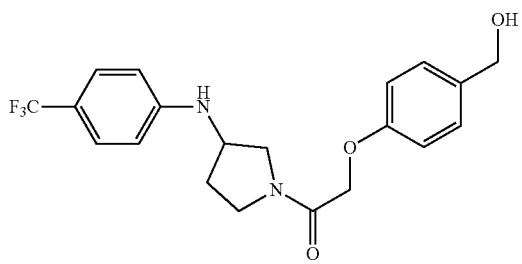

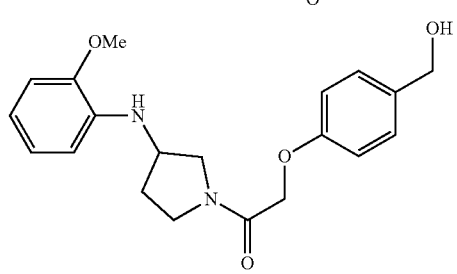

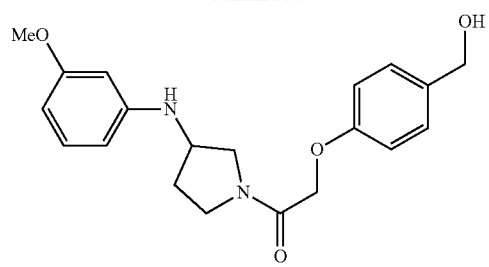
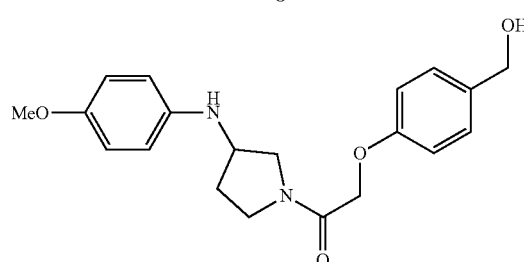
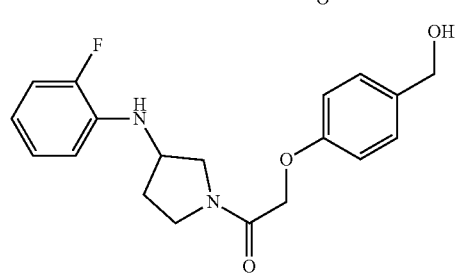
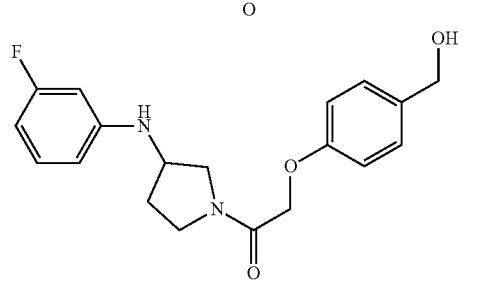
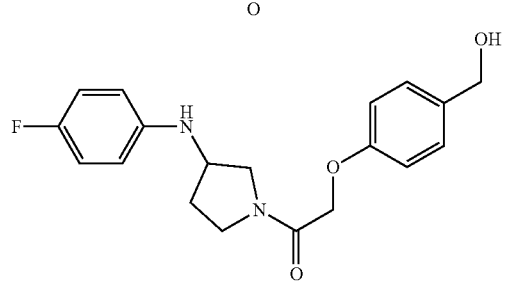
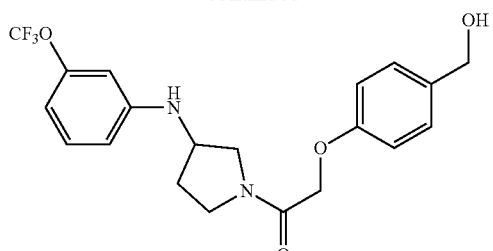
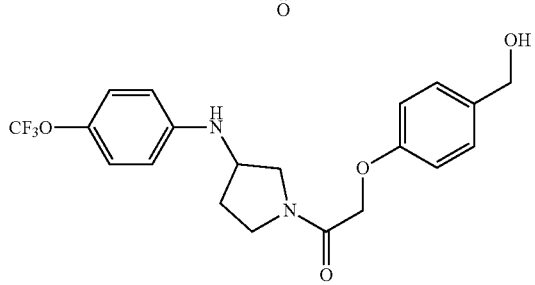
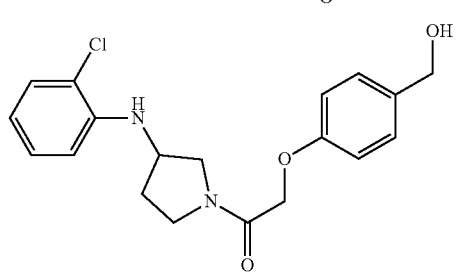
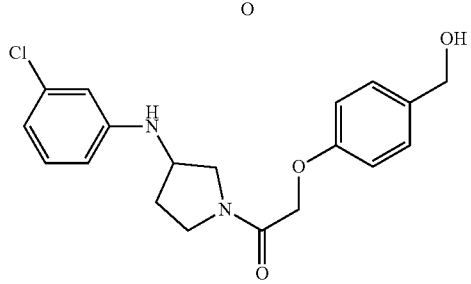
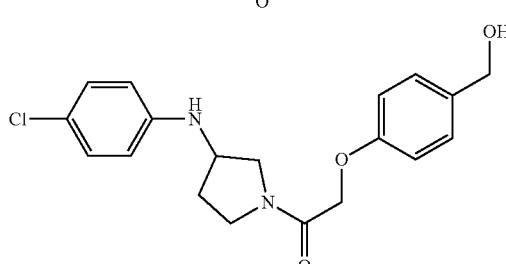
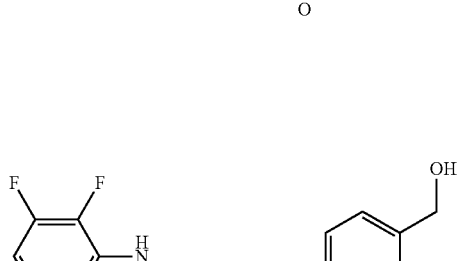
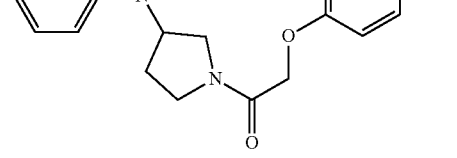

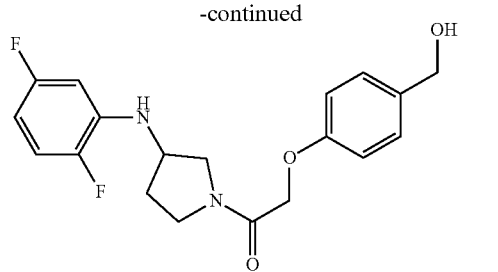
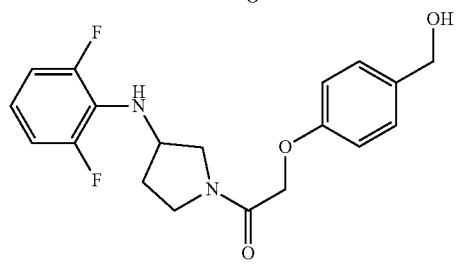
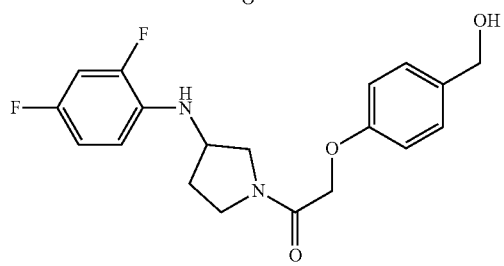
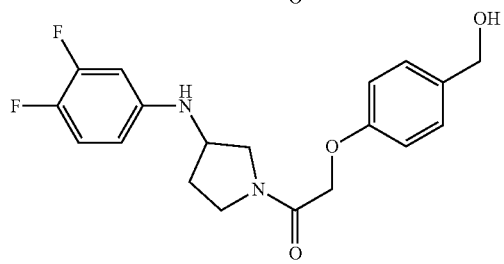
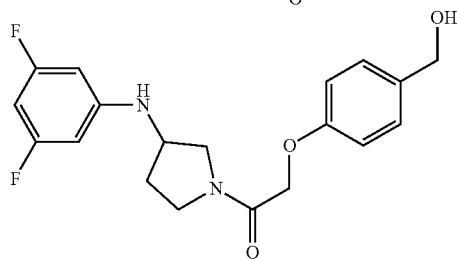
or a pharmaceutically acceptable salt, ester or prodrug form thereof.
In other embodiments, the compound is one of the following:
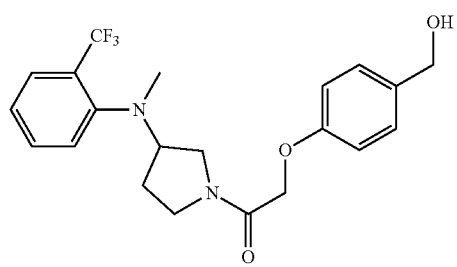
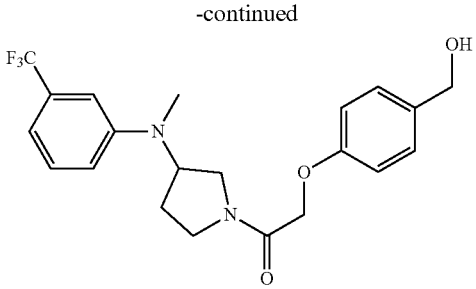
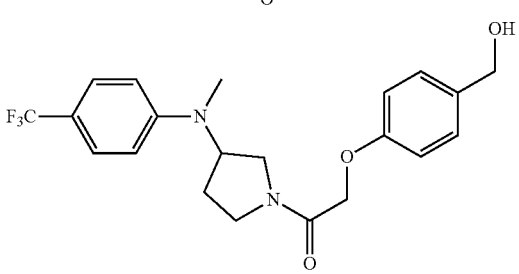
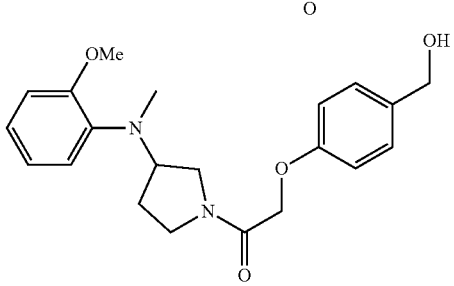
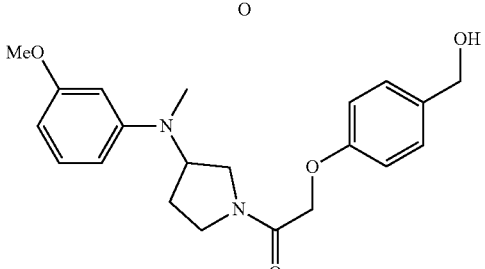
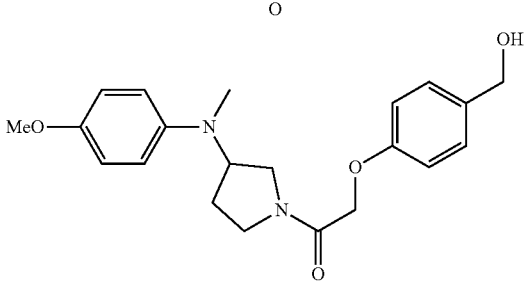
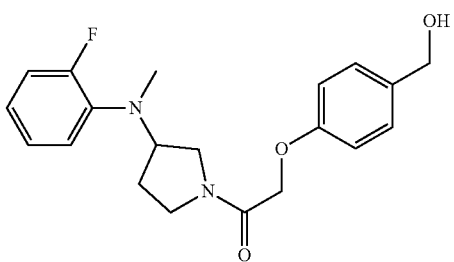

-continued
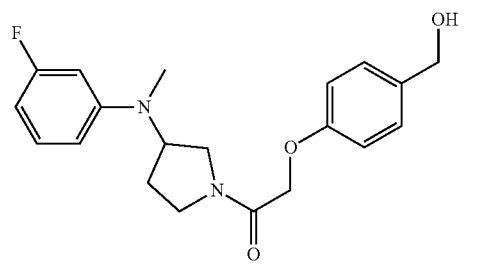
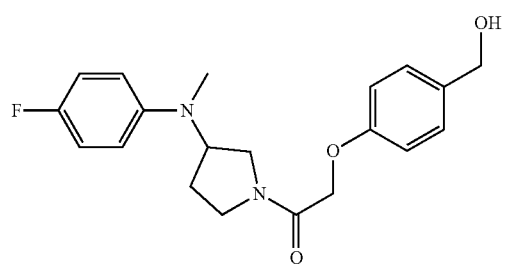
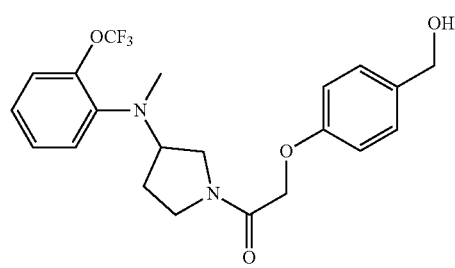
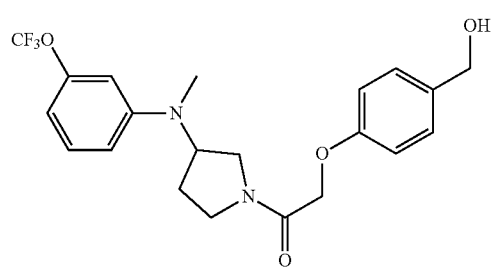
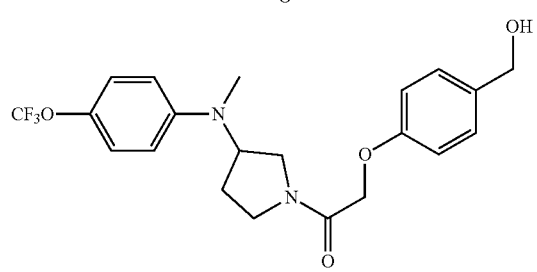
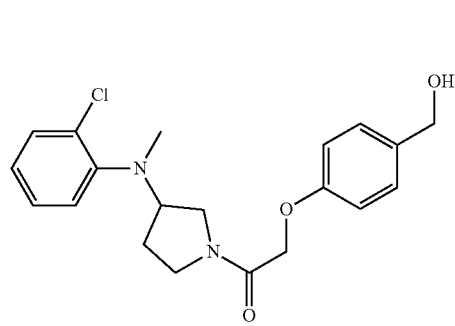
-continued
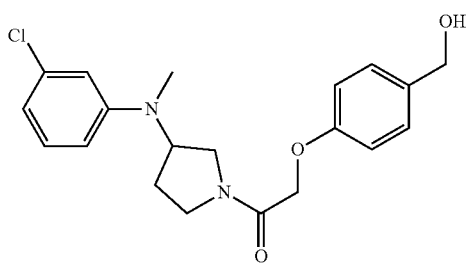
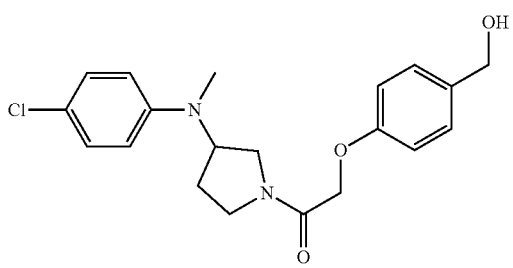
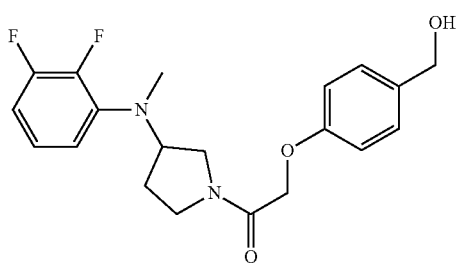
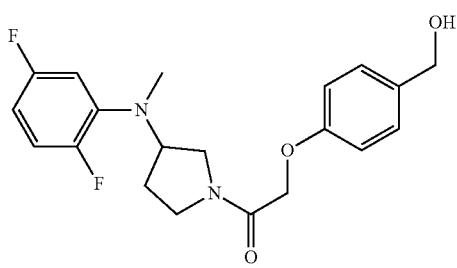
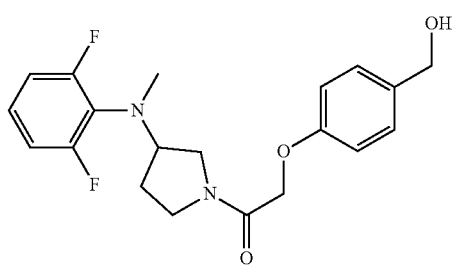
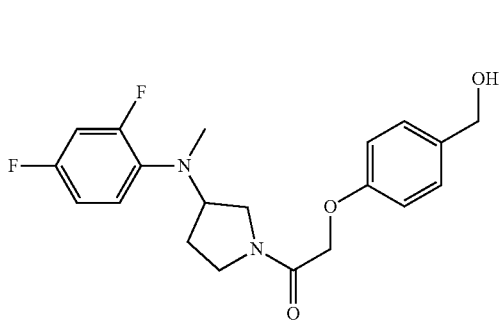

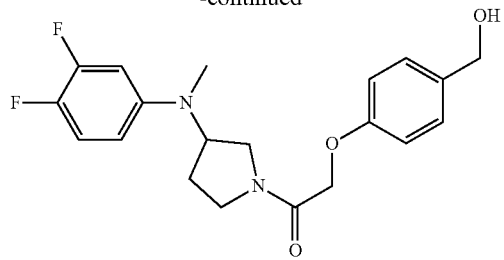
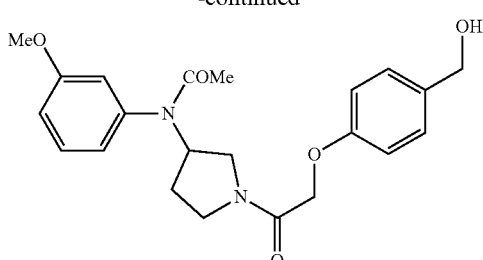
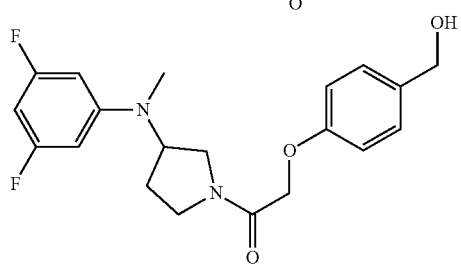
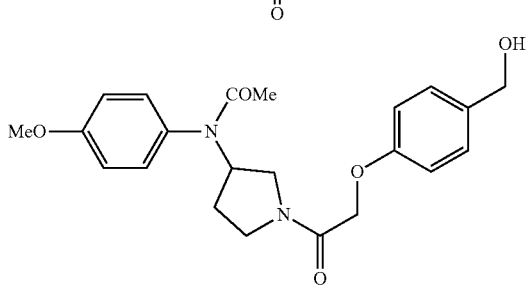
or a pharmaceutically acceptable salt, ester or prodrug form thereof.
In further embodiments, the compound is one of the following:
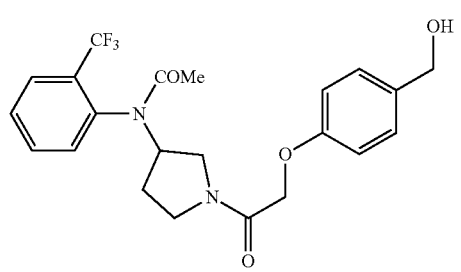
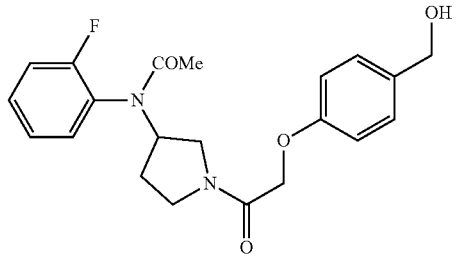
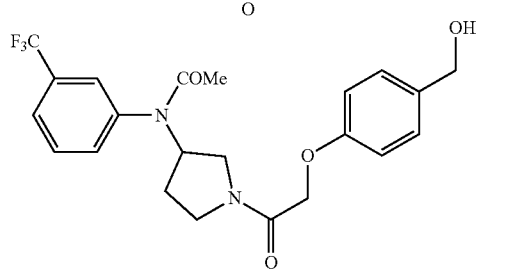
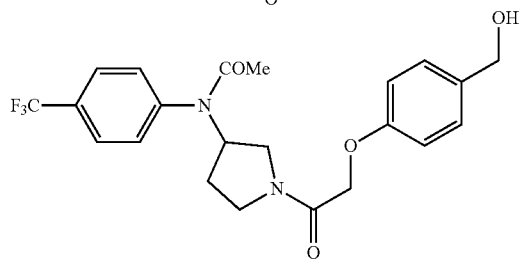
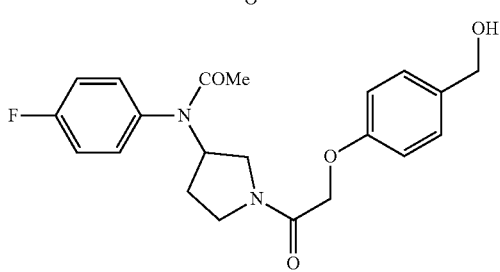
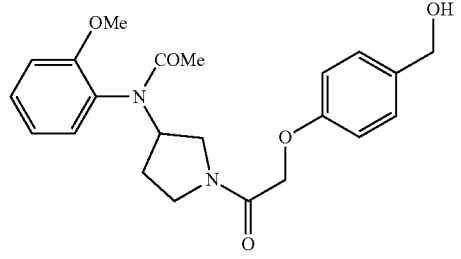
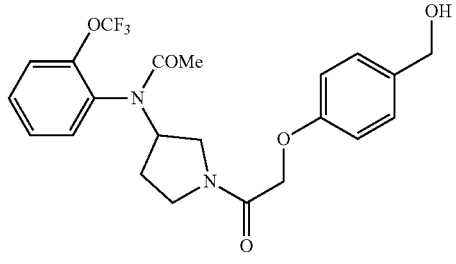

357
-continued
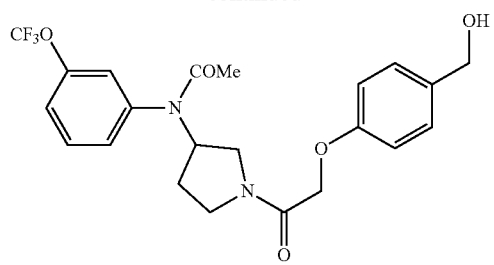
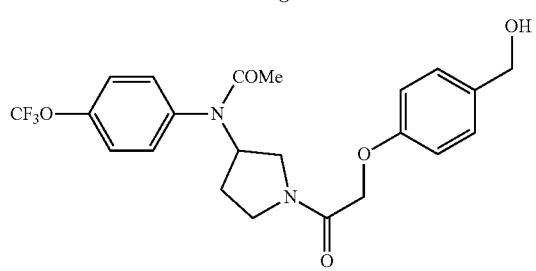
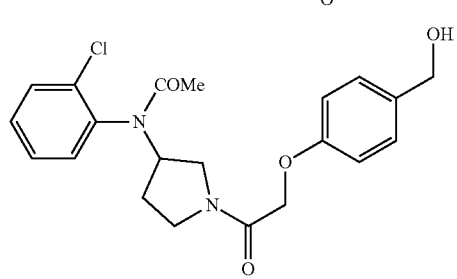
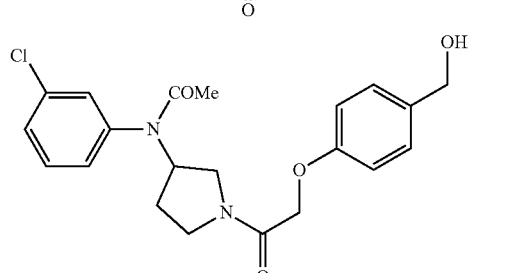
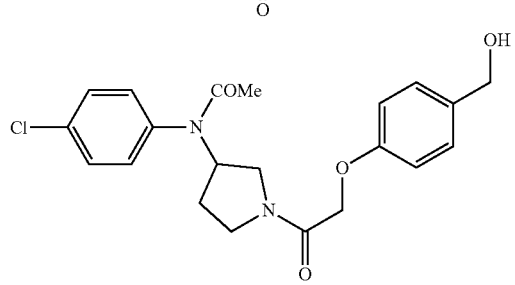
358
-continued
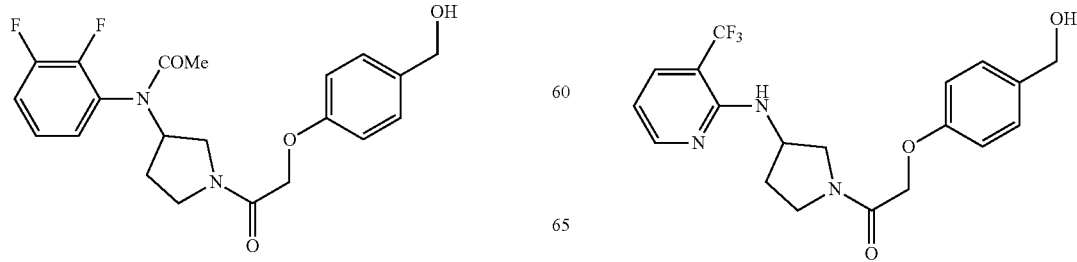
or a pharmaceutically acceptable salt, ester or prodrug form thereof.
In yet further embodiments, the compound is one of the following:
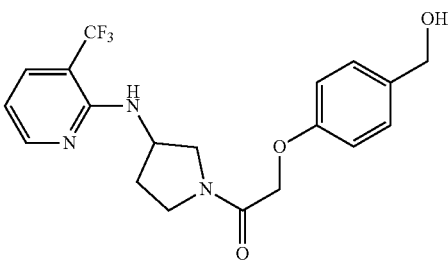

359
-continued
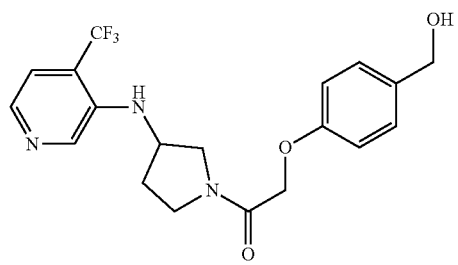
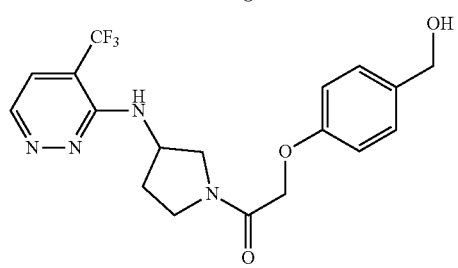
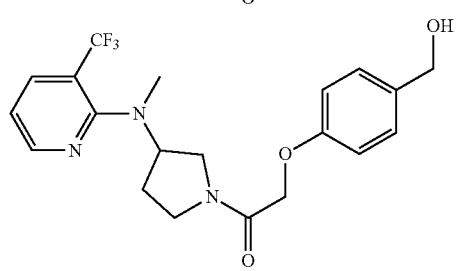
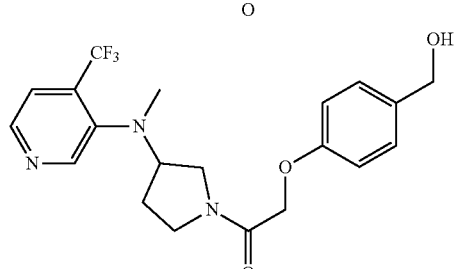
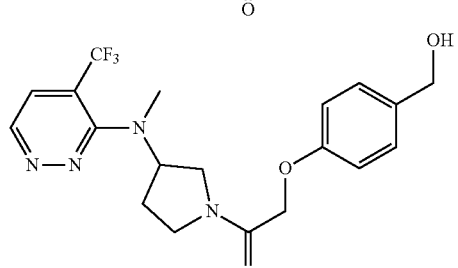
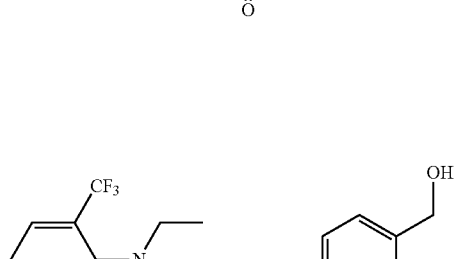
360
-continued
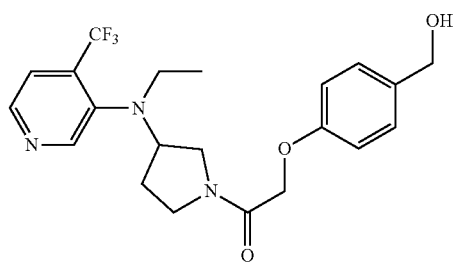
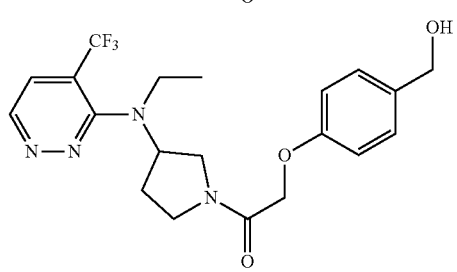
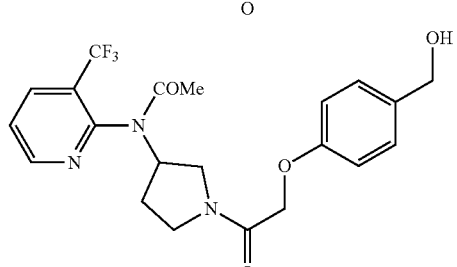
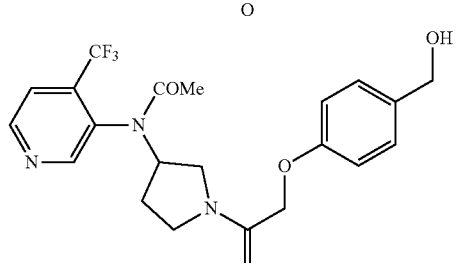
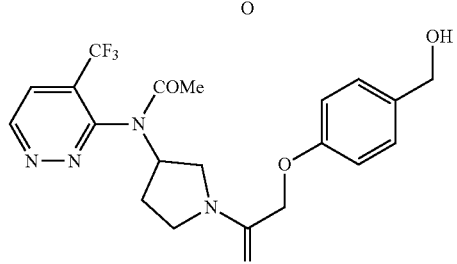
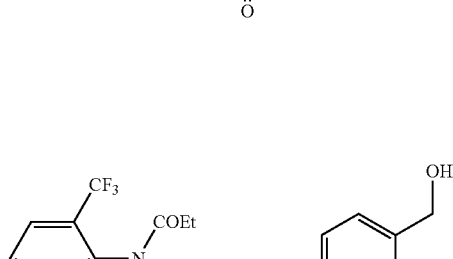

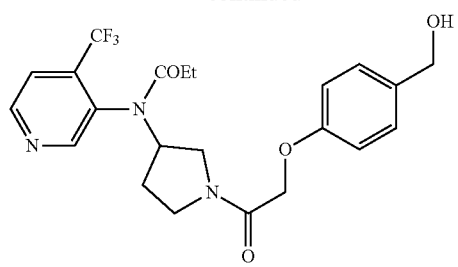
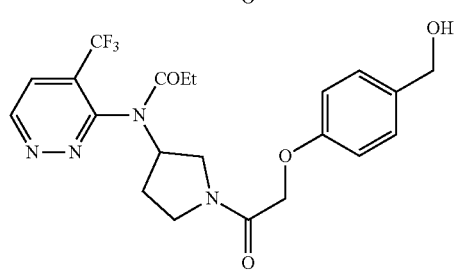
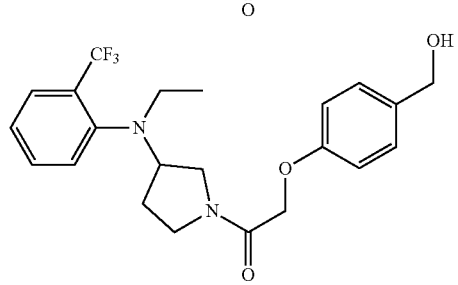
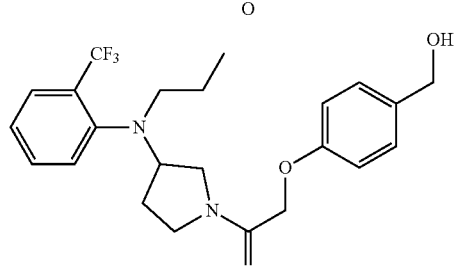
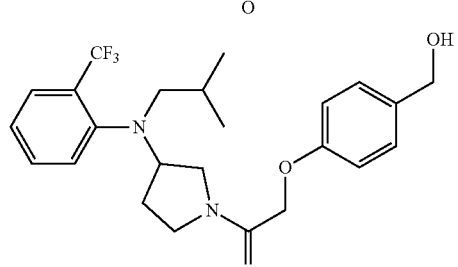
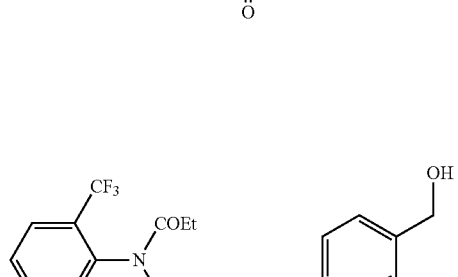
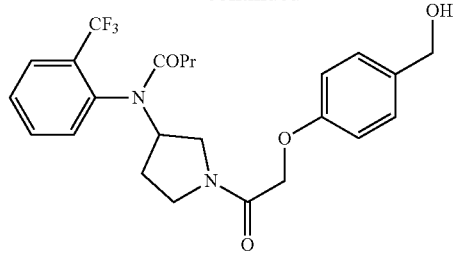
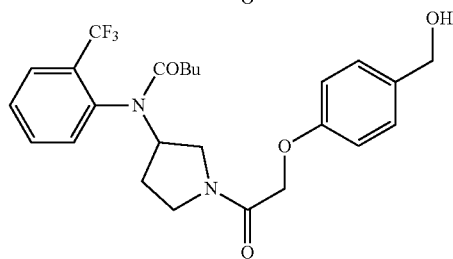
or a pharmaceutically acceptable sat, este r prodrug form thereof.
In yet other embodiments, the compound is one of the following:
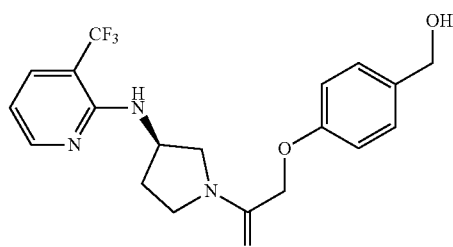
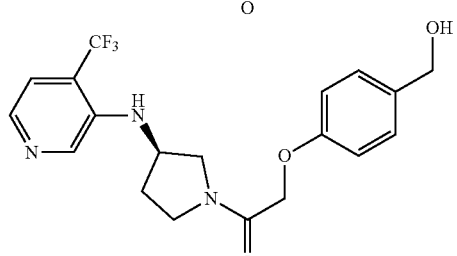
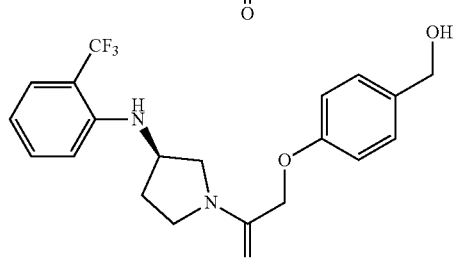
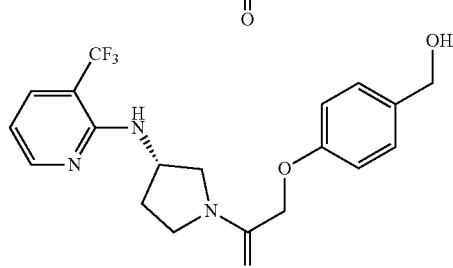

363
-continued
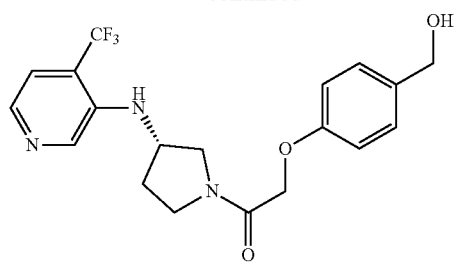
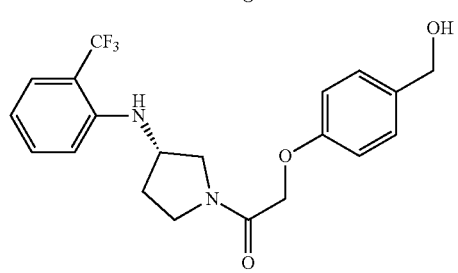
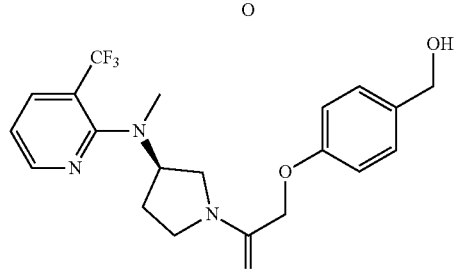
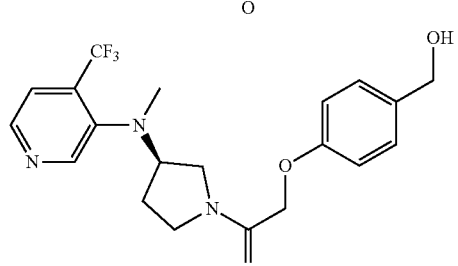
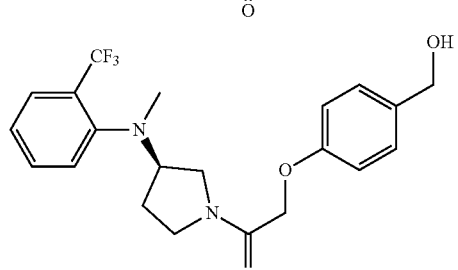
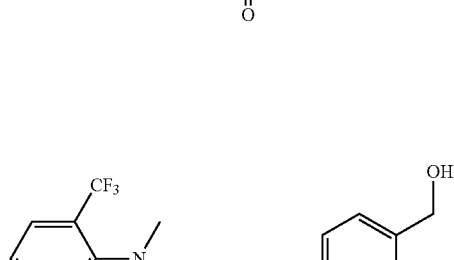
364
-continued
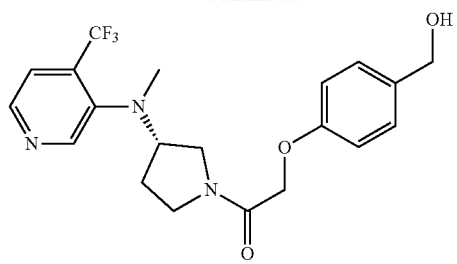
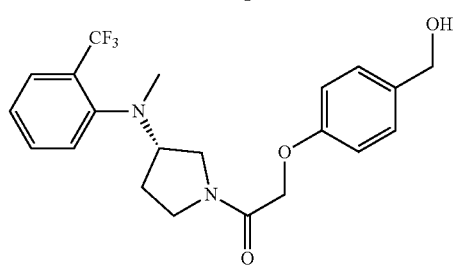
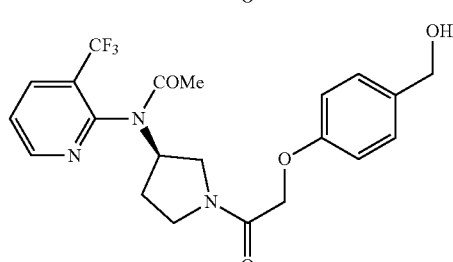
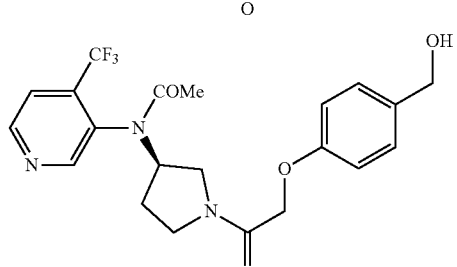
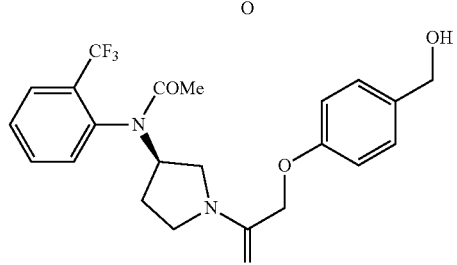
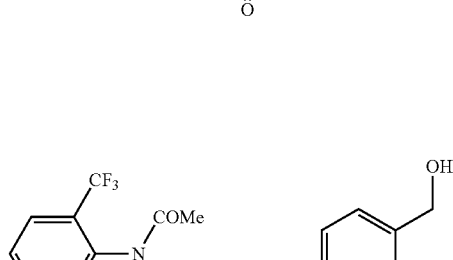

365

-continued

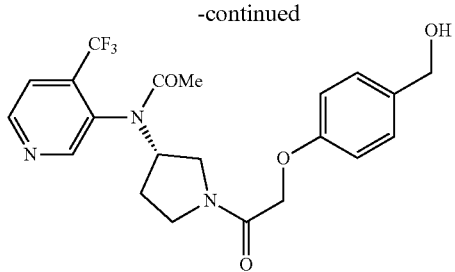

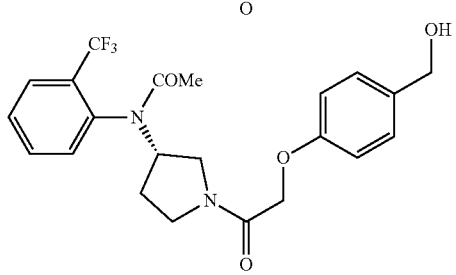

or a pharmaceutically acceptable salt, ester or prodrug form thereof.

In further embodiments, the compound is present in the composition at a concentration between about 0.005% and about 5% by weight.

In yet further embodiments, the compound is a racemic mixture, a diastereoisomeric mixture, a single enantiomer, an enantiomeric diastereomer, a meso compound, a pure epimer, or a mixture of epimers thereof.

In yet other embodiments, one or more double bonds present in the compound are cis or trans, E or Z, a cis/trans mixture, an E/Z mixture, a combination of E and Z geometries, a combination of E and Z geometric mixtures or other geometric isomers thereof.

The subject invention also provides a compound having the structure I, or pharmaceutically acceptable salts thereof,

I

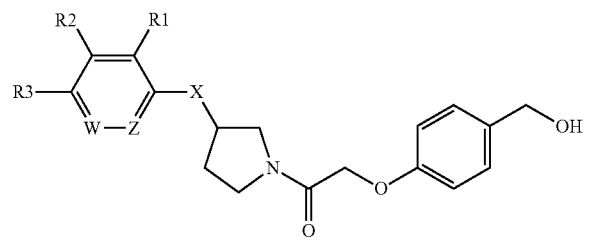

wherein:
X is S, SO or $SO_2$;
W is independently $CR_4$ or N;
Z is independently $CR_5$ or N;
wherein $R_1$, $R_2$ and $R_3$ and $R_4$ and/or $R_5$, if present, are independently:
H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ and esters thereof; $CO_2H$ and esters thereof;

366

$PO_2(OCH_3)H$ and phosphonates thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;

wherein adjacent substituents $R_1$, $R_2$ and $R_3$ and $R_4$ and/or $R_5$, if present, may form a saturated or unsaturated 5-membered or 6-membered carbocyclic or heterocyclic ring;

wherein $R_6$, $R_7$, $R_8$, $R_9$ and $R_{10}$, if present, are independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

and wherein Rx is alkyl, cycloalkyl, alkylcycloalkyl, acyl, ester, or thioester.

In some embodiments, X is S, SO or $SO_2$; W is independently $CR_4$ or N; Z is independently $CR_5$ or N; wherein $R_1$, $R_2$ and $R_3$ and $R_4$ and/or $R_5$, if present, are independently: H; OH; F; Cl; Br; I; Ca to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ and esters thereof; $CO_2H$ and esters thereof; $NO_2$; $NH_2$; NHCH(O); $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR)NR_9R_{10}$; wherein adjacent substituents $R_1$, $R_2$ and $R_3$ and $R_4$ and/or $R_5$, if present, may form a saturated or unsaturated 5-membered or 6-membered carbocyclic or heterocyclic ring; and wherein $R_6$, $R_7$, $R_8$, $R_9$ and $R_{10}$, if present, are independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In further embodiments, X is S. In other embodiments, X is SO or $SO_2$. In further embodiments, X is SO. In yet further embodiments X is $SO_2$.

In some embodiments, the compound is one of:

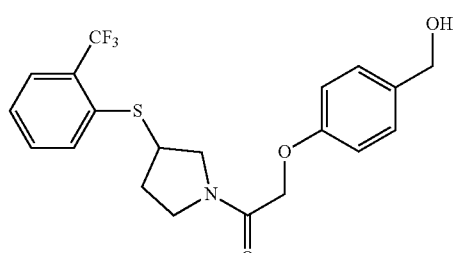

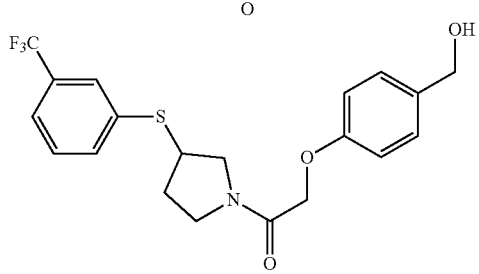

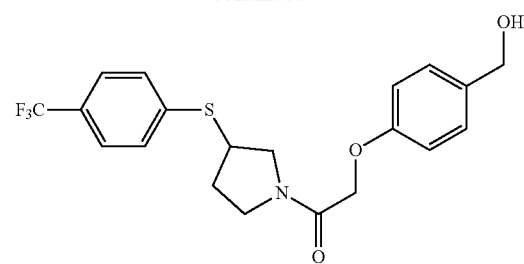
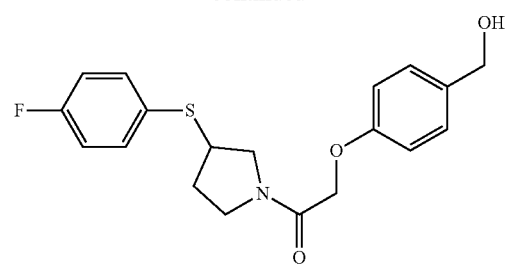
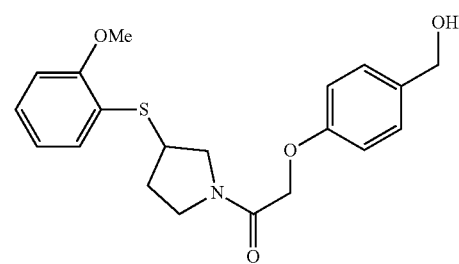
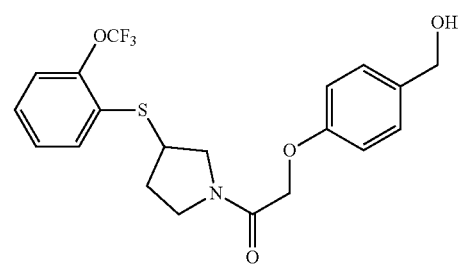
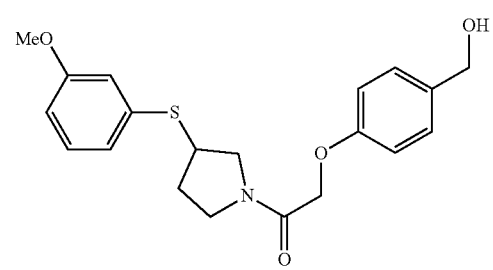
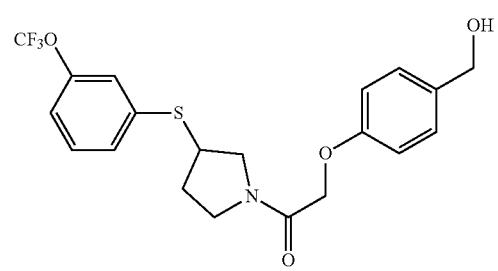
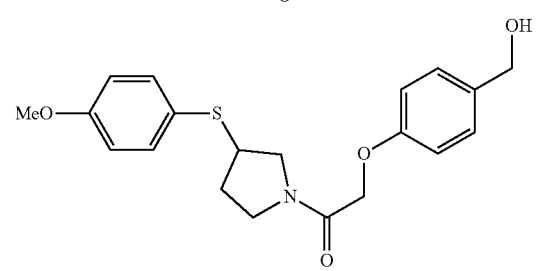
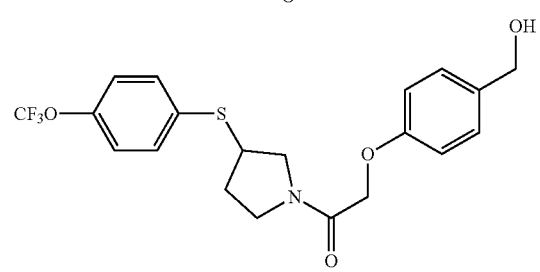
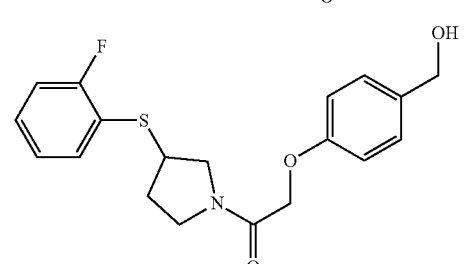
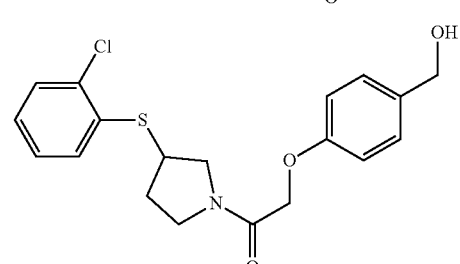
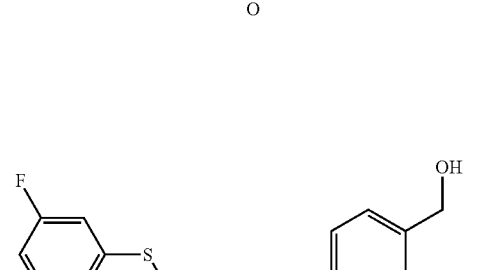
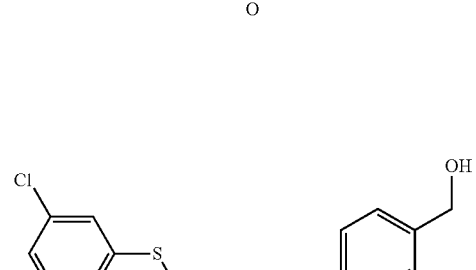

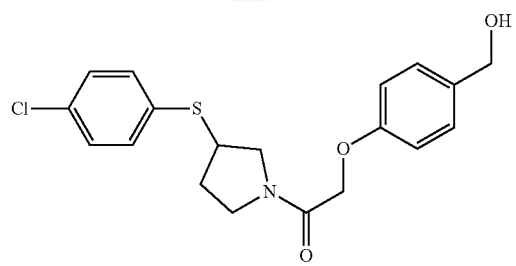
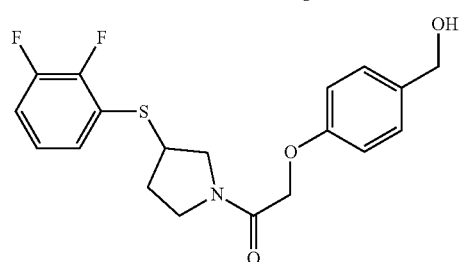
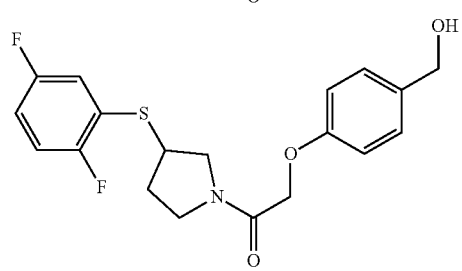
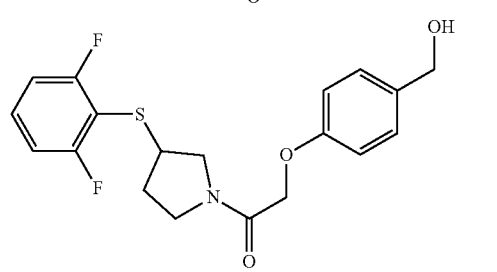
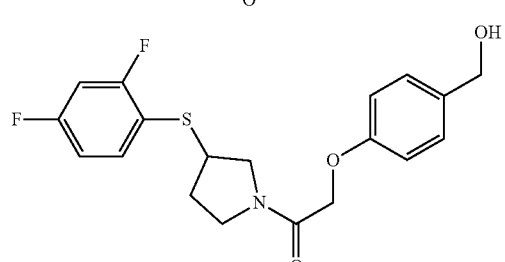
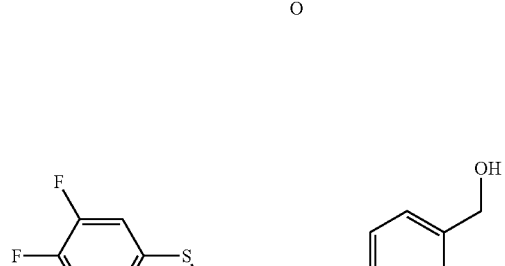
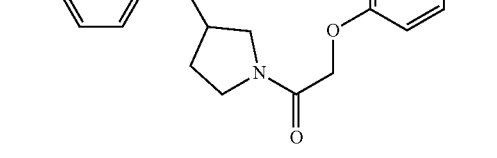
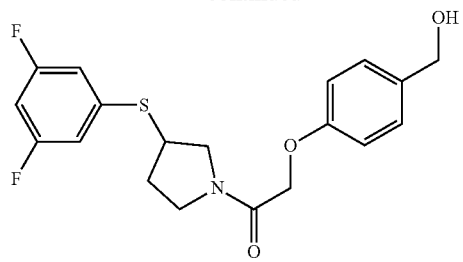
or a pharmaceutically acceptable salt, ester or prodrug form thereof.
In other embodiments, the compound is one of:
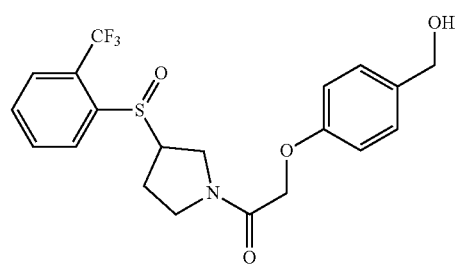
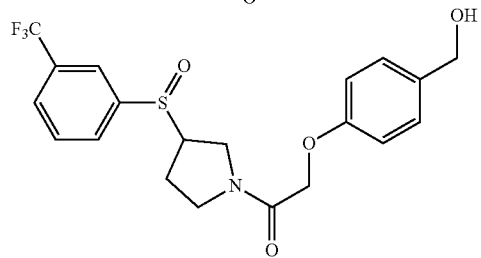
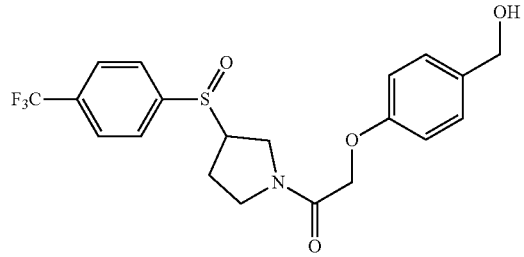
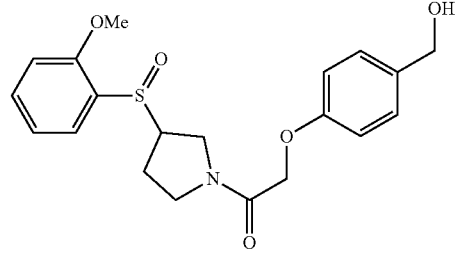
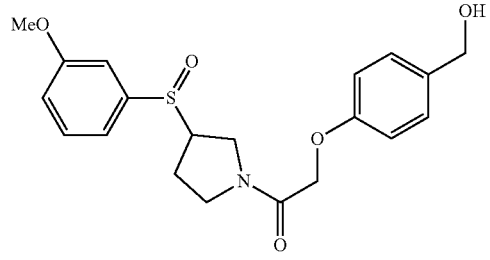

371
-continued
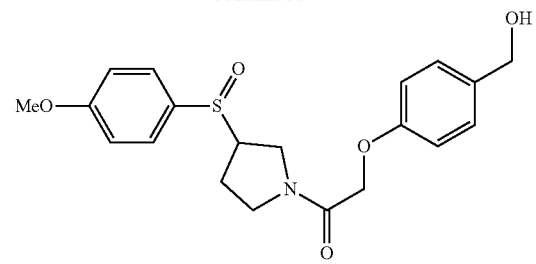
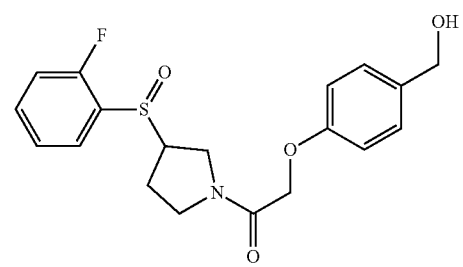
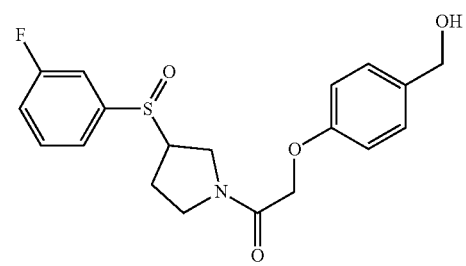
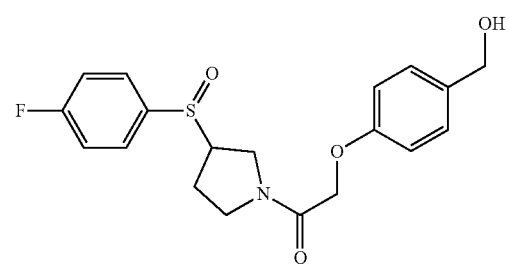
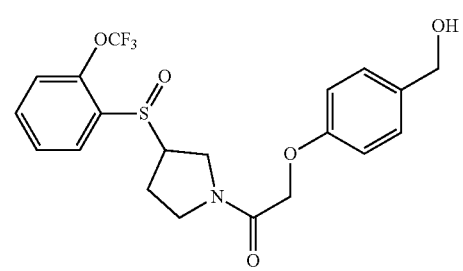
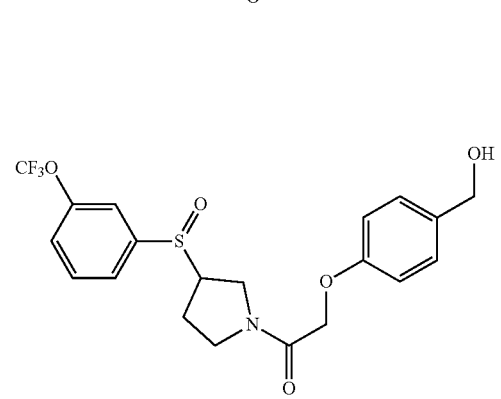
372
-continued
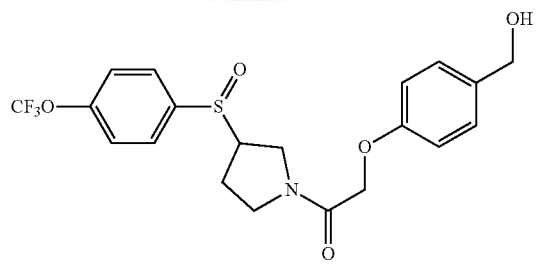
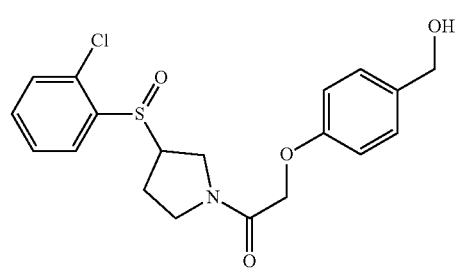
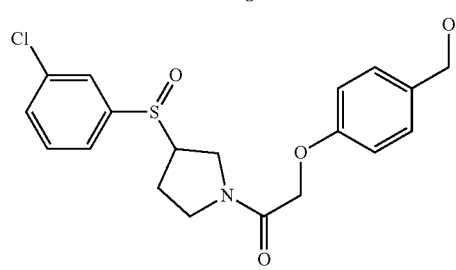
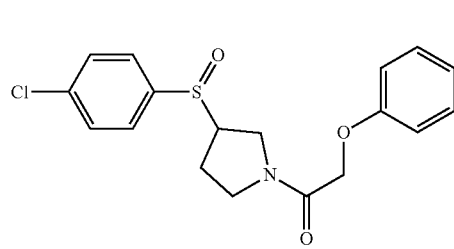
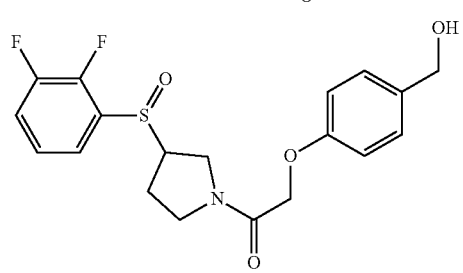
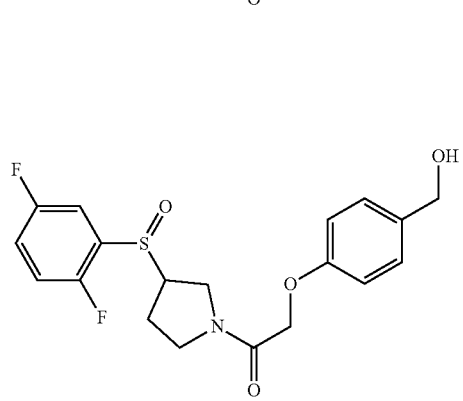

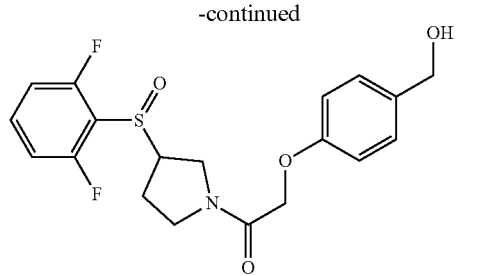
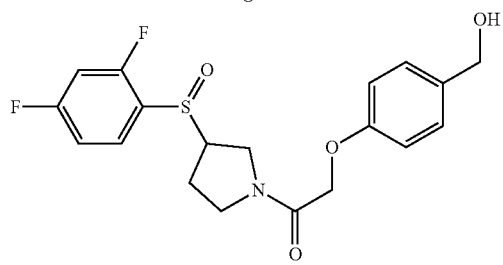
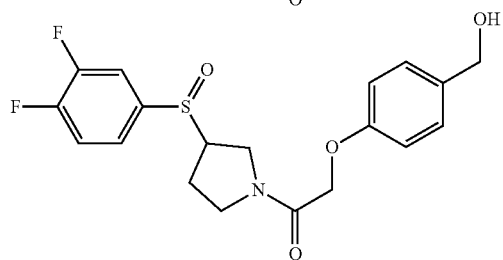
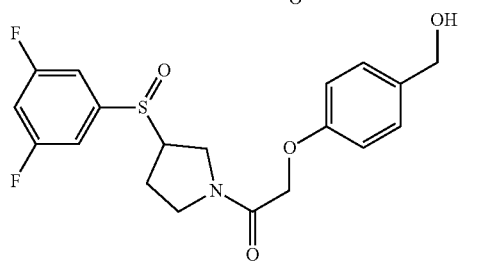
or a pharmaceutically acceptable salt, ester or prodrug form thereof.
In further embodiments, the compound is one of:
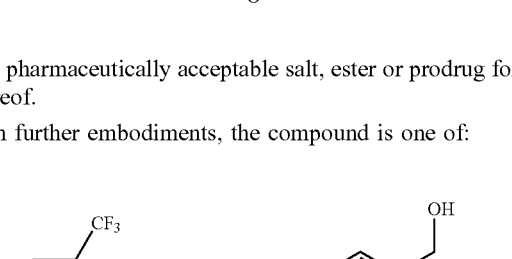
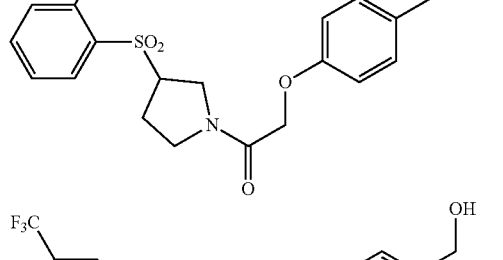
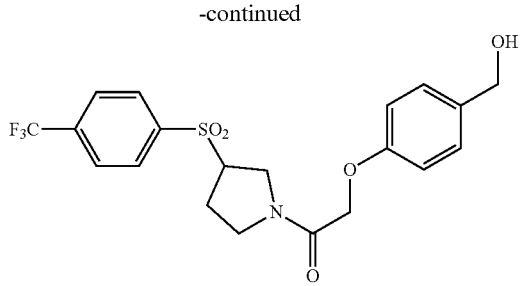
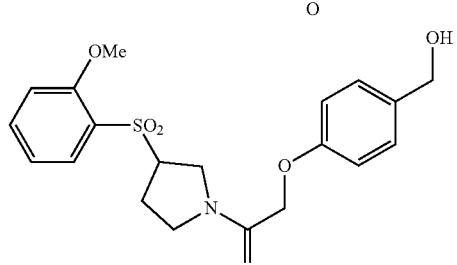
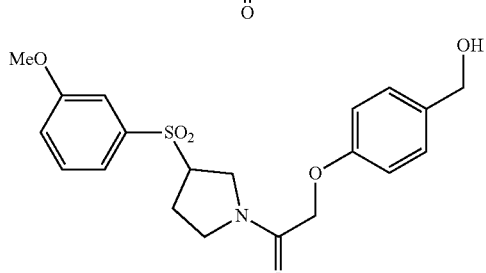
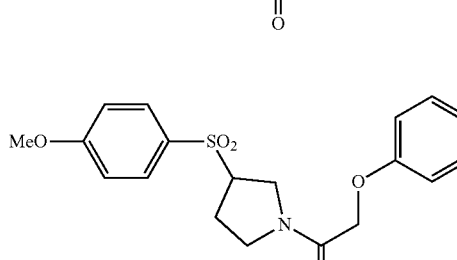
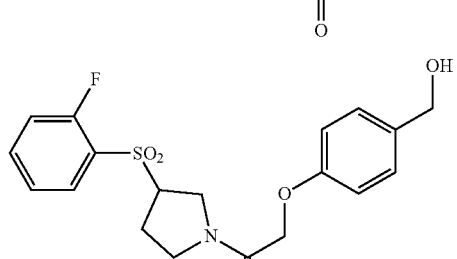
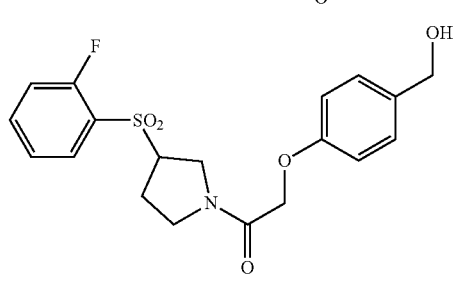
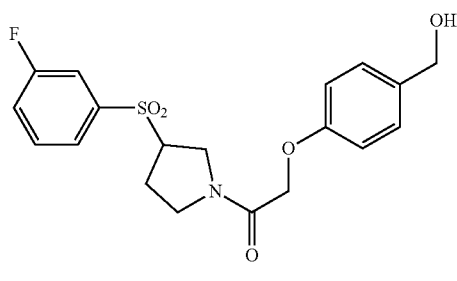

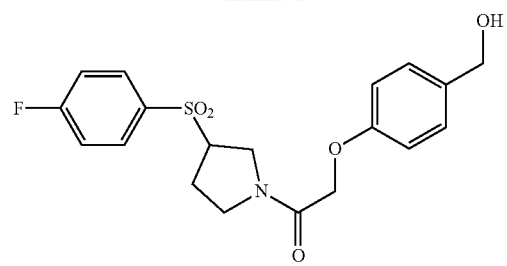
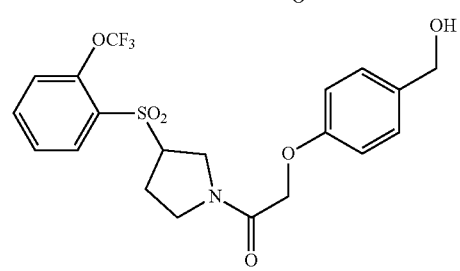
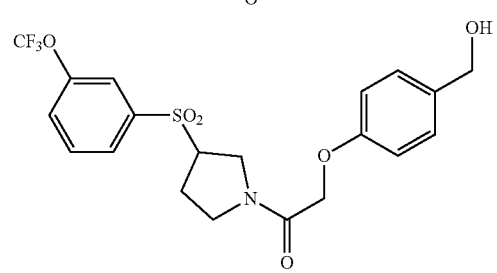
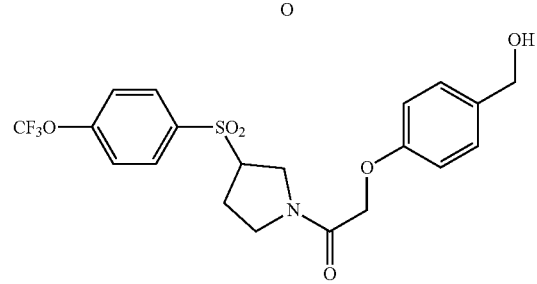
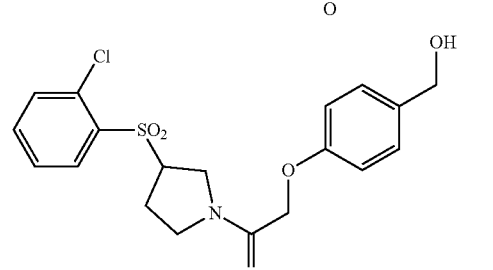
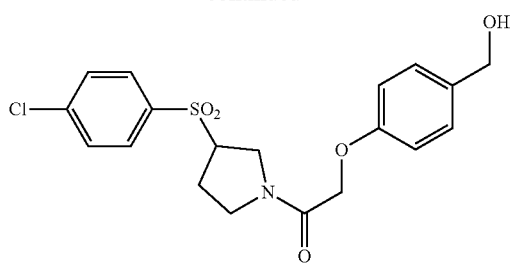
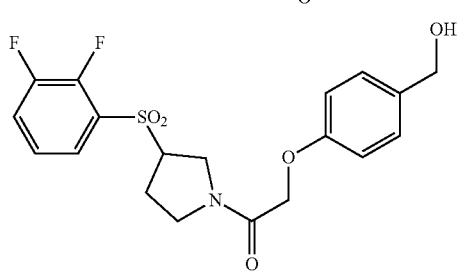
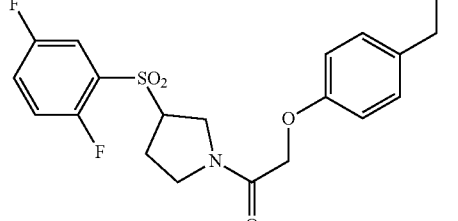
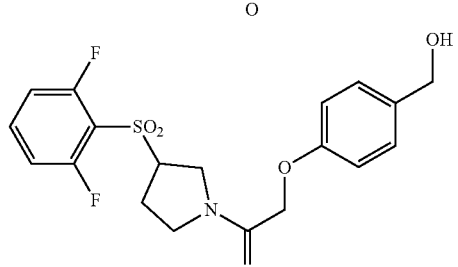
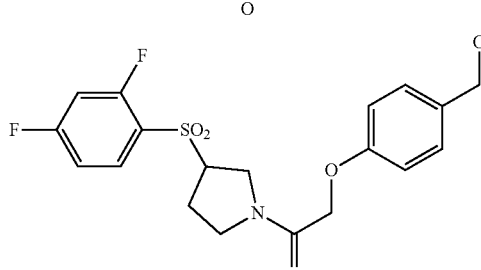

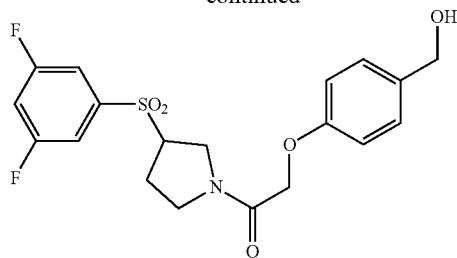
or a pharmaceutically acceptable salt, ester or prodrug form thereof.
In yet further embodiments, the compound is one of:
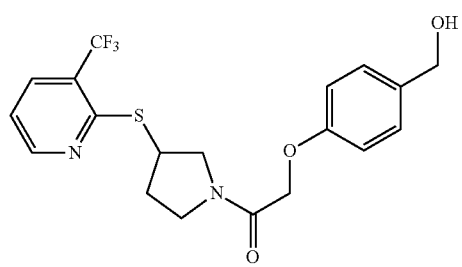
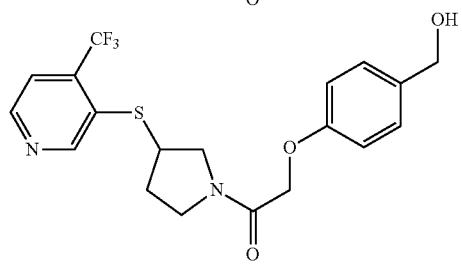
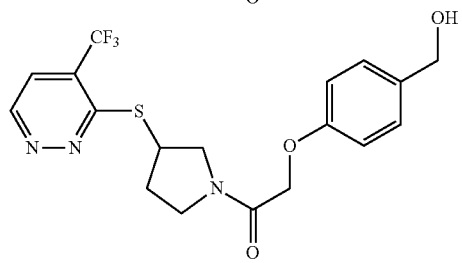
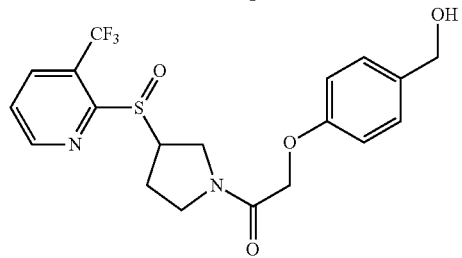
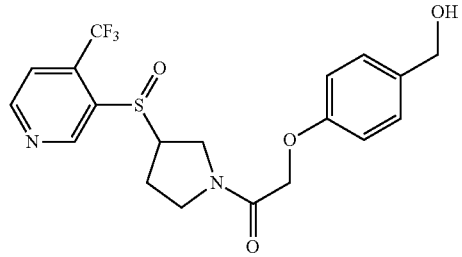
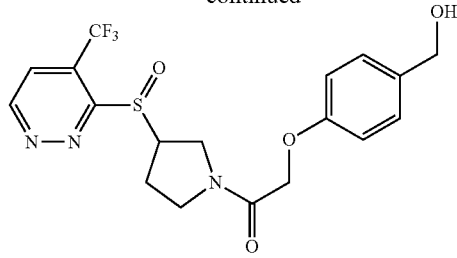
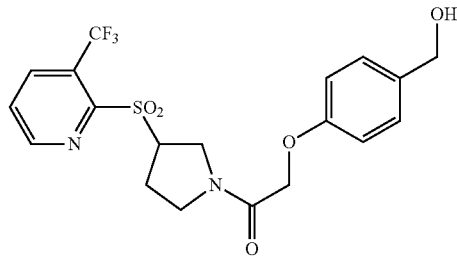
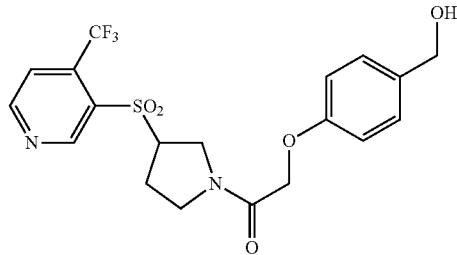
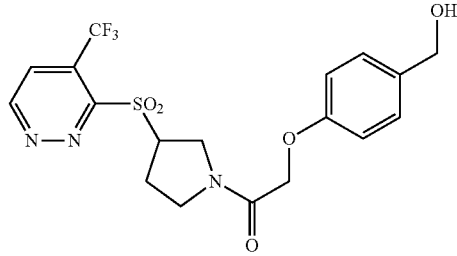
or a pharmaceutically acceptable salt, ester or prodrug form thereof.
In yet other embodiments, the compound is one of the following:
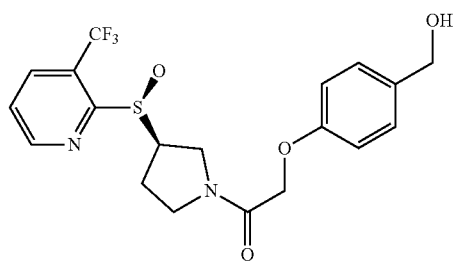
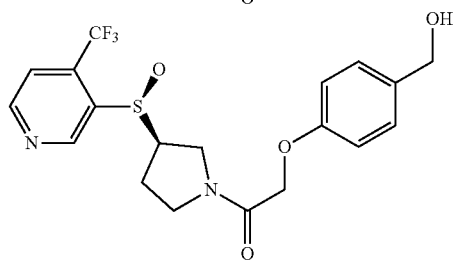

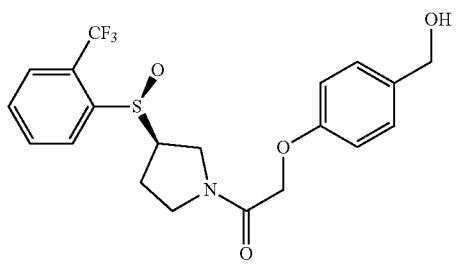

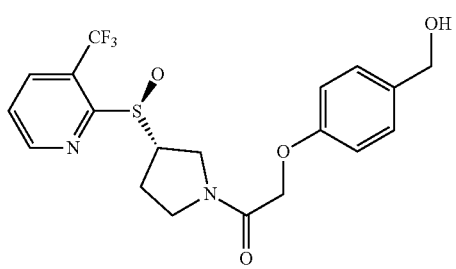

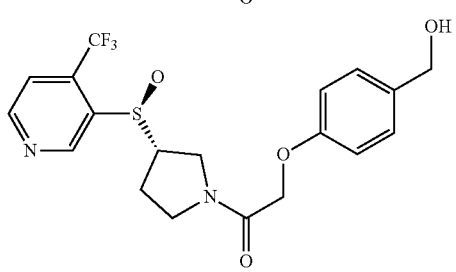

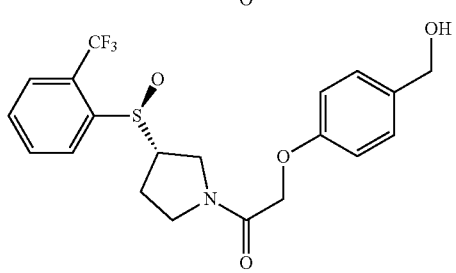

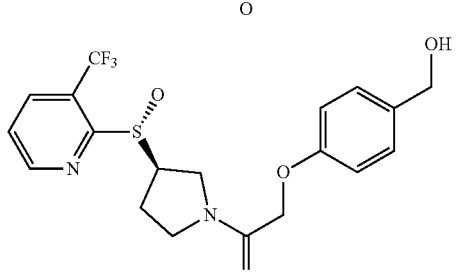

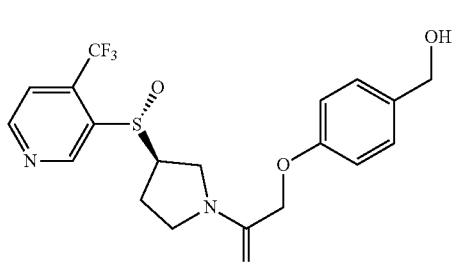

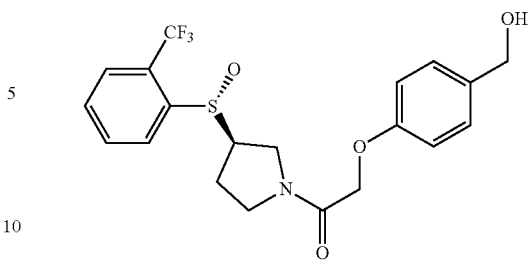

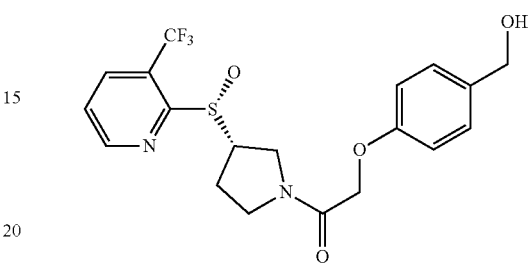

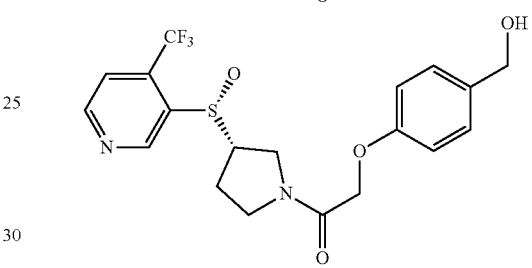

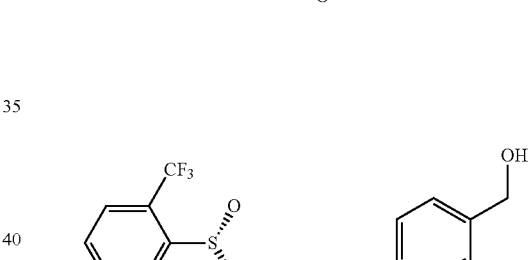

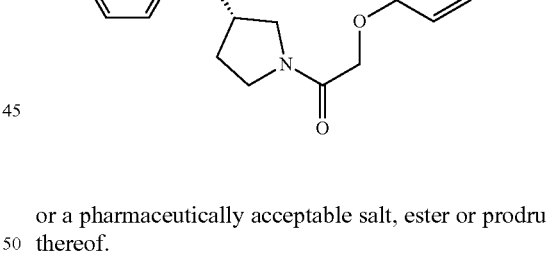

or a pharmaceutically acceptable salt, ester or prodrug form thereof.

In further embodiments, the compound is present in the composition at a concentration between about 0.005% and about 5% by weight.

In yet further embodiments, the compound is a racemic mixture, a diastereoisomeric mixture, a single enantiomer, an enantiomeric diastereomer, a meso compound, a pure epimer, or a mixture of epimers thereof.

In yet other embodiments, one or more double bonds present in the compound are cis or trans, E or Z, a cis/trans mixture, an E/Z mixture, a combination of E and Z geometries, a combination of E and Z geometric mixtures or other geometric isomers thereof.

The present invention still further provides a compound having the structure I, or a pharmaceutically acceptable salt, ester or prodrug form thereof,

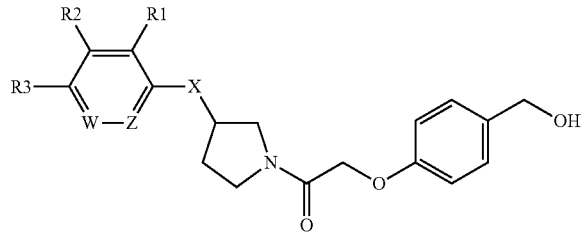

I wherein:
X is O;
W is CR$_4$ or N;
Z is CR$_5$ or N;
wherein at least one of W and Z is N;
wherein each of R$_1$, R$_2$ and R$_3$ and R$_4$ and R$_5$, if present, is independently:
H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;
wherein adjacent substituents R$_1$, R$_2$ and R$_3$ and R$_4$ and R$_5$, if present, may form a saturated or unsaturated 5-membered or 6-membered carbocyclic or heterocyclic ring;
wherein each of R$_6$, R$_7$, R$_8$, R$_9$ and R$_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;
wherein optionally substituted alkenyl, if present, may have one or more double bond and each double bond may independently be cis or trans, E or Z, a cis/trans mixture or an E/Z mixture; and
wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In some embodiments Z is N and in further embodiments Z is N and W is CR$_4$.

In other embodiments W is N and in yet further embodiments W is N and Z is CR$_5$.

In yet other embodiments Z is N and W is N.

The present invention also provides a compound having the structure I, or a pharmaceutically acceptable salt, ester or prodrug form thereof,

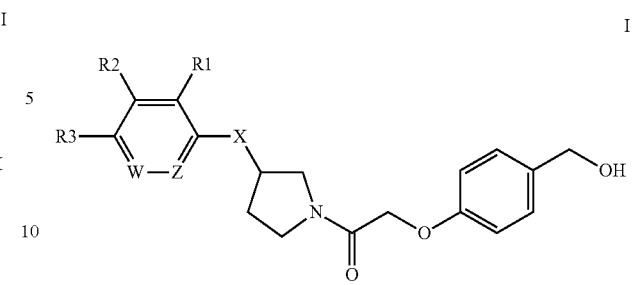

I wherein:
X is O;
W is CR$_4$;
Z is C$_5$;
wherein each of R$_1$, R$_2$, R$_3$, R$_4$ and R$_5$ is independently:
H; OH; F; Cl; Br; I; C$_1$ to C$_6$ straight chain or branched chain alkyl; CH$_2$F; CHF$_2$; CF$_3$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;
wherein at least two of R$_1$, R$_2$, R$_3$, R$_4$ and R$_5$ is other than H;
wherein adjacent substituents R$_1$, R$_2$, R$_3$, R$_4$ and R$_5$ may form a saturated or unsaturated 5-membered or 6-membered carbocyclic or heterocyclic ring;
wherein each of R$_6$, R$_7$, R$_8$, R$_9$ and R$_{10}$, if present, is independently:
H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;
wherein Rx, if present, is alkyl, cycloalkyl, alkylcycloalkyl, acyl, ester, or thioester;
wherein optionally substituted alkenyl, if present, may have one or more double bond and each double bond may independently be cis or trans, E or Z, a cis/trans mixture or an E/Z mixture; and
wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention further provides a compound having the structure I, or a pharmaceutically acceptable salt, ester or prodrug form thereof,

383

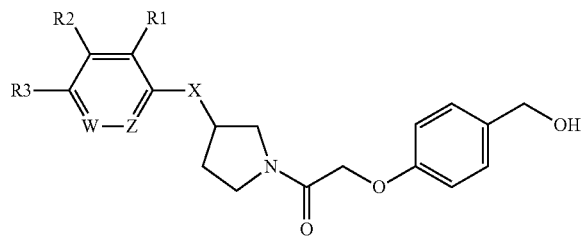

I wherein:
X is O;
W is CR$_4$;
Z is CR$_5$;
wherein one of R$_1$, R$_2$, R$_3$, R$_4$ and R$_5$ is independently: OH; O-alkyl; O-cycloalkyl; O-alkylcycloalkyl; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$; and the rest of R$_1$, R$_2$, R$_3$, R$_4$ and R$_5$ is H.

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

The present invention yet further provides a compound having the structure I, or a pharmaceutically acceptable salt, ester or prodrug form thereof,

I

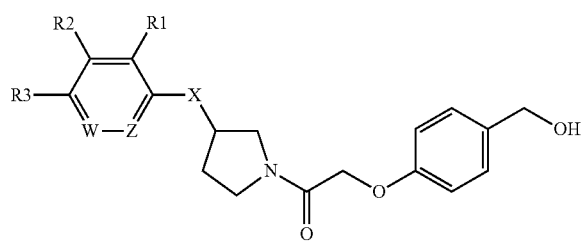

384 wherein:
X is O;
W is CR$_4$;
Z is CR$_5$;
wherein each of R$_1$ and R$_5$ is H;
wherein each of R$_2$, R$_3$, and R$_4$ is independently:

H; OH; F; Cl; Br; I; C$_1$ to C$_6$ straight chain or branched chain alkyl; CH$_2$F; CHF$_2$; CH$_2$CH$_2$F; CH$_2$CHF$_2$; CH$_2$CF$_3$; CHFCH$_2$F; CHFCHF$_2$; CHFCF$_3$; CF$_2$CH$_2$F; CF$_2$CHF$_2$; CF$_2$CF$_3$; O-alkyl; O-cycloalkyl; O-alkylcycloalkyl; OCH$_2$F; OCHF$_2$; OCF$_3$; OCH$_2$CH$_2$F; OCH$_2$CHF$_2$; OCH$_2$CF$_3$; OCHFCH$_2$F; OCHFCHF$_2$; OCHFCF$_3$; OCF$_2$CH$_2$F; OCF$_2$CHF$_2$; OCF$_2$CF$_3$; O—(CO)—R$_6$; O—(CNH)—R$_6$; O—(CNR$_6$)—R$_7$; SO$_3$H or a ester thereof; CO$_2$H or a ester thereof; PO$_2$(OCH$_3$)H or a phosphonate thereof; NO$_2$; NH$_2$; NHCH(O); NR$_6$CH(O); NHC(O)R$_6$; NR$_6$C(O)R$_7$; C(O)NR$_6$R$_7$; C(NH)NR$_6$R$_7$; C(NH)NR$_6$OH; C(NH)NR$_6$NO$_2$; or C(NR$_6$)NR$_7$C(NR$_8$)NR$_9$R$_{10}$;

wherein adjacent substituents R$_2$, R$_3$ and R$_4$ may form a saturated or unsaturated 5-membered or 6-membered carbocyclic or heterocyclic ring;

wherein each of R$_6$, R$_7$, R$_8$, R$_9$ and R$_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.

In certain embodiments each of R$_6$, R$_7$, R$_8$, R$_9$ and R$_{10}$, if present, is independently: H, optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl.

In other embodiments, the compound is one of the following:

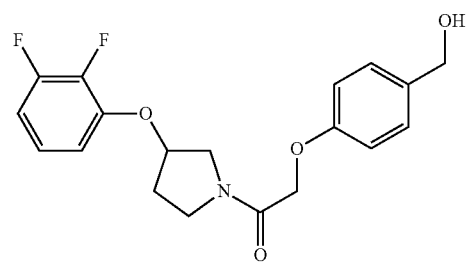

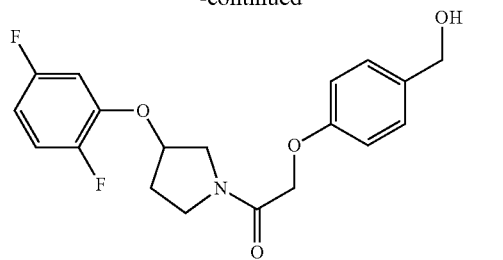
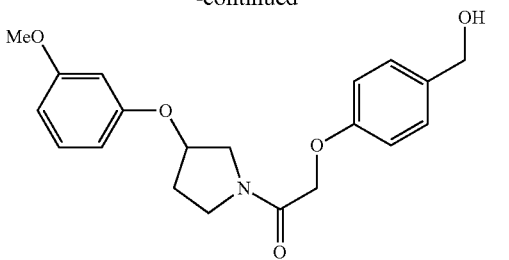
or a pharmaceutically acceptable salt, ester or prodrug form thereof.
In further embodiments, the compound is one of the following:
or a pharmaceutically acceptable salt, ester or prodrug form thereof.
In yet other embodiments, the compound is one of the following:
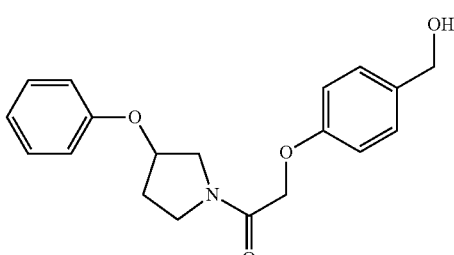
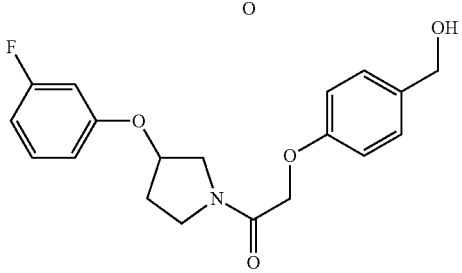

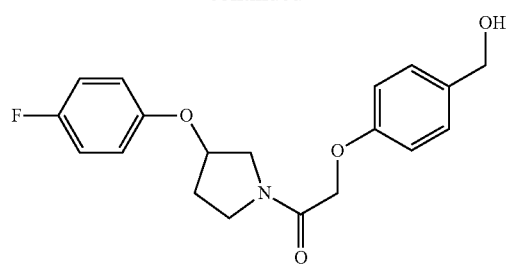
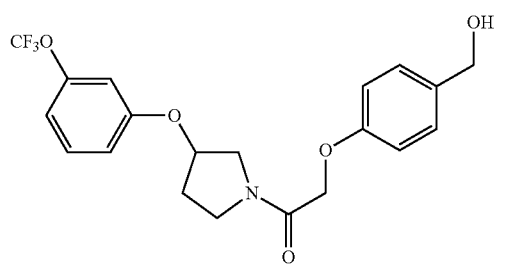
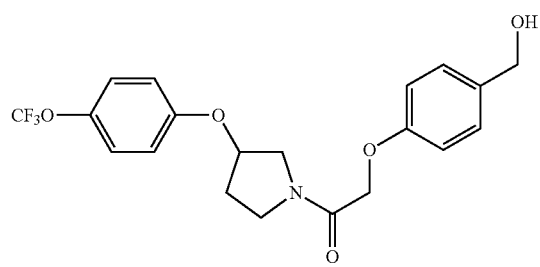
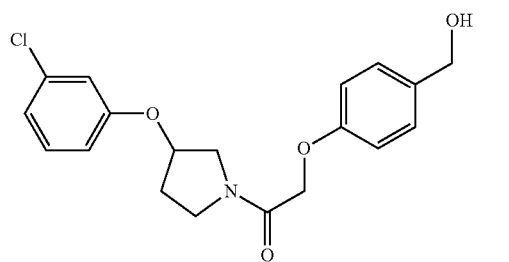
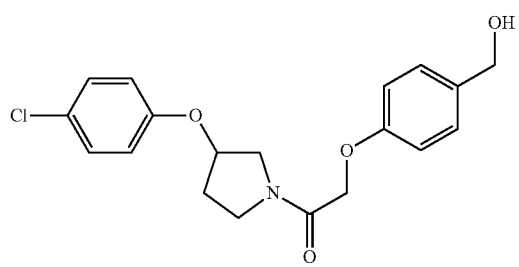
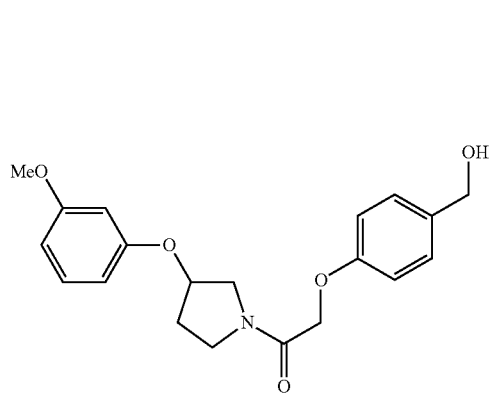
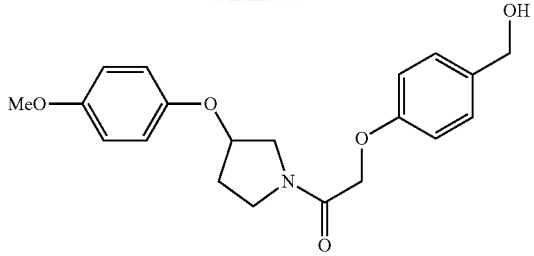
or a pharmaceutically acceptable salt, ester or prodrug form thereof.
In yet further embodiments, the compound is one of the following:
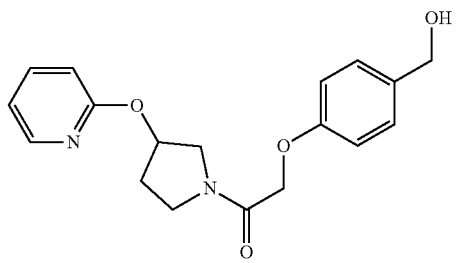
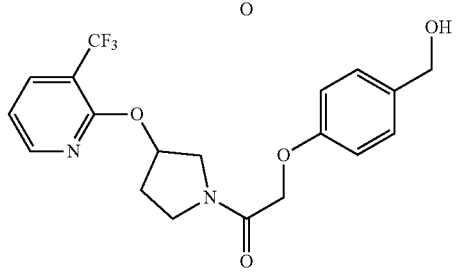
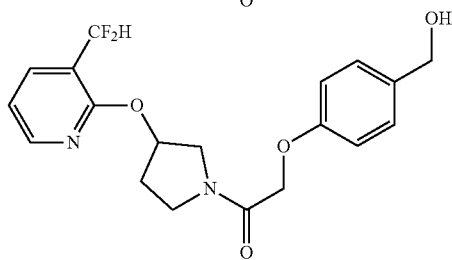
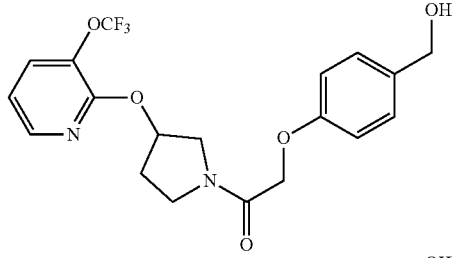
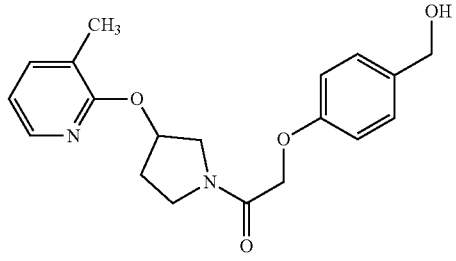

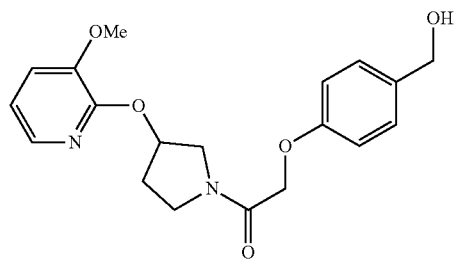
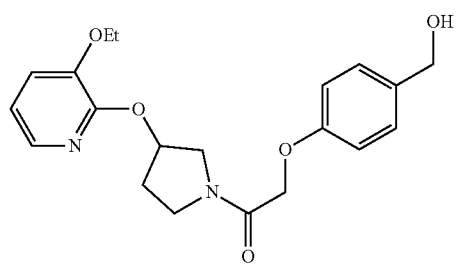
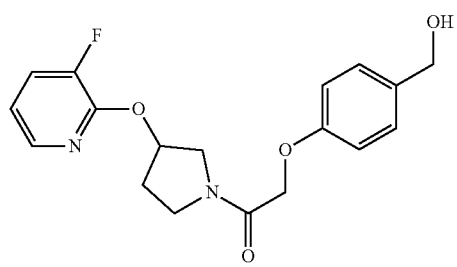
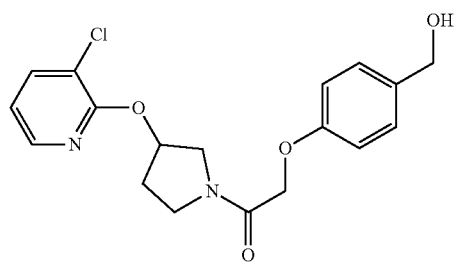
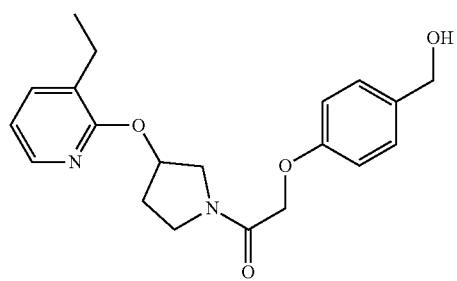
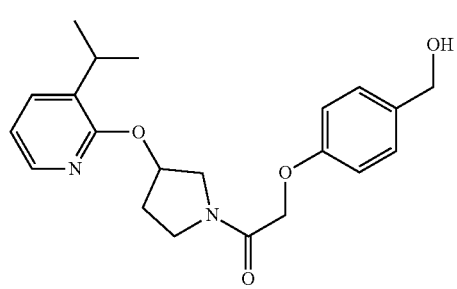
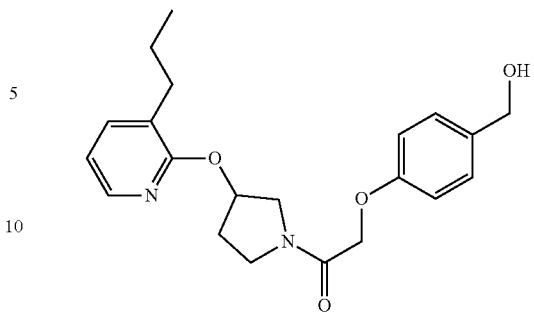
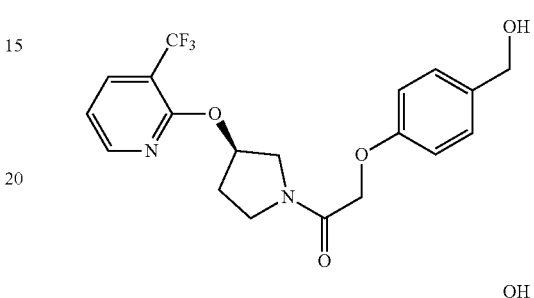
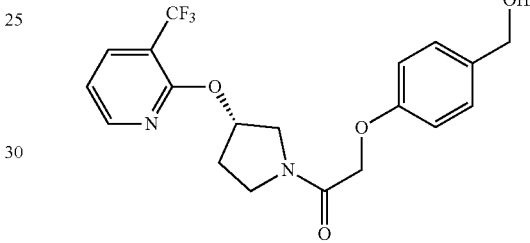
or a pharmaceutically acceptable salt, ester or prodrug form thereof.
In yet other embodiments, the compound is one of the following:
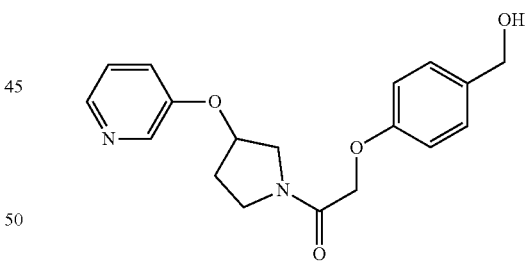
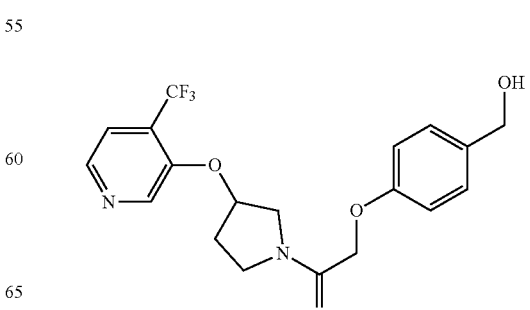

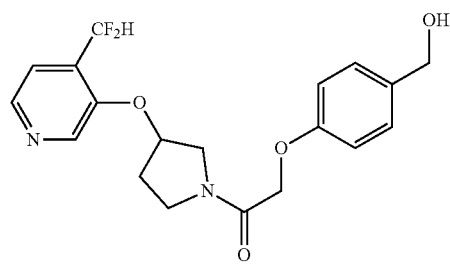
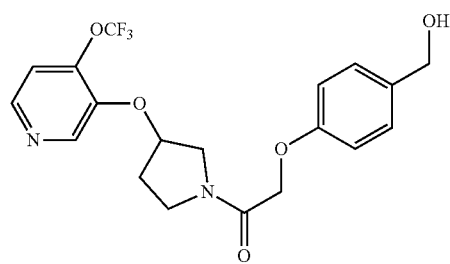
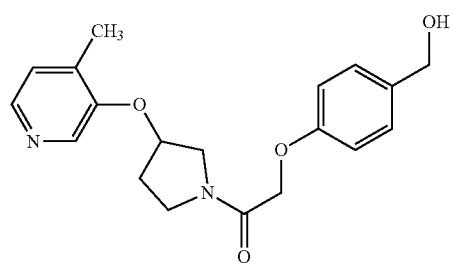
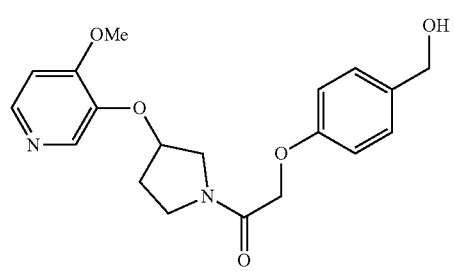
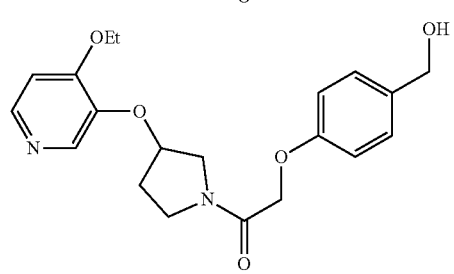
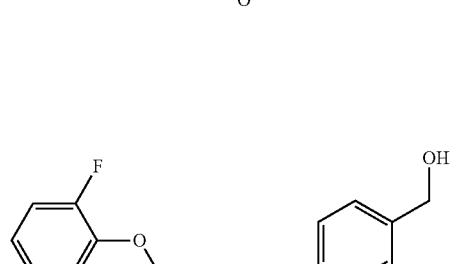
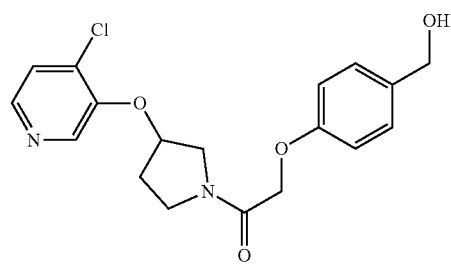
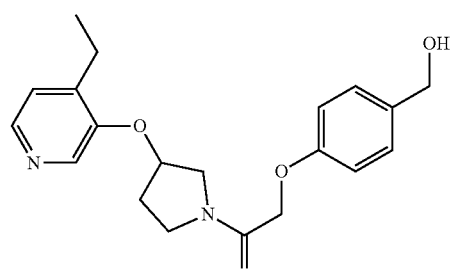
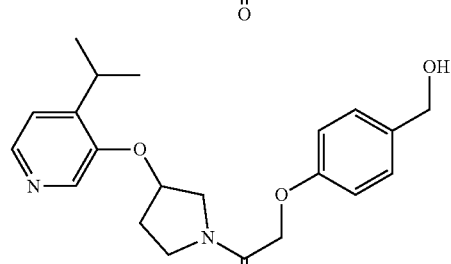
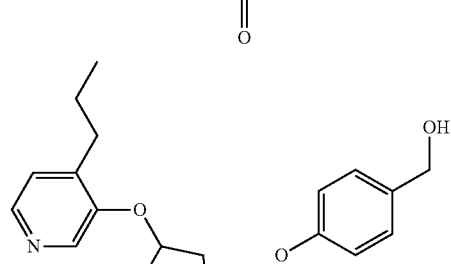
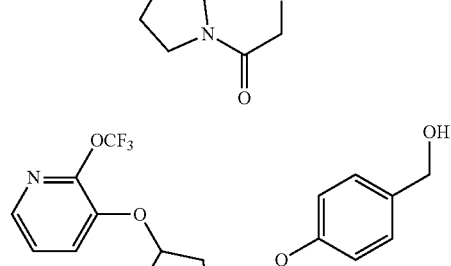
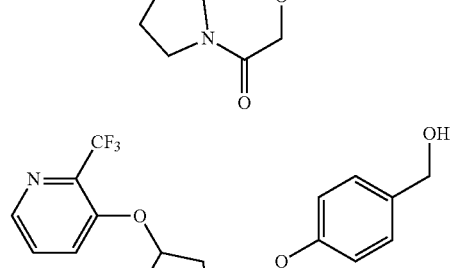

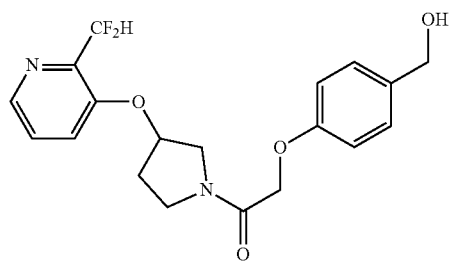
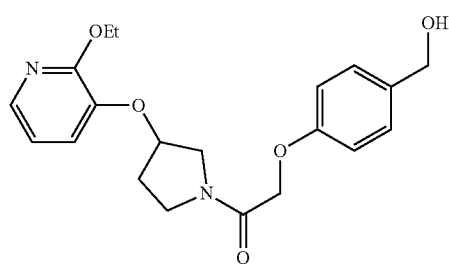 [SMILES: CCOc1ncccc1OC1CCN(C(=O)COc2ccc(CO)cc2)C1]
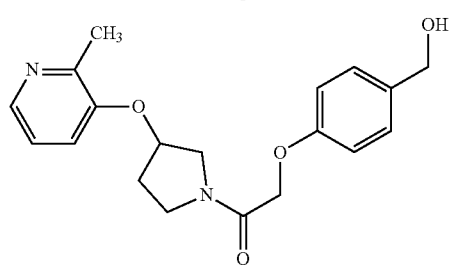 [SMILES: Cc1ncccc1OC1CCN(C(=O)COc2ccc(CO)cc2)C1]
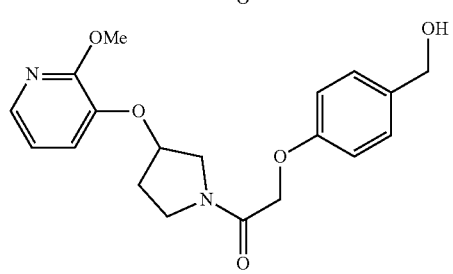 [SMILES: CC(C)c1ncccc1OC1CCN(C(=O)COc2ccc(CO)cc2)C1]
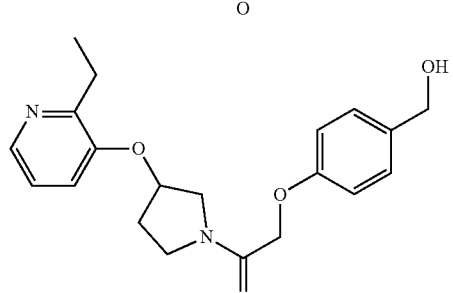
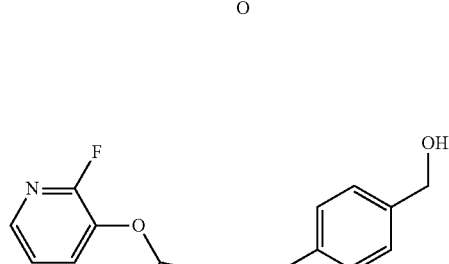
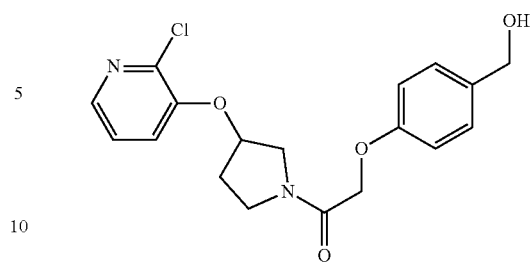
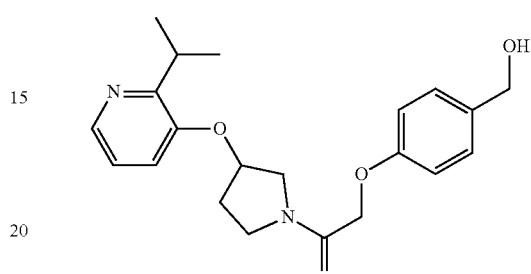
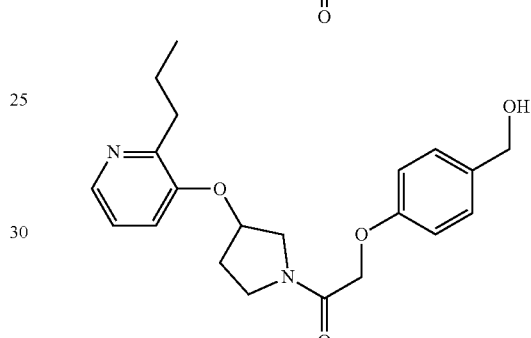
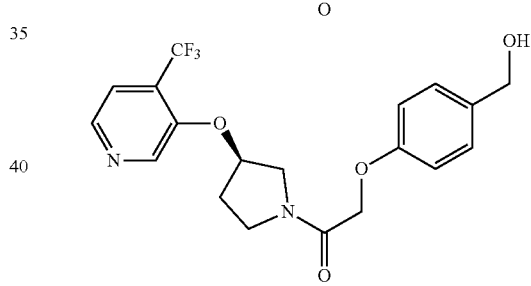
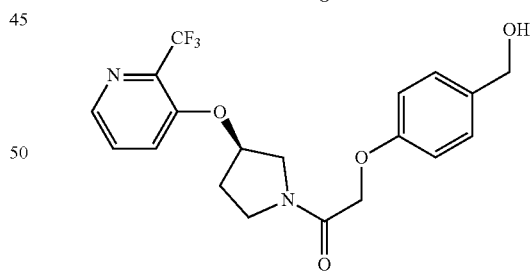
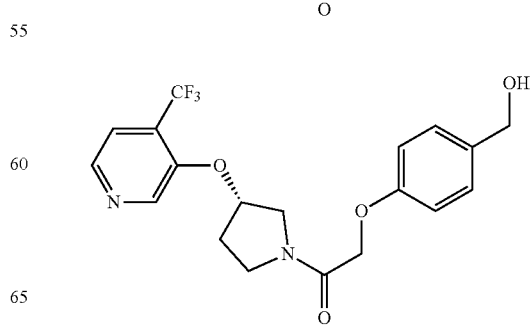

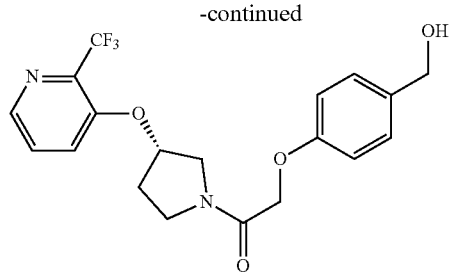
or a pharmaceutically acceptable salt, ester or prodrug form thereof.
In yet further embodiments, the compound is one of the following:
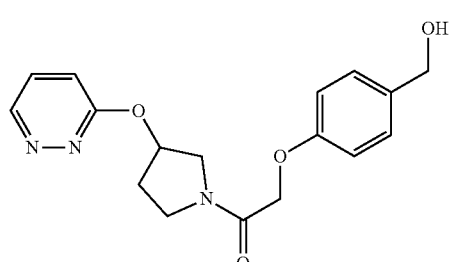
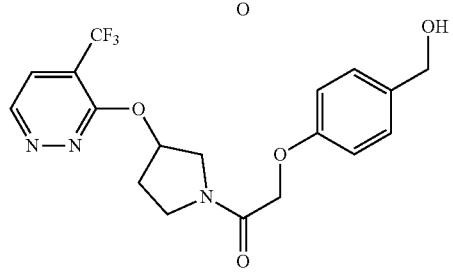
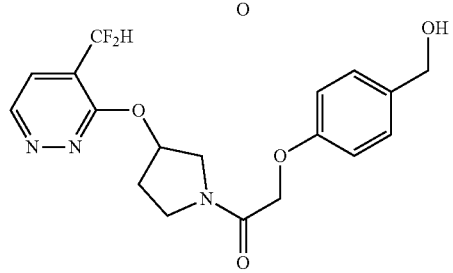
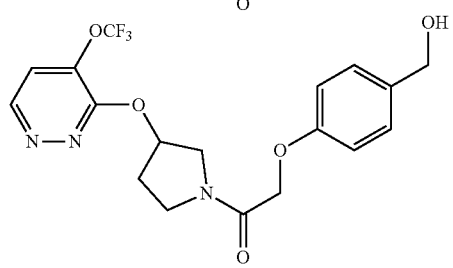
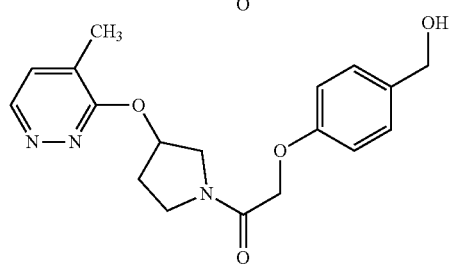
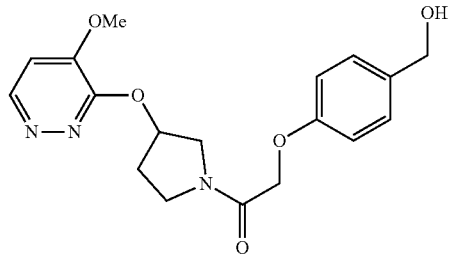 [SMILES: COc1ccnnc1OC1CCN(C(=O)COc2ccc(CO)cc2)C1]
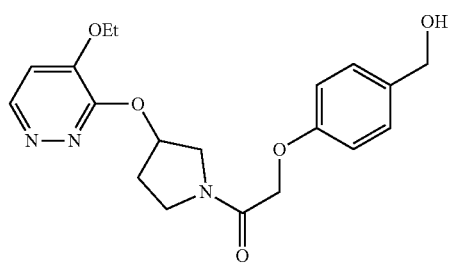
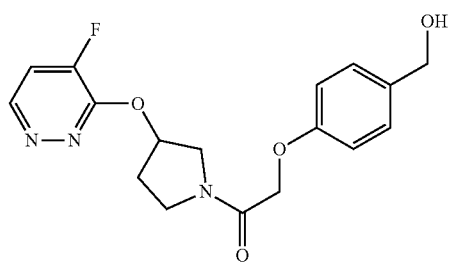 [SMILES: O=C(COc1ccc(CO)cc1)N1CCC(Oc2nnccc2F)C1]
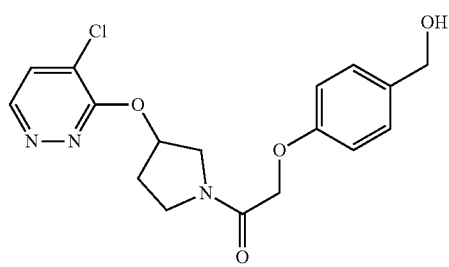 [SMILES: O=C(COc1ccc(CO)cc1)N1CCC(Oc2nnccc2Cl)C1]
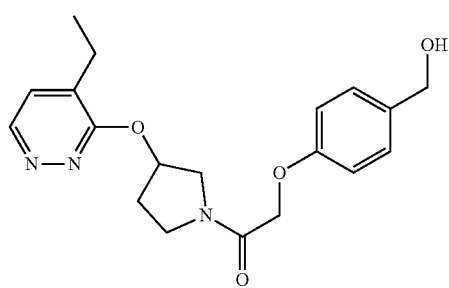 [SMILES: CCc1ccnnc1OC1CCN(C(=O)COc2ccc(CO)cc2)C1]
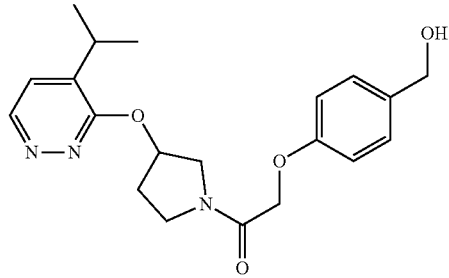 [SMILES: CC(C)c1ccnnc1OC1CCN(C(=O)COc2ccc(CO)cc2)C1]

-continued

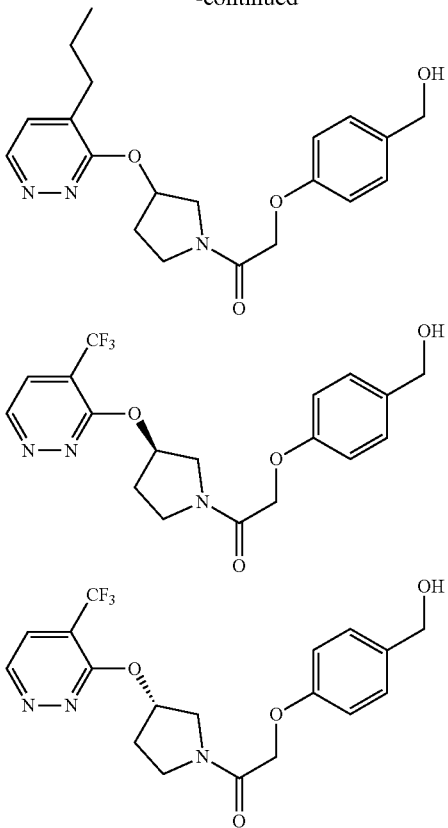

or a pharmaceutically acceptable salt, ester or prodrug form thereof.

In yet further embodiments, an asymmetric center is present in one or more substituent and the compound is in the form of a racemic mixture, a single enantiomer, a diastereoisomeric mixture, an enantiomeric diastereomer, a meso compound, a pure epimer, or a mixture of epimers thereof.

In yet other embodiments, an optionally substituted alkenyl having one or more double bond is present in the compound and each double bond is independently cis or trans, E or Z, a cis/trans mixture or an E/Z mixture.

The present invention also provides a compound having the structure I, or a pharmaceutically acceptable salt, ester or prodrug form thereof,

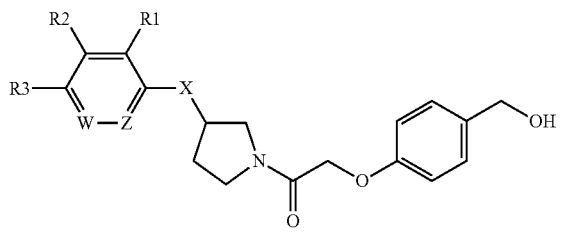

I wherein:
X is O;
W is independently $CR_4$ or N;
Z is independently $CR_5$ or N;
wherein each of $R_2$ and $R_3$ and $R_4$, if present, is independently:

H; OH; F; Cl; Br; I; $C_1$ to $C_6$ straight chain or branched chain alkyl; $CH_2F$; $CHF_2$; $CF_3$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; $NHCH(O)$; $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;

wherein when W is $CR_4$ and Z is $CR_5$, then each of $R_1$ and $R_5$ is independently:

H; OH; F; Cl; Br; I; $C_1$ to $C_6$ straight chain or branched chain alkyl; $CH_2F$; $CHF_2$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; $NHCH(O)$; $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$;

wherein when either or both of W and Z is N, then each of $R_1$, and $R_5$ if present, is independently:

H; OH; F; Cl; Br; I; $C_1$ to $C_6$ straight chain or branched chain alkyl; $CF_3$; $CH_2F$; $CHF_2$; $CH_2CH_2F$; $CH_2CHF_2$; $CH_2CF_3$; $CHFCH_2F$; $CHFCHF_2$; $CHFCF_3$; $CF_2CH_2F$; $CF_2CHF_2$; $CF_2CF_3$; O-alkyl; O-cycloalkyl; O-alkylcycloalkyl; $OCH_2F$; $OCHF_2$; $OCF_3$; $OCH_2CH_2F$; $OCH_2CHF_2$; $OCH_2CF_3$; $OCHFCH_2F$; $OCHFCHF_2$; $OCHFCF_3$; $OCF_2CH_2F$; $OCF_2CHF_2$; $OCF_2CF_3$; O—(CO)—$R_6$; O—(CNH)—$R_6$; O—($CNR_6$)—$R_7$; $SO_3H$ or a ester thereof; $CO_2H$ or a ester thereof; $PO_2(OCH_3)H$ or a phosphonate thereof; $NO_2$; $NH_2$; $NHCH(O)$; $NR_6CH(O)$; $NHC(O)R_6$; $NR_6C(O)R_7$; $C(O)NR_6R_7$; $C(NH)NR_6R_7$; $C(NH)NR_6OH$; $C(NH)NR_6NO_2$; or $C(NR_6)NR_7C(NR_8)NR_9R_{10}$ wherein adjacent substituents $R_1$, $R_2$ and $R_3$ and $R_4$ and $R_5$, if present, may form a saturated or unsaturated 5-membered or 6-membered carbocyclic or heterocyclic ring;

wherein each of $R_6$, $R_7$, $R_8$, $R_9$ and $R_{10}$, if present, is independently:

H; OH; O-Rx; optionally substituted alkyl; cycloalkyl; heterocycloalkyl; alkylheterocycloalkyl; optionally substituted alkenyl; optionally substituted alkynyl; optionally substituted aryl; optionally substituted alkylaryl; optionally substituted heteroaryl; or optionally substituted alkylheteroaryl;

wherein Rx, if present, is alkyl, cycloalkyl, alkylcycloalkyl, acyl, ester, or thioester;

wherein optionally substituted alkenyl, if present, may have one or more double bond and each double bond may independently be cis or trans, E or Z, a cis/trans mixture or an E/Z mixture; and wherein the compound may be in the form of a racemic mixture or a single enantiomer or, if an asymmetric center is present in one or more substituent, the compound may be in the form of a racemic mixture, a single enantiomer, a diastereoisomeric mixture, an enantiomeric diastereomer, a meso compound, a pure epimer, or a mixture of epimers thereof.
In some embodiments, the compound is one of the following:
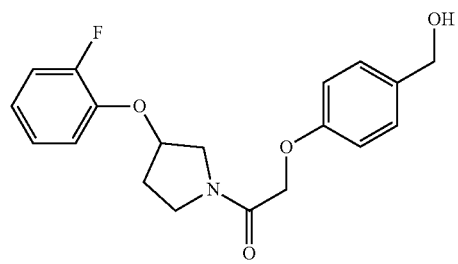
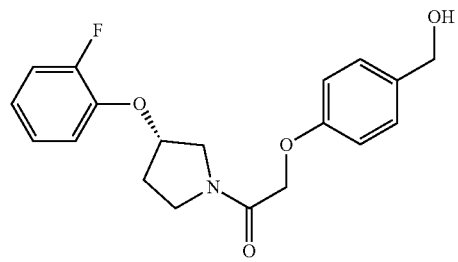
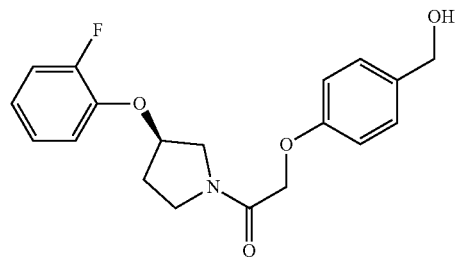
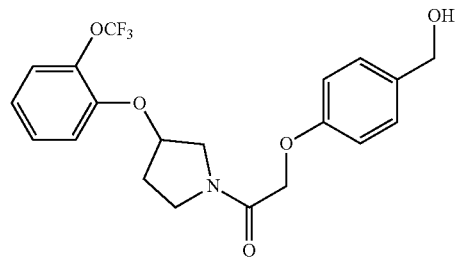
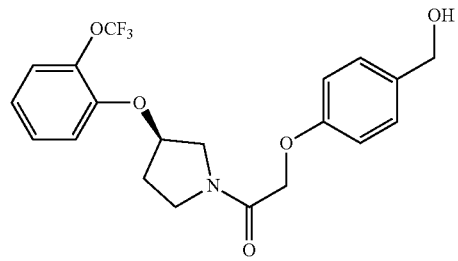
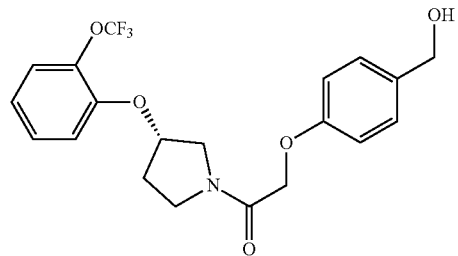
-continued
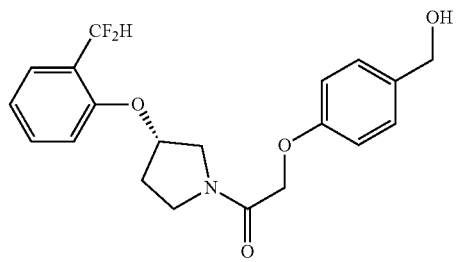
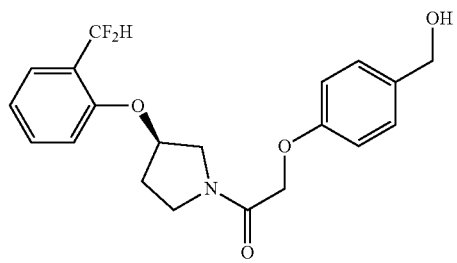
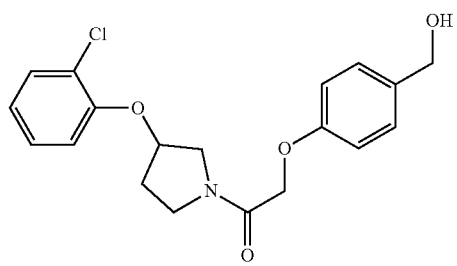
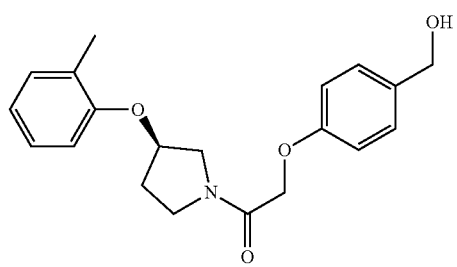
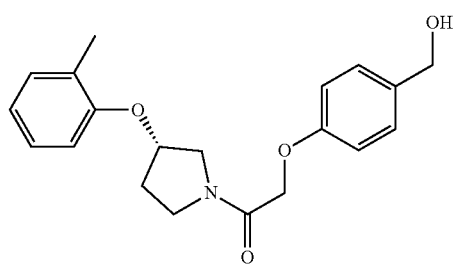
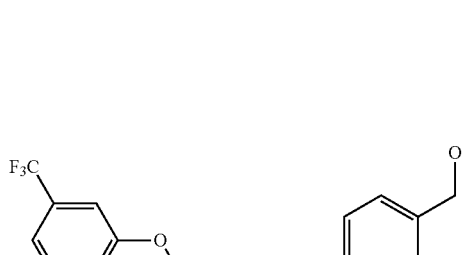

-continued

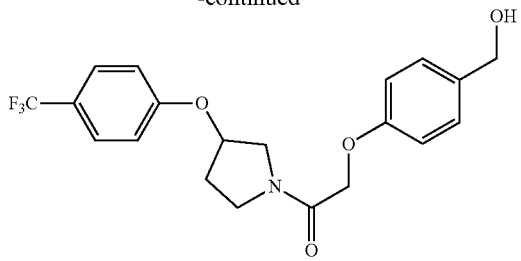

or a pharmaceutically acceptable salt, ester or prodrug form thereof.

Definitions

As used throughout this application, including the claims, the following terms have the meanings defined below, unless specifically indicated otherwise. The phrases "compounds of Structure I", "compound of the invention", and "compound" are used interchangeably throughout the application and should be treated as synonyms.

The phrase "pharmaceutically acceptable" indicates that the designated carrier, vehicle, diluent, excipient, solvate, salt or prodrug is generally chemically and/or physically compatible with the other ingredients comprising a formulation, and is physiologically compatible with the recipient thereof.

The terms "treat(s)", "treating", "treated", and "treatment" as used herein include preventative (e.g., prophylactic), ameliorative, palliative and curative uses and/or results. The terms preventative or prophylactic are used interchangeably and refer to treatment prior to the onset of one or more signs or symptoms of a particular condition or disease state. More specifically, these terms refer to the treatment of patients that are largely asymptomatic, i.e. where symptoms of a particular condition or disease state are not readily apparent or detectable, and which results in the substantial prevention, suppression or delay in the onset of one or more signs or symptoms of a particular condition or disease state. An ameliorative treatment is one that improves and/or lessens the severity of one or more signs or symptoms of a particular condition or disease state.

The phrases "therapeutic" and "therapeutically effective amount" as used herein respectively denote an effect and an amount of a compound, composition or medicament that (a) treats a particular disease, condition or disorder; (b) attenuates, ameliorates or eliminates one or more signs, symptoms of or complications arising from a particular disease, condition or disorder; (c) prevents or delays the onset of one or more signs, symptoms of or complications associated with a particular disease, condition or disorder. It should be understood that the terms "therapeutic" and "therapeutically effective amount" encompass any one of the aforementioned effects (a)-(c), either alone or in combination with any of the others (a)-(c). The terms "mammal", "patient" and "subject" refer to warm blooded animals such as, for example, guinea pigs, mice, rats, gerbils, cats, rabbits, dogs, monkeys, chimpanzees, and humans. The "therapeutically effective amount" will vary depending on the composition, the compound, the therapy, the course of treatment, the disease, disorder, or condition, and its severity and the age, weight, etc., of the subject to be treated.

A "humectant," as used herein, is an excipient that can increase the water level in the upper layers of the skin. Examples of humectants approved for use in topical drug products by the FDA include, but are not limited to, the following: hexylene glycol, propylene glycol, sorbitol, lactic acid, sodium lactate, methyl gluceth-10, methyl gluceth-20, and polyethylene glycols.

An "emollient," as used herein, is an excipient that can improve skin feel by softening, lubricating, and refatting the skin. Emollients may also improve the barrier function of skin and reduce water evaporation. Examples of emollients approved for use in topical drug products by the United States Food and Drug Administration (FDA) include, but are not limited to, the following: diisopropyl adipate, isopropyl myristate, isopropyl palmitate, cetearyl octonoate, isopropyl isostearate, myristyl lactate, octyldodecanol, oleyl alcohol, mineral oil, petrolatum, vegetable/plaint oils (e.g., peanut, soybean, safflower, olive, almond, coconut), PPG-15 stearyl ether, PPG-26 oleate, PEG-4 dilaurate, lecithin, lanolin, lanolin alcohol, polyoxyl 75 lanolin, cholesterol, cetyl esters wax, cetostearyl alcohol, glyceryl monostearate, medium chain triglycerides, dimethicone, and cyclomethicone.

An "pH buffering agent," as used herein, refers to, a chemical compound that alone or in combination with other compounds can be used to neutralize a vehicle base of a pharmaceutical composition comprising acidic components in aqueous-organic solvent mixtures and thereby facilitating stabilization the formulation both chemically and physically. Such agents can also be used in combination with an acceptable acidic polymer to provide enhanced viscosity and structure to the topical formulation. Typical pH buffering agents are basic salts or bases which are soluble in the aqueous-organic co-solvent that are non-irritant and have pKa's in the range of 8-10.0 for a topical formulation, or more preferably a pKa of 7.5-8.5 with the objective of buffering the pH with a less basic agents, thereby minimizing the skin sensitivity. Examples of pH buffering agents agents approved for use in topical drug products by the FDA include, but are not limited to: triethanolamine, ethanolamine, tromethamine, aminomethyl propanol, tetrahydroxypropyl ethylene diamine, triisopropanolamine, sodium hydroxide, potassium hydroxide, sodium bicarbonate, potassium bicarbonate.

A "nonaqueous solvent," as used herein, is a solvent other than water. It may be completely miscible with water or in the presence of other nonaqueous solvents above certain concentrations. Examples of nonaqueous solvents approved for use in topical drug products by the FDA include, but are not limited to: alcohol (ethanol), acetone, benzyl alcohol, phenoxyethanol, diethylene glycol monoethyl ether, glycerin, hexylene glycol, propylene glycol, isopropyl alcohol, polyethylene glycols, methoxypolyethylene glycols, diethyl sebacate, dimethyl isosorbide, propylene carbonate, and dimethyl sulfoxide. Many emollients that are liquid at room temperature can also be used as solvents. These include, but are not limited to: diisopropyl adipate, isopropyl myristate, vegetable/plant oils, mineral oil, and isopropyl palmitate.

An "antioxidant," as used herein, is a substance that inhibits oxidation of chemical compounds. Examples of typical antioxidants include alpha tocopherol (all isomers), beta tocopherol, delta tocopherol, gamma tocopherol, tocopherols, ascorbic acid, ascorbyl palmitate, butylated hydroxyanisol (BHA), butylated hydroxytoluene (BHT), fumaric acid, malic acid, methionine, propyl gallate, sodium ascorbate, sodium metabisulfate, sodium thiosulfate, sodium bisulfate. The chemical compounds protected from oxidation by an antioxidant include active pharmaceutical ingredients (API) and excipients containing moieties susceptible to oxidation.

A "chelator" as used herein, is a compound that is able to chelate or electrostatically interact with a range of transition metal ions (Fe, Cu, Co, Cr & Mn) which can facilitate and catalyze decomposition via oxidation. They are usually used in combination with an antioxidant. Examples of such chelators are Ethylene Diamine Tetra-acetic acid (EDTA) and its sodium salts, sodium pyrophosphate, Citric acid, Gluconic acid, Catechol and various thiol derivatives.

A "gelling agent," as used herein, is a compound that thickens (i.e. increases the viscosity of) a formulation. Examples are hydroxypropylcelluloses, carbomers, hydroxyethylcelluloses, carboxymethylcelluloses, xanthan gum, guar gum, chitosan, polyvinyl alcohol, povidone, carrageenan, methyl cellulose, hydroxypropyl methyl cellulose, fatty alcohols, cetyl alcohol, stearyl alcohol, cetostearyl alcohol, and myristyl alcohol. In a particular embodiment, the gelling agent is a pharmaceutical grade Carbomer Homopolymer Type C (Carbopol 980®) NF manufactured by Ashland Special Ingredients of Wilmington DE USA due to its ability to form nonaqueous gels which have more desirable cosmetic properties than those of the cellulose derivatives.

A "skin permeation enhancer," as used herein, is a compound that improves absorption of a pharmaceutically active ingredient through a cutaneous membrane, e, g, skin.

The "apparent pH" is that acidity or basicity measured directly in the topical formulation which may only contain 10-20% water in a mixture with nonaqueous solvents. The term "measured pH," as used herein, is that measured after diluting an aliquot of any pharmaceutical composition of the present invention as defined herein, with water to about 10% by volume.

As used herein, the term "therapeutically effective amount" refers to an amount of the API which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of compound administered to a subject will depend on the type and severity of the disease or condition and on the characteristics of the subject, such as general health, age, sex, body weight and tolerance to drugs. It will also depend on the degree, severity and type of the disorder being treated. The skilled artisan will be able to determine appropriate dosages depending on these and other factors. When co-administered with other agents, e. g., when co-administered with anti-infectives such as Benzoyl Peroxide or Vitamin A derivatives such as Retinoic acid, a "therapeutically effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of one or more pharmaceutical compositions of the present invention. In specific embodiments, the terms "treat", "treatment" and "treating" refer to the amelioration of at least one measurable physical parameter being treated. For example, for acne the total count of skin lesions and/or the count of skin pustules and associated inflammatory area under accepted Dermatological parameters will be used to measure the treatment effectiveness. In other embodiments the terms "treat", "treatment" and "treating" refer to the inhibition of the progression of a disorder being treated, either physically by, e.g., stabilization of a discernible symptom, physiologically by, e.g., stabilization of a physical parameter, or both. In the embodiments in which the disorder being evaluated An "ointment," as used herein, is a semisolid dosage form, usually containing less than 20% Water and volatiles and more than 50% hydrocarbons, waxes, or polyols as the vehicle. This dosage form is generally for external application to the skin or mucous membranes.

A "semisolid," as used herein refers to the aggregate state of matter which appears a liquid but which is not pourable; it does not flow or conform to its container shape at room temperature nor does it flow at low shear stress and generally exhibits plastic flow behavior.

A "gel," as used herein, is a semisolid dosage form that contains a gelling agent to thicken a solution or fine particle dispersion. The formulation can appear as a transparent or translucent fluid in a container, depending on how much fine particle dispersion is incorporated. Thickening the formulation aids in topical application and adherence to the skin in order to aid diffusion and film formation at the skin surface and to provide a matrix from which the water and nonaqueous solvents can exert their emollient, humectant, solubilization and permeation enhancement properties which are jointly responsible for the measured drug delivery to the skin tissues at specific sites on the body.

A "nonaqueous" gel as used herein, is a semisolid dosage form that contains a gelling agent to thicken a solution or fine particle dispersion but which is either completely comprised of nonaqueous solvents or with a minimal amount of water, typically less than 10% by weight or volume. These gels will generally solubilize higher concentrations of more lipophilic drugs than the aqueous gels A "cream" is a biphasic dispersion or emulsion that has an aqueous phase and an oil phase whereby significant energy and the use of surface active agents and stabilizers are required in order to prevent coalescence and separation. A Cream is typically a semisolid, thickened by the use of previously described gelling agents and long chain lipids used in the oil phase. The API if highly lipid soluble will tend to be located in the oil phase or solubilized by surfactants in the aqueous phase. Absorption at the skin surface is facilitated by the excellent cosmoses and spreadability that creams afford and the delivery of an oil rich film with high concentrations of drug once the aqueous phase has evaporated or been absorbed at the skin surface.

A "foam," as used herein, is a dosage form containing gas bubbles dispersed in a liquid that contains less than 50% Water, and several nonaqueous solvents and surfactants that cause rapid dispersion and film forming on the skin to facilitate coverage over the area of skin to be treated and rapid absorption.

As used herein, the term "sebaceous glands" refers to microscopic glands in the skin that secrete an oily/waxy matter, called sebum, to lubricate and waterproof the skin and hair of mammals. In humans, they are found in greatest abundance on the face and scalp, though they are distributed throughout all skin sites except the palms and soles. In the eyelids, meibomian sebaceous glands secrete a special type of sebum into tears.

As used herein, the term "skin" refers to the outer covering of the body. In humans, it is the largest organ of the integumentary system. The skin has multiple layers of ectodermal tissue and guards the underlying muscles, bones, ligaments and internal organs. Human skin is similar to that of most other mammals, except that it is not protected by a fur. Though nearly all human skin is covered with hair follicles, it can appear hairless. There are two general types of skin, hairy and glabrous skin. The adjective cutaneous means "of the skin" (from Latin cutis, skin).

As used herein, the term "acne" refers to acne vulgaris, a common human skin disease, characterized by areas of skin with comedones (blackheads and whiteheads), papules (pinheads), nodules (large papules), pimples, and possibly scarring. Acne affects mostly skin with the densest population of sebaceous follicles; these areas include the face, the upper part of the chest, and the back. Severe acne is inflammatory, but acne can also manifest in non-inflammatory forms. Severe acne also includes the condition known as 'nodulocystic acne'. Acne lesions are caused by changes in pilosebaceous units, skin structures consisting of a hair follicle and its associated sebaceous gland, changes that require androgen stimulation.

The term "seborrheic dermatitis" refers to a chronic disorder characterized by greasy or flaky scales overlying erythematous patches or plaques. The disorder is commonly located on areas of the skin in which sebaceous glands are located, including among other areas the scalp, face, auditory canal, and postauricular areas. The disorder may manifest itself in the first few weeks of life of humans, resolving before adolescence, but may also occur in adult life. It is typically treated with short-term therapies of low-potency steroids or topical anti-fungal agents such as ketoconazole cream or ciclopirox cream.

The term "rosacea" refers to a condition of reddening of the skin that occurs in the cheeks, nose, forehead, and chin. Patients with rosacea present with erythematous areas, telangiectases, papules, and/or pustules. The condition does not involve comedone formation, in distinction from acne, but may involve a vascular hyper-reactivity in the skin of the affected areas, and it may be accompanied by sebaceous overgrowth, especially on the nose. Previously, 'rosacea' has been referred to as 'acne rosacea'.

As used herein, the term "adipocyte" refers to cells, also known as lipocytes and fat cells, which are the cells that primarily compose adipose tissue, specialized in storing energy as fat. There are two principal types of adipose tissue, white adipose tissue (WAT) and brown adipose tissue (BAT), which are also known as white fat and brown fat, respectively, and comprise two types of fat cells. WAT is the predominant type. In addition, approximately 10% of fat cells are renewed annually at all adult ages and levels of body mass index (Spalding (2008)). Most recently, the presence of beige adipocytes with a gene expression pattern distinct from either white or brown adipocytes has been described. Also another special type of adipose tissue is being studied, pink adipose tissue, which seems to be involved in mammillary duct development in female breasts.

As used herein, "lipomas" refer to a common benign tumor involving the proliferation of fat cells (adipocytes). "Liposarcomas" refer to a highly malignant and aggressive cancer of adipocytes.

As used herein, the term "keratinocyte" refers to the predominant cell type in the epidermis, the outermost layer of the skin, constituting 90% of the cells found there. Those keratinocytes found in the basal layer (stratum basale) of the skin are sometimes referred to as "basal cells" or "basal keratinocytes".

As used herein, the term "hepatocyte" refers to a cell of the main tissue of the liver. Hepatocytes make up 70-85% of the liver's cytoplasmic mass. These cells are involved in protein synthesis, protein storage, transformation of carbohydrates, synthesis of cholesterol, bile salts and phospholipids, detoxification, modification, and excretion of exogenous and endogenous substances. The hepatocyte also initiates formation and secretion of bile.

As used herein the term "sebocyte" refers to epithelial cells that originate from a basal cell layer at the periphery of the sebaceous gland. Differentiation and maturation of sebocytes is accompanied by the accumulation of increasing amounts of a unique mixture of lipids (sebum). Approximately 25% of human sebaceous lipids are wax esters that are not synthesized by other cells in the body. With respect to lipogenesis, sebocyte differentiation may follow a similar program of differentiation as that observed in adipocytes. These lipid-laden cells then migrate towards the central excretory duct. Eventually, the cells disintegrate and release their lipid content. Most of the lipids of the skin surface come from sebaceous gland secretions.

Compounds embodied by Structure I have one or several asymmetric centers and therefore can exist in different stereoisomeric configurations. Consequently, the compound of Structure I can occur as individual (pure) enantiomers, individual pure enantiomeric diastereomers as well as a mixture of enantiomers or diastereomers. The scope of the present invention includes both single enantiomers and mixtures thereof in all ratios. The scope of the present invention further includes all tautomeric forms ("tautomers") of the compounds of Structure I, and all mixtures thereof in any ratio. It will be appreciated by one skilled in the art that a single compound may exhibit more than one type of isomerism.

The enantiomeric compounds of Structure I may be resolved into their pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers maybe synthesized by using an optically active starting material, by asymmetric synthesis using optically active reagents, substrates, catalysts or solvents, or by converting one stereoisomer into the other by asymmetric transformation or inversion.

The compounds of the present invention may exist in unsolvated as well as a variety of solvated forms with pharmaceutically acceptable solvents such as water, ethanol, and the like. In general, the solvated forms are considered equivalent to the unsolvated forms for the purposes of the present invention. It should be understood that pharmaceutically acceptable solvents further includes isotopically substituted solvents such as $D_2O$, dimethyl sulfoxide-d6 and the like. The term 'solvate' is used herein to describe a complex comprising the compound of the invention and one or more pharmaceutically acceptable solvent molecules, including water. As such, all manner of hydrates of the compound are included by the term 'solvate'. It is intended that the present invention embrace unsolvated forms, solvated forms and mixtures of solvated forms in any ratio.

The compound of the present invention and/or its salts and/or solvate may exist as amorphous solids or may exist in one or more crystalline states, i.e. polymorphs. Polymorphs of the compound of Structure I are encompassed in the present invention and may be prepared by crystallization under a number of different conditions such as, for example, using different solvents or different solvent mixtures; crystallization at different temperatures; and using various modes of cooling ranging from very fast to very slow during crystallization. Polymorphs may also be obtained by heating or melting a compound of Structure I followed by gradual or fast cooling. The presence of polymorphs may be determined by solid NMR spectroscopy, IR spectroscopy, differential scanning calorimetry, powder x-ray diffraction or other techniques. It should be understood that all such crystalline and amorphous forms of the compound of Structure I, and its salts, solvates and prodrugs thereof are encompassed by the invention and the claims.

The present invention also includes all pharmaceutically acceptable isotopically-labeled variations of the compound of Structure I. Such isotopically-labeled variations are compounds having the same structure and molecular formula as the compound of Structure I but wherein one or more atoms are replaced by atoms having an atomic mass or mass number different from the atomic mass or mass number usually found in nature. Examples of isotopes that may be incorporated into the compound of the present invention include isotopes of hydrogen, carbon, fluorine, nitrogen, and oxygen, such as $^2H$, $^3H$, $^{11}C$, $^{13}C$, $^{14}C$, $^{18}F$, $^{13}N$ $^{15}N$ $^{17}O$ and $^{18}O$, respectively.

Certain isotopically labeled variations of the compound of the present invention such as, for example, those incorporating a radioactive isotope such as $^3H$ and $^{14}C$, are useful in drug and/or substrate tissue distribution studies. Tritium, i.e. $^3H$, and carbon-14, i.e. $^{14}C$, are particularly preferred due their ease of preparation and detection. Further, substitution with heavier isotopes such as deuterium, i.e. $^2H$, can afford certain therapeutic advantages resulting from greater metabolic stability, for example, increased in vivo half-life or reduced dosage requirements, and hence may be preferred in some circumstances. Isotopically labeled compounds of Structure I of this invention and prodrugs thereof can generally be prepared by carrying out the procedures disclosed in the Schemes and/or in the Examples by substituting a readily available isotopically labeled reagent for a non-isotopically labeled reagent.

The compounds of Structure I may be administered as a prodrug. The term prodrug refers to a compound which is transformed in vivo to a compound of Structure I, or a pharmaceutically acceptable salt or solvate of the compound. The transformation may occur by various mechanisms, such as via hydrolysis in blood. A prodrug of the compound of Structure I may be formed in a conventional manner according to methods known in the art. A thorough discussion of prodrugs is provided by V. Stella in *Pro-drugs as Novel Delivery Systems*, Vol. 14 of the A.C.S. Symposium Series (Stella (1975)), and in *Bioreversible Carriers in Drug Design* (Roche (1987)), both of which are incorporated herein by reference.

"Alkyl" means a straight or branched chain, saturated hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, a straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl. Alkyl may be optionally substituted, e.g., optionally substituted with oxygen, silicon, sulphur or optionally substituted with OH, O-alkyl, SH, S-alkyl, $NH_2$, NH-alkyl. In another example, alkyl may be $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl.

"Alkylene" means a divalent alkyl, with alkyl as defined above.

"Aryl" means a monocyclic or bicyclic aromatic hydrocarbon radical, e.g., having from of 6 to 20 or 6 to 10 ring atoms e.g., phenyl or naphthyl. Aryl may be optionally substituted, e.g., substituted phenyl or substituted naphthyl.

"Alkylaryl" means a (alkylene)-R radical where R is aryl as defined above. Alkylaryl may be optionally substituted. In certain examples, alkylaryl may be alkylphenyl, alkylsubstituted phenyl, alkylnaphthyl or alkylsubstituted naphthyl.

"Alkenyl" means a straight or branched chain, saturated hydrocarbon radical which contains a carbon-carbon double bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkenyl" may refer to alkenyls having, e.g., two to six carbons, two to four carbons, etc. In certain examples, a straight chain alkenyl may have from two to six carbon atoms and a branched alkyl three to six carbon atoms, e.g., a vinyl group, an allyl group, butene (including all isomeric forms), pentene (including all isomeric forms), and the like. Alkenyl may be optionally substituted. In certain examples, alkenyl may be a $C_2$ to $C_{12}$ straight chain or branched chain hydrocarbon containing a carbon-carbon double bond, optionally substituted with oxygen, silicon or sulphur or optionally substituted with OH, O-alkyl, SH, S-alkyl, $NH_2$ or NH-alkyl.

"Alkynyl" means a straight or branched chain, saturated hydrocarbon radical which contains a carbon-carbon triple bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkynyl" may refer to alkynyls having, e.g., two to six carbons, two to four carbons, etc. In certain examples, a straight chain alkynyl may have from two to six carbon atoms and a branched alkyl three to six carbon atoms, e.g., an acetylene group, a propargyl group, butyne (including all isomeric forms), pentyne (including all isomeric forms), and the like. Alkynyl may be optionally substituted. In certain examples, alkynyl may be a $C_2$ to $C_{12}$ straight chain or branched chain hydrocarbon containing a carbon-carbon triple bond, optionally substituted with oxygen, silicon or sulphur or optionally substituted with OH, O-alkyl, SH, S-alkyl, $NH_2$ or NH-alkyl.

"Cycloalkyl" means a cyclic saturated or partially saturated hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to seven carbon atoms, from three to six carbon atoms, etc., wherein one or two carbon atoms may be replaced by an oxo group, e.g., admantanyl, cyclopropyl, cyclobutyl, cyclopentyl, cyclohexyl, cyclohexenyl, indanyl and the like.

"Alkylcycloalkyl" means a (alkylene)-R radical where R is cycloalkyl as defined above; e.g., cyclopropylmethyl, cyclobutylmethyl, cyclopentylethyl, or cyclohexylmethyl, and the like. In another example, alkylcycloalkyl has four to twelve carbon atoms, i.e., $C_4$-$C_{12}$ alkylcycloalkyl.

"O-alkyl" means an (oxygen)-R radical where R is alkyl as defined above. For example, O-alkyl may be an oxygen atom bonded to a $C_1$ to $C_6$ straight chain or branched chain alkyl.

"O-cycloalkyl" means an (oxygen)-R radical where R is cycloalkyl as defined above. For example, O-cycloalkyl is an oxygen atom bonded to a $C_3$ to $C_7$ cycloalkyl.

"O-alkylcycloalkyl" means an (oxygen)-R radical where R is alkylcycloalkyl as defined above. For example, O-cycloalkyl is an oxygen atom bonded to a $C_4$ to $C_8$ alkylcycloalkyl.

"Heterocyclyl" or "heterocycloalkyl" means a saturated or unsaturated monocyclic group, in which one or two ring atoms are heteroatom selected from N, O, or S, the remaining ring atoms being C. Heterocyclyl and heterocycloalkyl includes, e.g., where the heterocycle comprises one or two hetero atoms selected from O, S, or N, including a $C_2$ to $C_6$heterocycloalkyl. The heterocyclyl ring is optionally fused to a (one) aryl or heteroaryl ring as defined herein. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Alkylheterocycloalkyl" means an -(alkylene)-R radical where R is heterocyclyl ring as defined above e.g., tetrayhdrofuranylmethyl, piperazinylmethyl, morpholinylethyl, and the like. Alkylheterocycloalkyl also includes, e.g., where the heterocycle comprises one or two hetero atoms selected from O, S, or N and has three to eleven carbon atoms, i.e., $C_3$ to $C_{11}$ alkylheterocycloalkyl, and includes when N is present in the heterocyclic ring the nitrogen atom may be in the form of an amide, carbamate or urea.

"Heteroaryl" means a monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl (thiophenyl), thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl (pyridyl), pyrimidinyl, pyrazinyl, pyridazinyl, tetrazolyl, and the like. Heteroaryl may be optionally substituted.

"Oxo" or "carbonyl" means a =(O) group or C=O group, respectively.

The term "substituted" means that the referenced group is substituted with one or more additional group(s) individually and independently selected from groups described herein. In some embodiments, an optional substituent is selected from oxo, halogen, —CN, —NH2, —OH, —NH($CH_3$), —N($CH_3$)$_2$, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S-alkyl, —S(O)$_2$-alkyl, —CONH((substituted or unsubstituted alkyl) or (substituted or unsubstituted phenyl)), —CON(H or alkyl)$_2$, —OCON(substituted or unsubstituted alkyl)$_2$, —NHCONH((substituted or unsubstituted alkyl) or (substituted or unsubstituted phenyl)), —NHCOalkyl, —N(substituted or unsubstituted alkyl)CO(substituted or unsubstituted alkyl), —NHCOO(substituted or unsubstituted alkyl), —C(OH)(substituted or unsubstituted alkyl)$_2$, and —C(NH2)(substituted or unsubstituted alkyl)$_2$. In some embodiments, by way of example, an optional substituent is selected from oxo, fluorine, chlorine, bromine, iodine, —CN, —NH$_2$, —OH, —NH($CH_3$), —N($CH_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(O)$_2$—CH$_3$, —CONH$_2$, —CONHCH$_3$, —NHCONHCH$_3$, —COCH$_3$, —COOH and the like. In some embodiments, substituted groups are substituted with one, two or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

In some embodiments, an inhibitor of SCD-1 compound of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the lipid modulating compound described herein are reacted with an organic base, such as, but not limited to, ethanolamine, diethanolamine, triethanolamine, methylamine, dimethylamine, trimethylamine, ethylamine, diethylamine, triethylamine, N-methylglucamine, dicyclohexylamine, tris (hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

In the scope of the embodiments, the inhibitors of SCD-1 described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including but not limited to single enantiomers and enantiomeric diastereomers, meso compounds, stereoisomers, racemic mixtures and diastereoisomeric mixtures. Compounds described herein having one or more double bonds include cis/trans isomers, E/Z isomers and geometric isomers.

In some embodiments, sites on the inhibitors of SCD-1 disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group. Examples of such substituents can be found in Burger's Medicinal Chemistry, Drug Discovery and Development, 8 Volume Set (Abraham (2010)) and in Foye's Principles of Medicinal Chemistry (Lemke (2012)).

In some embodiments, sites on the inhibitors of SCD-1 disclosed herein are not susceptible to various metabolic reactions. Therefore incorporation of appropriate substituents at or near or distant from the places of a lack of metabolic reactions will modulate, enhance, or maximize the metabolic pathways. In specific embodiments, the appropriate substituent (metabolic handle) to enhance, or maximize the susceptibility of the aromatic ring to metabolic reactions is, by way of example only, is a phenolic or methoxy or carboxylate group. Examples of such substituents can be found in Burger's Medicinal Chemistry, Drug Discovery and Development, 8 Volume Set (Abraham (2010)) and in Foye's Principles of Medicinal Chemistry (Lemke (2012)).

Throughout the specification, groups and substituents thereof can be chosen by one skilled in the field to provide stable moieties and compounds.

Synthesis of the Compounds

In general, compounds of Structure I may be prepared using a number of methods known in the chemical arts, particularly in light of the description contained herein, in combination with the knowledge of the skilled artisan. Various starting materials, intermediates, and reagents may be purchased from commercial sources or made according to literature methods or adaptations thereof. Although other reagents, compounds or methods can be used in practice or testing, generalized methods for the preparation of the compound of Structure I are illustrated by the following descriptions and reaction Schemes. The methods disclosed herein, including those outlined in the Schemes, descriptions, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Although specific embodiments of various aspects of the invention will be described with reference to the Schemes, Preparations and/or Examples, it should be understood that such embodiments are by way of example only and are merely illustrative of a small number of the many possible specific embodiments which can represent applications of the principles of the present disclosure. The starting materials used for the synthesis of compounds described herein can be obtained from commercial sources, such as Aldrich Chemical Co. (Milwaukee, WI), Sigma Chemical Co. (St. Louis, Mo.), or the starting materials can be synthesized. The compounds described herein, and other related compounds having different substituents can be synthesized using techniques and materials known to those of skill in the art, such as described, for example, in March's Advanced Organic Chemistry: Reactions, Mechanisms, and Structure (Smith (2013)), Design and Strategy in Organic Synthesis (Hanessian (2013)) Greene's Protective Groups in Organic Synthesis (Wuts (2006)) and Fiesers' Reagents for Organic Synthesis (Volumes 1-27) (Ho (2013)), each of which are incorporated by reference in their entirety.

General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein.

The intermediate products described can be recovered by extraction, evaporation, or other techniques known in the art. The crude materials may then be optionally purified by chromatography, HPLC, recrystallization, trituration, distillation, or other techniques known in the art. In the discussions below, the following abbreviations were used: THF (tetrahydrofuran), DMF (N,N-dimethylformamide), BOC (tert-butoxycarbonyl), Cbz (carbobenzoxy), $Cs_2CO_3$ (Caesium Carbonate), DEPC (diethylcyano-phosphate), LDA (lithium Diisopropylamide), NMP (N-Methyl-2-pyrrolidone), TEA or $NEt_3$ (triethyl amine), p-TsOH (p-toluene sulfonic acid), i-PrOAc (isopropyl acetate), HOBT (1-hydroxybenzo-triazole), EDC (1-ethyl-3-(3-dimethylamino-propyl) carbodiimide), and EtOH (ethanol).

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. Methods of introducing and removing protecting groups are well known to those of ordinary skill in the art and are described in Greene's Protective Groups in Organic Synthesis (Wuts (2006)). Alternate reagents, starting materials, as well as methods for optimizing or adapting the procedures described herein would also be readily determined by one skilled in the art.

In Scheme 1 the starting pyrrolidine moiety C3 position is shown as the R-configuration. Initial formation of the chiral R mesylate followed by SN$_2$ type displacement with the anion derived from the suitable aromatic alcohol/phenol upon treatment with a suitable base such as Caesium Carbonate affords the BOC protected S derivative shown. In a separate transformation this can be readily hydrolyzed with p-toluene sulfonic acid in isopropyl acetate to the corresponding 3-substituted pyrrolidine.

ration for the key intermediates. The transformations shown in either Scheme 1 or Scheme 2 can be carried out with racemic material or material which has partial enrichment of one enantiomer over the other as well as the optically pure materials shown.

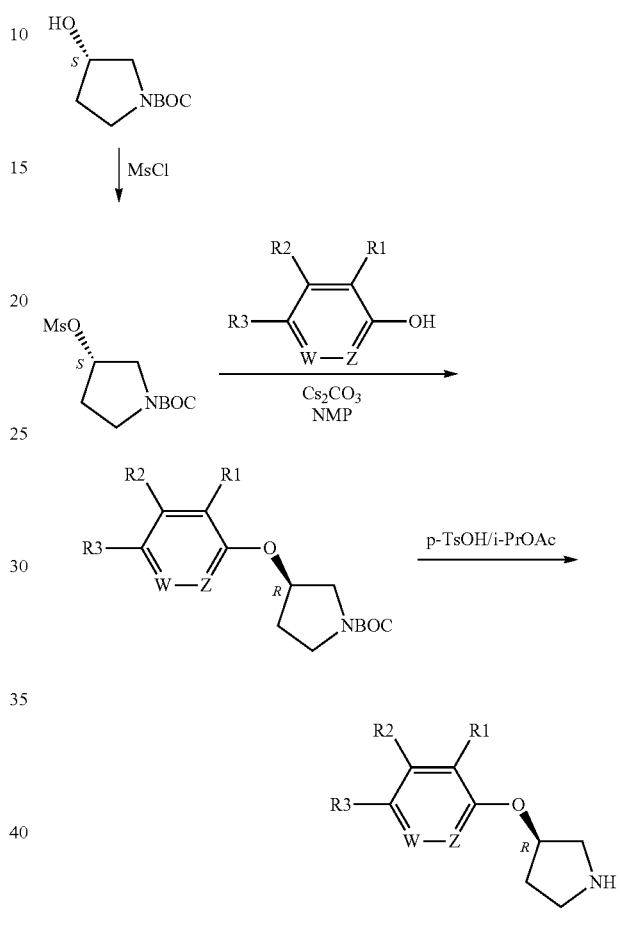

Scheme 2.

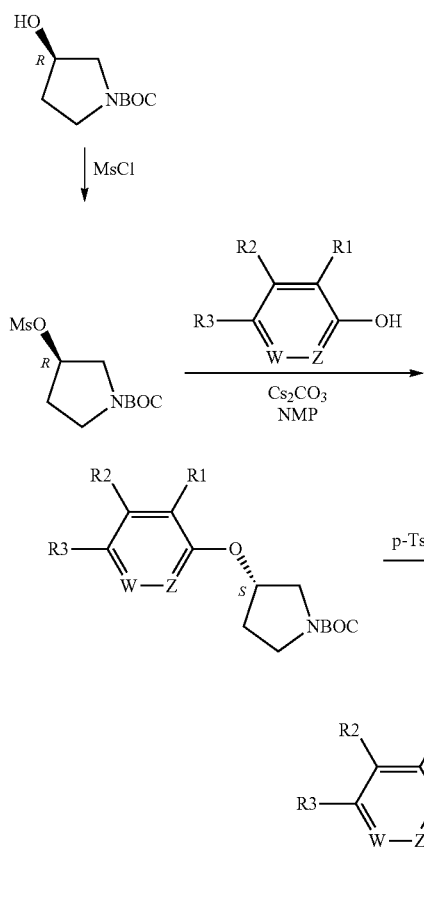

Scheme 1.

Scheme 2 outlines a similar set of transformations in the case wherein the C3 position of the starting pyrrolidine moiety is the S-configuration which leads to the R-configu- Scheme 3 outlines the general synthesis of representative compounds to be evaluated for topical formulation. In particular, this synthesis exploits relatively mild amide bond forming reactions such as with carbodiimides. The synthesis is completed by a Sodium Borohydride reduction of the side chain aldehyde to the alcohol. Again, these transformations can be carried out with racemic materials, partially optically enriched materials and optically pure materials.

Scheme 3.

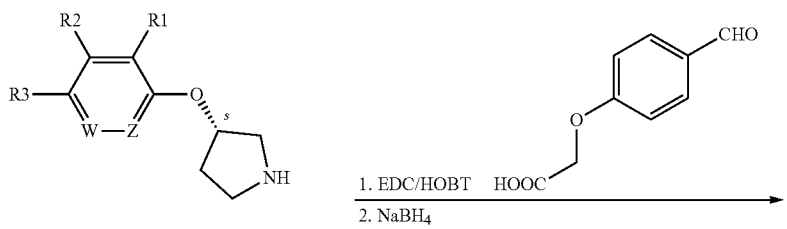

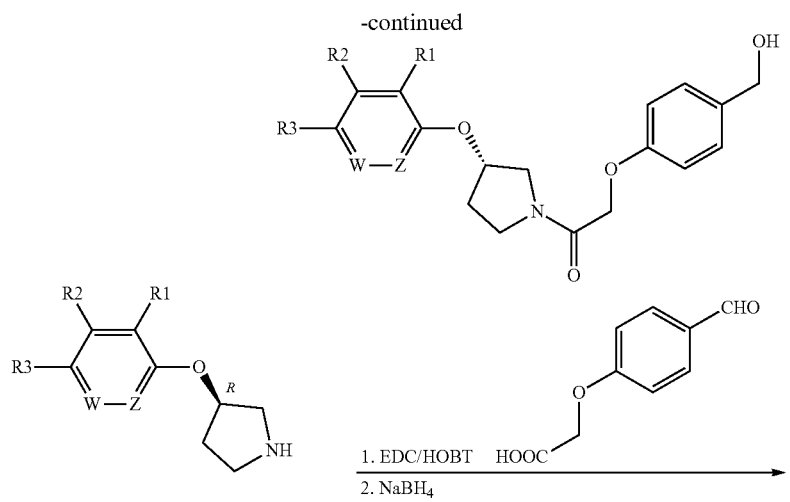

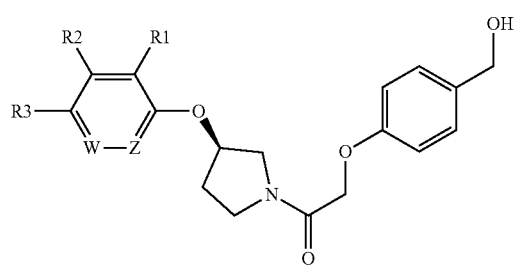

Scheme 4 is a simplified version of Scheme 3 where the amide bond formation is achieved in one step with the already reduced form of the side chain. Again, these transformations can be carried out with racemic materials, partially optically enriched materials and optically pure materials.

Scheme 4.

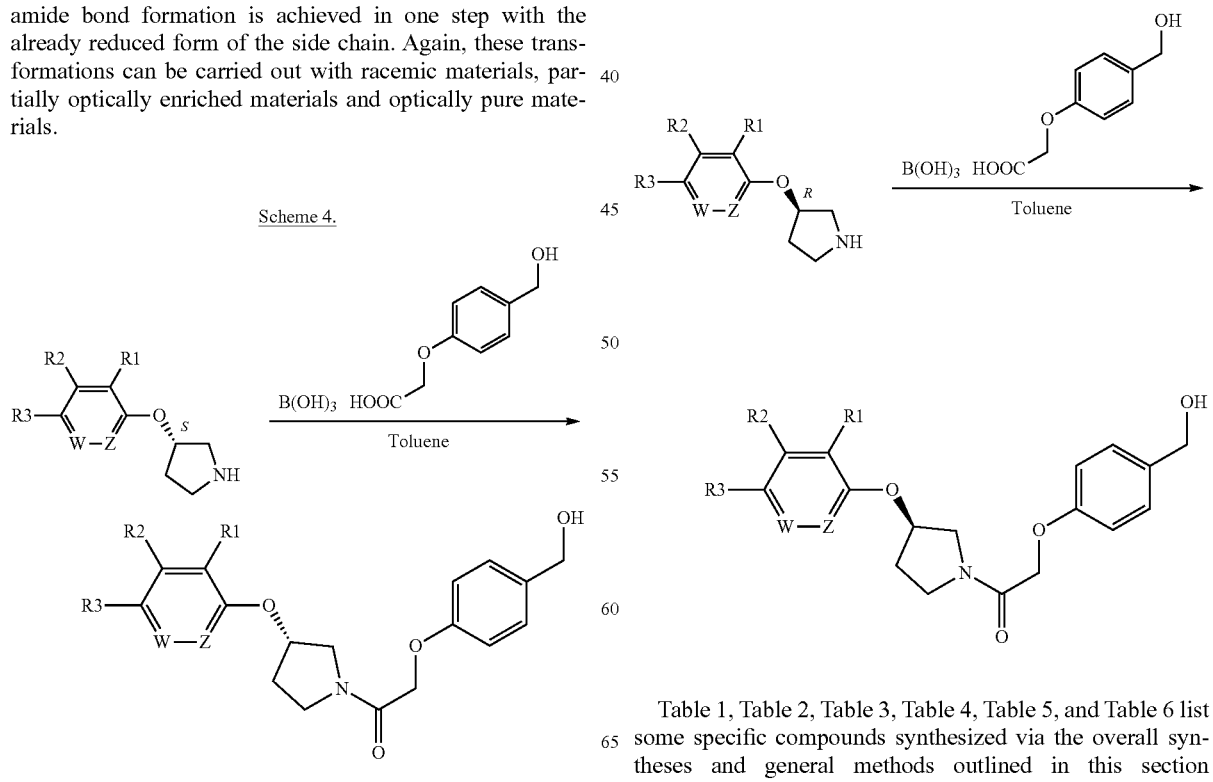

Table 1, Table 2, Table 3, Table 4, Table 5, and Table 6 list some specific compounds synthesized via the overall syntheses and general methods outlined in this section (Schemes 1-4)

TABLE 1-continued
Structure
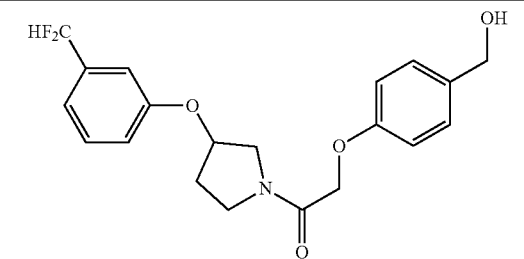
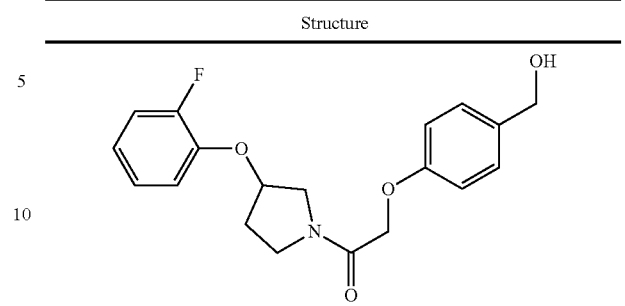
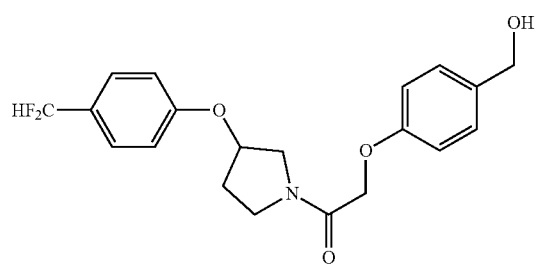
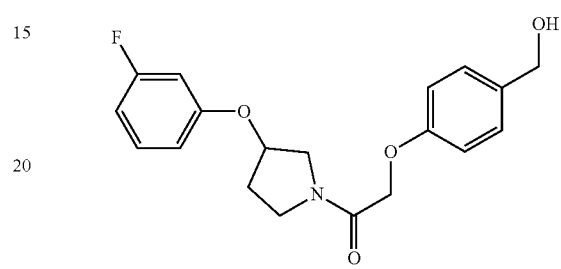
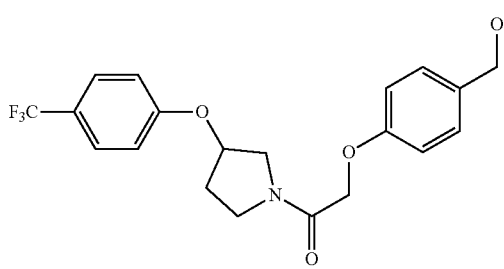
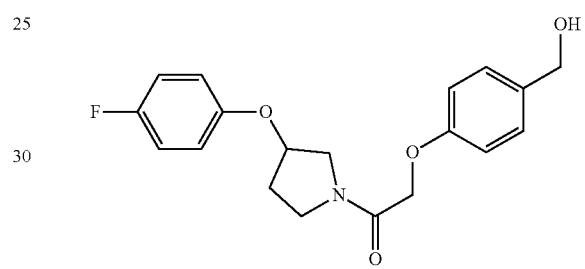
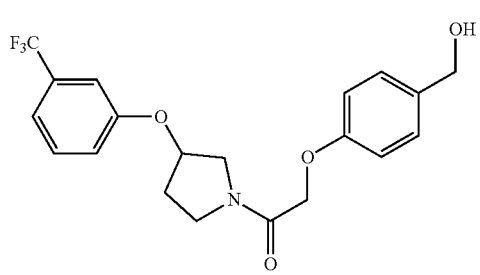
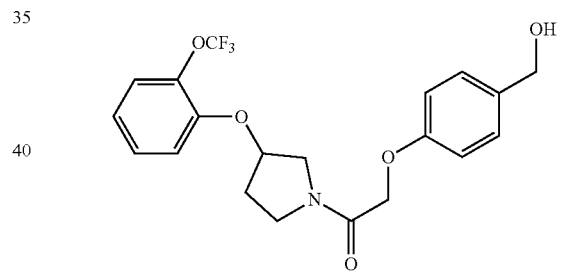
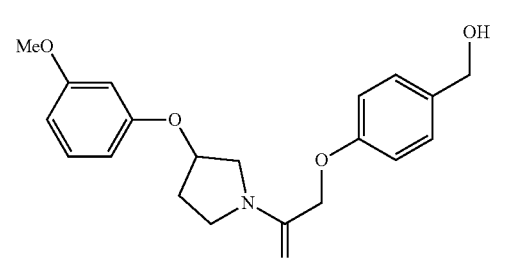
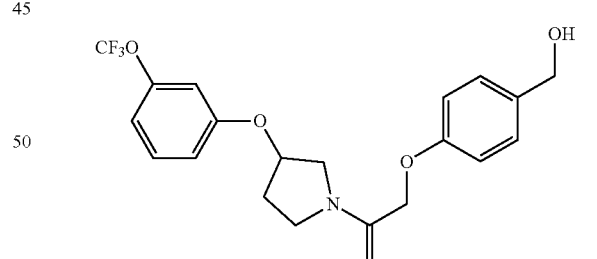
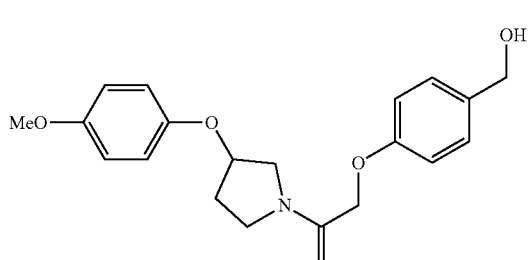
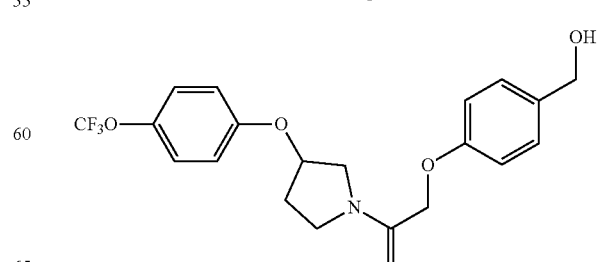

TABLE 1-continued

Structure

[chemical structure]

[chemical structure]

[chemical structure]

TABLE 2

Structure

[chemical structure]

[chemical structure]

TABLE 2-continued

Structure

[chemical structure]

[chemical structure]

[chemical structure]

[chemical structure]

[chemical structure]

[chemical structure]

TABLE 2-continued

Structure (Page contains chemical structure diagrams only.)

TABLE 2-continued
Structure
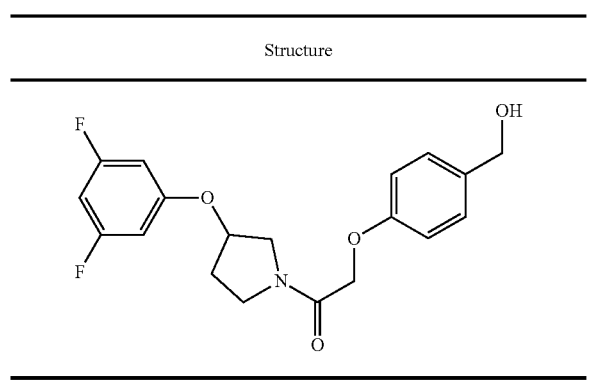
TABLE 3
Structure
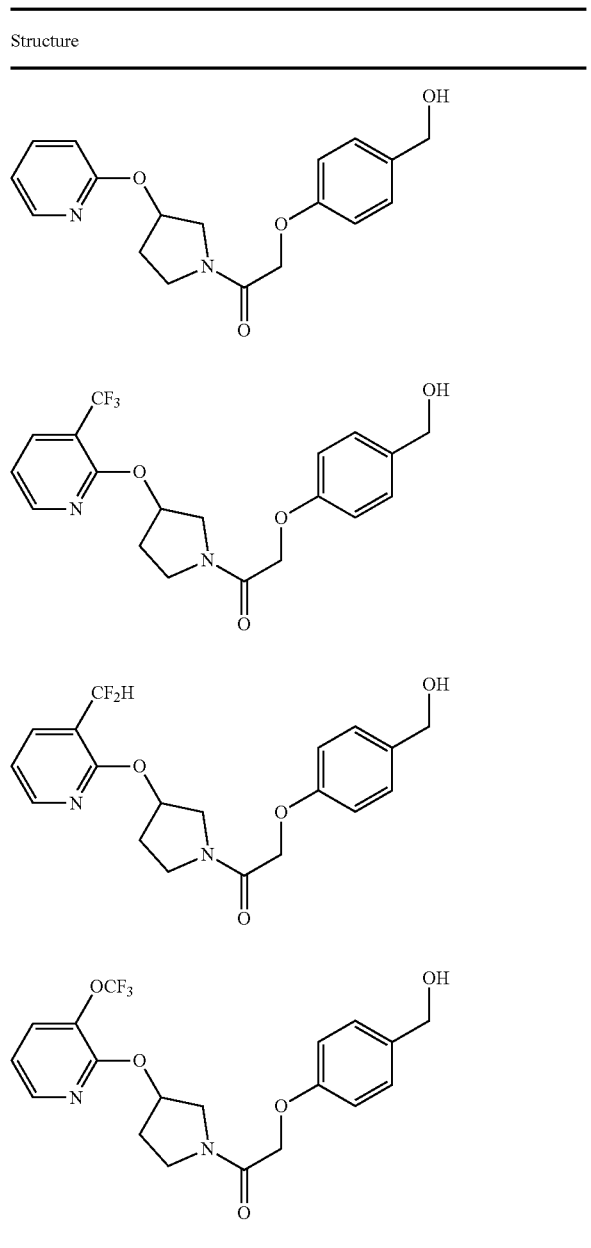
TABLE 3-continued
Structure
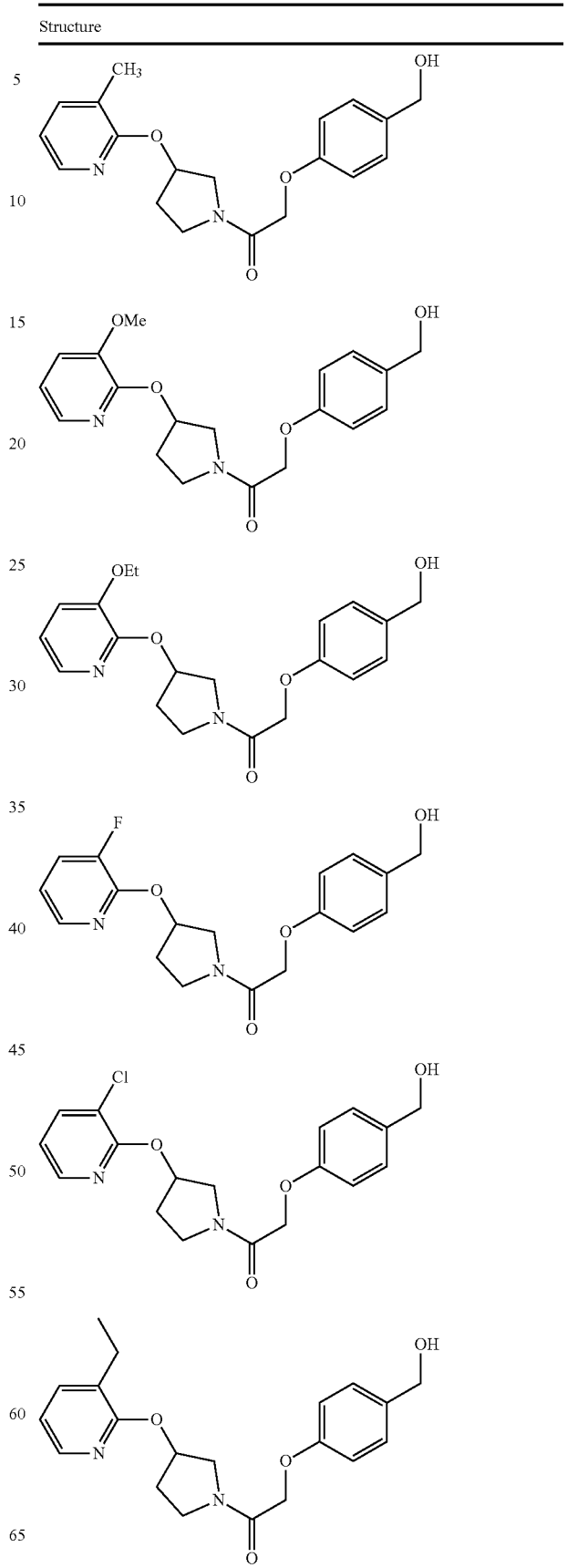

425
TABLE 3-continued
Structure
426
TABLE 4-continued
Structure
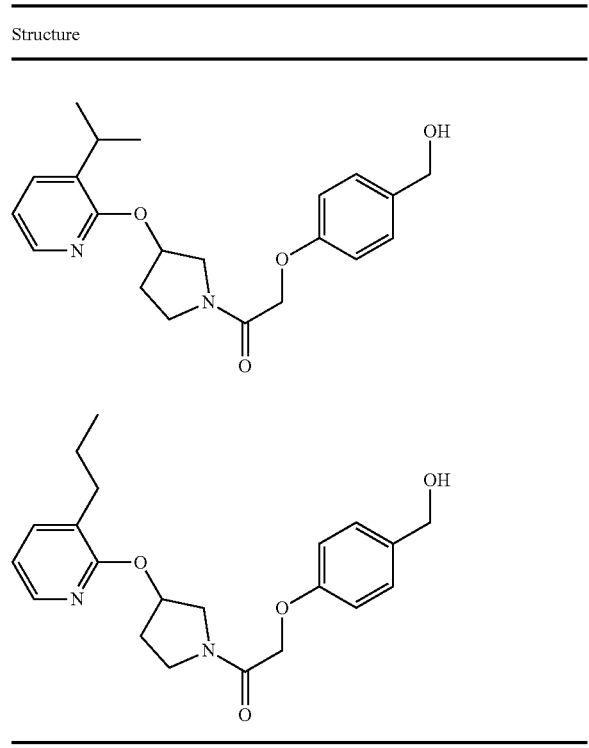
TABLE 4
Structure
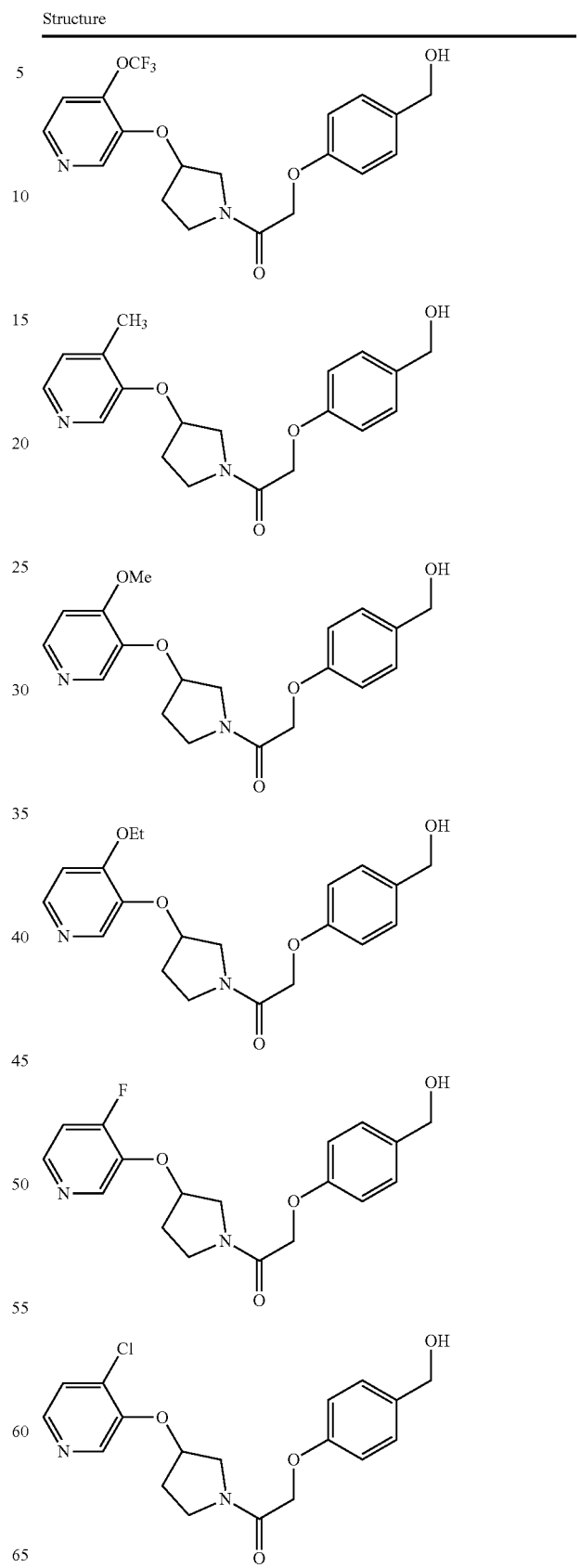

TABLE 4-continued
Structure
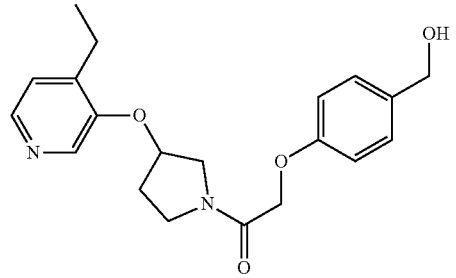
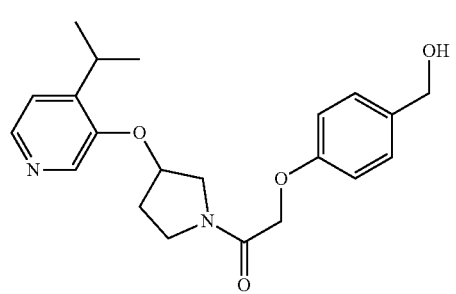
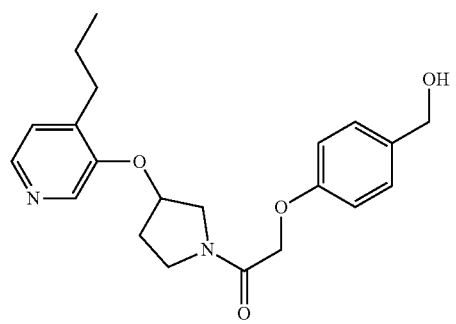
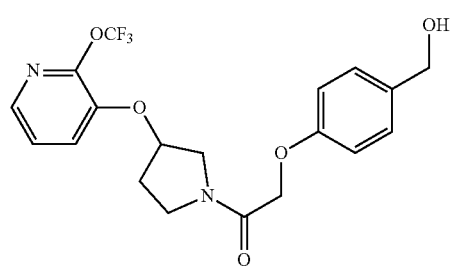
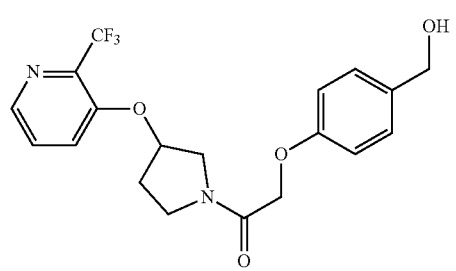
TABLE 4-continued
Structure
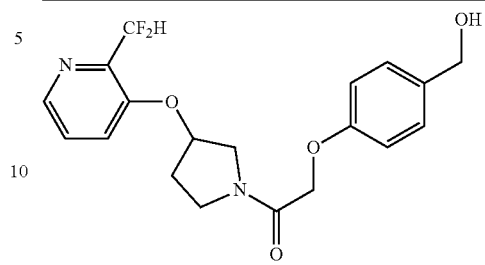
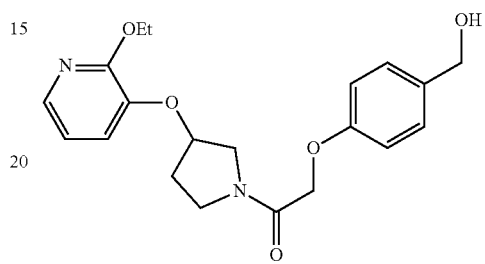
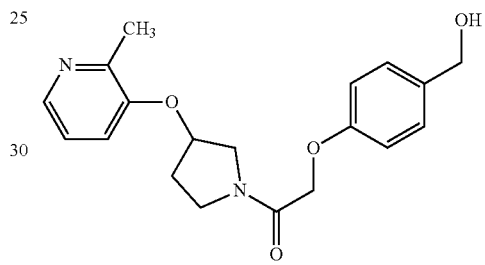
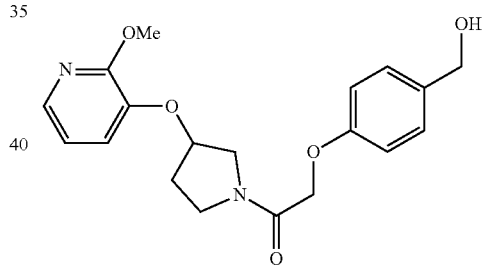
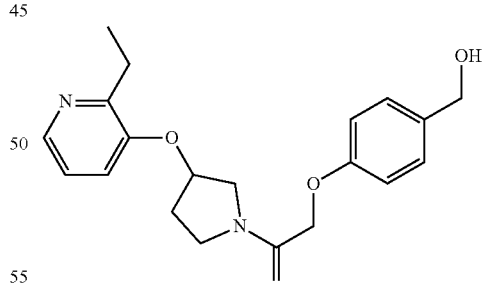
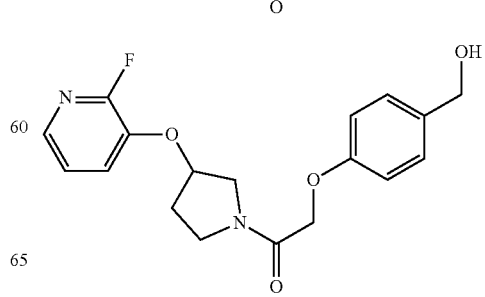

TABLE 4-continued
Structure
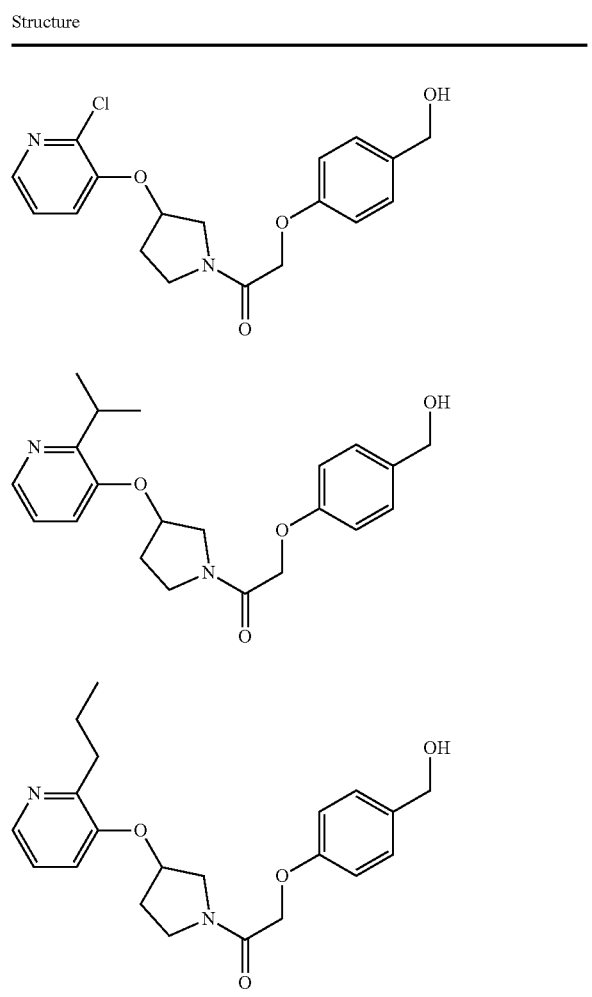
TABLE 5
Structure
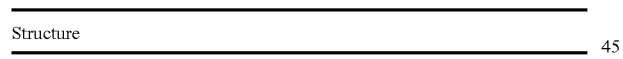
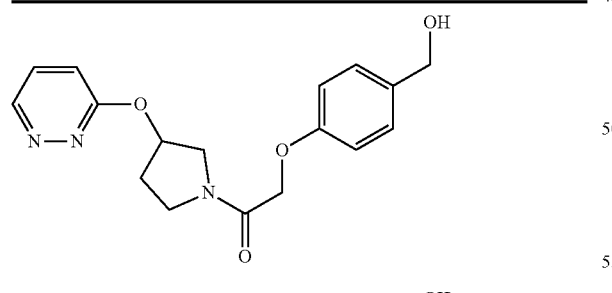
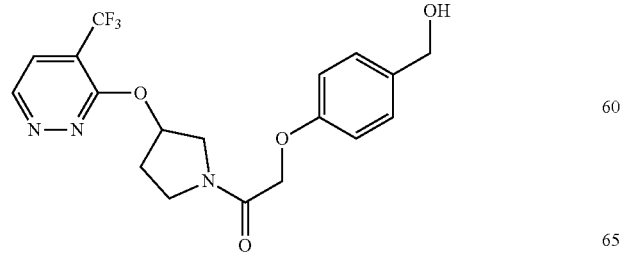
TABLE 5-continued
Structure
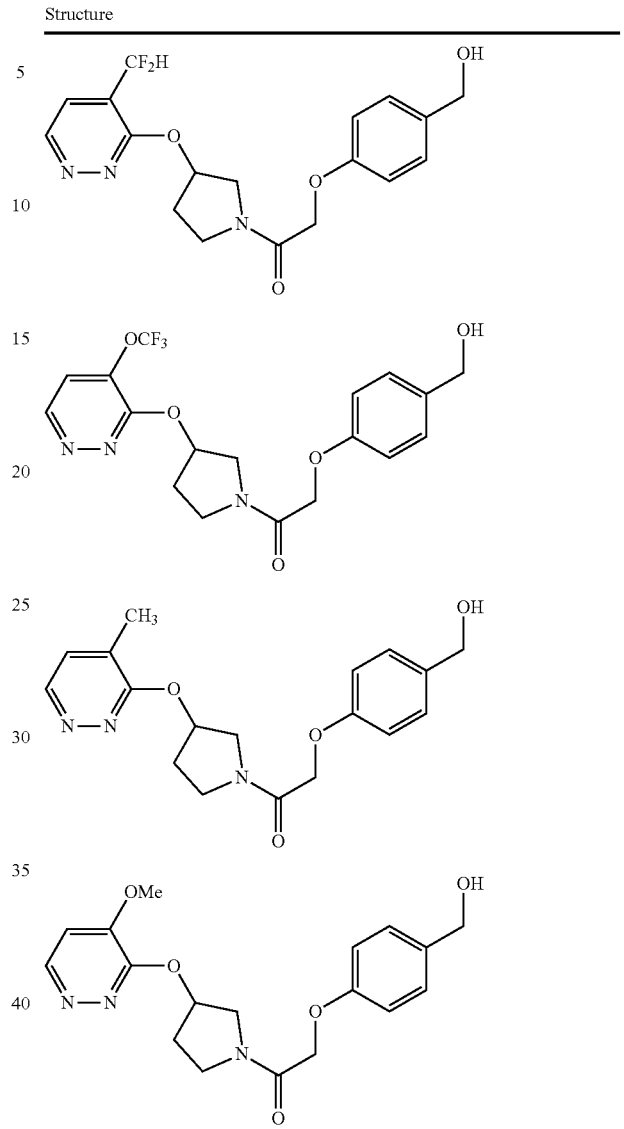
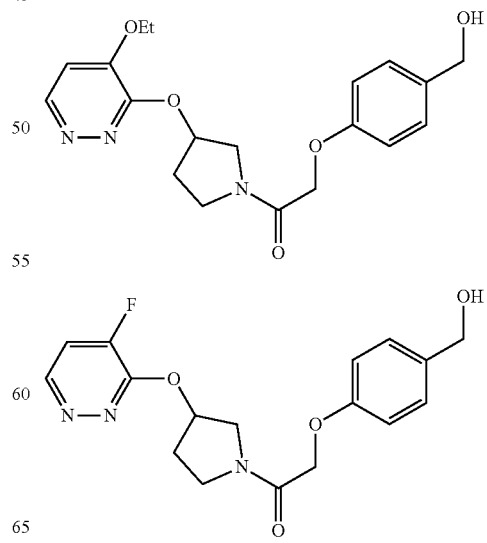

TABLE 5-continued
Structure
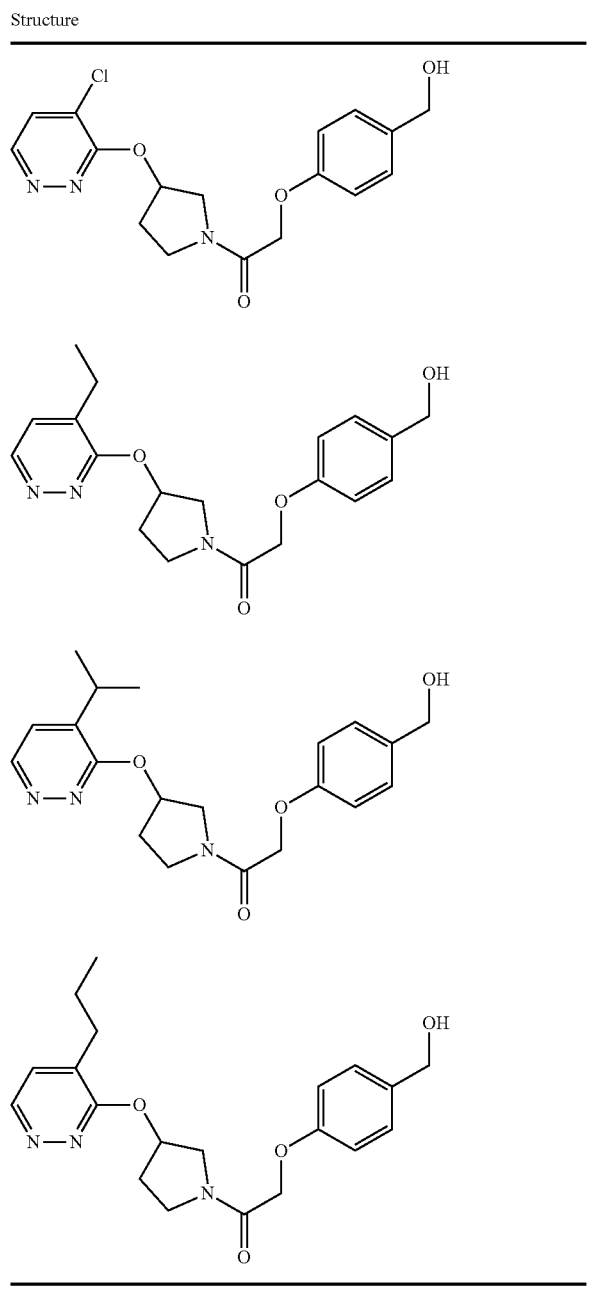
TABLE 6
Structure
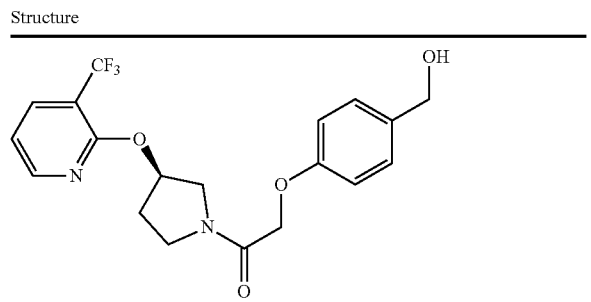
TABLE 6-continued
Structure
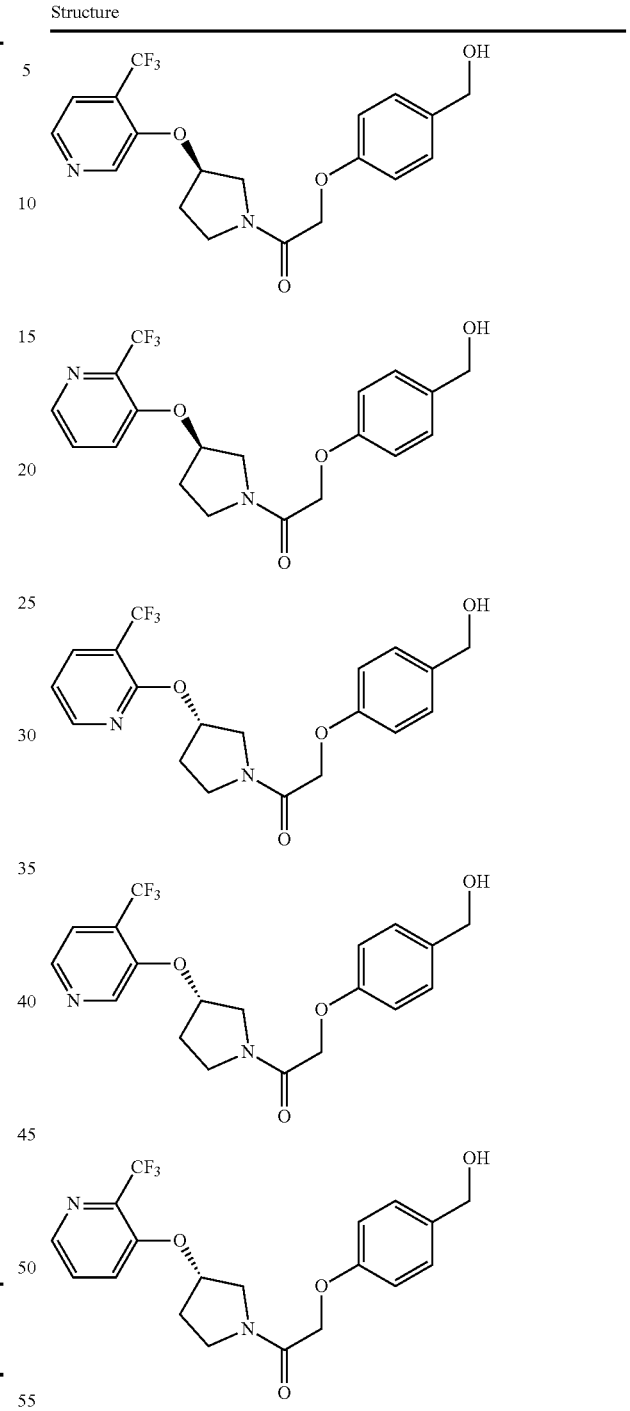
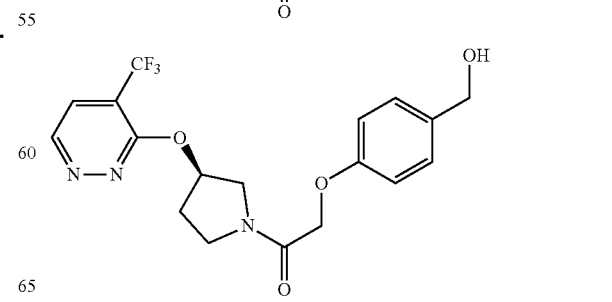

TABLE 6-continued

Structure

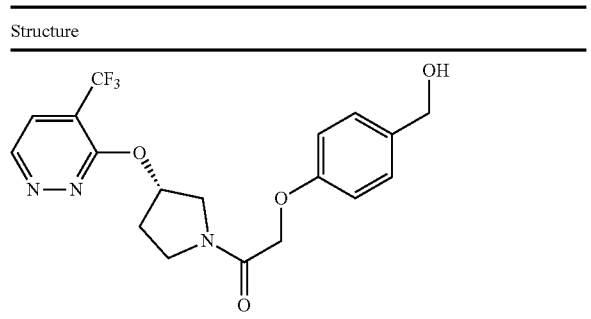

In Scheme 5 the starting pyrrolidine moiety C3 position is shown as the R-configuration. Initial formation of the chiral R mesylate followed by SN₂ type displacement with the anion derived from the carbobenzoxy (Cbz) protected suitable aromatic primary amine upon treatment with a suitable base such as Lithium Diisopropylamide affords the differentially bis-protected S derivative shown. In separate transformations this can be converted to key intermediates for the NH series, the N-alkyl series and the N-acyl series, each of which now have the S configuration around the key chiral center. Although the combination of Cbz and BOC protecting groups affords adequate differential protection for subsequent manipulations, other protecting groups are envisaged as described in Greene's Protective Groups in Organic Synthesis (Wuts (2006)).

Scheme 5.

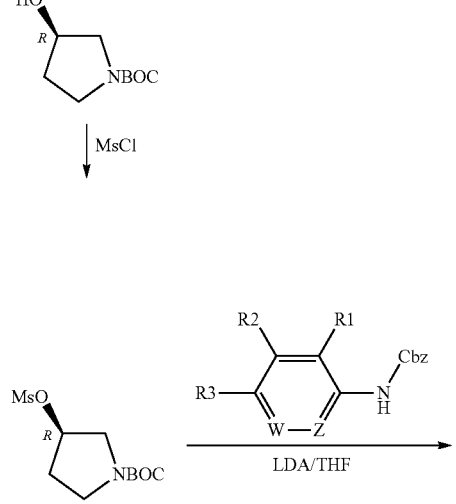

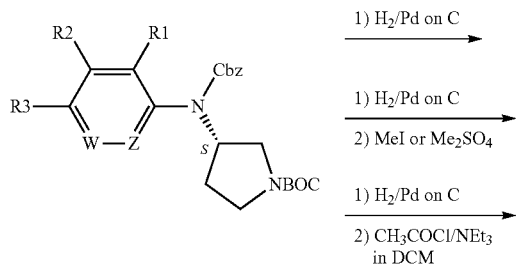

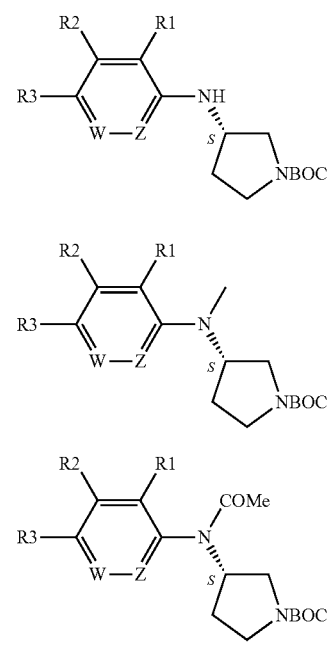

Scheme 6 outlines a similar set of transformations in the case wherein the C3 position of the starting pyrrolidine moiety is the S-configuration which leads to the R-configuration for the key intermediates. The transformations shown in either Scheme 5 or Scheme 6 can be carried out with racemic material or material which has partial enrichment of one enantiomer over the other as well as the optically pure materials shown.

Scheme 6.

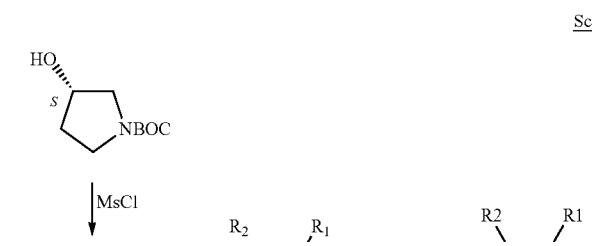

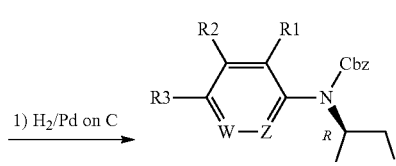

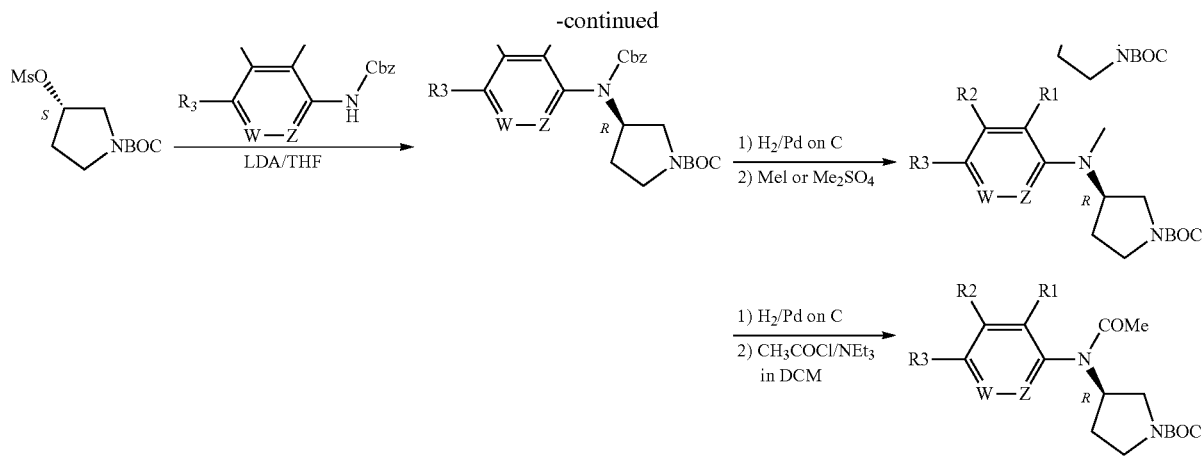

Scheme 7 outlines the general synthesis of some of the various compounds from the NH series to be evaluated for topical formulation. In particular, this synthesis exploits the differences in selectivity, well established in the art, between aromatic and alkyl amines under relatively mild amide bond forming reactions such as with carbodiimides. The synthesis is completed by a Sodium Borohydride reduction of the side chain aldehyde to the alcohol. Again, these transformations can be carried out with racemic materials, partially optically enriched materials and optically pure materials.

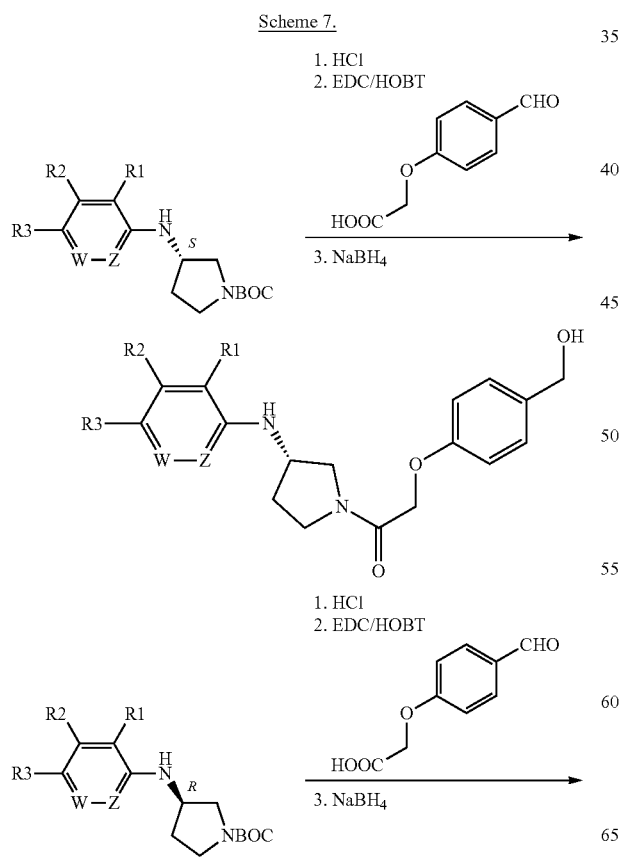

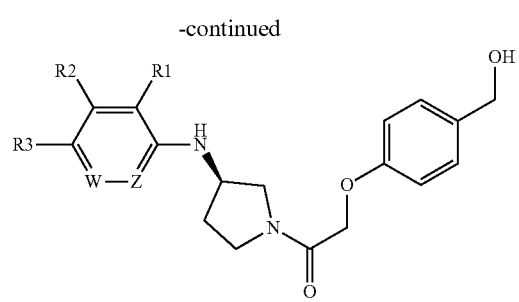

Scheme 8 is similar to Scheme 7 and is suitable for the N-alkyl series. Note that selectivity for amide bond formation is no-longer required due to the aromatic nitrogen atom being fully substituted. Again, these transformations can be carried out with racemic materials, partially optically enriched materials and optically pure materials.

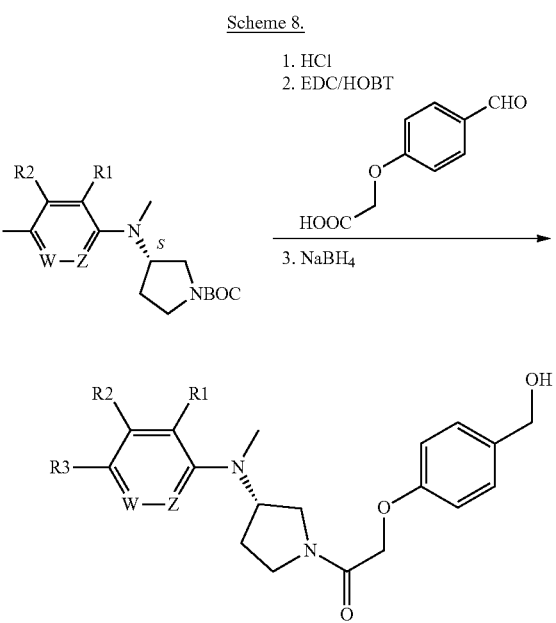

-continued

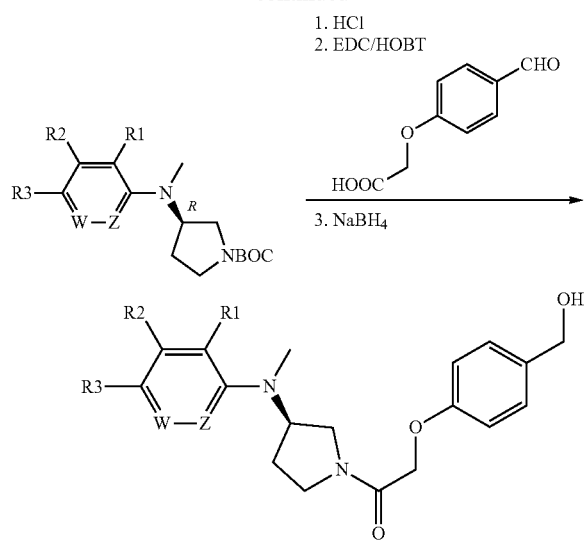

Scheme 9 outlines similar transformations suitable for the N-acyl series. Again, these transformations can be carried out with racemic materials, partially optically enriched materials and optically pure materials.

Scheme 9.

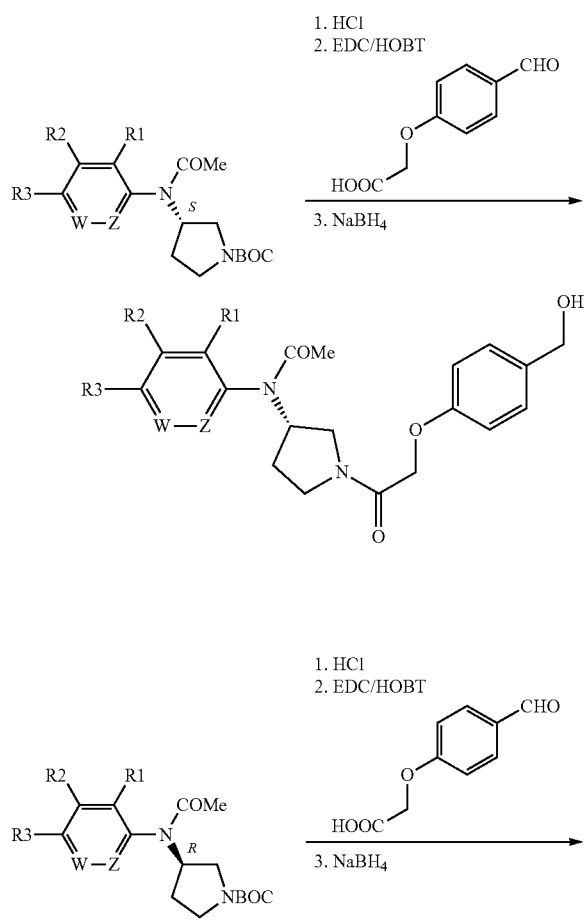

-continued

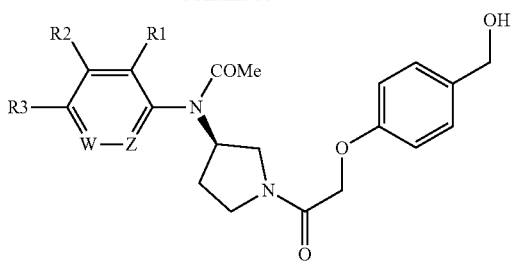

Table 7, Table 8, Table 9, Table 10, and Table 11 list some specific compounds synthesized via the overall syntheses and general methods outlined in this section (Schemes 5-9)

TABLE 7

Structure

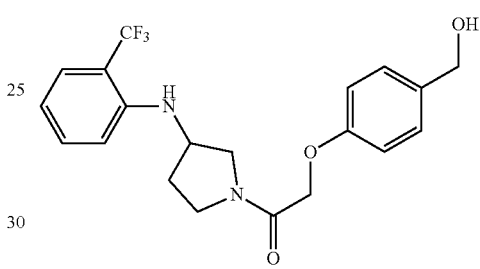

TABLE 7-continued
Structure
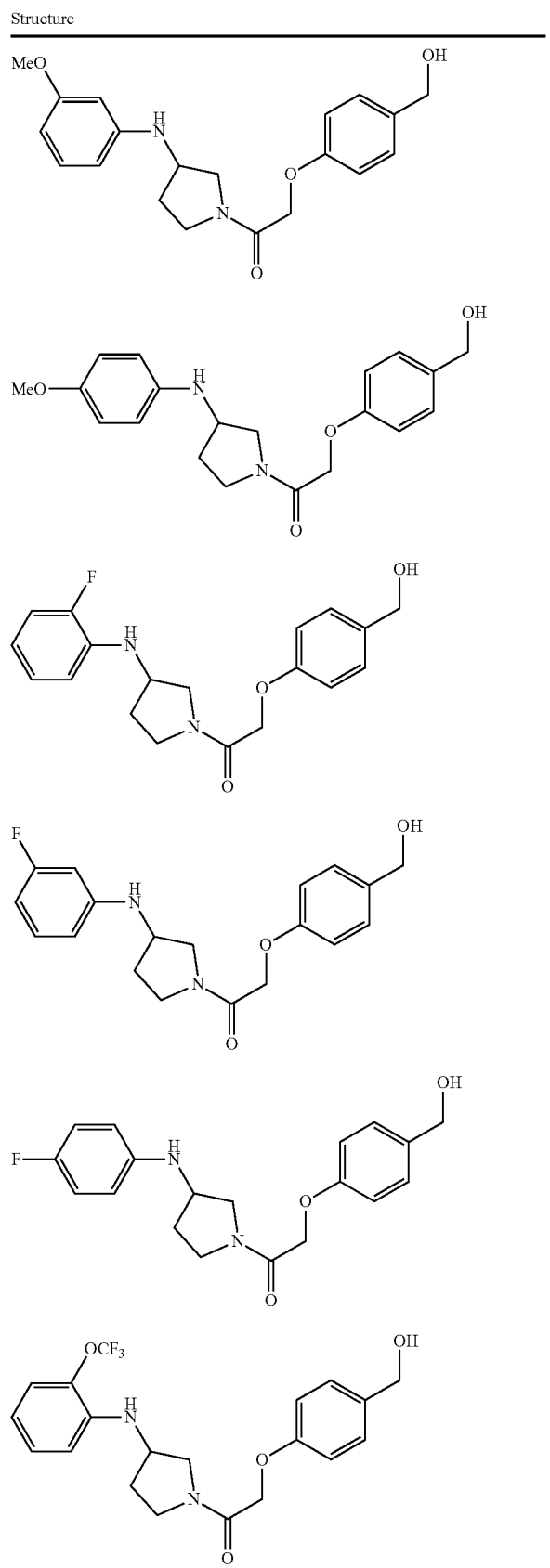
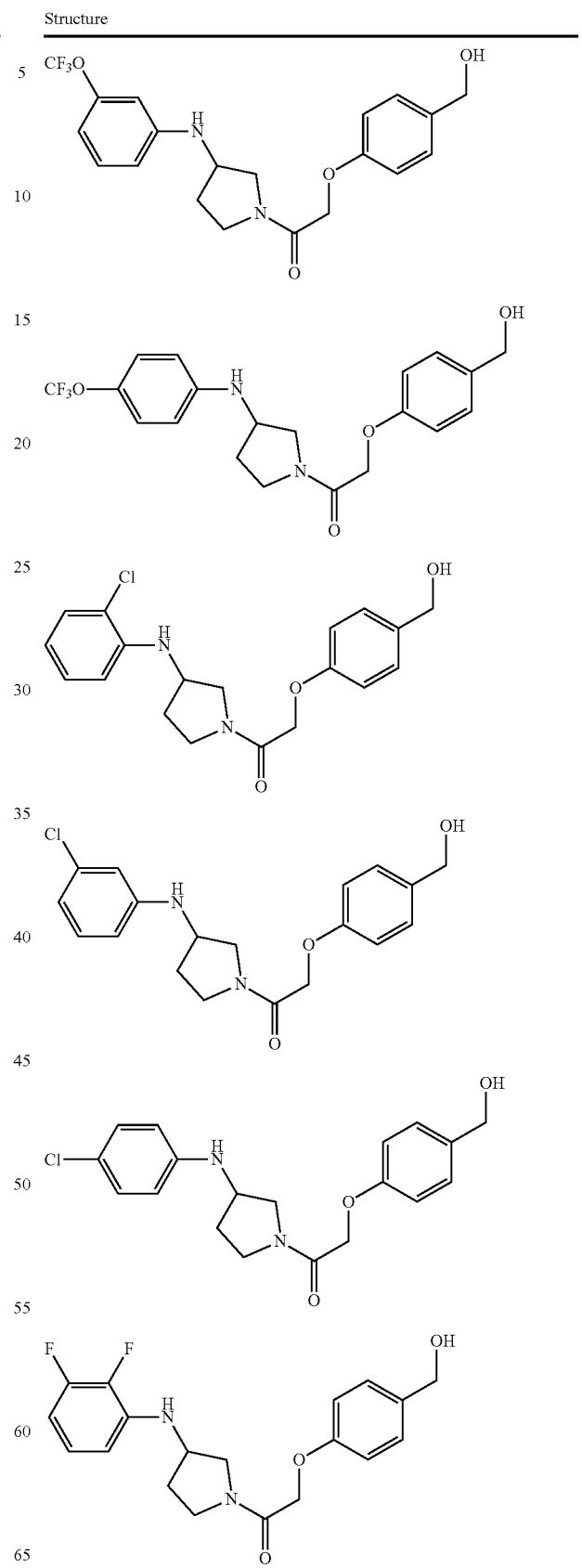

TABLE 7-continued
Structure
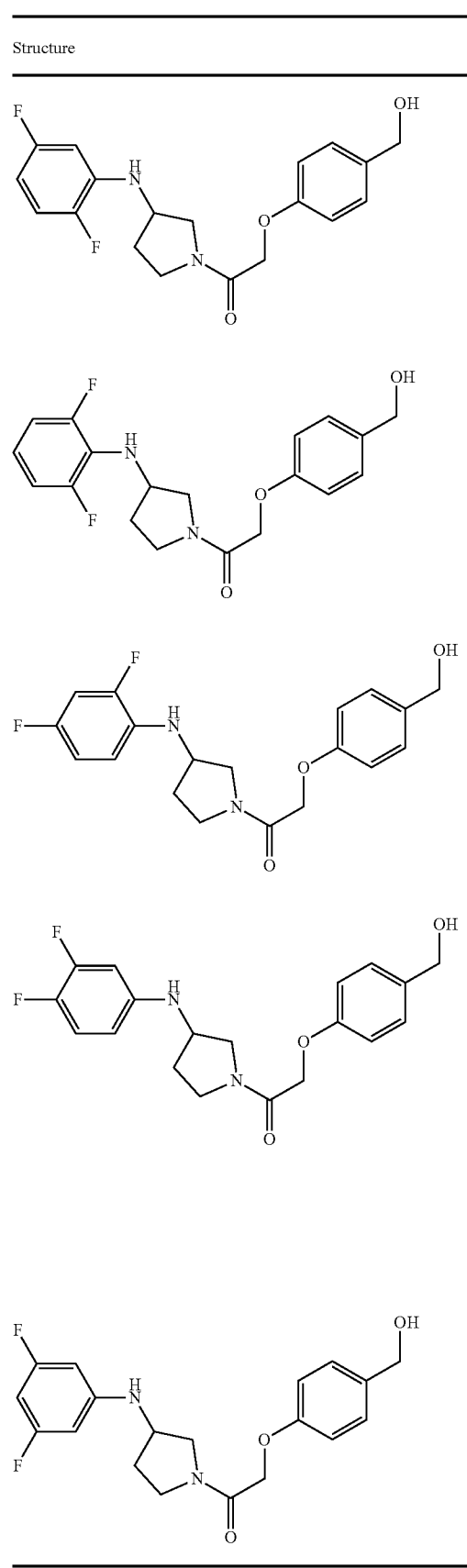
TABLE 8
Structure
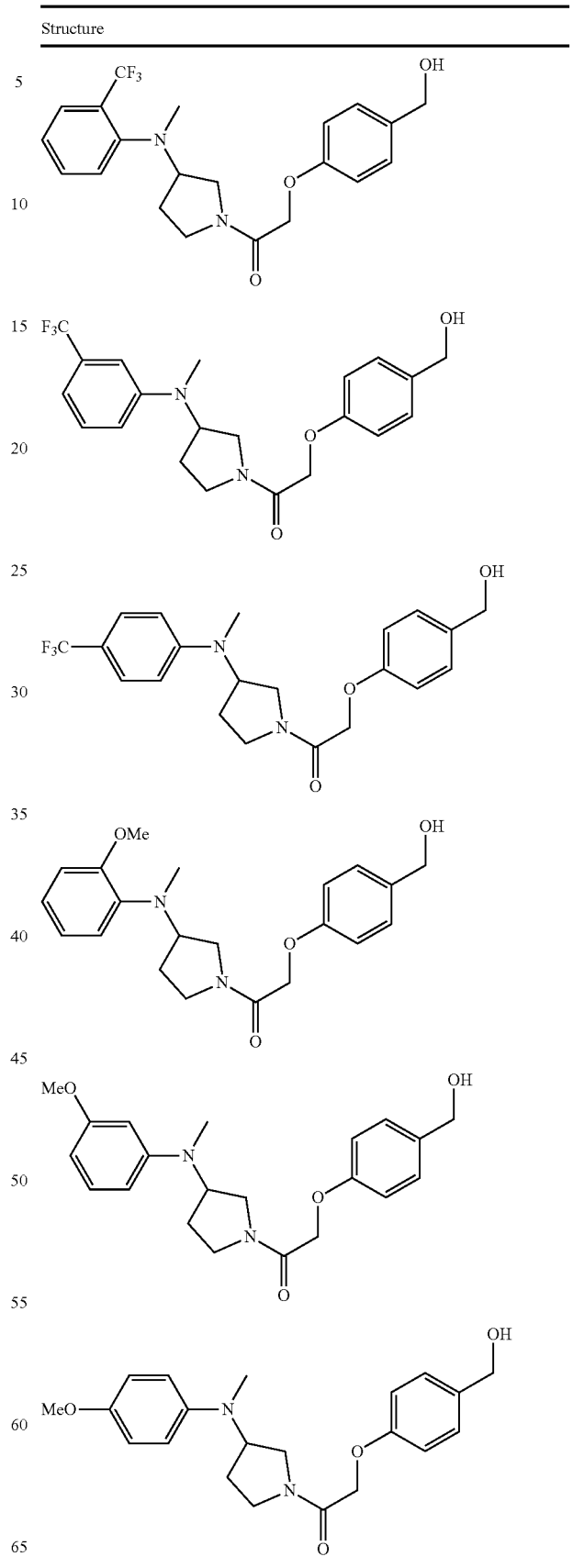

TABLE 8-continued
Structure

TABLE 8-continued
Structure
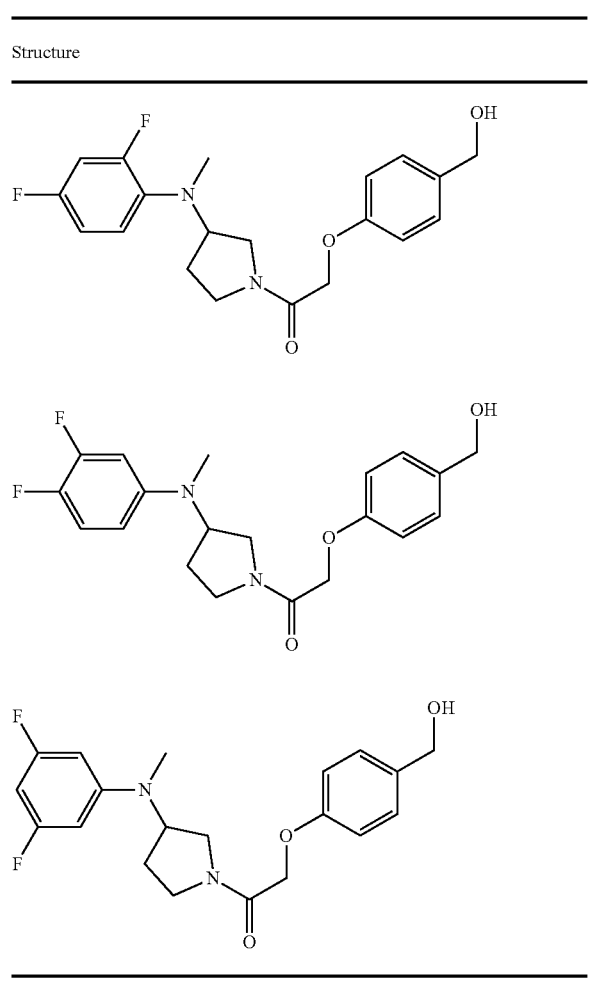
TABLE 9
Structure
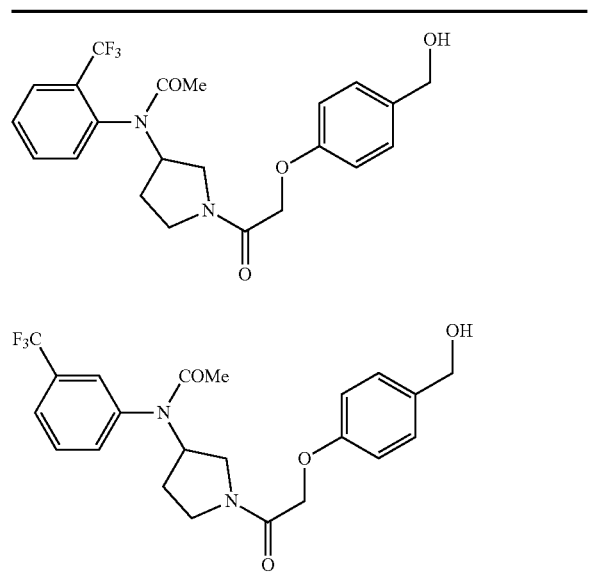
TABLE 9-continued
Structure
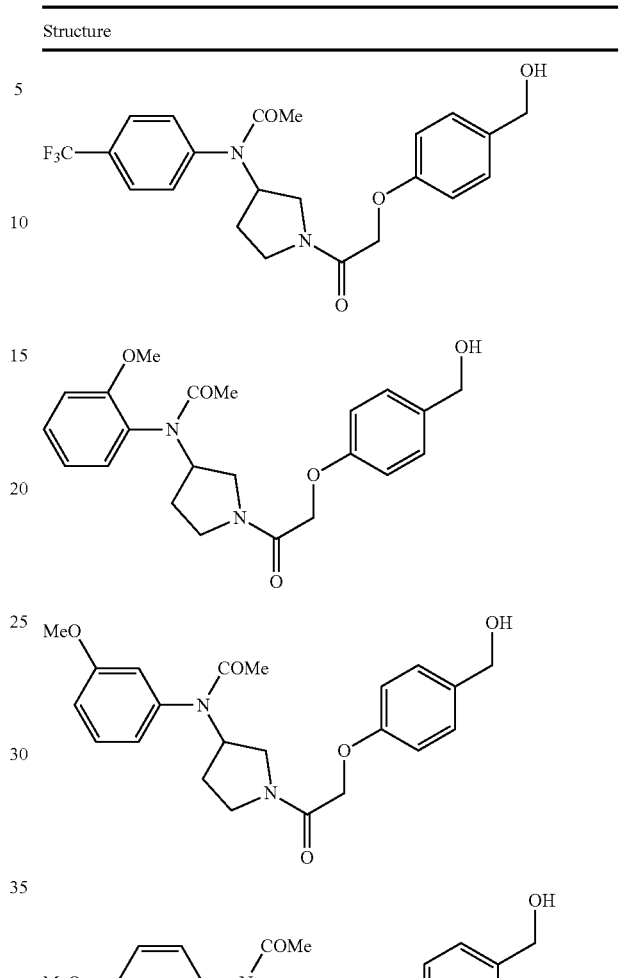
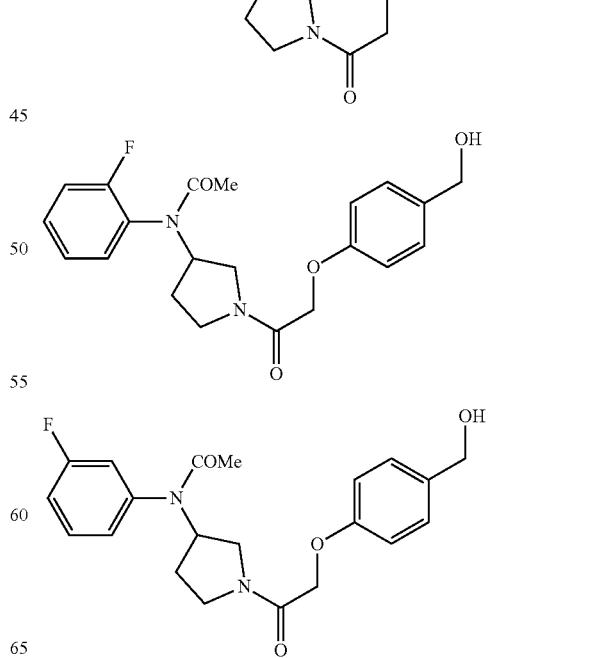

TABLE 9-continued
Structure
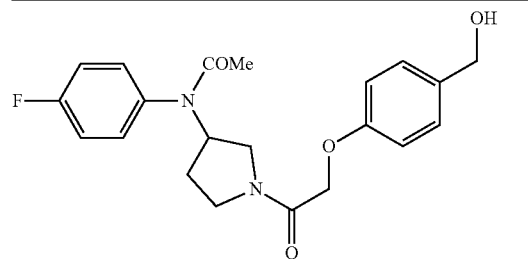
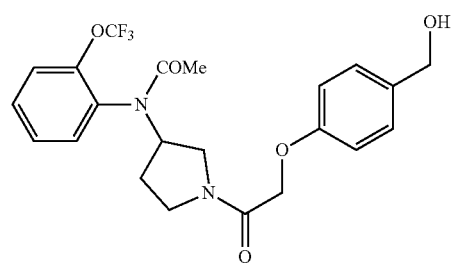
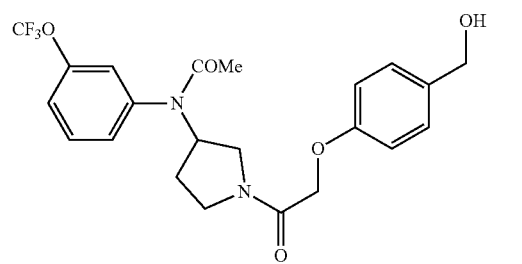
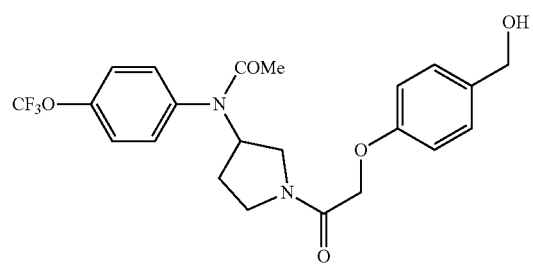
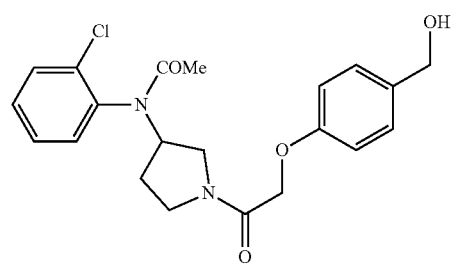
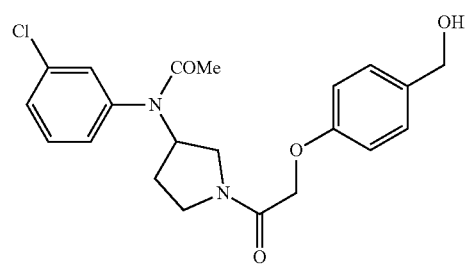
TABLE 9-continued
Structure
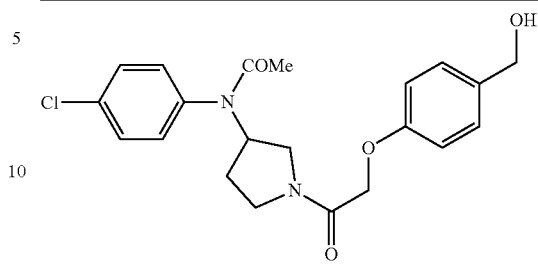
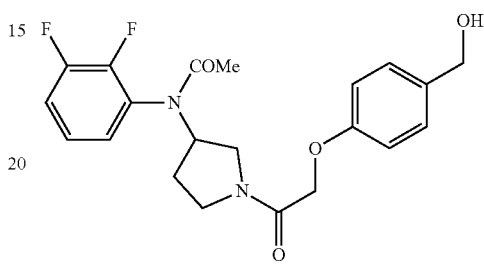
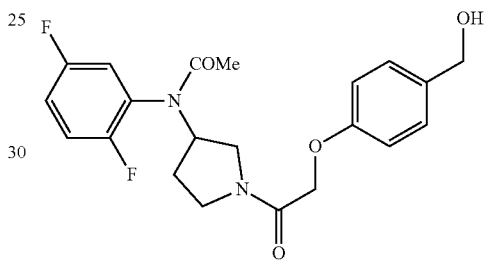
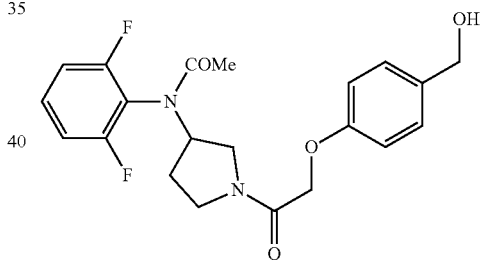
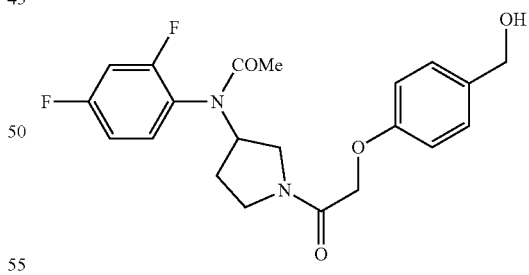
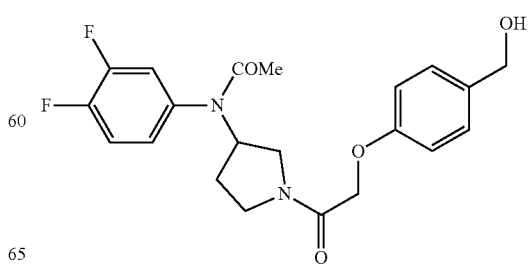

449
TABLE 9-continued
Structure
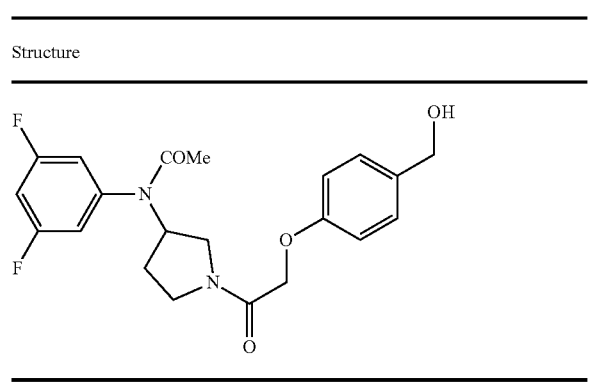
TABLE 10
Structure
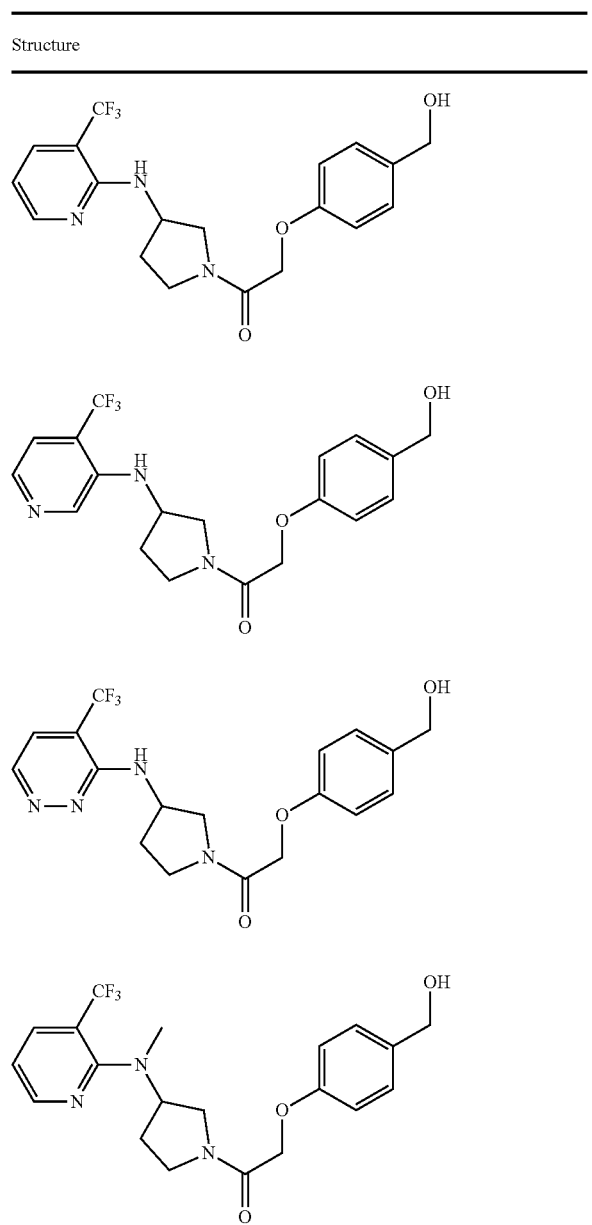
450
TABLE 10-continued
Structure
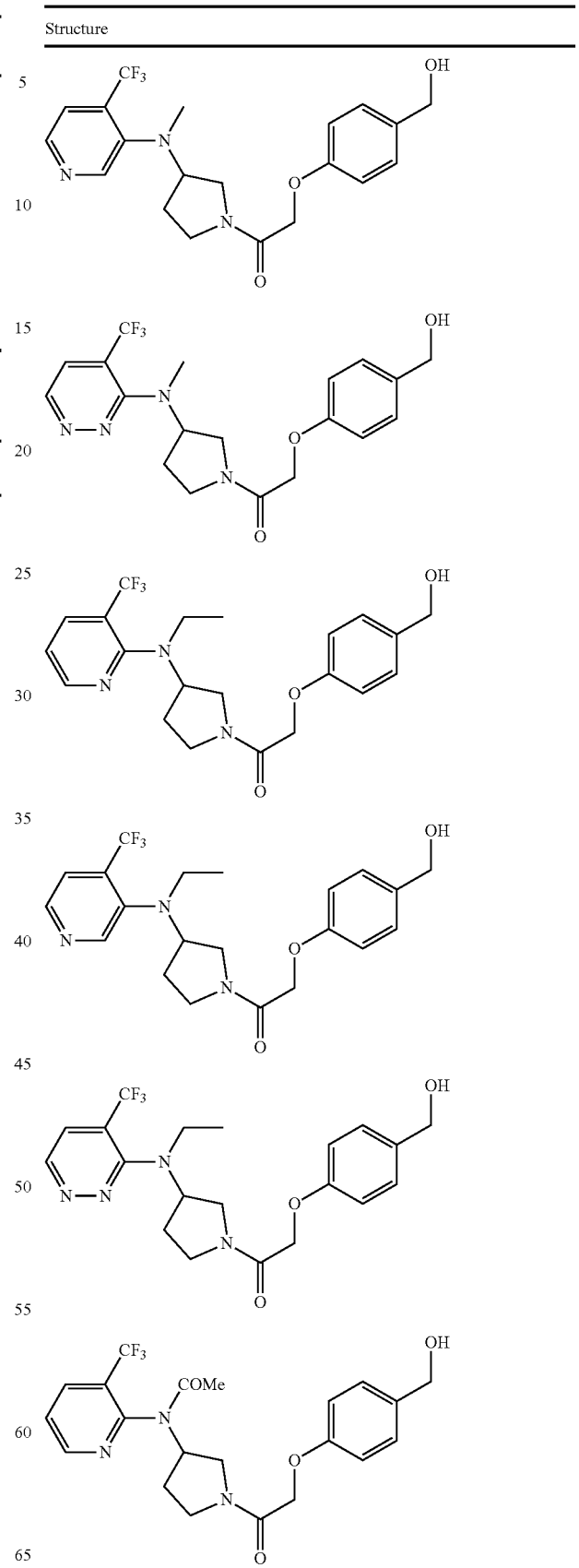

TABLE 10-continued
Structure
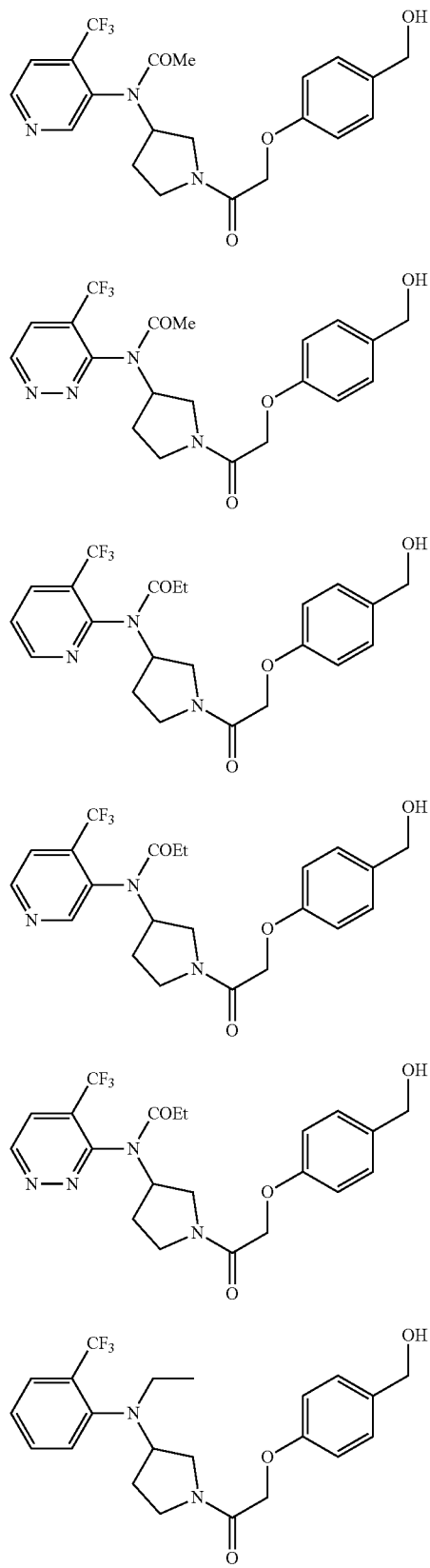
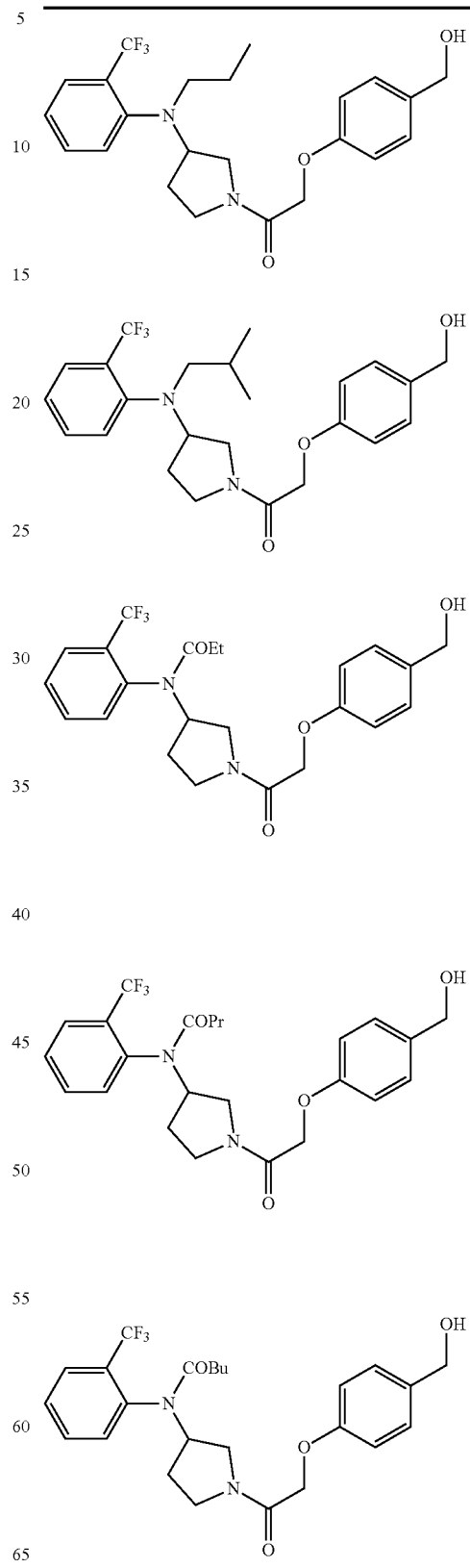

TABLE 11
Structure
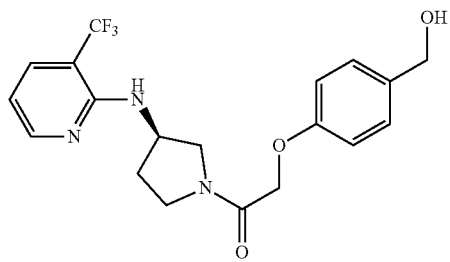 [SMILES: O=C(COc1ccc(CO)cc1)N1CC[C@@H](Nc2ncccc2C(F)(F)F)C1]
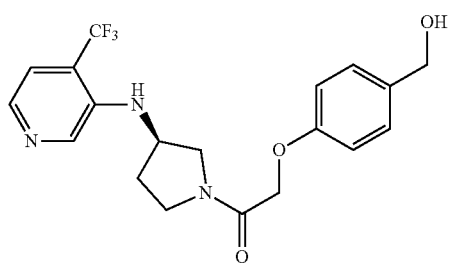 [SMILES: O=C(COc1ccc(CO)cc1)N1CC[C@@H](Nc2cnccc2C(F)(F)F)C1]
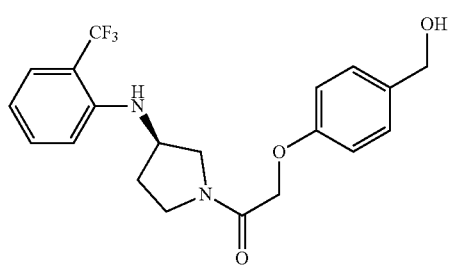 [SMILES: O=C(COc1ccc(CO)cc1)N1CC[C@@H](Nc2ccccc2C(F)(F)F)C1]
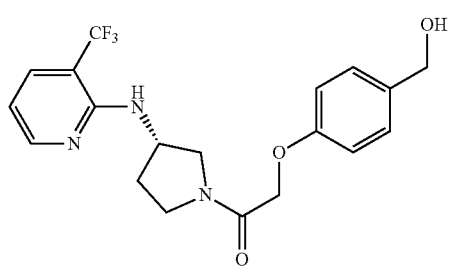 [SMILES: O=C(COc1ccc(CO)cc1)N1CC[C@H](Nc2ncccc2C(F)(F)F)C1]
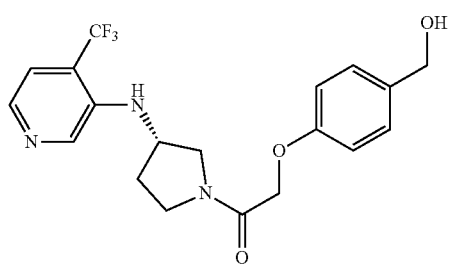
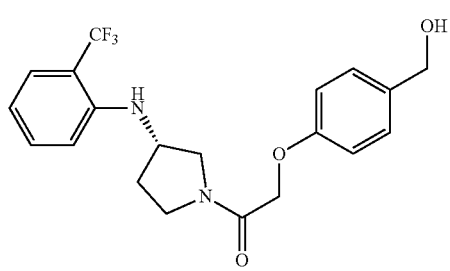
TABLE 11-continued
Structure
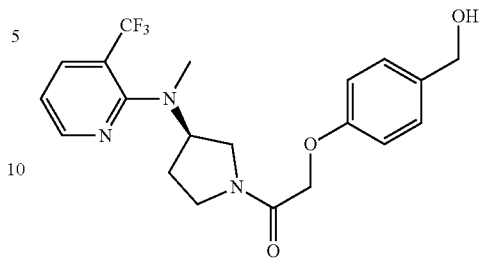
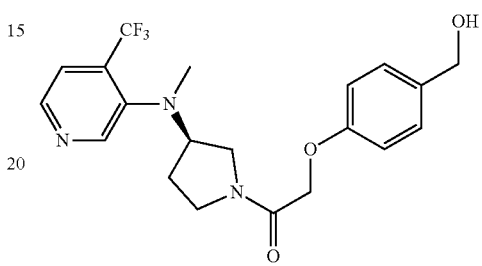
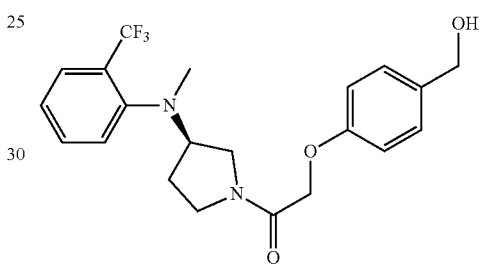
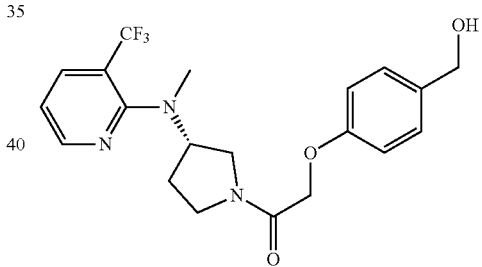
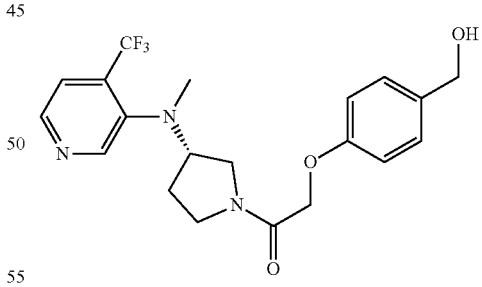
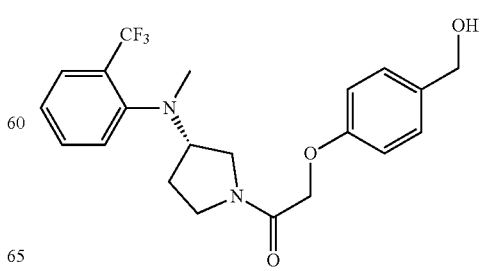

TABLE 11-continued

Structure

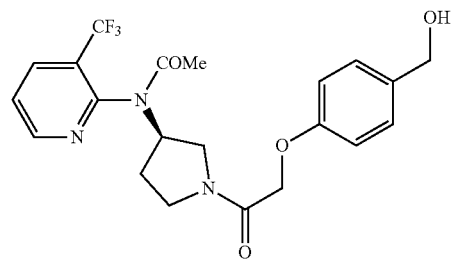

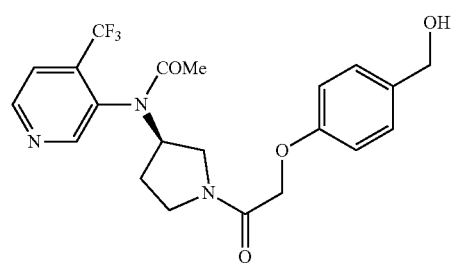

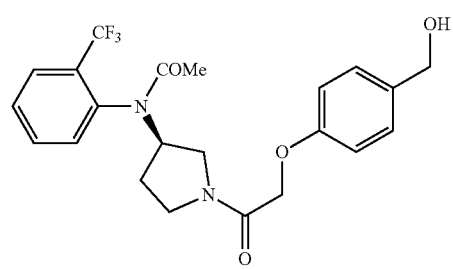

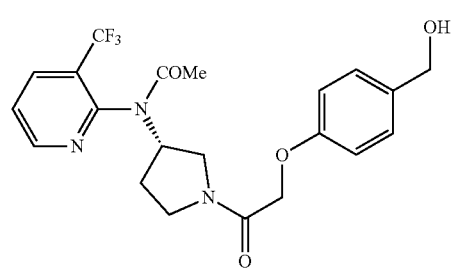

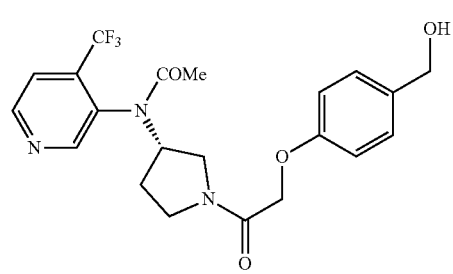

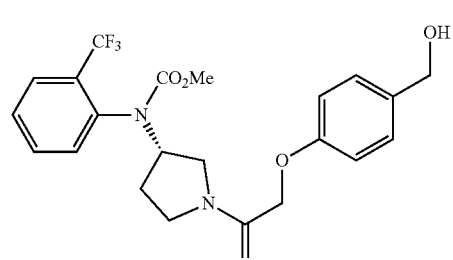

In Scheme 10 the starting pyrrolidine moiety C3 position is shown as the R-configuration. Chiral oxidizing agents ranging from chiral peracids to chiral ligand metal-mediated chiral oxidants, which are well known to those familiar with the art, are appropriate reagents not only for sulfur-selective oxidations, but also demonstrate suitable oxidizing control to stop the oxidation at the sulfoxide oxidation state. Depending upon the reagent used, either the R or S sulfur stereocenter will be formed in excess. This result is further enhanced, in terms of stereochemical control, by virtue of the fact the sulfur atom to be oxidized is adjacent to a chiral carbon atom of the pyrrolidine moiety.

Scheme 10.

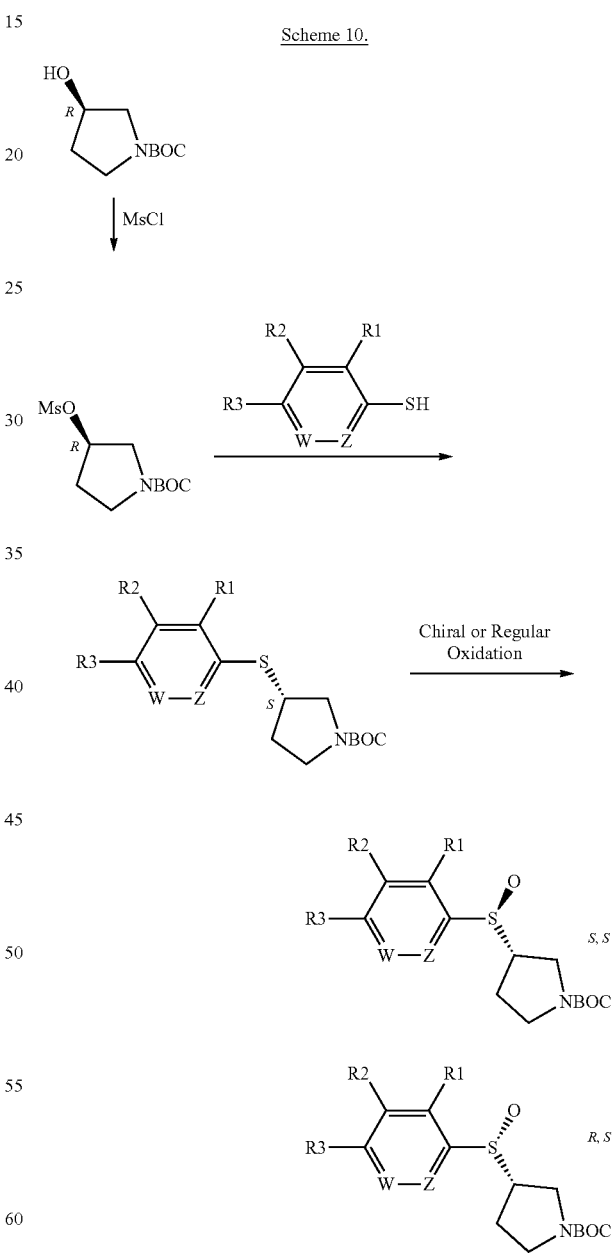

Scheme 11 outlines the transformation of the sulfur atom to its corresponding chiral sulfinyl functionality in the case wherein the C3 position of the starting pyrrolidine moiety is the S-configuration.

Scheme 11.
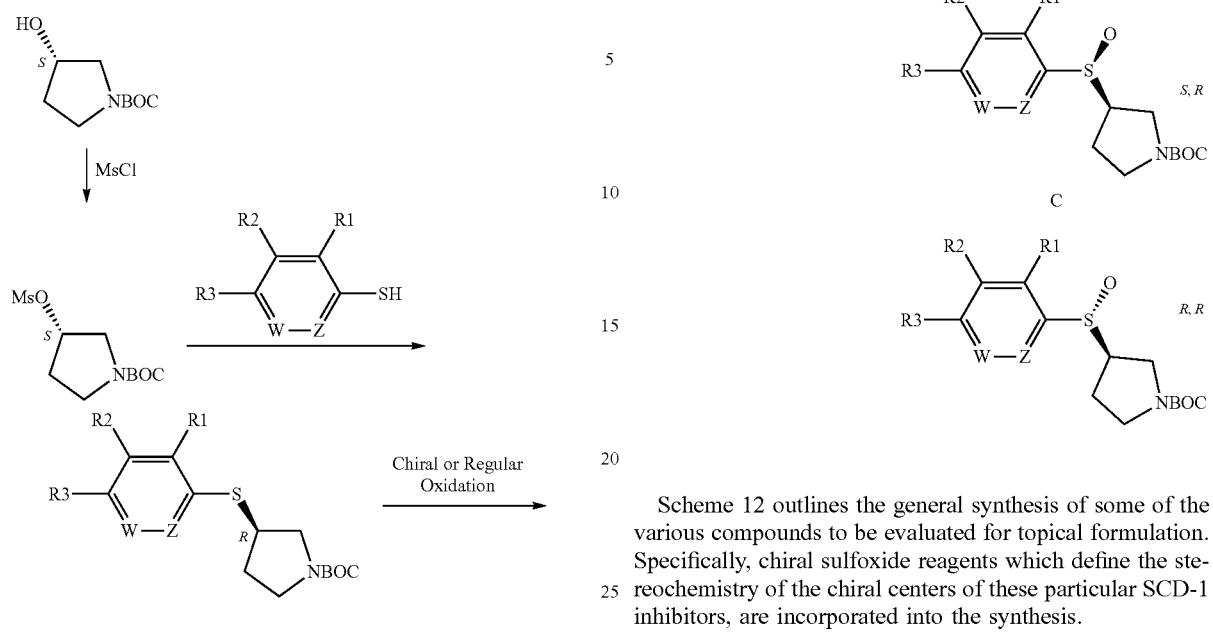
Scheme 12 outlines the general synthesis of some of the various compounds to be evaluated for topical formulation. Specifically, chiral sulfoxide reagents which define the stereochemistry of the chiral centers of these particular SCD-1 inhibitors, are incorporated into the synthesis.
Scheme 12.
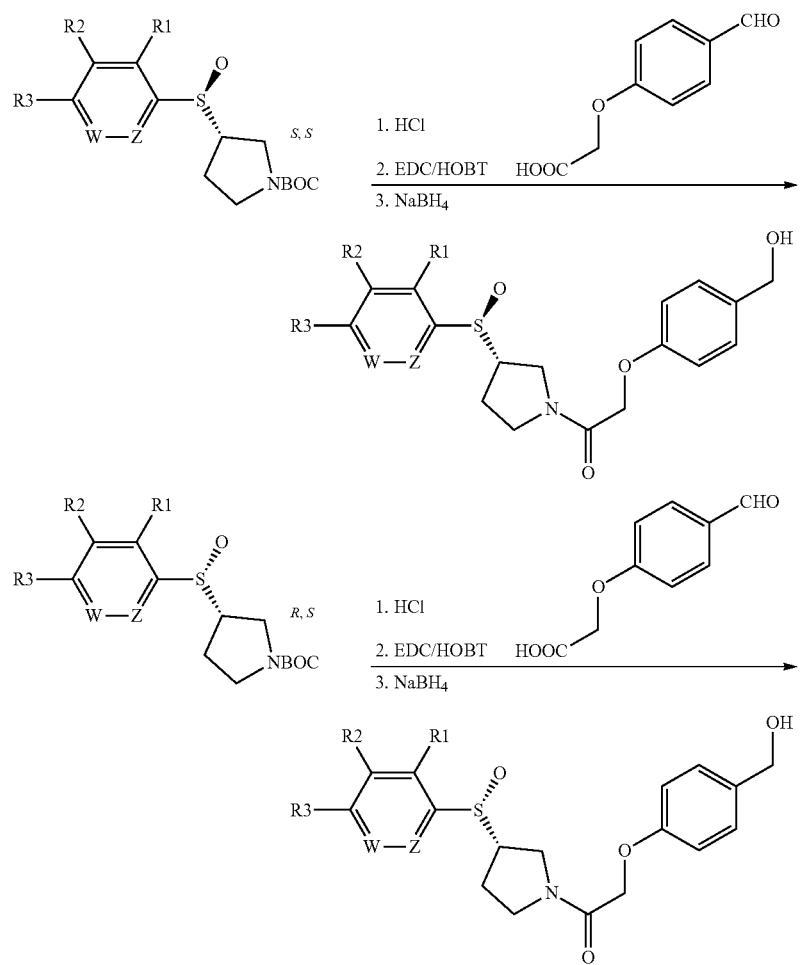

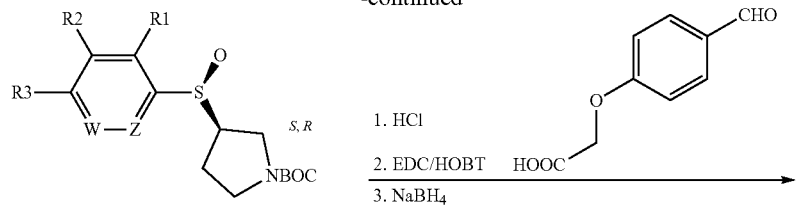

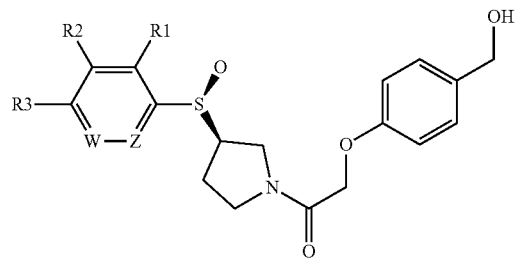

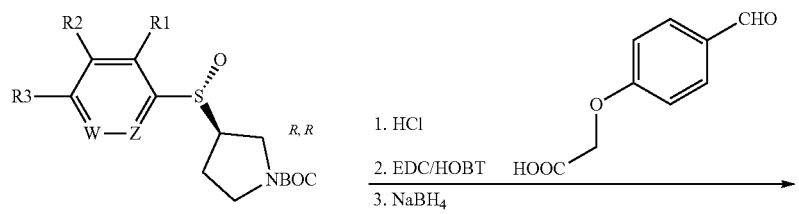

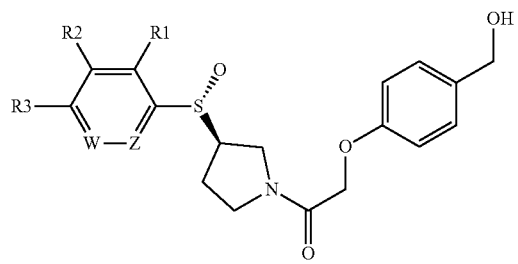

Schemes 11 and 12 can also be modified by using more demanding oxidation conditions to deliver the sulfone intermediates as shown in Schemes 13 and 14. Scheme 13 is similar to Scheme 10 in that the starting pyrrolidine moiety C3 position is shown as the R-configuration. Exhaustive oxidation which may be achieved with a variety of peracids delivers the desired chiral sulfone.

Scheme 13.

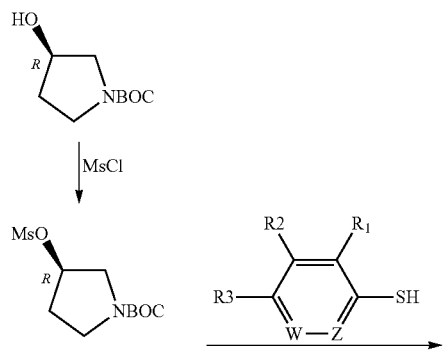

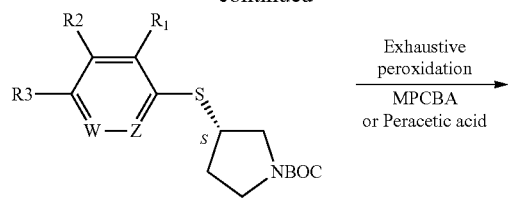

Scheme 14 outlines the transformation of the sulfur atom to its corresponding sulfone functionality in the case wherein the C3 position of the starting pyrrolidine moiety is the S-configuration.

Scheme 14.
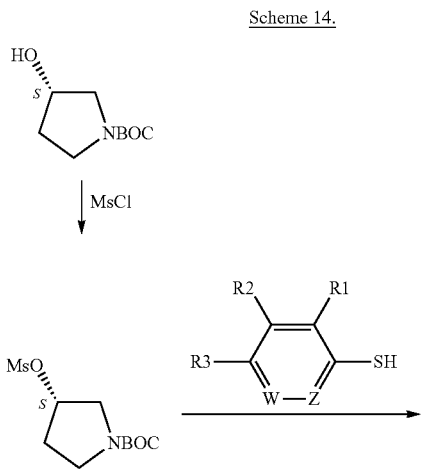
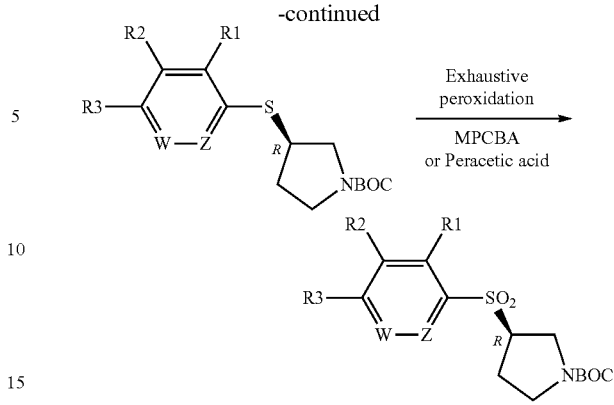
Each of these options can be further transformed into final sulfone products by protective group cleavage, coupling with the side chain acid and reduction of the aldehyde to the alcohol as shown in Scheme 15.
Scheme 15.
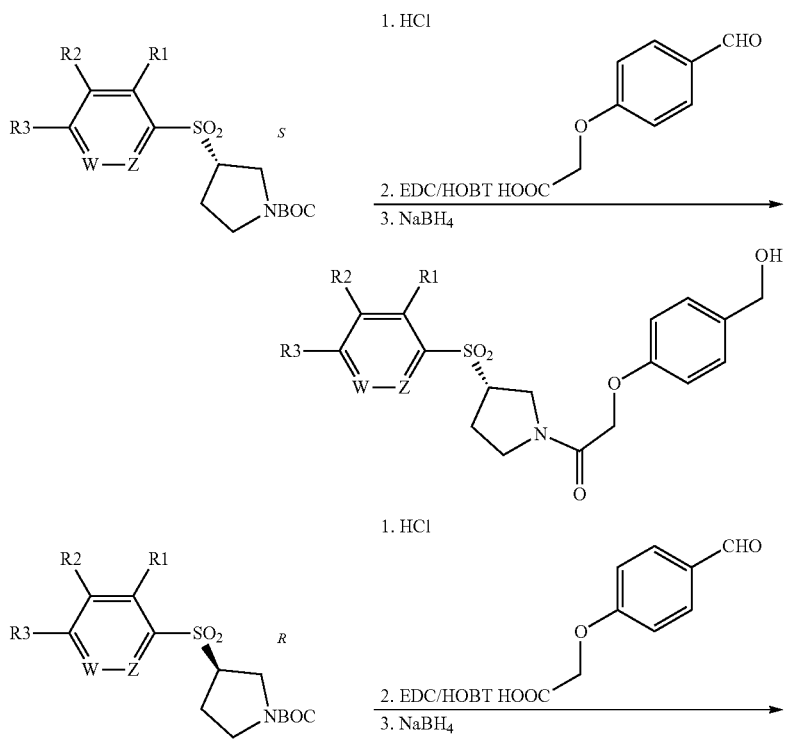
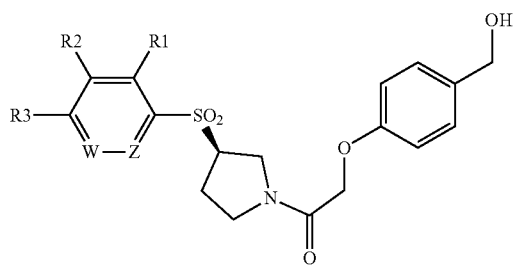

In order to synthesize the sulfide derivatives in this series then the key sulfide intermediates shown in several of the above schemes, prior to oxidation, can be used. Scheme 16 shows the transformation of the intermediate protected sulfide derivatives into final sulfides via protective group cleavage, coupling with the side chain acid and reduction of the aldehyde to the alcohol.

Scheme 16.

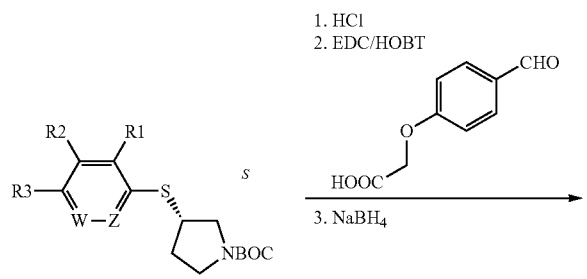

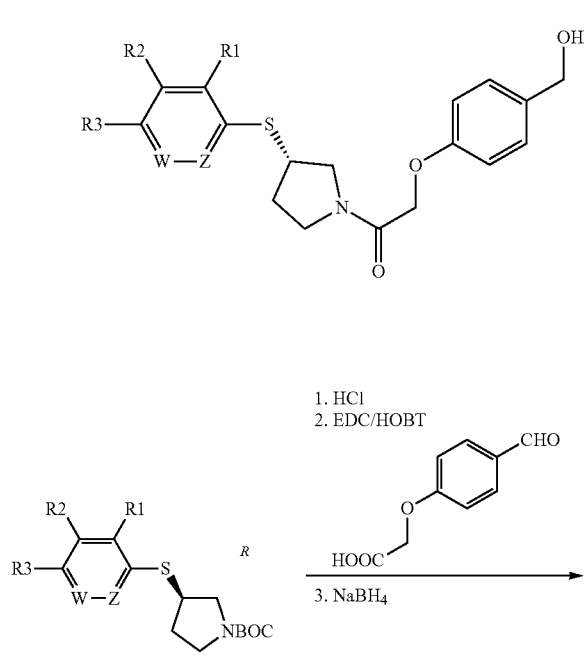

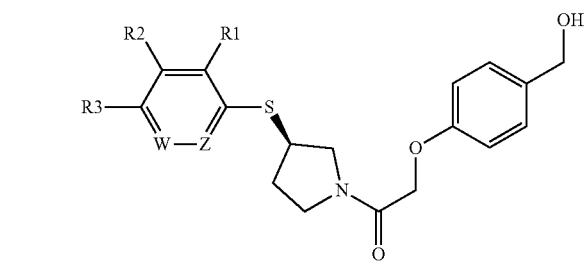

Table 12, Table 13, Table 14, Table 15, and Table 16 list some specific compounds synthesized via the overall syntheses and general methods outlined in this section (Schemes 10-16) Table 12.

TABLE 12

Structure

TABLE 12-continued
Structure
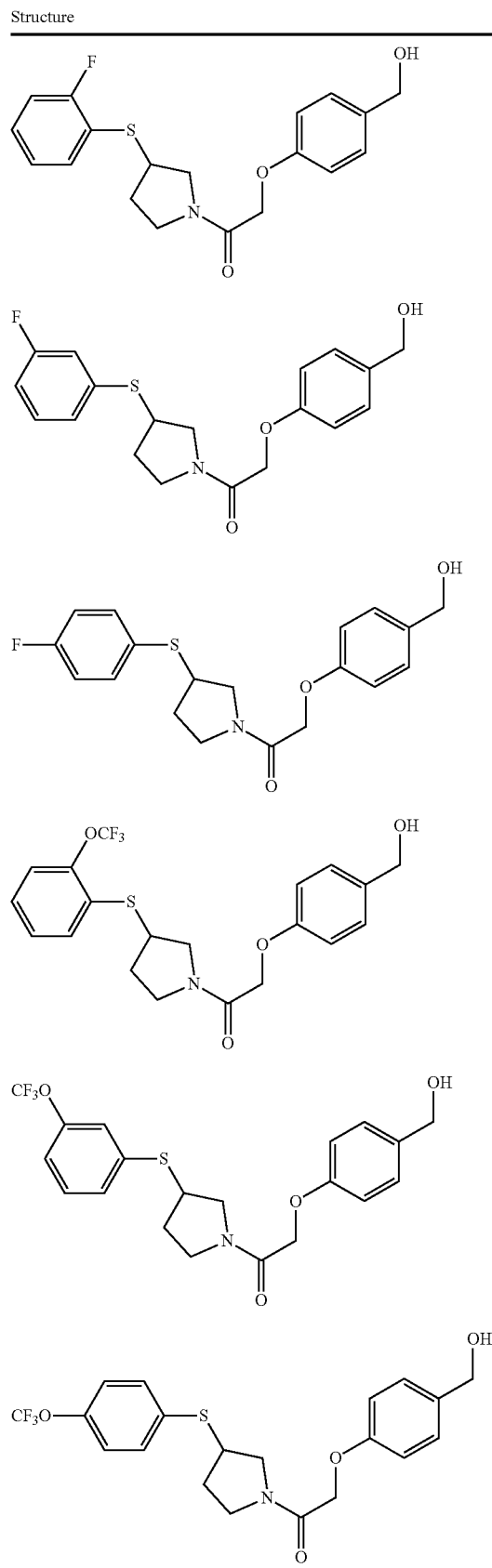
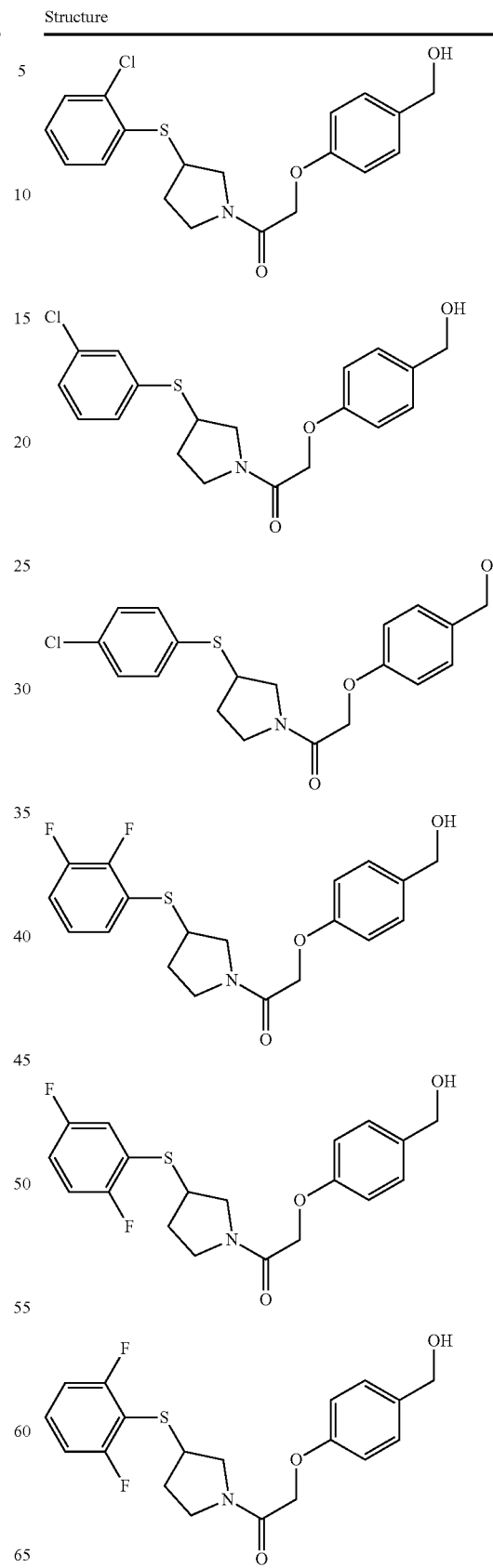

TABLE 12-continued
Structure
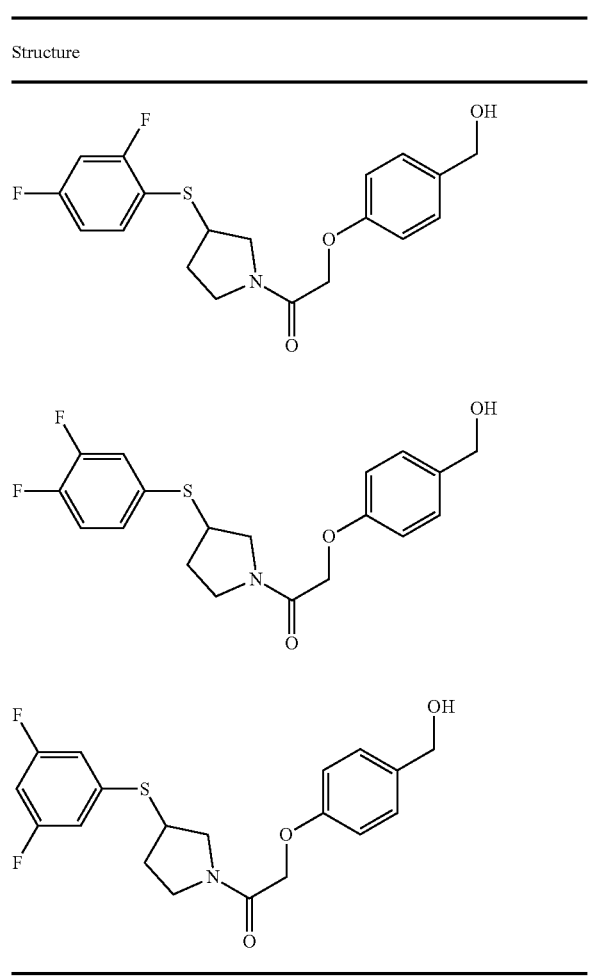
TABLE 13
Structure
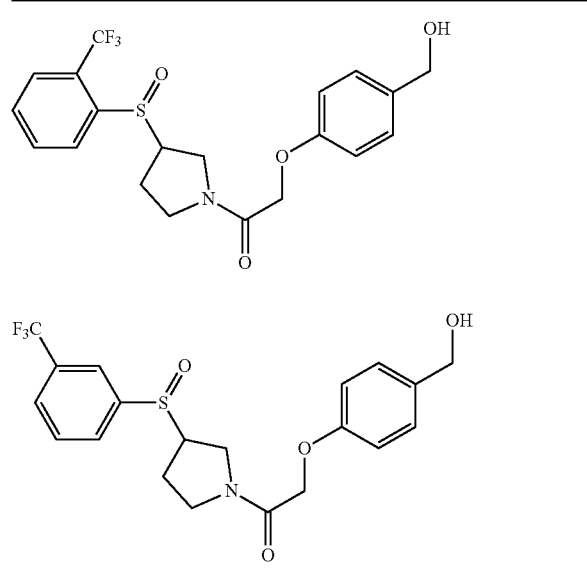
TABLE 13-continued
Structure
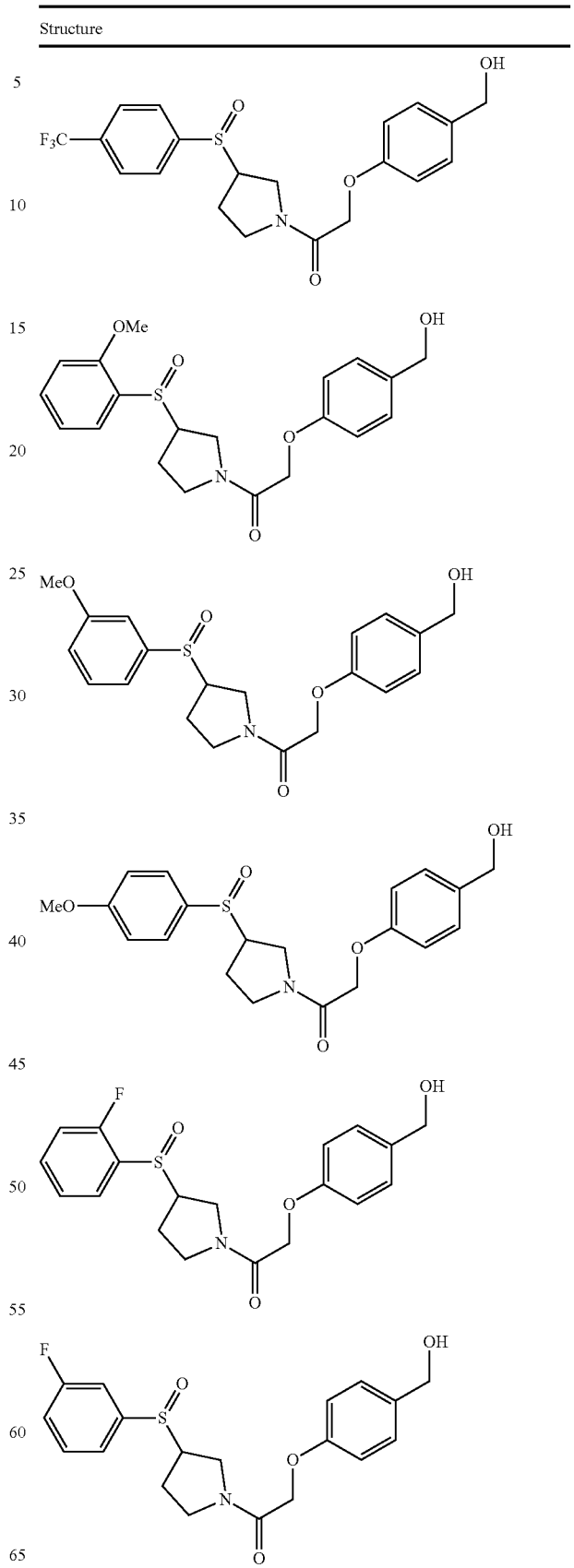

TABLE 13-continued
Structure
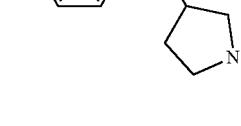

TABLE 13-continued
Structure
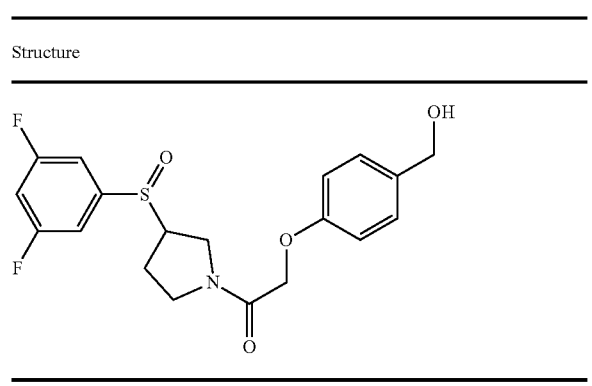
TABLE 14
Structure
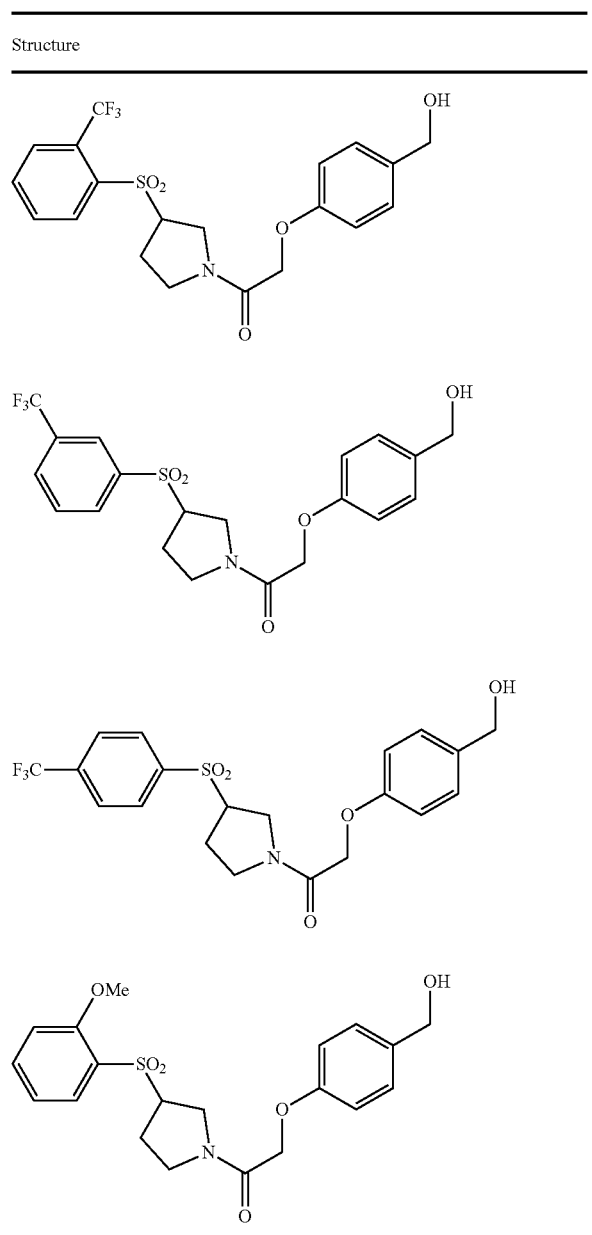
TABLE 14-continued
Structure
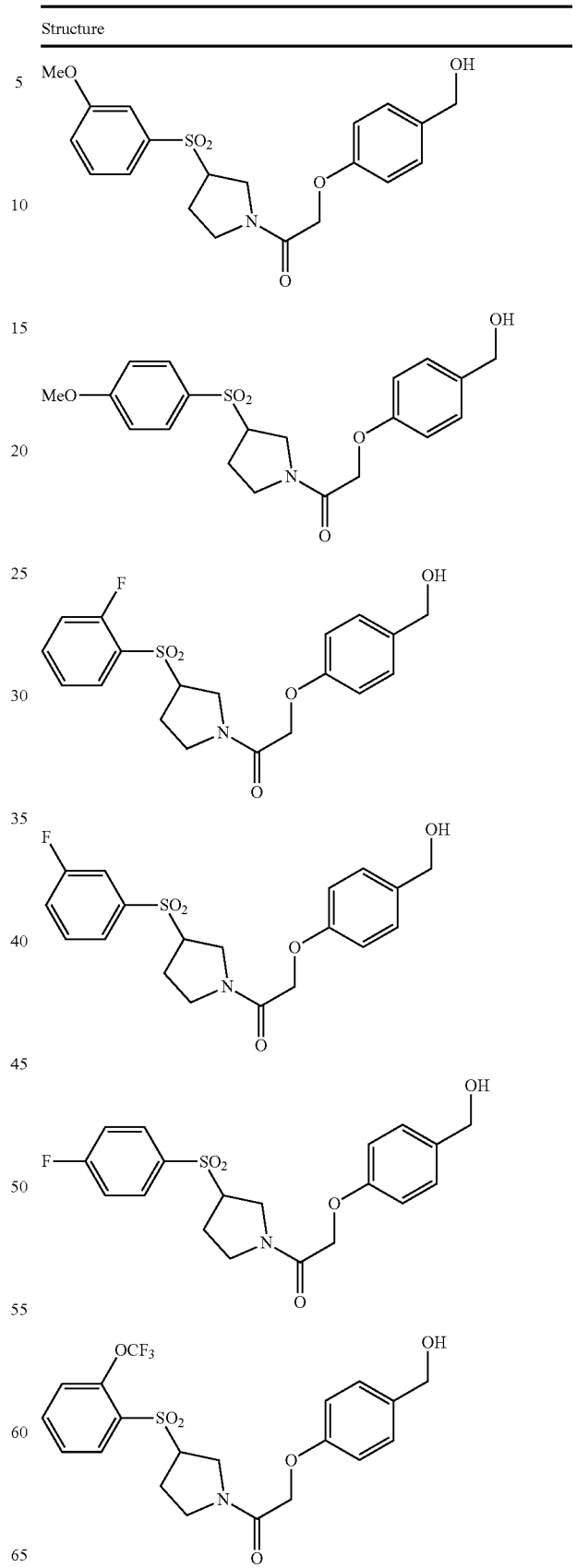

TABLE 14-continued
Structure
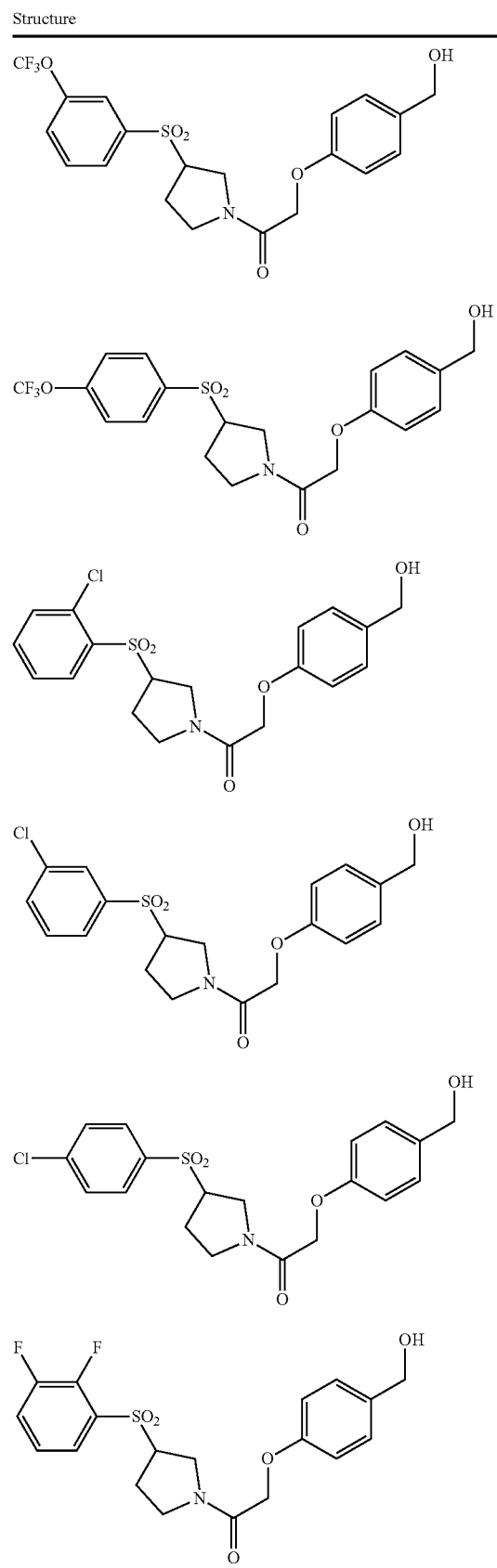
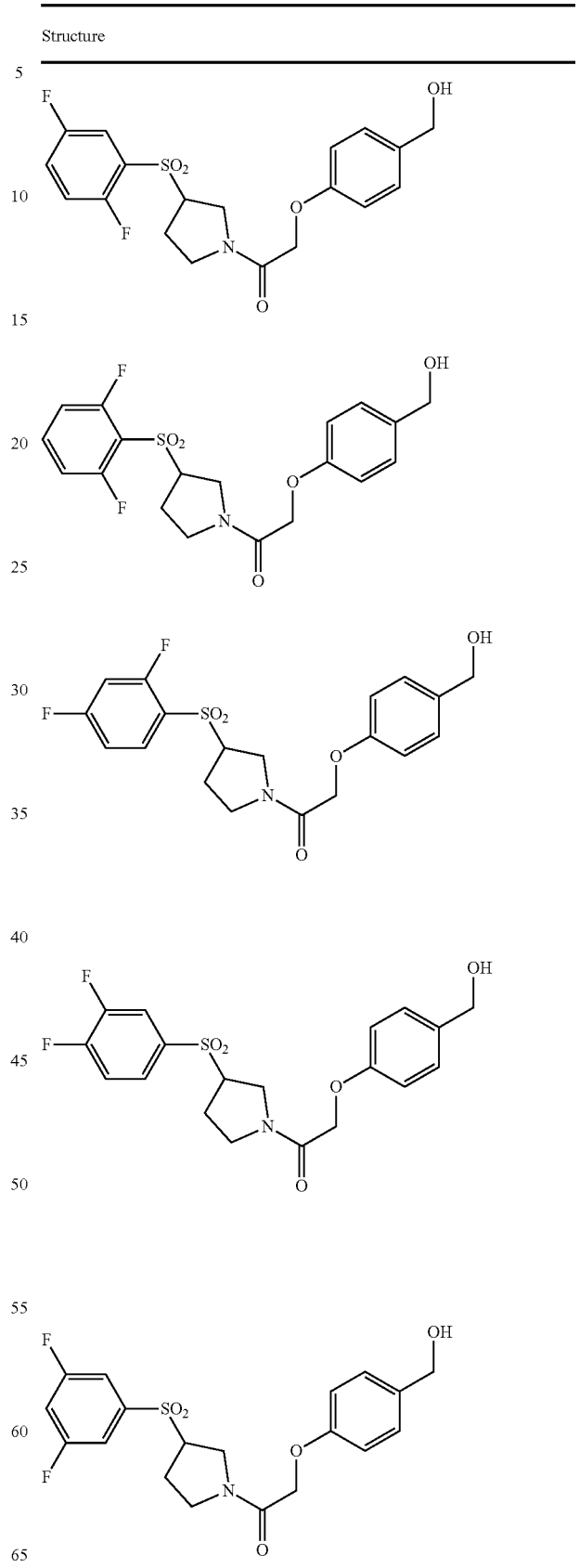

TABLE 15
Structure
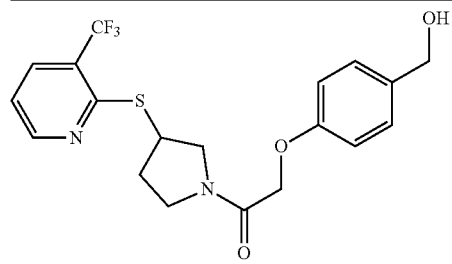
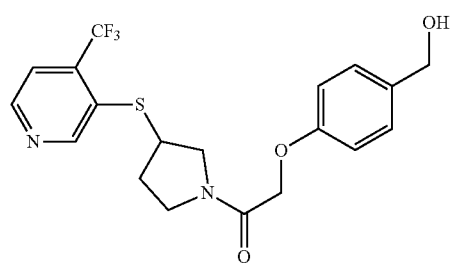
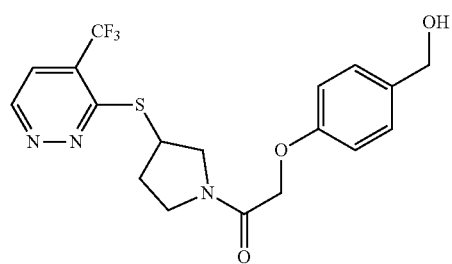 [SMILES: O=C(COc1ccc(CO)cc1)N1CCC(Sc2nnccc2C(F)(F)F)C1]
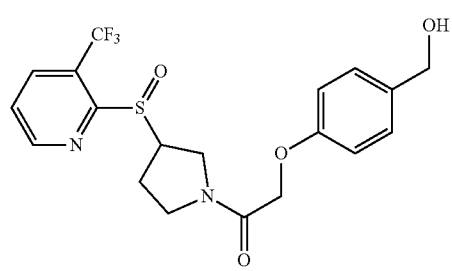 [SMILES: O=C(COc1ccc(CO)cc1)N1CCC(S(=O)c2ncccc2C(F)(F)F)C1]
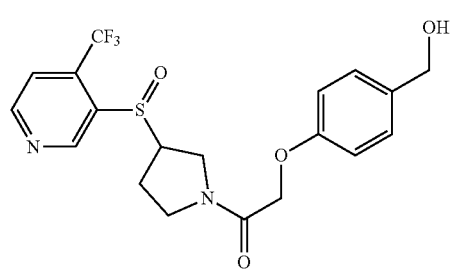 [SMILES: O=C(COc1ccc(CO)cc1)N1CCC(S(=O)c2cnccc2C(F)(F)F)C1]
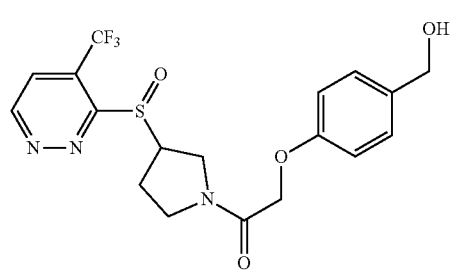 [SMILES: O=C(COc1ccc(CO)cc1)N1CCC(S(=O)c2nnccc2C(F)(F)F)C1]
TABLE 15-continued
Structure
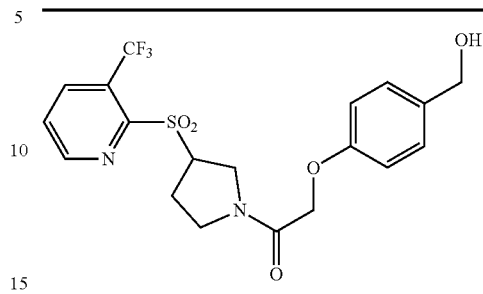
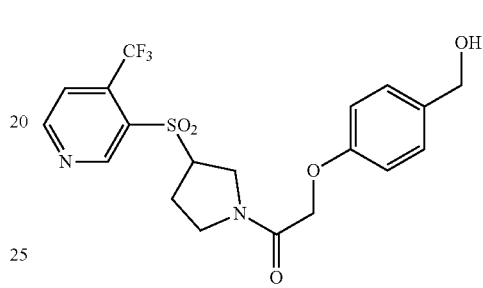
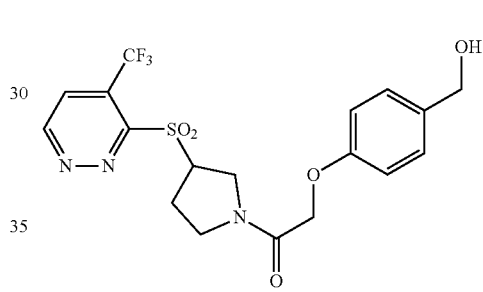
TABLE 16
Structure
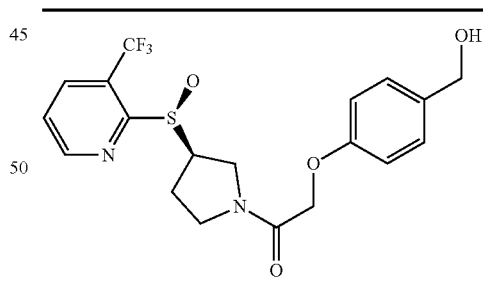
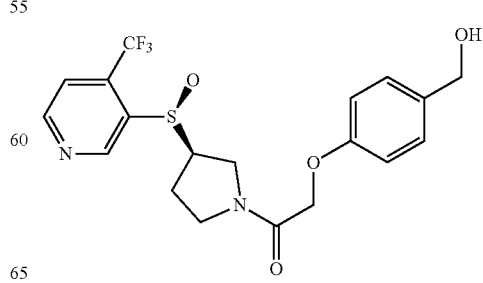

TABLE 16-continued

Structure

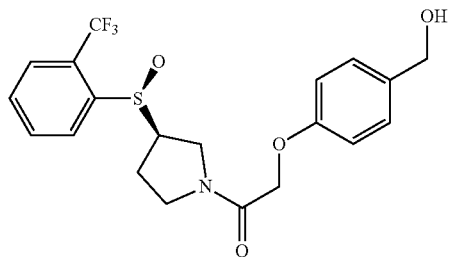

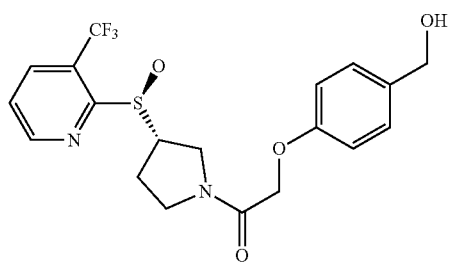

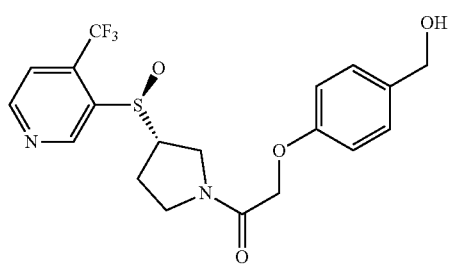

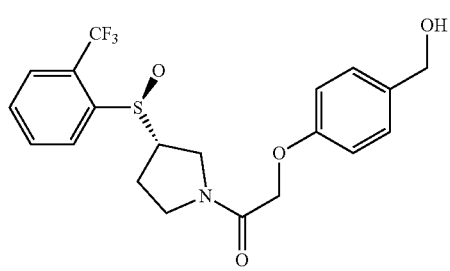

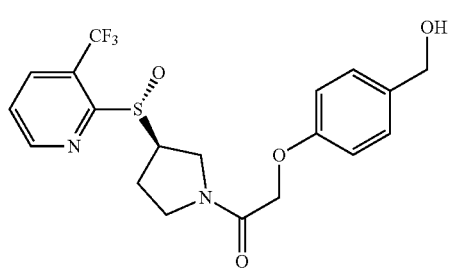

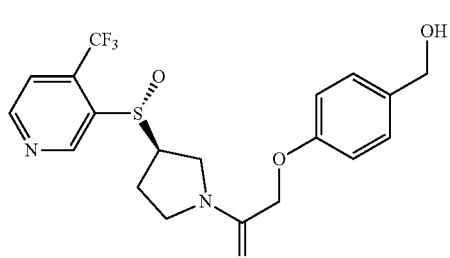

TABLE 16-continued

Structure

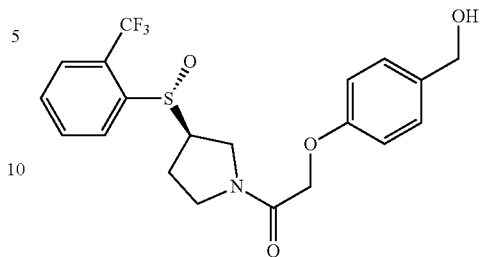

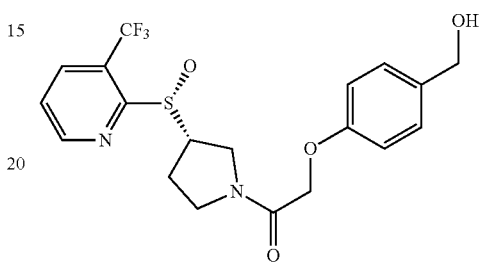

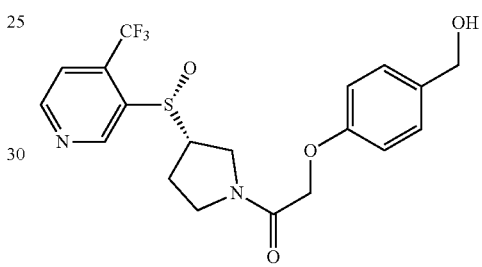

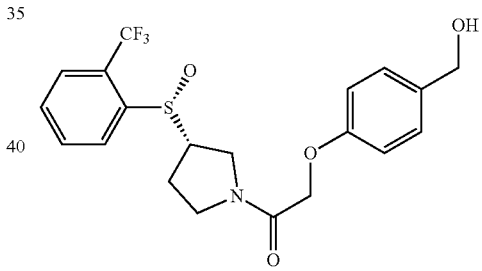

The modular synthesis of Schemes 1 through 16 can all be adapted to automated synthesis platforms, focused library platforms, solid phase organic synthesis platforms, combinatorial chemistry platforms, microwave chemistry platforms and other modern variants of synthetic organic chemistry suitable for high throughput.

Formulations

The formulations described in this application are primarily for dermatological and cosmetic use and may be formulated as a pharmaceutical composition and administered to a mammal, such as a human patient in a variety of forms adapted to a chosen route of administration, i.e. topically, intralesionally, or subcutaneously. It should be understood that the invention is not limited by the chosen route of administration. The compound present may be administered alone or in combination with one or more other therapeutic agents.

In a typical embodiment the compound will be administered as a formulation in association with a pharmaceutically acceptable carrier. The choice of carrier will largely depend on factors such as the particular mode of administration, the effect of the carrier on solubility and stability, and the nature of the dosage form.

In some embodiments, the compound will be formulated with a carrier suitable for administration directly to the skin or hair.

In other embodiments, the compound is topically applied to a subject. Topical application is especially appropriate for the treatment of acne, rosacea, excess sebum, oily skin or hair, and shiny or greasy looking skin. In certain embodiments, topical application refers to application of a compound, and optional carrier, directly to the skin and/or hair. The topical composition according to the present invention can be in the form of solutions, lotions, salves, creams, ointments, liposomes, sprays, gels, foams, roller sticks, or any other formulation routinely used in dermatology.

In other embodiments, compositions of the invention may be solid or semi-solid formulations which are suitable for use as cleansing soaps, gels or bars. These compositions are prepared according to the usual methods and may optionally contain additional excipients such as moisturizers, colorants, fragrances and the like.

The compound may also be formulated for application to the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the excipients in the various compositions according to the invention are those conventionally used in the fields considered.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Gennaro (1995)).

Dosage

The dose and dosing regimens of the compound present in the invention may be adjusted to provide the optimum desired response in accordance with methods and practices well known in the therapeutic arts. For example, a single bolus dose may be administered or several divided doses may be administered over time. The dose may also be proportionally reduced or increased as indicated by the exigencies of the therapeutic situation. The appropriate dosing regimen, the amount of each dose administered and/or the intervals between doses will depend upon a number of factors, including: the compound, the type of pharmaceutical composition, the characteristics of the subject in need of treatment and the severity of the condition being treated.

The dose of the compound will vary, but as a general guideline for dermatological administration, the compound will be present in a dermatologically acceptable formulation in an amount of from about 0.01 to 50 w/w %, and more typically from about 0.1 to 10 w/w %. In some embodiments, the formulation may be applied to the affected area from 1 to 4 times daily. A "dermatologically acceptable formulation" is one that may be applied to the skin or hair and will allow the drug to diffuse to the site of action.

The skilled artisan can also be expected to readily determine the maximum tolerable dose, the therapeutically effective amount which provides a detectable therapeutic benefit to a patient, and the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

The determination of optimal dosages for a particular patient is well-known to those skilled in the art. Certain non-limiting examples of pharmaceutically acceptable vehicles suitable for topical administration include propylene glycol:transcutanol:ethanol (20:20:60, v/v/v) and propylene glycol:ethanol (30:70, v/v). In some embodiments, the compound of Structure I may be present at concentrations of between about 1.5% to about 2.0% (w/v)

Co-Administration

In further embodiments of the invention, the compound is co-administered with other agents in order to enhance or complement the desired therapeutic effect or to minimize potential side effects. Non-limiting examples of such embodiments are described below. Acyl-CoA cholesterol acyl transferase (ACAT) inhibitors were initially evaluated for the treatment of elevated serum cholesterol. It was subsequently discovered that these compounds decrease sebum production (U.S. Pat. No. 6,133,326). Any such ACAT inhibitor can be co-administered with the compound(s) of Structure I to decrease sebum production, alleviate oily skin, etc.

Topical retinoids are used to treat acne by normalizing follicular keratinization, but do not effectively reduce sebum production. In an embodiment of the invention, a compound of Structure I is co-administered with a retinoid in order to decrease sebum production and to treat acne or seborrhea. Exemplary retinoids suitable for coadministration include, but are not limited to, etretinate, tretinoin, retinol, retinyl palmitate, adapalene, tazarotene, and aliretinoin.

Benzoyl peroxide has been a mainstay in the treatment of acne for many decades and works, at least in part, by reducing skin colonization with *Propionobacterium acnes*. In an embodiment of the invention, the compound(s) of Structure I is co-administered with benzoyl peroxide to enhance the treatment of acne.

Antibiotics, such as members of the tetracycline family (including minocycline and doxycycline), clindamycin, erythromycin, and dapsone have been used to treat acne. The antibiotic reduces or eradicates the microorganism, *Propionbacterium acnes*, leading to a reduction in the patient's acne. The compound(s) of Structure I can be co-administered with any antibiotic suitable for the treatment of acne.

Estrogen and progesterone have each been shown to decrease sebum production. These compounds, or any synthetic agonist of such compounds, may be co-administered with the compound(s) of Structure I in order to decrease sebum production.

As used in this application, the terms "co-administered" or "co-administration" refer to a dosing regimen where the compound of Structure I is administered with a second therapeutic agent, typically having a differing mechanism of action, to promote a desired result. It should be understood that "co-administration" is not limited by the route(s) of administration and can refer to simultaneous dosing, dosing at different times during a single day, or even dosing on different days. The compounds can be administered separately or can be combined into a single formulation (i.e. fixed combination).

In another embodiment, the medicinal and cosmetic formulations containing the compound and any additional therapeutic agents will typically be packaged for retail distribution (i.e. an article of manufacture or a kit). Such articles will be labeled and packaged in a manner to instruct the patient how to use the product. Such instructions will include the condition to be treated, duration of treatment, dosing schedule, etc. The compound(s) of Structure I may also be admixed with any inert carrier and utilized in laboratory assays in order determine the concentration of the compounds within the serum, urine, etc., of the patient as is known in the art. The compound may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data are being presented in order to further illustrate the invention. This disclosure should not be construed as limiting the invention in any manner.

For all of the foregoing embodiments, each embodiment disclosed herein is contemplated as being applicable to each of the other disclosed embodiments. Those skilled in the art will readily appreciate that the specific Experimental Details which follow are only illustrative of the invention as described more fully in the claims which follow thereafter.

EXPERIMENTAL DETAILS

The invention will be understood more clearly by those skilled in the art through the description hereinafter of several specific experiments, with reference to the corresponding examples as follows:

Example 1: Synthesis of Compounds

NMR spectra were recorded on Bruker Avance 400 MHz for $^1$H NMR and 100 MHz for $^{13}$C NMR. LCMS were taken on a single quadrupole Mass Spectrometer using Shimadzu LCMS 2010 (Column: sepax ODS 50×2.0 mm, 5 um) or Agilent 1200 HPLC, 1956 MSD (Column: Shim-pack XR-ODS 30×3.0 mm, 2.2 um) operating in ES (+) ionization mode. Chromatographic purifications were by flash chromatography using 100-200 mesh silica gel. SFC (Supercritical Fluid Chromatography) was carried out on a Thar Analytical SFC machine (column: Chiralpak AD-3 3 μm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar). Anhydrous solvents were pre-treated with 3A Molecular Sieves column before use. All commercially available reagents were used as received unless otherwise stated.

Compound A ($C_{20}H_{20}F_3NO_4$, shown below) is a Stearoyl CoA Desaturase-1 (SCD-1) inhibitor with a molecular weight of 395.4 gm/mol and e log $D_{7.4}$ of 3.4. The drug substance is resistant to chemical racemization, and no polymorphs are detected. It has a moderate melting point of 120.4° C. and low aqueous solubility at 0.02 mg/mL. The API is soluble in variety of polar ketone, alcohol, and glycol solvents (see solubility studies). The synthesis of compound A has been previously described in U.S. Pat. No. 8,242,286 B2 which discloses the aforementioned SCD-1 inhibitor 2-(4-(hydroxymethyl)phenoxy)-1-(3-(2-(trifluoromethoxy)phenoxy)pyrrolidin-1-yl)ethanone.

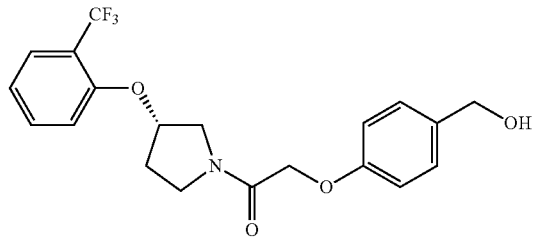 [SMILES: O=C(COc1ccc(CO)cc1)N1CC[C@H](Oc2ccccc2C(F)(F)F)C1]

Compound A
Compound B
General Procedure for Preparation of Intermediate B2

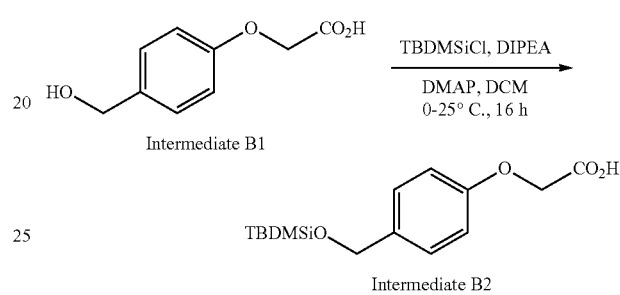

Intermediate B1 (40.0 g, 219 mmol), DIPEA (70.9 g, 548 mmol) and DMAP (10.7 g, 87.8 mmol) were dissolved in DCM (800 mL), then TBDMSiCl (72.8 g, 483 mmol) was added at 0° C. The reaction was stirred at 25° C. for about 16 h until TLC (DCM:MeOH=15:1, $R_f$=0.43) showed no starting material remaining. 5% citric acid (900 mL) was added and the whole was extracted with DCM (3×500 mL). The organic layer was concentrated to give Intermediate B2 (80 g, crude) which was used without further purification for the next step.

General Procedure for Preparation of Intermediate B3

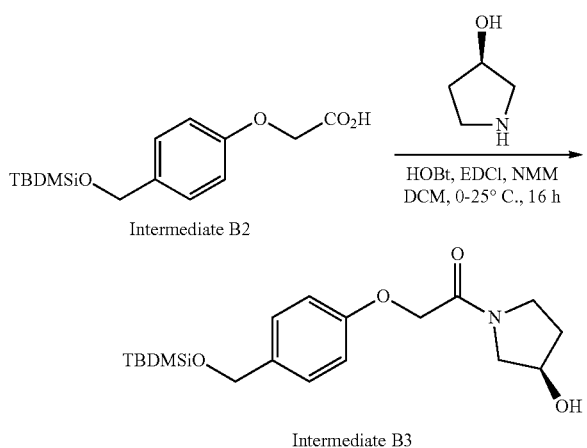

Intermediate B2 (89.0 g, 300 mmol), (3R)-pyrrolidin-3-ol (26.1 g, 300 mmol), HOBt (60.8 g, 450 mmol) and EDCl (86.3 g, 450 mmol) were dissolved in DCM (1.50 L), then NMM (151 g, 1.50 mol) was added at 0° C. The reaction was stirred at 25° C. for 16 h. LC-MS (Intermediate B3: RT=1.56 min) showed Intermediate B2 was completely consumed and the main product peak had the MS of Intermediate B3 (366.20 [M+1]$^+$). The mixture was added to 5% citric acid solution (800 mL) and extracted with DCM (3×500 mL), the organic layer washed with aq. NaHCO$_3$ (500 mL), separated then concentrated in vacuo. The residue was purified by column chromatography (SiO$_2$, 100-200 mesh, gradient elution petroleum ether/ethyl acetate=0:1 starting to 1:0 finishing) to give Intermediate B3 (45.0 g, 92% purity, 100% ee) as white solid.

LCMS: t=1.56 min, MS cal.: 365.20, [M+1]$^+$ 366.20. [a. mobile phase (solvent A: H$_2$O containing 0.0375% TFA; solvent B: Acetonitrile containing 0.018% TFA); gradient: 0.00:90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

HPLC: t=3.42 minutes (92% purity)

SFC: Enantiomeric purity as measured by enantiomeric excess: 100% (column: Chiralpak AD-3 3 μm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar).

General Procedure for Preparation of Intermediate B4

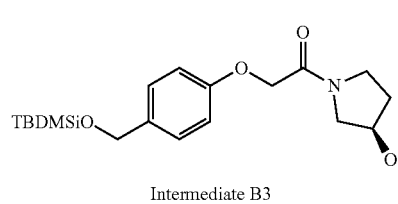

Intermediate B3

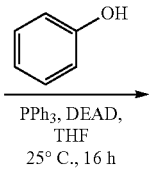

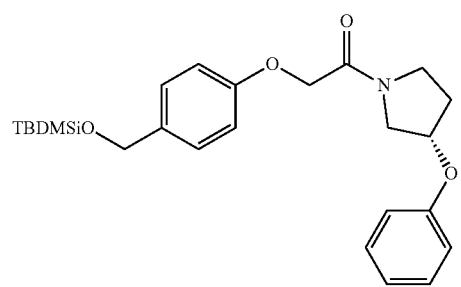

Intermediate B4

Intermediate B3 (5.00 g, 13.6 mmol), phenol (1.93 g, 20.5 mmol), and PPh$_3$ (5.38 g, 20.5 mmol) were dissolved in THF (100 mL), then DEAD (4.77 g, 27.3 mmol) was added at 25° C. The reaction was stirred at 25° C. for 16 h. LCMS (product: RT=1.82 min) showed Intermediate B3 was consumed completely and main peak has the MS (442.3 [M+1]$^+$) of Intermediate B4. The mixture was added to water (100 mL) and extracted with ethyl acetate (3×100 mL), the layers were separated and the organic layer was concentrated in vacuo. The residue was purified by silica gel chromatography (100-200 mesh silica gel, petroleum ether/ethyl acetate=1:0 starting, 3:1 finishing) to give Intermediate B4 (4.00 g, 53.6% yield) as white solid.

LCMS: t=1.82 min, MS cal.: 441.23.08, [M+1]$^+$=442.3, [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

General Procedure for Preparation of Compound B

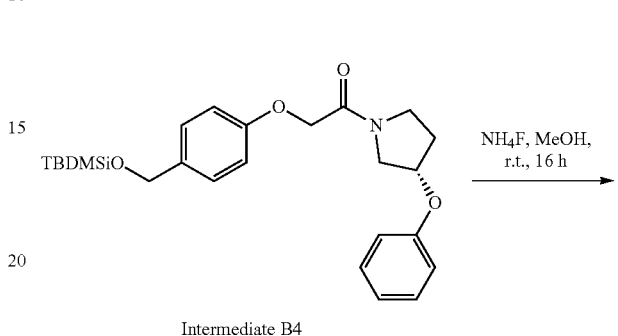

Intermediate B4

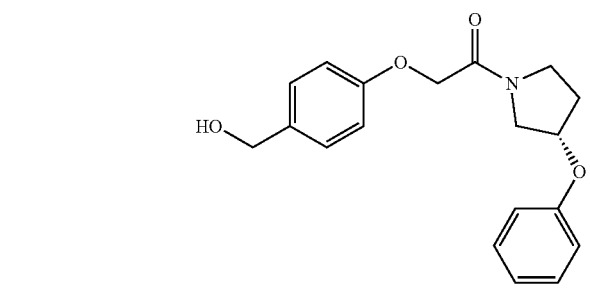

Compound B

Intermediate B4 (4.80 g, 10.8 mmol) and NH$_4$F (8.05 g, 217 mmol) were dissolved in MeOH (10.0 mL). The reaction was stirred at 25° C. for 16 h. LCMS (product as monitored RT=0.72 min) showed the main peak has MS of Compound B, ([M+1]$^+$=328.2). The mixture was directly concentrated. The residue was purified by prep-HPLC (neutral conditions) to give Compound B (1.80 g, 50% yield) as white solid.

LCMS: t=2.78 min, MS cal.: 327.15, ([M+1]$^+$=328.2), [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.28-7.34 (m, 4H), 6.85-6.98 (m, 5H), 4.97 (d, J=24.0 Hz, 1H), 4.63-4.72 (m, 4H), 3.75-3.92 (m, 4H), 2.06-2.38 (m, 2H)

SFC: Enantiomeric purity as measured by enantiomeric excess: 100% (column: Chiralpak AD-3 3 μm, 0.46 cm id×10 cm L, Mobile phase: A for SFC CO$_2$ and B for MeOH (0.05% IPAm), Gradient: B in A from 10% to 40% in 5 minutes, Flow rate: 4.0 mL/min, Wavelength: 220 nm, System Back Pressure: 100 bar).

Compound D

General Procedure for Preparation of Intermediate D1

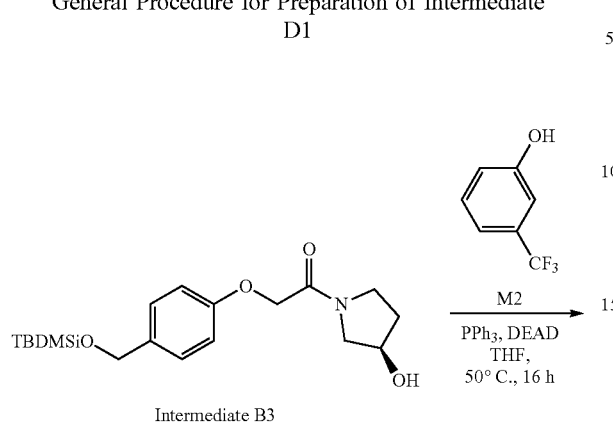

Intermediate B3

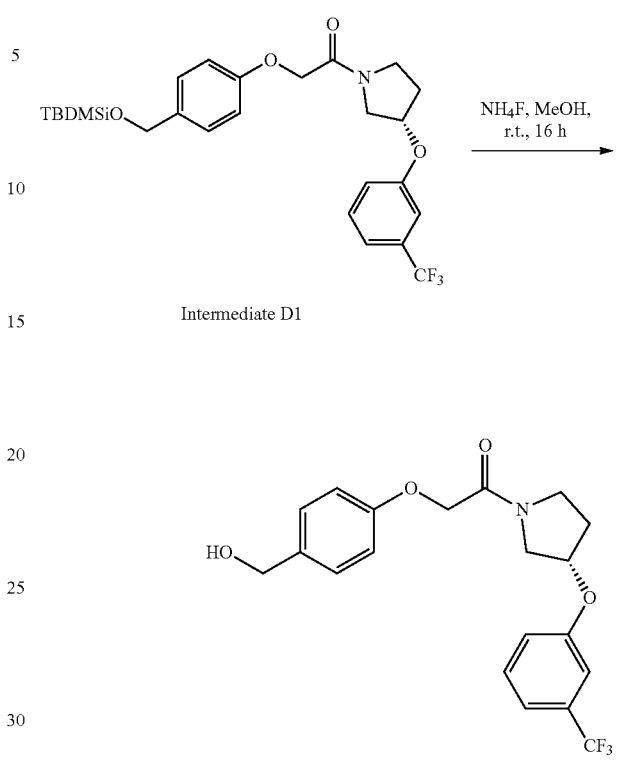

Intermediate D1

To a solution of Intermediate B3 (5.00 g, 13.6 mmol), compound M2 (3.33 g, 20.5 mmol, 2.46 mL) and PPh$_3$ (5.38 g, 20.5 mmol) in THF (100 mL) was added DEAD (4.77 g, 27.3 mmol, 4.96 mL) at 25° C. under N$_2$. The reaction was stirred at 50° C. for 16 h, LCMS showed no remaining Intermediate B3 (no presence of t=1.56 min, [M+1]$^+$ 366.20). The reaction mixture was partitioned between ethyl acetate (3×100 mL) and H$_2$O (100 mL). The organic phase was separated, washed with brine (100 mL), dried over Na$_2$SO$_4$, filtered and concentrated under reduced pressure to give a residue. The residue was purified by silica gel chromatography (100-200 mesh silica gel, petroleum ether/ ethyl acetate=1:0 starting, 10:1 finishing) to afford Intermediate D1 (6.50 g, 75% yield) as colorless oil.

LCMS: t=1.69 min, MS cal.: 509.22, [M+1]$^+$=510.2 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

General Procedure for Preparation of Compound D

To a solution of Intermediate D1 (6.50 g, 12.7 mmol) in MeOH (40.0 mL) was added NH$_4$F (9.45 g, 255 mmol) at 25° C., the reaction was stirred at 25° C. for 16 h. LCMS (monitoring product: RT=1.40 min, [M+1]$^+$=396.2) showed the reaction was complete, the whole was filtered and the organic phase concentrated under reduced pressure to give a residue. The residue was partitioned between ethyl acetate (3×100 mL) and H$_2$O (100 mL). The organic phase was separated, washed with brine (100 mL), dried over Na$_2$SO$_4$, filtered and concentrated under reduced pressure to give a residue, which was purified by prep-HPLC (ET6566-9-P1E, product: RT=2.46 min, condition: TFA) to afford the pure Compound D (1.73 g, 33% yield) as a white solid.

LCMS: t=2.75 min, MS cal.: 395.13, [M+1]$^+$=396.2 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.33-7.43 (m, 1H), 7.26-7.31 (m, 3H), 6.90-7.10 (m, 4H), 5.01 (d, J=22, 1H), 4.62-4.67 (m, 4H), 3.77-3.91 (m, 4H), 2.22-2.36 (m, 2H), 1.93-1.96 (m, 1H)

HPLC: t=2.47 minutes (88% purity)

SFC: Enantiomeric purity as measured by enantiomeric excess: 100% (column: Chiralpak AD-3 3 µm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar).

Compound E

General Procedure for Preparation of Intermediate E1

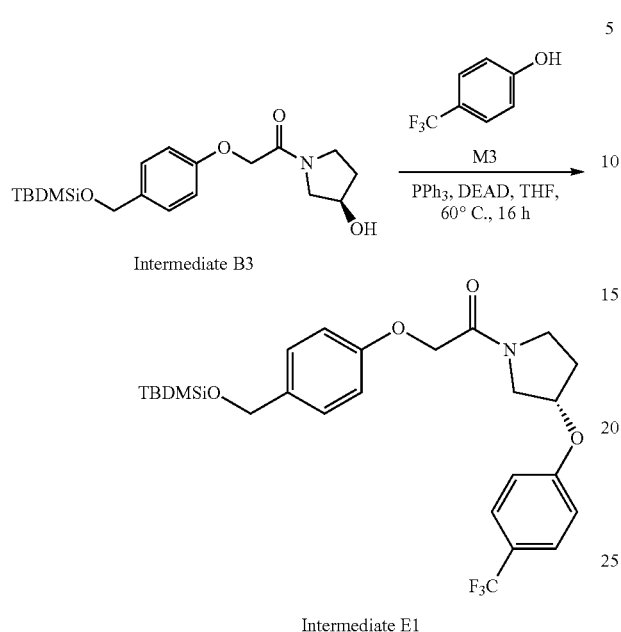

Intermediate B3

Intermediate E1

To a solution of Intermediate B3 (5.00 g, 13.7 mmol), M3 (3.33 g, 20.5 mmol) and PPh$_3$ (5.38 g, 20.5 mmol) in THF (50.0 mL) was added DEAD (4.77 g, 27.3 mmol, 4.96 mL) at 25° C., then the mixture was stirred at 60° C. for 16 h. TLC (ethyl acetate, R$_f$=0.3) showed no remaining Intermediate B3. H$_2$O (50.0 mL) was added, then the whole was extracted with ethyl acetate (3×50.0 mL), and purified by chromatography (100-200 mesh silica gel, petroleum ether/ethyl acetate=30:1 starting to 0:1 finishing) to give Intermediate E1 (2.80 g, 25% yield) as yellow oil.

LCMS: t=1.02 min, MS cal.: 509.22, [M+1]$^+$=510.3 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.45-7.48 (m, 2H), 7.13-7.17 (m, 2H), 6.79-6.85 (m, 4H), 6.81-6.83 (m, 1H), 4.90 (d, J=21.6, 1H), 4.52-4.59 (m, 4H), 3.61-3.81 (m, 4H), 2.11-2.24 (m, 2H), 0.85 (s, 9H), 0.01 (s, 6H)

General Procedure for Preparation of Compound E

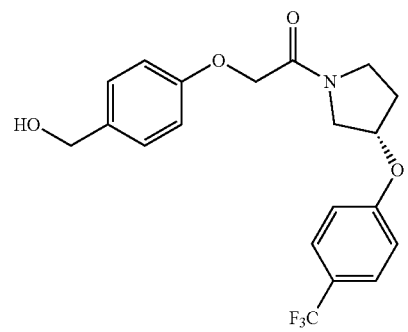

Compound E

To a solution of Intermediate E1 (2.80 g, 5.49 mmol) in MeOH (20.0 mL) was added NH$_4$F (4.07 g, 109 mmol) at 25° C., then the mixture was stirred at 25° C. for 16 hr. TLC (petroleum ether/ethyl acetate=1:1, R$_f$=0.3) showed Intermediate E1 was consumed. The mixture was concentrated, 100 mL of H$_2$O was added and the whole was extracted with ethyl acetate (3×50 mL), the organic layer was washed with brine (100 mL), dried over Na$_2$SO$_4$ and concentrated to give crude product. The crude was purified by prep-HPLC (neutral conditions) to give Compound E (1.10 g, 51% yield) as a white solid.

LCMS: t=2.75 min, MS cal.: 395.13, [M+1]$^+$=396.2 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.51-7.55 (m, 2H), 7.24-7.27 (m, 2H), 6.86-6.94 (m, 4H), 4.99 (d, J=23.2, 1H), 4.60-4.68 (m, 4H), 3.71-3.88 (m, 4H), 2.05-2.33 (m, 2H), 1.62-1.65 (m, 1H)

SFC: Enantiomeric purity as measured by enantiomeric excess: 99.77% (column: Chiralpak AD-3 3 µm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar).

Compound F

General Procedure for Preparation of Intermediate F1

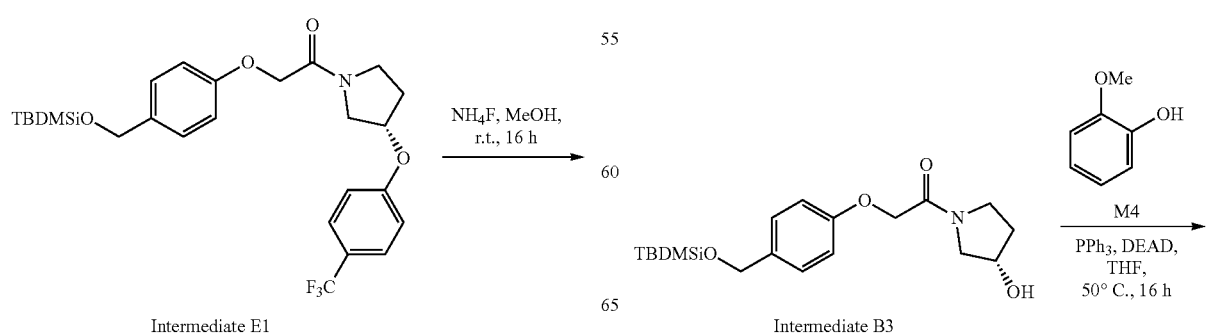

Intermediate B3

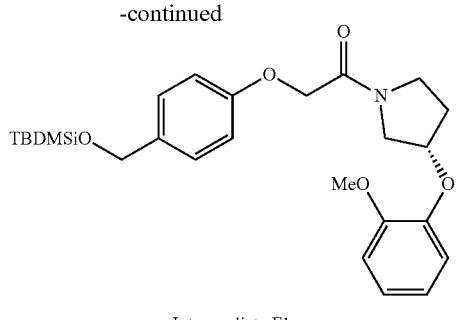

Intermediate F1

To a solution of Intermediate B3 (5.00 g, 13.6 mmol), compound M4 (3.61 g, 20.5 mmol) and PPh$_3$ (5.38 g, 20.5 mmol) in THF (100 mL) was added DEAD (4.77 g, 27.3 mmol, 4.96 mL) at 25° C. under N$_2$. The reaction was stirred at 50° C. for 16 h, upon when TLC (petroleum ether/ethyl acetate=1:1, Rf=0.6) showed the reaction was complete. The reaction mixture was partitioned between ethyl acetate (3×100 mL) and H$_2$O (100 mL). The organic phase was separated, washed with brine (100 mL), dried over Na$_2$SO$_4$, filtered and concentrated under reduced pressure to give a residue. The residue was purified by silica gel chromatography (100-200 mesh silica gel, petroleum ether/ethyl acetate=1:0 starting, 10:1 finishing) to afford Intermediate F1 (6.00 g, 66% yield) as colorless oil.

LCMS: t=0.95 min, MS cal.: 471.24, [M+1]$^+$=473.3 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

General Procedure for Preparation of Compound F

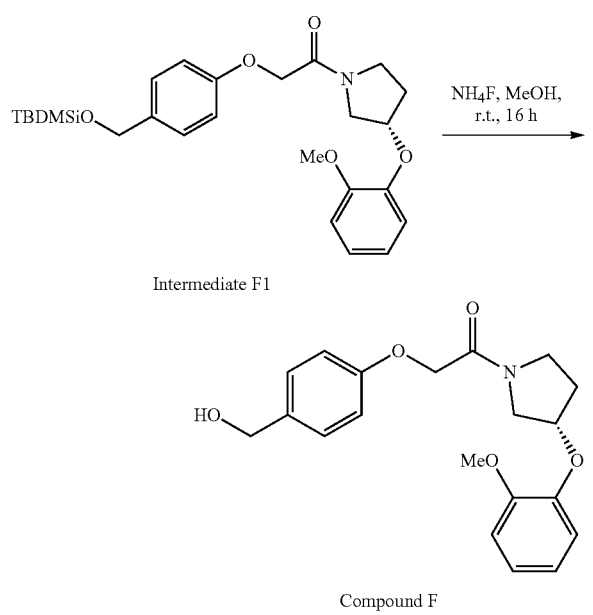

Compound F

To solution of Intermediate B4 (6.00 g, 12.7 mmol) in MeOH (40.0 mL) was added NH$_4$F (9.42 g, 254 mmol) at 25° C., the reaction was stirred at 25° C. for 16 h, LCMS (monitoring product: RT=1.22 min, [M+1]$^+$=358.2) showed the reaction was completed. The whole was filtered and the organic phase was concentrated under reduced pressure to give a residue which was partitioned between ethyl acetate (3×100 mL) and H$_2$O (100 mL). The organic phase was separated, washed with brine (100 mL), dried with Na$_2$SO$_4$, filtered and concentrated under reduced pressure to give a residue. The residue was purified by silica gel chromatography (100-200 mesh silica gel, DCM/MeOH=1:0 starting, 10:1 finishing) to afford Compound F (1.20 g, 25% yield) as a colorless oil.

LCMS: t=2.37 min, MS cal.: 357.16, [M+1]$^+$=358.2 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.23-7.26 (m, 2H), 6.81-6.96 (m, 6H), 4.91 (d, J=25.6, 1H), 4.51-4.60 (m, 4H), 3.62-3.84 (m, 7H), 2.20-2.35 (m, 1H), 1.96-2.10 (m, 2H)

SFC: Enantiomeric purity as measured by enantiomeric excess: 100% (column: Chiralpak AD-3 3 μm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar).

Compound G

General Procedure for Preparation of Intermediate G1

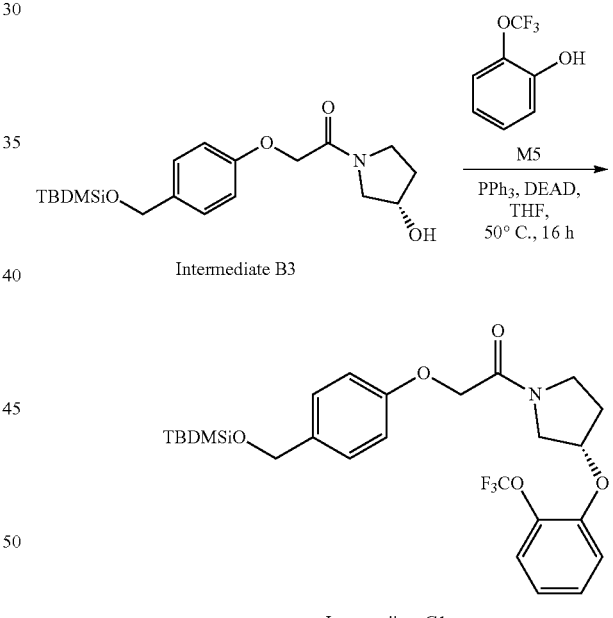

Intermediate G1

Intermediate B3 (5.00 g, 13.6 mmol), MS (2.44 g, 13.6 mmol) and PPh$_3$ (5.38 g, 20.5 mmol) were dissolved in THF (100 mL), then DEAD (4.77 g, 27.3 mmol) was added at 0° C. The reaction was stirred at 50° C. for 16 h. The mixture was detected by TLC (petroleum ether/ethyl acetate=1:1, R$_f$=0.51) and showed Intermediate B3 was consumed. The mixture was added water (50.0 mL), extracted with ethyl acetate (3×100 mL) and the organic layer was concentrated. The residue was purified by silica gel chromatography (100-200 mesh silica gel, petroleum ether/ethyl acetate=1:0 starting, 3:1 finishing) to give Intermediate G1 (4.00 g, 51% yield) as white solid.

General Procedure for Preparation of Compound G

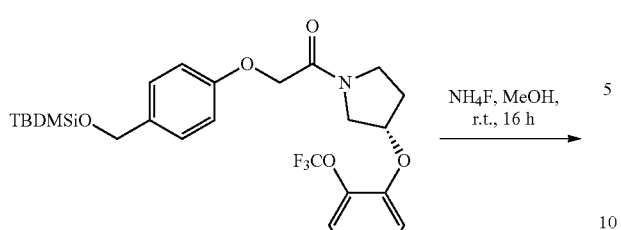

Intermediate G1

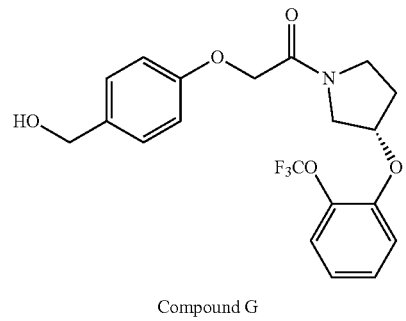

Compound G

Intermediate G1 (3.40 g, 6.47 mmol) and NH$_4$F (4.79 g, 129 mmol) were dissolved in MeOH (100 mL). The reaction was stirred at 25° C. for 16 h. LC-MS (monitoring product: RT=0.78 min, [M+1]$^+$=412.2) showed the main product peak had MS of Compound G. The mixture was directly concentrated. The residue was washed with hexane (20.0 mL) and filtered to give Compound G (1.20 g, 43% yield) as white solid.

LCMS: t=2.70 min, MS cal.: 411.13, [M+1]$^+$=412.1 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: (CDCl$_3$, 400 MHz): δ 7.26-7.32 (m, 4H), 6.92-6.97 (m, 4H), 5.00 (d, J=16.8 Hz, 1H), 4.58-4.66 (m, 4H), 3.69-3.93 (m, 4H), 2.06-2.41 (m, 2H), 1.90 (br, 1H)

SFC: Enantiomeric purity as measured by enantiomeric excess: 100% (column: Chiralpak AD-3 3 μm, 0.46 cm id×10 cm L, Mobile phase: A for SFC CO2 and B for MeOH (0.05% IPAm), Gradient: B in A from 10% to 40% in 5 minutes, Flow rate: 4.0 mL/min, Wavelength: 220 nm, System Back Pressure: 100 bar).

Compound H

General Procedure for Preparation of Intermediate H1

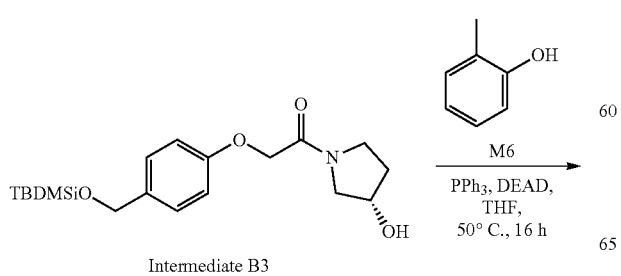

Intermediate B3

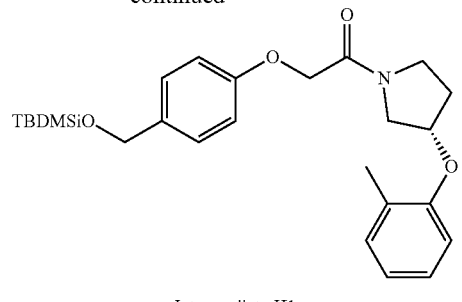

Intermediate H1

To a solution of Intermediate B3 (5.00 g, 13.6 mmol), compound M6 (2.22 g, 20.5 mmol, 2.13 mL) and PPh$_3$ (5.38 g, 20.5 mmol) in THF (100 mL) was added DEAD (4.77 g, 27.3 mmol, 4.96 mL) at 25° C. under N$_2$, and the reaction was stirred at 50° C. for 16 h. TLC (petroleum ether/ethyl acetate=1:1, R$_f$=0.6) showed the reaction was complete. The reaction mixture was partitioned between ethyl acetate (3×100 mL) and H$_2$O (100 mL). The organic phase was separated, washed with brine (100 mL), dried over Na$_2$SO$_4$, filtered and concentrated under reduced pressure to give a residue. The residue was purified by silica gel chromatography (100-200 mesh silica gel, petroleum ether/ethyl acetate=1:0 starting, 10:1 finishing) to afford Intermediate H1 (3.80 g, 53% yield) as colorless oil.

LCMS: t=1.69 min, MS cal.: 455.25, [M+1]$^+$=456.2 [a. mobile phase (solvent A: H$_2$O containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

General Procedure for Preparation of Compound H

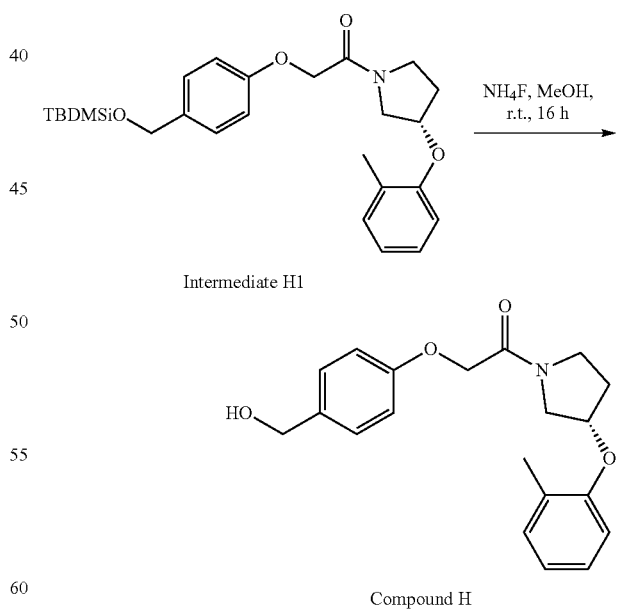

To a solution of Intermediate H1 (3.80 g, 8.34 mmol) in MeOH (40.0 mL) was added NH$_4$F (6.18 g, 166 mmol) at 25° C., and the reaction was stirred at 25° C. for 16 h. LCMS (monitoring product: RT=1.11 min, [M+1]$^+$=342.2) showed the reaction was complete. The whole was filtered and the organic phase was concentrated under reduced pressure to give a residue, which was partitioned between ethyl acetate (3×100 mL) and $H_2O$ (100 mL). The organic phase was separated, washed with brine (100 mL), dried over $Na_2SO_4$, filtered and concentrated under reduced pressure to give a residue, which was purified by HPLC purification to afford the pure Compound H (1.10 g, 38% yield) as colorless oil.

LCMS: t=2.60 min, MS cal.: 341.16, $[M+1]^+$=342.2 [a. mobile phase (solvent A: $H_2O$ containing 0.0375% TFA; solvent B: Acetonitrile containing 0.018% TFA); gradient: 0.00: 90% A; 0.40: 90% A; 3.40: 0% A; 3.85: 0% A; 3.86: 90% A; 4.50: 90% A; flow rate: 0.8 mL/min; column: Venusil XBP-C18; column temperature: 50° C.].

$^1$H NMR: ($CDCl_3$, 400 MHz): δ 7.28-7.33 (m, 2H), 7.15-7.17 (m, 2H), 6.91-6.98 (m, 3H), 6.81-6.83 (m, 1H), 4.99 (d, J=25.6, 1H), 4.63-4.69 (m, 4H), 3.75-3.91 (m, 4H), 2.09-2.38 (m, 5H), 1.69-1.71 (m, 1H)

SFC: Enantiomeric purity as measured by enantiomeric excess: 100% (column: Chiralpak AD-3 3 µm, 0.46 cm id×10 cm L, Mobile phase: A for SFC $CO_2$ and B for MeOH (0.05% IPAm), Gradient: B in A from 10% to 40% in 5 minutes, Flow rate: 4.0 mL/min, Wavelength: 220 nm, System Back Pressure: 100 bar).

Figure 1B:
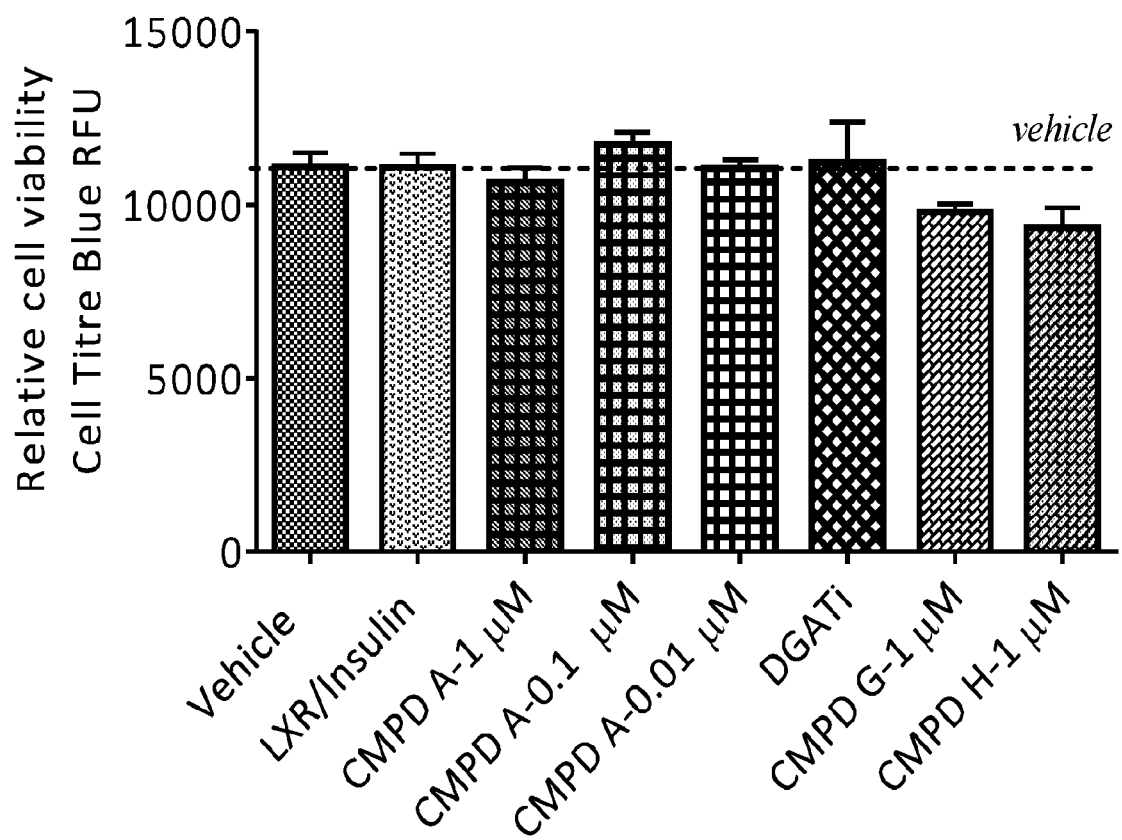

Example 2: Inhibition of Neutral Lipid Accumulation in Primary Human Sebocytes Human primary sebocytes (Zenbio, RTP, NC) were cultured (10,000 cells/well) in black clear bottom 96-well plates and allowed to reach confluence. Once the cells reached confluence the growth medium was removed and replaced with medium containing compounds and controls together with an agonist of the Liver X receptor (LXR) T0901317 (1 µM) and insulin. An inhibitor of acyl-CoA diacylglycerol acyltransferase inhibitor (DGATi) A922500 (2 µM) was included as a positive control. The cells were re-dosed with fresh treatments every 24 hours. After three days, medium was removed and replaced with 100 µl of Nile Red in PBS at a concentration of 1 µg/ml and the cells allowed to incubate for 30 minutes at 37° C., 5% $CO_2$. After 30 minutes, the Nile red was removed and replaced with 50 µl of PBS. The relative fluorescence (RFU) of the incorporated stain was determined under 2 parameters: 540ex/620em with no cutoff (Total Lipid), and 485ex/555em with a 515 cutoff (Neutral Lipid). Compound A dose-dependently reduced neutral lipid in three different sebocyte donors. FIG. 1 shows a representative experiment from a single donor in which Compound A reduced LXR/insulin stimulated neutral lipid accumulation with an $EC_{50}$ of 70 nM.

Figure 2:
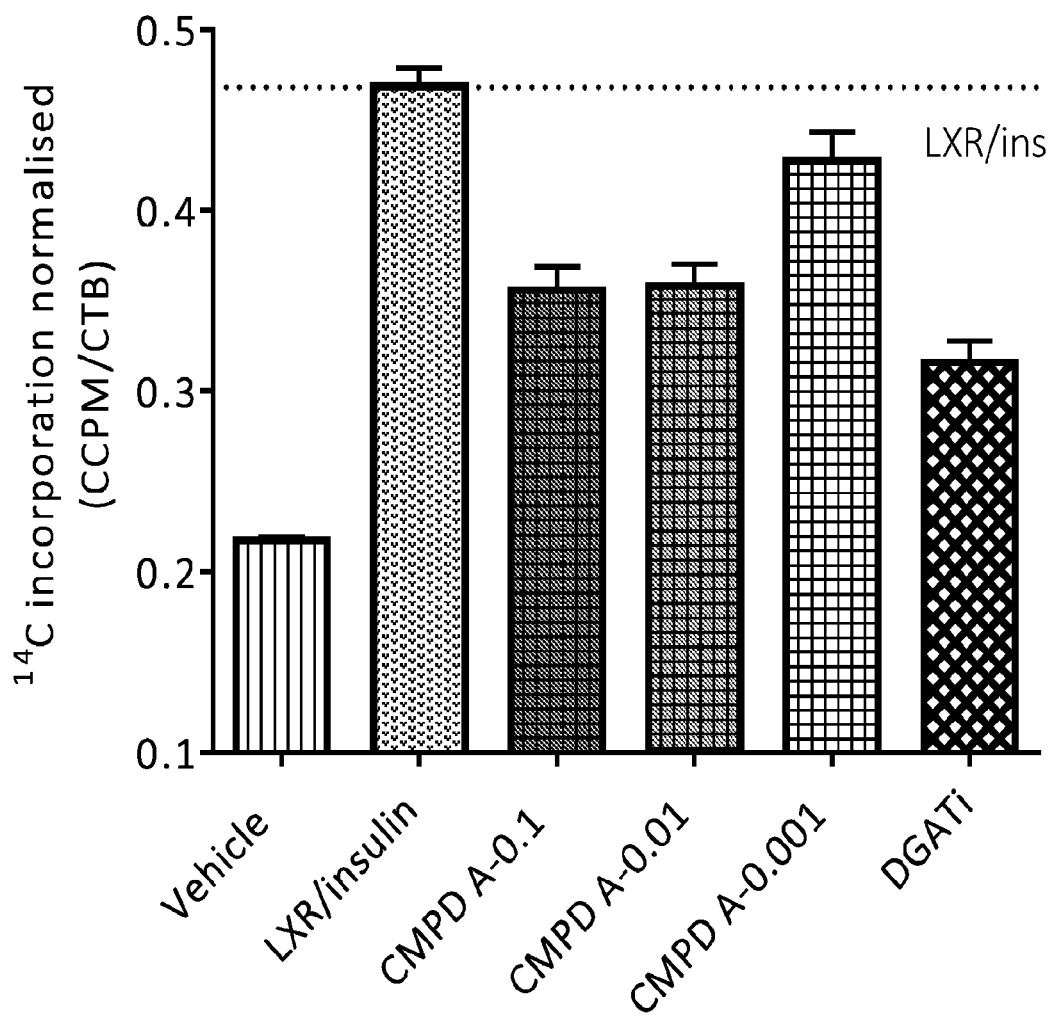
FIG. 2 shows incorporation of $^{14}$C-acetate into human sebocytes as a measure of de novo lipogenesis following incubation of sebocytes with Compound A at the concentrations indicated in the presence of the LXR agonist and insulin. Data shown is from a single experiment as mean±s.e.m. with each point in quadruplicate.

Example 3: Inhibition of $^{14}$C Acetate Incorporation in Primary Human Sebocytes Human primary sebocytes (Zenbio, RTP, NC) were plated at confluence on 96 well Scintiplates and allowed to adhere overnight. Cells were treated with the SCD1 inhibitor Compound A prepared in media containing the LXR agonist and insulin and cultured overnight. The DGAT inhibitor A922500 (2 µM) was included as a positive control. The following day $^{14}$C-acetate was added to each well and the plate was gently mixed. Cells were placed in the incubator at 37° C. for 4 hours total. After 2 hours of incubation the Cell Titer Blue (CTB) assay was started, 10 µl of CTB reagent was added to each well and incubated for the remaining 2 hours at 37° C. Following the 4 hour incubation, the RFU was determined using the SpectraMax Gemini EM under the following parameters: 560ex/590em with a 570 cutoff, top read. The medium was removed and cells were washed 3× with PBS. All of the PBS was removed from the wells and the plates were allowed to air dry. The plate was read in the MicroBeta TriLux counter and data was analyzed as CPM and normalized to CTB readout. Data is shown in FIG. 2.

Example 4: Cytotoxicity of SCD1 Inhibitors in Mouse Melanoma Cells

Figure 3:
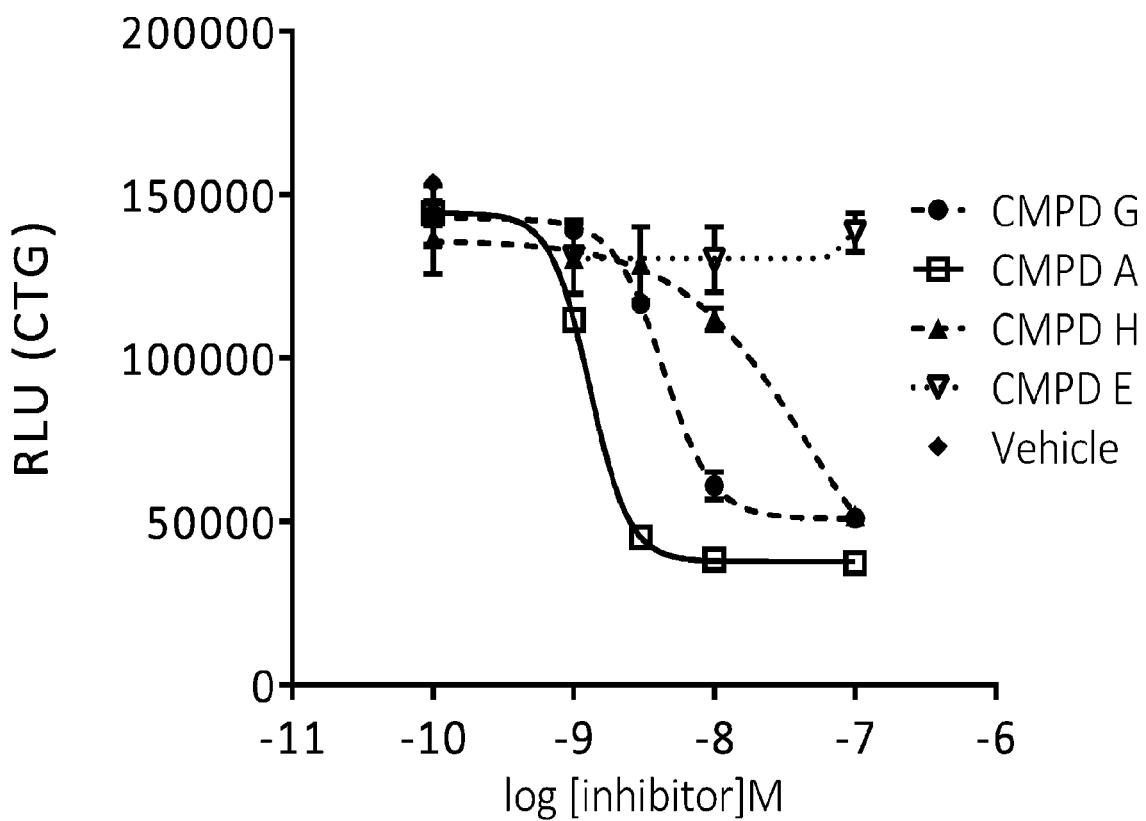
FIG. 3 shows that SCD1 inhibition results in cytotoxicity of B16F10 mouse melanoma cells. Quantitation of cell viability using CellTiter-Glo following 48 h treatment with vehicle, Compound A, Compound E, Compound G or Compound H. Data is shown as mean relative luminescence units (RLU)±StDev.

Mouse melanoma cells (B16F10) (American Type Culture Collection (ATCC), Manassas, VA) were cultured in Dulbecco's minimal essential media (DMEM) containing 10% fetal bovine serum, (Thermofisher, Waltham, MA). Cells were plated at a density of 5,000 cells per well into a 96-well plate and allowed to attach for 24 h in a 37° C. humidified incubator with a 5% $CO_2$ atmosphere. Media was replaced with that containing test agents or vehicle (0.1% dimethylsulphoxide) and cells incubated for a further 48 h. Cell viability was assessed using CellTiter-Glo® (Promega). Incubation of cells with compound A and analogs compound G and compound H resulted in dose-dependent increases in cytotoxicity (FIG. XX3). Analog compound E did not reduce the viability of the cells up to 100 nM. FIG. 3 shows a representative experiment where the $EC_{50}$ of compounds A, G and H for cytotoxicity was 1.3 nM, 4.3 nM and 46 nM respectively.

Figure 4:
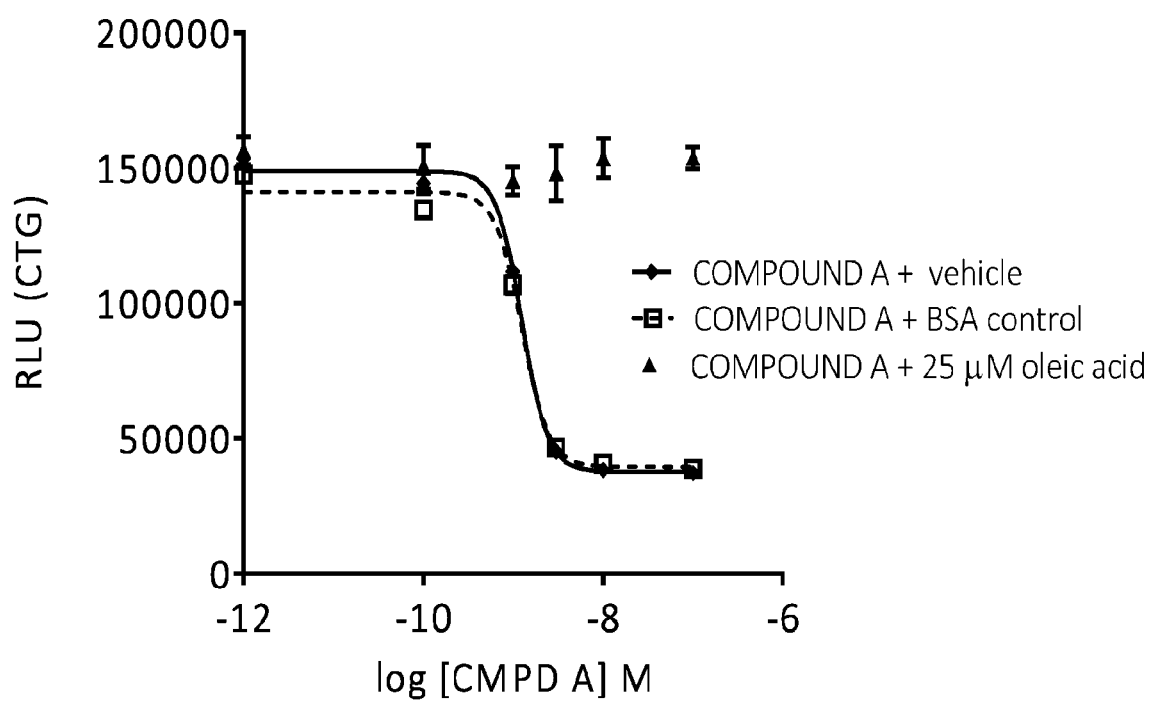
FIG. 4 shows that oleic acid prevents the cytotoxicity of Compound A. Co-incubation of B16F10 cells with Compound A in the presence of 25 μM oleic acid prevents the cytotoxicity. Data is shown as mean relative luminescence units (RLU)±StDev.

The effect of co-incubation with oleic acid, the product of the SCD1 mediated desaturation of stearic acid is shown in FIG. 4. An oleate-bovine serum albumin (BSA) conjugate was prepared by dissolving sodium oleate to 100 mM in methanol. The oleate was diluted to 20 mM with PBS and further diluted 1:1 with 30% fatty acid free albumin and incubated overnight at 37° C. The solution was sterile filtered prior to treating cells. The BSA control was prepared in the same manner, without the fatty acid. The presence of oleic acid at 25 µM in the media prevented the cytotoxic effect of compound A (FIG. 4), compound G and compound H (not shown). Non-linear regression analysis was performed using GraphPad PRISM®.

Figure 5:
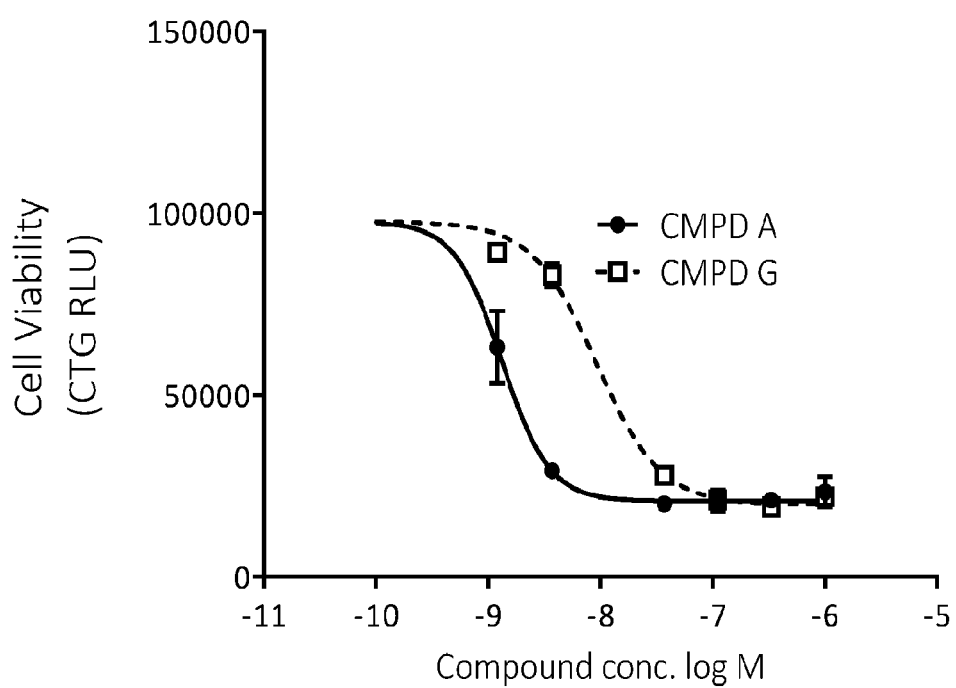
FIG. 5 shows that SCD1 inhibition results in cytotoxicity of HSC-1 human squamous carcinoma cells. Quantitation of cell viability using CellTiter-Glo following 72 h treatment with COMPOUND A OR COMPOUND G. Data is shown as mean relative luminescence units (RLU)±StDev (n=2-4).

Example 5: Cytotoxicity of SCD1 Inhibitors in Human Squamous Carcinoma Cells The human skin squamous carcinoma line (HSC) (Japanese Collection of Research Bioresources Cell Bank (JCRB)) was cultured in Dulbecco's minimal essential media (DMEM) containing 20% fetal bovine serum (FBS), (Thermofisher, Waltham, MA). Cells were plated at a density of 5,000 cells per well into a 96-well plate and allowed to attach for 24 h in a 37° C. humidified incubator with a 5% $CO_2$ atmosphere. Media was replaced with that containing test agents or vehicle (0.1% dimethylsulphoxide) in 1% FBS and cells incubated for a further 72 h. Cell viability was assessed using CellTiter-Glo® (Promega). Non-linear regression analysis was performed using GraphPad PRISM®. FIG. 5 shows a representative experiment where the $EC_{50}$ of COMPOUND A, was 5.2 nM and that of COMPOUND G was 9.2 nM.

Example 6: Cytotoxicity of SCD1 Inhibitors in Human Colon Cancer Cells

Figure 6A:
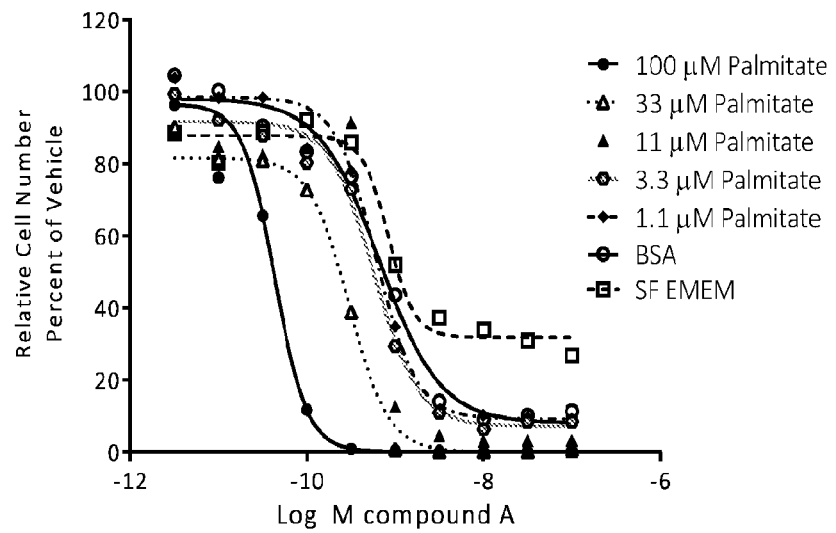
FIG. 6A-B show that addition of palmitate increases potency of Compound A for inhibiting viability of HCT-116 cells. HCT-116 cells in serum-free media were treated with COMPOUND A at concentrations indicated for 96 h in the presence of palmitate. (A) Dose-response curves of relative number of cells in compound A-treated wells as % of those in vehicle-treated wells. Table shows the $EC_{50}$ of COMPOUND A for decreasing relative cell number in the presence of different concentrations of palmitate (B) Relative number of cells in wells treated with palmitate only for 96 h. These data show that SCD1 inhibition with Compound A results in cytotoxicity of HCT-116 cells and that addition of palmitate increases potency of Compound A for inhibiting viability of HCT-116 cells
Figure 6B:
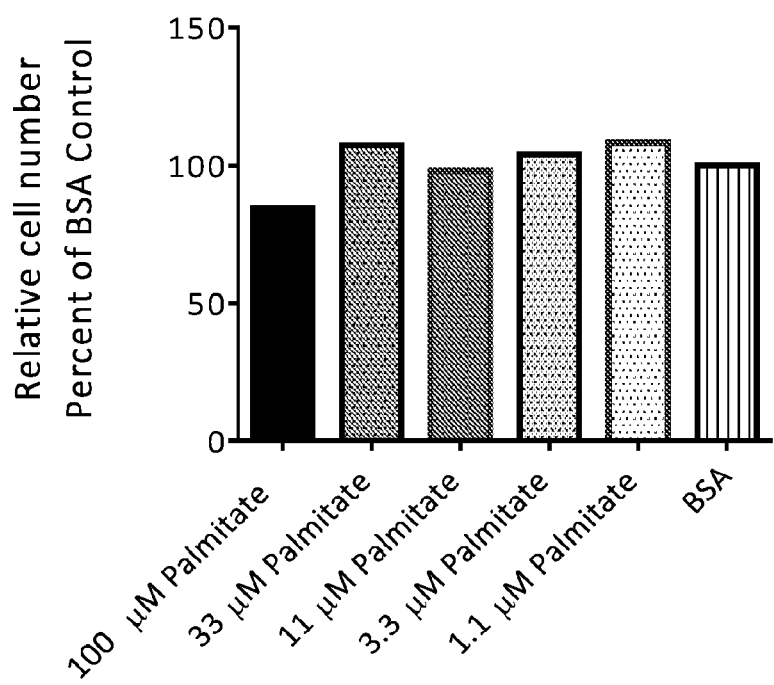
Figure 7:
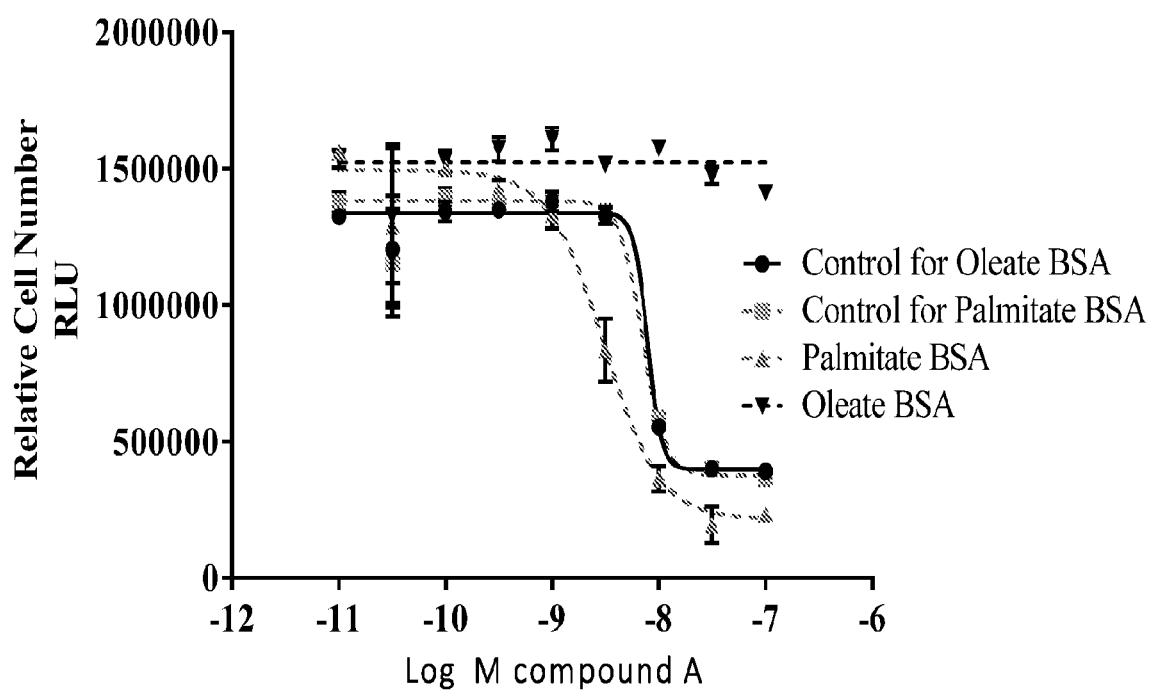
FIG. 7 shows that the potency of Compound A on HCT-116 cell viability is altered in the presence of exogenous substrate (palmitate) or product (oleate). Data is shown as dose-response curves of relative cell number.

Human colon cancer HCT-116 cells (ATCC (Manassas, VA, U.S.A.)) were plated at 20,000 cells/cm² in a 96-well the day prior to the start of the study (Day −1) in McCoys modified media 5A (Sigma-Aldrich (St. Louis, MO, U.S.A.)) containing 10% FCS. At the start of the study (Day 0) Compound A at concentrations from 1 μM to 100 nM or vehicle (0.1% DMSO final) was added to cells as indicated in serum-free McCoy's 5A media in the presence or absence of palmitate (FIG. 6) or with either palmitate or oleate and respective controls (FIG. 7). Sodium palmitate or oleate was conjugated to BSA for use in experiments. Palmitate-BSA conjugate was prepared by dissolving sodium palmitate to 100 mM in 200 proof ethanol. The palmitate was diluted to 20 mM with D-PBS. The palmitate was then further diluted 1:1 with 30% fatty acid free albumin and incubated overnight at 37° C. The solution was then sterile filtered with a 0.22 micron syringe filter prior to treating cells. The BSA control was prepared in the same manner, without the fatty acid. Sodium oleate was dissolved to 100 mM in methanol prior to dilution in the same manner as palmitate. Following 96 h of incubation (Day 4) the number of cells present in each well was assessed using Cell-titre Glo™. Cell-titre Glo™ was diluted 1:1 in serum free McCoy's 5A media. 50 μl of diluted Cell-titre Glo™ was added to each well and the plate contents mixed by placing on a plate shaker at 400 r.p.m. for 5 min prior to reading the luminescence on an i3 SpectraMax plate reader. Compound A inhibited the relative HCT-116 cell number in a concentration-dependent manner with a $EC_{50}$ of 838 μM (FIG. 6A). The potency of Compound A in reducing the relative HCT-116 cell number increased in the presence of increasing concentrations of palmitic acid. Palmitate alone had no effect on relative cell number (FIG. 6B). FIG. 7 shows concentration-dependent reductions in relative HCT-116 cell number per well with Compound A in the presence of 25 μM oleate or palmitate and respective controls. The $EC_{50}$ of Compound A in reducing relative cell number increased from 7.1 nM in the presence of the palmitate control to 3.1 nM with 25 μM palmitate. While the $EC_{50}$ of Compound A for the reduction in relative cell number was 7.9 nM in the presence of the oleic acid control, the presence of 25 μM oleate completely prevented the cytotoxicity of Compound A. These data demonstrate that inhibition of SCD1 with Compound A results in cytotoxicity to HCT-116 cells, consistent with studies reducing SCD1 activity using siRNA or another SCD1 inhibitor (Mason et al. 2012). Compound A and active analogs may therefore have the potential as anti-cancer agents particularly in colon cancer. The observed decrease in potency of Compound A in reducing HCT-116 relative cell number in the presence of increased product, Oleic acid supports the inhibition of SCD1 as the mechanism of action. The finding that increasing the concentration of one of the substrates for SCD1, Palmitate, tends to increase the potency of COMPOUND A for HCT-116 cytotoxicity suggests that compound A may act uncompetitively. It is possible that diet therefore may affect the potency of Compound A as a therapeutic in the treatment of colon cancer.

Example 7: Melanin Production in B16F10 Melanoma Cells

Figure 8A:
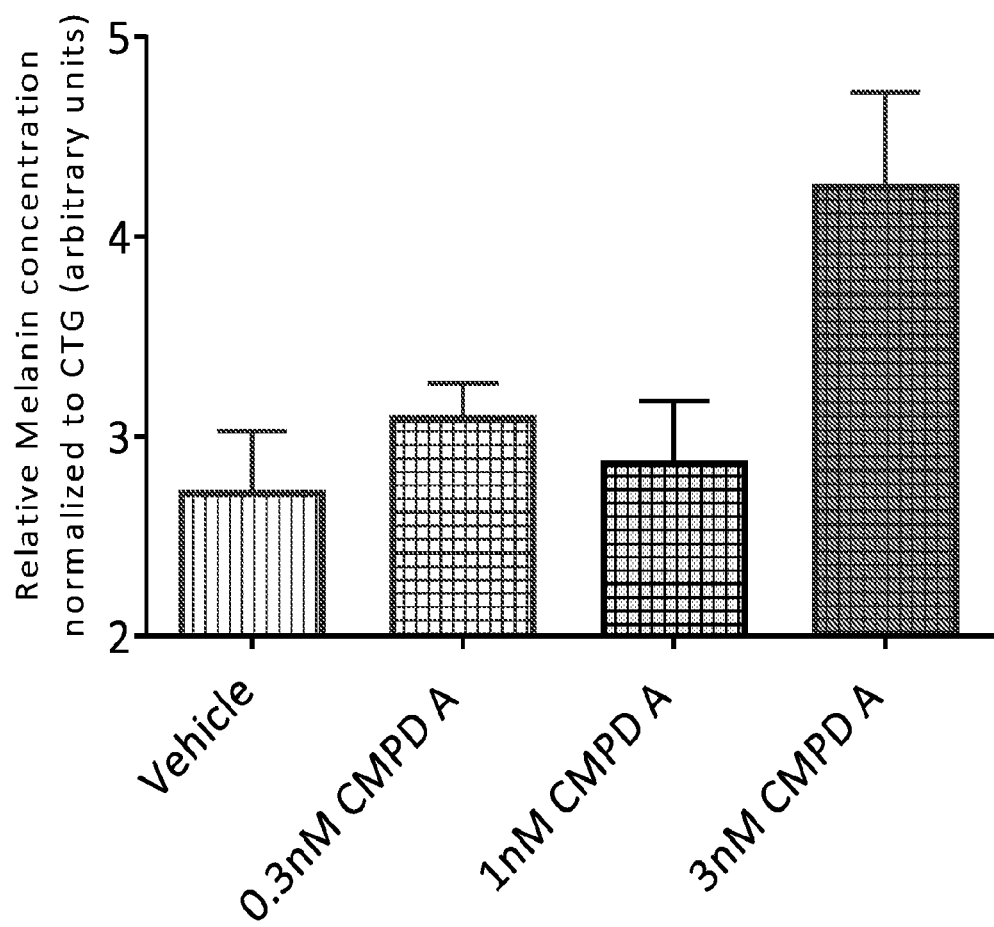
FIG. 8 shows the increase in melanin following SCD1 inhibition in B16F10 cells. B16F10 cells were treated with Compound A, Compound E, Compound G or Compound H at concentrations indicated and melanin determined (A) Normalization to manual cell counting, (B) Normalized to number of viable cells using CellTitre Glo®. Data is shown as mean±StDev.
Figure 8B:
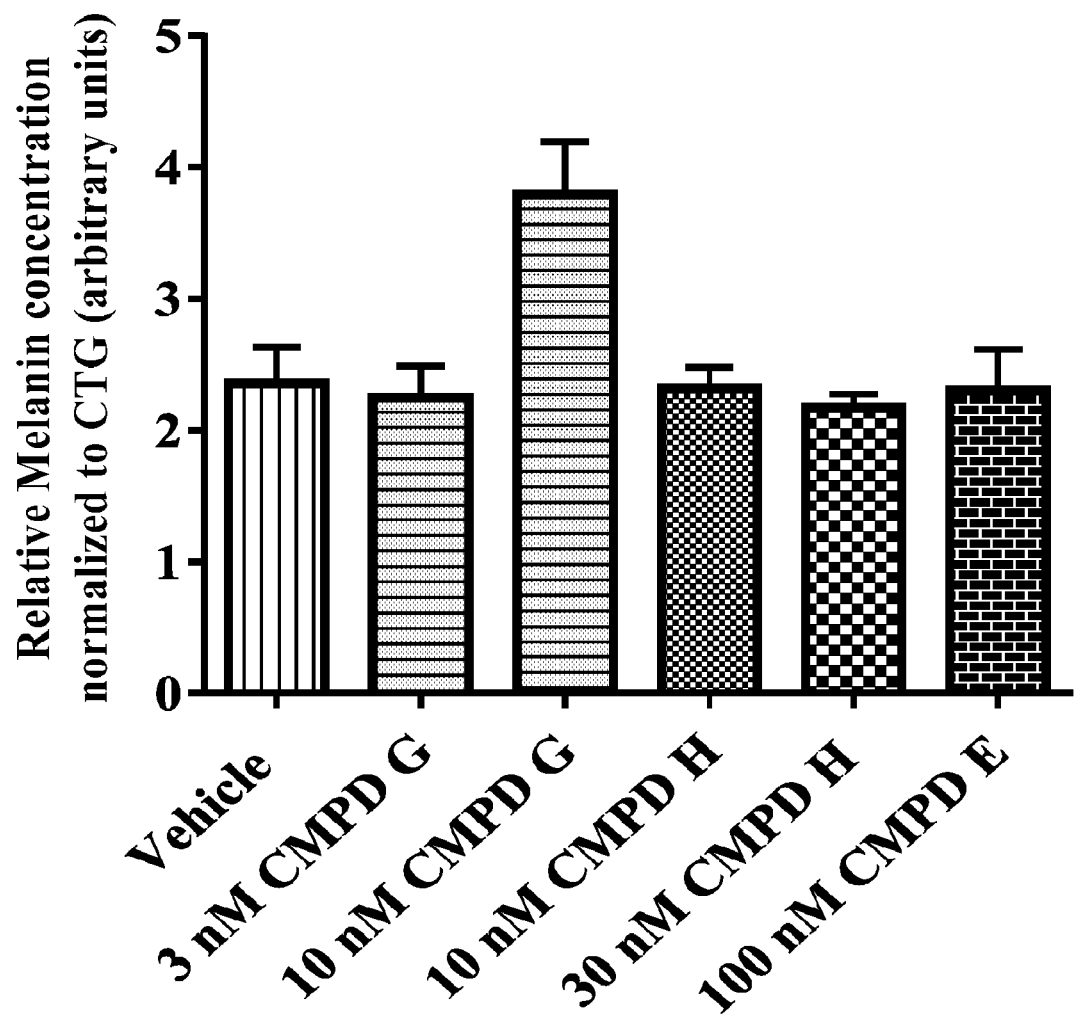

B16F10 cells were plated at 150,000 cells per well into a 6-well plate and allowed to attach for 24 h in a 37° C. humidified incubator with a 5% $CO_2$ atmosphere. Media was replaced with that containing test agents or vehicle (0.1% DMSO) and cells incubated for a further 48 h. Wells were washed once with PBS and cells removed by trypsinization and transferred to eppendorf tubes. Tubes were centrifuged at 1000 g for 10 minutes and the cell pellet resuspended in 0.5 mls PBS. Since compound A and analogs caused a reduction in cell viability the relative cell number per well was determined by taking an aliquot of the cell suspension in PBS and using CellTiter Glo® to determine the relative number of viable cells (Figure XX5). The PBS/cell suspension was centrifuged at 1000 g for 10 mins and the cell pellet resuspended in 1N NaOH/10% DMSO (v/v) and the tubes heated in a dry heating block at 80° C. with occasional vortexing to mix. In parallel a standard curve of melanin was prepared in 1N NaOH/10% DMSO using Sepia melanin (Sigma, St. Louis, MO) and standards also heated at 80° C. for 1 h. Samples and standards were centrifuged at 3000 g for 5 minutes and aliquots of the supernatant transferred to a 96-well plate for determination of melanin using Abs 475 nm. Melanin cellular content was interpolated from a standard curve and corrected based on the relative cell number in the sample. FIG. 8 shows representative experiments in which treatment of cells with 3 nM COMPOUND A and 10 nM COMPOUND G resulted in an increase in melanin.

Brief Discussion of Examples 2 Through 7

Compound A and analogs have the potential to treat a variety of cancers. Tumor cells are heavily dependent on lipid for their survival. A significant body of recent work has supported the role of SCD1 in the growth and survival of tumor cells of many origins. Furthermore, knockdown of SCD1 activity is cytotoxic to tumor cells, but not to non-transformed cells (Minville-Walz 2010) or to human primary sebocytes (see for example FIGS. 1 and 2) or adipocytes (not shown). Compounds A, G and H were cytotoxic to a mouse melanoma cell line and a human squamous cell carcinoma line. Compound A was cytotoxic to a human colon carcinoma line, moreover the cytotoxicity was reduced by adding exogenous oleic acid. Topical or subcutaneously injected compound A, G or H for melanoma and/or squamous cell carcinoma or Actinic Keratosis (a precursor to squamous cell carcinoma) could provide an effective therapy to the disease. Saturated fatty acids are activators of key steps in the melanin synthesis pathway. The potential treatment of skin diseases associated with decreased melanogenesis with topically applied SCD1 inhibitors, such as compounds A and G, is supported by studies showing increased melanin content in the mouse melanoma cells line B16F10. Thus inhibition of SCD1 with compounds such as compound A and G could also serve as a novel treatment for diseases of hypopigmentation such as vitiligo.

Example 8: Inhibition of Primary Human Adipocyte Differentiation

Figure 9:
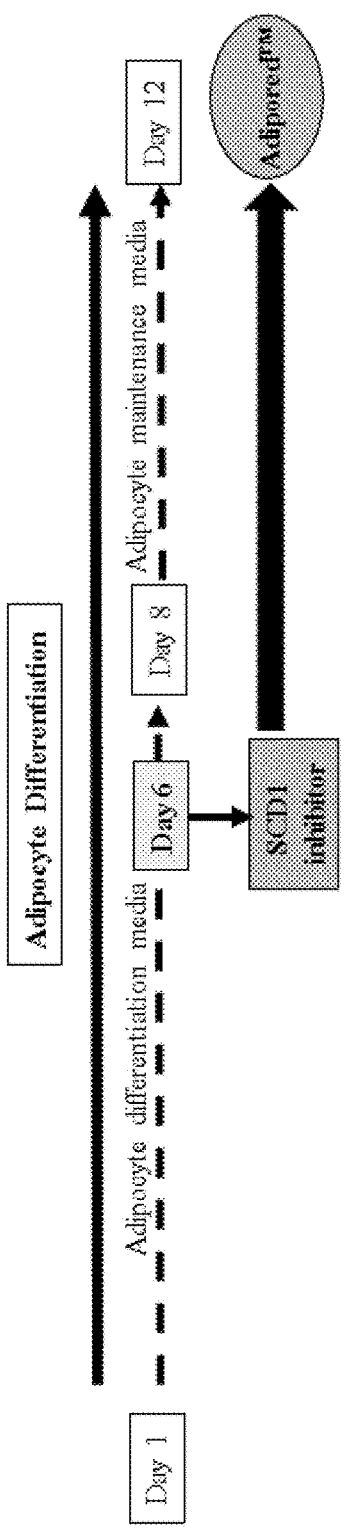
FIG. 9 shows a schematic of the protocol for determining effects of SCD1 inhibitors on adipocyte lipid accumulation in human primary differentiating adipocytes

Human subcutaneous pre-adipocytes (Zenbio (RTP, NC, U.S.A.)) were received pre-plated in white-walled 96-well plates. A schematic description of the protocol used for examining the effects of Compound A on lipid accumulation in differentiating human adipocytes is shown in FIG. 9. Upon arrival of cells (Day 1) 150 μL media in the wells was replaced with adipocyte differentiation media (Zenbio (RTP, NC, U.S.A.)). The following day media was replaced as described for Day 1. Media was subsequently replaced as described every two to three days. On Day 6, 150 μL of the adipocyte differentiation media was replaced with vehicle (0.1% DMSO), or the SCD1 inhibitors at the concentrations indicated. After two days (Day 8) 150 μL media was replaced with 150 μL adipocyte maintenance media containing vehicle (0.1% DMSO) or the SCD1 inhibitors at the concentrations indicated as described above. Following a further four days of incubation (Day 12) cells were stained with AdipoRed™ (Lonza Bioscience (Walkersville, MD, U.S.A.)) according to the manufacturer's instructions. Cytotoxicity following incubation of adipocytes with Compound A was determined in separate wells, not used for Adipored™ staining, and was measured using CellTiter-Glo® (Promega (Madison, WI)) according to the manufacturer's instructions. Following a 10 min room temperature incubation the luminescence measured as relative light units (RLU) was determined in a luminescent plate reader. For adipocytes treated with concentrations of 1.2-100 nM Compound A for 6 days, cell viability as determined by RLU following CellTiter-Glo® remained greater than 75% of the value obtained with vehicle-treated adipocytes. The RLU dropped to 72% of vehicle in adipocytes treated with 1 µM Compound A (data not shown). These findings indicate that the decrease in lipid accumulation in the differentiating primary human adipocytes following Compound A treatment is not associated with cytotoxicity at least up to 100 nM Compound A.

Figure 10:
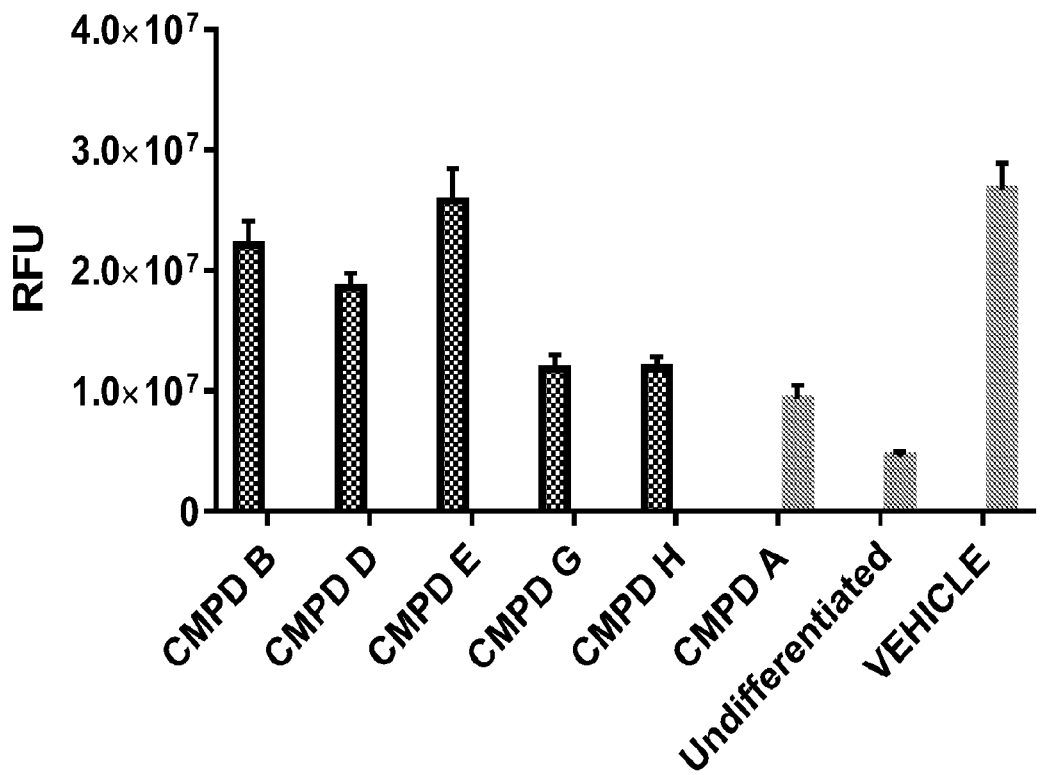
FIG. 10 shows the inhibition of lipid accumulation with Compounds A, B, D, E, G and H at 100 nM. Inhibition of lipid accumulation in differentiating primary human adipocytes following six days of exposure. Data is shown as mean RFU±STDev. (n=3 replicates).
Figure 11:
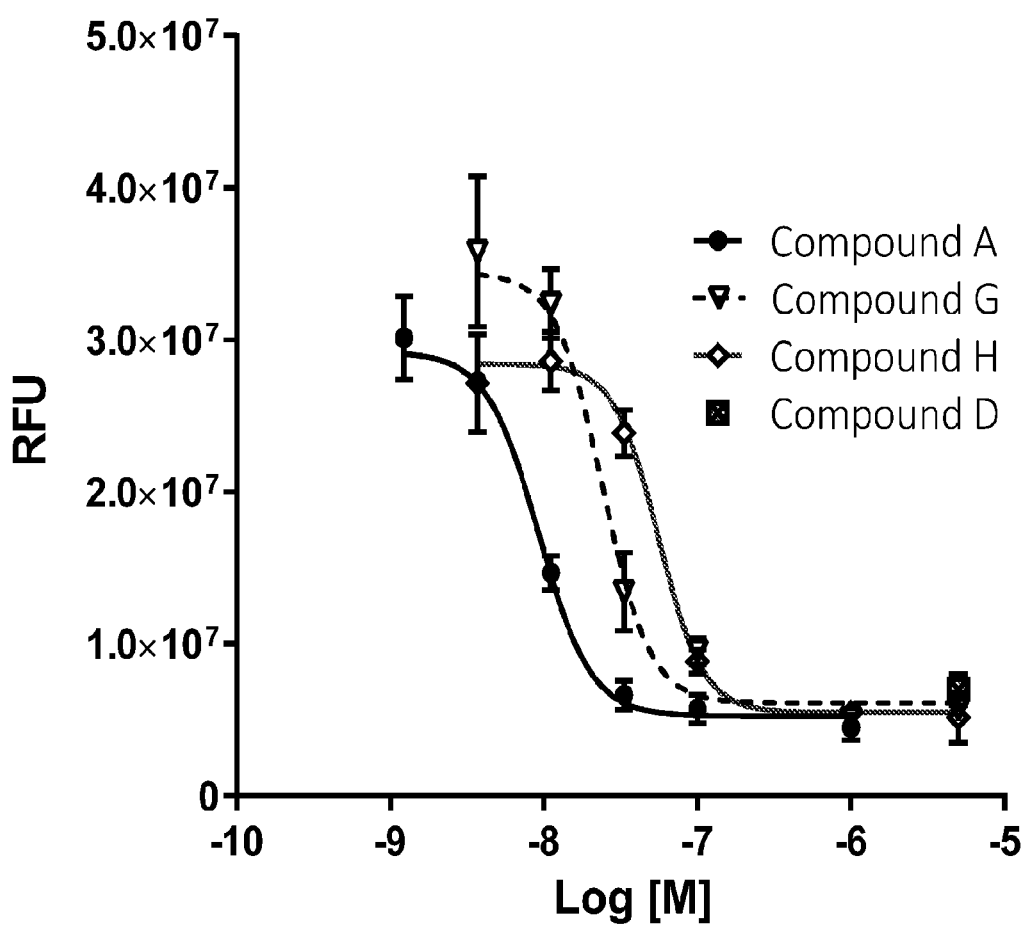
FIG. 11 shows the concentration dependent decreases in lipid accumulation following treatment of differentiating human adipocytes with Compounds A, G, H and D for six days. Data are shown from a single experiment and are depicted as mean RFU±STDev, (n=3 replicates).

Calculation of the $IC_{50}$ for inhibition of triglyceride accumulation in human adipocytes was determined by non-linear regression analysis of the RFU, using a variable slope, 4-parameter fit (GraphPad PRISM®). FIG. 10 Shows the reduction in lipid accumulation following treatment of differentiating primary human adipocytes with 100 nM Compound A and analogs Compounds B, D, E, G and H for six days. FIG. 11 shows a representative study comparing the concentration-dependent reduction in lipid accumulation with Compounds A, G and H. Compound D was tested at 5 µM only. The relative $IC_{50}$ values for Compound A, G and H in this study were 9.3 nM, 24.2 nM and 56 nM respectively.

Example 9: Inhibition of Mouse 3T3-L1 Differentiation and Cell Viability

Figure 12:
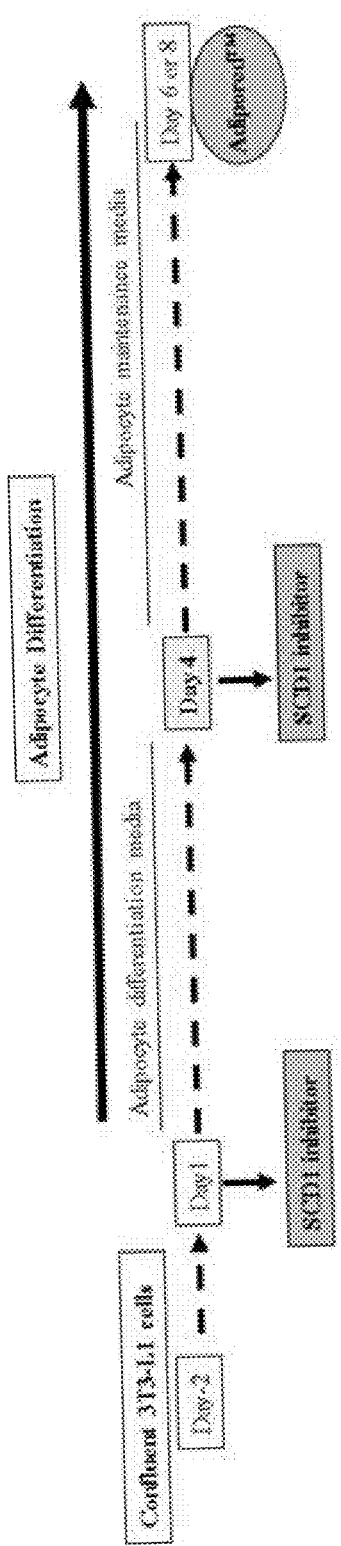
FIG. 12 shows a schematic of protocol for determining effects of SCD1 inhibitors on adipocyte lipid accumulation in mouse 3T3L-1 differentiating adipocytes

Viability of mouse 3T3 L1 preadipocytes (ATCC, Mannassas, VA) cultured in a 96-well plate following treatment with 10 µM Compound A and analogs Compounds B, D, E, G and H was assessed using Cell Titer Blue (Promega (Madison, WI)) according to manufacturer's instructions. No loss in cell viability compared to vehicle treated cells was observed (data not shown). To evaluate how the efficacy of Compound A in reducing lipid accumulation altered with substrate availability, studies were performed in differentiating mouse 3T3-L1 pre-adipocytes using charcoal stripped serum to reduce substrate concentration and also with added exogenous palmitate as the substrate. 3T3-L1 cells were plated at 6000 cells/cm² and cultured until confluence at 37° C. in a humidified incubator in 95% air/5% $CO_2$. Two days post-confluence pre-adipocyte differentiation was initiated using adipocyte differentiation medium containing DMEM with high glucose, 10% fetal bovine serum, insulin (1.7 µM), dexamethasone (1 µM), IBMX (0.5 mM), PPARγ agonist Rosiglitazone, (1 µM) with penicillin and streptomycin with 10 nM compound A or vehicle (0.1% DMSO). Seventy two hours following the initiation of differentiation, media was replaced with adipocyte maintenance media containing DMEM with high glucose and insulin (1.7 µM) with 10 nM compound A or vehicle (0.1% DMSO) (FIG. 12). Serum composed of 100% FCS or that containing 20, 40, 60, 80 or 100% charcoal stripped serum (cFCS). For experiments where sodium palmitate was added the serum comprised of a 90:10 ratio of FCS:cFCS with 5.0 or 50 µM palmitate/bovine-serum albumin (BSA) complex. Sodium palmitate was conjugated to BSA for use in experiments and was prepared by dissolving to 100 mM in 200 proof ethanol. The palmitate was diluted to 20 mM with D-PBS. The palmitate was then further diluted 1:1 with 30% fatty acid free albumin and incubated overnight at 37° C. The solution was sterile filtered with a 0.22 micron syringe filter prior to treating cells. The BSA control was prepared in the same manner, without the fatty acid. For the studies in which palmitate was added the media additionally contained palmitate/BSA complex at the same concentration as that used during the differentiation stage. Following a further forty-eight hours or ninety-six hours of incubation (Day 6 or Day 8 respectively) the media was removed, wells rinsed with PBS, and 200 µL PBS was added. Five microliters of AdipoRed™ reagent was added to each well, mixed, and allowed to stand at room temperature for 10 mins. Triglyceride was quantitated in a fluorimeter (i3 SpectraMax, Molecular Devices) using $\lambda_{ex}$ 530 nm and $\lambda_{em}$ 590 nm to determine relative fluorescent units (RFU). Percent inhibition of triglyceride accumulation in Compound A treated 3T3-L1 adipocytes compared to those treated with vehicle under each condition was calculated by using the formula; % Triglyceride Compound A treated adipocytes=100*(RFU Compound A treated adipocytes/RFU vehicle treated adipocytes).

Figure 13:
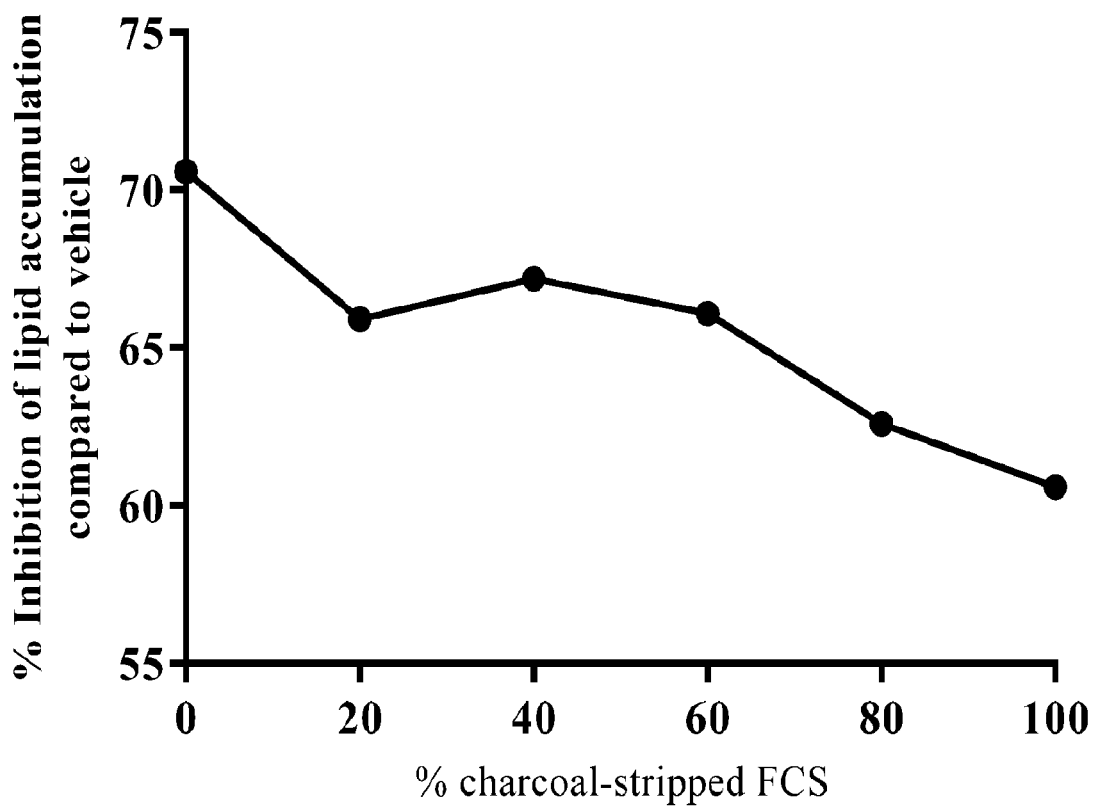
FIG. 13 shows that increasing percentage of charcoal-stripped serum during 3T3-L1 preadipocyte differentiation decreases compound A-mediated reduction in lipid accumulation. Data are shown from a single experiment and are depicted as mean % inhibition of lipid accumulation compared to vehicle treated adipocytes (n=3).
Figure 14:
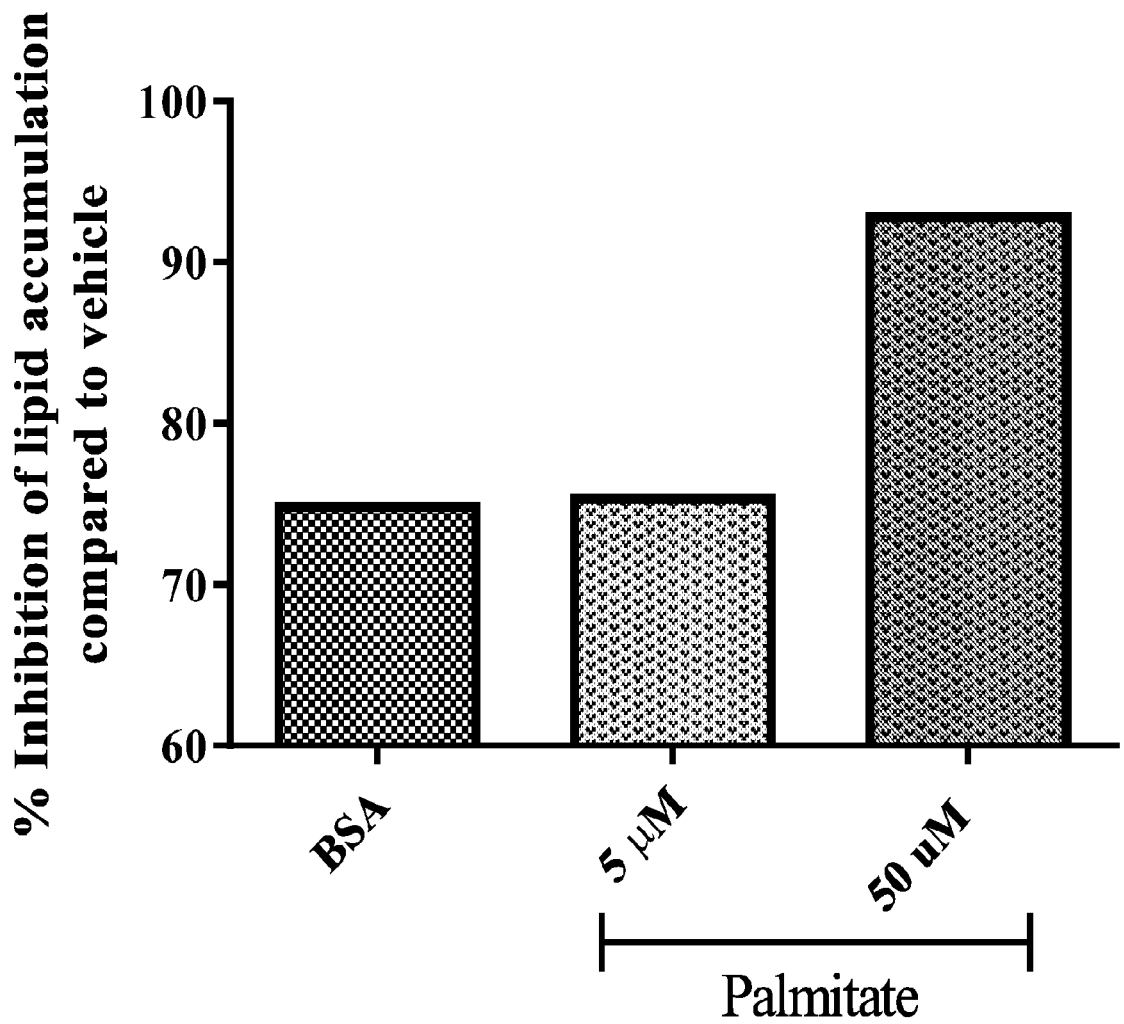
FIG. 14 shows that increasing palmitate during 3T3-L1 preadipocyte differentiation augments Compound A-mediated reduction in lipid accumulation. Eight days of exposure to 10 nM Compound A produced a decrease in lipid accumulation in differentiating mouse 3T3-L1 adipocytes which was augmented with 50 μM added palmitate. Data shown are from a single experiment and are depicted as mean % inhibition of lipid accumulation compared to vehicle treated adipocytes (n=8).

Treatment of 3T3-L1 pre-adipocytes with compound A for 6 days resulted in a 71% inhibition of triglyceride accumulation as determined by AdipoRed™ staining (FIG. 13). Increasing the percentage of csFCS such that less SCD-1 substrate was available resulted in a reduction in the ability of Compound A to inhibit lipid accumulation. Following 6 days of adipocyte differentiation Compound A in the presence of 80:20% FCS:csFCS resulted in a 66% inhibition of lipid accumulation and in the presence of 100% csFCS lipid accumulation was inhibited by 61% compared to vehicle (FIG. 13). In a separate experiment in which the exogenous SCD-1 substrate palmitate was added to the differentiating 3T3-L1 adipocytes in the presence of compound A, the % inhibition of lipid accumulation compared to that of vehicle treated cells was 75% in the presence of compound A with BSA compared to 93% in the presence of 50 µM palmitate/BSA determined on day 8 of differentiation (FIG. 14). Compound A, G and H were able to reduce accumulation of lipid and differentiation of primary human adipocytes. Compound A also reduced lipid accumulation in mouse 3T3-L1 adipocytes. No indication of the compounds having cytotoxic effects on the adipocytes was observed. Since accumulation of saturated fatty acids is key to the differentiation of adipocytes, compounds A, G and H may be a therapeutic approach to diseases involving accumulation of fat such as obesity and related complications such as NAFLD and NASH.

Example 10: Determination of In Vitro Potency in Rat Liver Microsomes

Sprague Dawley rats are fasted for 40 hours, after which the diet is replaced with free fatty acid deficient chow to increase SCD-1 activity. Rats are then euthanized using $CO_2$ asphyxiation and their livers removed. Livers are weighed and minced. Microsomes are isolated by homogenization with a polytron and several centrifugation steps. Following final centrifugation, the resulting pellet is resuspended in buffer and protein concentration is determined. Aliquots are stored at −80° C.

Rat liver microsomes are incubated with deuterium labeled stearoyl coenzyme A in the presence of putative inhibitor to test the compound's ability to inhibit the conversion of stearoyl-coenzyme A to oleoyl coenzyme A. The reaction is terminated using acetonitrile. Free fatty acids are extracted and the sample is then acidified with formic acid before final extraction with chloroform. The organic layer is transferred and evaporated under nitrogen gas. Samples are then reconstituted and analyzed by LC/MS/MS. The ability to inhibit the conversion of stearoyl-CoA to oleoyl-CoA is expressed as an $IC_{50}$.

Example 11: In Vitro Activity Using Hepatocytes, Keratinocytes, Adipocytes, and/or Sebocytes The biochemical function of SCD-1 is believed to be similar in hepatocytes, keratinocytes, adipocytes, and sebocytes. The ability of a given compound to inhibit the SCD-1 enzyme in intact human cells is determined using the Human AdipoRed™ assay. An example of hepatocytes that are used in these assays is the HepG2 cell line. An example of keratinocytes that are used in these assays is the A431 keratinocyte cell line. An example of sebocytes that are used in these assays is the SEB-1 cell line. In the case of human adipocytes, cells are received as pre-adipocytes and then differentiated for 5 days. All cells are grown as confluent monolayer cultures. Compounds tested are then added at various concentrations and incubated for up to 5 days. The production of triglycerides is assessed by a unique dye (AdipoRed™, a proprietary formulation of Nile Red from Lonza Walkersville, Inc., www.lonza.com, Document # AA-1038-7 04/11, Walkersville, MD 21793-0127 USA) which specifically binds to secreted triglycerides generating a fluorescent signal in a lipophilic environment.

The lipophilic AdipoRed™ specifically partitions into the fat droplets, binds to triglycerides and the latter is simply quantified by measuring fluorescence at 572 nm. The ability to inhibit the production of triglycerides is expressed as an IC50. All inhibitors are also tested in cell based assays for viability using standard methods well known in the art such as MTT, to distinguish between selective inhibition of SCD-1 versus secondary decreases in TG levels due to non-specific cytotoxicity. Mass spectrometry methods are employed to evaluate the conversion of either [U-14C]—or deuterated stearoyl-CoA to oleoyl-CoA and to evaluate the exact lipid profile in the presence of such modulators, as is well established by those skilled in the art (Camera (2010)).

Example 12: Rodent Ear Assay for Determination of Sebum Secretion In Vivo

Rodent ear models (e.g., Luderschmidt (1977)) such as the hamster ear and mouse ear are validated and represent convenient animal models for testing whether compounds are capable of modulating sebaceous gland function and sebum secretion in vivo. Putative SCD-1 inhibitors are screened by dosing topically to the ventral surfaces of both the right and left ears BID for 1-4 weeks. At sacrifice, samples of ear tissue are taken for lipid analysis, histology, and skin concentrations of the test compound. Lipid analysis is performed using either HPLC and/or LC/MS. To avoid confusion with epidermal lipids, wax esters, which are a unique product of sebaceous glands, are analyzed as one surrogate of sebum production. Other sebaceous lipids, such as cholesterol esters and triglycerides, are also measured. Automated tissue imaging analysis is employed to determine the number of active sebaceous glands per ear, the relative surface of the section occupied by sebaceous glands, and/or the number of differentiated and mature sebocytes per square millimeter within the sebaceous glands of a section. Inhibition of SCD-1 activity in skin tissue is measured by decrease in the conversion of stearoyl-CoA (18:0) to oleoyl-CoA (18:1). Good biological activity in these animal models is reflected by a decrease in the surface area of sebaceous glands and may be the function of increased drug potency, improved skin penetration, improved partitioning into sebum with enhanced access to sebaceous glands, or a variety of other factors.

Example 13: In Vivo Activity Using Cynomologous Monkey Model

Cynomologous monkeys have sebaceous glands very similar in size to those of human facial skin and at a depth from the skin surface approximating that of the human (~500 μm). SCD-1 inhibitors are screened by dosing topically to the upper back of monkeys BID for up to 3 months. Sebum production is analyzed by various methods. SebuTape is used for timed sebum collection and extracted lipids are quantified. Skin biopsies are obtained and changes in sebaceous gland size and surface area are monitored by standard histological evaluation. In both the extracted lipids from SebuTape and the skin biopsies, SCD-1 inhibition is also quantified by measuring inhibition of the conversion of stearoyl-CoA (18:0) to oleoyl-CoA (18:1). Good biological activity in this model is indicated by substantial inhibition of the conversion of stearoyl-CoA (18:0) to oleoyl-CoA (18:1) and substantial reduction in sebaceous gland size and sebum-specific lipids such as wax esters.

Example 14: Topical Dosing of Compound a Reduces in Weight in High-Fat Fed Rats

Compound A has been shown to inhibit lipid accumulation in adipocytes and mice lacking SCD1 in the skin exhibit a reduction in weight gain on a high-fat diet. Fatty acids themselves as well as lipid related molecules are known to play an important role in the maintenance of energy homeostasis. A topically applied inhibitor of SCD1 such as compound A therefore may be considered as a possible therapy to modify weight.

Figure 15:
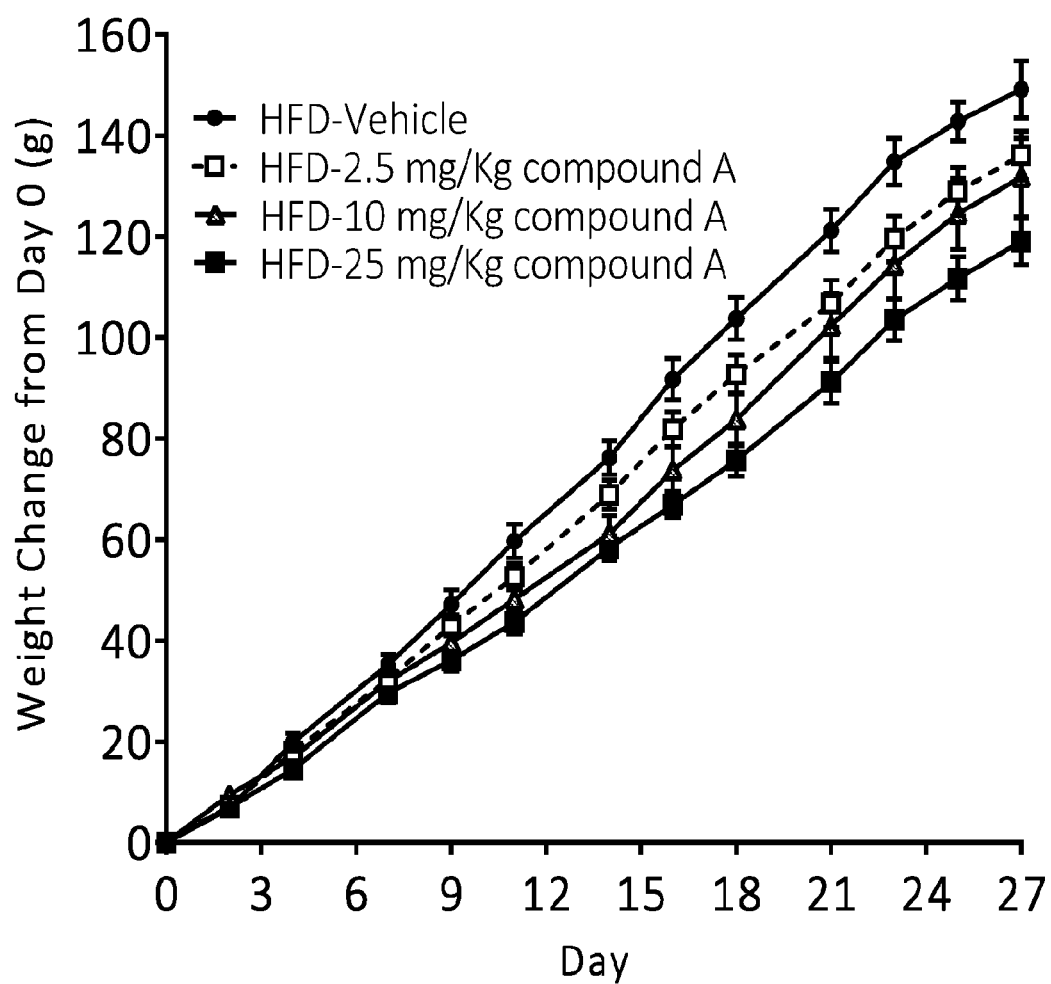
FIG. 15 shows that topical treatment of rats on a high-fat diet with compound A for 28 days results in a dose dependent reduction in weight gain. Rats were dosed twice-daily with compound A at the doses indication on 10% BSA. Data shown is mean weight change from Day 0±s.e.m. Doses of 2.5, 10 and 25 mg/Kg twice daily resulted in weight gains that were 91%, 88% and 80% respectively compared to vehicle after 28 days of dosing.

The effect of topical dosing on weight gain in male SD rats on a high-fat diet or normal chow was assessed in studies conducted at Pharmaron (Beijing, China). SD rats, 6-8 weeks of age were fed normal chow or placed on a high-fat diet (HFD) (D12492, Research Diets) for three weeks before dosing started. Rats were randomly assigned to groups based on body weight following the lead-in period. Rats fed high-fat diet were dosed topically with compound A at 2.5 mg/Kg (0.25% w/v gel), 10 mg/Kg (1% w/v gel) and 25 mg/Kg (2.5% w/v gel) twice-daily to 10% body-surface area (BSA) (n=10). Rats on normal chow were dosed topically with compound A at 25 mg/Kg (2.5% w/v gel) twice-daily to 10% BSA. Weight, food intake and water intake were determined three times weekly. Administration of compound A to HFD Rats resulted in a dose-dependent reduction in weight gain. Groups treated with 2.5, 10 and 25 mg/Kg twice daily exhibited weight gain that was 91%, 88% and 80% of that in vehicle treated rats respectively (FIG. 15).

Figure 16:
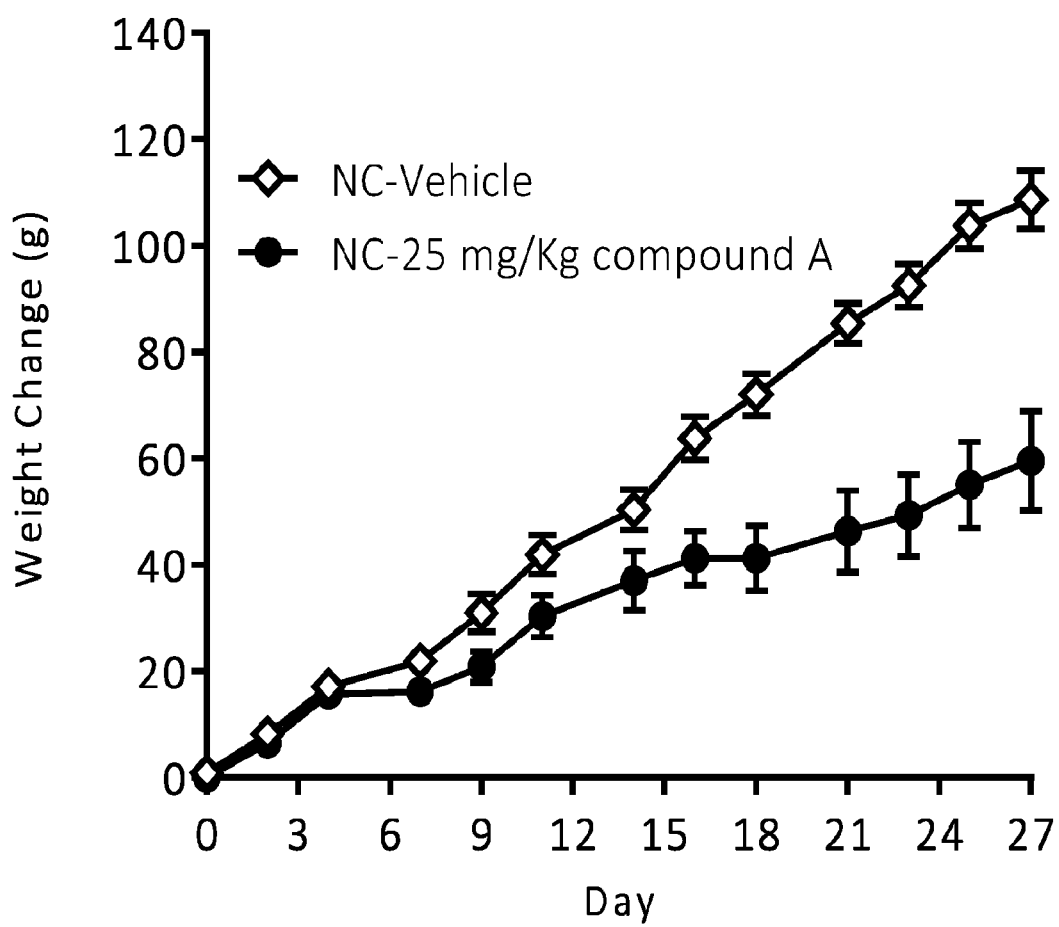
FIG. 16 shows that Compound A dosed topically twice daily in rats fed normal chow for 4 weeks results in a dose-dependent reduction in weight gain. Male rats were dosed topically, twice daily with vehicle or compound A at 25 mg/Kg (n=10 per group). After 28 days of dosing the weight gain in the rats treated with compound A was 53% of that in the vehicle treated group.

Compound A also led to reductions in weight gain in rats fed normal chow with treated rats gaining 53% as much weight of the vehicle treated rats (FIG. 16). No changes in food intake or water consumption were observed.

Figure 17:
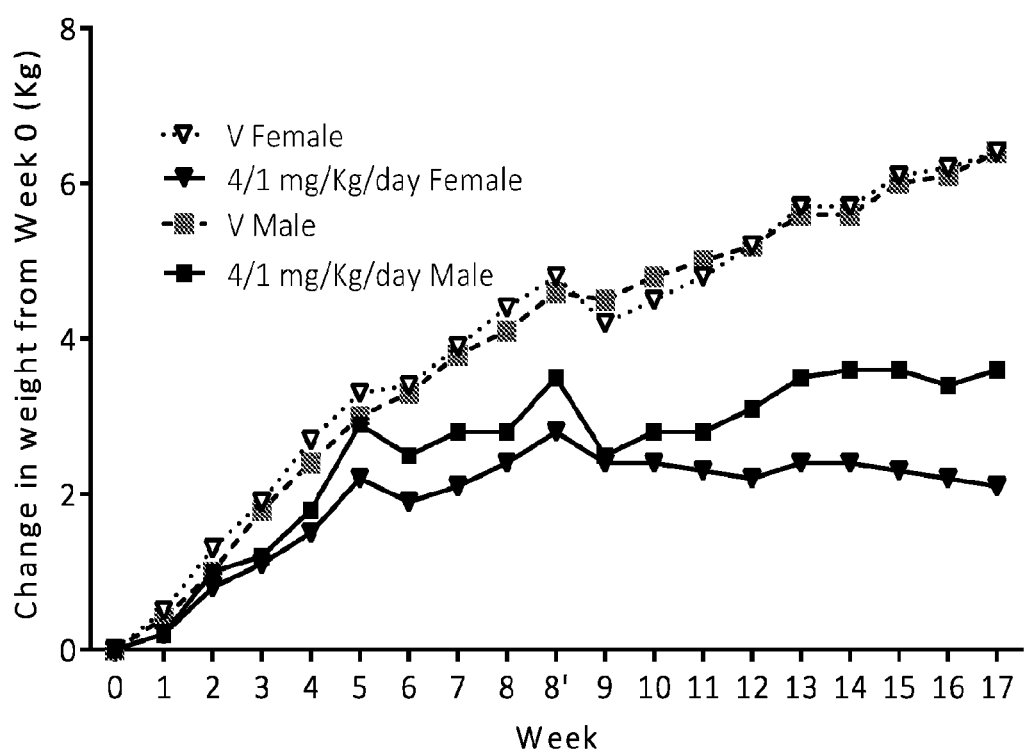
FIG. 17 show that compound A reduces weight gain in male and female growing minipigs. Male and female minipigs were dosed topically twice-daily with compound A at 4 mg/Kg for 61 days and then at 1 mg/Kg for the remaining 59 days. Weight gain in male and female minipigs that received compound A was essentially prevented following 35 days of dosing.

Example 15: Topical Dosing of Compound a Reduces Weight Gain in Growing Mini-Pigs on a Restricted Diet The effect of compound A on weight gain in young, growing minipigs was determined in a study conducted by WIL research (Ashland, Ohio). 3-4 month male and female minipigs were randomized to treatment groups based on body weight. Minipigs were dosed topically to 10% BSA twice daily with vehicle or 4 mg/Kg compound A (up to week 9-day 61) and with 1 mg/Kg compound A (week 9 to week 17). All minipigs were diet restricted. Following week 5 of dosing the weight gain in the minipigs treated with compound A plateaued, in comparison that in the vehicle treated groups continued to increase (FIG. 17).

Brief Discussion of Examples 14 Through 15

Surprisingly, given the likelihood that little of these compounds get into the peripheral circulation after topical application, the data shown (FIGS. 10 through 17) in both adipocyte differentiation models in vitro and in vivo in rats and minipigs strongly supports the topical use of these compounds to treat obesity.

Animal models for NAFLD and NASH are at an early stage of development and it is not yet clear whether these currently challenging models are suitable predictors of an outcome in humans. Nevertheless, the obesity data above ((FIGS. 15 through 17) plus other observations regarding the role of SCD-1 in NAFLD and NASH and a very strong connection between obesity and NAFLD/NASH strongly suggests the topical application of these SCD-1 inhibitors would be beneficial to NAFLD/NASH patients (Sanyal (2002), Rinella (2015)).

Example 16: Analytical Methods for Compound A

API used was the Compound A. All excipients used are listed in the United States Pharmacopeia-National Formulary (USP/NF) unless indicated. Water and acetonitrile for HPLC analysis were HPLC grade. A standard pH meter with a combined electrode was used to measure pH. The samples were measured for Apparent pH directly with $\frac{1}{10}^{th}$ dilution with water. Measured pH was performed only where indicated. Viscosity (at 25±1° C.) was measured with a Brookfield LV-DV-1+ viscometer using the Helipath spindle E (595) just below the surface and the speed set to ensure a torque of between 50-90%, once stabilized for 1 minute. Since the samples were stored at different temperatures, they were allowed to equilibrate at the viscosity measurement temperature for at least 24 hours.

HPLC analysis was performed using a variable Wavelength UV/Vis diode array detector. A gradient HPLC method is summarized in Tables 17 & 18.

TABLE 17

Chromatographic conditions used for Compound A formulation assessment

| | |
|---|---|
| HPLC System | Waters photodiode array detector |
| | Waters Separations Module |
| | Waters Empower$^3$ Pro (Version 7.00.00.99) |
| Column | Waters XBridge C18, 4.6 × 150 mm, 3.5 μm, 130 Å (PN: 186003034) |
| Guard Column | Waters XBridge C18, Sentry Guard Cartridge (PN: 186003061) |
| Detection | 220 nm (Diode array detector)/269 nm for phenxyethanol |
| Sample Temperature | Ambient |
| Column Temperature | 30° C. ± 2° C. |
| Flow Rate | 1.0 mL/min |
| Mobile Phase | A: 0.1% Phosphoric acid in water |
| | B: 0.1% Phosphoric acid in acetonitrile |
| Gradient | Summarised in Table 4 |
| Injection Volume | 10 μL |
| Run Time | 45 min |
| Needle Wash | 50:50 HPLC grade acetonitrile/deionised water |
| Pump Wash | 60:40 HPLC grade methanol/deionised water |

TABLE 18

Gradient conditions used in HPLC method

| Run time (min) | % Mobile Phase A | % Mobile Phase B |
|---|---|---|
| 0 | 90 | 10 |
| 20 | 40 | 60 |
| 30 | 0 | 100 |
| 33 | 0 | 100 |
| 39 | 100 | 0 |
| 41 | 90 | 10 |
| 45 | 90 | 10 |

Example 17: Solubility Studies of Compound A

Solubility assessment of Compound A in up 30 vehicles comprising pure solvents and co-solvent mixtures and excipient systems with a potential to be incorporated into topical formulations was performed as part of a pre-formulation screen. These solubility measurements were performed by suspending excess compound A above its visual solubility to a known weight of solvent which was then stirred for a minimum of 24 hours at 25° C. prior to centrifugation and HPLC analysis of the supernatant. The results are shown in Table 19.

TABLE 19

Compound A solubility in various pharmaceutical solvents used in topical products

| Solvent Type | Solvent | Density (g/mL) at 20-25° C. | Compound A Solubility (% w/w) | Compound A Solubility (mg/mL) |
|---|---|---|---|---|
| Aqueous | Water[a] | 1 | 0.005 | 0.05 |
| | pH 7.4 Buffer | 1 | 0.0002 | 0.02 |
| | Brij 98 (0.5%) | 1 | 0.022 | 0.22 |
| Water Miscible | Ethanol | 0.789 | 3.43 | 43.5 |
| | Propylene Glycol | 0.965 | 1.39 | 13.5 |
| | PEG400 | 1.128 | 2.92 | 25.9 |
| | Arasolve (Di-Methyl isosorbide) | 1.17 | 3.75 | 43.9 |
| | Transcutol P(2-[2-Ethoxyethoxy]ethanol) | 0.988 | 4.88 | 48.2 |
| | DMSO | 1.092 | 9.16 | >100 |
| | Pharmasolve (N-Methyl Pyrrolidone) | 1.03 | 37.5 | 386.3 |
| | Kolliphor EL | 1.05 | 1.43 | 15.0 |
| Water Immiscible | Benzyl Alcohol | 1.04 | 7.04 | 73.2 |
| | Phenoxyethanol[a] | 1.1 | 4.45 | 49.0 |
| | Di-isopropyl Adipate | 0.97 | 0.78 | 7.5 |
| | Oleoyl Alcohol | 0.85 | 0.06 | 0.5 |
| | Isopropyl Myristate | 0.85 | <0.01 | <0.09 |
| | Mineral Oil | 0.91 | <0.01 | <0.09 |
| | Castor Oil | 0.956 | 0.13 | 1.24 |

Abbreviations:

DMSO = dimethyl sulfoxide,

PEG 400 = polyethylene glycol 400

[a]Present in TSAG3 aqueous gel formulations

Results showed that Compound A is practically insoluble in aqueous systems but highly soluble in semi-polar organic solvents which are miscible with water such as ethanol, propylene glycol, PEG400, diethylene glycol monoethyl ether (DEGEE or Transcutol P®), DMSO, di-methyl isosorbide (Arasolve®) and N-methyl pyrrolidone (Pharmasolve®) in the range of 14 to 386 mg/ml. For partially water miscible, semi-polar solvents such as benzyl alcohol and phenoxyethanol, the same high solubility was noted but for long chain or ester type of solvents, the solubility was considerably lower. This suggested that nonaqueous and aqueous co-solvent gel formulations could have the dissolved drug concentration range to deliver a broad range of doses. However, cream, lotion and ointment formulations which rely more heavily on drug dissolved in lipid and surfactant phases, would be more limited.

For acne treatment, moderately drying, non-oily formulations are preferred therapeutically and cosmetically as the patient's skin typically over-secretes sebum and the formulation should function to both minimize oil production and maximize drug delivery to sebum-producing sebaceous glands in hair follicles. These solubility results are particularly encouraging with regard to the development of a suitable set of formulations.

Example 18: Solubility Studies on Selected Analogs

In order to assess the compatibility with the modified TSAG3 gel formulation, several analogs were saturated in the gel components at room temperature (20-23° C.). The method used was as follows: Each analog at the equivalent of 30 mg/g was added to 500 microliters of the gel vehicle (minus the 1% w/w Carbopol as this made the gel too viscous) and allowed to equilibrate using a gently rotating, rotisserie sample holder that was allowed to come to equilibrium over 4 days. The samples were visually observed, filtered and diluted for analysis via HPLC in a concentrations range predetermined to be in a linear range for analyte detection. It is believed that Carbopol makes little difference to the equilibrium solubility at the 1% w/w level but may possibly prevent precipitation of super-saturated solutions of drug initially over 24-48 hours which is a further reason for taking it out to better assess the drug solubility in the remainder of the formulation. The results obtained are shown in Table 20.

TABLE 20 absolute and relative solubility measurement s of analog solubilities
and visual appearance of suspension/solution after 4 days in TSAG3
gel vehicle (minus 1% w/w Carbopol) after equilibration over 4 days
at Room Temperature (20-23° C.), filtered and assayed by HPLC.

| Analog Compound | Supernatant concentration Mean (N = 2-3) mg/g at RT after 4 days equilibration | Visual observation of sample after 4 days | Relative solubility in TSAG3 gel formulation |
| --- | --- | --- | --- |
| A Reference | 30.3 | Yellowish, clear Liquid | 1.0 |
| B | 28.46 | Clear solution | >0.94 |
| D | 28.35 | Clear solution | >0.936 |
| E | 23.18 | Visible precipitate | 0.765 |
| G | 28.78 | Clear solution | >0.92 |
| H | 27.89 | Clear solution | >0.92 |
| Acid Metabolite of A | 30.68 | Clear solution | >1.01 |

Compound A was assessed as having an approximate solubility of 3% w/w or 30 mg/g in the modified TSAG3 gel. As the gel has a viscosity of around 100,000 cP when first prepared, it is virtually impossible to physically equilibrate solids in such a viscous gel in order to generate a consistent solubility estimates. Hence, the thickening agent Carpopol was taken out of the gel formulation in order to estimate the relative solubilities of all the analogs. Virtually all the analog compounds tested showed clear solutions which means they could dissolve >30 mg/g (or >3% w/w) which is as good as or better estimate than that of Compound A in this formulation. The only exception was Compound E which was only about 77% of Compound A solubility. The conclusion is that all of the analogs tested, with the possible exception of THE000090X, showed equivalent gel solubility characteristics and compatibility with modified TSAG3 gel, demonstrating its utility across the majority of analogs tested. As the thermodynamic drug solubility in the vehicle is a major determining factor in topical absorption, it is likely that the majority of the analogs tested will behave in a similar manner to that of Compound A in the modified TSAG3 formulation.

Example 19: Gel Formulation Preparation Methods

Figure 18:
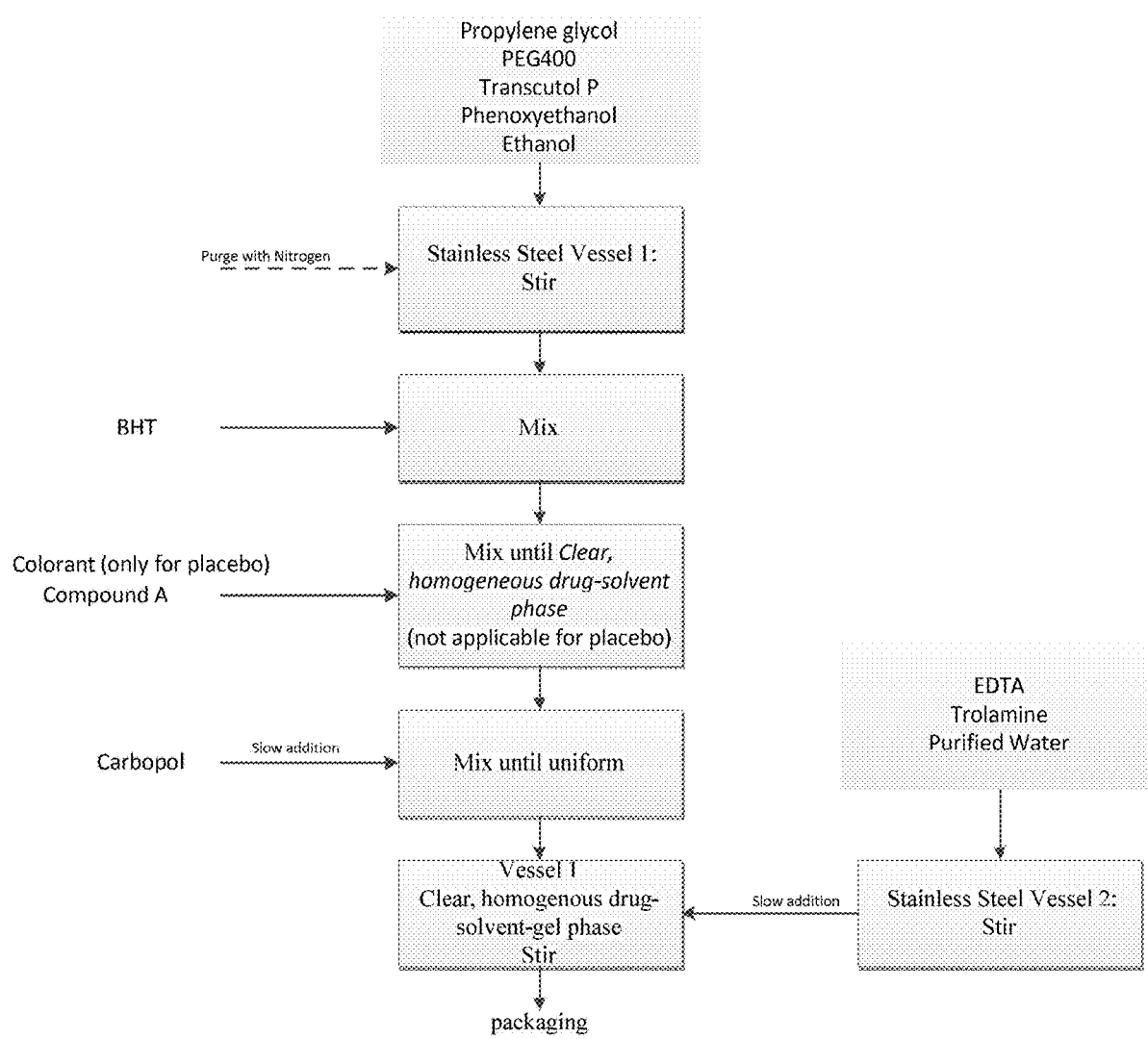
FIG. 18 shows the general process flow for manufacturing all compound A topical gel formulations (depicted here as being for a specific gel formulation)

The Gel formulations were all manufactured in a similar way. A flow diagram for a typical manufacturing run is shown in FIG. 18. An aqueous phase is used to dissolve or disperse the water soluble materials which typically comprise the chelator, the pH buffering agent and the purified water components. These are dissolved in a stainless steel container and purged with nitrogen. The non-aqueous phase is typically prepared by first adding propylene glycol, polyethylene glycol 400, Transcutol P, phenoxyethanol, and ethanol together and stirring under a purge of nitrogen with an overhead mixer in another stainless steel container protected from light. The non-aqueous phase solution is then pumped into a larger stainless steel mixing vessel and antioxidant(s) is/are added and mixed until completely dissolved. Compound A is then added while the vessel is purged with nitrogen and the contents mixed using a turbine mixer with a side sweep mechanism until all the API is completely dissolved. Carbomer or other gelling agent is then slowly added to the nonaqueous solution carefully to ensure minimal adherence to the sides of the vessel and to the mixer agitator arms. The contents are then stirred for 8-12 hours while simultaneously purging with nitrogen to ensure a uniform dispersion free of lumps. When both the aqueous and drug-containing nonaqueous phases are prepared completely, the aqueous phase is slowly added into the gel phase under continuous stirring and under a nitrogen purge. Gelation occurs rapidly and stirring is continued and controlled in order for the gel to form without segregation and entrainment of air or nitrogen until a visually homogenous, clear gel is obtained. The final gel is then packaged into suitable containers, typically plastic laminate or coated aluminum tubes in 5 g, 10 g, 15 g or 30 g amounts under a blanket of nitrogen while protecting from direct sunlight. Each are weight checked to comply with container weight uniformity tests. This process has been developed from the laboratory scale of 0.1-1 kg scale up to 80 kg scale.

Example 20: Preliminary Gel Excipient Compatibility Studies

Preliminary stability studies to evaluate the compatibility of Compound A with solvent systems employed in solubility experiments were assessed at 40° C. and 50° C. over a 4 week time frame. The data in Table 21 indicates that Compound A was stable under test conditions within the variability of the assay and throughout the 4 weeks in most of the tested systems. The exceptions were Arlasolve dimethyl isosorbide (DMI) and Pharmasolve N-methyl pyrrolidone (NMP) where the peak purity decreased significantly from the initial value. The remaining excipients were used to provide different prototype Gel or Cream Formulations which are summarized in Example 21 and Example 29.

TABLE 21

Percentage peak purity of Compound A in solvents and solvent systems

| Excipients and Solvent Systems | t = 0 | t = 2 weeks | | t = 4 weeks | |
| --- | --- | --- | --- | --- | --- |
| | | 40° C. | 50° C. | 40° C. | 50° C. |
| Propylene Glycol | 99.98 | 100.00 | 100.00 | 99.83 | 99.84 |
| Kolliphor EL | 99.94 | 99.67 | 99.67 | 99.63 | 99.94 |
| Ethanol | 99.87 | 100.00 | 100.00 | 99.84 | 99.84 |
| PEG400 | 99.83 | 99.82 | 99.56 | 99.55 | 98.90 |
| Arlasolve DMI | 97.58 | 96.66 | 96.53 | 96.28 | 96.17 |
| Transcutol P | 99.97 | 99.87 | 99.84 | 99.77 | 99.42 |
| Benzyl Alcohol | 99.88 | 100.00 | 100.00 | 99.84 | 99.84 |
| Phenoxyethanol | 100.00 | 100.00 | 100.00 | 99.80 | 99.58 |
| Pharmasolve NMP | 100.00 | 96.03 | 96.18 | 95.51 | 95.17 |

Further preliminary solubility and stability studies were then conducted with the three solutions, solution 1, solution 2, and solution 3 using the methodology and analytical methods described above. The details of these three solutions and the solubility of Compound A in each are summarized in Table 22 below. The stability of Compound A in each of the three solutions over a 4 week time frame was excellent and is shown in Table 23

The overall conclusions of the solubility and compatibility studies are that Arasolve DMI and Pharmasolve NMP are to be avoided due to some underlying instability of Compound A, despite promoting high solubility of compound A. The basic combination of ethanol, PEG400, propylene glycol and Transcutol P co-solvents in an aqueous system provides reasonable drug loading potential for Compound A

TABLE 22

Compound A solubility in various solvent systems

| Formulation Code | Major Solubilizer(s) | Approx. Formulation Composition at saturation (% w/w) | COMPOUND A Solubility (% w/w) At Ambient | COMPOUND A Solubility (mg/mL) At Ambient |
| --- | --- | --- | --- | --- |
| Solution 1 | Ethanol/PEG400/ Transcutol P | Ethanol (10); Benzyl Alcohol(2); Prop. Glycol(10); PEG400(30); Water(21); Transcutol P (25) | 2.89 (2.87-2.91) | 28.9 (28.70-29.07) |
| Solution 2 | Ethanol/PEG400/ Transcutol P + Arasolve DMI | Ethanol (10); Benzyl alcohol(1); Phenoxyethanol (1); Propylene Glycol(10); PEG400(30); Water(7); Transcutol P (25); Arasolve DMI (15) | 5.18 (5.18-5.19) | 51.84 (51.83-51.86) |
| Solution 3 | Ethanol/PEG400 | Ethanol (40); PEG400(40); Kolliphor EL (20) | 4.76 (4.73-4.79) | 47.57 (47.28-47.86) |

Abbreviations:
DMI = Di-Methyl Isosorbide,
PEG400 = polyethylene glycol 400,
w/w = weight/weight

TABLE 23

Percentage peak purity of Compound A in solvents and solvent systems (cont'd)

| Excipients and Solvent Systems | t = 0 | t = 2 weeks | | t = 4 weeks | |
| --- | --- | --- | --- | --- | --- |
| | | 40° C. | 50° C. | 40° C. | 50° C. |
| Solution 1 | 99.99 | 99.86 | 99.85 | 99.79 | 99.45 |
| Solution 2 | 99.94 | 99.57 | 99.49 | 99.38 | 99.19 |
| Solution 3 | 100.00 | 99.85 | 99.75 | 99.73 | 99.58 |
| 50:50 Water:Ethanol | 100.00 | 99.87 | 99.87 | 99.83 | 99.79 | at low stability risk. Ethanol/PEG400/KolliphorEL provides a non-aqueous option of higher solubility with similar low stability risk.

Example 21: Prototype Gel Formulations

Over 20 formulations of both non-aqueous and aqueous based gel systems were developed and evaluated. The primary focus of this preliminary gel formulation evaluation was to maximize drug load to facilitate topical toxicology and early clinical studies. The basis of the gel formulations was combining the use of co-solvents and excipients to best solubilize Compound A and simultaneously to provide good gelation properties for both aqueous and non-aqueous systems. Several non-aqueous (TSNG) and aqueous gel (TSAG) formulations were selected from physico-chemical and cosmetic screening for subsequent stability and in-vitro release—permeation studies, and are described in detail in Examples 22 through Example 28. A reference formulation used during discovery evaluation is also included in these evaluations.

alcohol did not provide added drug saturation solubility. However, apart from the trend that aqueous inclusion lowers the solubilized drug loading in the gel formulations, the inherent drug loadings found to be possible were not predicted a priori when the complex interactions with water was included. The gelling agent Carbopol was generally preferred to HPC for aqueous gels as the latter provided a sticky deposit and stringy texture on skin, rendering it unacceptable cosmetically. For non-aqueous gels, HPC was found to be a better gelling agent than Carbopol due to the lower solubility and gelling capacity of the latter. For aqueous gels, increasing ethanol levels allowed reduction in Propylene Glycol levels for a more drying preparation and maintained Compound A solubility.

Example 22: Formulation Stability Study Design and Summary of Results

Selected formulations from Example 21 (Table 24) were placed on stability for testing at t=0, 2 weeks and 4 weeks

TABLE 24

Composition (% w/w) of gel formulations selected for in depth stability and in vitro transport studies

| Excipient | Composition (% w/w) | | | | | | | | |
|---|---|---|---|---|---|---|---|---|---|
| | TSNG 13 | TSNG 10 | TSAG 3 | TSAG 4 | TSAG 7a | TSAG 8a | TSAG 9 | TSAG 9a | Reference Formulation |
| Ethanol (200 proof) | 30.00 | 30.00 | 10.00 | 10.00 | 20.00 | 10.00 | 10.00 | — | 67.90 |
| Isopropyl alcohol | — | — | — | — | — | — | — | 10.00 | — |
| Benzyl alcohol | — | — | — | — | 2.00 | 2.00 | — | 2.00 | — |
| Phenoxyethanol | — | — | 1.00 | 1.00 | — | — | 1.00 | — | — |
| Propylene Glycol | 20.00 | — | 20.00 | 20.00 | — | 10.00 | 21.25 | 20.30 | 29.10 |
| PEG400 | 45.00 | 39.50 | 21.00 | 47.00 | 26.75 | 26.85 | — | — | — |
| Water 1 | — | — | 19.50 | 19.50 | 30.00 | 30.00 | 21.10 | 21.00 | — |
| 0.1M NaOH | — | — | — | — | To pH 6 | To pH 6 | To pH 6 | To pH 6 | — |
| Transcutol P | — | 25.00 | 25.00 | — | — | — | 25.00 | 25.00 | — |
| Carbopol 980 NF | — | — | 1.00 | 1.00 | 1.00 | 1.00 | 1.00 | 1.00 | — |
| HPC | 1.00 | 1.00 | — | — | — | — | — | — | 0.5 |
| Water 2 | — | — | — | — | q.s. 100 | q.s. 100 | q.s. 100 | q.s. 100 | — |
| Compound A | 4.00 | 4.50 | 2.50 | 1.50 | 0.25 | 0.15 | 0.65 | 0.70 | 2.5 |

(Abbr. HPC = hydroxypropyl cellulose , PEG400 = polyethylene glycol 400)

All gel formulations were assessed macroscopically for appearance, stability, viscosity, texture, and residue upon applying to a glove and drug loading potential. The solubility of compound A was lower in aqueous gels (0.2-2.5% w/w) versus that in non-aqueous gels (4-4.50% w/w). In both gel systems, drug solubility increased when propylene glycol is substituted with Transcutol P or PEG400. Benzyl at 25° C. and 40° C. In addition, freeze thaw testing (samples stored at −20° C.) was performed at t=2 (1 freeze/thaw cycle) and 4 (2 freeze/thaw cycles) weeks. The formulations were stored in a single packaging type (Type I borosilicate vials) and the chemical stability data, as established by the analytical methods described in Example 16, is summarized in Table 25.

TABLE 25

Peak Purity of Prototype Gel Formulations described in Table 24 after storage at −20° C., 25° C. and 40° C.

| Formulation | Compound A Concentration (% w/w) | T = 0 | Peak purity of Compound A (% a/a), n = 3 T = 2 weeks | | |
|---|---|---|---|---|---|
| | | | −20° C. | 25° C. | 40° C. |
| TSAG3 | 2.5 | 98.17 (97.71-98.44) | 98.20 (98.19-98.21) | 98.42 (98.32-98.57) | 98.23 (98.20-98.27) |
| TSAG4 | 1.5 | 98.53 (98.40-98.60) | 98.21 (98.16-98.24) | 98.44 (98.37-98.51) | 98.17 (98.16-98.19) |
| TSAG 7a | 0.25 | 97.91 (97.18-98.51) | 98.72 (98.23-99.68) | 98.33 (98.28-98.39) | 98.34 (98.32-98.37) |
| TSAG 8a | 0.15 | 97.41 (96.35-98.34) | 98.27 (98.21-98.30) | 98.39 (98.28-98.49) | 98.39 (98.36-98.42) |
| TSAG 9 | 0.65 | 98.40 (98.37-98.42) | 98.15 (97.80-98.42) | 98.40 (98.37-98.42) | 97.96 (97.24-98.35) |
| TSAG 9a | 0.7 | 97.78 (96.55-98.46) | 98.23 (98.21-98.25) | 98.05 (97.36-98.43) | 98.27 (98.24-98.29) |
| TSNG 10 | 4.5 | 98.44 (98.39-98.49) | 98.12 (98.03-98.18) | 98.44 (98.39-98.49) | 98.06 (97.96-98.11) |
| TSNG 13 | 4.0 | 98.58 (98.47-98.64) | 98.19 (98.17-98.21) | 98.47 (98.42-98.52) | 98.18 (98.16-98.21) |

| Formulation | Peak purity of Compound A (% a/a), n = 3 T = 4 weeks | | |
|---|---|---|---|
| | −20° C. | 25° C. | 40° C. |
| TSAG3 | 98.24 (98.20-98.26) | 98.01 (97.77-98.13) | 98.19 (98.12-98.26) |
| TSAG4 | 98.22 (98.17-98.27) | 98.14 (98.11-98.19) | 98.19 (98.07-98.27) |
| TSAG 7a | 98.17 (98.13-98.24) | 98.22 (98.18-98.26) | 98.35 (98.29-98.45) |
| TSAG 8a | 98.18 (98.12-98.27) | 98.22 (98.18-98.26) | 98.40 (98.38-98.44) |
| TSAG 9 | 98.16 (98.10-98.27) | 98.31 (98.26-98.37) | 98.26 (97.89-98.42) |
| TSAG 9a | 98.18 (98.14-98.21) | 98.23 (98.21-98.27) | 98.35 (98.31-98.38) |
| TSNG 10 | 98.20 (98.08-98.26) | 98.08 (98.03-98.12) | 98.13 (98.10-98.16) |
| TSNG 13 | 98.14 (98.01-98.23) | 98.12 (98.08-98.15) | 98.15 (98.12-98.19) |

The data shows that that chemical stability of Compound A was largely similar across all temperatures, time points, and selected solvents. No trend in chemical instability was obvious at the conditions tested and none of the formulations tested exhibited a visual change in appearance or crystallization of Compound A under the studied conditions. The pH and viscosity showed no obvious change in any of the formulations under all conditions. From forced degradation studies, exposing the drug substance and formulated drug to oxidizing, acidic, basic, thermal and UV light conditions, there was a potential concern for the interaction with peroxides and UV light. However, using standard quality excipients and research grade API, the pre-formal studies using Compound A alone and in formulations described in Table 24 showed no evidence of requiring protection from oxygen or excipient generated peroxides. Thus the need for anti-oxidant and/or chelating agents was not examined in depth at this stage of development. Also, the exposure to normal light was minimized during preparation and subsequent storage in light impermeable aluminum tubes. In addition, physical appearance, pH and viscosity of all the selected gels showed no evidence of change even under extreme storage conditions. Based on all the above data, the TSAG3 formulation was selected as the lead development formulation for subsequent GLP and clinical studies.

Example 23: Further Gel Formulations

Figure 19:
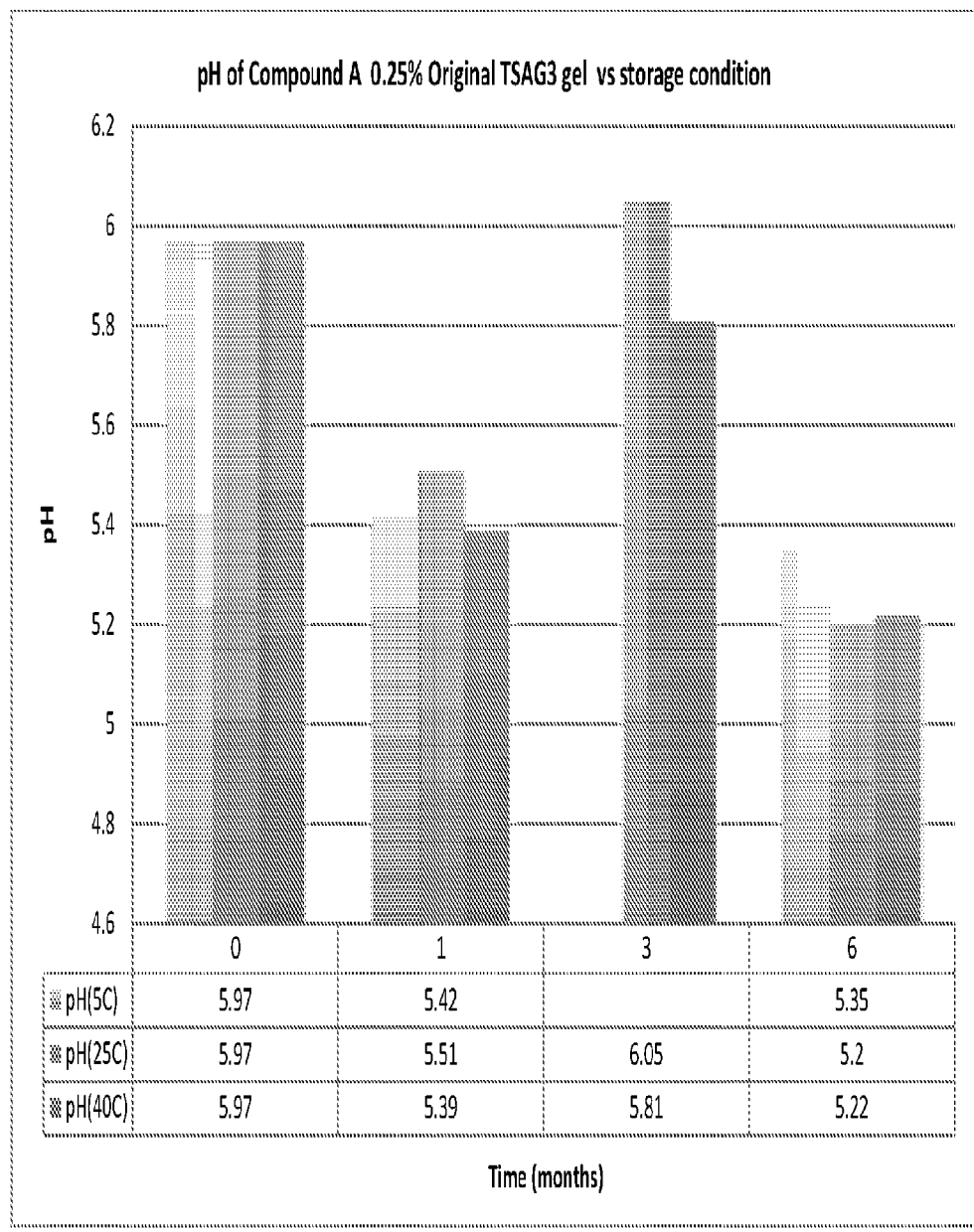
FIG. 19 shows six month formal stability data for the Original TSAG3 formulation as measured by apparent pH reductions when stored at 5° C., 25° C./60% relative humidity, and 40° C./75% relative humidity

Based on longer term, formal ICH protocols, the TSAG3 topical Gel formulation selected for formal development demonstrated a chemical (Compound A degradation) and physical (inconsistent and unstable gelling) instability that surprisingly was not predicted from pre-formal studies or forced degradation studies described above. Analytical evidence suggested that an impurity, identified as the aldehyde oxidation product of the primary alcohol of Compound A (referred to as C-4 which is also a synthetic precursor of the drug and analogs and is shown in Scheme 17), was accumulating at rates which were much faster than previously projected from the pre-formal studies. In addition, both the pH and the viscosity of the TSAG3 gel formulation were dropping at all storage conditions as shown numerically in Table 26 and graphically in FIGS. 19 and 20.

Scheme 17: Structure of C-4 and its potential formation from Compound A via oxidation

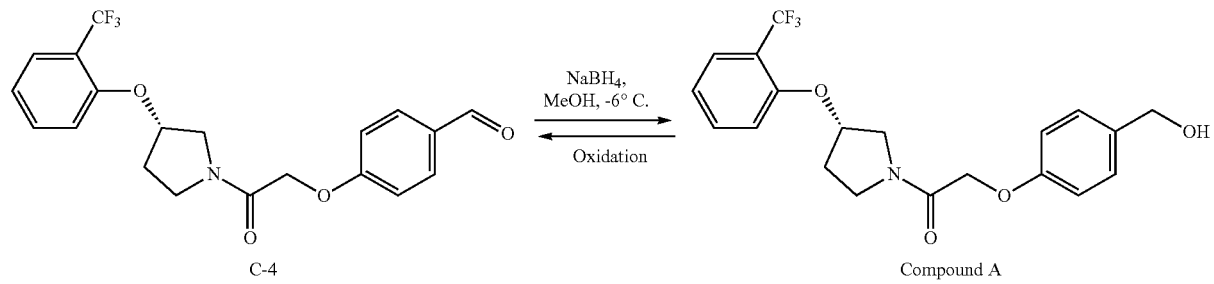

TABLE 26

Six month formal stability data showing accumulation of C-4 and total impurities when stored at 5° C., 25° C./60% Relative Humidity, and 40° C./75% Relative Humidity for the TSAG3 formulation.

| | 6 Month C-4 impurity level (area %) Storage condition | | | 6 Month TOTAL impurity level (area %) Storage condition | | |
|---|---|---|---|---|---|---|
| Formulation | 5° C. | 25° C./60% RH | 40° C./75% RH | 5° C. | 25° C./60% RH | 40° C./75% RH |
| 0.25% w/w TSAG3 | 0.13 | 0.27 | 0.87 | 0.24 | 0.33 | 1.85 |
| 1.75% w/w TSAG3 | 0.19 | 0.44 | 0.94 | 0.37 | 0.54 | 1.1 |

These new data, in contrast with initial studies, now indicated that the TSAG3 formulation would not sustain a required two year shelf life at controlled room temperature (15-30° C.), having a projected 6-7 month shelf life at this condition based on a specification of not more than 0.5% individual impurity being allowed. Furthermore, the apparent pH was dropping from 5.97 to 5.22-5.35 which in turn reduced the effectiveness of the Carbomer gelling agent resulting in a viscosity drop and changing application properties of the formulation resulting in a negative cosmetic effect. Re-formulation studies therefore focused on two areas: a) understanding and controlling the sources of chemical decomposition b) providing improved pH buffering within the formulation. Table 27 shows the antioxidant-chelator combinations selected for evaluation within the TSAG3 gel formulation base using a 2% w/w Compound A drug loading in order to suppress or eliminate the unanticipated instability seen above. The evidence strongly suggested that oxidation was the primary route of decomposition which could be driven or catalyzed by a number of parameters such as low level impurities, peroxides, metal ions coming from the excipients, the same occurring via different API sources, oxygen gas in the headspace and light exposure. While TSAG3 formulations did not seem to be highly sensitive to these parameters in screening, different lots of excipients and API as well as the increase of exposure to oxygen and light during scale up could be responsible for this. Thus, to develop these compounds commercially, a more stable modified version was required which retained the advantages of the original TSAG3 yet also proved stable over prolonged periods of time.

Figure 21:
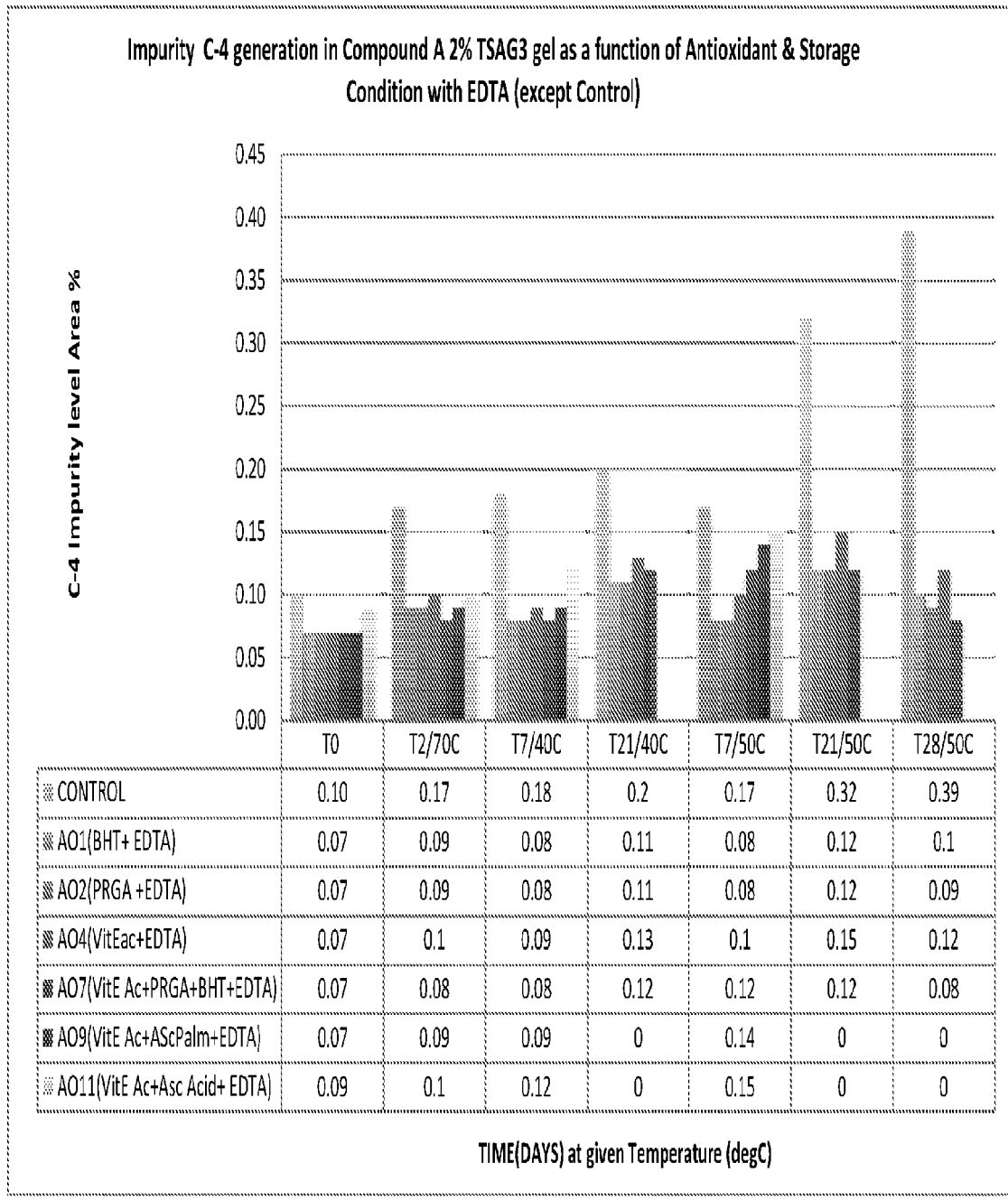
FIG. 21 shows levels of Impurity C-4 in combination antioxidant/chelator formulations of TSAG3 variants (2% w/w Compound A) as a function of storage temperature and time in days.
Figure 22:
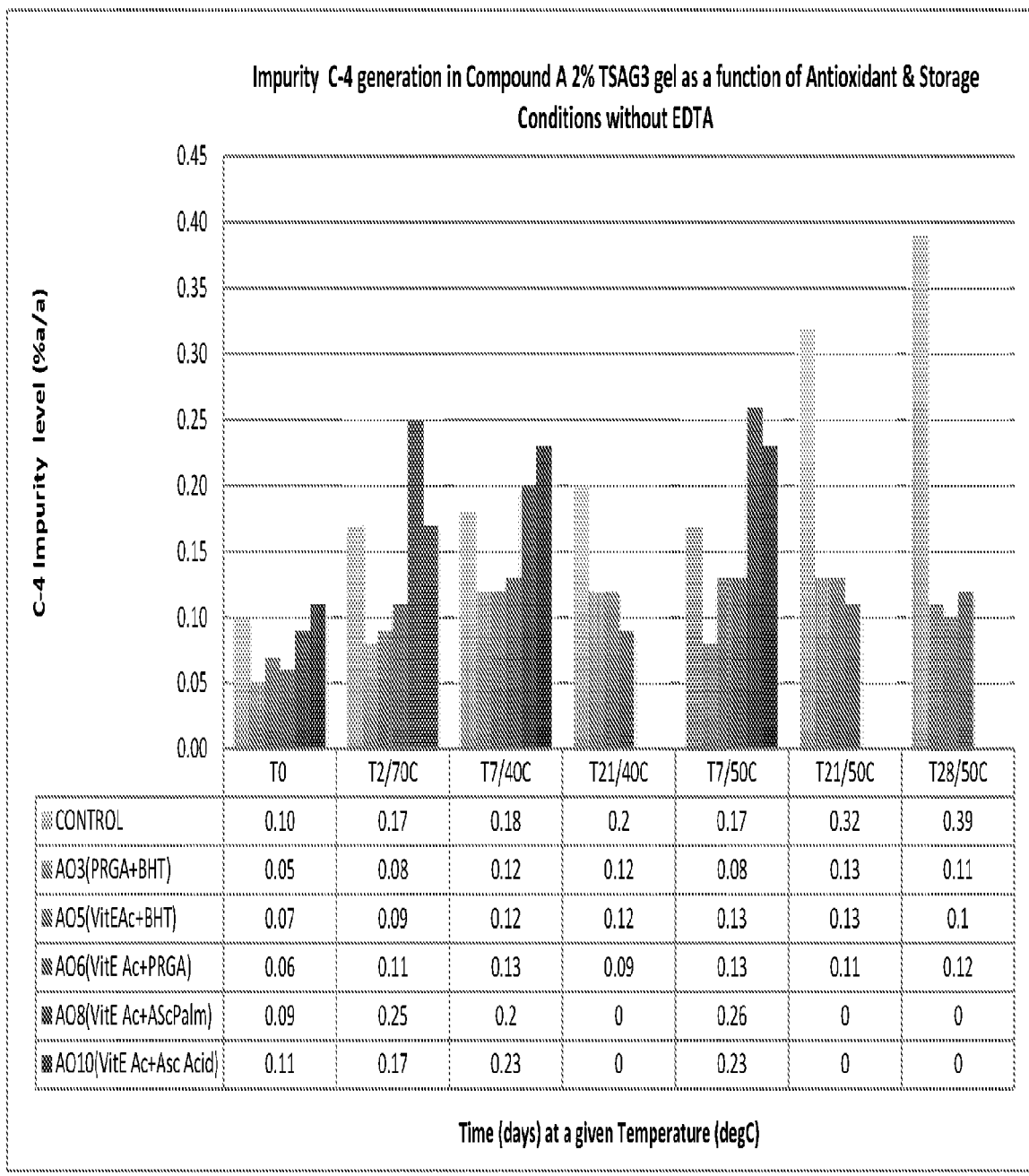
FIG. 22 shows levels of Impurity C-4 in antioxidant only formulations of TSAG3 variants (2% w/w Compound A) as a function of storage temperature and time in days.

The formulations described in Table 27 were stored in glass vials protected from light at 40° C., 50° C. and 70° C. Stability was measured at time zero and after 2 days for the 70° C. samples, time zero and after 7 days, 21 days and 28 days for the 50° C. samples, time zero and after 7 days and 21 days for the 40° C. samples. The data is shown graphically for levels of impurity C-4 with respect to anti-oxidant and EDTA presence in FIG. 21 and for levels of impurity C-4 with respect to presence of anti-oxidant alone in FIG. 22. The majority of the antioxidant/chelator formulations provided improved relative stability (as judged by the rate of appearance of impurity C-4 shown in FIGS. 21 and 22 and Table 27) than the control TSAG3 formulation with the exception of the Vitamin E Acetate+Ascorbyl palmitate or Ascorbic acid combination without EDTA. The latter were not measured at 50° C., 21 days and 50° C., 28 days due to the much higher decomposition at earlier time points. There is also evidence that C-4 may be a transient impurity degrading to other products at higher temperatures over the longer periods of the experiment. Additional findings from this study are summarized below:

BHT+EDTA (TSAG3 A01) and Propyl Gallate+EDTA (TSAG3 A02) combinations provided the highest levels of protection but BHT is inherently a more stable antioxidant than all the other antioxidants which can themselves degrade and cause unintended reaction with the drug under long term storage while offering no added advantage. TSAG3 AO1 appears 7-8 fold more stable than the TSAG3 control at 50° C.

Super Refined Excipients PEG400 SR and Transcutol HP were chosen in TSNAG3 SR as they potentially have

TABLE 27

Estimated relative rates of Impurity formation at 50° C./7 days for the various antioxidant/chelator variants of TSAG3 including SR containing super refined grades of Transcutol P (HR grade) and PEG400. Different sources of Compound A were also tested in TSAG3 base

| Formulation[1] | BHT (% w/w) | Propyl gallate (% w/w) | VitaminE acetate (% w/w) | Ascorbyl palmitate (% w/w) | Ascorbic Acid (% w/w) | EDTA (% w/w) | Rate of Impurity gen. (%/day × 10³) at 50° C. |
|---|---|---|---|---|---|---|---|
| TSAG3 (Control) | No antioxidant | | | | | | 10.0 |
| TSAG3 SR | Contains super refined excipients | | | | | | 2.9 |
| TSAG3 AO1 | 0.1 | — | — | — | — | 0.005 | 1.4 |
| TSAG3 AO2 | — | 0.025 | — | — | — | 0.005 | 1.4 |
| TSAG3 AO3 | 0.1 | 0.025 | — | — | — | — | 4.3 |
| TSAG3 AO4 | — | — | 0.002 | — | — | 0.005 | 4.3 |
| TSAG3 AO5 | 0.1 | — | 0.002 | — | — | — | 8.6 |
| TSAG3 AO6 | — | 0.025 | 0.002 | — | — | — | 10.0 |
| TSAG3 AO7 | 0.1 | 0.025 | 0.002 | — | — | 0.005 | 7.1 |
| TSAG3 AO8 | — | — | 0.002 | 0.02 | — | — | 24.3 |
| TSAG3 AO9 | — | — | 0.002 | 0.02 | — | 0.005 | 10.0 |
| TSAG3 AO10 | — | — | 0.002 | — | 0.05 | — | 17.1 |
| TSAG3 AO11 | — | — | 0.002 | — | 0.05 | 0.005 | 8.6 |

[1]Antioxidants added to formulation with levels of ethanol, phenoxyethanol, propylene glycol, PEG 400 and Transcutol P reduced to compensate and q.s. 100%.
[2]Two different suppliers of API (1 & 2) were tested in TSAG3 formulation base - API(2) corresponds to Control.

less peroxide/free radical inducing impurities which are often an issue in oxidation. While appearing to provide some advantage at 50° C., conflicting results were seen at 40° C. and 70° C. suggesting a complex temperature dependency. (e.g. SR was seen to be less stable by a factor of 2 than control at 40° C. over 3 weeks, but at 50° C. for the same period, SR was more stable by a factor of 3.5 from Table 27.

The impact of the source of Compound A was particularly surprising with alternate supplier (Compound A API2) used in the TSAG3 formulation with no antioxidants/chelators showed a decomposition rate estimated to be 3.7 fold that of the control. Hence, the variation of small amounts of synthetic impurities in the API, despite meeting the same specifications, appear to be responsible for decreased stability of the drug product once mixed with excipients. This is potentially one reason why little decomposition was seen in earlier pre-formal studies and also why an antioxidant/chelator is necessary As the improvement in stability for the modified re-formulation, TSAG3A01, was calculated to be 7-8 fold at 50° C. vs. the TSAG3 control, a broader, accelerated stability evaluation was performed using Arrhenius modelling software and data produced at by FreeThink Technologies Inc using ASAPrime® software over a wider range of temperatures and conditions to validate our results in Example 23.

Example 24: Accelerated Stability Predictions

ASAPrime® Studies (Accelerated Stability Assessment Program) is a registered product of FreeThink Technologies Inc., Branford CT, USA. The purpose of these studies was to compare the original TSAG3 2% Compound A gel formulation to the lead modified formulation containing BHT and EDTA. Formulation strengths in the range 0.25 and 2.5% w/w were used to compare TSAG3 and Modified TSAG3 across a range of temperatures (50° C., 60° C., 70° C., 75° C., 80° C.) to get a more accurate estimate of the improvement in product shelf life conferred by the addition of stabilizers via the production rate of the C-4 impurity. Additionally, the impact of an oxygen absorber was also assessed to understand the role of oxygen in any instability observed plus the effect of replacing regular grade Transcutol® P with the purified grade Transcutol® HP. A validated HPLC analytical method was used based on the method described in Example 16 to assess the appearance of C-4 and any other peaks of unidentified origin. In all cases, the added excipients were demonstrated not to interfere with the assay. A summary of results is shown in Table 28 and Table 29 including calculated mean shelf life at 25° C./60% Relative Humidity compared to actual data obtained and shelf life extrapolated in ICH studies for 0.25% and 2.5% gels under the same conditions stored in aluminum tubes.

TABLE 28

Summary of ASAPrime ® Studies on the TSAG3 Gel Formulation (Compound A 2.0%)

| Formulation of cpd A Gel | Experimental Conditions[a] | C-4 Spec. Limit | $E_a$ (kcal/mol) | Corr. Coeff. ($R^2$) for Arrhenius | Mean Shelf-Life(yrs) @25° C./60% RH |
|---|---|---|---|---|---|
| TSAG3 (2% w/w) | No $O_2$ absorber + Transcutol ®P | 0.5% | 19.7 | 1.00 | 0.49 |
| TSAG3 (2% w/w) | $O_2$ absorber + Transcutol ®P | 0.5% | 4.4 | 0.93 | 1.2 |
| TSAG3 (2% w/w) | No $O_2$ absorber + Transcutol ®HP | 0.5% | 15.6 | 0.87 | 0.59 |
| TSAG3 (2% w/w) | $O_2$ absorber + Transcutol ®HP | 0.5% | 5.1 | 0.89 | 1.3 |
| TSAG3 (0.25% w/w) | Actual GMP lot[b] on ICH stability | 0.5% | Not calculated | 0.96[c] | 0.63 |
| TSAG3 (2.5% w/w) | Actual GMP lot[b] on ICH stability | 0.5% | Not calculated | 0.9418[c] | 0.37 |

[a]For ASAPrime ® studies run for 21 days and no. of samples (n) 50° C.(4), 60° C.(5), 65° C.(5), 70° C.(4), 75° C.(3), 5° C. control (3)
[b]Data from ICH stability samples stored at 25° C./60% RH in aluminum tubes for up to 3 months with n = 4 time points.
[c]$R^2$ data for C-4 appearance rate at 25° C./60% Relative Humidity, not Arrhenius projections

TABLE 29

Summary of ASAPrime ® Studies on the Modified TSAG3 Gel Formulation (Compound A at 0.25% and 2.5%)

| Formulation of Compound A Gel | Experimental Conditions[a] | C-4 Spec. Limit | $E_a$ (kcal/mol) | Correlation Coefficient ($R^2$) for Arrhenius | Mean Shelf-Life (yrs) 25° C./60% RH |
|---|---|---|---|---|---|
| TSAG3 Modified (0.25% w/w) | No $O_2$ absorber + Transcutol ®P | 0.5% | 28.928 | 0.951 | >10 |

TABLE 29-continued

Summary of ASAPrime ® Studies on the Modified TSAG3
Gel Formulation (Compound A at 0.25% and 2.5%)

| Formulation of Compound A Gel | Experimental Conditions[a] | C-4 Spec. Limit | $E_a$ (kcal/mol) | Correlation Coefficient ($R^2$) for Arrhenius | Mean Shelf-Life (yrs) 25° C./60% RH |
|---|---|---|---|---|---|
| TSAG3 Modified (2.5% w/w) | No $O_2$ absorber + Transcutol ®P | 0.5% | 49.086 | 0.94 | >10 |

[a]For ASAPrime ® studies run for 21-28 days and no. of samples (N) 50° C. (3), 60° C. (4), 70° C.(6), 75° C.(4), 80° C.(4), 5° C. control (3)
[b]Data from ICH stability samples stored at 25° C./60% RH in aluminum tubes for up to 3 M with N = 4 time points
[c]$R^2$ data for C-4 appearance rate at 25° C./60% RH, not Arrhenius projection Summarizing the results for this study
- The ASAPrime® technology is predictive of shelf life for the current formulation based on C-4 impurity appearance rate within a reasonable error.
- The prevention of contact with oxygen from the current product improves the projected shelf-life at 25° C./60% RH by a factor of 2-3 fold from 0.49 to 1.2 years but the use of the purer Transcutol® HP makes little difference to the shelf life in either case which is consistent with the erratic results found previously for super refined excipients
- The Modified TSAG3 formulation at both the 0.25% and 2.5% strength have projected shelf-lives at 25° C./60% Relative Humidity of greater than 10 years (15-20 fold increase over the original TSAG3 formulation), confirming that Controlled Room Temperature storage is now much more viable.
- Both the Pre-formal Antioxidant and the ASAPrime® studies for the Modified TSAG3 formulation predict significant improvement in shelf-life at 25° C./60% RH (8× vs 15-20×) over that of the original TSAG3 formulation with the ASAPrime® prediction likely to be more accurate. Even in the most pessimistic case a shelf life of 3-4 years is predicted for the modified TSAG3 formulation versus 6 months for the unmodified TSAG3 formulation at 25° C./60% Relative Humidity.
- Transition Metal impurities did not seem to vary much between lots and spiked samples of TSAG3 with Chromium and Ferric ions did not show dramatic differences in rates of oxidation from control. EDTA does however provide some benefit in the case of Chromium and when combined with an antioxidant. For example, with CrCl3/EDTA at 60° C. for 2 weeks the level of C-4 accumulation was 0.814% vs. 1.381% for control, an improvement of about 1.7 fold based on single assay point. However, the effect was neutral for corresponding Ferric ion studies.
- Nitrogen purging of gel solvents during manufacture and headspace application during packaging demonstrated some benefit (a factor of 2× decreased rate of C-4 production at 50° C. storage for 4 weeks using nitrogen headspace in tubes) and had already been applied to the current Compound A gel manufacturing process. The experimental use of an oxygen absorber (more efficient than Nitrogen purging) demonstrated a 2-3 fold improvement of shelf life.

Thus the benefit of oxygen exclusion has been retained for the Modified formulation.

Example 25: Photo-Stability Studies of Gel Formulations

Photo-stability was initially evaluated for the Original TSAG3 formulation of Compound A gel at 2.0% w/w under exposure to ICH light conditions for both Visible and UVA light as shown in Table 30. Using the same formulations and strengths of the Modified TSAG3 formulation (0.25% and 2.5% Compound A gel) as used for the ASAPrime® studies in Example 24, photo-stability was also evaluated under exposure to ICH light conditions for both Visible and UVA light as shown in Table 31. The analytical methods used were as described in Example 16.

TABLE 30

Photo-stability Results for Original TSAG3 formulation (Compound A 2.0% w/w) Gels and Controls using ICH irradiation conditions

| 1 × ICH irradiation condition | Area % C-4 impurity in Original TSAG3 formulation (Compound A 2% w/w) Gel with Transcutol ®-P | | | Area % C-4 impurity in Original TSAG3 formulation (Compound A 2% w/w) Gel with Transcutol ®-HP | | |
|---|---|---|---|---|---|---|
| | Unstressed | Control | Exposed | Unstressed | Control | Exposed |
| Vis: 1.2 m lux-hrs | 0.01% | 0.14% | 9.12%[a] | 0.09% | 0.14% | 12.62%[a] |
| UVA: 200 Whrs/m$^2$ | 0.01% | 0.14% | 0.5% | 0.11% | 0.14% | 0.6% |

[a]Other peaks reported at RRT 0.85; 1.03; 1.30 totaling < 3.0%

TABLE 31

Photo-stability Results for Modified TSAG3 formulation (Compound A 0.25% and 2.5% w/w) Gels and Controls using ICH irradiation conditions

| 1 x ICH irradiation condition | Area % C-4 impurity in Modified TSAG3 formulation (Compound A 0.25% w/w) Gel with Transcutol ®-P | | | Area % C-4 impurity in Modified TSAG3 formulation (Compound A 2.5% w/w) Gel with Transcutol ®-P | | |
|---|---|---|---|---|---|---|
| | Unstressed | Control | Exposed | Unstressed | Control | Exposed |
| Vis: 1.2 m lux-hrs | 0.075% | N/A | 0.28% | 0.08% | 0.07% | 0.67% |
| UVA: 200 Whrs/m$^2$ | 0.075% | N/A | 0.23% | 0.08% | 0.07% | 1.23% |
| | Area % RRT 1.30 in Modified TSAG3 formulation (Compound A 0.25% w/w) Gel with Transcutol ®-P | | | Area % RRT 1.30 in Modified TSAG3 formulation (Compound A 2.5% w/w) Gel with Transcutol ®-P | | |
| Vis: 1.2 m lux-hrs | ND | N/A | 0.52 | ND | ND | ND |
| UVA: 200 Whrs/m$^2$ | ND | N/A | 0.06 | ND | ND | ND |

$^a$No other peaks detected

The results of these photo-stability studies are summarized below.

For the Original TSAG3 formulation (Compound A 2%), irradiation with visible light showed significantly more production of the C-4 impurity (9-13% depending on grade of Transcutol) versus that produced under UVA irradiation (0.5-0.6%). Both levels were significantly greater than controls.

Several other impurities (totaling less than 3.0%) were seen in the Original TSAG23 formulation exposed to both of the above conditions.

For the Modified TSAG3 formulations the corresponding levels of C-4 produced under irradiation with visible light and UVA for Compound A at 0.25% were only 0.28 and 0.23%, respectively and for Compound A at 2.5% were only 0.67 and 1.23%, respectively.

The only other major impurity appearing with the Modified TSAG3 formulation was at RRT 1.30, which appeared in the Compound A at 0.25% strength under visible irradiation (0.52%) but was minimally present under UVA irradiation; whereas the Compound A at 2.5% strength showed no detectable levels of this impurity under either visible or UVA irradiation.

Overall, the Modified TSAG3 formulation demonstrates an 18-33 fold improvement in photo-stability under the visible ICH irradiation conditions exposure and an equivalent profile when subjected to UVA irradiation conditions.

The data for the Original TSAG3 formulation provides the additional insight that Transcutol®-HP potentially delivers less stable product than the lower grade Transcutol®-P under conditions of oxidative stress, although this was not examined for the Modified TSAG3 formulation.

Example 26: Physical Stability of Compound a Gels

Figure 20:
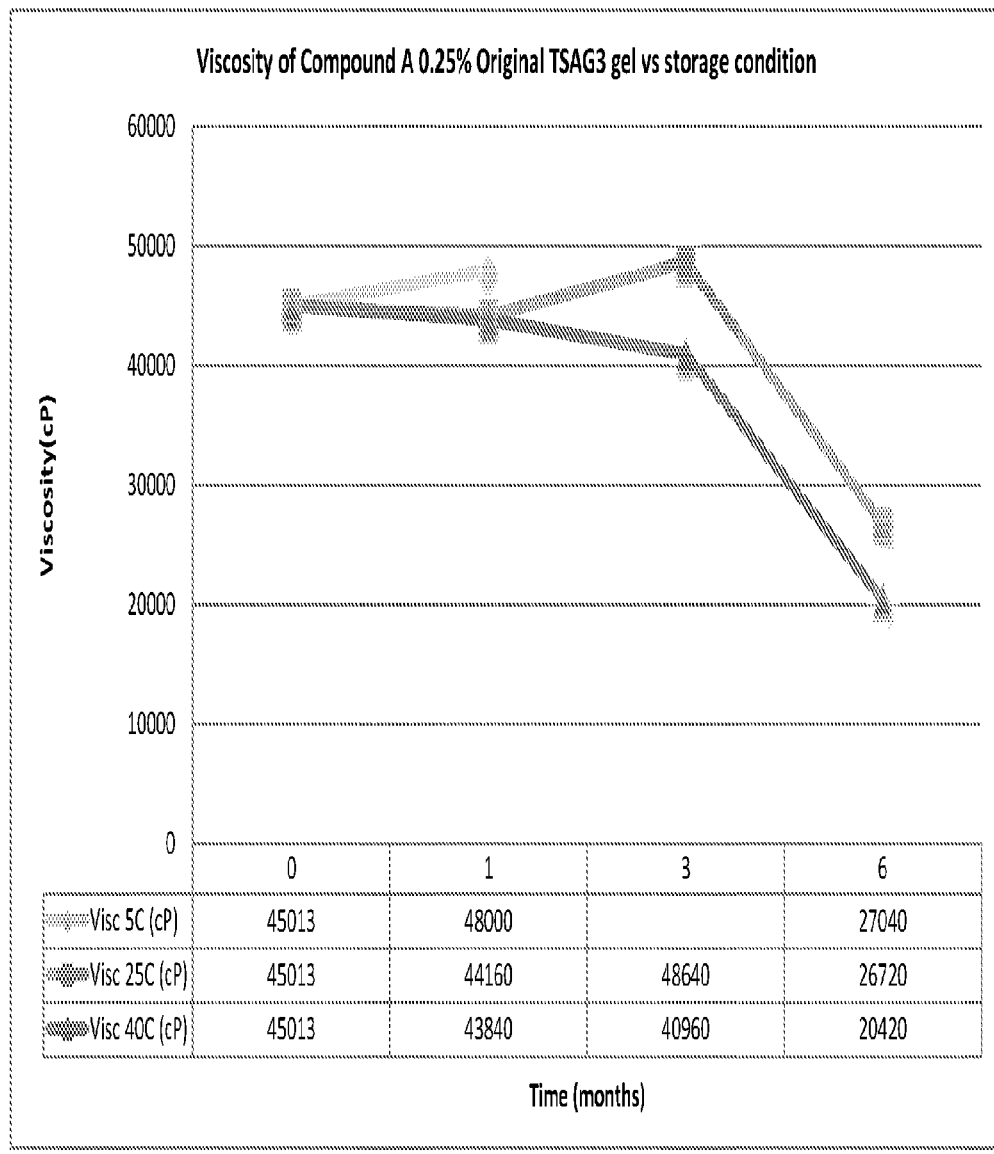
FIG. 20 shows six month formal stability data for the Original TSAG3 formulation as measured by apparent viscosity reductions when stored at 5° C., 25° C./60% relative humidity, and 40° C./75% relative humidity
Figure 23:
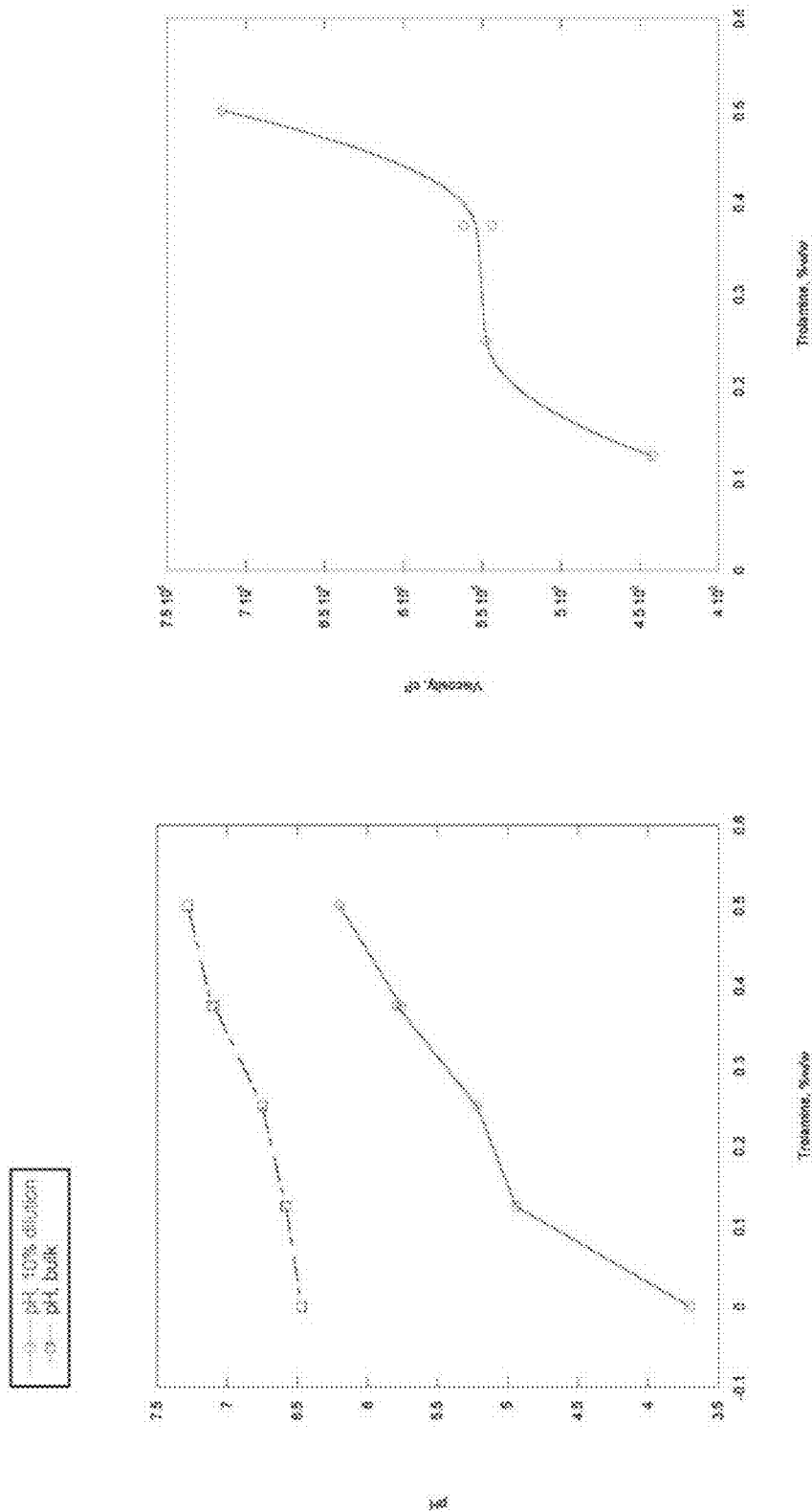
FIG. 23 shows the effect of Trolamine Levels on both the apparent and measured pH values with corresponding measurements of viscosity of the Modified TSAG3 Gel (containing compound A)

The physical instability of the Original TSAG3 formulations as indicated by drop in the gel viscosity and apparent pH is described in Example 23 and FIG. 20 and the probable cause is insufficient buffer capacity in the Original TSAG3 formulation. Based on pre-formal evaluations, despite the low aqueous content of the TSAG3 formulation (19-20%), it was considered that the 1% Carbomer loading was solvated well enough to remain stable, especially as there are no components other than the Carbomer which are ionizable. In order to resolve both the drop in apparent pH and viscosity resulting from it, a commonly used neutralizing/buffering agent, Trolamine NF (primarily triethanolamine), was evaluated rather than sodium hydroxide due to the high level of non-aqueous solvent (75%) in the gel and the chance of inorganic sodium chloride precipitation. FIG. 23 shows how increasing levels of trolamine result in changes to both pH control and viscosity. Based on this data a Trolamine NF level of 0.375% was selected for the Modified TSAG3 formulation providing an ability to buffer at the measured (diluted) pH above 5.5, which is close to the pKa of the carbomer polymer. This level also conferred a viscosity "plateau" between approximately 0.3 and 0.4% trolamine. During manufacture of the gels, it is recommended that aqueous phase containing trolamine is added using high shear mixing to the non-aqueous phase containing all of the other ingredients in order to achieve a homogeneous gel.

Figure 24:
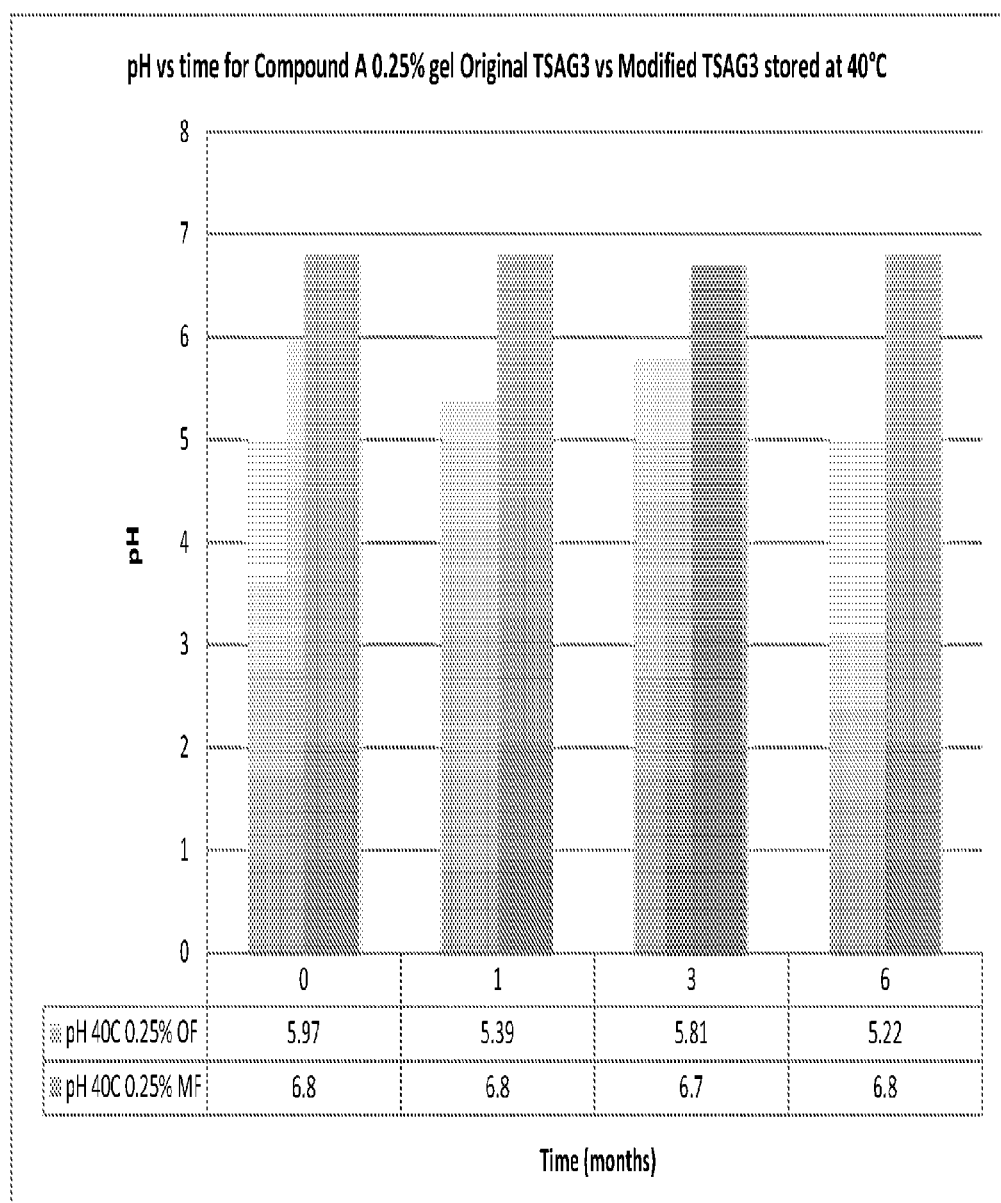
FIG. 24 shows the apparent pH physical stability data for Original TSAG3 and Modified TSAG3 (both containing compound A at 0.25% w/w) gels stored at 40° C. in lacquered aluminum tubes for 6 months under ICH stability protocols
Figure 25:
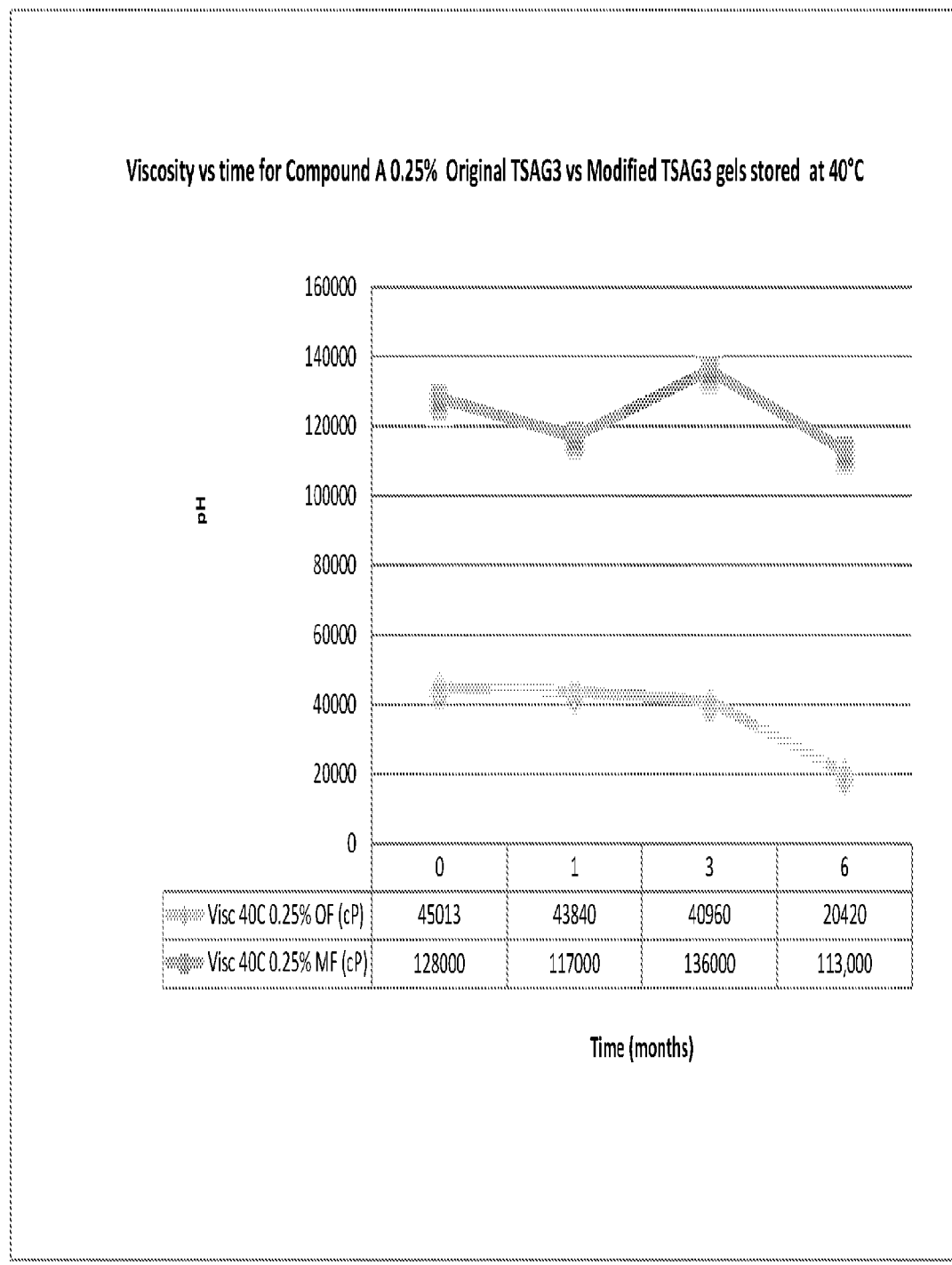
FIG. 25 shows the viscosity physical stability data for Original TSAG3 and Modified TSAG3 (both containing compound A at 0.25% w/w) gels stored at 40° C. in lacquered aluminum tubes for 6 months under ICH stability protocols

Longer term ICH stability studies were also carried out in lacquered aluminum tubes. The comparative long term ICH physical stability as measured by apparent pH (FIG. 24) and viscosity (FIG. 25) for the Original TSAG3 and Modified TSAG3 gels (0.25% w/w compound A) show significant improvements in control of both parameters for the Modified TSAG3. These longer term ICH stability studies in tubes demonstrates that the Modified TSAG3 gel is able to maintain both the apparent pH and viscosity under accelerated conditions at 40° C. compared to the much lower viscosity provided by the Original TSAG3 formulation and inability to control drop in pH. Aqueous gels of 10-20% water are rarely gelled using Carbomer due to the difficulty of providing the pH buffering and hydration of the polymer in order to provide the gel structure. Trolamine is ideal in that it is soluble within the non-aqueous solvent base used in TSAG3 variants. The ranges of Trolamine and Carbomer used are critical to being able to produce consistent gels which will apply to the skin evenly and deliver drug consistently and reproducibly. This is not determined or predicted a priori due to the very complex interactions and behavior of the gel excipients in this formulation.

Example 27. In Vitro Human Cadaver Skin Permeation Studies and In Vitro Artificial Membrane Release Studies In vitro human cadaver skin permeation studies are readily performed by those skilled in the art using a Franz skin transport-diffusion measurement apparatus in order to measure flux and deposition within skin tissue from excised human skin having the key features of stratum corneal, epidermal and dermal tissue. In vitro artificial membrane release studies are virtually identical methodologically to that of the human cadaver skin in that both use the same apparatus and analytical methods but differ in what they measure. The former is used measure the release of drug from the formulation in a way that attempts to simulate what happens in vivo, using an artificial membrane that is not rate limiting. The Human Cadaver skin model is designed to evaluate drug diffusion into the skin, the distribution within the skin and the permeation rate through it whereby the skin is the rate limiting barrier. The two values are used to optimize both the release and transport across the prototype formulations.

A set suitable of analytical conditions were developed on an Agilent G6120 LC/MS system with a mass spectrometer detector ("MS"), for analyzing Compound A as follows:

TABLE 32

Analytical conditions for the method used for detecting Compound A. The calibration curves were made using pure Compound A reference standard

| Instrument: | Agilent G6120MS |
| --- | --- |
| Column: | Eclipse Plus C8. 5 um, 4.6 × 100 mm |
| Mobile Phase: | A: Water w/0.1% Formic Acid |
| | B: Acetonitrile |

| Gradient: | Time (minutes): | % B |
| --- | --- | --- |
| | 0 | 10% |
| | 1 | 10% |
| | 9 | 95% |
| | 10.5 | 95% |

| Flow Rate: | 1.0 ml/min |
| --- | --- |
| Column Temp: | 30° C. |
| MS Detection: | Negative Ion, SIM: 430 |
| Injection Vol: | 25 μl |
| Retention time: | ~7.2 minutes |

Based on the results of solubility studies, a receptor chamber fluid of phosphate buffered saline ("PBS") at pH 7.4 with 0.01% wt. $NaN_3$ (added as a preservative) and 4% wt. hydroxypropylbetacyclodextrin (HPBCD) was chosen. The solubility of the actives in the receptor chamber fluid was found to be ~36 μg/ml which is sufficient to maintain sink conditions for the flux study. The receptor chamber solution was prepared at an appropriate pH and degassing was carried out by filtering the receptor chamber fluid through a ZapCap CR 0.2 m membrane while pulling vacuum.

Custom made Franz diffusion cells ("FDCs") with a receptor chamber volume of 3.3 ml were used for the experiment. The available diffusional surface area of the skin for each cell is 0.55 $cm^2$. The receptor chamber fluid was maintained at 32° C.±0.5° C. during the experiment using a stirring dry block heater and the fluid was continuously agitated with a stir bar. The steps for assembling the diffusion cells are outlined below:

For the in vitro release measurement, a cellulose acetate membrane was selected and the terms skin and membrane will be used synonymously in the following sections apart from the skin deposition measurements which are not relevant to in vitro release. Dermatomed intact human cadaver skin was purchased from the New York Firefighters Tissue Bank ("NYFFTB"). Upon receipt of the skin from the tissue banks, the skin was stored frozen at −20° C. until the morning of the experiment. The cadaver skin was removed from the freezer and allowed to defrost in a bio-safety hood for 30 minutes. The thoroughly defrosted skin was removed from the package and placed on the bio-safety hood countertop with the stratum corneum side up. The skin was patted dry with a Kimwipe, then sprayed with fresh PBS and patted dry four times to remove any residues present on the skin.

The receptor chamber wells were then filled with the previously prepared degassed receptor chamber fluid. A Teflon coated stir bar was added to each receptor chamber well. The defrosted cadaver skin was examined and only areas with even thickness and no visible damage to the surface were used. The skin was cut into ~2 cm×2 cm squares and each skin piece was centered on the donor chamber wells, stratum corneum ("SC") side up. The skin was centered again and the edges flattened out. The donor chamber and receptor chamber wells were then aligned and clamped together with a pinch clamp. Additional receptor chamber fluid was added where necessary. Any air bubbles present were removed by tilting the cell, allowing air to escape along the sample port. The fully loaded Franz diffusion cells were then placed in the stirring dry block heaters and allowed to rehydrate for 20 minutes from the receptor chamber fluid. The block heaters were maintained at 329C±0.5° C. throughout the experiment with continuous stirring. After 20 minutes, the surface of the skin was examined. If the skin was wet or showed signs of "sweating", the FDC was considered compromised and discarded.

Once the cells had been assembled and the skin allowed to hydrate for 20 minutes, the barrier integrity of each skin section was tested using a tritiated water test prior to the dosing of the formulation to the skin as follows: an aliquot of 150 μl of tritiated water (spiked with 25 μCi tritiated water/10 ml water) was added to each FDC donor chamber well. After 5 minutes, the tritiated water from the donor chamber wells was removed and the skin tapped dry using a Kimwipe. The receptor chamber wells were further agitated for an additional 1 hour after the tritiated donor chamber fluid was removed. A 300 μl aliquot sample was then taken from each receptor chamber well. The remaining receptor chamber fluid was discarded and replaced with fresh PBS (membrane integrity studies use only PBS in receptor chamber fluid). 600 μl of scintillation cocktail (Ultima Gold XR) was then added to each sample aliquot and the tritium content of the receptor chamber aliquot was then measured using a liquid scintillation counter ("LSC"). Any FDCs showing anomalously high water flux were discarded. The remaining FDCs were then ranked according to tritiated water flux and then distributed such that each formulation was assigned to FDCs with nearly equivalent average tritiated water flux values. Once the membrane integrity check study was complete, the entire receptor chamber volume of each FDC was replaced with receptor chamber fluid prepared above.

After the membrane integrity test was complete, and the cells appropriately sorted, the formulations were applied to the stratum corneum of the skin. The test articles were applied as 5 μl doses to the skin using a positive displacement Nichiryo pipette, then spread across the surface of the skin using a glass rod. Donor chamber wells were left uncapped during the experiment. At 1-2, 4, 6-8, 22-24, 30 and 46-48 hours, a 300 μl sample aliquot was drawn from the receptor chamber wells using a graduated Hamilton type injector syringe. Fresh receptor chamber medium was added to replace each 300 μl sample aliquot. The samples were then filtered with a 0.2 μm GHP membrane filter plate.

At 46-48 hrs, the skin was washed with a PBS/EtOH 50/50 vol % solution, then wiped clean using PBS/EtOH soaked KimWipes. After the residual formulation was wiped off and the skin tapped dry with KimWipes, the stratum corneum was tape stripped three times—each tape stripping consisting of applying cellophane tape to the skin with uniform pressure and peeling the tape off. The epidermis of each piece was then separated from the underlying dermal tissue using tweezers. If necessary, the skin pieces were briefly heated for two minutes on a hot plate maintained at 60° C. to facilitate separation of the epidermis and dermis. The epidermal and dermal tissues were collected and separately placed in to 4 ml borosilicate glass vials. After all the skin pieces were separated, 2 ml of the extraction solvent (pure DMSO) was added to each vial. The vials were then allowed to incubate for 24 hours at 40° C. with gentle shaking. After 24 hours, sample aliquots were taken and filtered with the 0.20 μm GHP membrane filter plate. Sample aliquots were analyzed using the analytical method as outlined above. Samples were refrigerated at 4-8° C. prior to analysis to help prevent any unwanted degradation of the actives.

In Vitro Performance Evaluation: Drug Release

Several studies were performed using the in vitro release rate and human cadaver skin model described. The first was an in vitro release study through a cellulose acetate membrane, designed to evaluate the variation of release in order to select a more limited number of formulations for the in vitro human cadaver skin permeation and deposition studies. Formulations were selected based on pre-formal evaluations. A summary of the results are shown in Table 33. Compound A release rates from 6 prototype gel formulations described in Table 24 were evaluated in the in vitro drug release experiment. Based on these results, in vitro permeation and penetration experiment was carried out in order to compare Compound A permeation and penetration characteristics.

All formulations were thermodynamically optimized to the predicted 80% of Compound A saturation in each case. It was apparent that flux through an inert membrane has virtually a direct, dependence on Compound A formulation concentration or loading and plays a significant part in determining the transport rate in this model. However, when normalized for drug loading, the normalized flux was relatively consistent across formulations with the exception of the Reference formulation which was designed as a high flux transdermal application. This is almost certainly driven by co-diffusion of solvents altering the kinetics of release. In general, the higher loaded Non-Aqueous gel formulations (TSNG) released faster than the Aqueous gels (TSNAG's) which in turn released faster than the Cream formulations (TSC's). The Cream formulations are discussed in Example 29. On the basis of this, several Nonaqueous and Aqueous gels were selected for the in vitro human cadaver skin permeation and deposition studies in order to put in context the in vitro release rate data obtained.

In Vitro Performance Evaluation: Human Cadaver Skin Permeation and Deposition Studies Based on the data obtained (Table 33), four gel formulations and one control were selected for study in in vitro human cadaver skin penetration and permeation experiments using the Franz Diffusion cell methodology described above, the results of which are shown in Table 34. Penetration data into the Stratum Corneum (SC), the Epidermis and the Dermis were assessed using methodology described in this section for tissue separation (tape stripping for SC; heat treatment to separate the Epidermis and Dermis and separate extractions) and validated extraction and HPLC analytical methodology.

TABLE 33

Summary of results from Franz Diffusion cell release of Compound A through a cellulose acetate membrane over 6 hours from several gel prototypes listed in Table 9 (±Standard Deviation; n = 5-6)

| Formulation | Amount of drug applied (μg, based on 300 μg dose of formulation) | Steady State Drug Release (μg/cm$^2$/h) | Steady State Drug Release (μg/cm$^2$/√h) | Rank based on parameters A and B | C. Steady State Drug Release normalised for 1% w/w (μg/cm$^2$/h) |
|---|---|---|---|---|---|
| TSNG13 (4% w/w) | 12.00 | 154.08 ± 30.43 | 556.59 ± 110.50 | 1 | 38.52 |
| TSNG10 (4.5% w/w) | 13.50 | 138.98 ± 20.24 | 513.07 ± 82.06 | 2 | 31.12 |
| Reference (2.5% w/w) | 7.50 | 137.50 ± 19.51 | 496.46 ± 67.59 | 3 | 55.00 |
| TSAG3 (2.5% w/w) | 7.50 | 91.20 ± 17.04 | 318.91 ± 62.01 | 4 | 36.48 |
| TSC10 (SS5) (1.4% w/w) | 4.20 | 42.60 ± 9.21 | 144.57 ± 28.66 | 5 | 30.43 |
| TSAG4 (1.5% w/w) | 4.50 | 36.02 ± 11.84 | 128.71 ± 44.67 | 6 | 24.01 |
| TSAG7a (0.25% w/w) | 0.75 | 9.83 ± 3.93 | 31.25 ± 13.95 | 7 | 39.32 |
| TSC10a (0.22% w/w) | 0.66 | 9.82 ± 0.61 | 22.56 ± 2.86 | 8 | 44.64 |
| TSC10c (0.3% w/w) | 0.90 | 5.48 ± 1.81 | 17.47 ± 7.33 | 9 | 18.27 |
| TSC16 (0.25% w/w) | 0.75 | 5.14 ± 2.08 | 14.53 ± 6.74 | 10 | 20.56 |

TABLE 34

Summary results from Franz Cell in vitro human cadaver skin permeation and deposition study using Compound A gel prototypes (±SD; n = 6)

| Formulation | Flux (µg/cm²/h) | Flux Measurement Location | $R^2$ | Flux Normalized for 1% w/w (µg/cm²/h) |
|---|---|---|---|---|
| TSAG3 (2.5% w/w) | 0.33 ± 0.10 | 4-30 h | 0.98 | 0.13 |
| TSAG4 (1.5% w/w) | 0.08 ± 0.02 | 6-30 h | 0.97 | 0.05 |
| TSNG10 (4.5% w/w) | 0.32 ± 0.13 | 6-30 h | 0.95 | 0.07 |
| TSNG13 (4% w/w) | 0.67 ± 0.34 | 4-30 h | 0.99 | 0.17 |
| Ref Form (2.5% w/w) | 2.22 ± 0.27 | 2-24 h | 0.99 | 0.89 |

Abbreviations:
h = hours,
Ref Form = reference formulation,
w/w = weight/weight

Of the various formulation prototypes TSAG3 was the best performing aqueous gel in both flux experiments. Overall, the total recovery of drug from the skin surface after 48-hour exposure in this study ranged from 52% to 87% of applied dose. The rank ordering of flux across skin does suggest an influence of formulation type and the concentration applied between the different gels but this is not as clear as that shown for in vitro release through an artificial membrane.

Table 35 shows the mean concentrations found for the human cadaver skin penetration estimated in mM (millimolar) concentrations for the drug in the stratum corneum, epidermal and dermal layers. The half-maximal inhibitory concentration ($IC_{50}$) value of Compound A vs. SCD-1 is reported to be <5 nM, thus the $IC_{50}$ value is exceeded by >80,000 fold for all formulations across all skin layers.

TABLE 35

Mean (n = 6) concentrations (mM) of compound A extracted from skin tissue after 48 hours exposure to selected formulations

| | Concentration (mM) of compound A in tissue | | |
|---|---|---|---|
| Formulation | Stratum Corneum | Epidermis | Dermis |
| TSAG3 | 10.83 | 1.10 | 0.56 |
| TSAG4 | 8.43 | 1.01 | 0.42 |
| TSNG10 | 32.37 | 1.37 | 1.78 |
| TSNG13 | 13.87 | 1.44 | 3.76 |
| Ref Form | 10.12 | 0.84 | 1.33 |

Abbreviation:
Ref Form = reference formulation

Thus, all applied formulations in this experimental model appear to provide concentrations of drug that are well over the $IC_{50}$ value. The balance between penetration and flux therefore became the key focus as a topical formulation should be designed to optimize local tissue penetration and delivery while minimizing the transdermal flux and greater systemic exposure.

The overall conclusions for the in vitro release and Human Cadaver skin permeation and deposition studies are:
  The Human Cadaver skin in vitro release rate is highly dependent on Compound A loading in the formulation but less so for the Human Cadaver skin permeation rate.
  Skin deposition data suggests that all of the formulations are capable of providing the concentration range to significantly exceed the $IC_{50}$ value of Compound A for SCD-1 enzyme inhibition and therefore provide adequate exposure to test both the in vivo pharmacology in humans and the toxicology in the animal model selected.
  Balancing in vitro flux rates with skin layer deposition, the Non-Aqueous gel TSNG10 and Aqueous gel TSAG3 offer the best options.
  TSAG3 was subsequently selected due to superior cosmetic properties and its balance of physico-chemical and biopharmaceutical characteristics amongst all the Gel formulations studied.

Example 28—Validation of the Modified Gel Formulation Performance

As expressed and demonstrated in the Examples above, the initially selected, Original TSAG3 formulation required further stabilization chemically and physically to provide a topical gel formulation capable of minimally delivering a two year shelf life at controlled room temperature. The Modified TSAG3 formulation has been demonstrated to provide this in terms of resistance to oxidation, photo instability, pH drop and loss in viscosity stability in comparison with the Original TSAG3 formulation. For comparison the two formulations are shown in Table 36.

TABLE 36

Formulation Composition for the Original TSAG3 and the Modified TSAG3 gels of Compound A covering all strengths from 0% w/w(vehicle) to the maximum attainable strength of drug dissolved in vehicle (2.5% w/w)

| | | TSAG3 | | Modified TSAG3 | |
|---|---|---|---|---|---|
| Component | Function | % w/w | mg/g | % w/w | mg/g |
| Compound A | API | 0-2.50 | 0-25.0 | 0-2.50 | 0-25.0 |
| Dehydrated Alcohol (Ethanol) USP | Solvent | 10.00 | 100.00 | 10.00 | 100.00 |
| Propylene Glycol USP | Solvent | 20.00 | 200.00 | 20.00 | 200.00 |
| Polyethylene Glycol (PEG 400) NF | Solvent | 21.00 | 210.00 | 21.00 | 210.00 |
| Diethylene glycol monethyleether (Transcutol P) NF | Solvent | 25.00 | 250.00 | 25.00 | 250.00 |

TABLE 36-continued

Formulation Composition for the Original TSAG3 and the Modified TSAG3 gels of Compound A covering all strengths from 0% w/w(vehicle) to the maximum attainable strength of drug dissolved in vehicle (2.5% w/w)

| Component | Function | TSAG3 % w/w | TSAG3 mg/g | Modified TSAG3 % w/w | Modified TSAG3 mg/g |
|---|---|---|---|---|---|
| Phenoxyethanol USP | Preservative/solvent | 1.00 | 10.00 | 1.00 | 10.00 |
| Butylated hyrdoxytoluene (BHT) NF | Antioxidant | 0.00 | 0.00 | 0.10 | 1.00 |
| Edeetate disodium diydrate USP | Chelating agent | 0.00 | 0.00 | 0.005 | 0.05 |
| Carbomer Homopolymer TypeC (Carbopol 980) NF | Gelling agent | 1.00 | 10.00 | 1.00 | 10.00 |
| Trolamine NF | pH adjuster | 0.00 | 0.00 | 0.375 | 3.75 |
| Water for Irrigation or Purified Water USP | Gel phase solvent | 22-19.5 | 220-195.00 | 21.52-19.02 | 215.2-190.20 |
| Total | | 100.00 | 1000.00 | 100.00 | 1000.00 |

Variants of TSAG3 and the Modified TSAG3 were also conceived and Table 37 and Table 38 below show a comparison between the variants.

TABLE 37

Variants of TSAG3 and the Modified TSAG3 gels of Compound A covering strengths from 0.005% w/w to 5% w/w

| Component | Function | TSAG3 % w/w | Modified TSAG3 % w/w |
|---|---|---|---|
| Compound A | API | 0.005-5.0 | 0.005-5.0 |
| Dehydrated Alcohol (Ethanol) USP | Solvent | 1.0-20.0 | 1.0-20.0 |
| Propylene Glycol USP | Solvent | 5.0-40.0 | 5.0-40.0 |
| Polyethylene Glycol (PEG 400) NF | Solvent | 5.0-40.0 | 5.0-40.0 |
| Diethylene glycol monethyleether (Transcutol P) NF | Solvent | 5.0-40.0 | 5.0-40.0 |
| Phenoxyethanol USP | Preservative/solvent | 0.1-5.0 | 0.1-5.0 |
| Butylated hyrdoxytoluene (BHT) NF | Antioxidant | 0.00 | 0.05 or more |
| Edeetate disodium diydrate USP | Chelating agent | 0.00 | 0.001 or more |
| Carbomer Homopolymer TypeC (Carbopol 980) NF | Gelling agent | 0.5-2.0 | 0.5-2.0 |
| Trolamine NF | pH adjuster | 0.00 | amount needed to provide an apparent pH in the range of 6.5 to 7.5 |
| Water for Irrigation or Purified Water USP | Gel phase solvent | remainder | remainder |
| Total | | 100.00 | 100.00 |

TABLE 38

Further variants of TSAG3 and the Modified TSAG3 gels of Compound A covering strengths from 0.1% w/w to 2.5% w/w

| Component | Function | TSAG3 % w/w | Modified TSAG3 % w/w |
|---|---|---|---|
| Compound A | API | 0.1-2.5 | 0.1-2.5 |
| Dehydrated Alcohol (Ethanol) USP | Solvent | 5.0-15.0 | 5.0-15.0 |
| Propylene Glycol USP | Solvent | 15.0-25.0 | 15.0-25.0 |
| Polyethylene Glycol (PEG 400) NF | Solvent | 15.0-25.0 | 15.0-25.0 |
| Diethylene glycol monethyleether (Transcutol P) NF | Solvent | 20.0-30.0 | 20.0-30.0 |

TABLE 38-continued

Further variants of TSAG3 and the Modified TSAG3 gels of
Compound A covering strengths from 0.1% w/w to 2.5% w/w

| Component | Function | TSAG3 % w/w | Modified TSAG3 % w/w |
|---|---|---|---|
| Phenoxyethanol USP | Preservative/solvent | 0.5-2.0 | 0.5-2.0 |
| Butylated hyrdoxytoluene (BHT) NF | Antioxidant | 0.00 | 0.1 or more |
| Edeetate disodium diydrate USP | Chelating agent | 0.00 | 0.005 or more |
| Carbomer Homopolymer TypeC (Carbopol 980) NF | Gelling agent | 0.75-1.5 | 0.75-1.5 |
| Trolamine NF | pH adjuster | 0.00 | amount needed to provide an apparent pH in the range of 6.5 to 7.5 |
| Water for Irrigation or Purified Water USP | Gel phase solvent | remainder | remainder |
| Total | | 100.00 | 100.00 |

Figure 26:
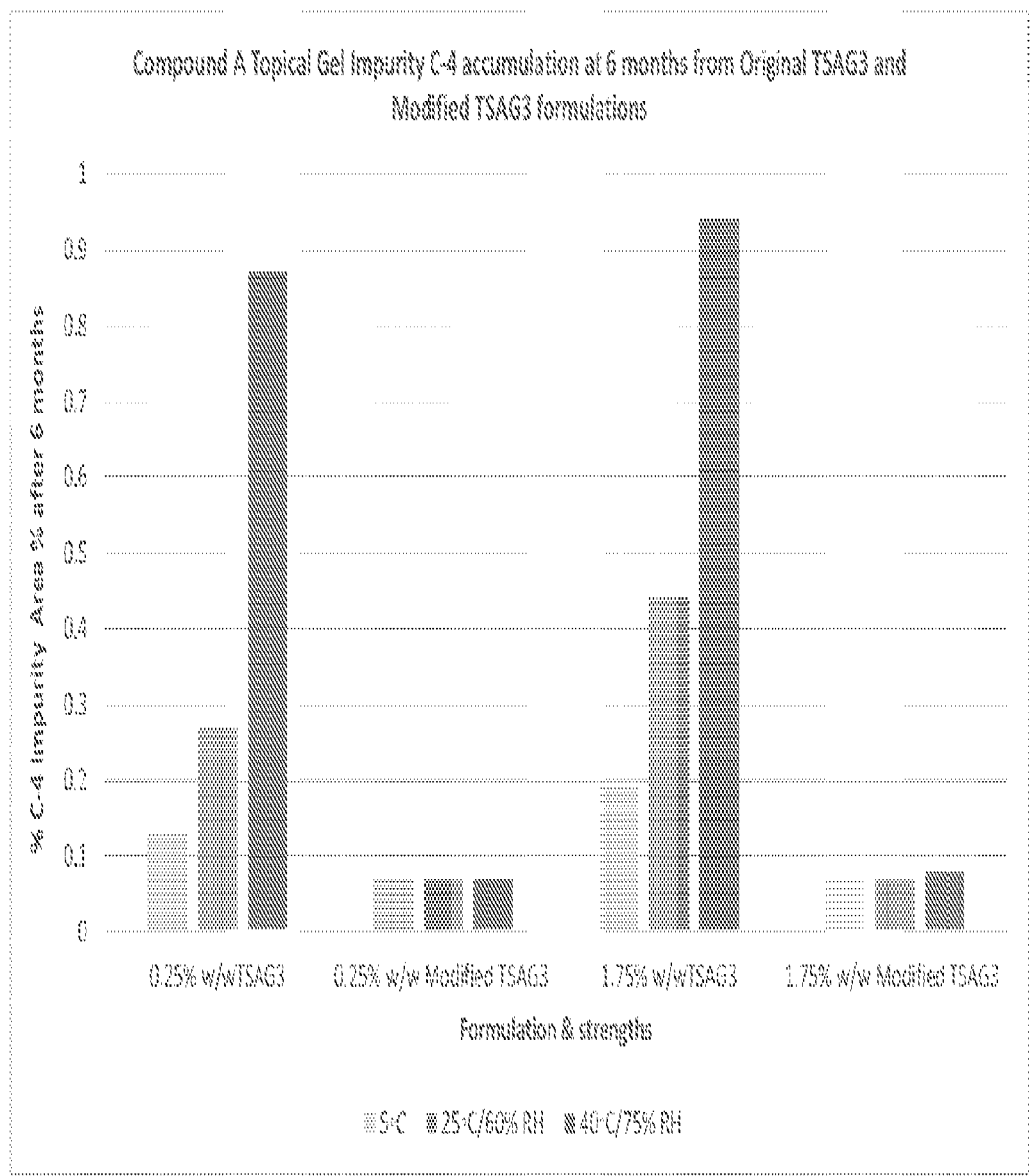
FIG. 26 shows the charted summary of data from Table 39 for comparative ICH stability results at 6 months for Original TSAG3 and Modified TSAG3 formulations at 0.25% and 1.75% w/w concentrations of Compound A indicating measured quantities of the specific Impurity C-4.
Figure 27:
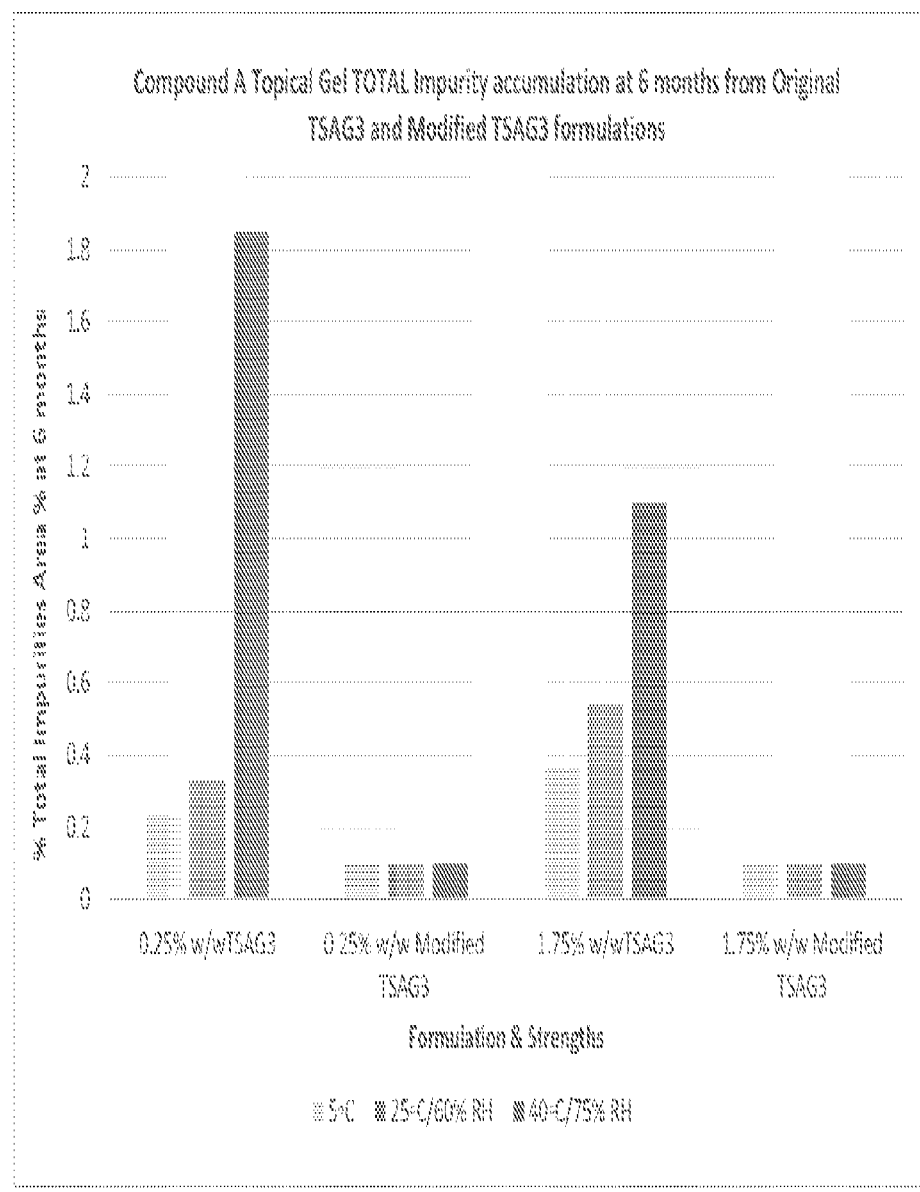
FIG. 27 shows the charted summary of data from Table 39 for comparative ICH stability results at 6 months for Original TSAG3 and modified TSAG3 formulations at 0.25% and 1.75% w/w concentrations of Compound A indicating total impurities.

Both of the TSAG3 formulations have been placed on official ICH stability study in order to support the ongoing clinical studies and to provide an estimation of shelf life. Table 39 and FIG. 26 and FIG. 27 summarizes the results of ICH stability studies in 10-15 g lacquered aluminum tubes up to 6 months' storage at 5° C., 25° C./60% Relative Humidity and 40° C./75% Relative Humidity.

TABLE 39

Summary of comparative ICH stability results for the Original TSAG3 and Modified TSAG3 formulations of Compound A at 0.25% and 1.75% w/w after 6 months at various conditions and showing the measurements of the specific impurity C-4 and Total impurities. The projected or actual shelf lives based on the C-4 specification displayed is taken from Tables 28 & 29.

| | 6 M C4 impurity level (area %) | | | 6 M TOTAL impurity level (area %) | | |
|---|---|---|---|---|---|---|
| | Specification | | | | | |
| | Spec NMT 0.5% Storage condition | | | Spec NMT 2.0% Storage condition | | |
| Formulation | 5° C. | 25° C./60% RH | 40° C./75% RH | 5° C. | 25° C./60% RH | 40° C./75% RH |
| 0.25% w/w TSAG3 | 0.13 | 0.27 | 0.87 | 0.24 | 0.33 | 1.85 |
| 0.25% w/w Modified TSAG3 | 0.07 | 0.07 | 0.07 | 0.1 | 0.1 | 0.1 |
| 1.75% w/w TSAG3 | 0.19 | 0.44 | 0.94 | 0.37 | 0.54 | 1.1 |
| 1.75% w/w Modified TSAG3 | 0.07 | 0.07 | 0.08 | 0.1 | 0.1 | 0.1 |
| | Projected Shelf Life (Years) | | | Projected Shelf Life (Years) | | |
| TSAG3 formulation | | | | | | |
| predicted | 0.49-0.59 | | | TBD | | |
| determined | 0.37-0.63 | | | TBD | | |
| TSAG3 Modified Formulation | >10 | | | TBD | | |

In order to further study the relationship of Compound A flux versus total skin deposition in human skin and how this compares to resulting pharmacokinetic profiles and bioavailability in-vivo in humans of the original and modified formulations, additional studies were carried out in human cadaver skin. The additional in-vitro human cadaver skin permeation and deposition data, generated under the same conditions and via the same methods as referenced in Example 27, are summarized in Table 40.

TABLE 40

Additional in vitro permeation (flux) and deposition studies carried out on Compound A gels using human cadaver skin showing (a) Study 2 comparing the original TSAG3 formulation versus the modified TSAG3 formulation at the highest clinical strength tested (1.75% w/w) and (b) Study 3 demonstrating the effect of increasing the concentration of Compound A in modified TSAG3 gel across a wide range of concentrations

| Formulation | Strength (% w/w) | Skin Flux[1] ($\mu g/cm^2$)[3] | Epidermal Deposition[1,2] ($\mu g/cm^2$)[3] | $mM^2$ | Dermal Deposition[1,2] ($\mu g/cm^2$)[3] | $mM^2$ | Total Skin Deposition[1,2] ($\mu g/cm^2$)[3] | $mM^2$ |
|---|---|---|---|---|---|---|---|---|
| a) Study 2 | | | | | | | | |
| Original TSAG3 | 1.75 | 0.214 ± 0.14 | 21.15 ± 3.9 | 3.22 | 1.53 ± 0.65 | 0.061 | 22.68 | 3.28 |
| Modified TSAG3 | 1.75 | 0.352 ± 0.13 | 14.3 ± 3.3 | 1.99 | 1.58 ± 0.47 | 0.063 | 15.88 | 1.96 |
| b) Study 3 | | | | | | | | |
| Modified TSAG3 | 0.05 | ND | 0.55 ± 0.13 | 0.08 | 0.2 ± 0.04 | 0.01 | 0.75 | 0.08 |
| Modified TSAG3 | 0.25 | 0.08 ± 0.02 | 1.93 ± 0.33 | 0.27 | 0.16 ± 0.07 | 0.01 | 2.09 | 0.27 |
| Modified TSAG3 | 0.75 | 0.36 ± 0.11 | 4.04 + 0.62 | 0.56 | 1.45 ± 0.76 | 0.06 | 5.49 | 0.62 |
| Modified TSAG3 | 1.75 | 0.73 ± 0.17 | 14.8 ± 3.15 | 2.06 | 1.77 ± 0.40 | 0.07 | 16.6 | 2.13 |

Figure 28:
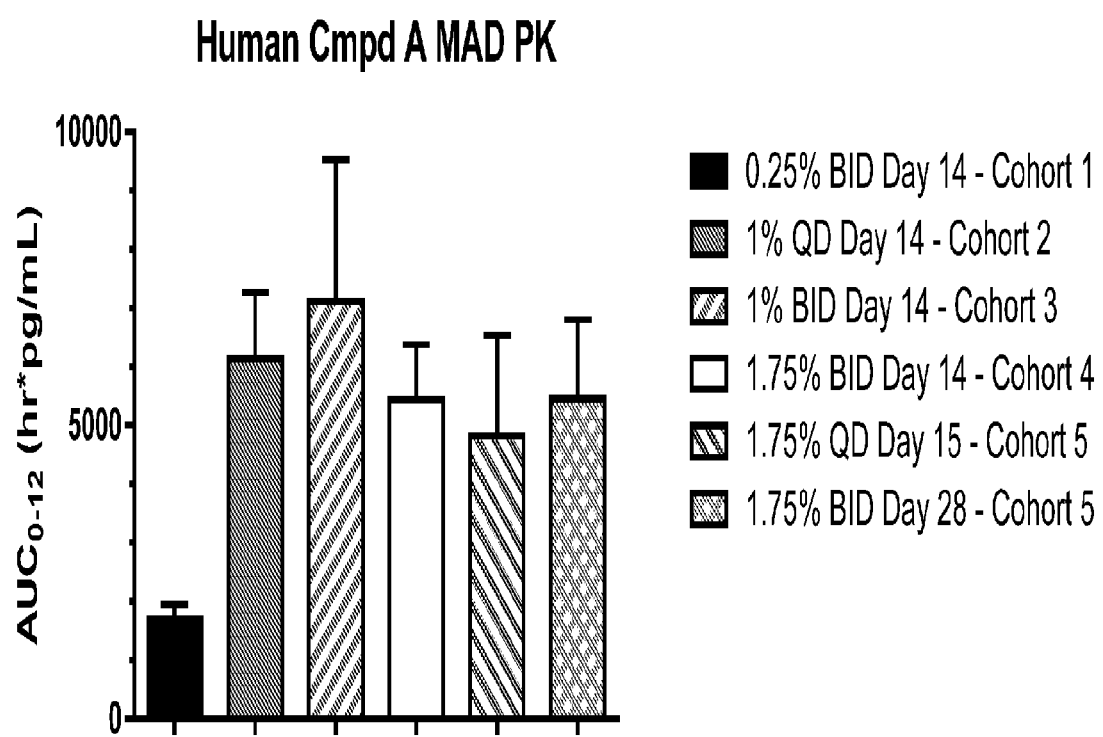
FIG. 28 shows the human Multiple Ascending Dose (MAD) PK data from Phase 1 studies comparing the Original TSAG3 formulation in Cohorts 1-4 (treated QD or BID for 14 days) and the Modified TSAG3 formulation in Cohort 5 (treated QD for days 1-14 and BID for days 15-28)

[1] over 46-48 hrs;
[2] for 10 mg skin sample;
[3] Standard Error of the Mean of n = 6 replicates The in-vitro results show very good reproducibility of data at the highest strength of modified gel (1.75% w/w) between two different studies using to different human cadaver skin samples in Study (2). It also demonstrated no significant difference in-vitro between the original and modified formulations of gel in terms of permeation (flux) or deposition in the Epidermis or Dermis. This correlates well with Human in-vivo shown in FIG. 28 which compares the bioavailability (Plasma AUC) of increasing amounts and strengths of Original Formulation (Cohorts 1-4) with of the Modified Formulation (Cohorts 5& 6) at steady state. Cohort 4 (1.75% w/w original formulation once per day at 14 days) can be compared directly with Cohort 5 (1.75% w/w modified formulation once per day for 15 days) and shows no significant difference in plasma exposure or bioavailability, similar to the results found for permeation found in-vitro. Indeed, the subsequent application in Cohort 6 to the same set of volunteers using modified 1.75% w/w formulation twice per day (ie doubling the dose applied) for a further 13 days to 28 days, did not increase the plasma exposure of Cohort 6 significantly, implying that there is a saturation effect in the skin barrier which limits the in vivo bioavailability. This is most likely due to the gel reaching the physical limits of delivering the drug through the skin in-vivo and being efficiently metabolized.

Figure 29:
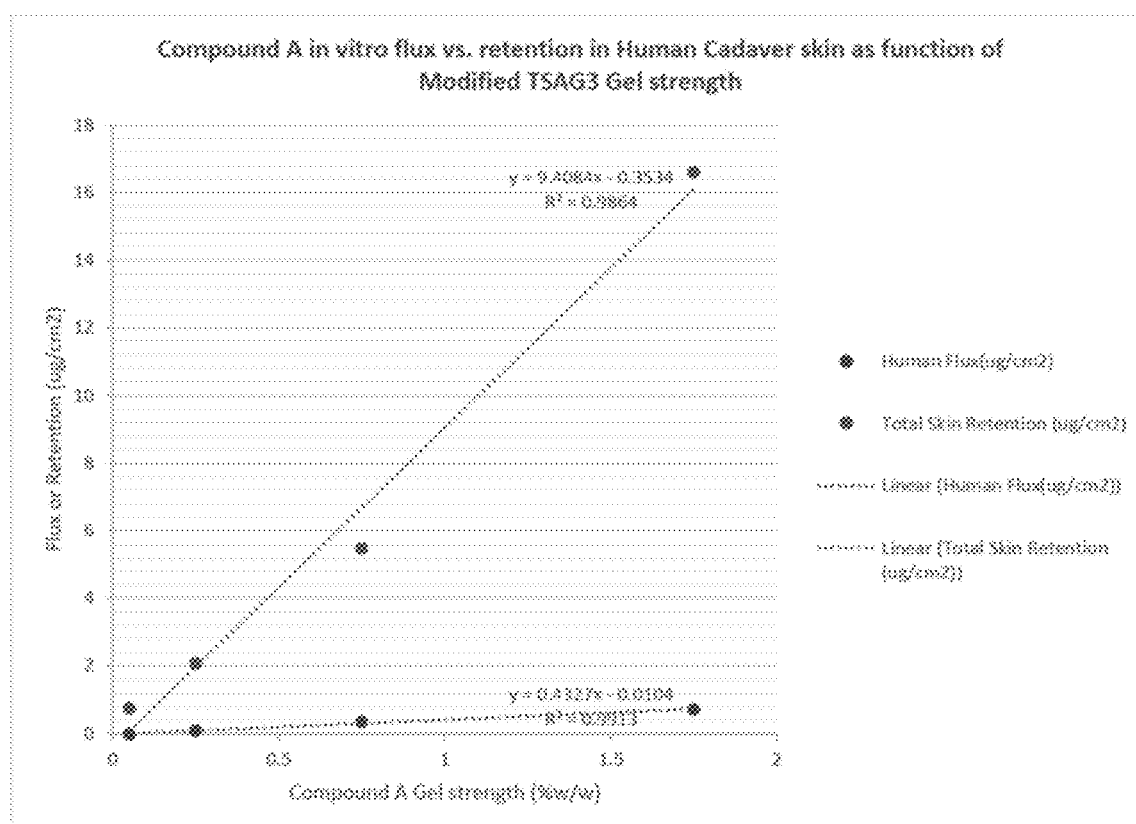
FIG. 29 shows the Linear Correlation of in-vitro permeation (flux) through and total skin retention (deposition) in human cadaver skin with applied gel strength of Compound A in modified TSAG3 formulation showing the high deposition in the epidermis and Dermis combined with relatively low permeation rate.

However, in-vitro a different pattern of behavior is seen whereby, in the ranges of modified gel strengths tested (0.05, 0.25, 0.75 and 1.75% w/w), the permeation or flux through the skin and total drug retention or deposition in the skin over 46-48 hrs is seen to be highly linearly correlated with the strength of gel applied ($R^2$ values are 0.99134 and 0.98635 respectively) as shown in FIG. 29. This suggests no physical saturation of transport mechanisms through the skin occurs within the same concentration range as tested in-vivo and the limiting factor in-vivo is most likely to be metabolic, especially as enzymatic activity is typically very low in excised skin samples used in-vitro.

What is, however, unexpected and unanticipated is that the deposition rate within the skin is proportionately much higher than the permeation rate for this type of formulation which contains a high proportion of transdermal enhancers (25% w/w Transcutol-P, 20% w/w Propylene Glycol and 10% w/w Ethanol). Thus, the modified TSAG3 formulation is providing very high levels of Compound A in the Epidermis and Dermis which are $10^3$-$10^5$ fold above the $IC_{50}$ for the SCD-1 enzyme while providing unexpectedly low permeation rates in-vitro, with the lack of increased exposure further amplified in-vivo by built in metabolic clearance of Compound A. This is highly desirable for a topical medication delivery system, providing the active drug at high concentrations in the target tissue without exposing the rest of the body systemically, thereby lowering the potential for side effects and systemic safety concerns.

Example 29: Creams

The compositions of the creams prepared during the formulation development are summarized in Table 41. The Cream formulations were prepared using the following procedure which is similar to that used for gels: The aqueous phase solvents were sequentially weighed into a suitably sized container and the contents stirred until completely miscible. Into a separate suitably sized glass container the oil phase components (stearic acid, IPP, cetostearyl alcohol, liquid paraffin, Brij 72, paraffin oil, white soft paraffin, hard paraffin, Crodamol GTCC, Dow Corning Emulsifier 10, Tween 60, Span 60 or cetomacrogol 100) were weighed and the oil phase heated in a water bath previously calibrated at 65° C. The oil phase was stirred until a clear melt was observed and any antioxidants were added at this point and dissolved in the oil phase. In a separate suitably sized stainless steel container, the Compound A followed by the aqueous phase were weighed and heated in a water bath previously calibrated at 65° C. using nitrogen blanketing and protection from light. The oil phase was added to the vessel containing the aqueous phase mixture and the formulation homogenized on the maximum speed setting for 3 min using a suitable high shear homogenizer, the head of which was pre-warmed to 65° C. The dimethicone (where applicable) was added to the formulation during homogenization and the formulation was subsequently gently stirred until it was at approximately ambient temperature and the cream base given a chance to stabilize. Once cooled, the cream formulations can be packaged into suitable containers, typically plastic laminate or coated aluminum tubes in 5, 10, 15 or 30 g amounts under a blanket of nitrogen while protecting from direct sunlight and are weight checked to comply with container weight uniformity tests. Preliminary cream excipient compatibility studies were carried out. Many excipients and combinations of excipient were used to evaluate the ability to solubilize drug and obtain the required drug loading as well as both physical and chemical stability of prototype cream combinations using the methodology described above. A key parameter used was the ability to withstand centrifugation at 13,000 RPM (16,060 g) at 2 minute intervals and the cumulative time taken to separate the phases and the extent to which the drug loading was impacted by this. Based on solvent data obtained and multiple physical evaluations, the Cream formulations shown in Table 41 were selected for more in depth stability evaluation.

In order to obtain the higher drug loading, the aqueous phase had to be reduced significantly and co-solvents such as PEG400, Transcutol P and ethanol had to be increased. Following storage at −20° C., 25° C. and 40° C. after two weeks Cream 3, Cream 4 and Cream 10 showed a tendency to phase separate. The higher drug loading coupled with the low nonaqueous to aqueous solvent ratio for Cream 10 was likely the reason for this. Also the Tween/Span combination as an alternative to the Brij 72 surfactant to modify the HLB value and the low viscosity associated with Cream 3 make it feasible as a lotion preparation. Cream 4 was the preferred cream cosmetically but this contained stearic acid which may impact the effectiveness of the drug on SCD-1 and therefore several variants were developed for which Cream 11 is most promising. Table 42 shows the relative chemical stability data obtained. It was concluded that there were no obvious trends in chemical stability and all appear equally stable within the limits of the assay employed and the un-optimized extraction procedures used for at this stage. Although Cream 11 has physical instability challenges and further work will be necessary to improve this, its cosmesis and drug loading potential can be further optimized.

TABLE 41

Composition of Cream Formulations selected for Pre-Formal stability

| Excipient | Composition (% w/w) | | | | | | | |
|---|---|---|---|---|---|---|---|---|
| | Cream4 | Cream 3 | Cream10 | Cream10a | Cream10c | Cream 10e | Cream 11 | Cream16 |
| Stearic acid | 2.00 | — | — | — | — | — | — | — |
| White soft paraffin | 1.00 | 10.00 | 2.00 | 2.00 | 2.00 | 2.00 | 2.00 | — |
| Crodamol GTCC | 9.00 | — | 8.00 | 8.00 | 8.00 | 8.00 | 8.00 | — |
| Medium Chain Triglycerides | — | — | — | — | — | — | — | 7.00 |
| Liquid paraffin | 5.00 | 5.00 | 3.00 | 3.00 | 3.00 | 3.00 | 3.00 | — |
| Cetostearyl alcohol | 3.00 | 4.00 | 2.00 | 2.00 | 2.00 | 2.00 | 2.00 | 5.75 |
| Tween 60 | — | 5.00 | — | — | — | — | — | — |
| Cetomacrogol 1000 | — | 8.00 | — | — | — | — | — | — |
| Span 60 | — | 2.00 | — | — | — | — | — | — |
| Brij 721 | — | — | 2.00 | 2.00 | 2.00 | 2.00 | 2.00 | — |
| Ethanol | 10.00 | 8.00 | 10.00 | 10.00 | 10.00 | — | 10.00 | 10.00 |
| Benzyl alcohol | 2.00 | 1.60 | 2.00 | — | — | — | — | — |
| Phenoxyethanol | — | — | — | 1.00 | 1.00 | 1.00 | 1.00 | 1.00 |
| Propylene glycol | 10.00 | 8.00 | 10.00 | 10.00 | — | 10.00 | — | 10.00 |
| PEG400 | 18.75 | 16.00 | 20.00 | 21.00 | 26.00 | 26.00 | 21.00 | 21.00 |
| Buffer pH 5.5 | 30.00 | 27.15 | 32.75 | 32.78 | 32.70 | 32.80 | 21.60 | 32.75 |
| Transcutol P | — | — | — | — | 5.00 | 5.00 | 15.00 | — |
| Glycerol | 5.00 | 4.00 | 5.00 | 5.00 | 5.00 | 5.00 | 10.00 | 5.00 |
| Brij 72 | 3.00 | — | 3.00 | 3.00 | 3.00 | 3.00 | 3.00 | — |
| Arlacel 165 | — | — | — | — | — | — | — | 6.00 |
| Carbopol 980 NF | — | — | — | — | — | — | — | 0.25 |
| Dimethicone 350 | 1.00 | 1.00 | — | — | — | — | — | 1.00 |
| Compound A | 0.25 | 0.25 | 0.25 | 0.22 | 0.30 | 0.20 | 1.40 | 0.25 |

TABLE 42

Relative chemical stability of compound A cream formulations at −20° C., 25° C. & 40° C.

| Formulation | Compound A concentration (% w/w) | T = 0 | Peak purity of Compound A (% a/a), Mean n = 3 | | | | | |
|---|---|---|---|---|---|---|---|---|
| | | | T = 2 weeks | | | T = 4 weeks | | |
| | | | −20° C. | 25° C. | 40° C. | −20° C. | 25° C. | 40° C. |
| Cream 3 | 0.25 | 98.44 | 98.40 | 98.4 | 98.30 | 98.32 | 98.39 | 98.30 |
| Cream 4 | 0.25 | 98.99 | 98.44 | 98.66 | 98.13 | 98.07 | 98.06 | 98.29 |
| Cream10 | 0.25 | 98.61 | 98.39 | 98.47 | 98.30 | 98.48 | 98.38 | 98.38 |
| Cream10a | 0.22 | 98.44 | 98.41 | 98.49 | 98.47 | 98.48 | 98.50 | 98.21 |
| Cream 10c | 0.3 | 98.38 | 98.48 | 98.34 | 98.63 | 98.47 | 98.45 | 98.38 |
| Cream 10e | 0.2 | 98.48 | 98.51 | 98.68 | 98.54 | 98.47 | 98.51 | 98.50 |
| Cream 11 | 1.4 | 98.47 | 98.34 | 98.40 | 98.36 | 98.35 | 98.23 | 98.34 |
| Cream 16 | 0.25 | 97.70 | 98.50 | 98.11 | 98.54 | 98.53 | 98.50 | 98.57 |

Discussion

Pharmaceutical formulations of the present invention unexpectedly provide chemically and physically stable products at controlled room temperature and above while also combining the ability to dissolve and deliver large concentrations of API topically to a patient's skin in order to treat Acne Vulgaris and related conditions. The vehicle base also provides desired cosmetic properties in terms of rapid rub-in, provision of some emolliency, lack of greasy deposit or excessive drying of the skin.

The inclusion of certain, key antioxidants and chelators and critical pH buffering agents together with the exclusion of oxygen and protection from light exposure, retard degradation of the API via oxidative pathways to an unexpectedly large extent. Furthermore, the pH buffering agent unexpectedly maintains the apparent pH in the range of 6.5-7.0 in a solvent of low water content which enables the acidic gelling agent to provide a structured gel of high viscosity above at least 50,000 cP. This correspondingly provides consistent cosmetic properties and consistent drug delivery to the skin tissues.

Pharmaceutical formulations of the present invention have the following advantages:

(a) the ability to dissolve enough drug in a pharmaceutically acceptable, non-irritating vehicle base to enable drug to be driven into the skin tissues locally;

(b) the potential to modulate the delivery parameters balancing efficient delivery into the skin tissue with a corresponding low levels of accumulated drug in the systemic circulation where the drug is typically not required for activity and can therefore become a safety liability for no therapeutic benefit to the patient;

(c) acceptable cosmetic properties for a topical agent in terms of rapid rub-in, emolliency, lack of greasy deposit or excessive drying of the skin; and (d) a chemically and physically stable formulation matrix that can provide at least a two year shelf life at controlled room temperature (15-30° C.) to facilitate manufacture, storage, distribution and patient usage in the field.

A technical challenge for topical drug formulations can be that success in areas (a), (b) and (c) may be in conflict with (d) or alternatively, the required physico-chemical and biopharmaceutical properties imparted by specific formulation ingredients or excipients, individually or in combination in effectively delivering the topical product may lead to unanticipated instability that cannot be predicted by screening studies.

As a result, the complexity of the resulting gel or cream formulations, due to complex and subtle interactions at the molecular level between drug and excipients, are very difficult to predict a priori with respect to product stability.

The compounds of the subject application can be formulated in many ways as gel, cream or Lotion preparations, but it was discovered that certain antioxidants in combination with certain metal chelators at controlled apparent pH of around neutrality by certain buffering agent types provide acceptable chemical and physical stability without interfering with the drug solubility, delivery and cosmetic properties important for the treatment of Acne Vulgaris or related conditions.

Surprisingly, the combination of certain key antioxidants with a chelator and certain pH buffering agents in a mixture of nonaqueous and aqueous solvents provides excellent stabilization in order to yield a 2 year shelf life whereas other combinations will either provide no benefit or make the product more unstable. This unpredictability of antioxidant behavior is also confounded by the fact that the source of some of the oxidative impurities are believed to be provided by the formulation excipients themselves and even the API itself. The discovery of the key combinations of excipients and stabilizers was therefore both difficult and unexpected as all aspects of the formulation excipient and API supply chain had to be carefully evaluated in order to provide effective stabilization.

LIST OF REFERENCES

1. M. Miyazaki et al. (2001) "Targeted disruption of stearoyl-CoA desaturase1 gene in mice causes atrophy of sebaceous and meibomian glands and depletion of wax esters in the eyelid" *Journal of Nutrition* 131(9): 2260-2268
2. Y. Zheng et al. (1999) "Scd1 is expressed in sebaceous glands and is disrupted in the asebia mouse" *Nat. Genet.*, 23, 268-270
3. H. Sampath et al. "Skin-specific deletion of stearoyl-CoA desaturase-1 alters skin lipid composition and protects mice from high fat diet-induced obesity" *J Biol Chem.*, 284, 19961-73
4. M. Miyazaki et al. (2003) "Role of stearoyl-coenzyme A desaturase in lipid metabolism" *Prostaglandins Leukot. Essent. Fatty Acids*, 68, 113-21
5. U.S. Pat. No. 8,242,286 B2
6. A. L. Zaenglein et al. (2012). "Acne vulgaris and acneiform eruptions" *Fitzpatrick's Dermatology in General Medicine*, 8th ed., vol. 1, pp. 897-917

7. J. K. L. Tan (2008) "Current Measures for the Evaluation of Acne Severity" *Expert Rev. Dermatol.*, 3(5), 595-603
8. N. Janiczek-Dolphin et al., (2010) "Can sebum reduction predict acne outcome?" *Br. J. Dermatology*, 163(4), 683-688
9. K. L. Spalding et al. (2008) "Dynamics of fat cell turnover in humans" *Nature*, 453, 783-787
10. V. Stella (1975) "Pro-drugs: An Overview and Definition" *Pro-drugs as Novel Drug Delivery Systems*, T. Higuchi Ed., Vol. 14, Chapter 1, 1-115
11. E. B. Roche (1987) "Bioreversible carriers in drug design: theory and application" *Pergamon Press*, 1st Edition
12. D. J. Abraham et al. (2010) "Burger's Medicinal Chemistry, Drug Discovery and Development" Wiley, 7th Edition
13. T. L. Lemke et al. (2013) "Foye's Principles of Medicinal Chemistry" Wiley, $7^{th}$ Edition
14. M. B. Smith (2013) "March's Advanced Organic Chemistry: Reactions, Mechanisms, and Structure" Wiley, 7th Edition
15. S. Hanessian et al. (2013) "Design and Strategy in Organic Synthesis" Wiley-VCH, 1st Edition
16. P. G. M. Wuts et al. "Greene's Protective Groups in Organic Synthesis" Wiley-Interscience, 4th Edition
17. T. L. Ho "Fiesers' Reagents for Organic Synthesis" Wiley, Volume 27 Edition
18. A. R. Gennaro "Remington's Pharmaceutical Sciences" Mack Pub. Co, $19^{th}$ Edition
19. U.S. Pat. No. 6,133,326
20. E. Camera et al. (2010) "Comprehensive analysis of the major lipid classes in sebum by rapid resolution high-performance liquid chromatography and electrospray mass spectrometry" *J. Lipid Res.*, 51(11), 3377-3388
21. C. Luderschmidt et al. (1977) "Effects of cyproterone acetate and carboxylic acid derivatives on the sebaceous glands of the Syrian hamster" Arch. Dermatol. Res., 258(2), 185-191
22. Shaker M; et al. (2014). "Liver transplantation for nonalcoholic fatty liver disease: New challenges and new opportunities". *World journal of gastroenterology: WJG.* 20 (18): 5320.
23. Rinella M E (June 2015). "Nonalcoholic fatty liver disease: a systematic review". *JAMA* (*Systematic review*). 313 (22): 2263-73.
24. Sanyal, A J (2002). "AGA Technical Review on Nonalcoholic Fatty Liver Disease.". *Bethesda, MD: American Gastroenterological Association.*
25. Clark J M, Diehl A M (2003). "Nonalcoholic fatty liver disease: an underrecognized cause of cryptogenic cirrhosis". *JAMA.* 289 (22): 3000-4.
26. McCulough, Arthur J (August 2004). "The clinical features, diagnosis and natural history of nonalcoholic fatty liver disease". *Clinics in Liver Disease.* 8 (3): 521-33.
27. Werner, R N; Stockfleth, E; Connolly, S M; et, al. (2015). "Evidence- and consensus-based (S3) Guidelines for the Treatment of Actinic Keratosis—International League of Dermatological Societies in cooperation with the European Dermatology Forum—Short version.". *Journal of the European Academy of Dermatology and Venereology.* 29: 2069-2079.
28. McKenna J K, Florell S R, Goldman G D, Bowen G M (April 2006). "Lentigo maligna/lentigo maligna melanoma: current state of diagnosis and treatment". *DermatolSurg.* 32 (4): 493-504.
29. Ando, H., Watabe, H., Valencia, J. C., Yasumoto, K., Furumura, M., Funasaka, Y., Oka, M., Ichihashi, M., and Hearing, V. J. (2004) "Fatty acids regulate pigmentation via proteasomal degradation of tyrosinase: a new aspect of ubiquitin-proteasome function." *J Biol Chem* 279, 15427-15433
30. Koizume, S., and Miyagi, Y. (2016) "Lipid Droplets: A Key Cellular Organelle Associated with Cancer Cell Survival under Normoxia and Hypoxia." *Int J Mol Sci* 17
31. Mason, P., Liang, B., Li, L., Fremgen, T., Murphy, E., Quinn, A., Madden, S. L., Biemann, H. P., Wang, B., Cohen, A., Komarnitsky, S., Jancsics, K., Hirth, B., Cooper, C. G., Lee, E., Wilson, S., Krumbholz, R., Schmid, S., Xiang, Y., Booker, M., Lillie, J., and Carter, K. (2012) "SCD1 inhibition causes cancer cell death by depleting mono-unsaturated fatty acids." *PLoS One* 7, e33823
32. Peck, B., Schug, Z. T., Zhang, Q., Dankworth, B., Jones, D. T., Smethurst, E., Patel, R., Mason, S., Jiang, M., Saunders, R., Howell, M., Mitter, R., Spencer-Dene, B., Stamp, G., McGarry, L., James, D., Shanks, E., Aboagye, E. O., Critchlow, S. E., Leung, H. Y., Harris, A. L., Wakelam, M. J., Gottlieb, E., and Schulze, A. (2016) "Inhibition of fatty acid desaturation is detrimental to cancer cell survival in metabolically compromised environments." *Cancer Metab* 4, 6
33. Shabani, F. a. S. R. (2010) "Increase of Melanogenesis in the Presence of Fatty Acids." *Pharmacologyonline* 1, 314-323
34. Sumantran, V. N., Mishra, P., and Sudhakar, N. (2015) "Microarray analysis of differentially expressed genes regulating lipid metabolism during melanoma progression." *Indian J Biochem Biophys* 52, 125-131
35. Vargas, T., Moreno-Rubio, J., Herranz, J., Cejas, P., Molina, S., González-Vallinas, M., Mendiola, M., Burgos, E., Aguayo, C., Custodio, A. B., Machado, I., Ramos, D., Gironella, M., Espinosa-Salinas, I., Ramos, R., Martín-Hernandez, R., Risueño, A., De Las Rivas, J., Reglero, G., Yaya, R., Fernández-Martos, C., Aparicio, J., Maurel, J., Feliu, J., and Ramirez de Molina, A. (2015) "ColoLipid-Gene: signature of lipid metabolism-related genes to predict prognosis in stage-II colon cancer patients." *Oncotarget* 6, 7348-7363
36. Yoon, W. J., Kim, M. J., Moon, J. Y., Kang, H. J., Kim, G. O., Lee, N. H., and Hyun, C. G. (2010) "Effect of palmitoleic acid on melanogenic protein expression in murine b16 melanoma." *J Oleo Sci* 59, 315-319
37. Minville-Walz, M., Pierre, A. S., Pichon, L., Bellenger, S., Févre, C., Bellenger, J., Tessier, C., Narce, M., and Rialland, M. (2010) "Inhibition of stearoyl-CoA desaturase 1 expression induces CHOP-dependent cell death in human cancer cells." *PLoS One* 5, e14363

What is claimed is:

1. A method of treating a patient afflicted with Non-alcoholic Steatohepatitis (NASH) which comprises applying to a patient's skin a pharmaceutical composition effective to treat the patient and alleviate the patient's NASH, wherein the pharmaceutical composition comprises a pharmaceutically acceptable carrier and a compound which has the structure:

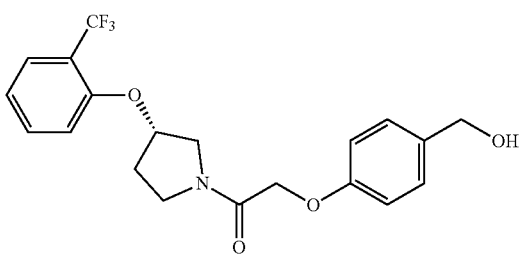 [SMILES: O=C(COc1ccc(CO)cc1)N1CC[C@H](Oc2ccccc2C(F)(F)F)C1]

or a pharmaceutically acceptable salt or ester of the compound in an amount effective to treat the patient, and wherein the pharmaceutically acceptable carrier (A) provides an environment of physical and chemical stability, (B) enables retention of the amount of the compound effective to treat the patient in the patient's skin, (C) permits only a low level of the compound to enter and accumulate in the patient's systemic circulation, and (D) comprises:
(i) ethanol at a concentration of 10.00% w/w;
(ii) phenoxyethanol at a concentration in the range 0.1-5.0% w/w;
(iii) diethylene glycol mono-ethyl ether (otherwise known as DEGEE or Transcutol P®) at a concentration in the range 5.0-40.0% w/w;
(iv) propylene glycol at a concentration in the range 5.0-40.0% w/w;
(v) PEG400 at a concentration in the range 5.0-40.0% w/w;
(vi) carbomer homopolymer type C980 at a concentration in the range of 0.5 to 2.0% w/w;
(vii) butylated hydroxytoluene (BHT) at a concentration of at least 0.05% w/w;
(viii) di-sodium EDTA at a concentration of at least 0.001% w/w;
(ix) trolamine at a concentration sufficient to provide an apparent pH in the range 6.50 to 7.50; and
(x) water at a concentration of 19.02-22% w/w.

2. The method of claim 1 wherein the pharmaceutically acceptable carrier comprises:
(i) ethanol at a concentration of 10.0% w/w;
(ii) phenoxyethanol at a concentration of 1% w/w;
(iii) diethylene glycol mono-ethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w; and
(vii) water at a concentration of 19.5-22% w/w.

3. The method of claim 2, wherein the pharmaceutically acceptable carrier comprises:
(i) ethanol at a concentration of 10.0% w/w;
(ii) phenoxyethanol at a concentration of 1% w/w;
(iii) diethylene glycol mono-ethyl ether (otherwise known as DEGEE or Transcutol P®) at a concentration of 25.0% w/w;
(iv) propylene glycol at a concentration of 20.0% w/w;
(v) PEG400 at a concentration of 21.0% w/w;
(vi) carbomer homopolymer type C980 at a concentration of 1.0% w/w;
(vii) butylated hydroxytoluene (BHT) at a concentration of 0.1% w/w;
(viii) di-sodium EDTA at a concentration of 0.005% w/w;
(ix) trolamine at a concentration of 0.375% w/w; and
(x) water at a concentration of 19.02-21.52% w/w.

4. The method of claim 1, wherein the amount of the compound present in the pharmaceutical composition is a concentration of the compound up to 2.50% w/w.

5. The method of claim 4, wherein the amount of the compound present in the pharmaceutical composition is a concentration of the compound of 0.25%, 0.75% or 1.75% w/w.

6. The method of claim 5, wherein the amount of the compound present in the pharmaceutical composition is a concentration of the compound of 1.75% w/w.

7. The method of claim 3, wherein the amount of the compound present in the pharmaceutical composition is a concentration of the compound up to 2.50% w/w.

8. The method of claim 7, wherein the amount of the compound present in the pharmaceutical composition is a concentration of the compound of 0.25%, 0.75% or 1.75% w/w.

9. The method of claim 8, wherein the amount of the compound present in the pharmaceutical composition is a concentration of the compound of 1.75% w/w.

* * * * *